(12) United States Patent
Park et al.

(10) Patent No.: US 11,917,907 B2
(45) Date of Patent: Feb. 27, 2024

(54) ORGANIC ELECTROLUMINESCENT DEVICE

(71) Applicant: ROHM AND HAAS ELECTRONIC MATERIALS KOREA LTD., Chungcheongnam-do (KR)

(72) Inventors: Kyoung-Jin Park, Gyeonggi-do (KR); Tae-Jin Lee, Gyeonggi-do (KR); Jae-Hoon Shim, Seoul (KR); Yoo Jin Doh, Gyeonggi-do (KR); Hee-Choon Ahn, Gyeonggi-do (KR); Young-Kwang Kim, Gyeonggi-do (KR); Doo-Hyeon Moon, Gyeonggi-do (KR); Jeong-Eun Yang, Gyeonggi-do (KR); Su-Hyun Lee, Gyeonggi-do (KR); Chi-Sik Kim, Gyeonggi-do (KR); Ji-Song Jun, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 0 days.

(21) Appl. No.: 17/532,294

(22) Filed: Nov. 22, 2021

(65) Prior Publication Data

US 2022/0102633 A1 Mar. 31, 2022

Related U.S. Application Data

(63) Continuation of application No. 15/327,664, filed as application No. PCT/KR2015/007607 on Jul. 22, 2015, now abandoned.

(30) Foreign Application Priority Data

Jul. 22, 2014 (KR) .................. 10-2014-0092763

(51) Int. Cl.
| | | |
|---|---|---|
| H01L 51/54 | (2006.01) |
| H10K 85/60 | (2023.01) |
| C09K 11/06 | (2006.01) |
| H05B 33/20 | (2006.01) |
| C07D 209/86 | (2006.01) |
| C07D 405/14 | (2006.01) |
| C07D 409/14 | (2006.01) |
| C09K 11/02 | (2006.01) |
| H10K 50/11 | (2023.01) |
| H10K 50/15 | (2023.01) |
| H10K 101/10 | (2023.01) |
| H10K 101/00 | (2023.01) |

(52) U.S. Cl.
CPC ......... *H10K 85/633* (2023.02); *C07D 209/86* (2013.01); *C07D 405/14* (2013.01); *C07D 409/14* (2013.01); *C09K 11/025* (2013.01); *C09K 11/06* (2013.01); *H05B 33/20* (2013.01); *H10K 85/631* (2023.02); *H10K 85/636* (2023.02); *H10K 85/654* (2023.02); *H10K 85/6572* (2023.02); *H10K 85/6574* (2023.02); *H10K 85/6576* (2023.02); *C09K 2211/1007* (2013.01); *C09K 2211/1029* (2013.01); *C09K 2211/1088* (2013.01); *C09K 2211/1092* (2013.01); *C09K 2211/185* (2013.01); *H10K 50/11* (2023.02); *H10K 50/15* (2023.02); *H10K 50/156* (2023.02); *H10K 85/615* (2023.02); *H10K 85/624* (2023.02); *H10K 85/626* (2023.02); *H10K 2101/10* (2023.02); *H10K 2101/90* (2023.02)

(58) Field of Classification Search
None
See application file for complete search history.

(56) References Cited

U.S. PATENT DOCUMENTS

| | | | |
|---|---|---|---|
| 2007/0093643 A1 | 7/2007 | You et al. | |
| 2013/0207046 A1* | 8/2013 | Pflumm | H10K 85/626 252/500 |
| 2013/0234119 A1 | 9/2013 | Mizuki et al. | |
| 2013/0256645 A1 | 10/2013 | Min et al. | |
| 2014/0034929 A1 | 2/2014 | Hamada et al. | |
| 2014/0042469 A1 | 2/2014 | Seo et al. | |
| 2014/0070204 A1* | 3/2014 | Nagao | H10K 85/6572 548/440 |
| 2014/0306207 A1 | 10/2014 | Nishimura et al. | |
| 2014/0364625 A1 | 11/2014 | Ahn et al. | |
| 2015/0337197 A1 | 11/2015 | Jatsch et al. | |
| 2016/0308146 A1 | 10/2016 | Parham et al. | |

FOREIGN PATENT DOCUMENTS

| | | |
|---|---|---|
| CN | 1657588 A | 8/2005 |
| JP | 3139321 B2 | 2/2001 |
| JP | 2013-183036 A | 9/2013 |
| KR | 20120013173 A | 2/2012 |
| KR | 101170666 B1 | 8/2012 |
| KR | 10-1502316 A1 | 3/2015 |
| WO | 2009/060757 A1 | 5/2009 |

(Continued)

OTHER PUBLICATIONS

Notice of Reason for Refusal from JPO for Japanese application No. 2020-110380; dated Jun. 26, 2020.

*Primary Examiner* — Andrew K Bohaty
(74) *Attorney, Agent, or Firm* — G. Creston Campbell

(57) ABSTRACT

The present disclosure relates to an organic electroluminescent device. The organic electroluminescent device of the present disclosure shows high luminous efficiency and good lifespan by comprising a specific combination of the plural kinds of host compounds and a specific hole transport compound.

11 Claims, No Drawings

(56) References Cited

FOREIGN PATENT DOCUMENTS

| WO | WO-2012034627 A1 | * | 3/2012 | ........... | C07C 209/10 |
| WO | WO-2012150826 A1 | * | 11/2012 | ........... | C07D 231/26 |
| WO | 2013/112557 A1 | | 8/2013 | | |
| WO | 2013/168688 A1 | | 11/2013 | | |
| WO | 2015/156587 A1 | | 10/2015 | | |

* cited by examiner

ORGANIC ELECTROLUMINESCENT DEVICE

CLAIM OF BENEFIT OF PRIOR APPLICATION

This application claims priority under 35 U.S.C. § 120 from U.S. patent application Ser. No. 15/327,664, filed Jan. 20, 2017, which is the National Stage Entry of PCT/KR2015/007607, filed Jul. 22, 2015, both of which are incorporated by reference herein in their entirety.

TECHNICAL FIELD

The present disclosure relates to an organic electroluminescent device.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

The organic EL device converts electric energy into light when electricity is applied to an organic light-emitting material(s). Generally, the organic EL device has a structure comprising an anode, a cathode, and an organic layer disposed between the anode and the cathode. The organic layer of the organic EL device comprises a hole injection layer, a hole transport layer, an electron blocking layer, a light-emitting layer (comprising a host material and a dopant material), an electron buffering layer, a hole blocking layer, an electron transport layer, an electron injection layer, etc. Depending on its function, materials for forming the organic layer can be classified as a hole injection material, a hole transport material, an electron blocking material, a light-emitting material, an electron buffering material, a hole blocking material, an electron transport material, an electron injection material, etc. When a voltage is applied to the organic EL device, holes and electrons are injected from an anode and a cathode, respectively, to the light-emitting layer. Excitons having high energy are formed by recombinations between the holes and the electrons. The energy of excitons puts the light-emitting organic compound in an excited state, and the decay of the excited state results in a relaxation of the energy level into a ground state, accompanied by light-emission.

The most important factor determining luminous efficiency in the organic EL device is light-emitting materials. The light-emitting material needs to have high quantum efficiency, high electron mobility, and high hole mobility. Furthermore, the light-emitting layer formed by the light-emitting material needs to be uniform and stable. Depending on colors visualized by light-emission, the light-emitting materials can be classified as a blue-, green-, or red-emitting material, and a yellow- or orange-emitting material can be additionally included therein. Depending on its function, the light-emitting materials can be classified as a host material and a dopant material. Recently, the development of an organic EL device providing high efficiency and long lifespan is an urgent issue. Particularly, considering EL characteristic requirements for a middle or large-sized panel of OLED, materials showing better characteristics than conventional ones must be urgently developed. The host material acts as a solvent in a solid state and transfers energy, and thus needs to have high purity and a molecular weight appropriate for vacuum deposition. Furthermore, the host material needs to have high glass transition temperature and high thermal degradation temperature to achieve thermal stability, high electro-chemical stability to achieve long lifespan, easiness of forming amorphous thin film, good adhesion to materials of adjacent layers, and non-migration to other layers.

In order to enhance color purity, luminous efficiency and stability, the light-emitting material may be used as a mixture of a host and a dopant. Generally, devices showing good electroluminescent characteristics comprise a light-emitting layer in which a dopant is doped into a host. In the dopant/host material system, efficiencies and lifespan of the device are highly affected by the host material, and thus selection of the host material is important.

WO 2013/168688 A1, WO 2009/060757 A1, and Japanese Patent Application Laying-Open No. 2013-183036 A1 disclose an organic electroluminescent device in which a biscarbazole derivative is employed as a host material. However, the references fail to specifically disclose an organic electroluminescent device employing the following compounds: as a plurality of hosts, a biscarbazole derivative in which the nitrogen atoms of carbazoles are linked to aryls, respectively, and a carbazole derivative in which the nitrogen atom of carbazole is linked to a nitrogen-containing heteroaryl; and as a hole transport compound, a fluorene or spirobifluorene derivative which is linked to a diarylamino.

DISCLOSURE OF INVENTION

Technical Problem

The object of the present disclosure is to provide an organic electroluminescent device having high efficiency and long lifespan.

Solution to Problems

The present inventors found that the above object can be achieved by an organic electroluminescent device comprising an anode, a cathode, and an organic layer between the anode and the cathode, wherein the organic layer comprises one or more light-emitting layers and one or more hole transport layers; at least one of the one or more light-emitting layers comprises one or more dopant compounds and two or more host compounds; a first host compound of the two or more host compounds is represented by the following formula 1; a second, host compound is represented by the following formula 2; and at least one of the one or more hole transport layers comprises the compound represented by the following formula 3:

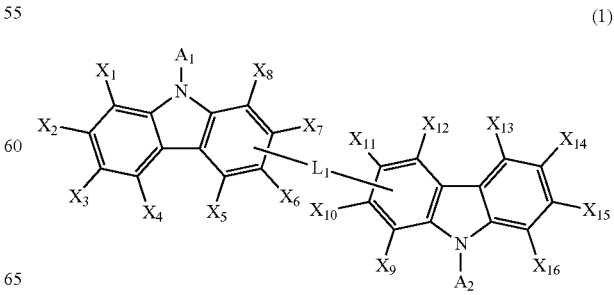

(1)

wherein

A₁ and A₂, each independently, represent a substituted or unsubstituted (C6-C30)aryl, provided that a nitrogen-containing heteroaryl is excluded from the substituent for $A_1$ and $A_2$;

$L_1$ represents a single bond or a substituted or unsubstituted (C6-C30)arylene;

$X_1$ to $X_{16}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3-to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur;

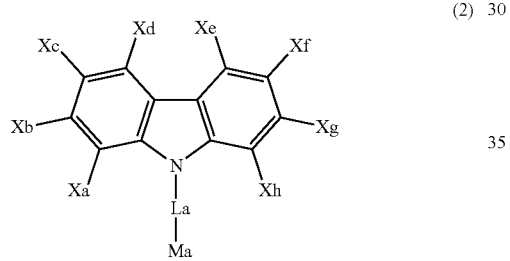

(2)

wherein

Ma represents a substituted or unsubstituted nitrogen-containing 5- to 11-membered heteroaryl;

La represents a single bond, or a substituted or unsubstituted (C6-C30)arylene;

Xa to Xh, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3-to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur;

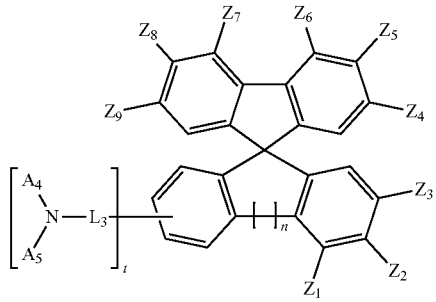

(3)

wherein $A_4$ and $A_5$, each independently, represent a substituted or unsubstituted (C6-C30)aryl;

$L_3$ represents a single bond or a substituted or unsubstituted (C6-C30)arylene;

$Z_1$ to $Z_9$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3-to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur;

n represents an integer of 0 or 1;

t represents an integer of 0, 1, or 2; and the heteroaryl contains at least one hetero atom selected from B, N, O, S, Si, and P.

Advantageous Effects of Invention

An organic electroluminescent device of the present disclosure has high efficiencies and long lifespan. A display system or lighting system using the organic electroluminescent device can be manufactured.

MODE FOR THE INVENTION

Hereinafter, the present disclosure will be described in detail. However, the following description is intended to explain the invention, and is not meant in any way to restrict the scope of the invention.

The details of the organic electroluminescent device of the present disclosure are as follows.

According to one embodiment of the organic electroluminescent device of the present disclosure, the compound of formula 1 may be represented by the following formula 5, 6, 7, or 8.

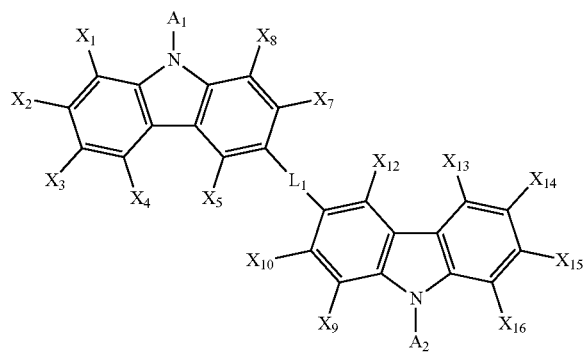

(5)

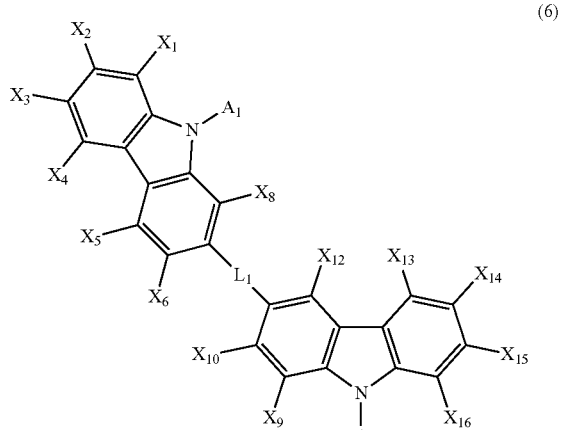

(6)

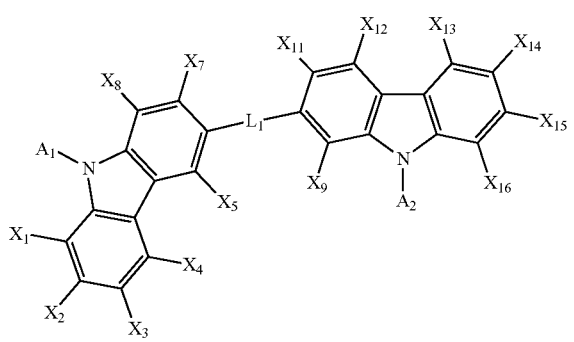

(7)

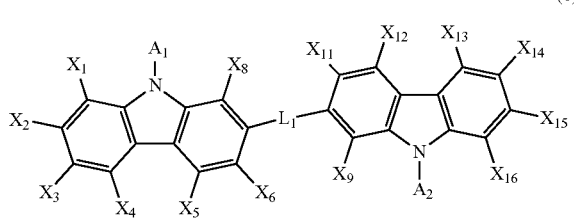

(8)

wherein, $A_1$, $A_2$, $L_1$ and $X_1$ to $X_{16}$ are as defined in formula 1.

In formula 1, $A_1$ and $A_2$, each independently, represent a substituted or unsubstituted (C6-C30)aryl. $A_1$ and $A_2$, each independently, may represent preferably, a substituted or unsubstituted (C6-C18)aryl; and more preferably, a (C6-C18)aryl unsubstituted or substituted with a cyano, a halogen, a (C1-C6)alkyl, a (C6-C12)aryl, or a tri(C6-C12)arylsilyl. Specifically, $A_1$ and $A_2$, each independently, may be selected from the group consisting of a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted benzofluorenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted phenylnaphthyl, a substituted or unsubstituted naphthylphenyl, and a substituted or unsubstituted fluoranthenyl. Herein, the substituent for the substituted phenyl, etc. may be a cyano, a halogen, a (C1-C6)alkyl, a (C6-C12)aryl, or a tri(C6-C12)arylsilyl. $A_1$ and $A_2$ may be the same or different.

In formula 1, $X_1$ to $X_{16}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur. $X_1$ to $X_{16}$, each independently, may represent preferably, hydrogen, a cyano, a substituted or unsubstituted (C1-C10)alkyl, a substituted or unsubstituted (C6-C20)aryl, a substituted or unsubstituted 5- to 20-membered heteroaryl, or a substituted or unsubstituted tri(C6-C12)arylsilyl; and more preferably, hydrogen, a cyano, a (C1-C10)alkyl, a (C6-C20)aryl unsubstituted or substituted with a cyano, a (C1-C10)alkyl, or a tri(C6-C12)arylsilyl, a 5- to 20-membered heteroaryl unsubstituted or substituted with a (C1-C10)alkyl, a (C6-C15)aryl, or a tri(C6-C12)arylsilyl, or a tri(C6-C12)arylsilyl unsubstituted or substituted with a (C1-C10)alkyl. Specifically, $X_1$ to $X_{16}$, each independently, may represent hydrogen; a cyano; a (C1-C6)alkyl; phenyl, biphenyl, terphenyl, or naphthyl, unsubstituted or substituted with a cyano, a (C1-C6)alkyl, or triphenylsilyl; dibenzothiophene or dibenzofuran, unsubstituted or substituted with a (C1-C6)alkyl, phenyl, biphenyl, naphthyl, or triphenylsilyl; or triphenylsilyl unsubstituted or substituted with a (C1-C6)alkyl.

In formula 1, $L_1$ represents a single bond, or a substituted or unsubstituted (C6-C30)arylene. Preferably, $L_1$ may represent a single bond, or a substituted or unsubstituted (C6-C15)arylene.

$L_1$ may represent a single bond, or one selected from the following formulae 9 to 21.

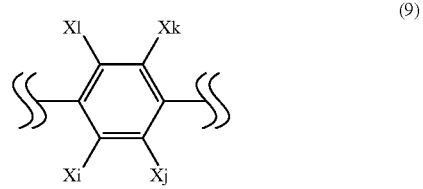

(9)

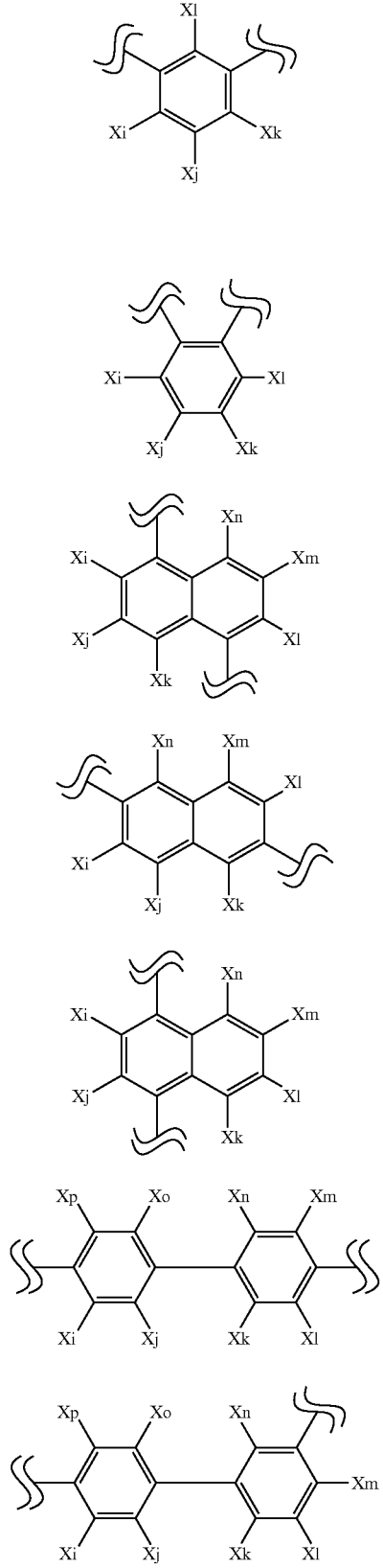
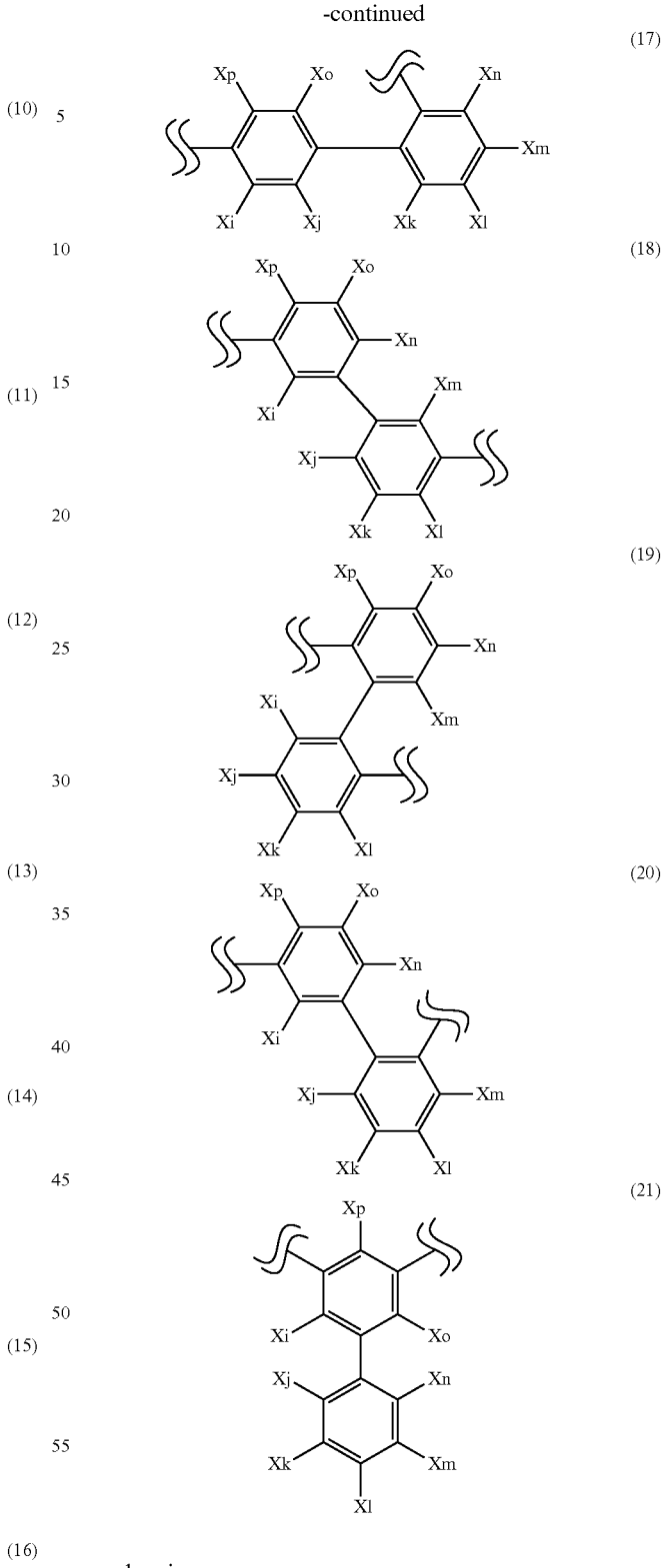

wherein
Xi to Xp, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3-to 30-membered heteroaryl, a substituted or unsubunsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur; and  represents a bonding site. Xi to Xp, each independently, may represent preferably, hydrogen, a halogen, a cyano, a (C1-C10)alkyl, a (C3-C20)cycloalkyl, a (C6-C12)aryl, a (C1-C6)alkyldi(C6-C12)arylsilyl, or a tri(C6-C12)arylsilyl; and more preferably, hydrogen, a cyano, a (C1-C6)alkyl, or a tri(C6-C12)aryl silyl.

In formula 2, Ma represents a substituted or unsubstituted nitrogen-containing 5- to 11-membered heteroaryl. Ma may represent preferably, a substituted or unsubstituted nitrogen-containing 6- to 10-membered heteroaryl. Ma may represent more preferably, a nitrogen-containing 6- to 10-membered heteroaryl substituted with the following: an unsubstituted (C6-C18)aryl; a (C6-C12)aryl substituted with a cyano; a (C6-C12)aryl substituted with a (C1-C6)alkyl; a (C6-C12) aryl substituted with a tri(C6-C12)arylsilyl; or a 6- to 15-membered heteroaryl.

Specifically, Ma may represent a substituted or unsubstituted monocyclic ring-type heteroaryl selected from the group consisting of a substituted or unsubstituted pyrrolyl, a substituted or unsubstituted imidazolyl, a substituted or unsubstituted pyrazolyl, a substituted or unsubstituted triazinyl, a substituted or unsubstituted tetrazinyl, a substituted or unsubstituted triazolyl, a substituted or unsubstituted tetrazolyl, a substituted or unsubstituted pyridyl, a substituted or unsubstituted pyrazinyl, a substituted or unsubstituted pyrimidinyl, and a substituted or unsubstituted pyridazinyl, or a substituted or unsubstituted fused ring-type heteroaryl selected from the group consisting of a substituted or unsubstituted benzimidazolyl, a substituted or unsubstituted isoindolyl, a substituted or unsubstituted indolyl, a substituted or unsubstituted indazolyl, a substituted or unsubstituted benzothiadiazolyl, a substituted or unsubstituted quinolyl, a substituted or unsubstituted isoquinolyl, a substituted or unsubstituted cinnolinyl, a substituted or unsubstituted quinazolinyl, a substituted or unsubstituted naphthyridinyl, and a substituted or unsubstituted quinoxalinyl. Preferably, Ma may represent a substituted or unsubstituted triazinyl, a substituted or unsubstituted pyrimidinyl, a substituted or unsubstituted pyridyl, a substituted or unsubstituted quinolyl, a substituted or unsubstituted isoquinolyl, a substituted or unsubstituted quinazolinyl, a substituted or unsubstituted naphthyridinyl, or a substituted or unsubstituted quinoxalinyl. The substituent for the substituted pyrrolyl, etc. of Ma may be selected from a (C6-C18) aryl, a (C6-C12)aryl substituted with a cyano, a (C6-C12) aryl substituted with a (C1-C6)alkyl, a (C6-C12)aryl substituted with a tri(C6-C12)arylsilyl, a cyano, a (C1-C6) alkyl, a tri(C6-C12)arylsilyl, or a 6- to 15-membered heteroaryl. Specifically, the substituent may be selected from phenyl, biphenyl, terphenyl, naphthyl, phenyl naphthyl, naphthylphenyl, phenanthrenyl, anthracenyl, dibenzothiophenyl, or dibenzofuranyl, unsubstituted or substituted with a cyano, a (C1-C6)alkyl, or triphenylsilyl.

In formula 2, La represents a single bond, or a substituted or unsubstituted (C6-C30)arylene. Preferably, La may represent a single bond, or a substituted or unsubstituted (C6-C12)arylene. Specifically, La may represent a single bond, or one of formulae 9 to 21.

In formula 2, Xa to Xh, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30) alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino, or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur. Preferably, Xa to Xh, each independently, may represent hydrogen, a cyano, a substituted or unsubstituted (C6-C15)aryl, a substituted or unsubstituted 10- to 20-membered heteroaryl, or a substituted or unsubstituted tri(C6-C10)arylsilyl, or may be linked to an adjacent substituent(s) to form a substituted or unsubstituted (C6-C20), mono- or polycyclic aromatic ring, whose carbon atom(s) may be replaced with at least one hetero atom selected from nitrogen, oxygen, and sulfur. More preferably, Xa to Xh, each independently, may represent hydrogen, a cyano, a (C6-C15)aryl unsubstituted or substituted with a tri(C6-C10) arylsilyl, or a 10- to 20-membered heteroaryl unsubstituted or substituted with a (C6-C12)aryl; or may be linked to an adjacent substituent(s) to form a substituted or unsubstituted benzene, a substituted or unsubstituted indole, a substituted or unsubstituted benzindole, a substituted or unsubstituted indene, a substituted or unsubstituted benzofuran, or a substituted or unsubstituted benzothiophene.

In formula 3, $A_4$ and $A_5$, each independently, represent a substituted or unsubstituted (C6-C30)aryl. Specifically, $A_4$ and $A_5$, each independently, may be selected from the group consisting of a substituted or unsubstituted phenyl, a substituted or unsubstituted biphenyl, a substituted or unsubstituted terphenyl, a substituted or unsubstituted naphthyl, a substituted or unsubstituted phenanthrenyl, a substituted or unsubstituted anthracenyl, a substituted or unsubstituted pyrenyl, a substituted or unsubstituted tetracenyl, a substituted or unsubstituted chrysenyl, a substituted or unsubstituted fluorenyl, a substituted or unsubstituted benzofluorenyl, a substituted or unsubstituted fluoranthenyl, a substituted or unsubstituted triphenylenyl, and a substituted or unsubstituted spirobifluorenyl. Specifically, the substituent for the substituted aryl such as the substituted phenyl of $A_4$ and $A_5$ may be selected from a (C1-C10)alkyl, a cyano, a halogen, a (C6-C18)aryl, or a 6- to 18-membered heteroaryl; and more specifically, a (C1-C6)alkyl, a cyano, a halogen, phenyl, biphenyl, terphenyl, naphthyl, phenanthrenyl, anthracenyl, pyrenyl, tetracenyl, chrysenyl, fluorenyl, fluorenyl substituted with two (2) methyl groups, fluorenyl substituted with two (2) phenyl groups, fluorenyl substituted with a methyl group and a phenyl group, dibenzothiophenyl, dibenzofuranyl, or carbazolyl. $A_4$ and $A_5$ may be the same or different.

In formula 3, $L_3$ represents a single bond, or a substituted or unsubstituted (C6-C30)arylene; preferably, a single bond, or a substituted or unsubstituted (C6-C18)arylene; and more preferably, a single bond, or a (C6-C18)arylene unsubstituted or substituted with a (C1-C6)alkyl or phenyl. Specifically, $L_3$ may represent a single bond or phenyl.

In formula 3, $Z_1$ to $Z_9$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30) alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino, or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur. Preferably, $Z_1$ to $Z_9$, each independently, may represent hydrogen, deuterium, a halogen, a cyano, a substituted or unsubstituted (C1-C30)alkyl, a substituted or unsubstituted (C6-C30)aryl, a substituted or unsubstituted 6- to 30-membered heteroaryl, or a substituted or unsubstituted mono- or di-(C6-C30)arylamino; or one to three pairs selected from $Z_1$ and $Z_2$, $Z_2$ and $Z_3$, $Z_4$ and $Z_5$, $Z_5$ and $Z_6$, $Z_7$ and $Z_8$, and $Z_8$ and $Z_9$, as a pair of adjacent substituents, may form a substituted or unsubstituted (C3-C30), mono- or polycyclic aromatic ring, whose carbon atom(s) may be replaced with one to three hetero atoms selected from nitrogen, oxygen, and sulfur. Specifically, $Z_1$ to $Z_9$, each independently, may represent hydrogen, a (C1-C6)alkyl, or a mono- or di-(C6-C18)arylamino; or one to two pairs selected from $Z_1$ and $Z_2$, $Z_2$ and $Z_3$, $Z_4$ and $Z_5$, $Z_5$ and $Z_6$, $Z_7$ and $Z_8$, and $Z_8$ and $Z_9$, as a pair of adjacent substituents, may form a substituted or unsubstituted benzene, a substituted or unsubstituted indene, a substituted or unsubstituted cyclopentanaphthalene, a substituted or unsubstituted benzothiophene, or a substituted or unsubstituted benzofuran. Herein, the substituent for the substituted alkyl, the substituted aryl, etc., for $Z_1$ to $Z_9$ may be specifically selected from deuterium, a halogen, a cyano, a (C1-C6)alkyl, a (C6-C18) aryl, a 6- to 18-membered heteroaryl or a mono- or di-(C6-C18)arylamino; and more specifically selected from a (C1-C6)alkyl or a mono- or di-(C6-C18)arylamino.

In formula 3, n represents an integer of 0 or 1.

In formula 3, t represents an integer of 0, 1, or 2. Preferably, where t is 0, at least one of $Z_1$ to $Z_9$ is a substituted or unsubstituted mono- or di-(C6-C30)arylamino. More preferably, t is an integer of 1 or 2.

Herein, "(C1-C30)alkyl" indicates a linear or branched alkyl having 1 to 30, preferably 1 to 20, and more preferably 1 to 10 carbon atoms, and includes methyl, ethyl, n-propyl, isopropyl, n-butyl, isobutyl, tert-butyl, etc. "(C2-C30) alkenyl" indicates a linear or branched alkenyl having 2 to 30, preferably 2 to 20, and more preferably 2 to 10 carbon atoms and includes vinyl, 1-propenyl, 2-propenyl, 1-butenyl, 2-butenyl, 3-butenyl, 2-methylbut-2-enyl, etc. "(C2-C30) alkynyl" indicates a linear or branched alkynyl having 2 to 30, preferably 2 to 20, and more preferably 2 to 10 carbon atoms and includes ethynyl, 1-propynyl, 2-propynyl, 1-butynyl, 2-butynyl, 3-butynyl, 1-methylpent-2-ynyl, etc. "(C3-C30)cycloalkyl" indicates a mono- or polycyclic hydrocarbon having 3 to 30, preferably 3 to 20, and more preferably 3 to 7 carbon atoms and includes cyclopropyl, cyclobutyl, cyclopentyl, cyclohexyl, etc. "3- to 7-membered heterocycloalkyl" indicates a cycloalkyl having 3 to 7, preferably 5 to 7 ring backbone atoms including at least one hetero atom selected from the group consisting of B, N, O, S, Si, and P, preferably O, S, and N, and includes tetrahydrofuran, pyrrolidine, thiolan, tetrahydropyran, etc. Furthermore, "(C6-C30)aryl(ene)" indicates a monocyclic or fused ring radical derived from an aromatic hydrocarbon and having 6 to 30, preferably 6 to 20, and more preferably 6 to 15 ring backbone carbon atoms, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluranthenyl, etc. "3- to 30-membered heteroaryl" indicates an aryl group having 3 to 30 ring backbone atoms including at least one, preferably 1 to 4, hetero atom selected from the group consisting of B, N, O, S, Si, and P; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzindolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Nitrogen-containing 5- to 30-membered heteroaryl" indicates an aryl group having 5 to 30, preferably 5 to 20, and more preferably 5 to 15, ring backbone atoms including at least one, preferably 1 to 4, nitrogen atom; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as pyrrolyl, imidazolyl, pyrazolyl, triazinyl, tetrazinyl, triazolyl, tetrazolyl, pyridyl, pyrazinyl, pyrimidinyl, pyridazinyl, etc., and a fused ring-type heteroaryl such as benzoimidazolyl, isoindolyl, indolyl, indazolyl, benzothiadiazolyl, quinolyl, isoquinolyl, cinnolinyl, quinazolinyl, quinoxalinyl, carbazolyl, phenanthridinyl, etc. Furthermore, "halogen" includes F, Cl, Br, and I.

Herein, "substituted" in the expression, "substituted or unsubstituted," means that a hydrogen atom in a certain functional group is replaced with another atom or group, i.e. a substituent. In the formulae of the present disclosure, each of the substituents for the substituted alkyl, the substituted alkenyl, the substituted alkynyl, the substituted cycloalkyl, the substituted aryl(ene), the substituted heteroaryl, the substituted trialkylsilyl, the substituted arylsilyl, the substituted dialkylarylsilyl, the substituted mono- or di-arylamino, the substituted nitrogen-containing heteroaryl in $A_1$, $A_2$, $L_1$, $X_1$ to $X_{16}$, Ma, La, and Xa to Xh of formulae 1 and 2, each independently, may be at least one selected from the group consisting of deuterium, a halogen, a cyano, a carboxy, a nitro, a hydroxy, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a 3- to 7-membered heterocycloalkyl, a (C6-C30)aryloxy, a (C6-C30)arylthio, a 3- to 30-membered heteroaryl unsubstituted or substituted with a (C6-C30)aryl, a (C6-C30)aryl unsubstituted or substituted with a cyano, a 3- to 30-membered heteroaryl or a tri(C6-C30)arylsilyl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl (C6-C30)aryl; and preferably, a cyano, a (C1-C6)alkyl, a 5- to 15-membered heteroaryl, a (C6-C18)aryl unsubstituted or substituted with a cyano, or a tri(C6-C12)arylsilyl, a tri(C6-C12)arylsilyl and a (C1-C6)alkyl(C6-C12)aryl.

In formula 1, triarylsilyl for $X_1$ to $X_{16}$ is preferably triphenylsilyl.

The first host compound represented by formula 1 includes the following, but is not limited thereto.

H1-1

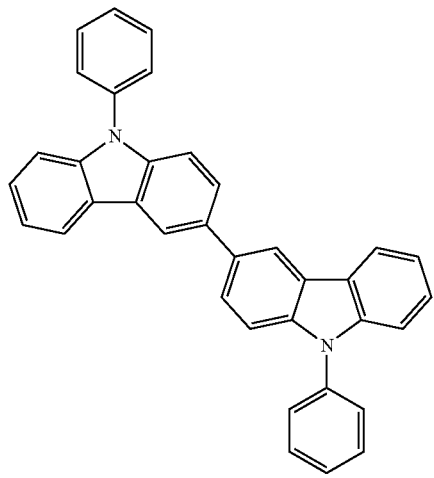

H1-2

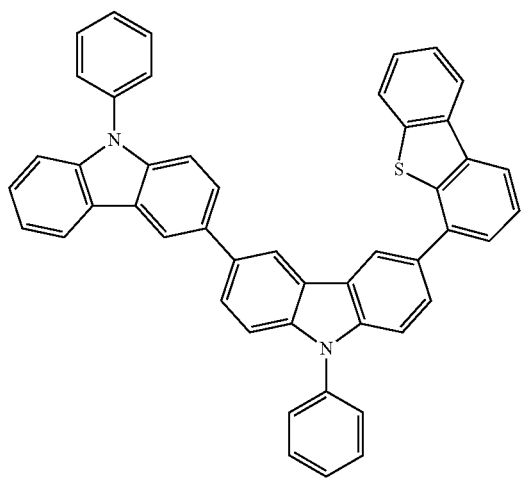

H1-3

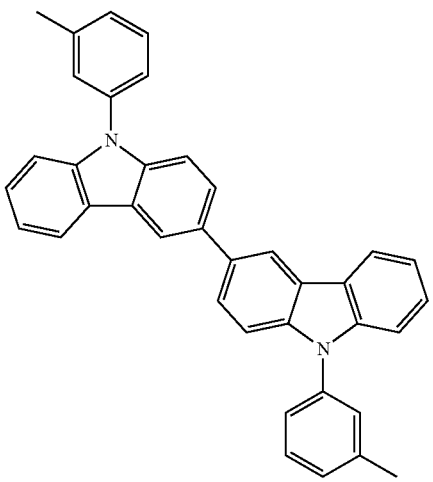

H1-4

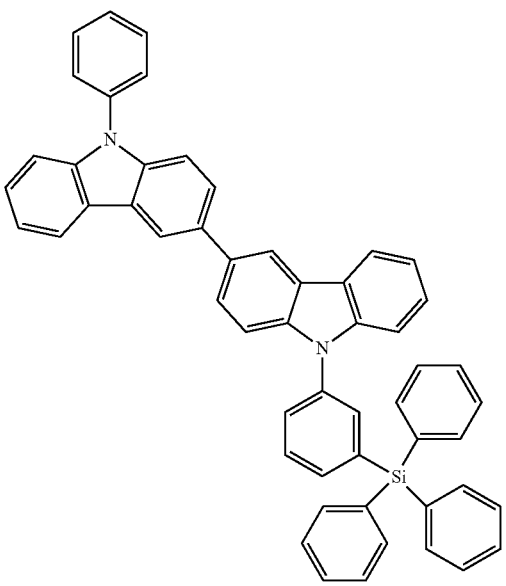

H1-5

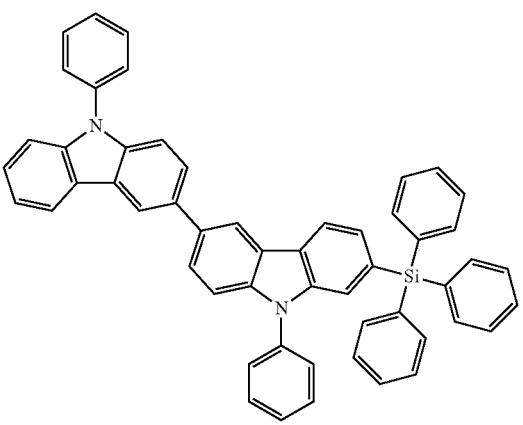

H1-6
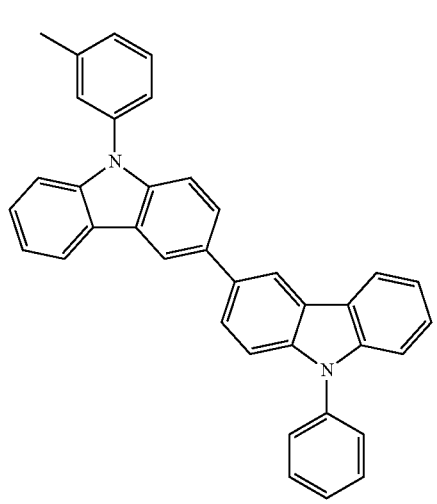
H1-7
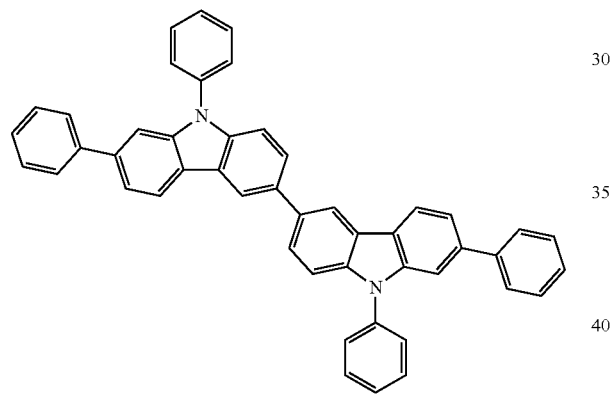
H1-8
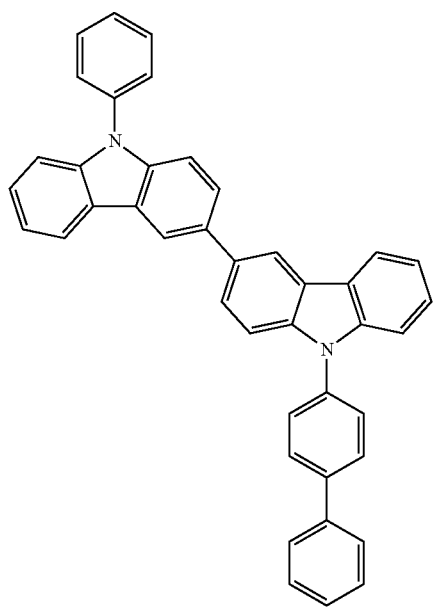
H1-9
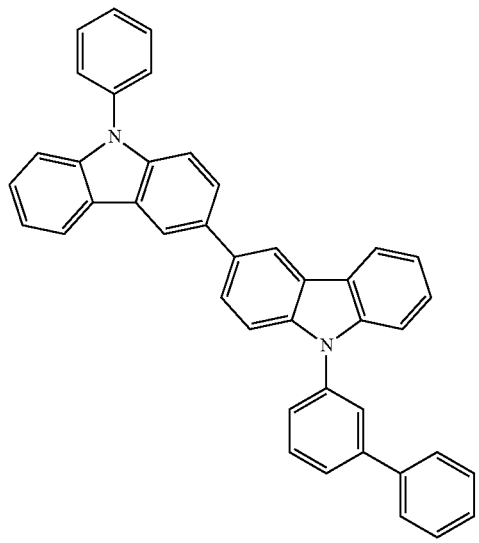
H1-10
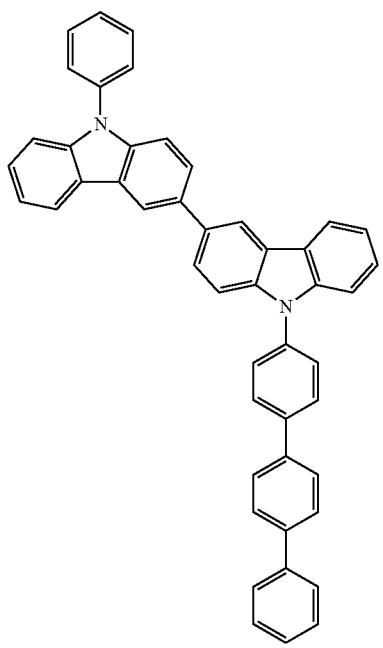

H1-11
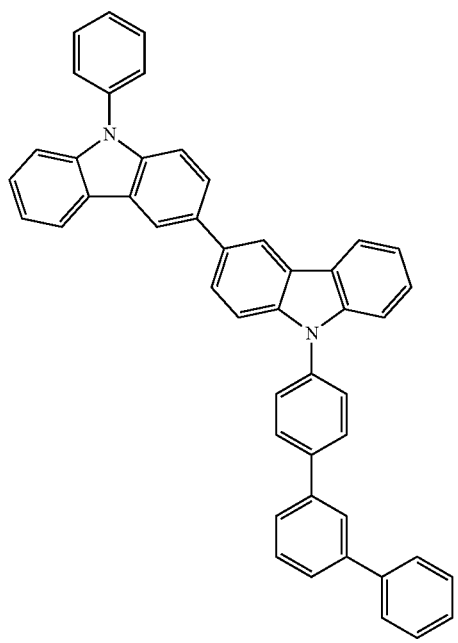
H1-12
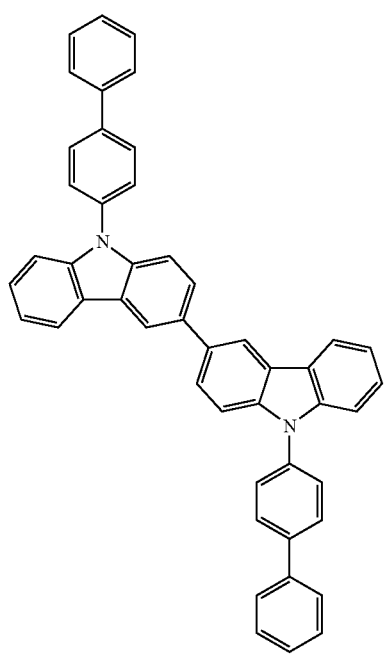
H1-13
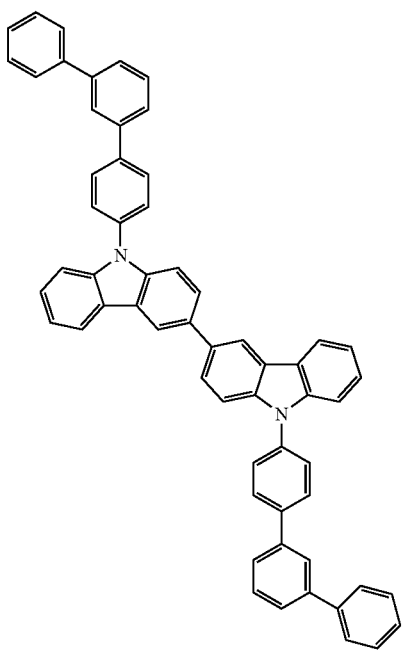
H1-14
H1-15

H1-16
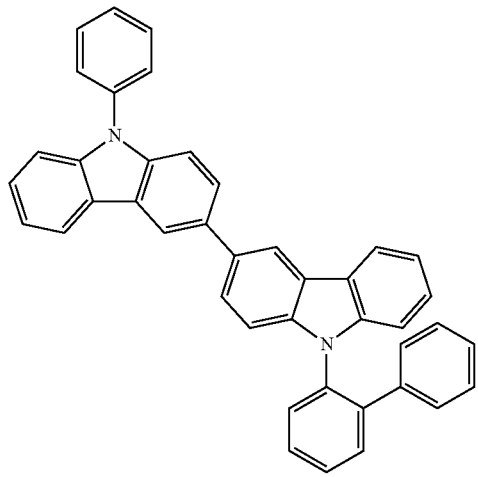
H1-17
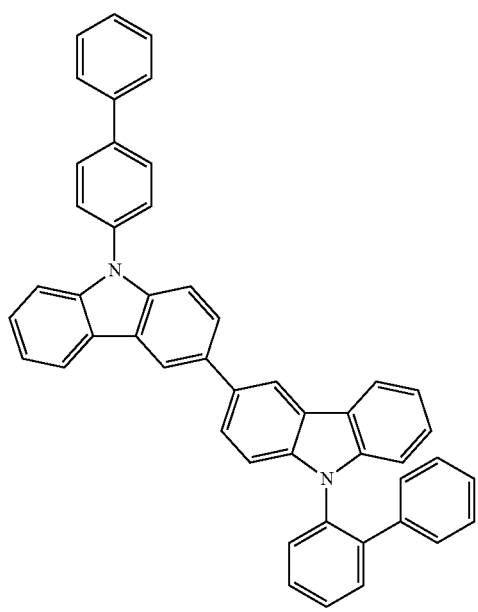
H1-18
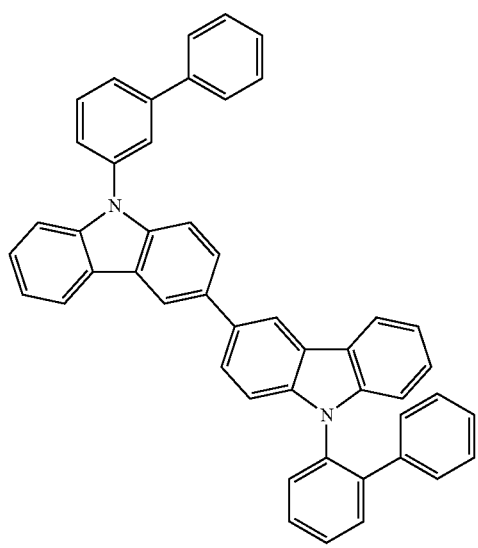
H1-19
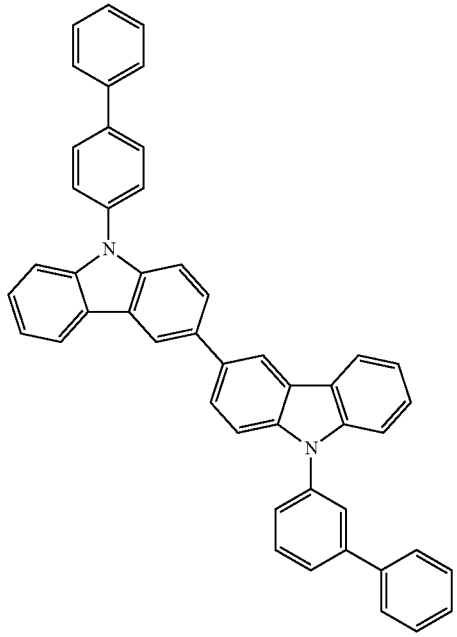
H1-20
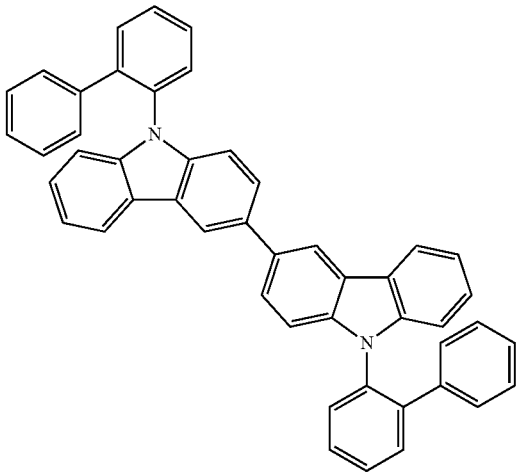
H1-21
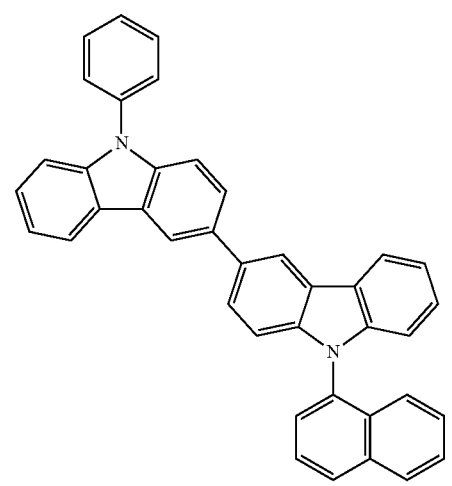

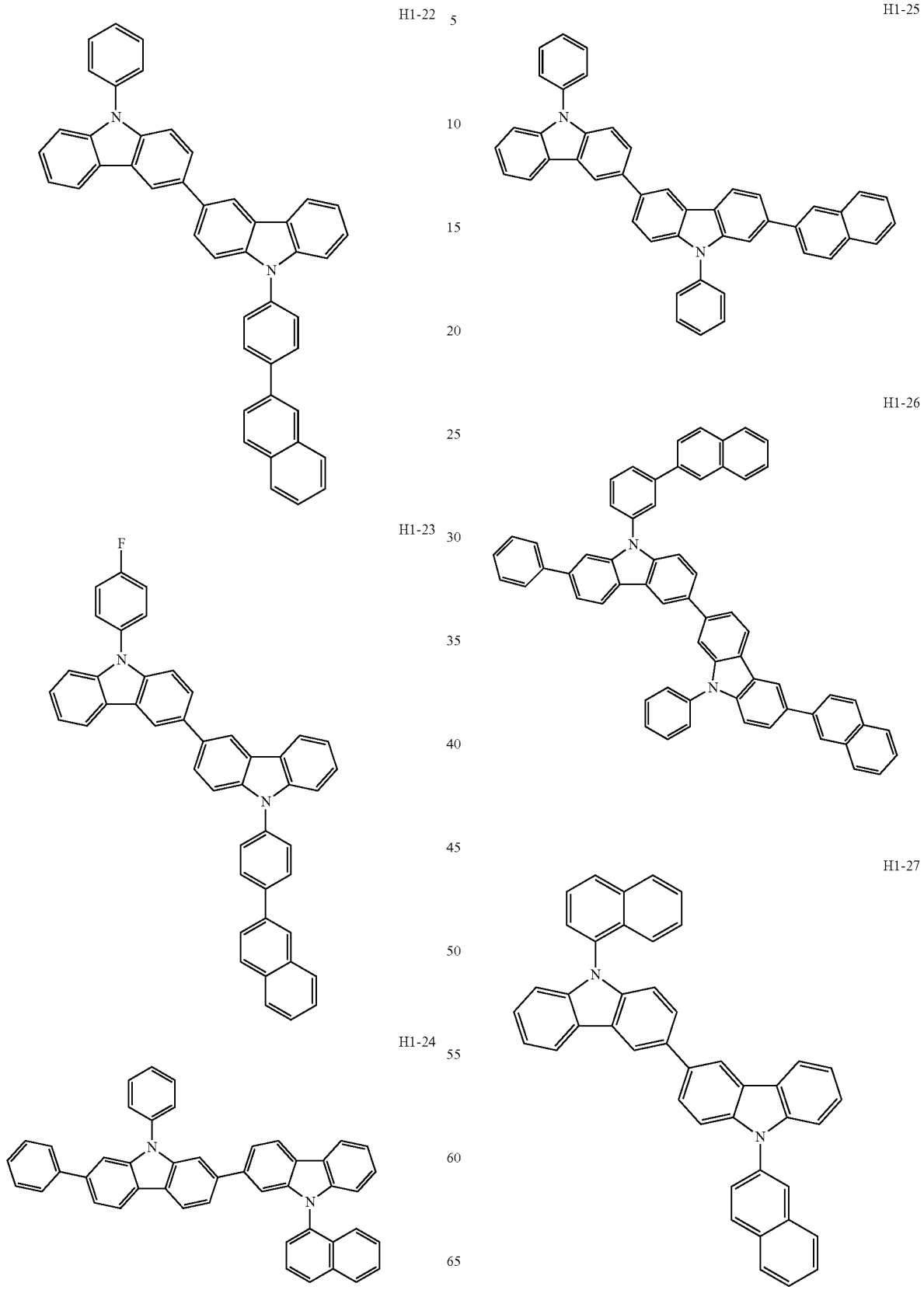

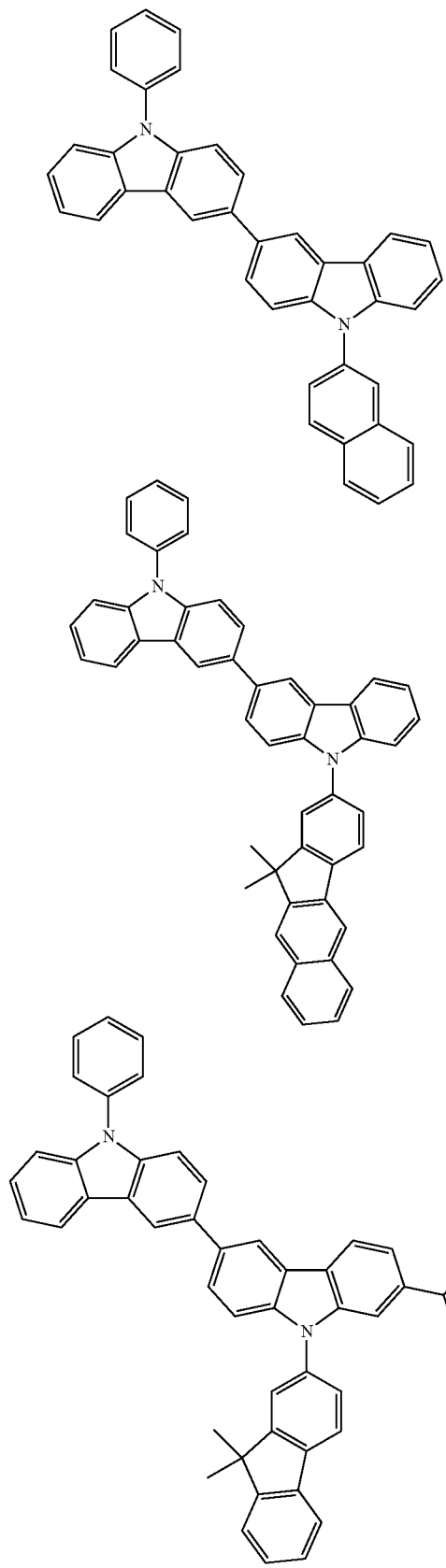
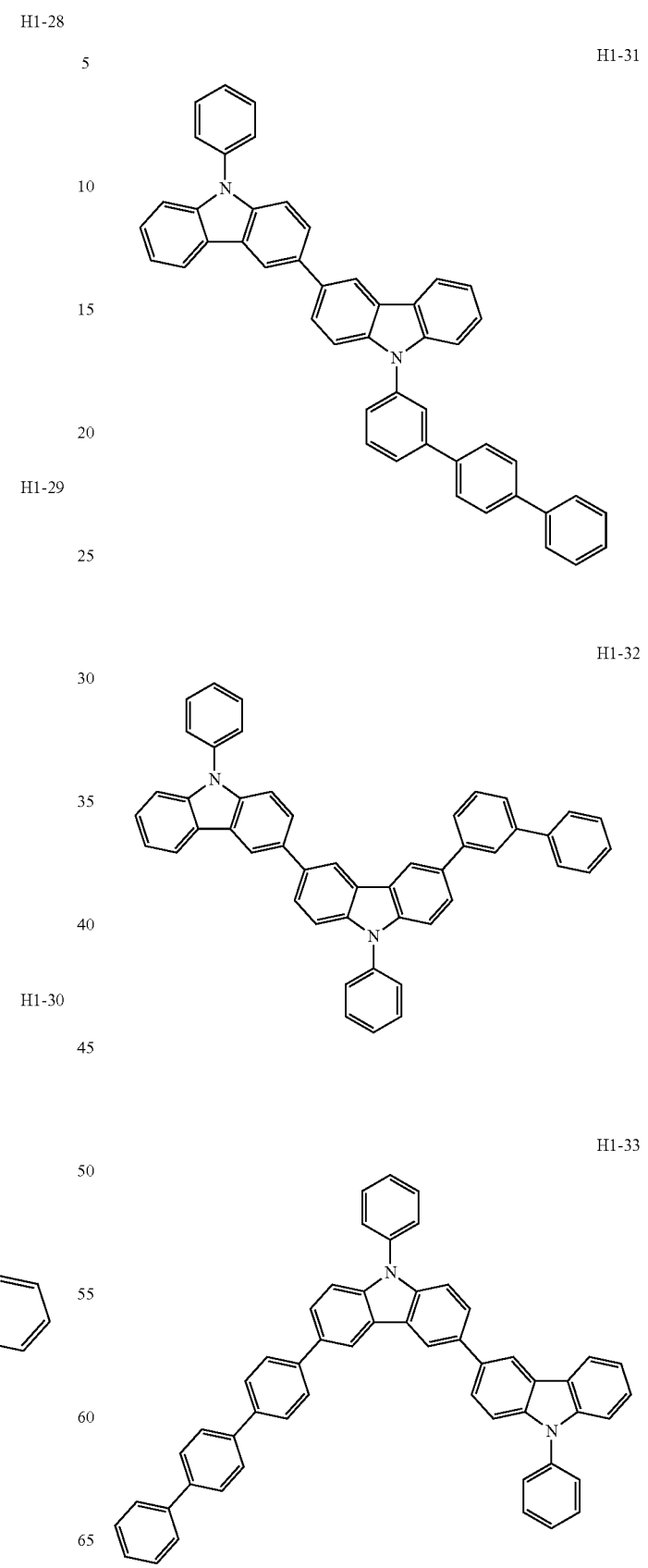

H1-34
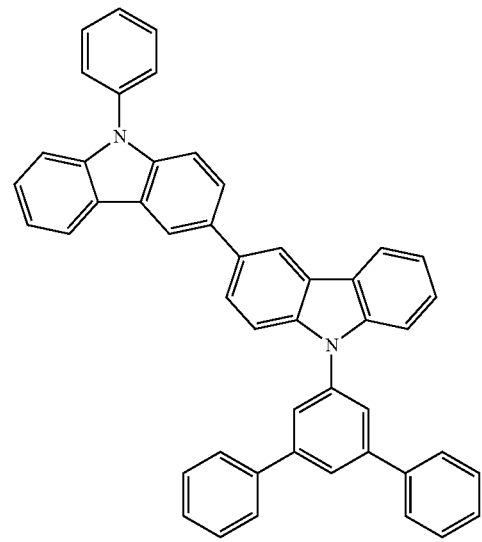
H1-35
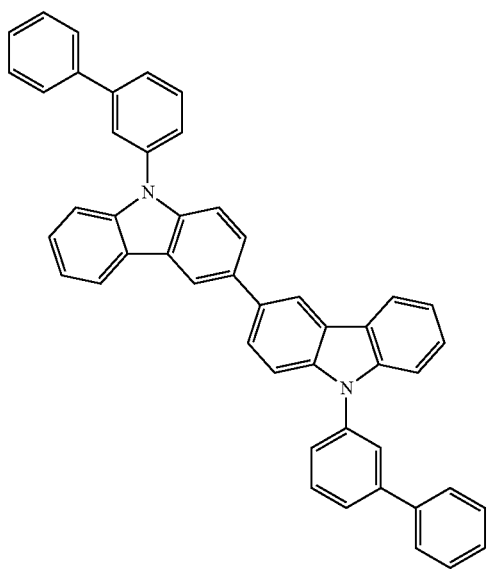
H1-36
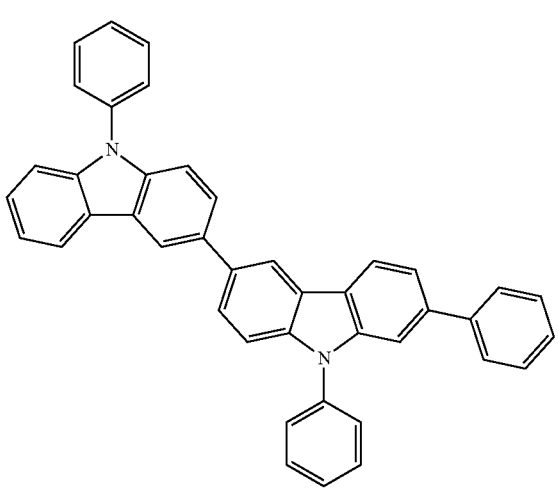
H1-37
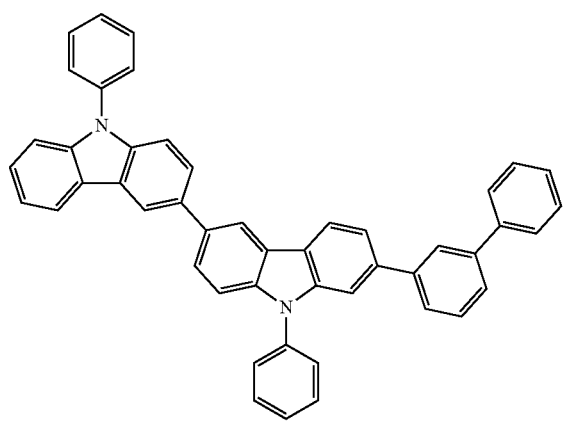
H1-38
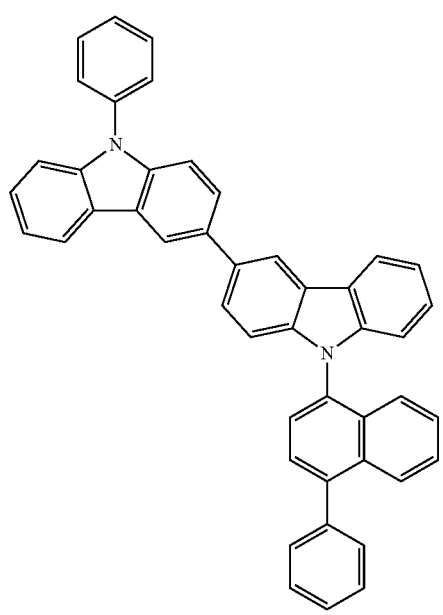
H1-39
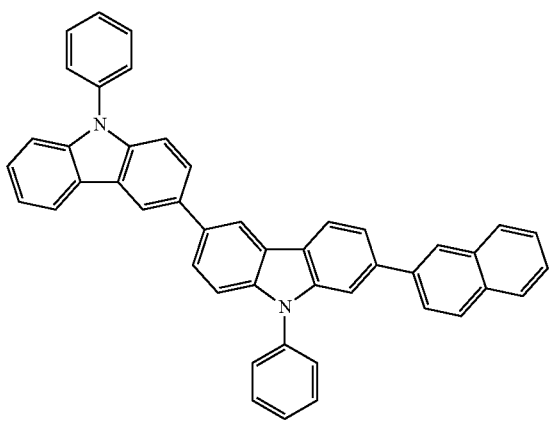

H1-40
H1-41
H1-42
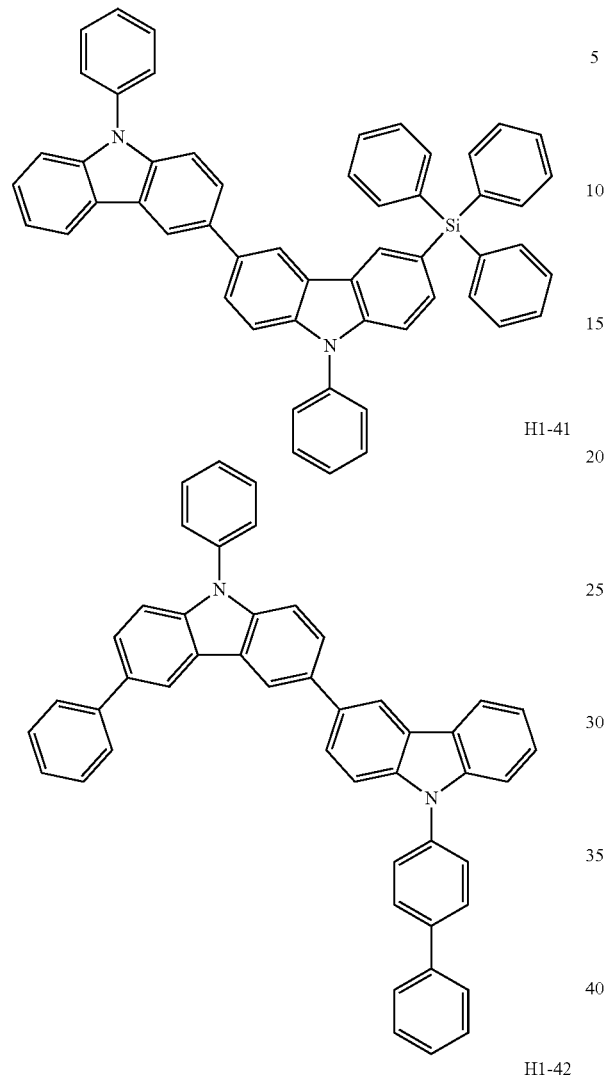
H1-43
H1-44
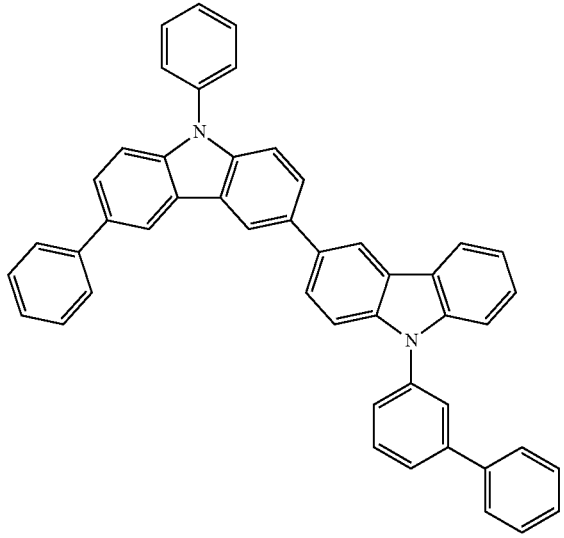
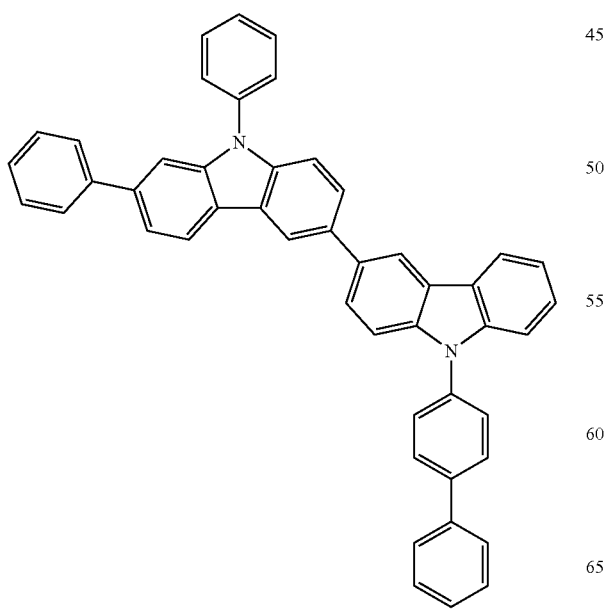

H1-45
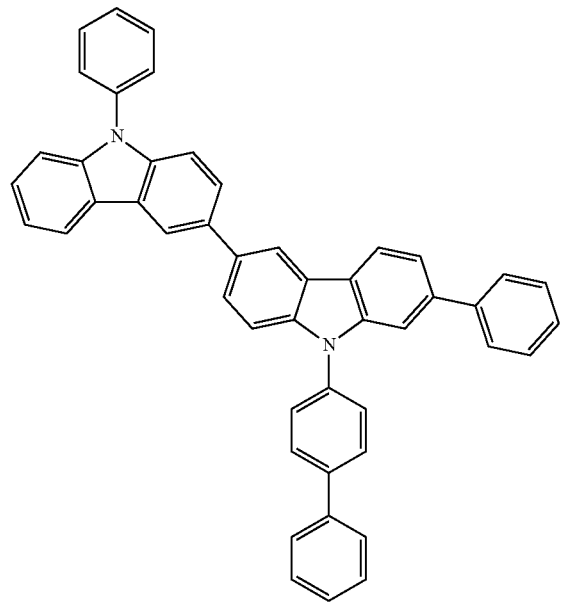
H1-46
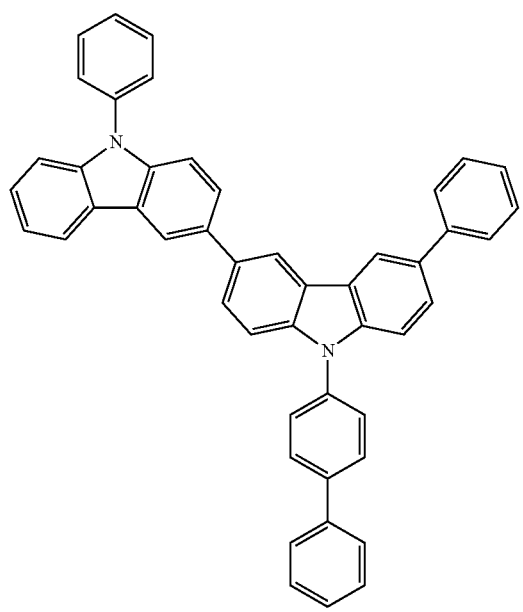
H1-47
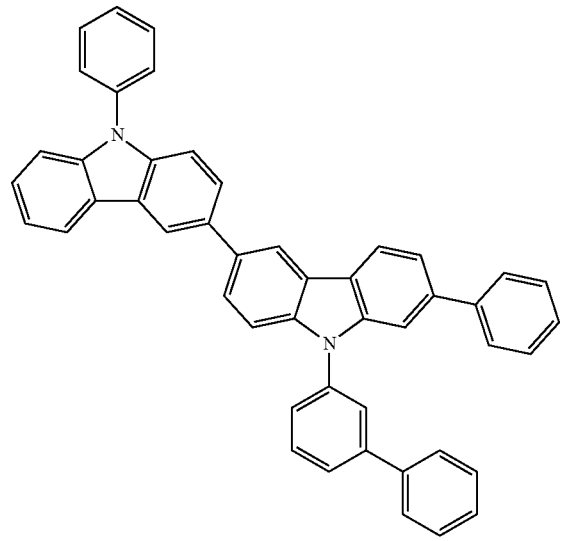
H1-48
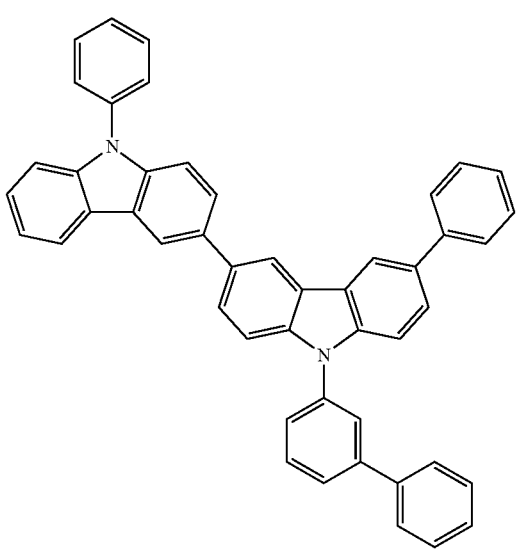
H1-49
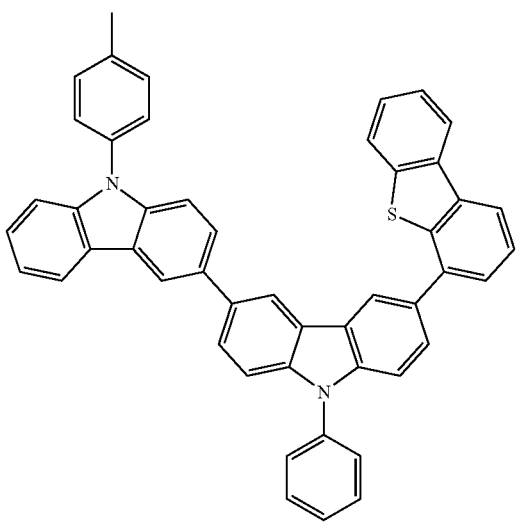

-continued
H1-50
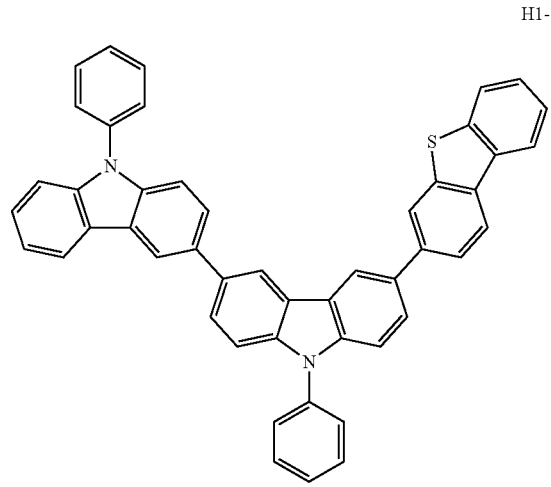
H1-51
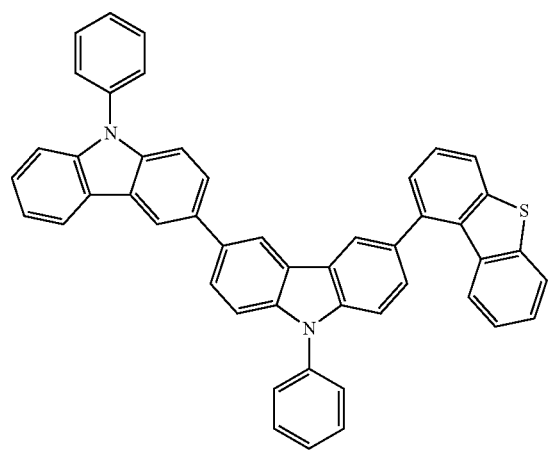
H1-53
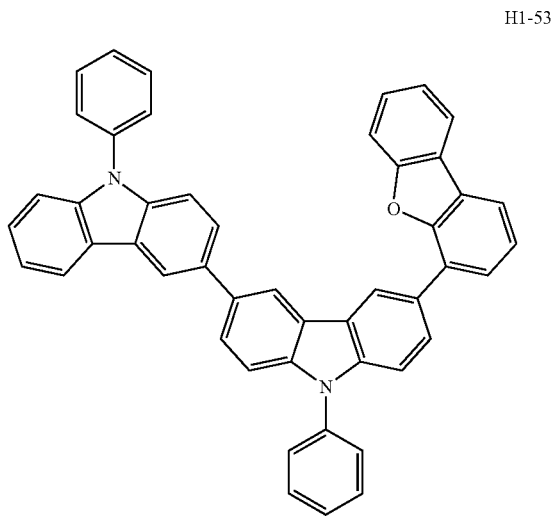
H1-52 H1-54
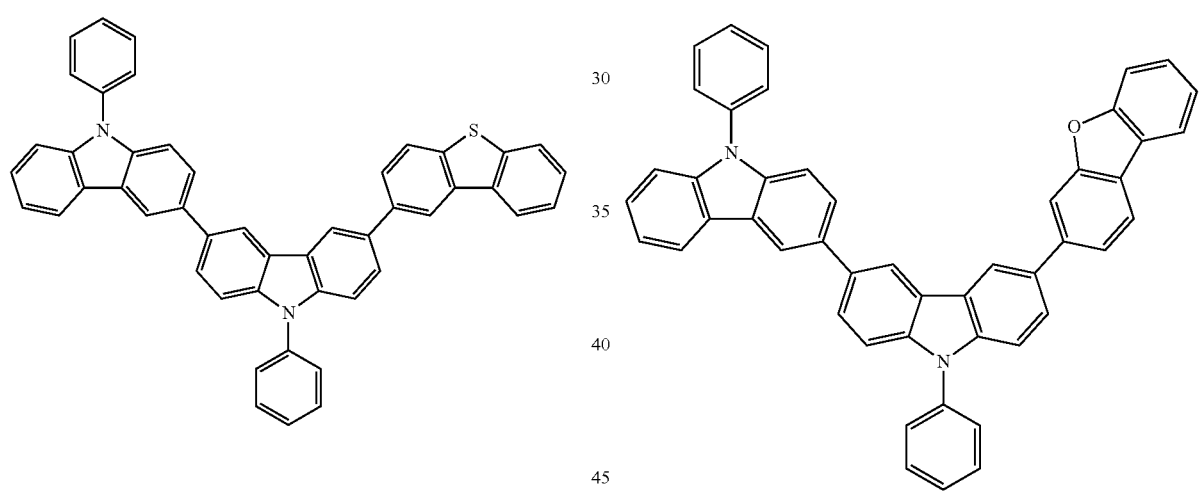
H1-55
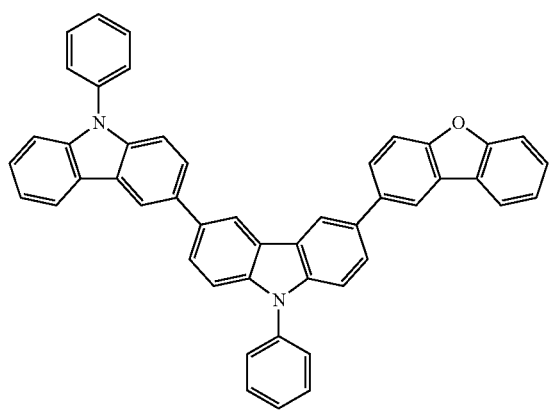

-continued
H1-56
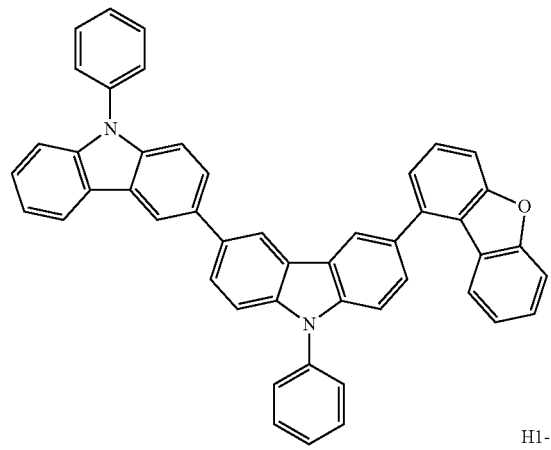
H1-57
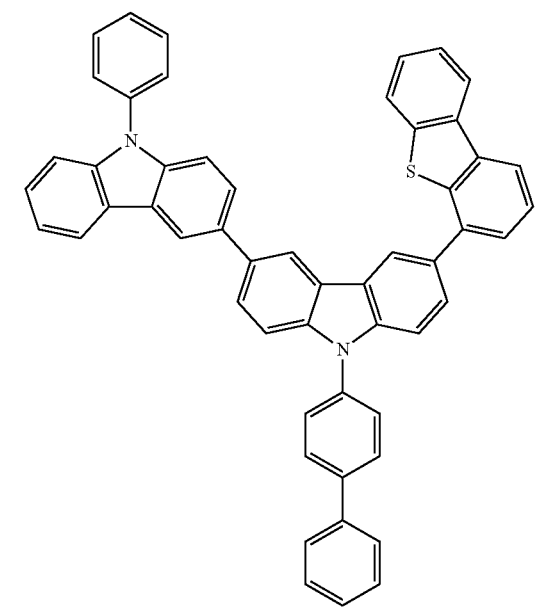
H1-58
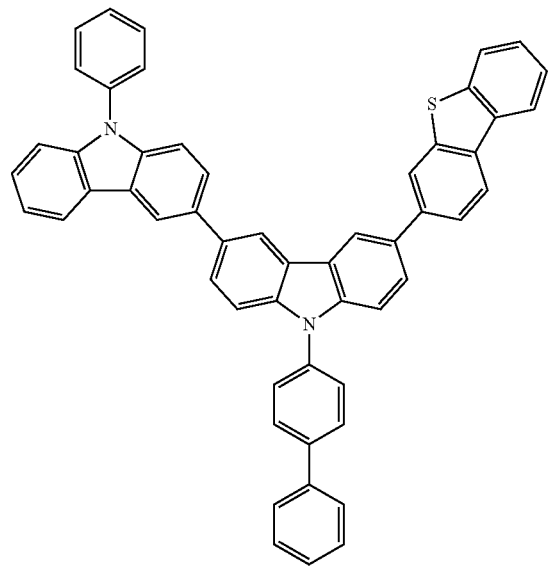
-continued
H1-59
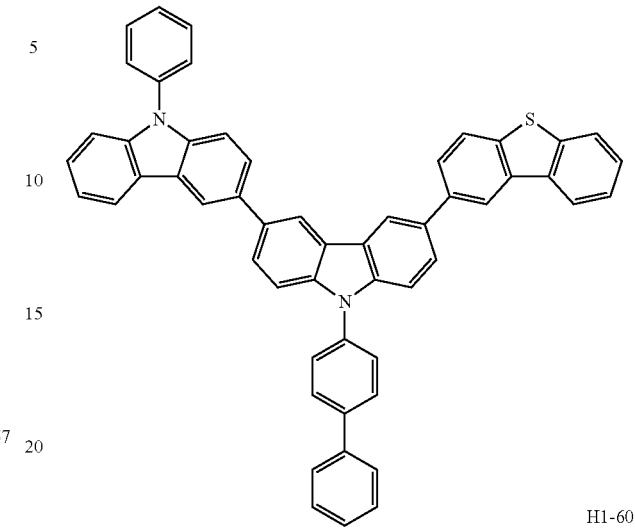
H1-60
H1-61
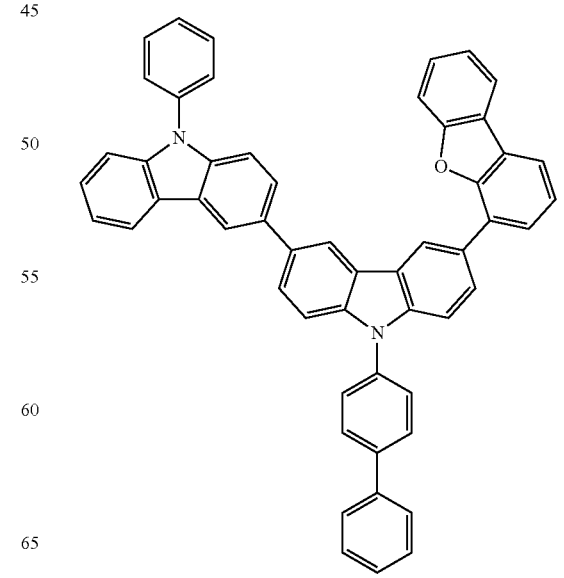

H1-62
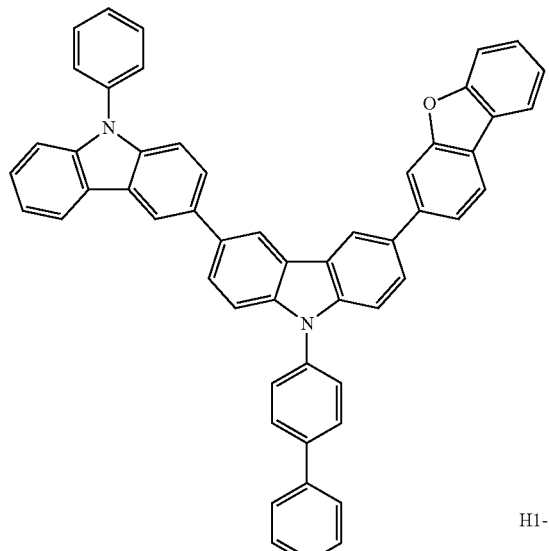
H1-63
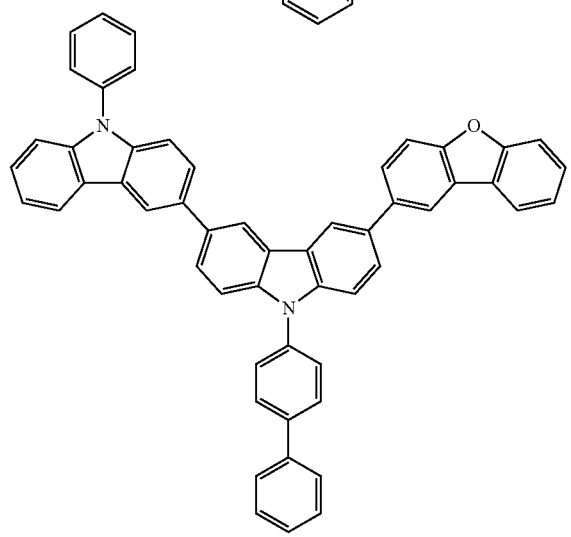
H1-64
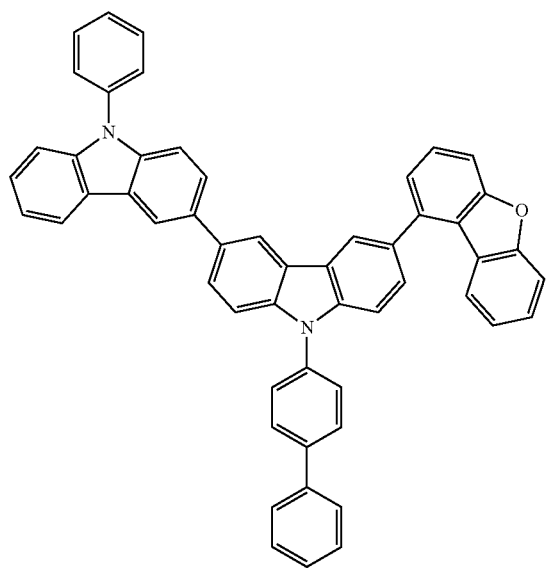
H1-65
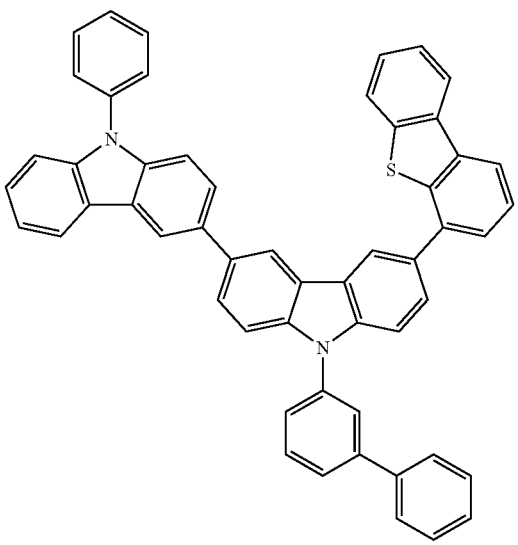
H1-66
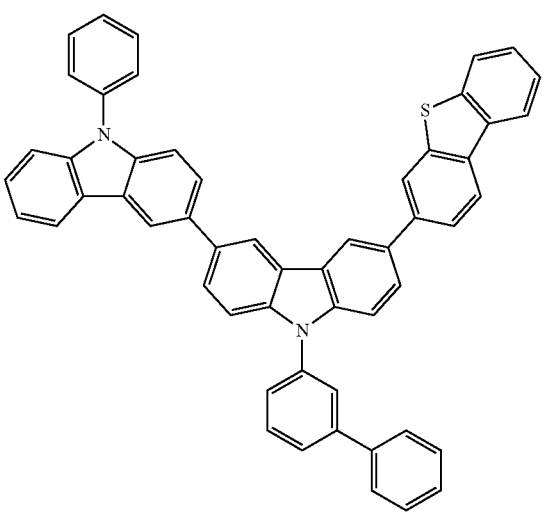
H1-67
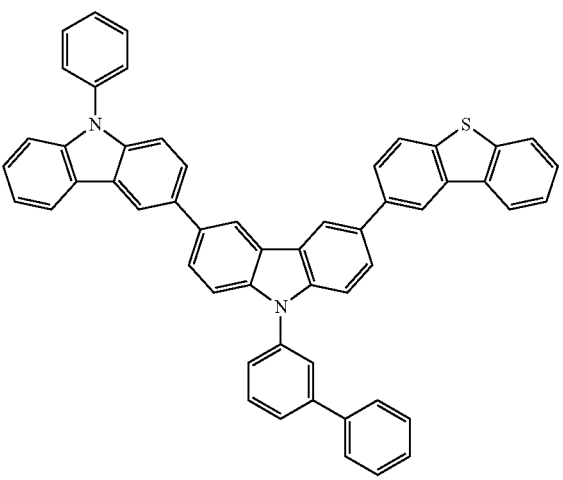

H1-68
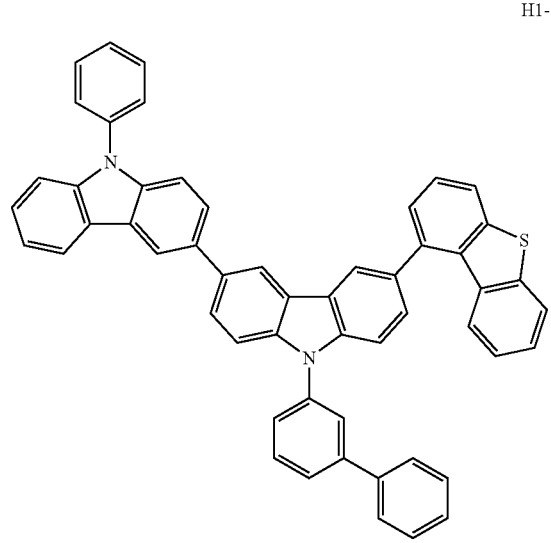
H1-69
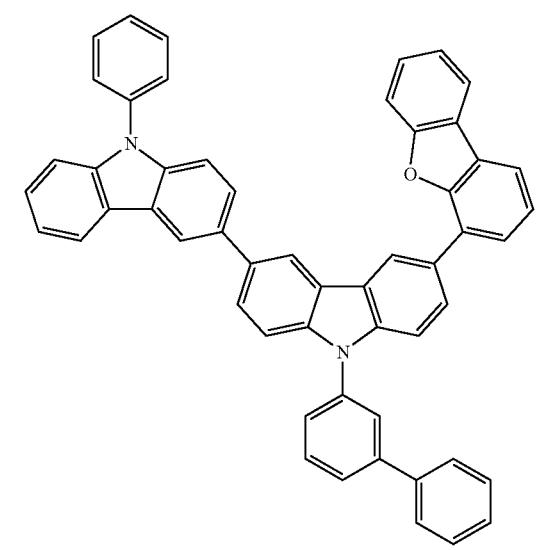
H1-70
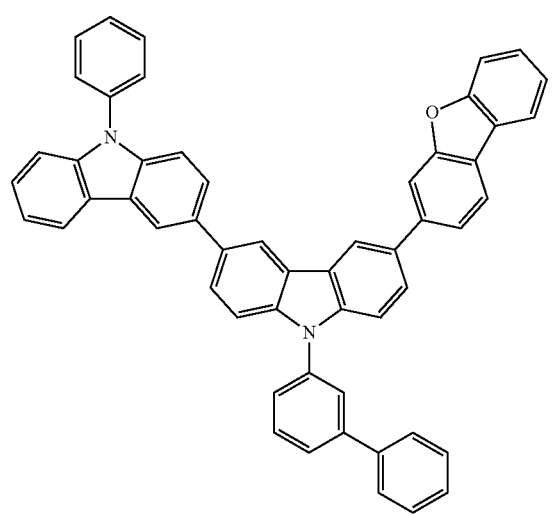
H1-71
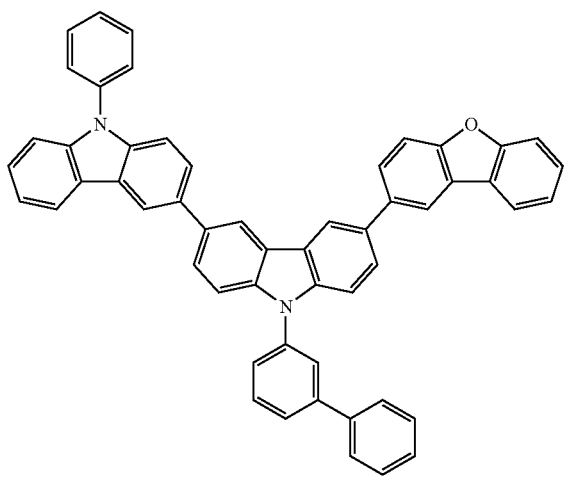
H1-72
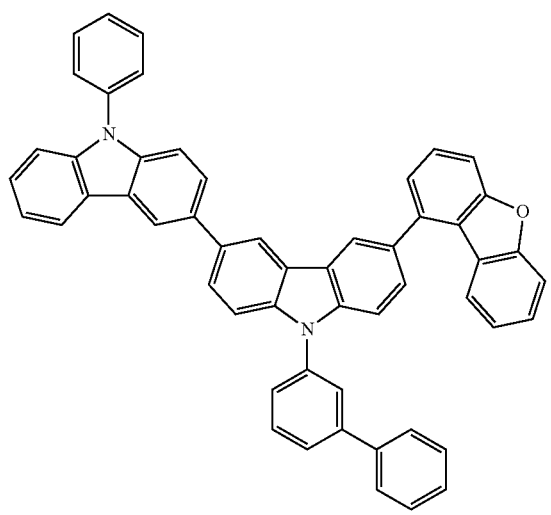
H1-73
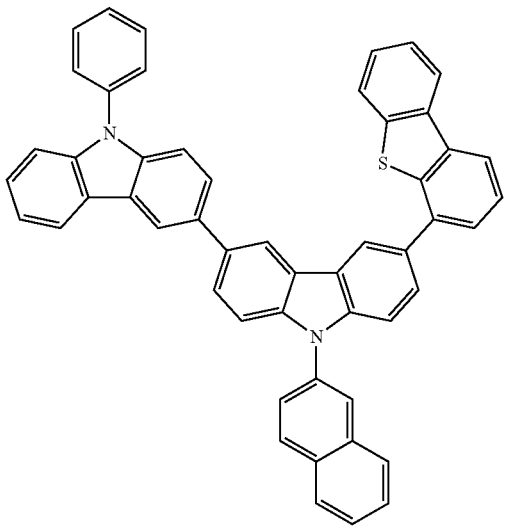

H1-74
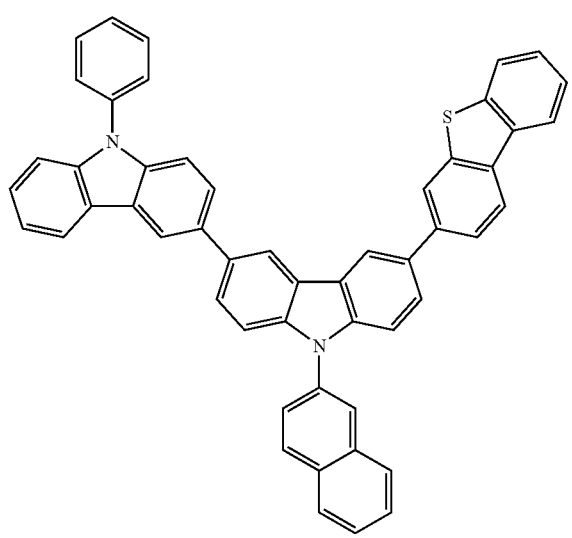
H1-75
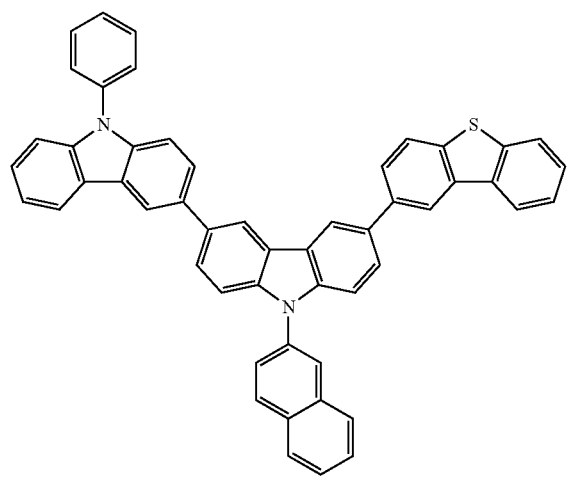
H1-76
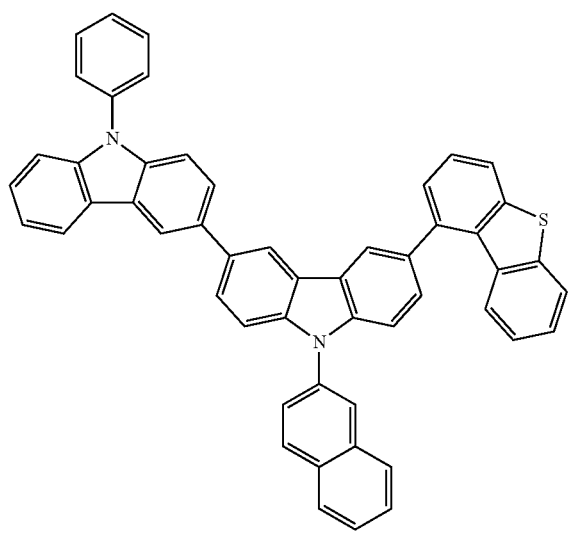
H1-77
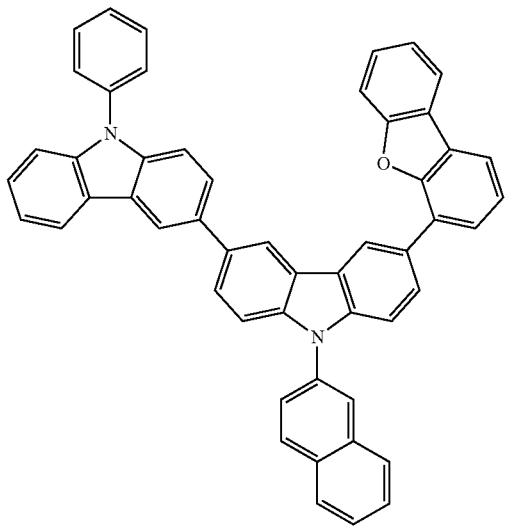
H1-78
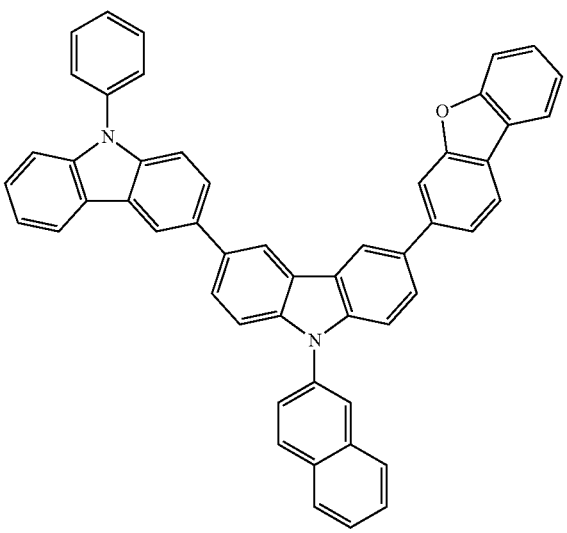
H1-79
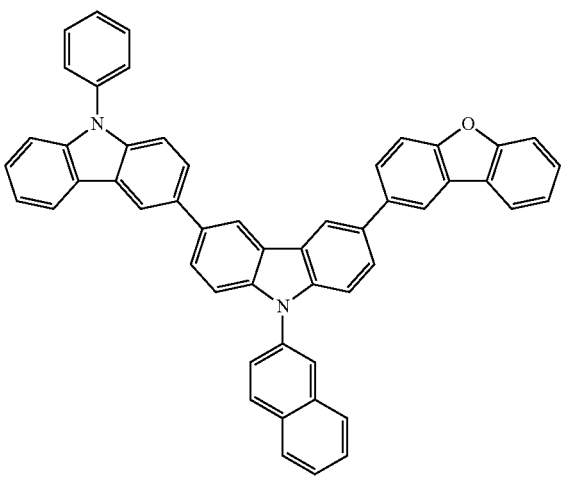

H1-80
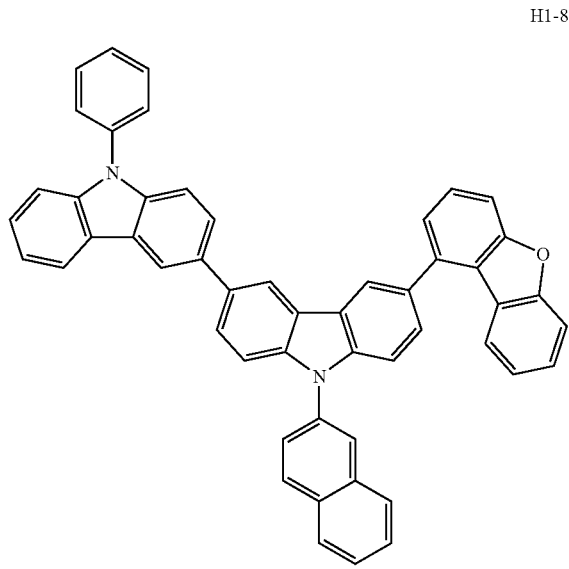
H1-81
H1-82
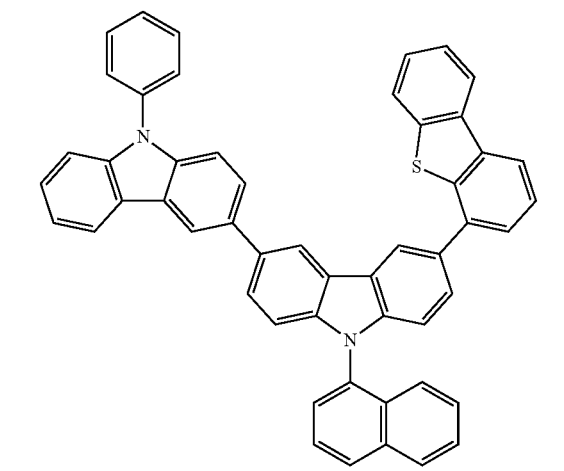
H1-83
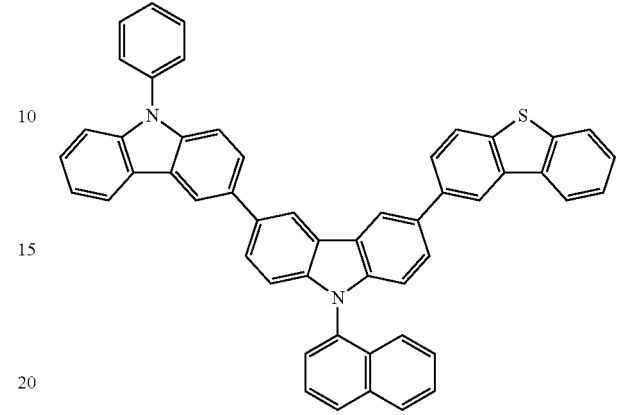
H1-84
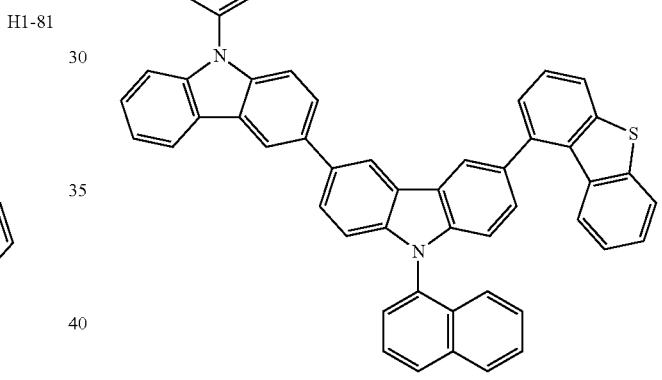
H1-85
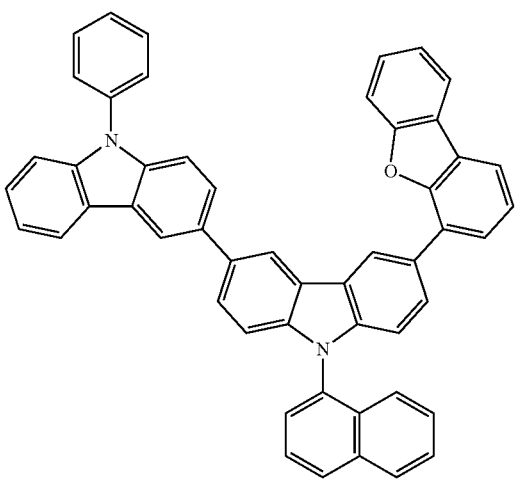

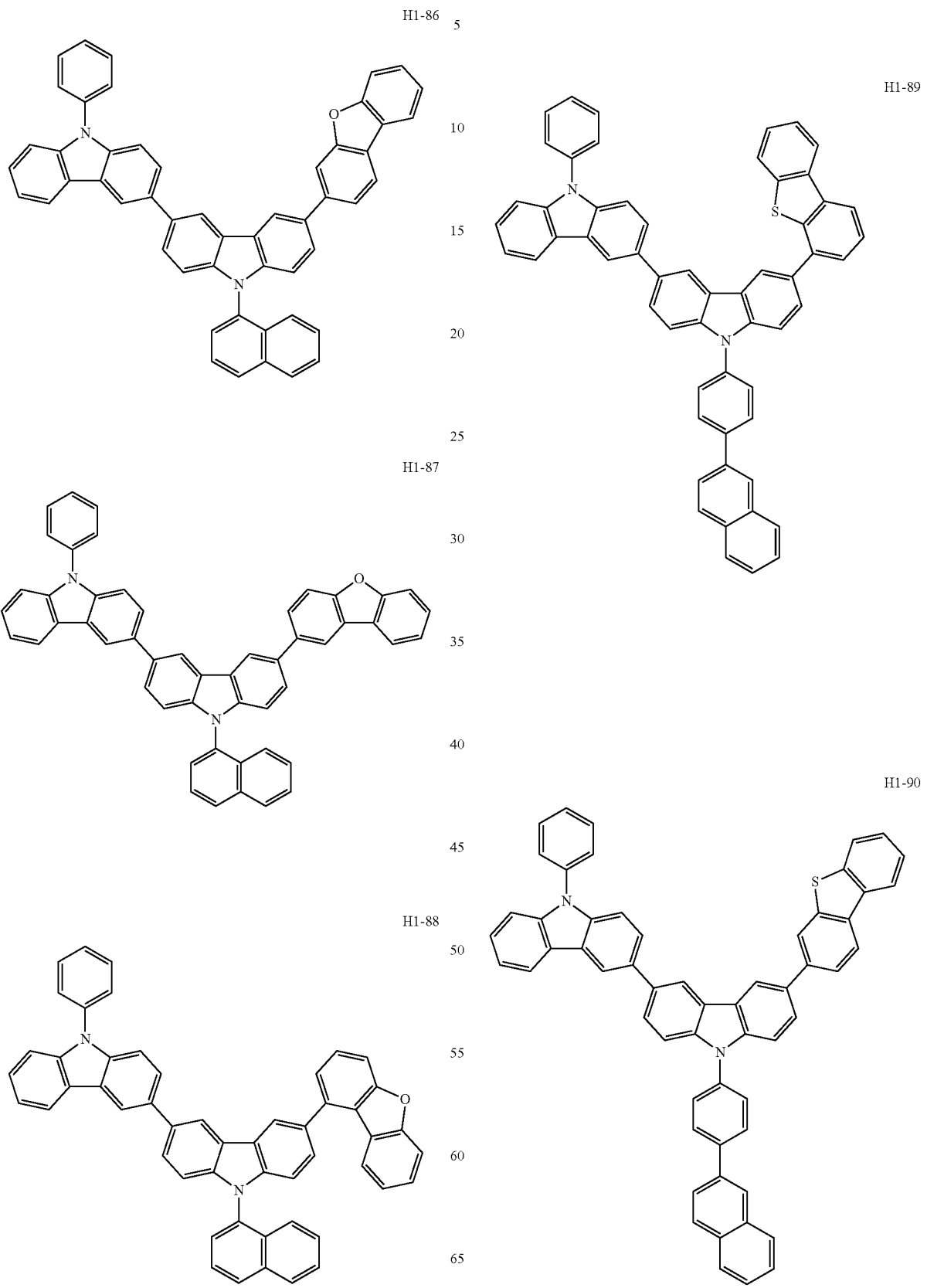

H1-91
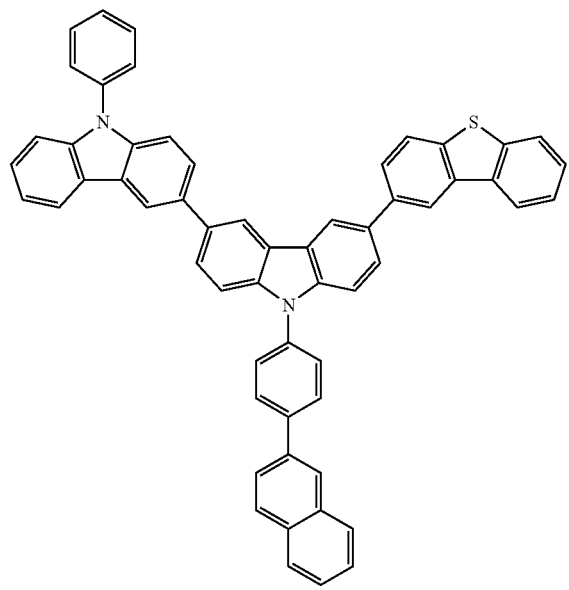
H1-93
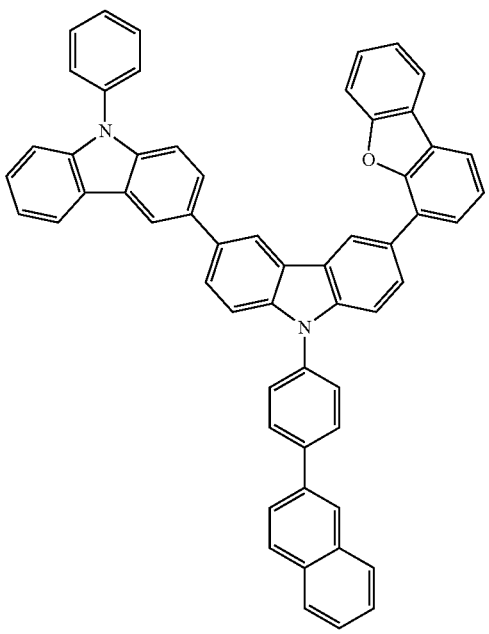
H1-92
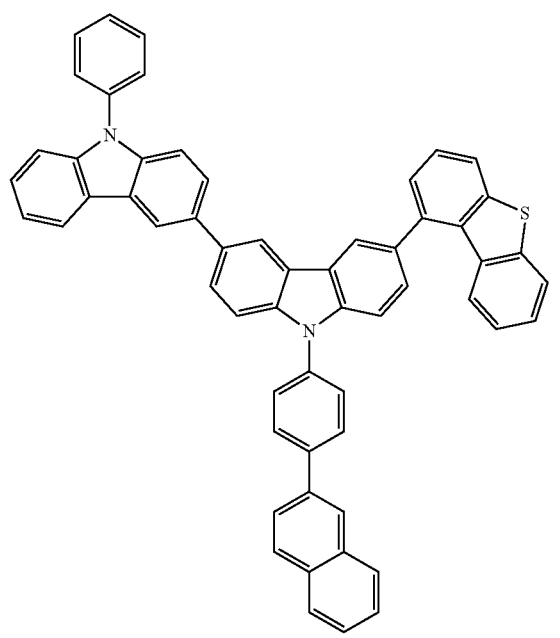
H1-94
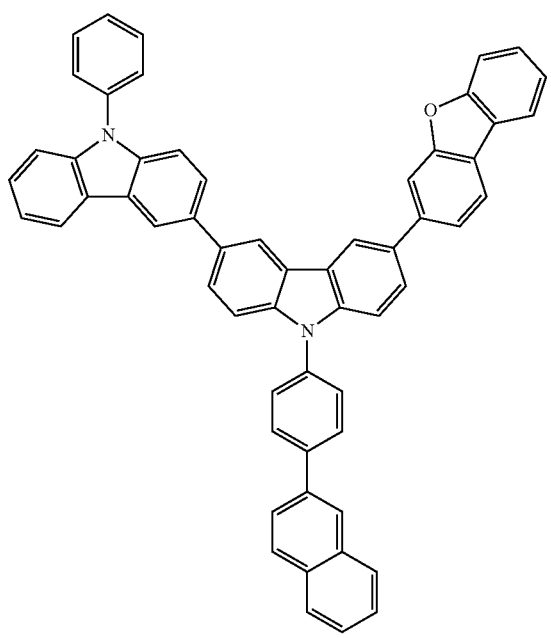

H1-95
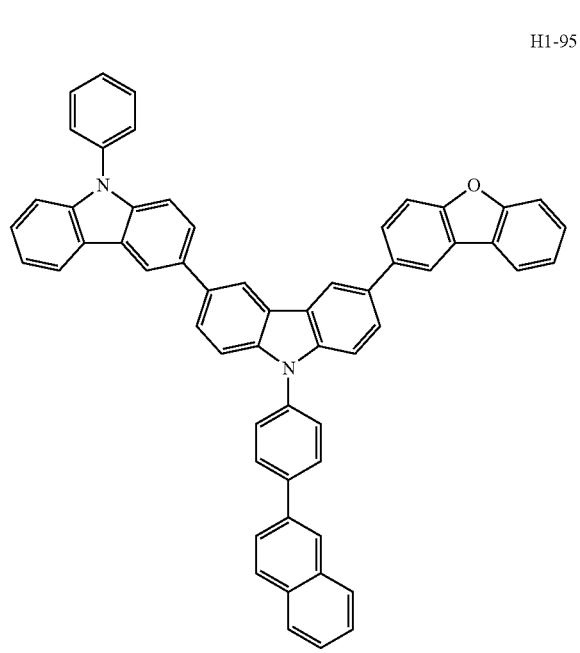
H1-96
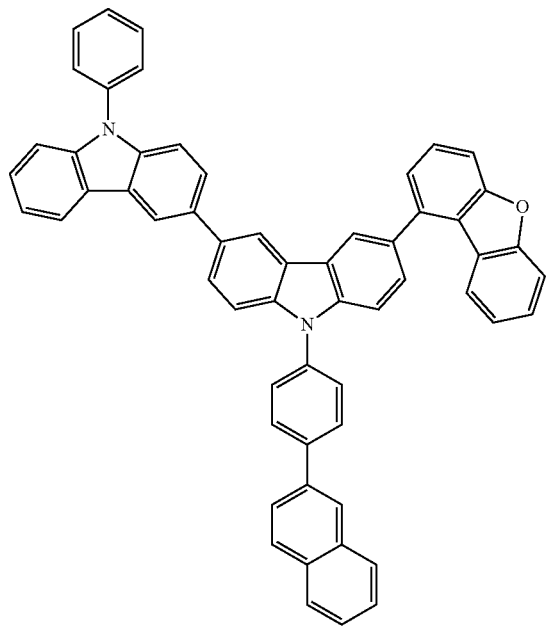
H1-97
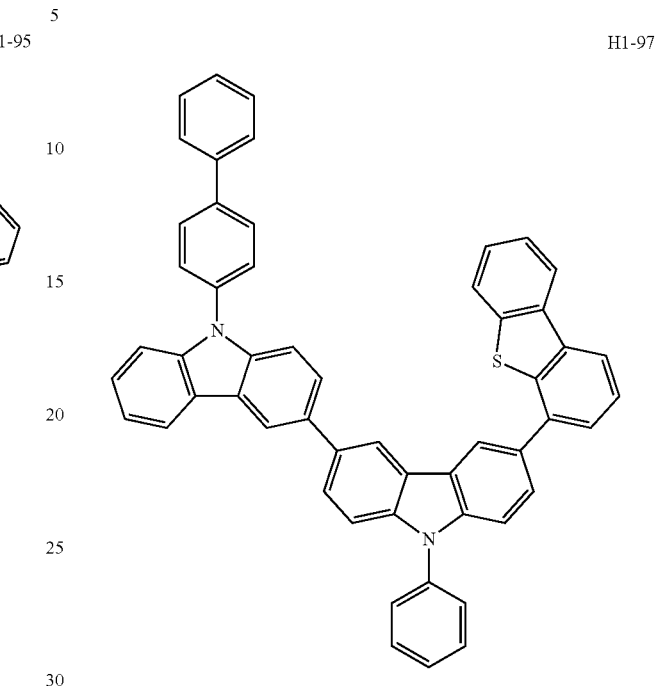
H1-98
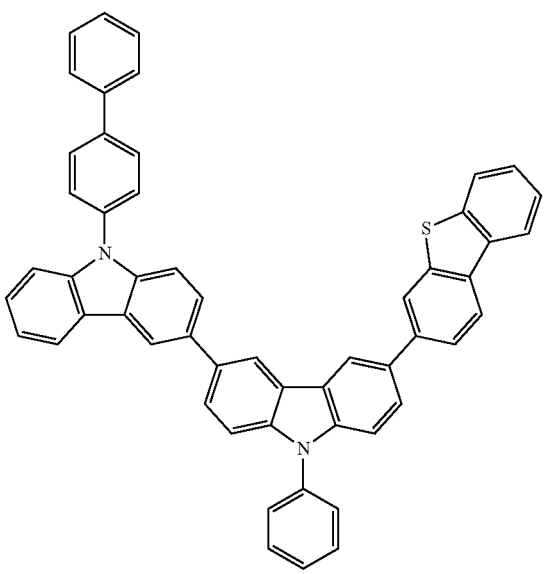

H1-99
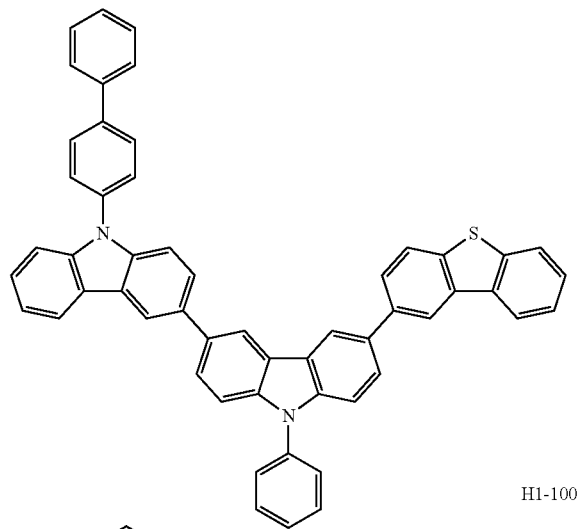
H1-100
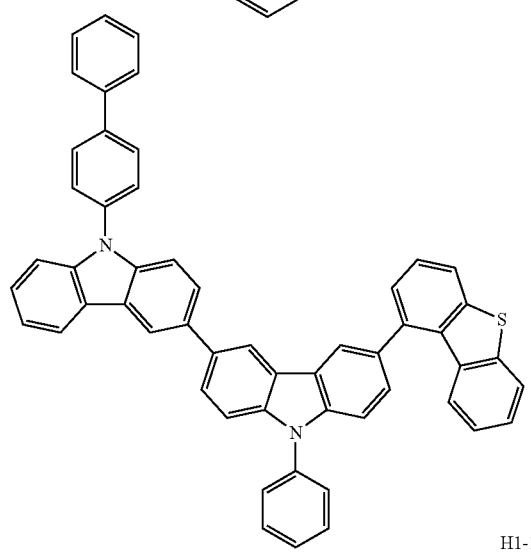
H1-101
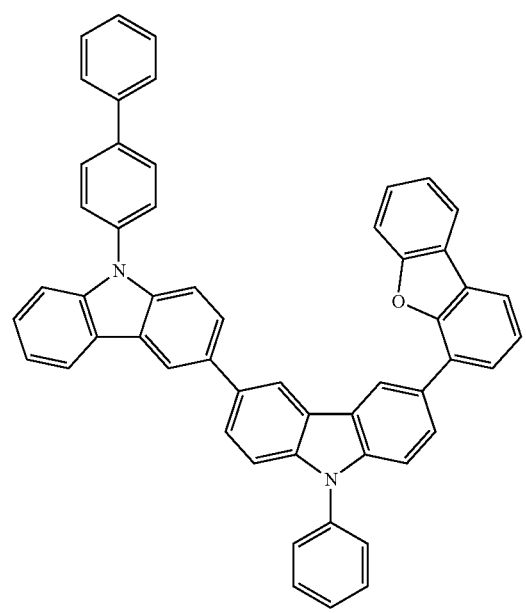
H1-102
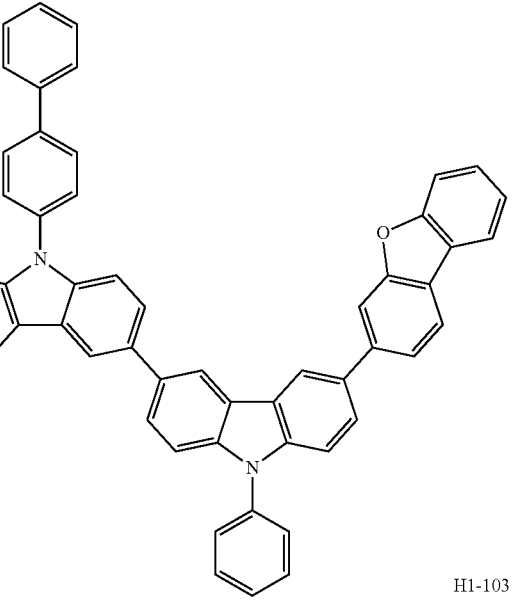
H1-103
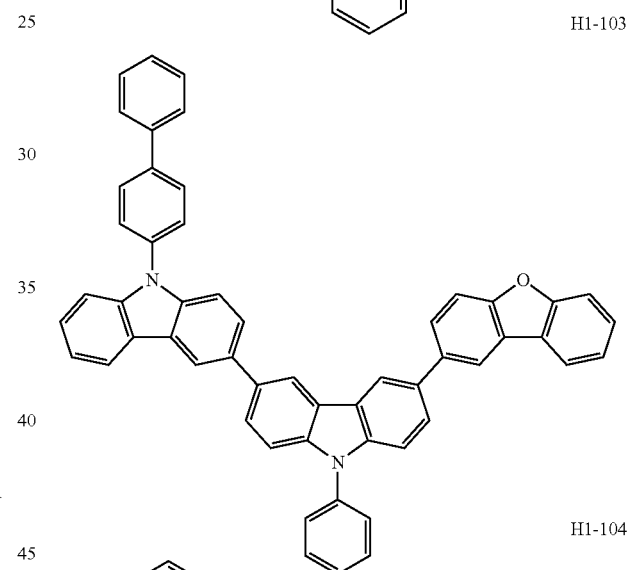
H1-104
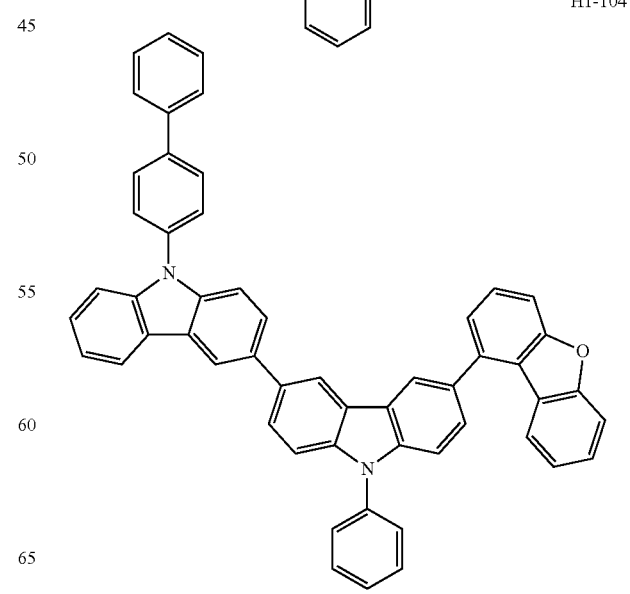

-continued
H1-105
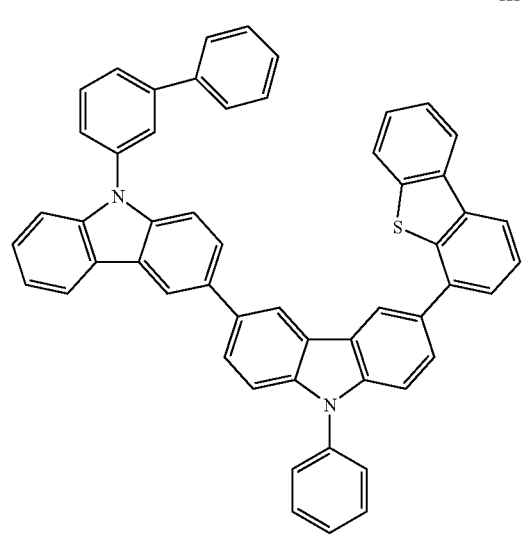
H1-106
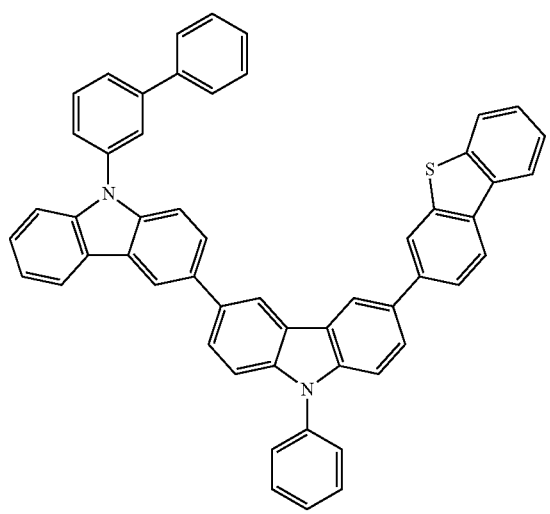
H1-107
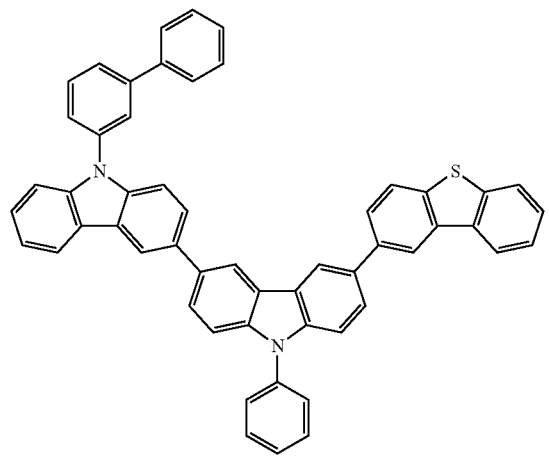
-continued
H1-108
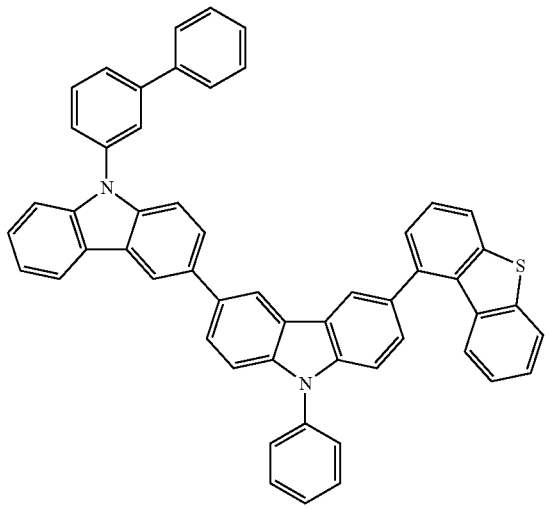
H1-109
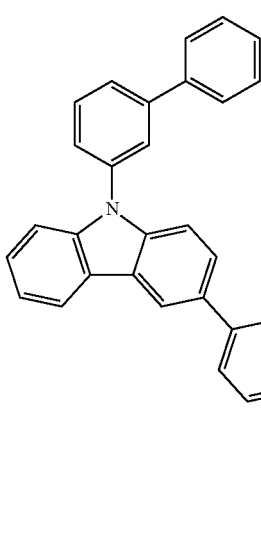
H1-110
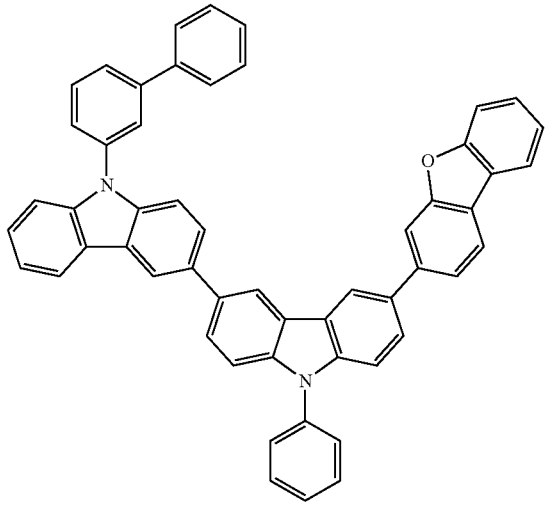

H1-111
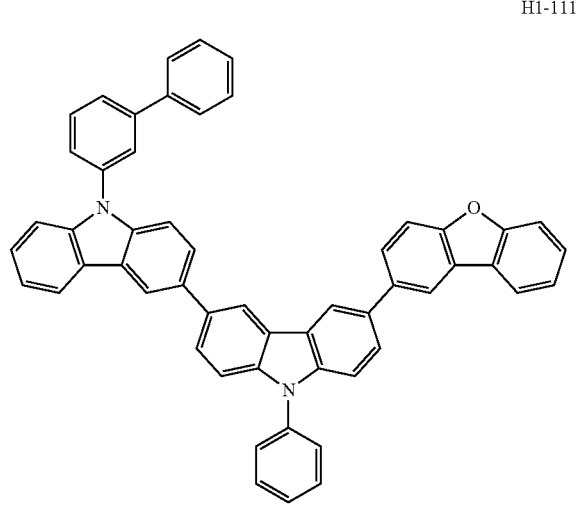
H1-114
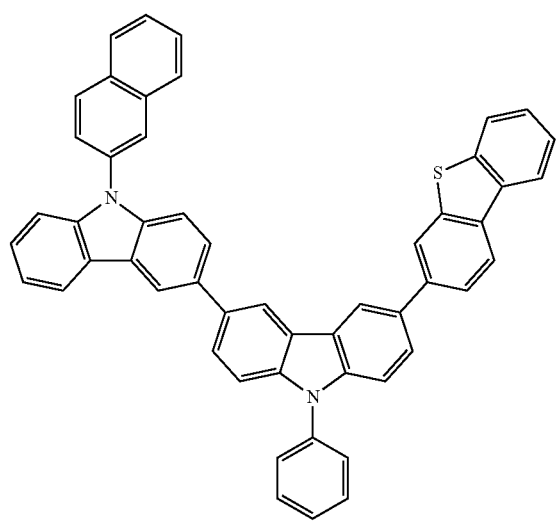
H1-112
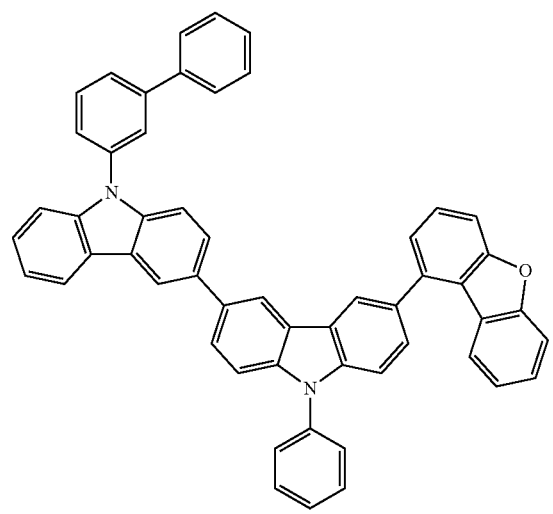
H1-115
H1-113
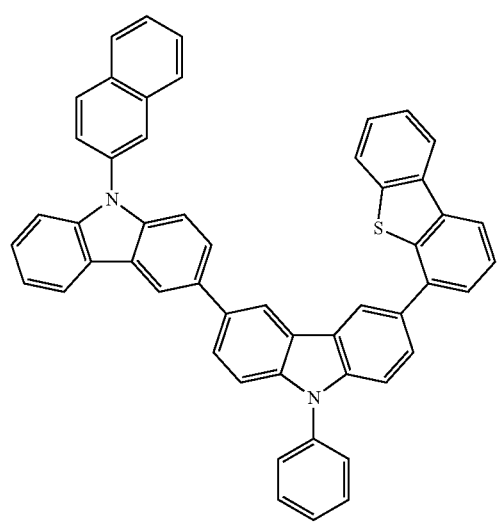
H1-116
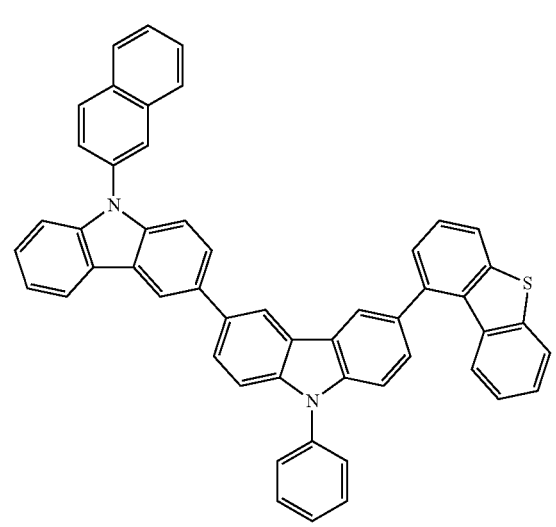

H1-117
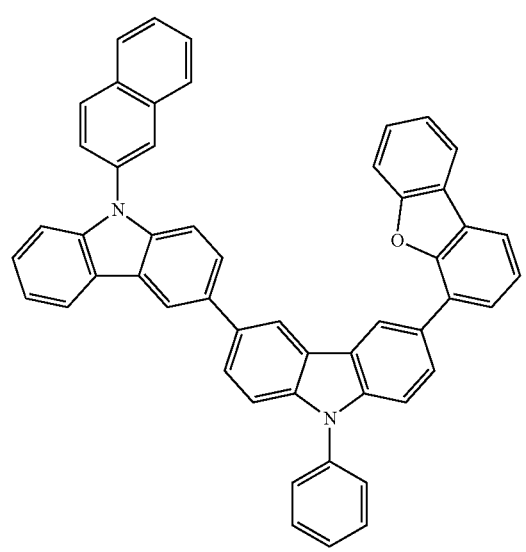
H1-120
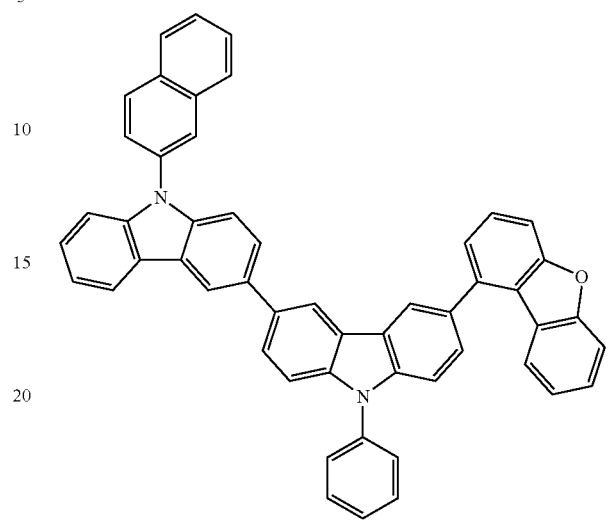
H1-118
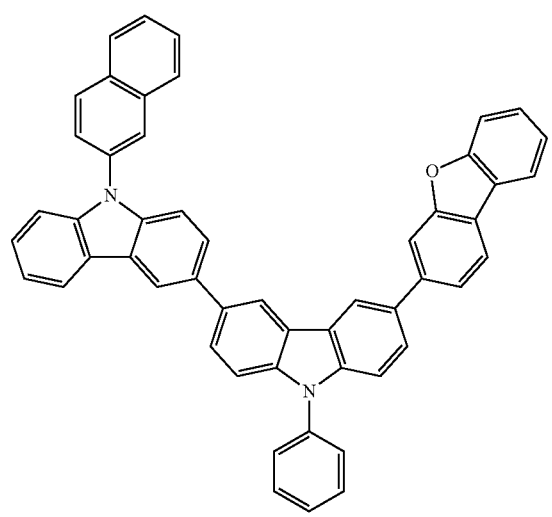
H1-121
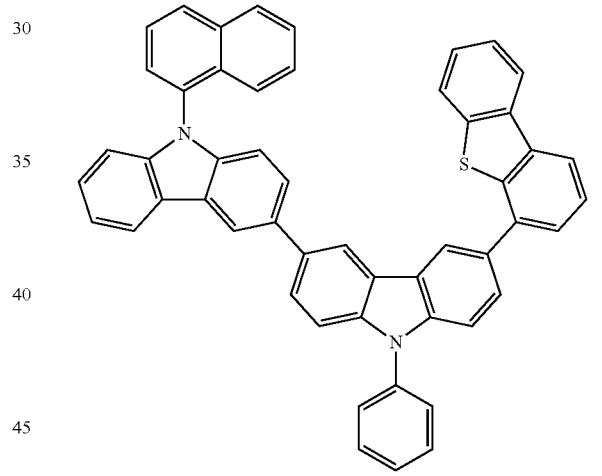
H1-119
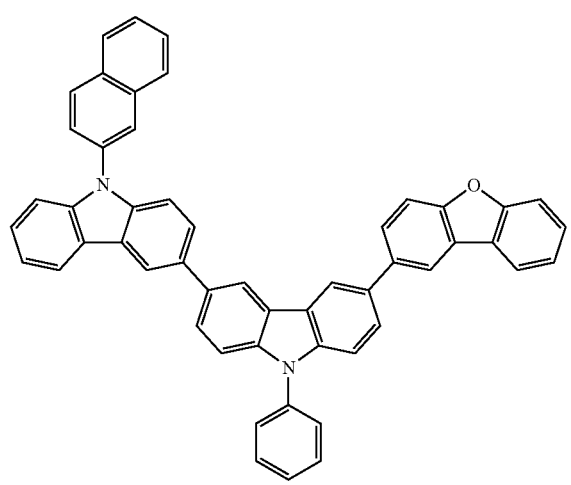
H1-122
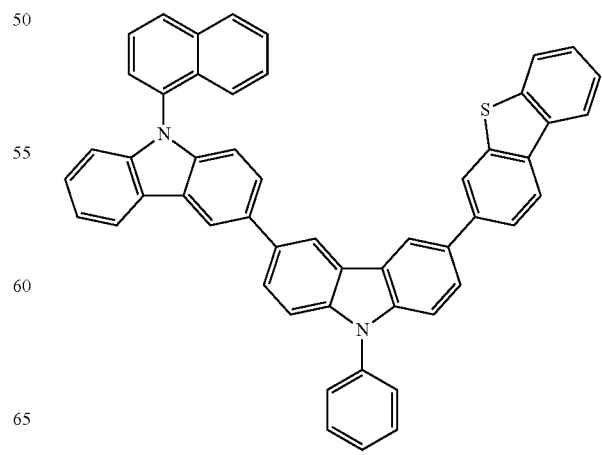

-continued
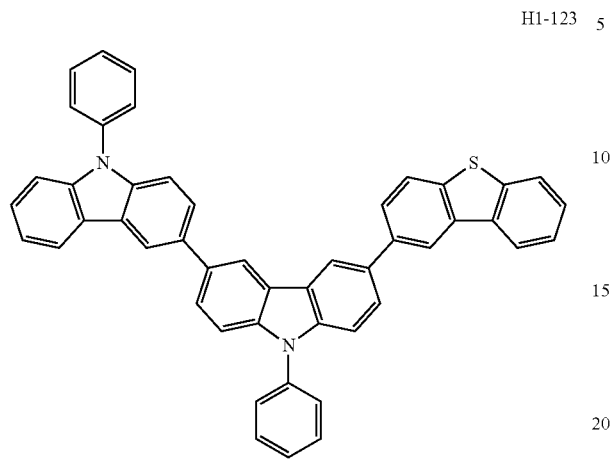
H1-123
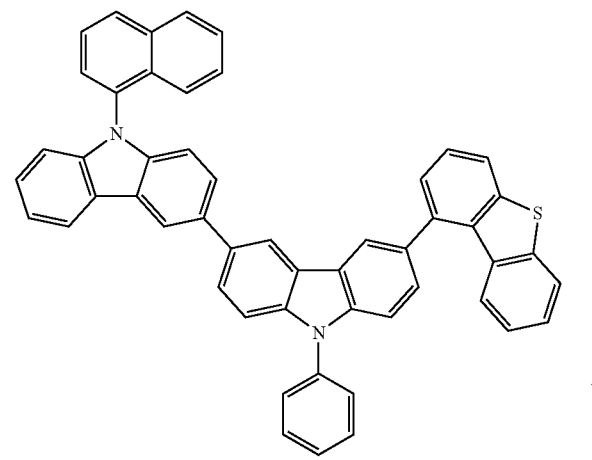
H1-124
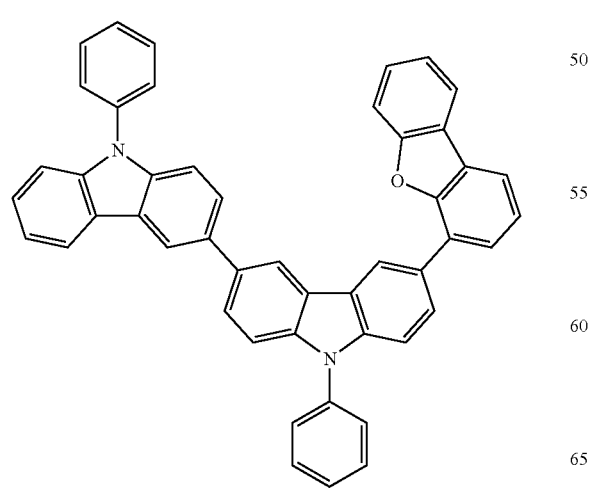
H1-125
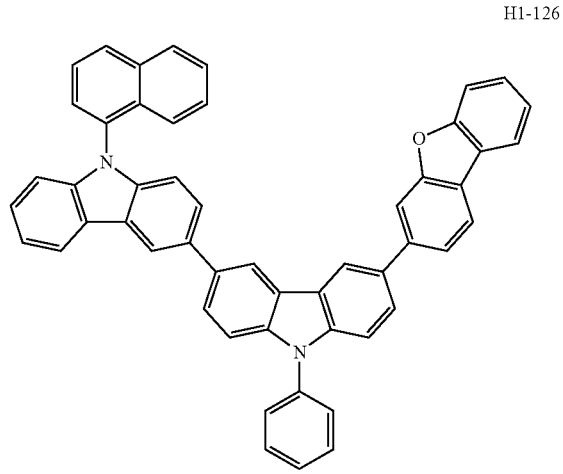
H1-126
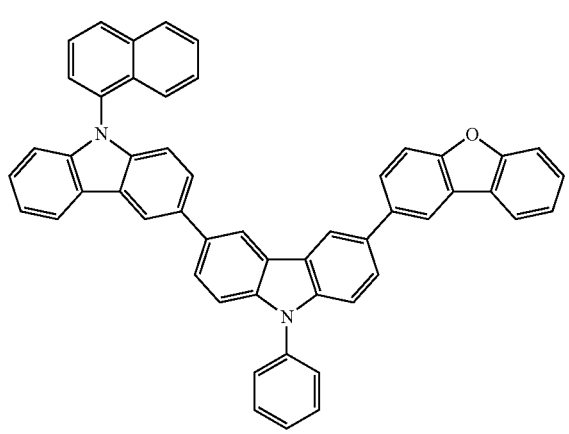
H1-127
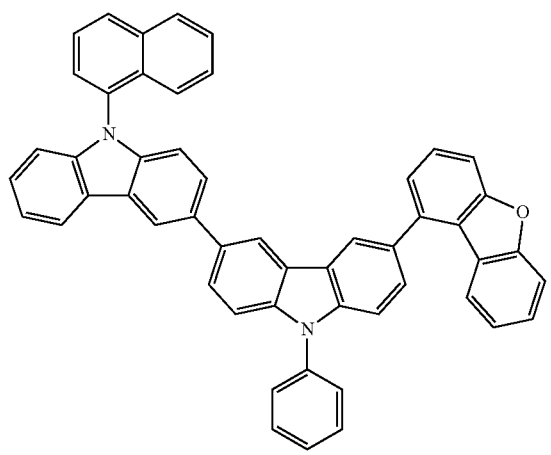
H1-128

H1-129
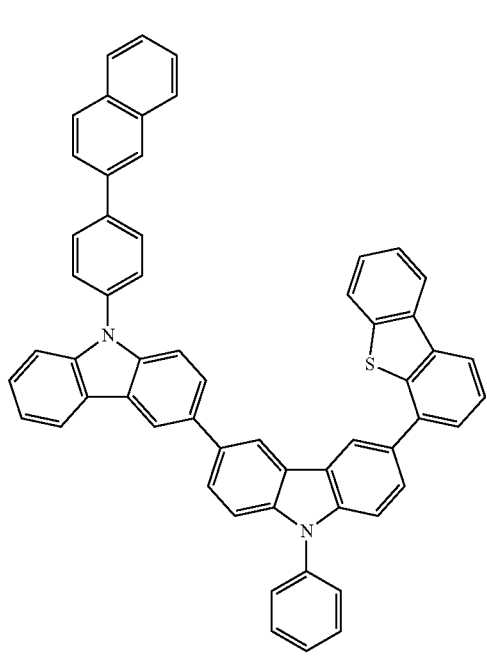
H1-130
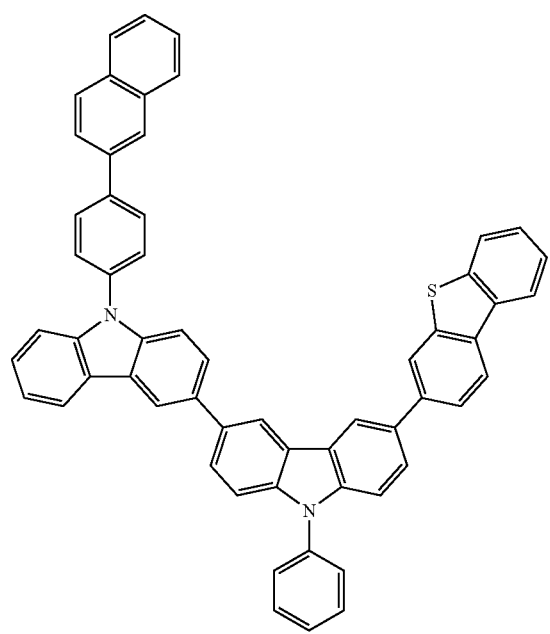
H1-131
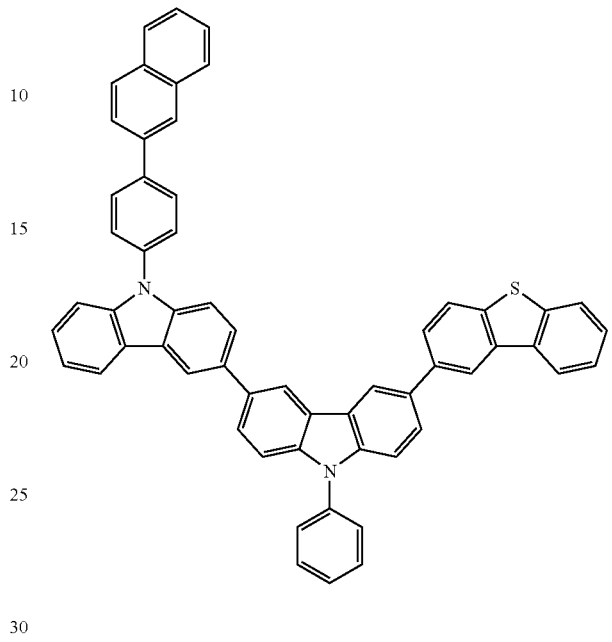
H1-132
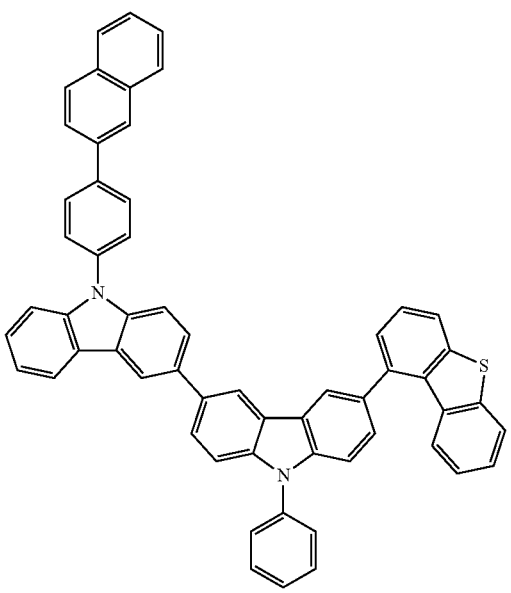

-continued
H1-133
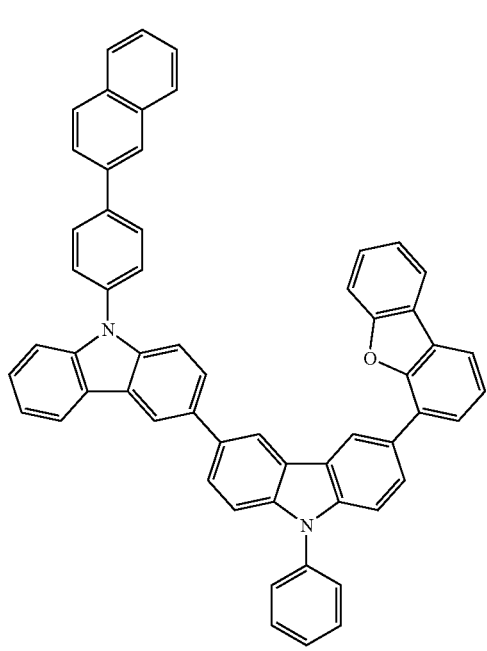
H1-134
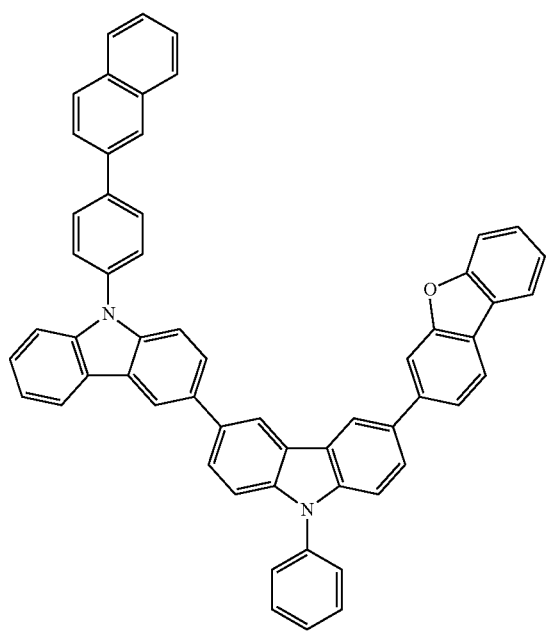
-continued
H1-135
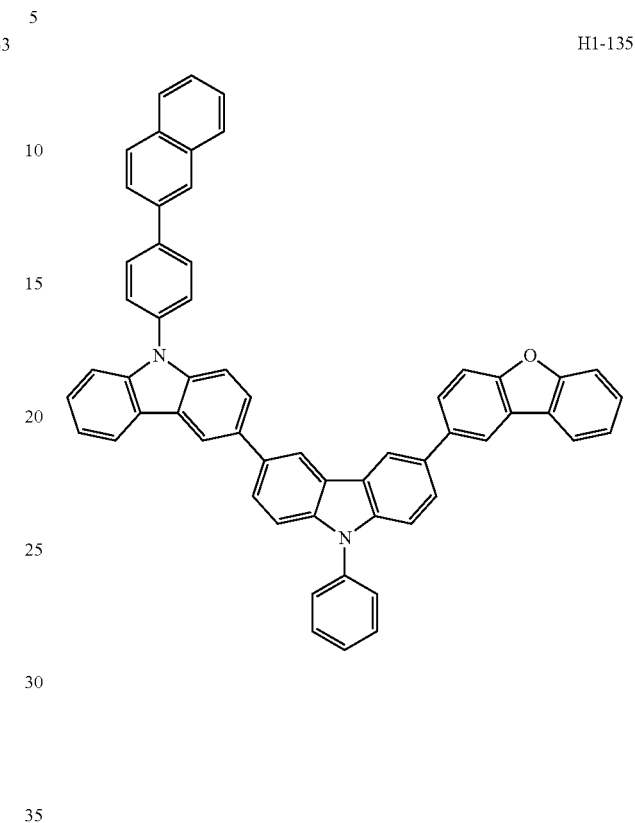
H1-136
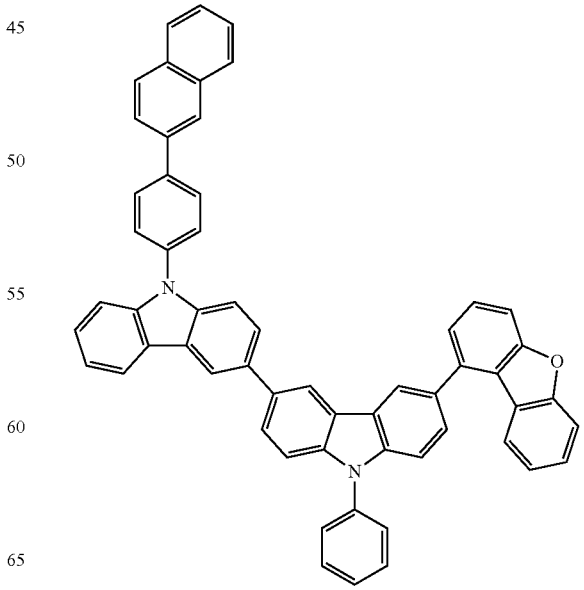

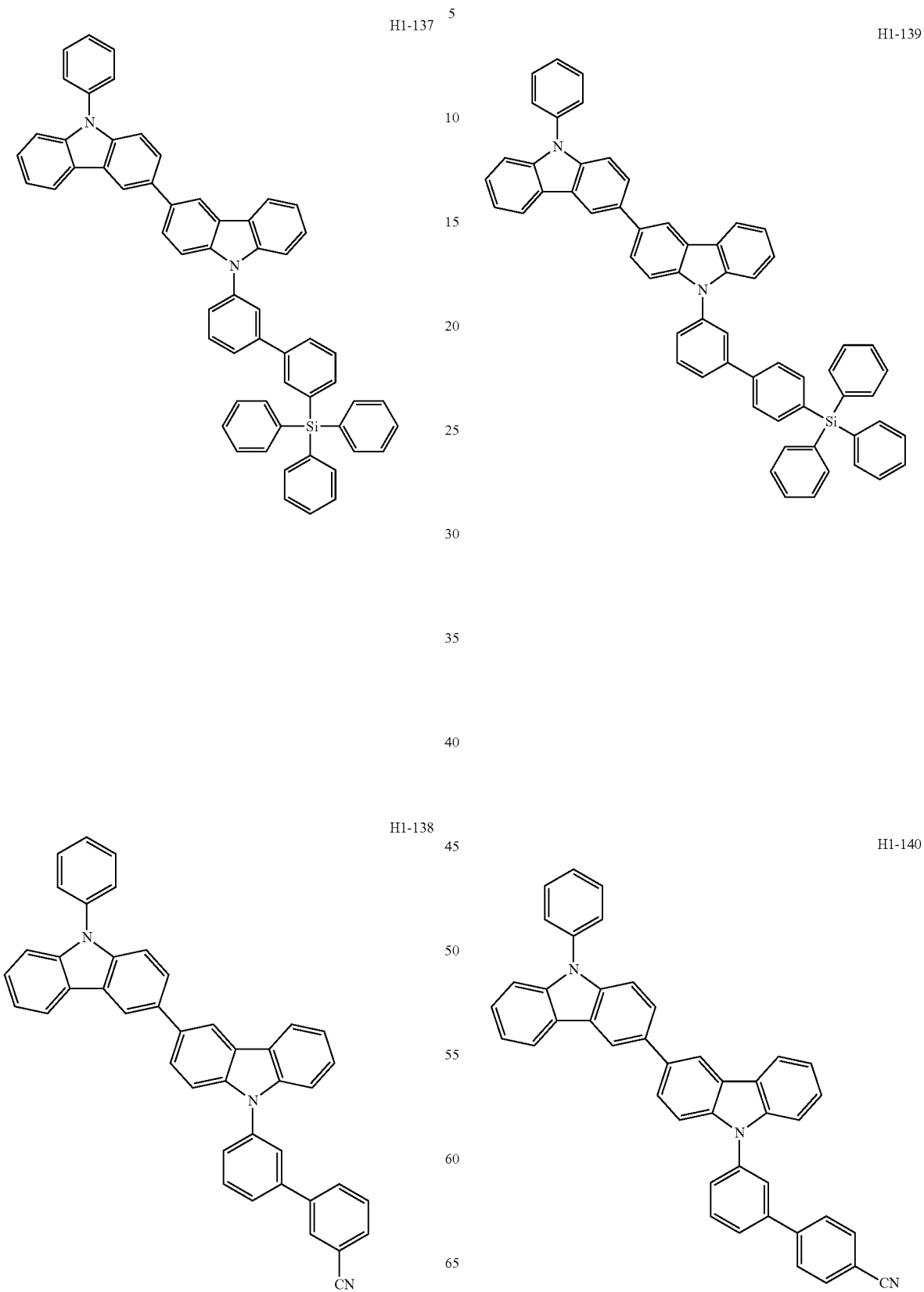

H1-141
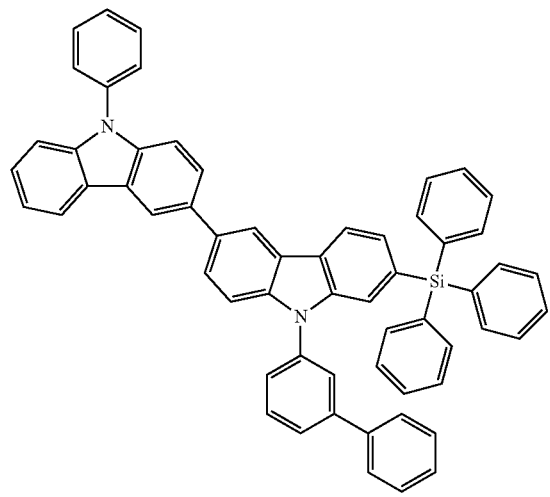
H1-142
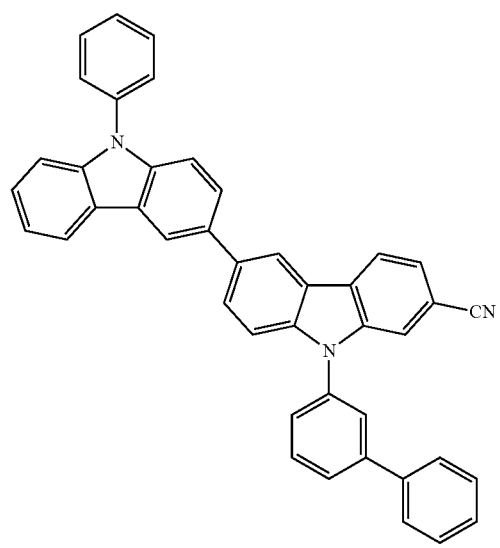
H1-143
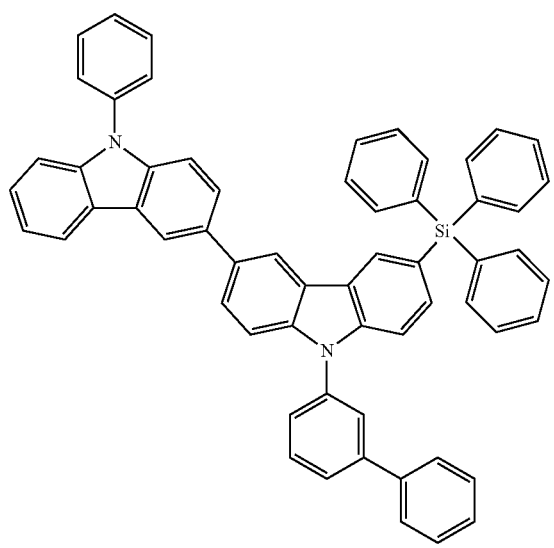
H1-144
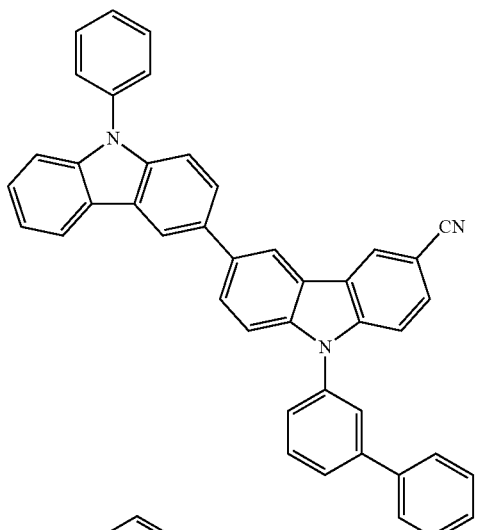
H1-145
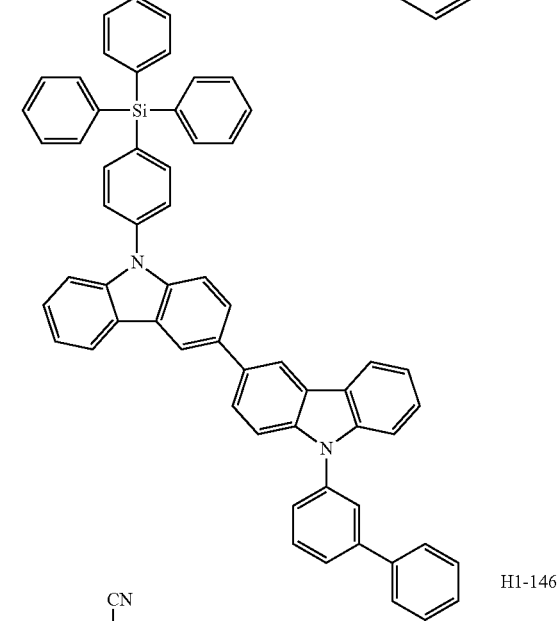
H1-146
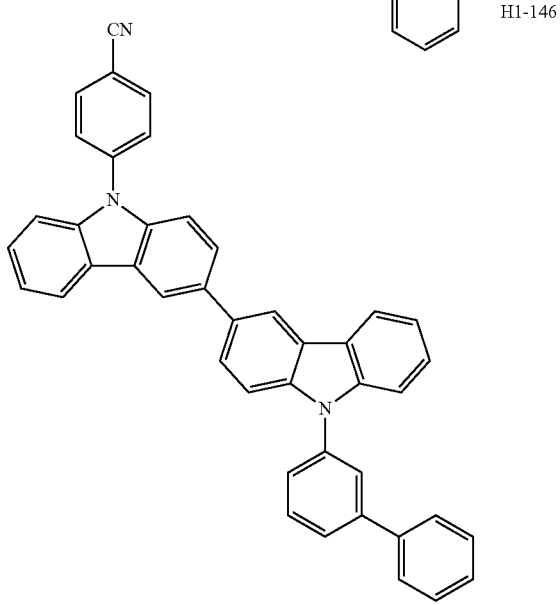

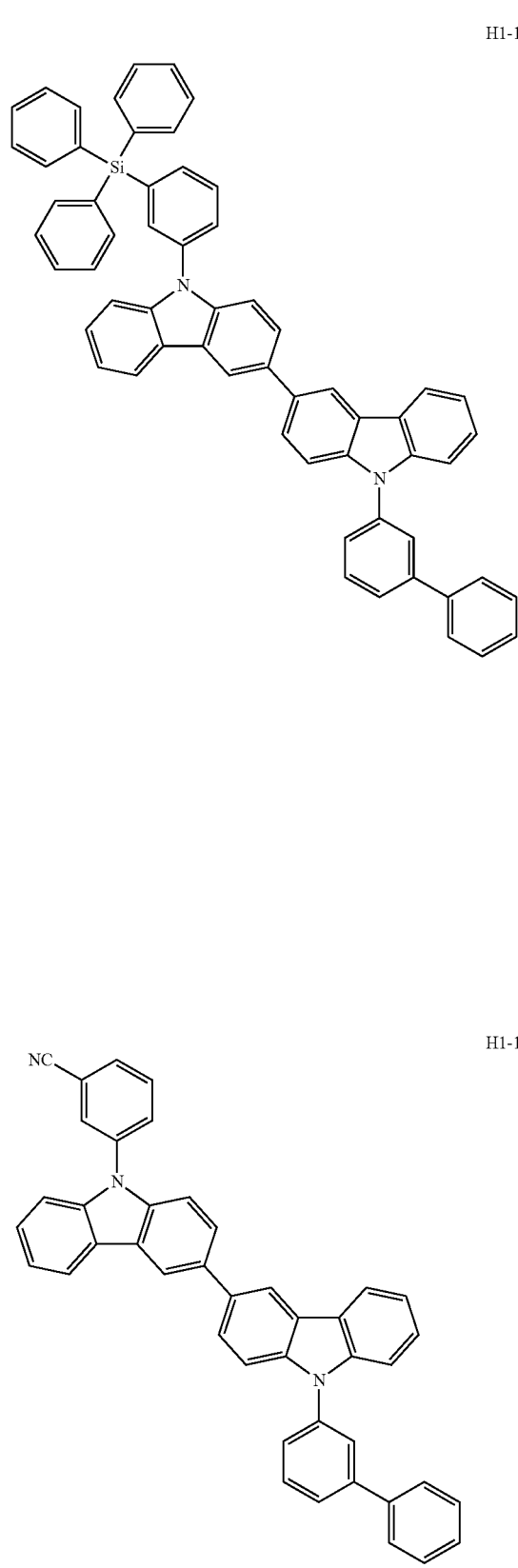
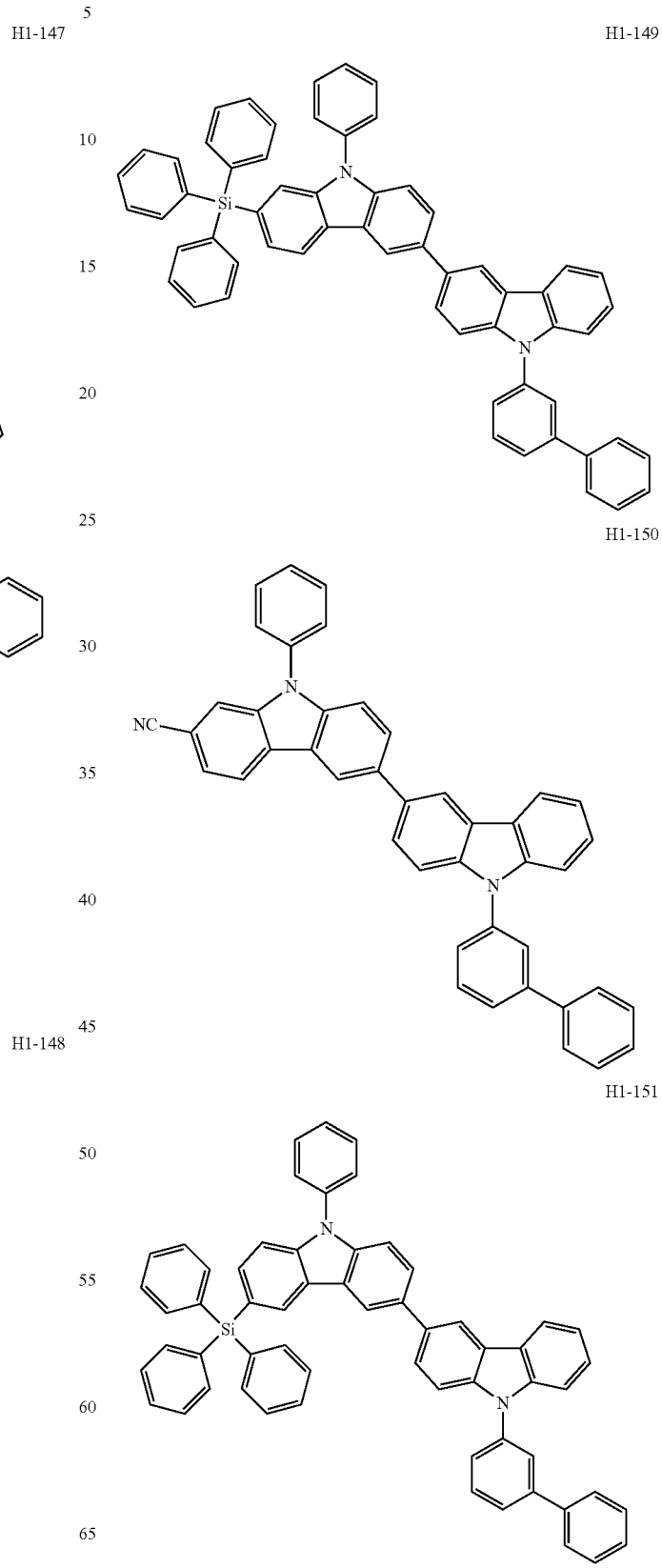

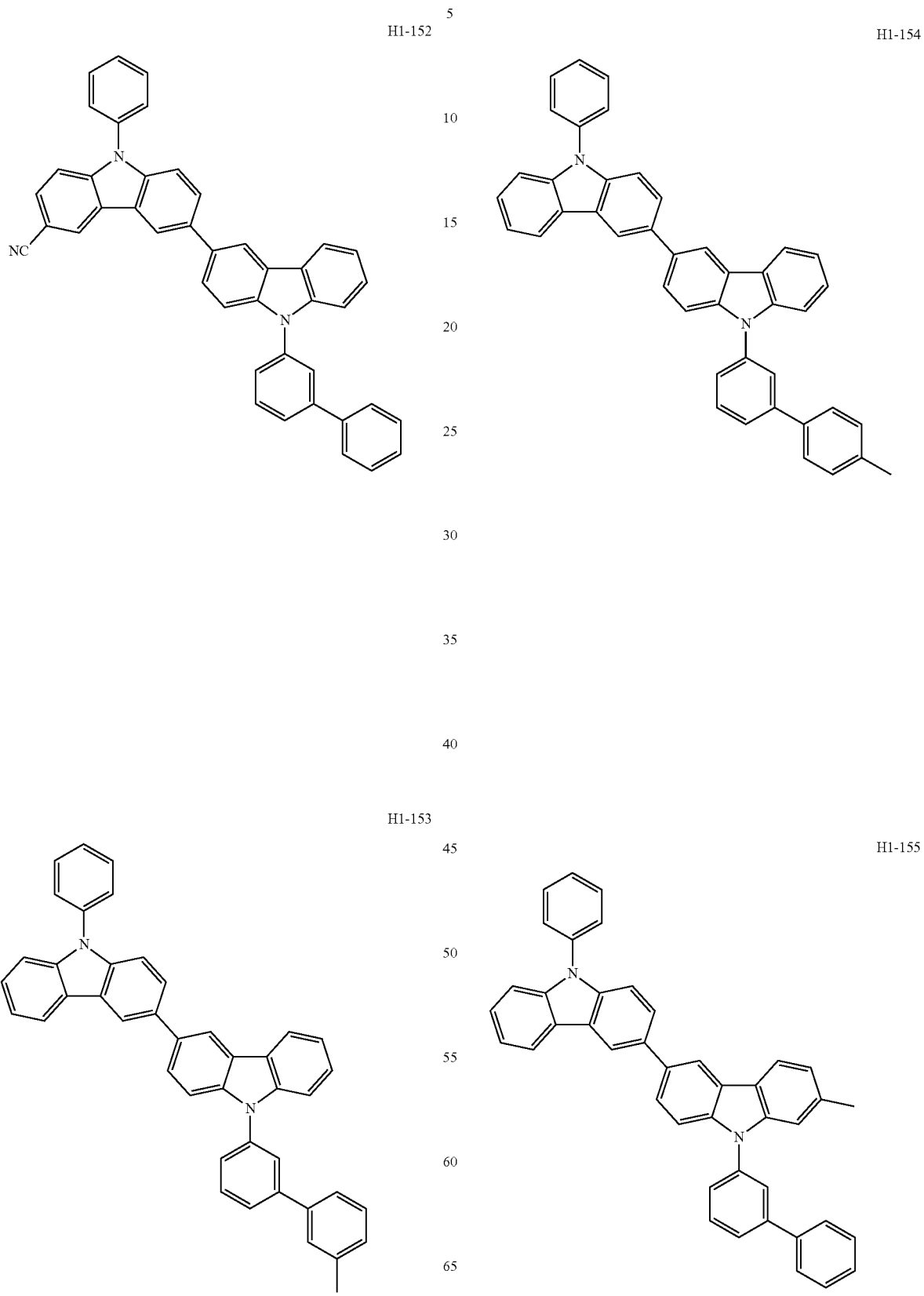
H1-152
H1-153
H1-154
H1-155

H1-156
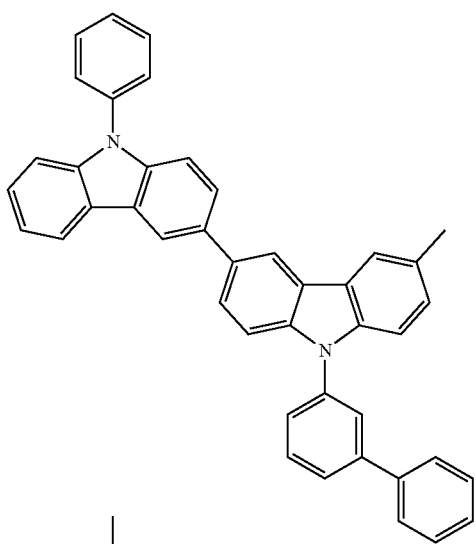
H1-159
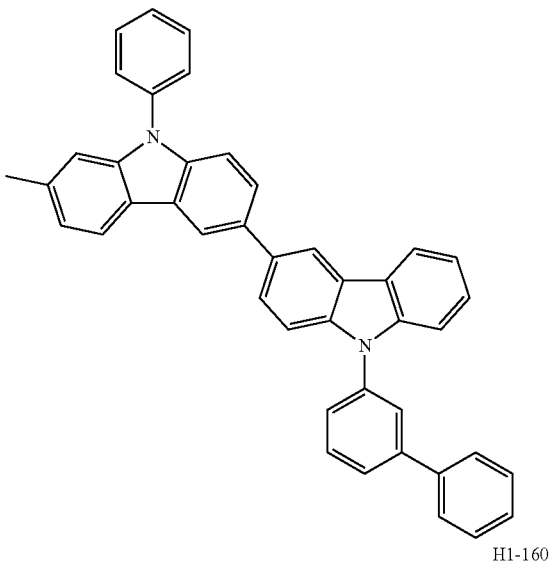
H1-157
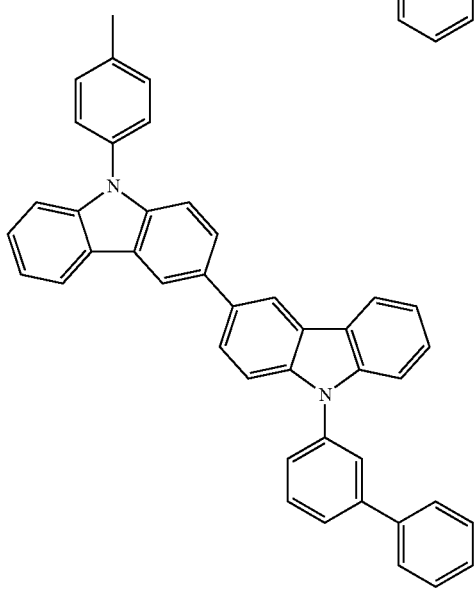
H1-160
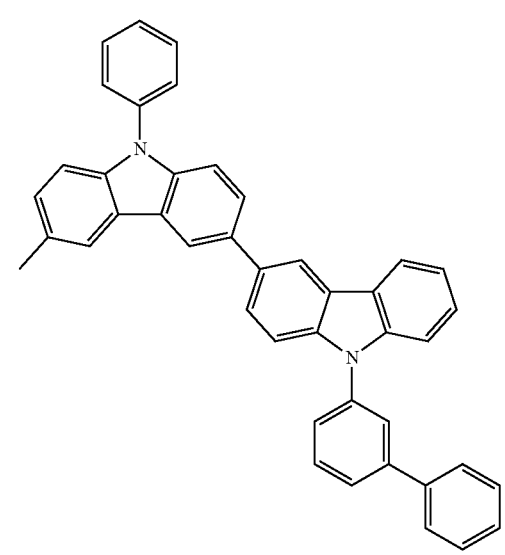
H1-158
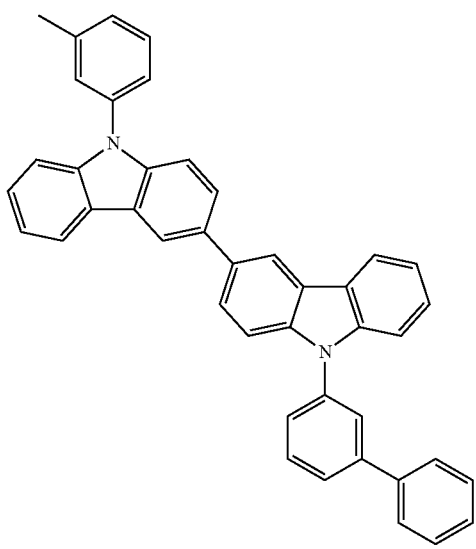
H1-161
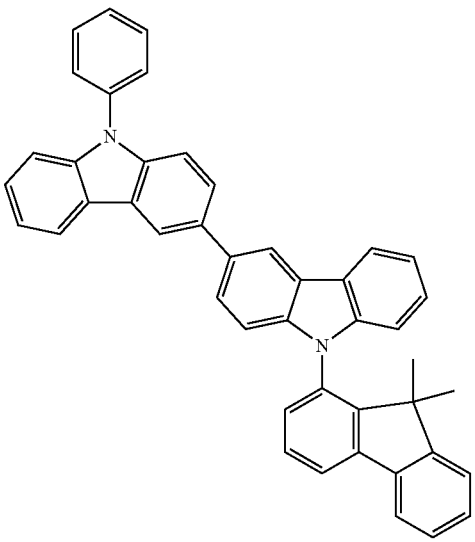

H1-162
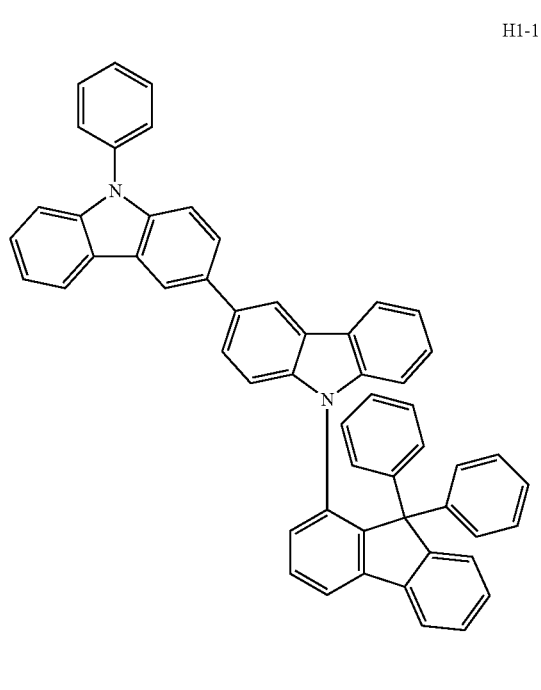
H1-164
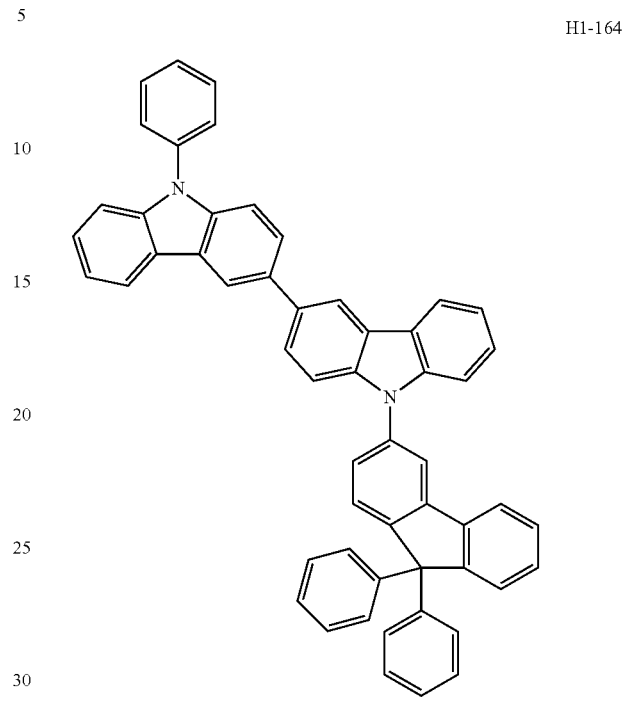
H1-163
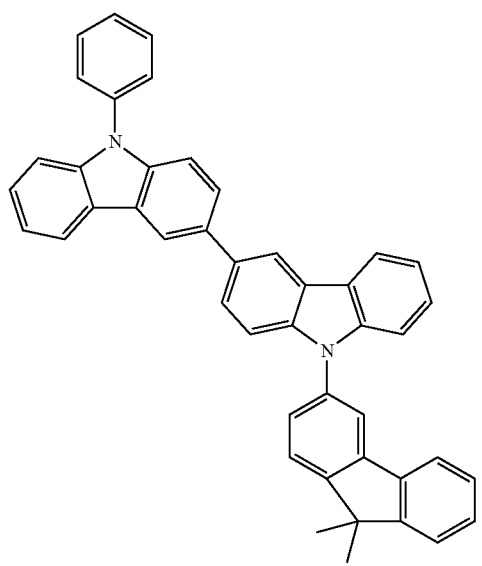
H1-165
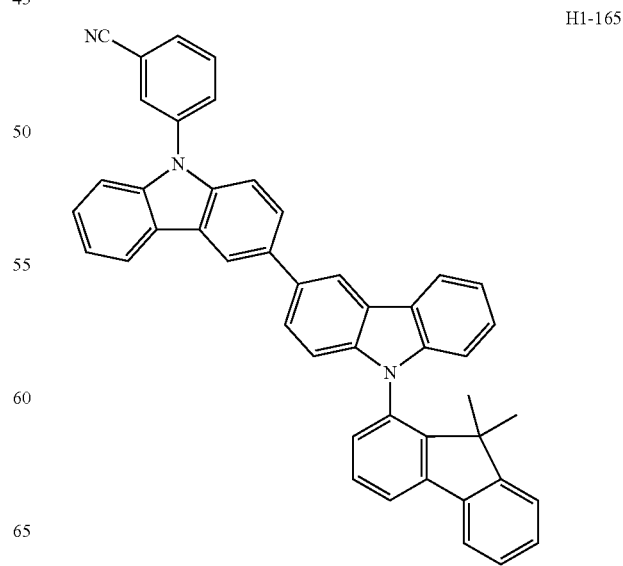

-continued
H1-166
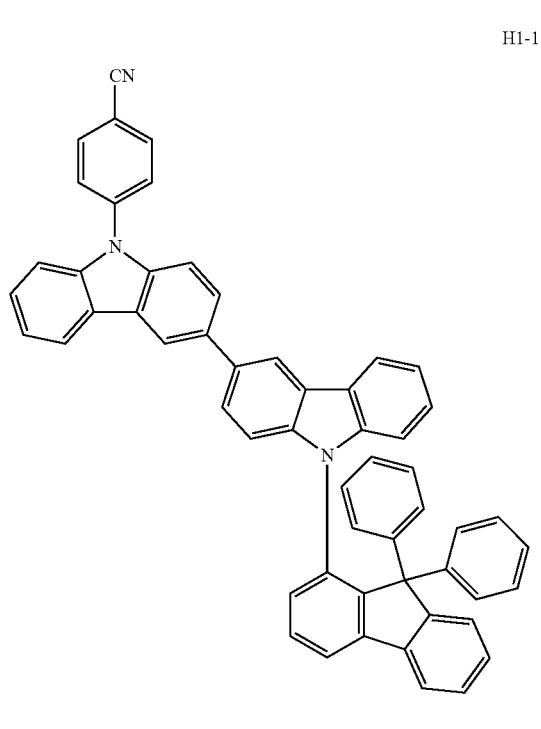
H1-168
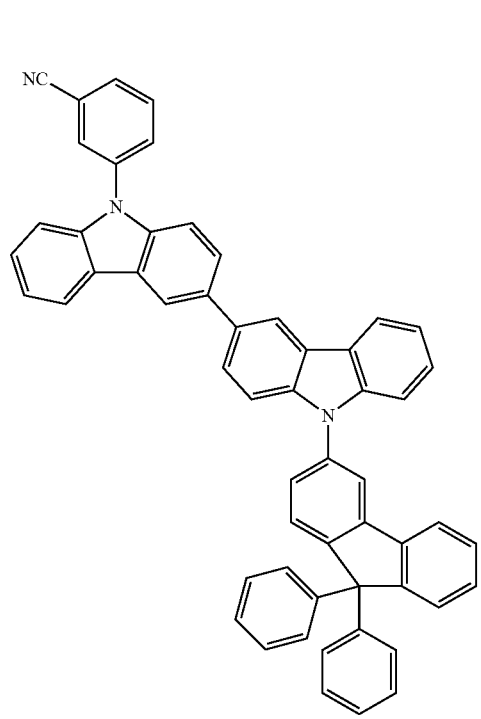
H1-167
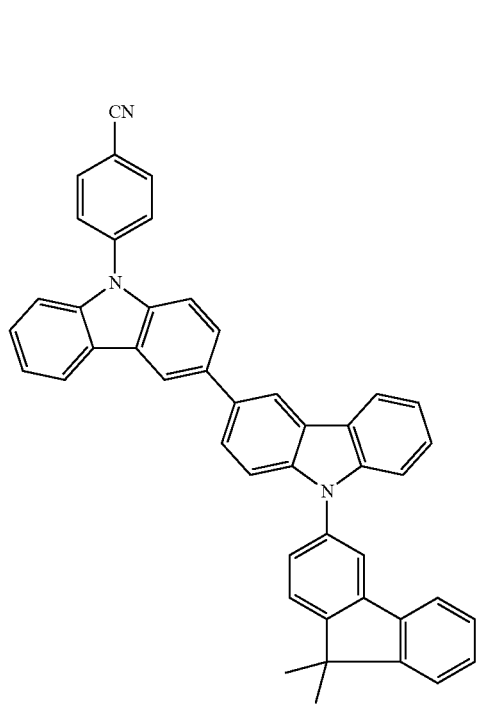
H1-169
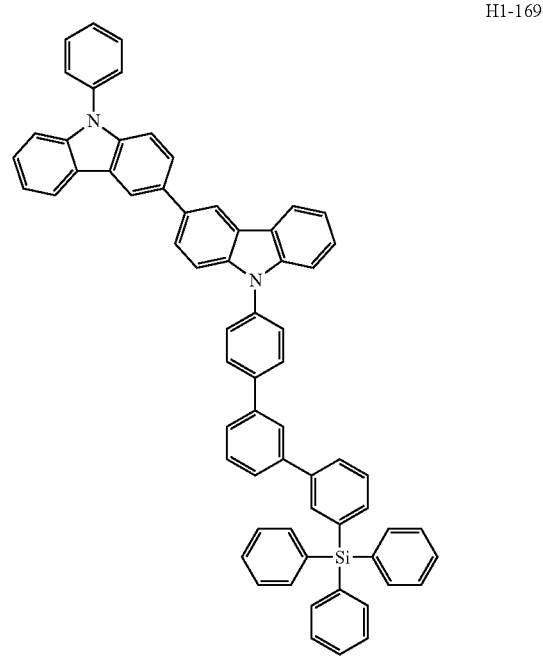

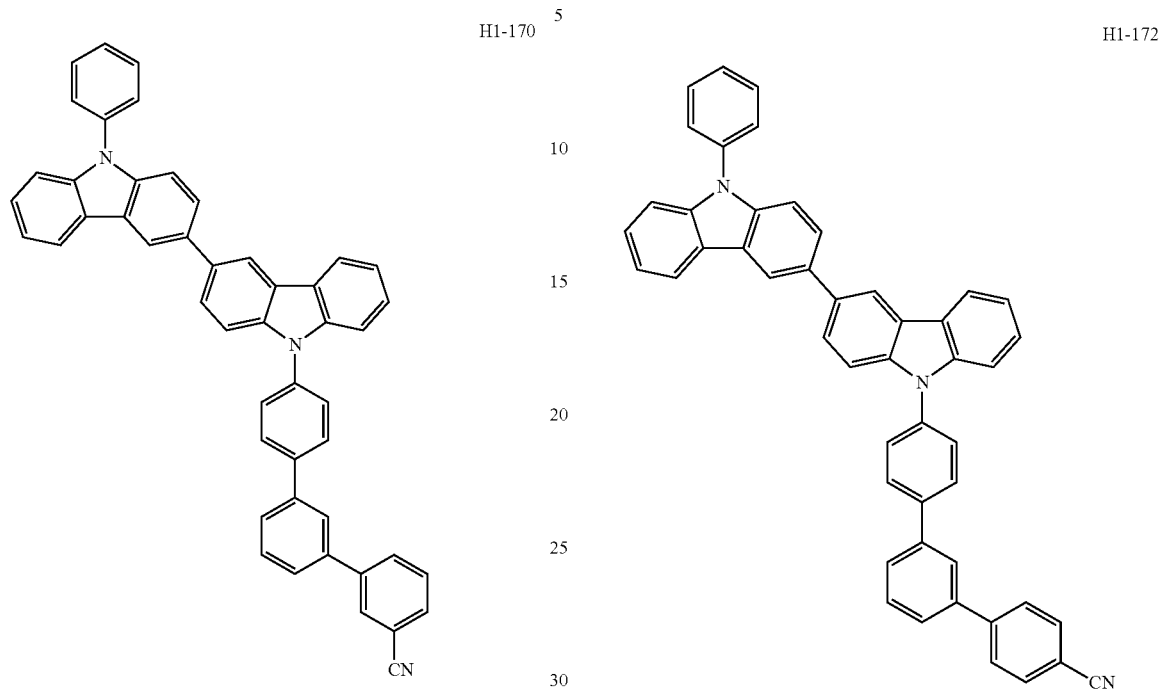
H1-170
H1-172
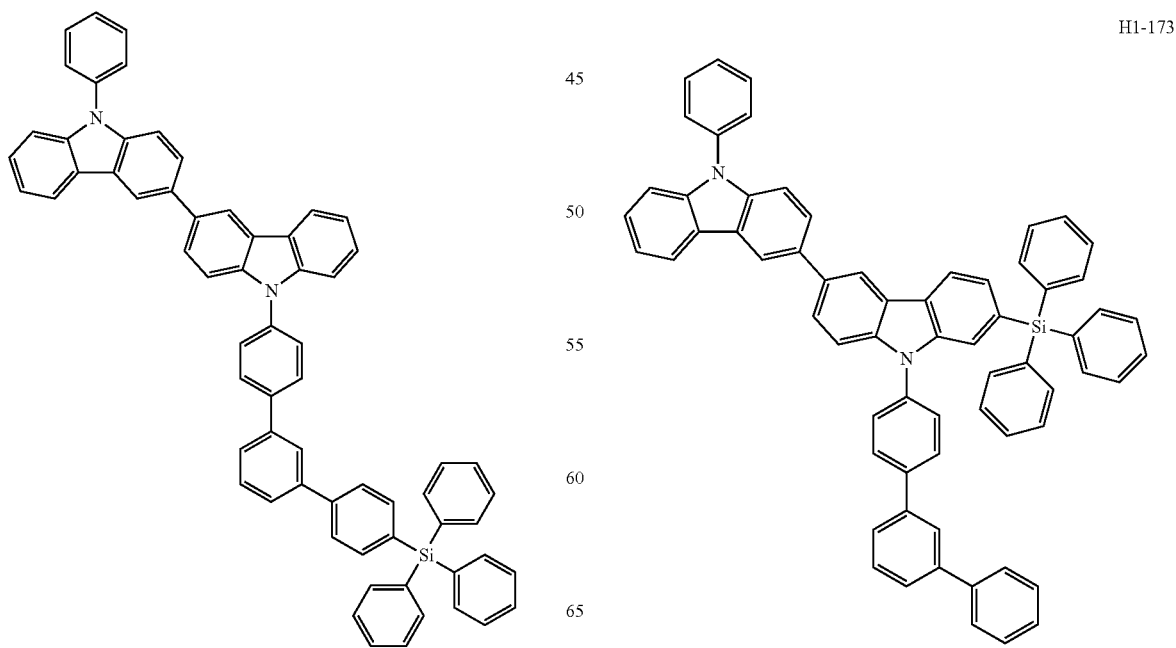
H1-171
H1-173

-continued
H1-174
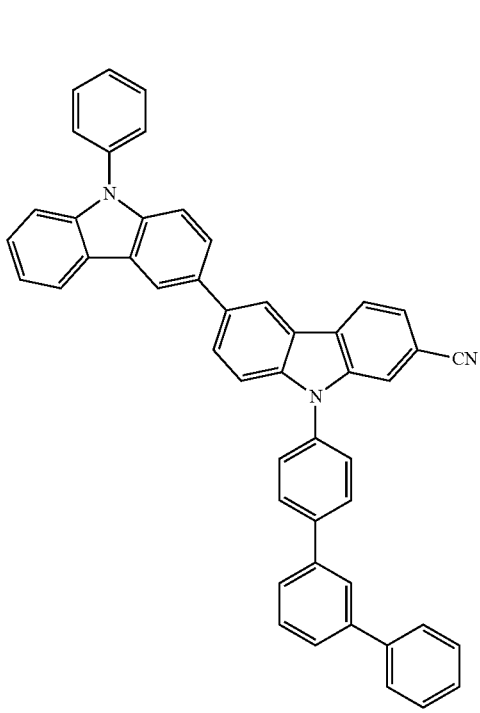
H1-176
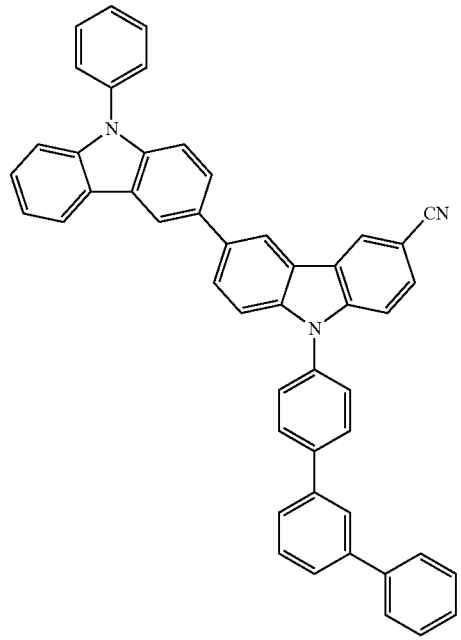
H1-175
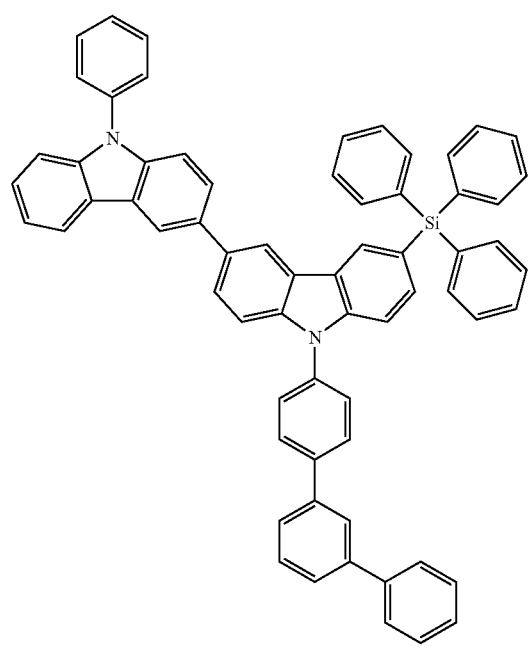
H1-177
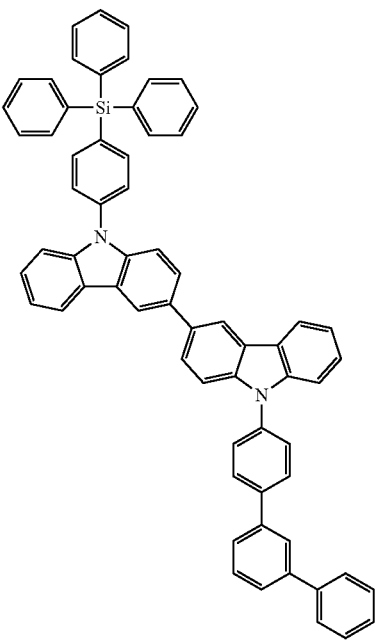

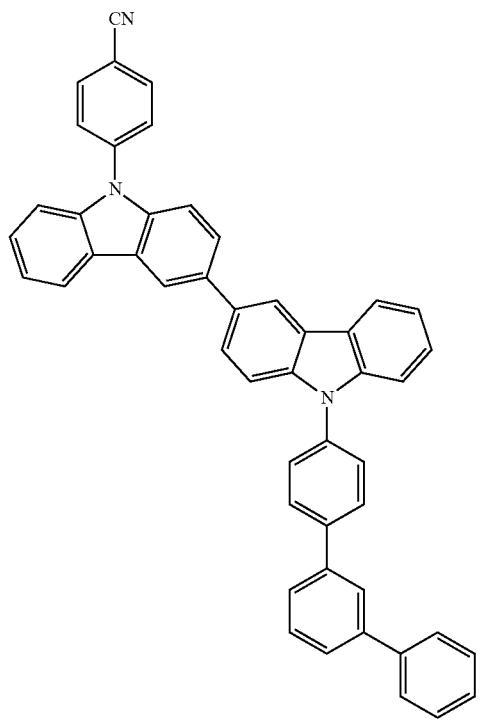
H1-178
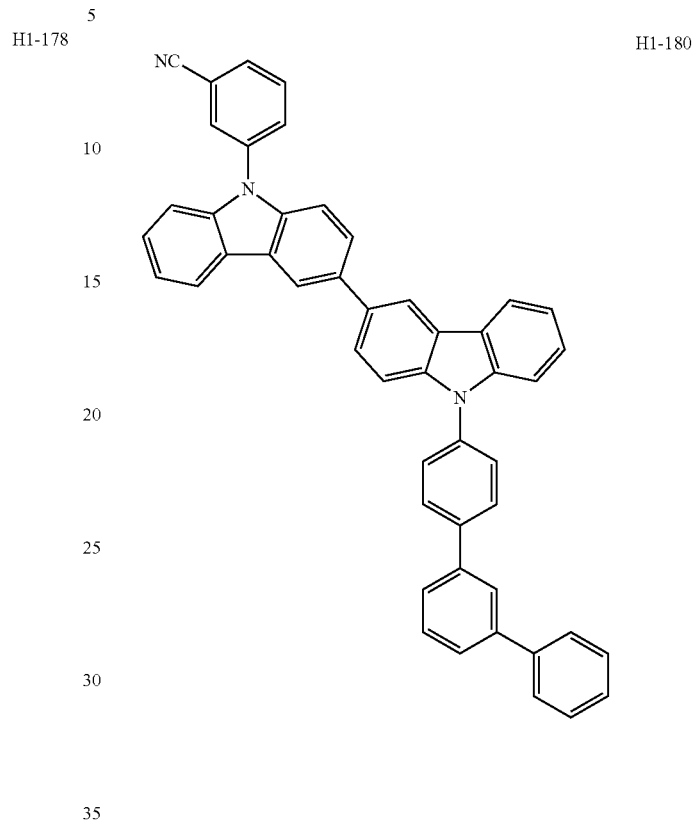
H1-180
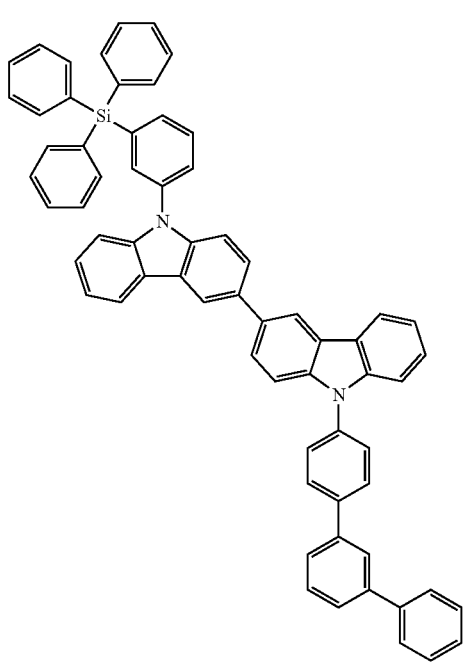
H1-179
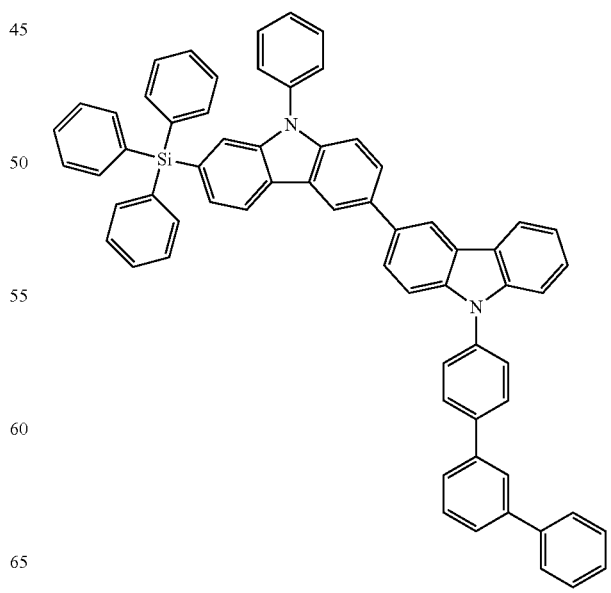
H1-181

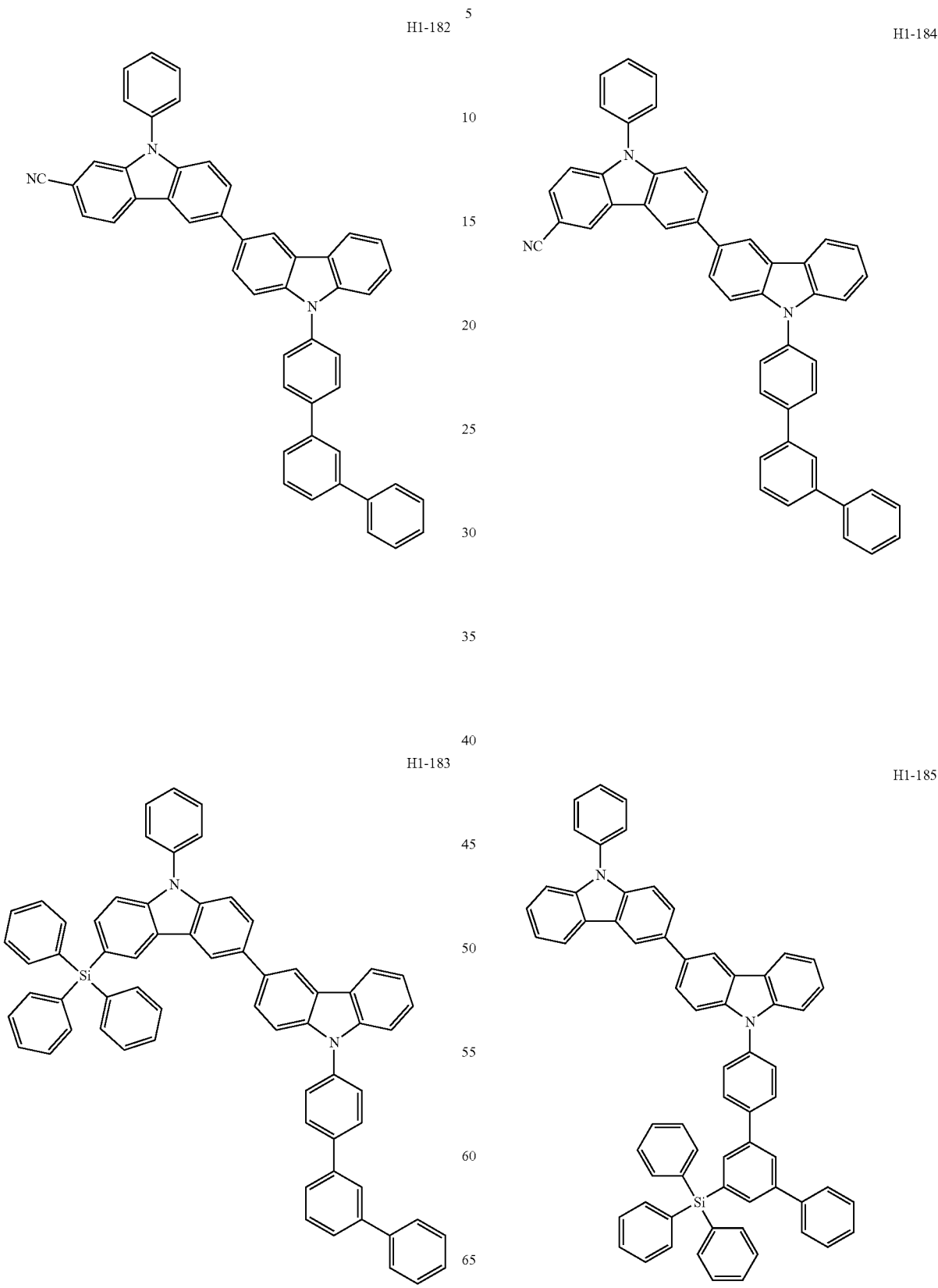

H1-186
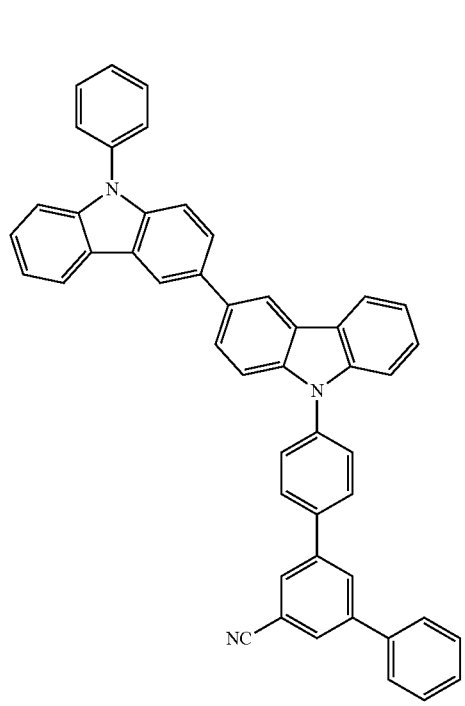
H1-188
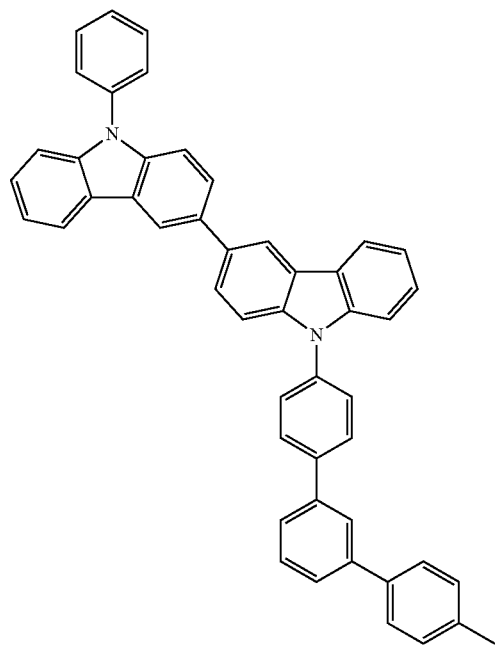
H1-187
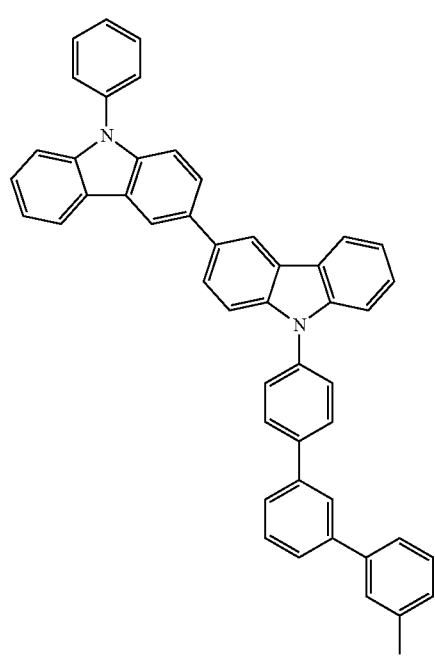
H1-189
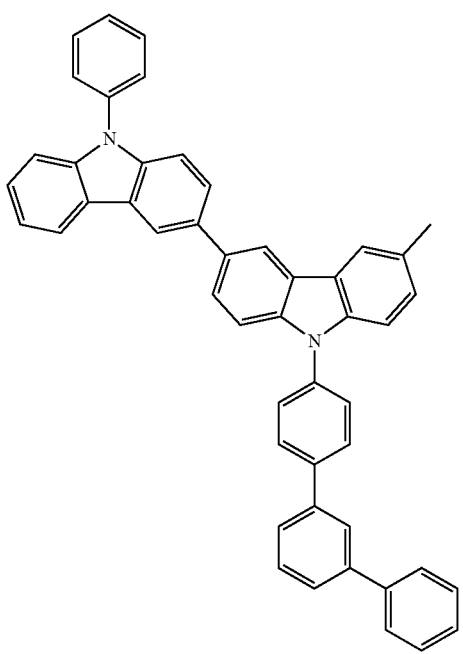

H1-190
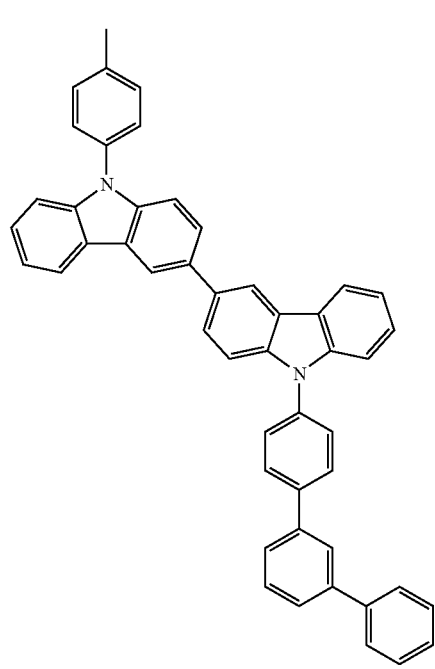
H1-192
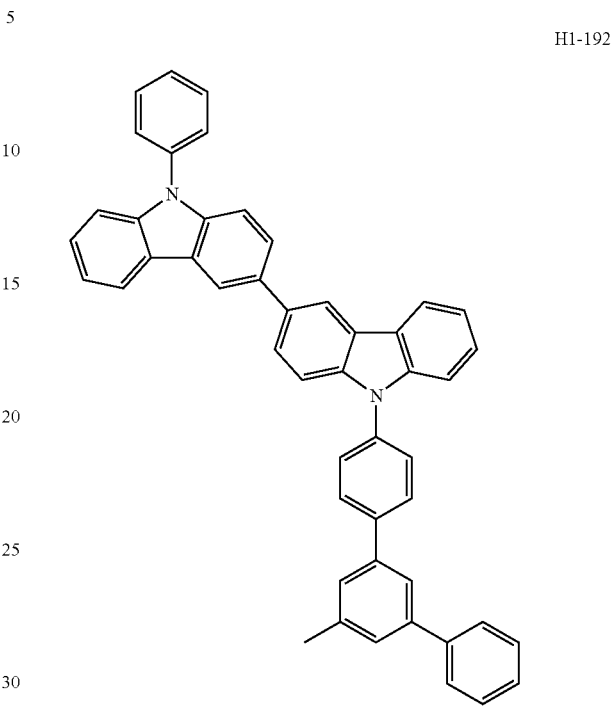
H1-191
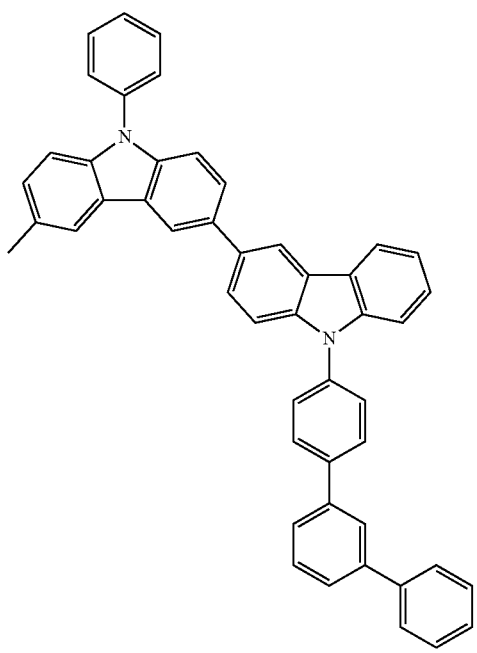
H1-193
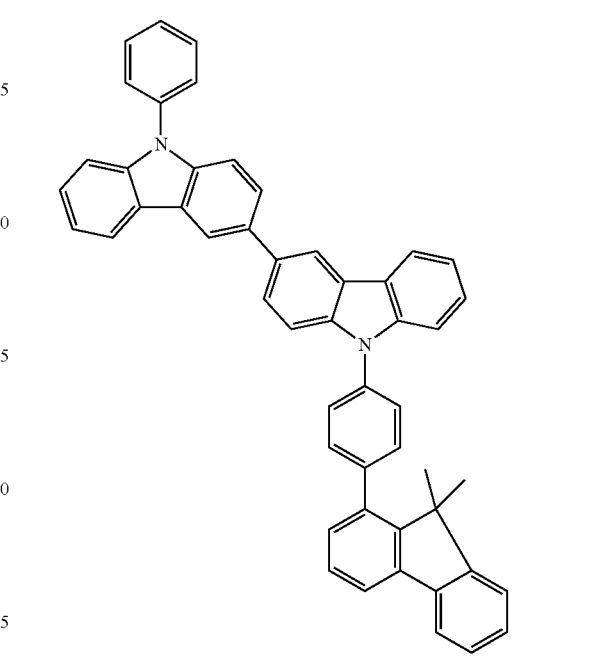

-continued
H1-194
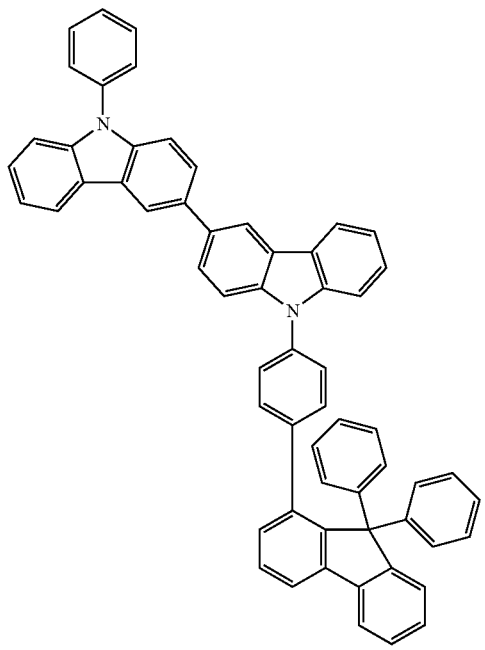
H1-195
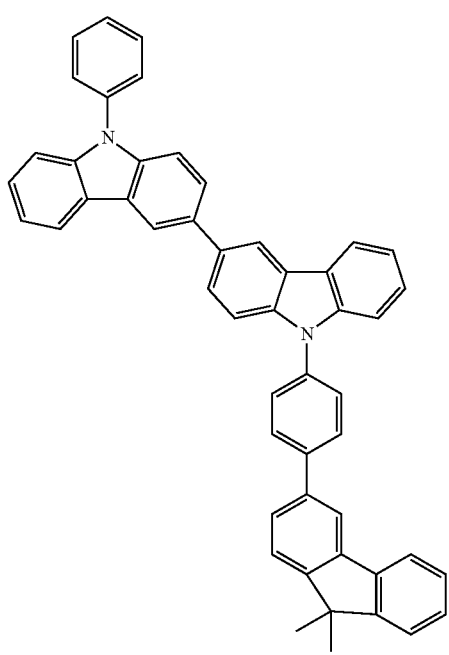
-continued
H1-196
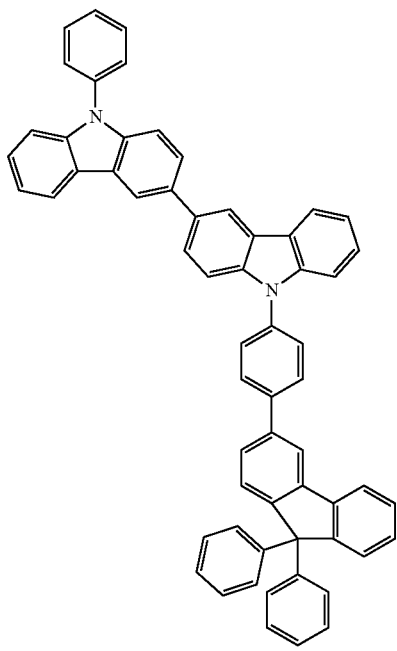
H1-197
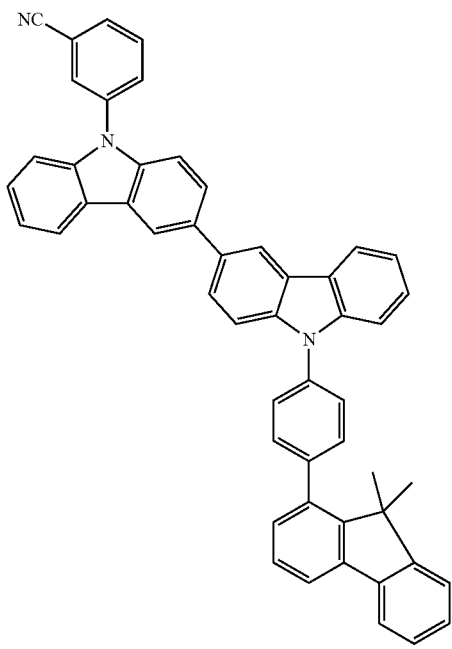

H1-198
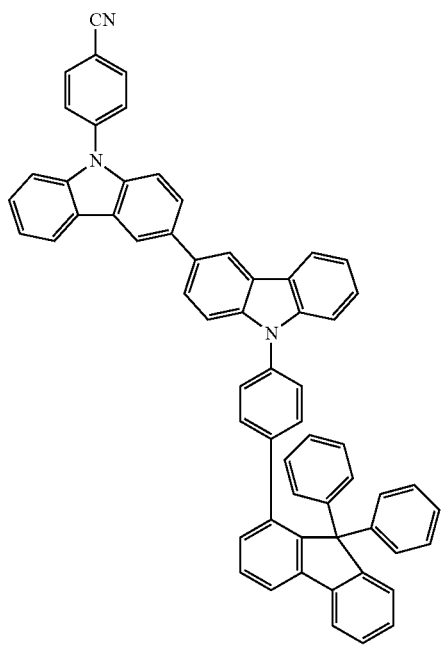
H1-199
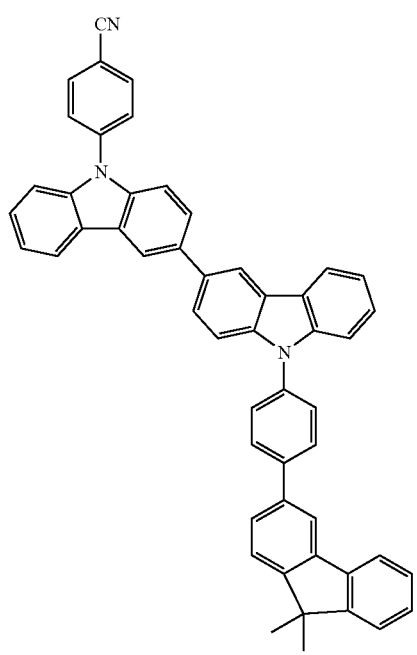
H1-200
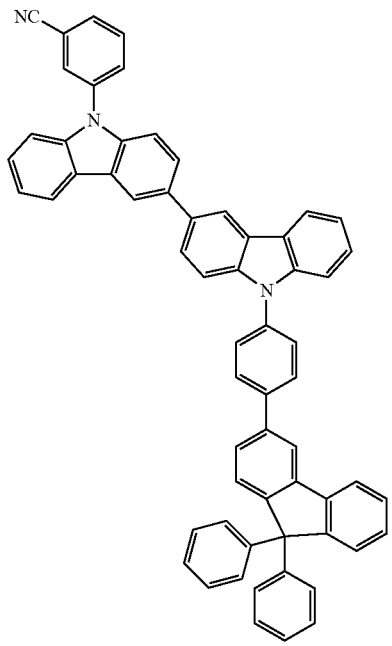
H1-201
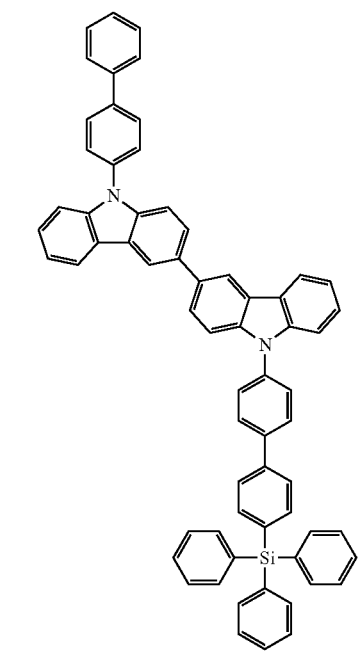

H1-202
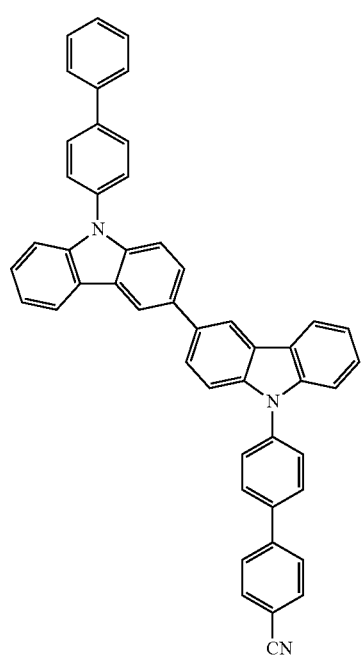
H1-204
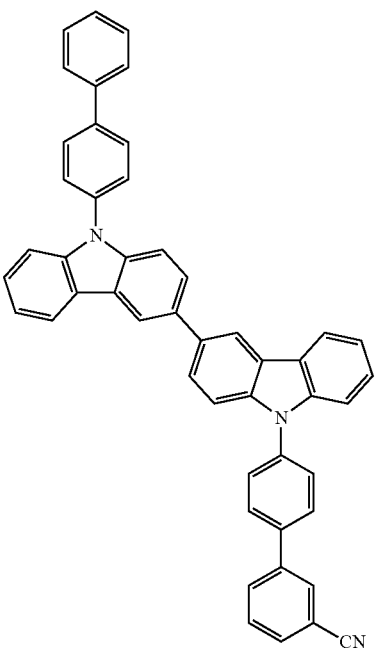
H1-203
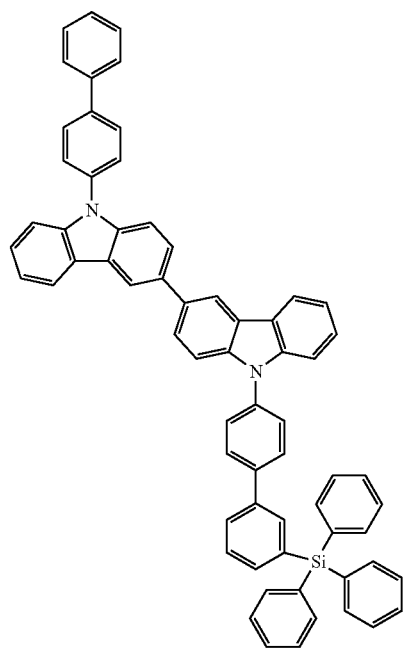
H1-205
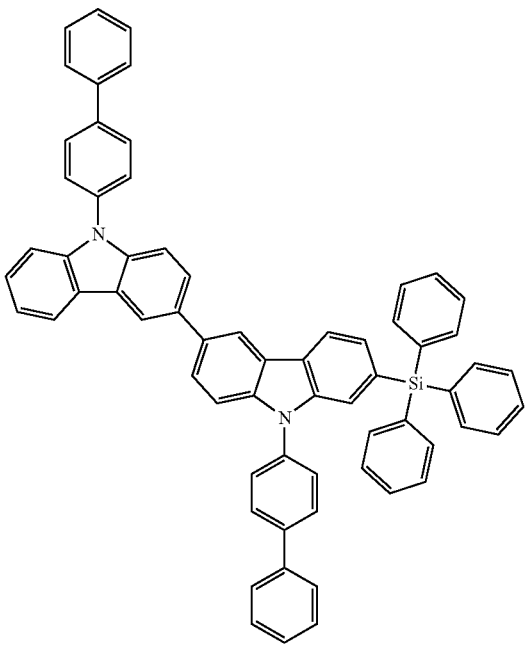

H1-206
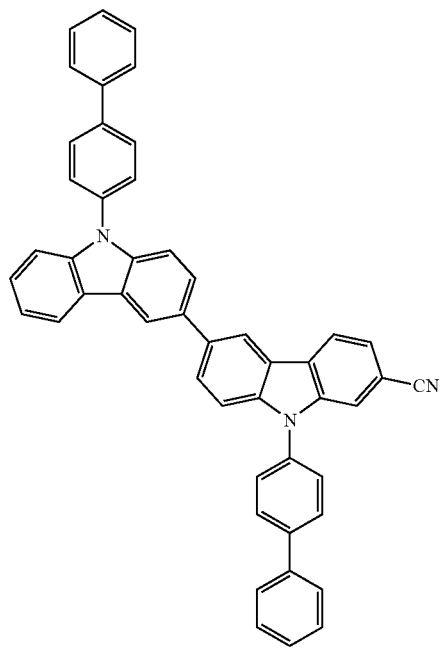
H1-208
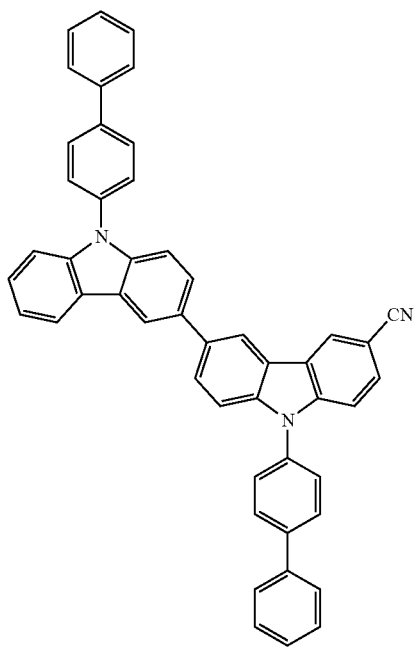
H1-207
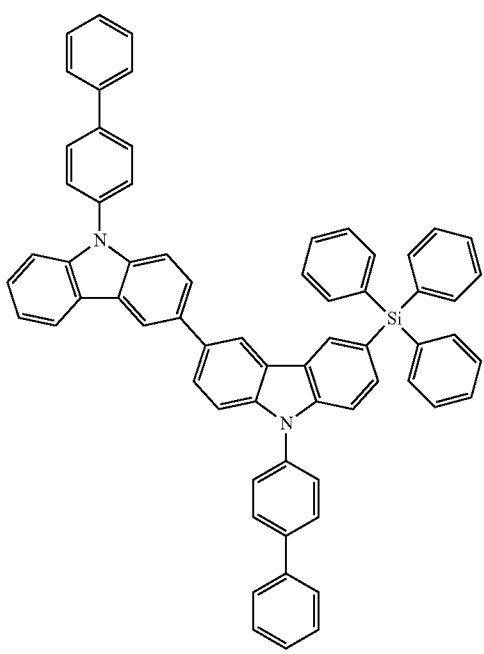
H1-209
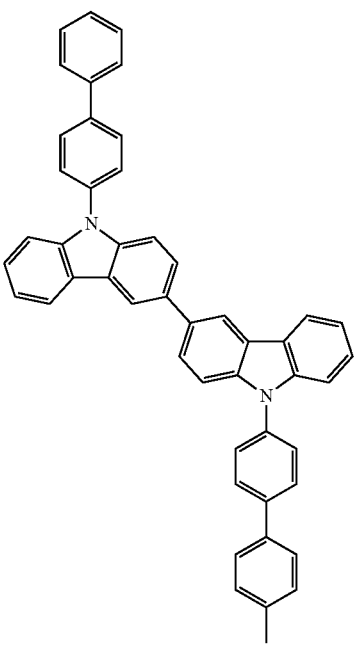

H1-210
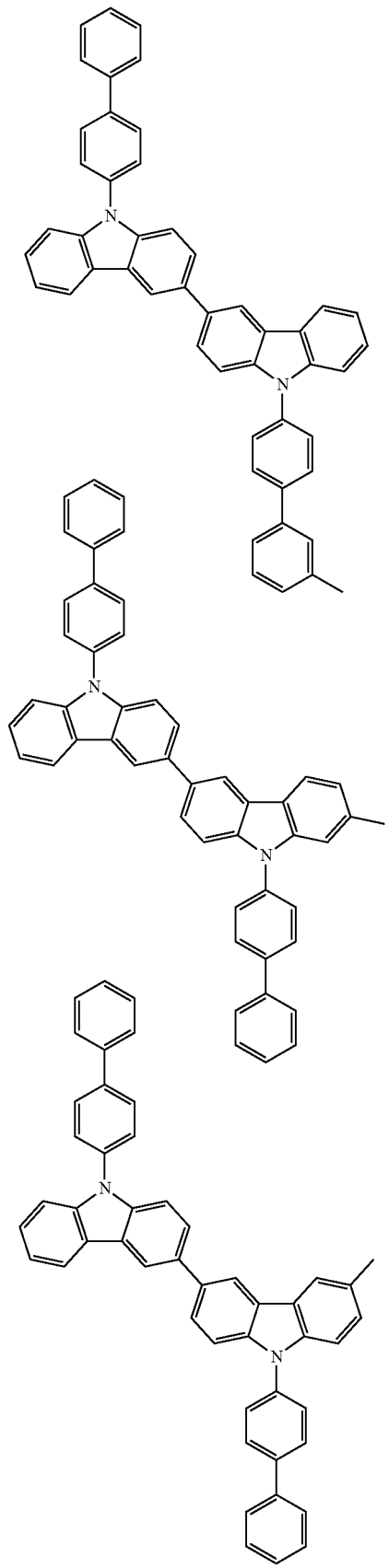
H1-211
H1-212
H1-213
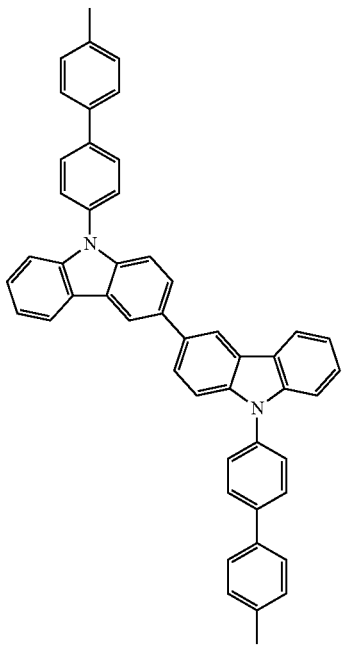
H1-214
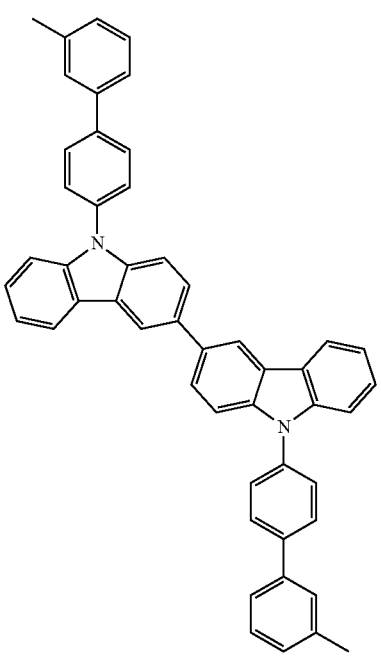

H1-215
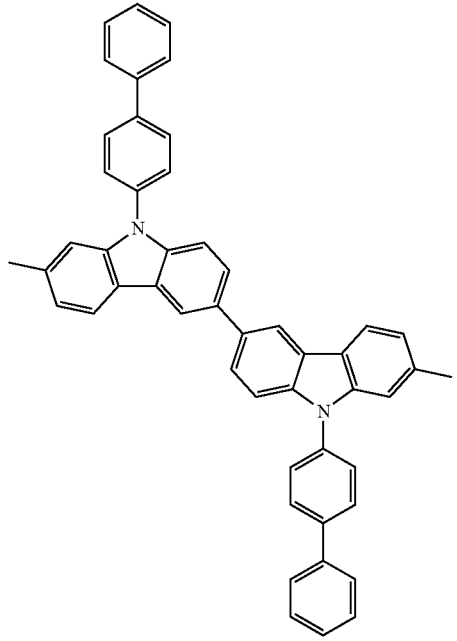
H1-216
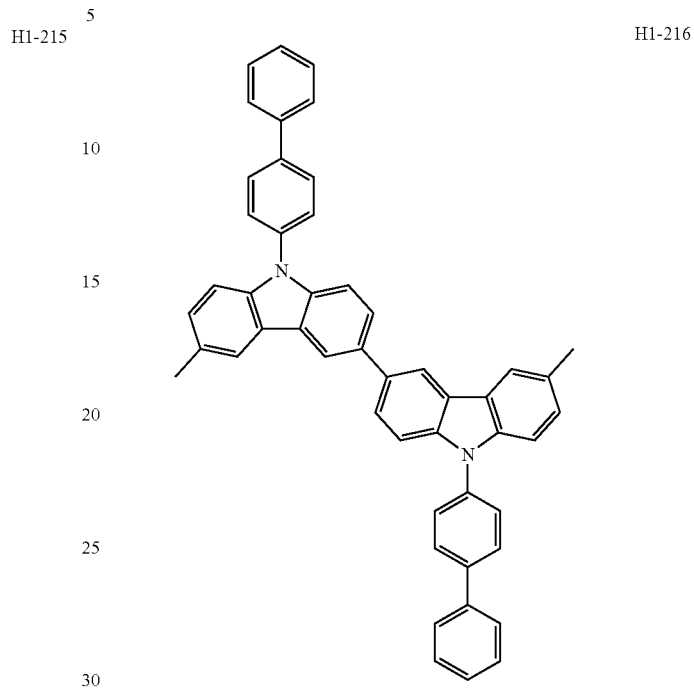
H1-217
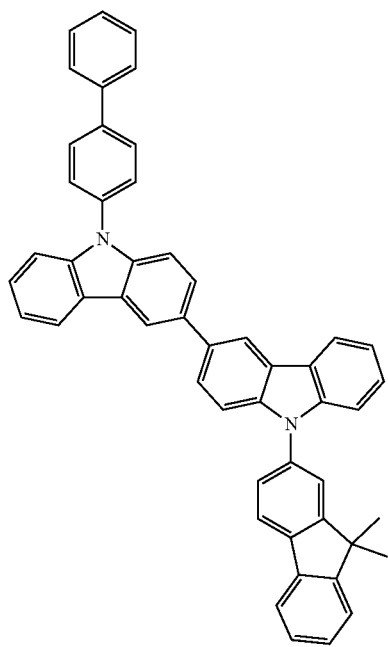
H1-218
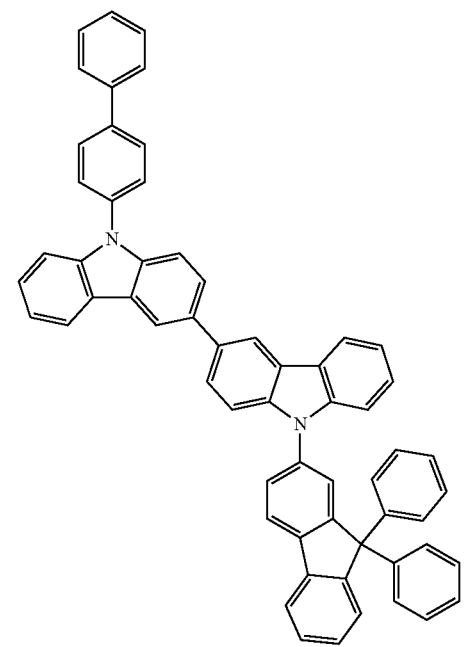

-continued
H1-219
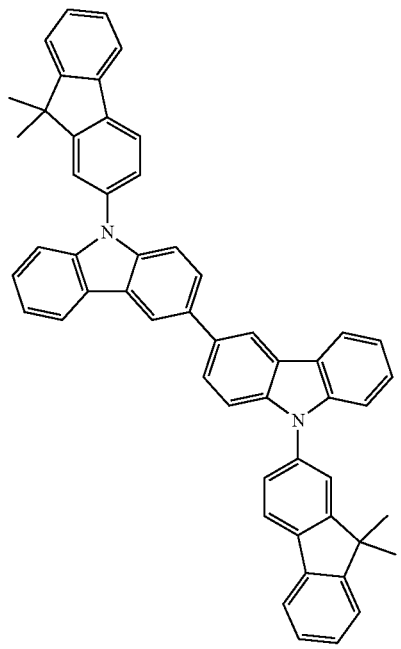
H1-220
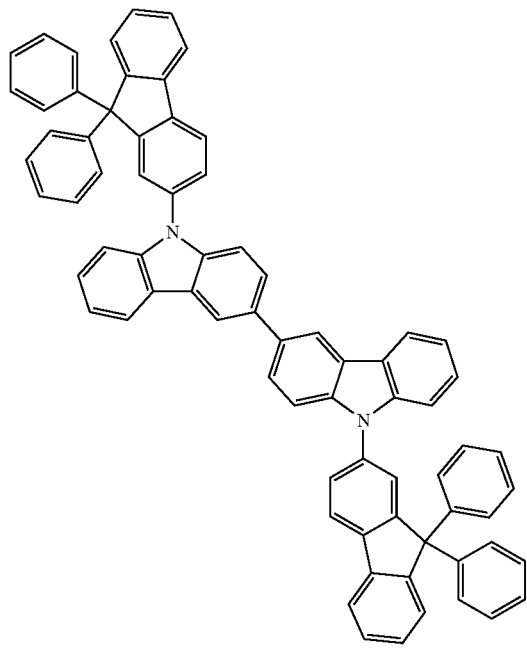
H1-221
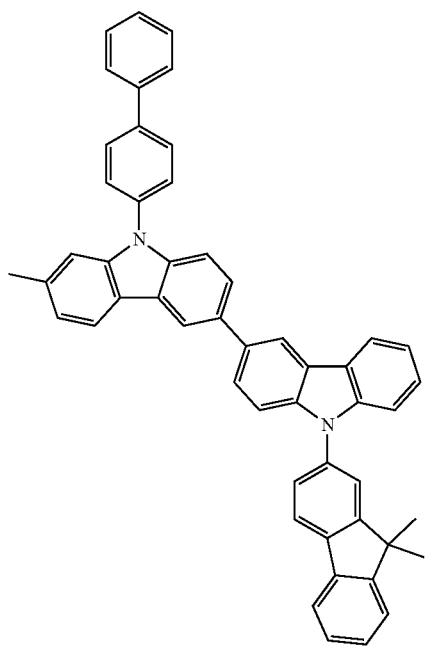
H1-222
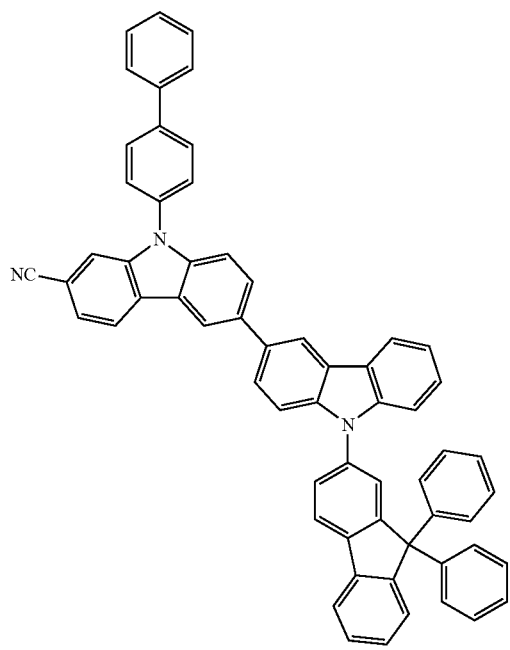

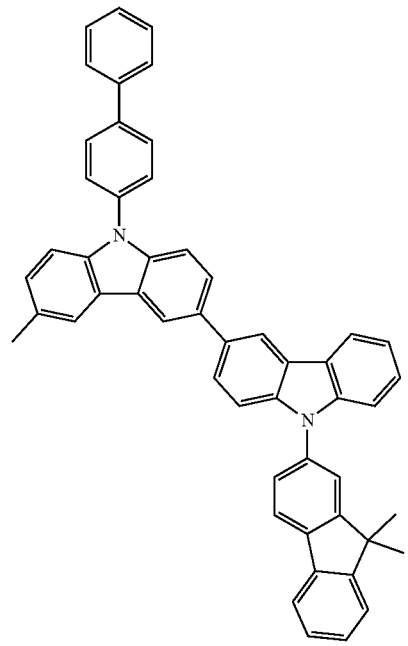
H1-223
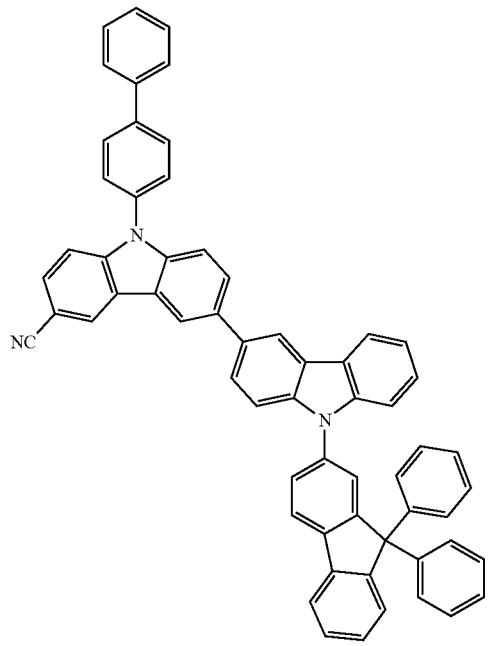
H1-224
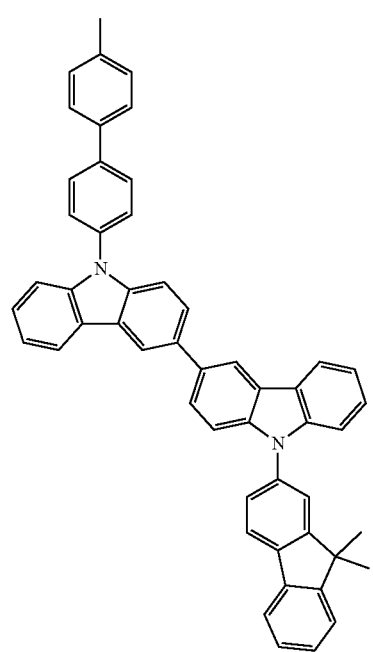
H1-225
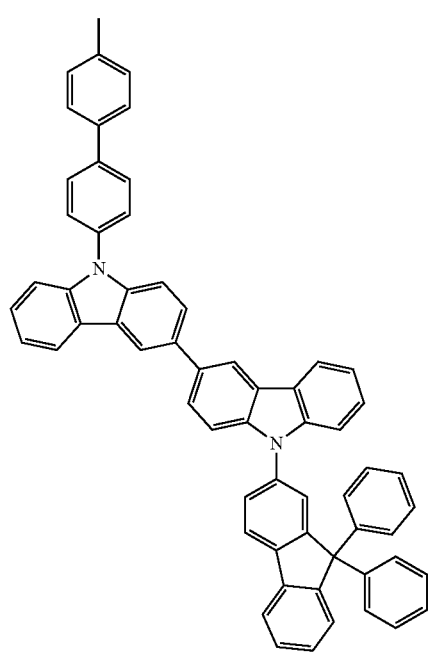
H1-226

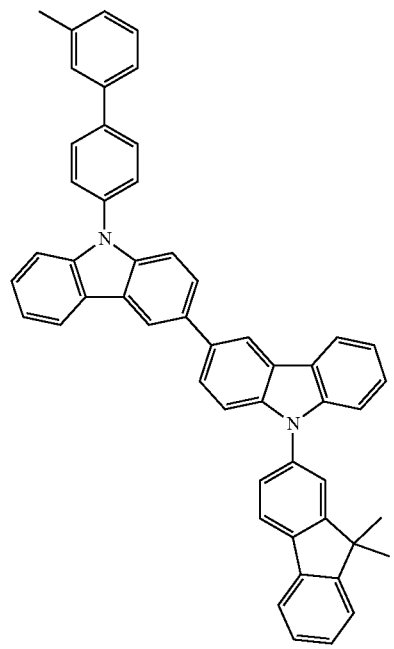
H1-227
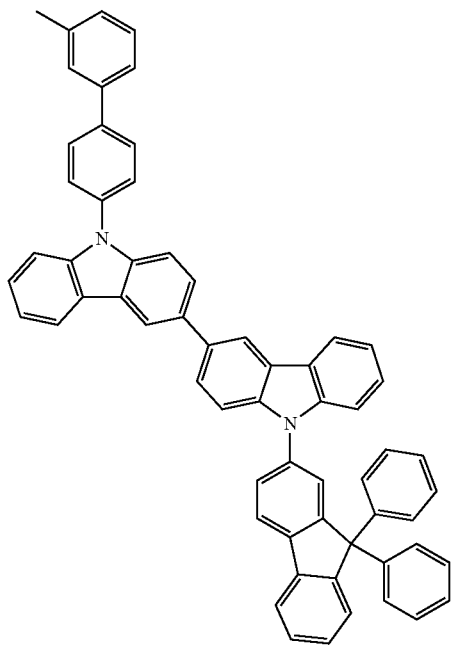
H1-228
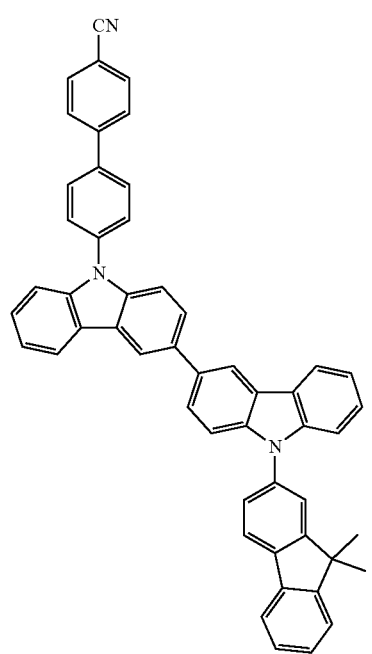
H1-229
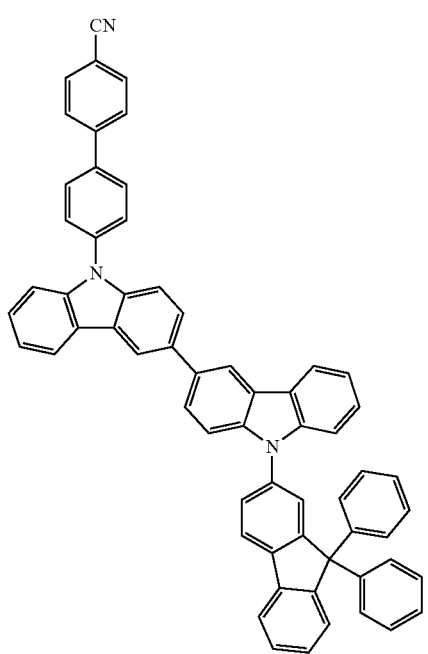
H1-230

H1-231 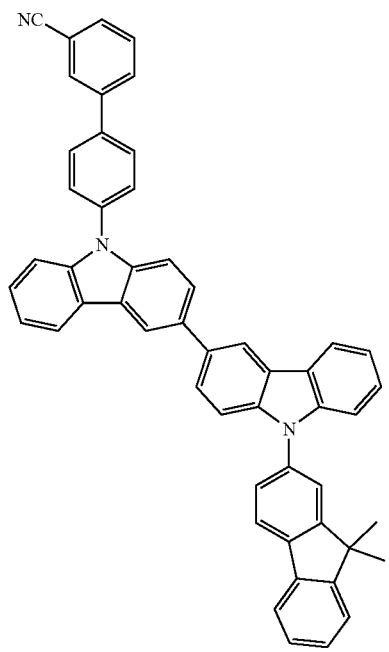
H1-232 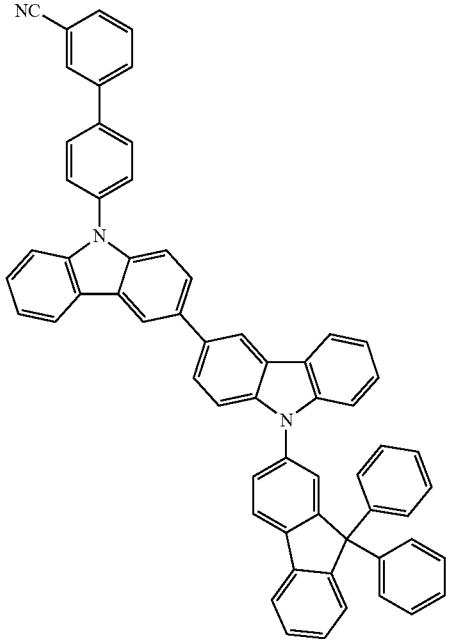
H1-233 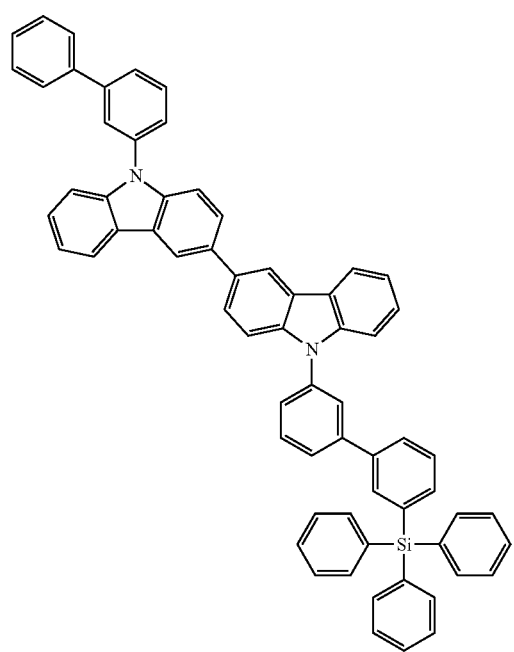
H1-234 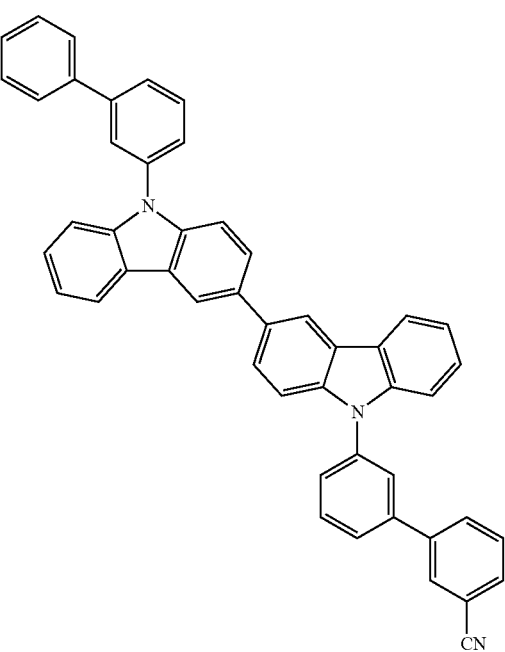

H1-235 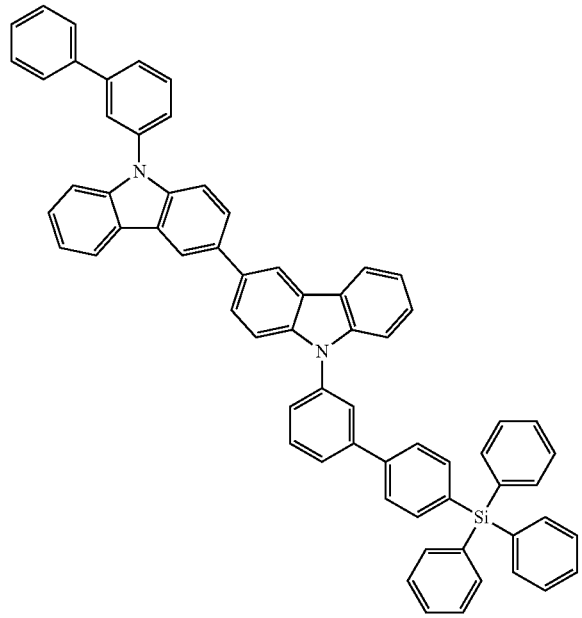
H1-236 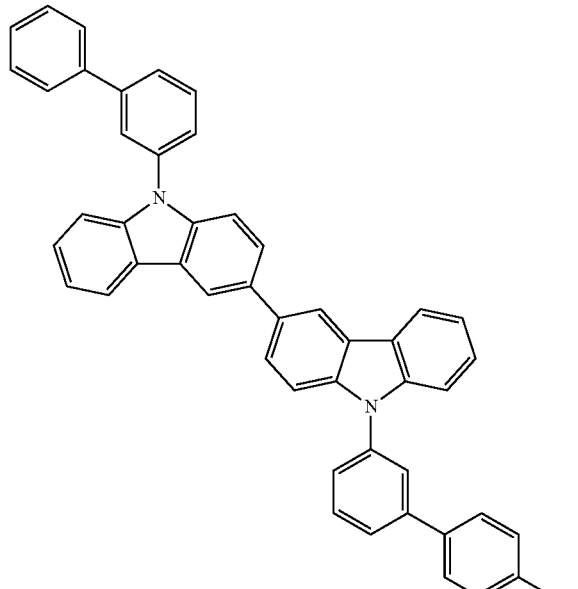
H1-237 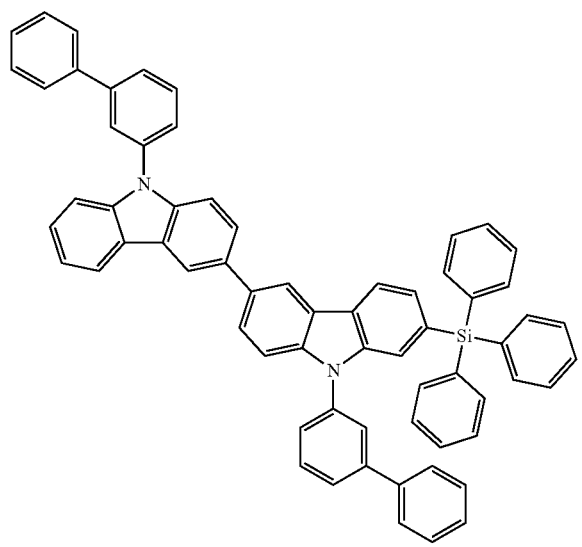
H1-238 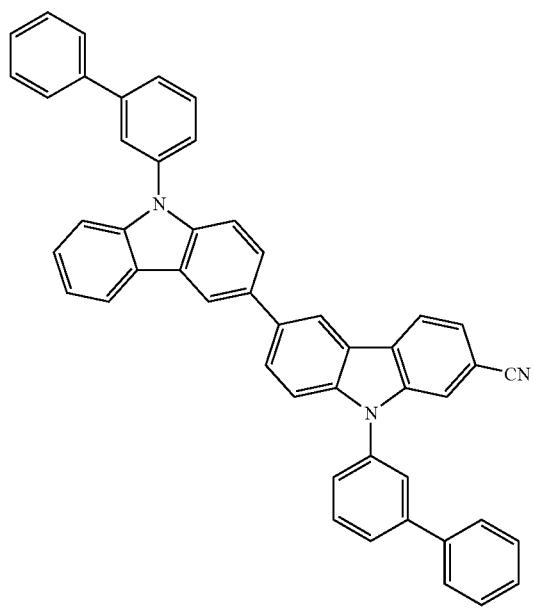

H1-239
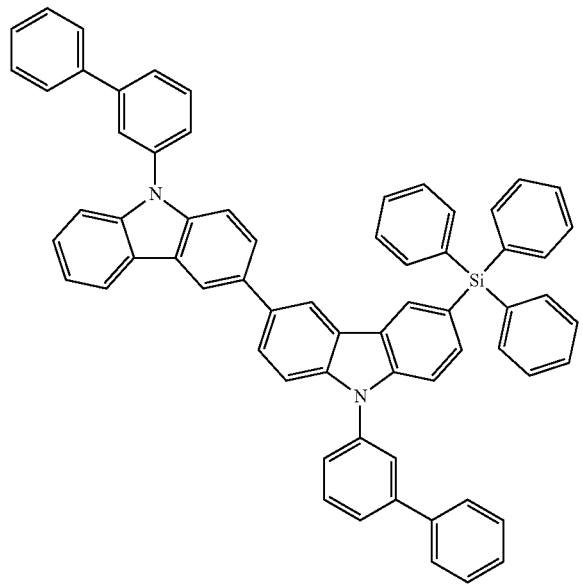
H1-240
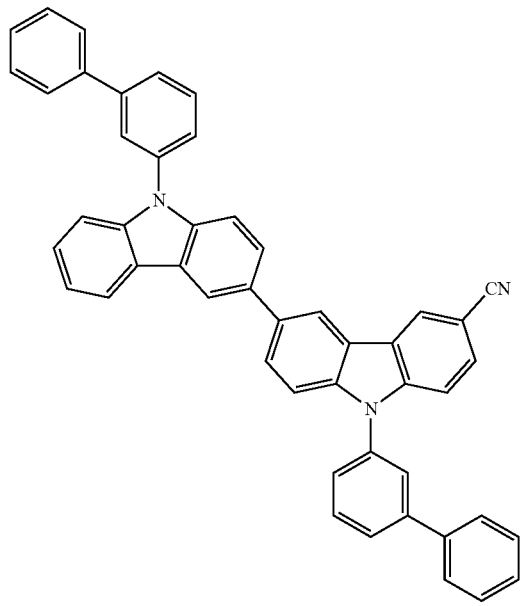
H1-241
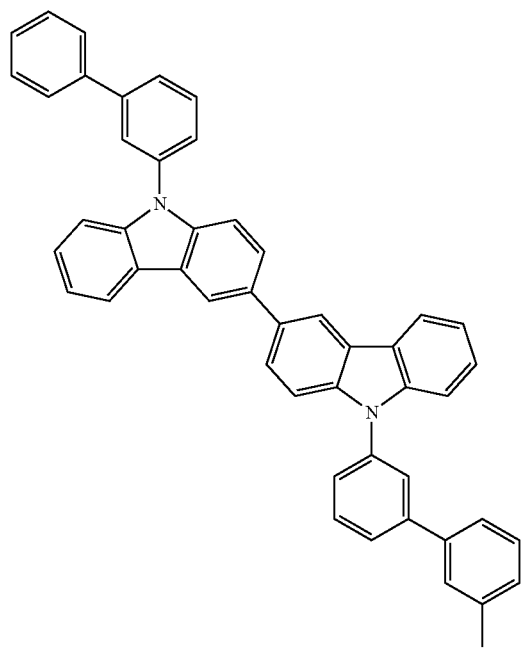
H1-242
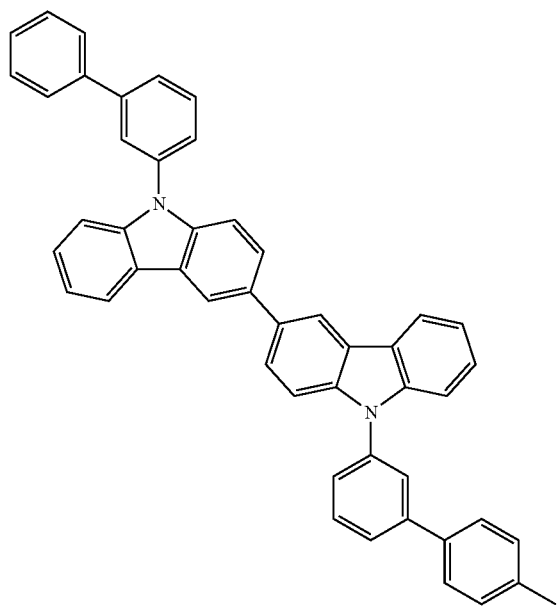

-continued
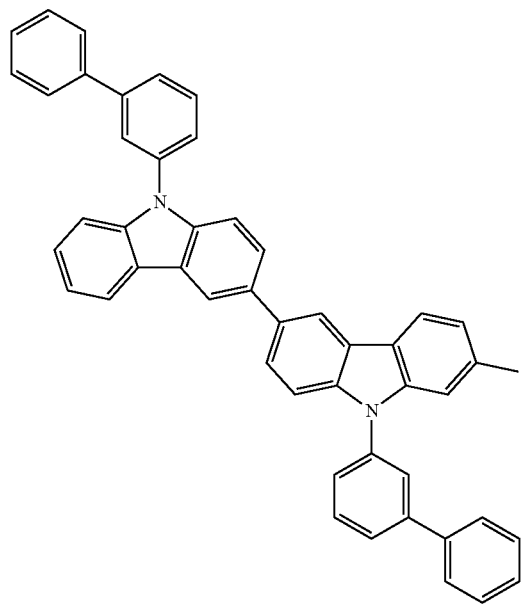
H1-243
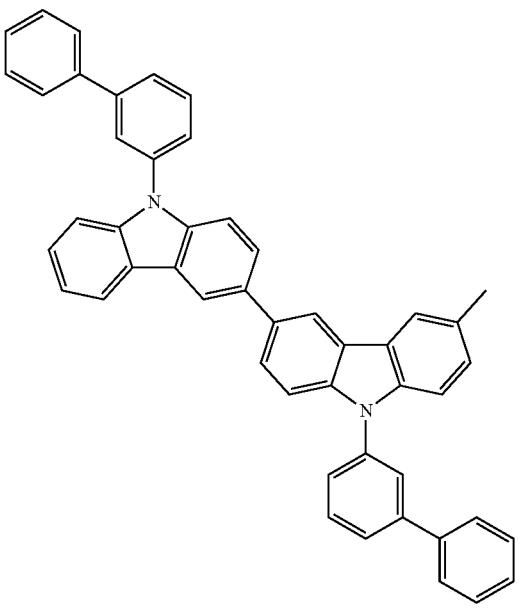
H1-244
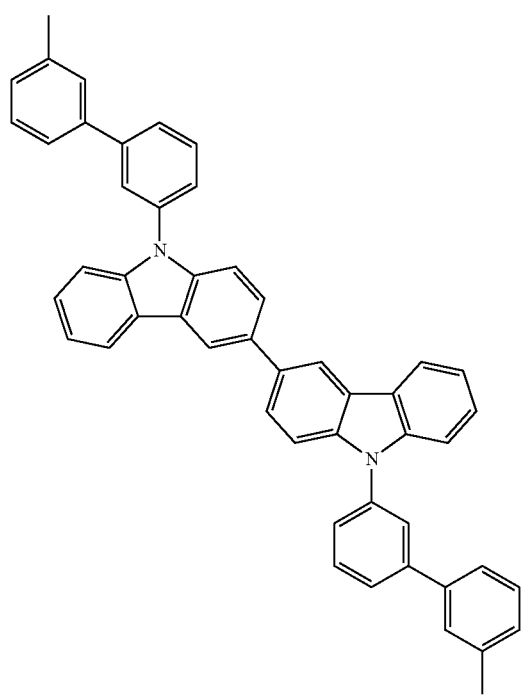
H1-245
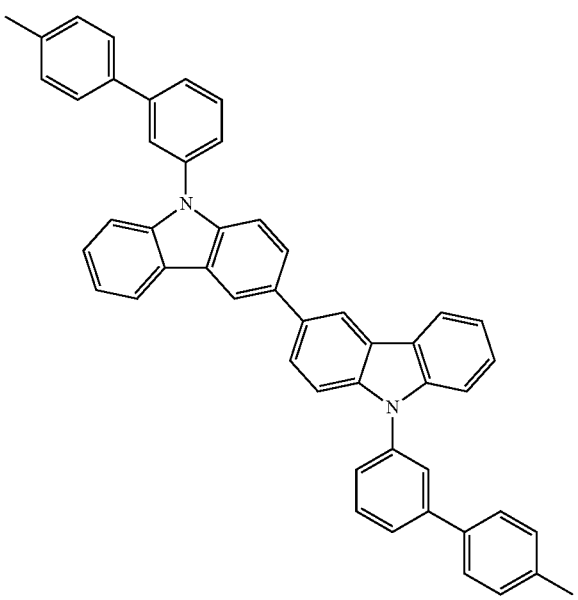
H1-246

H1-247 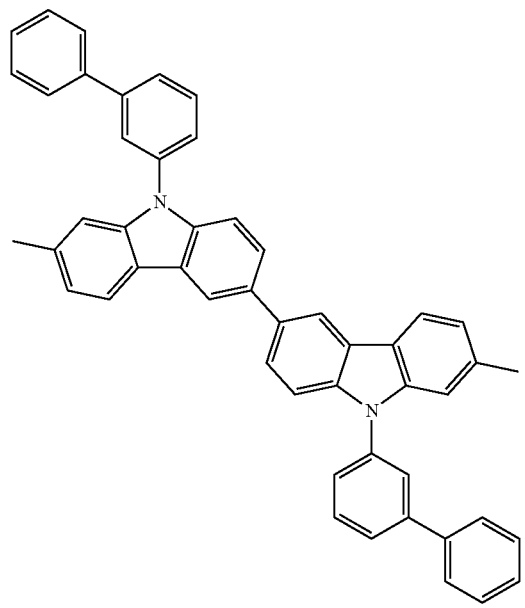
H1-248 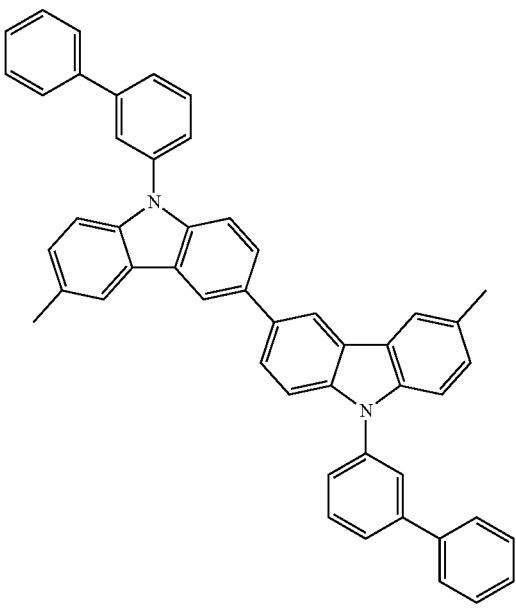
H1-249 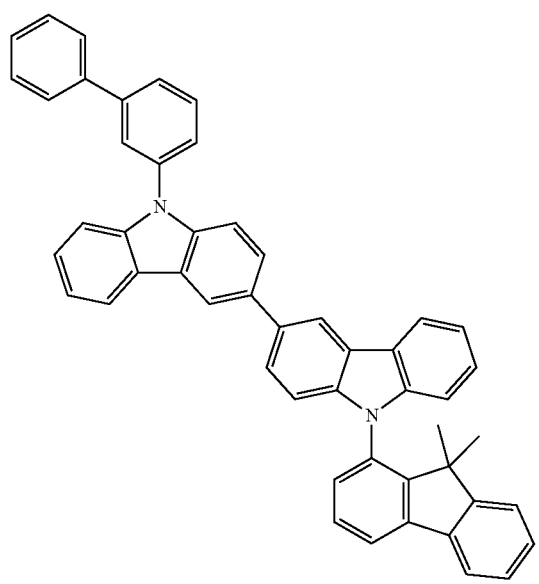
H1-250 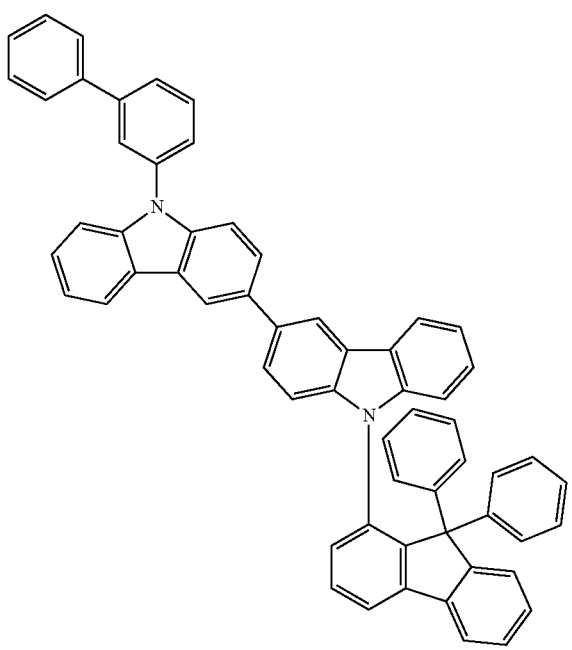

H1-251
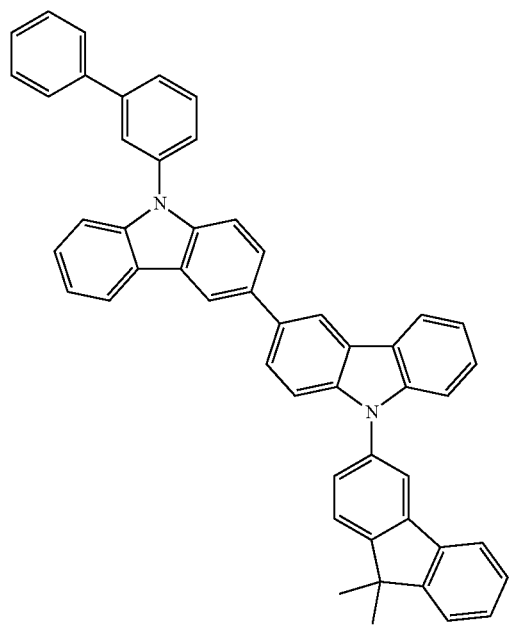
H1-252
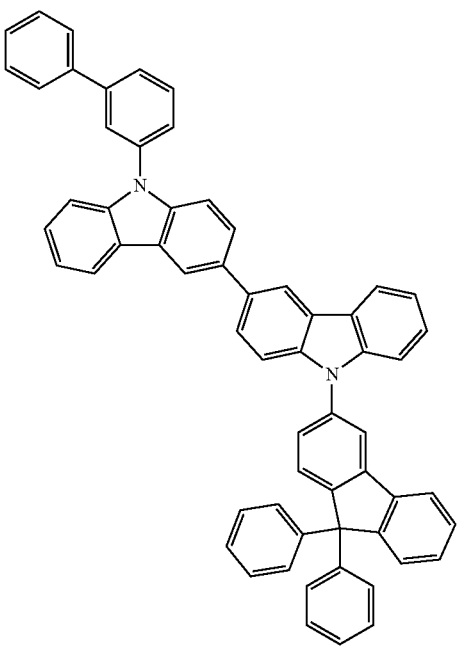
H1-253
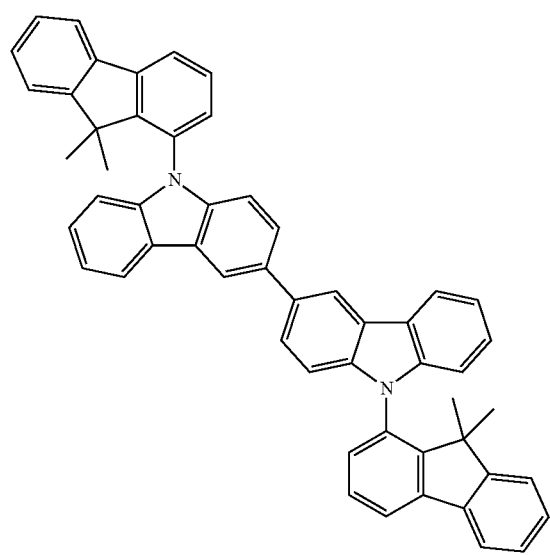
H1-254
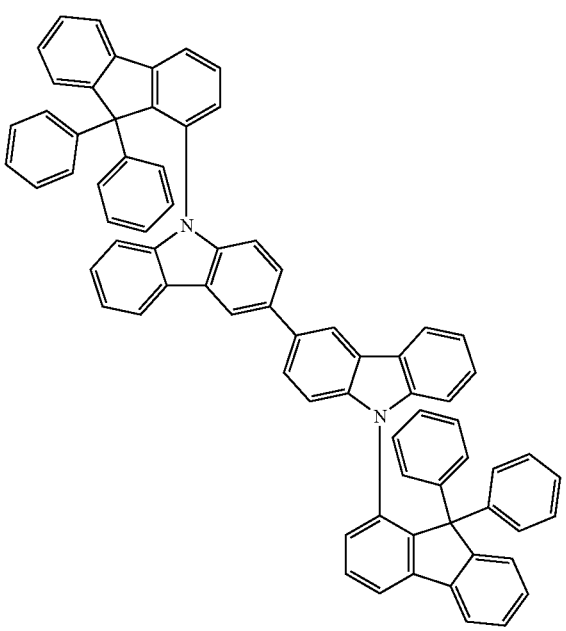

H1-255
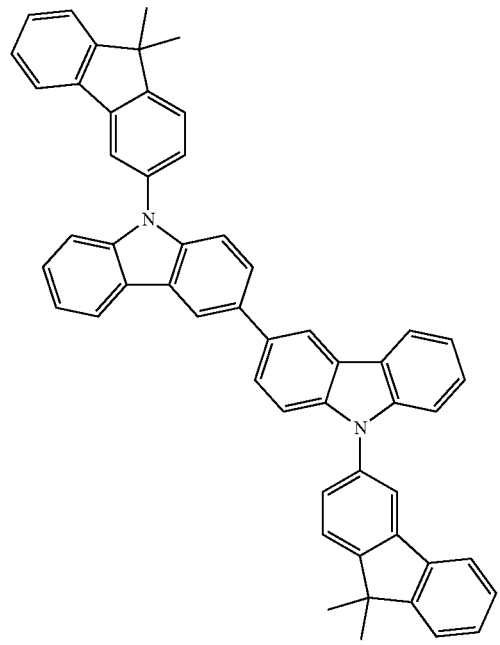
H1-256
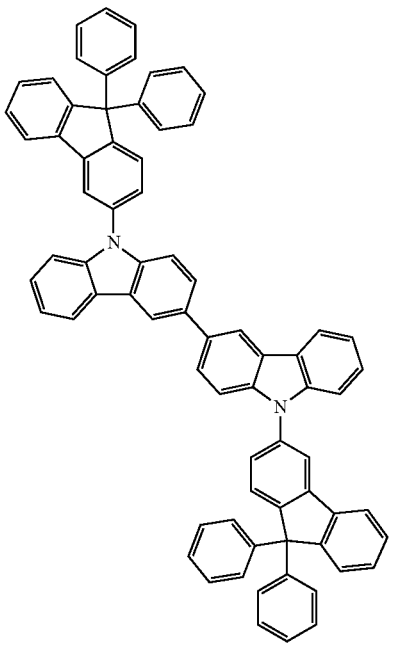
H1-257
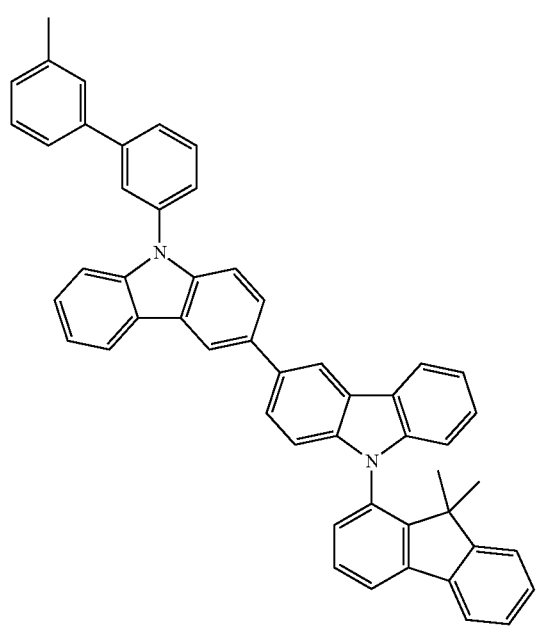
H1-258
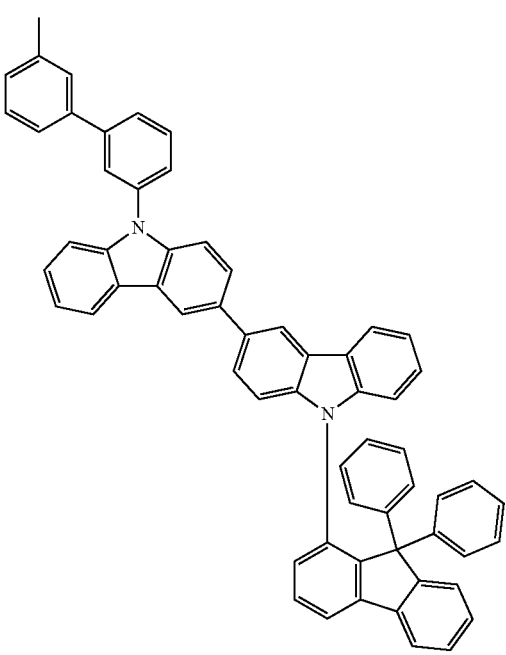

-continued
H1-259
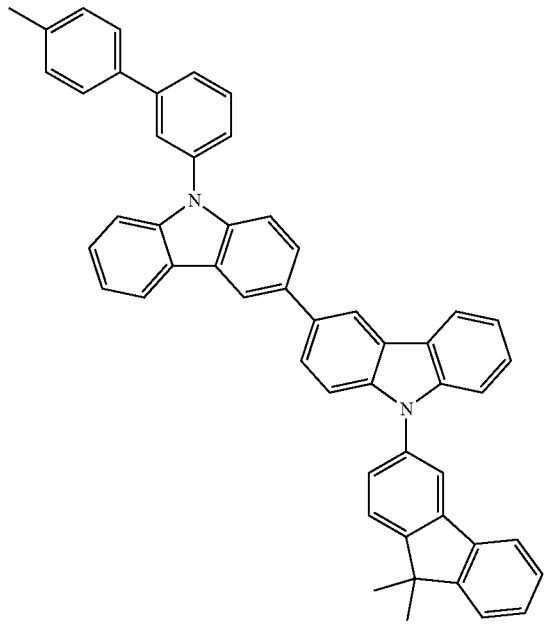
H1-260
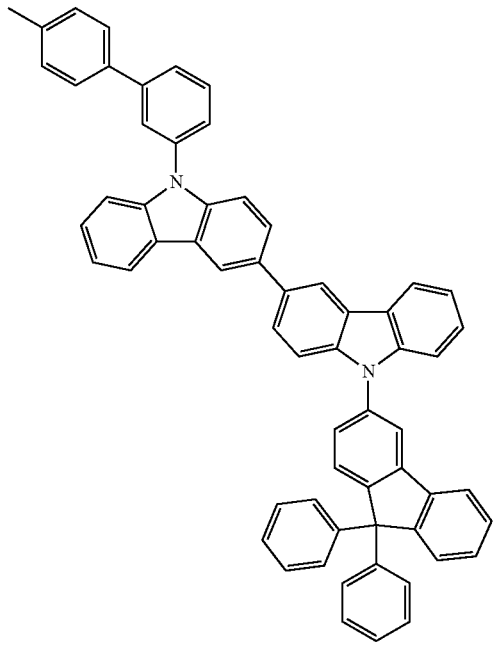
H1-261
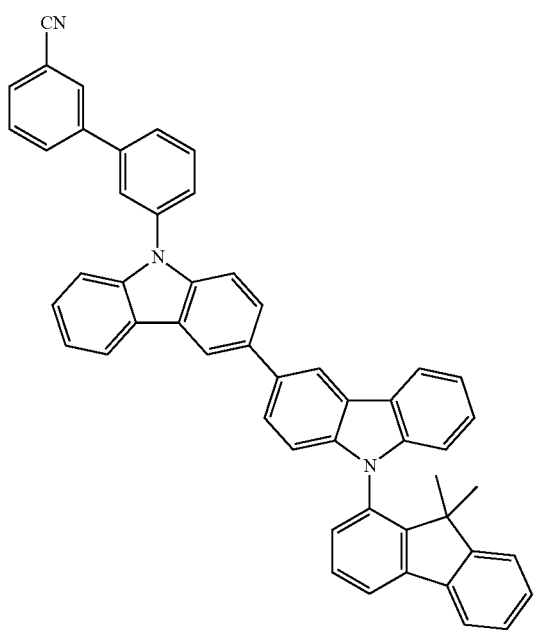
H1-262
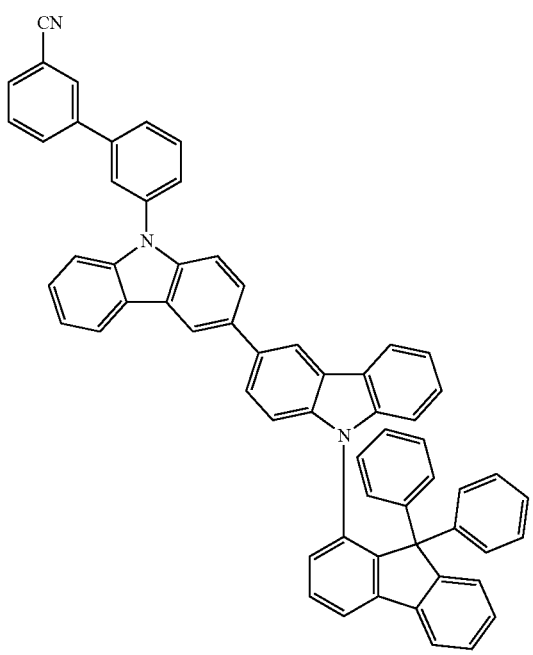

H1-263
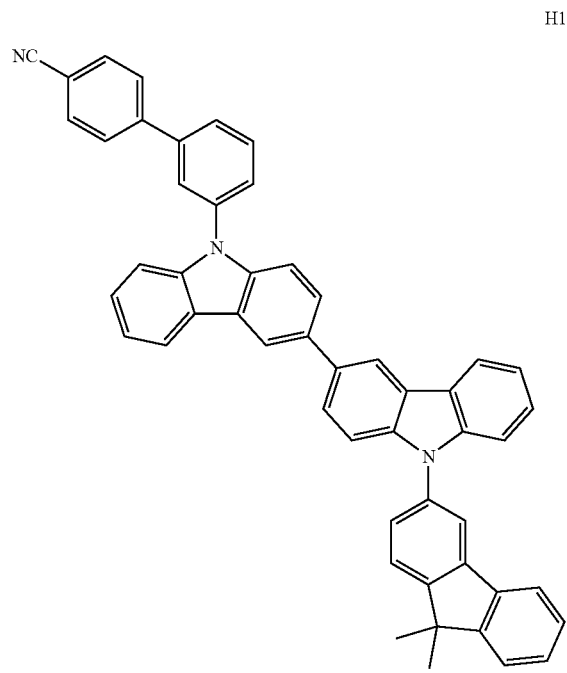
H1-264
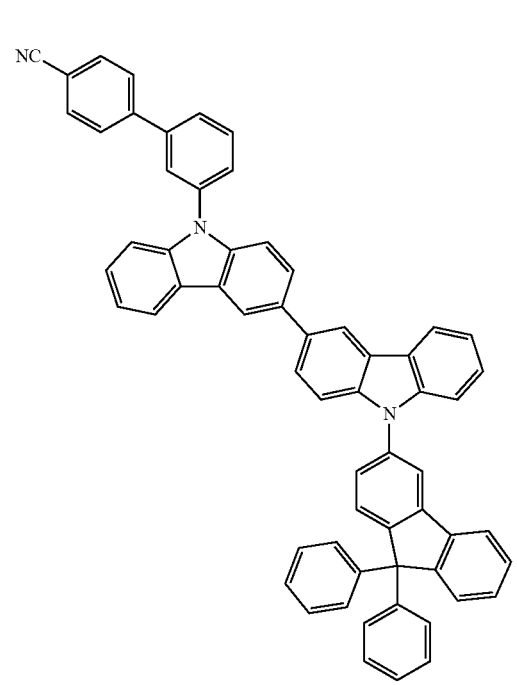
H1-265
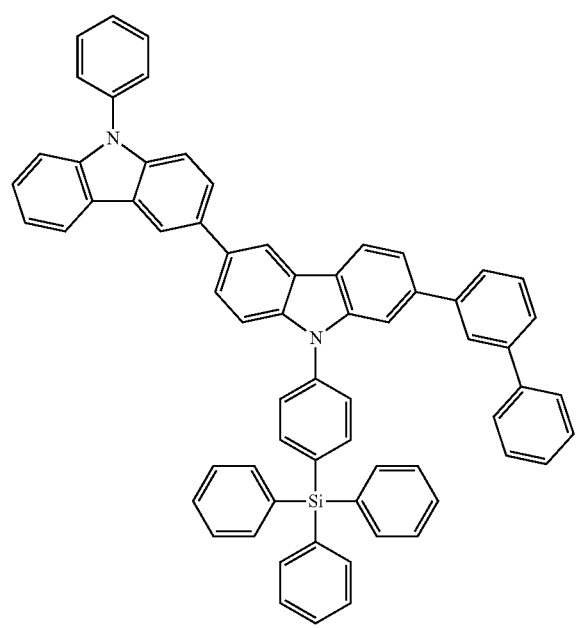
H1-266
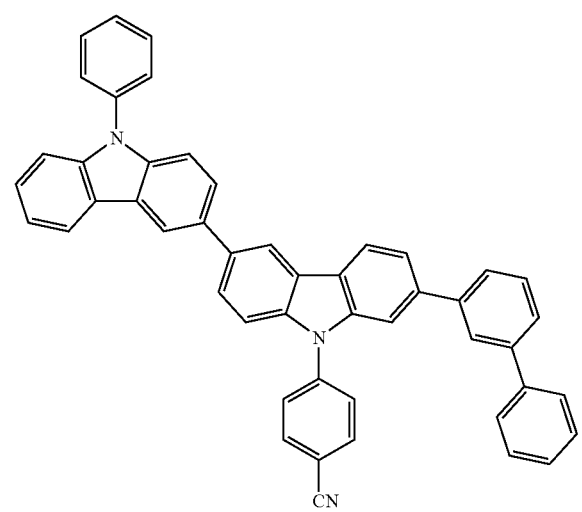

-continued
H1-267
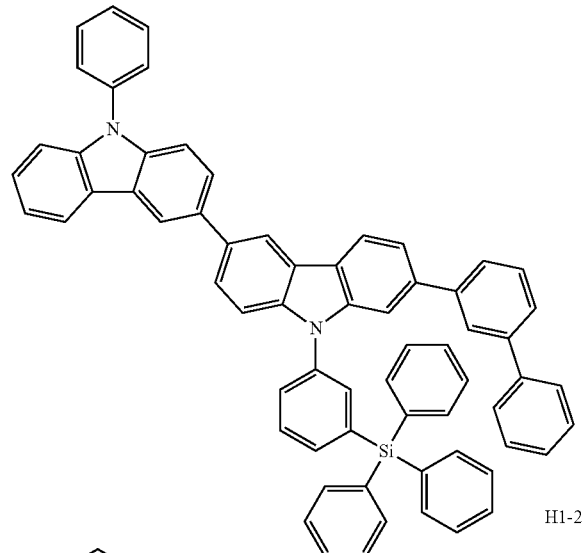
H1-268
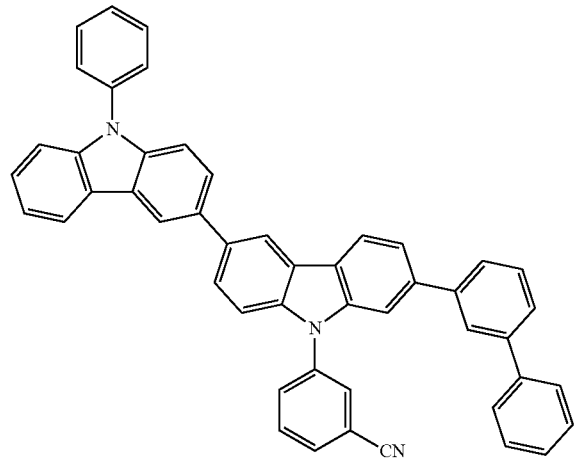
H1-269
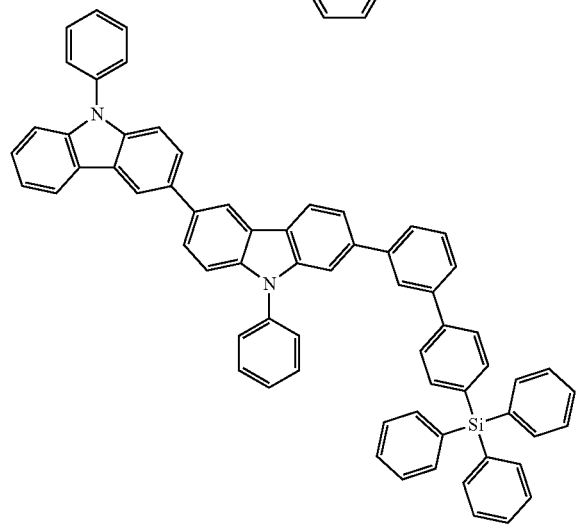
H1-270
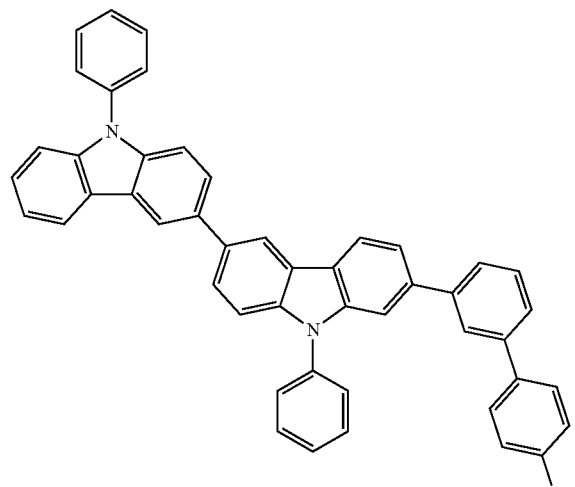
H1-271
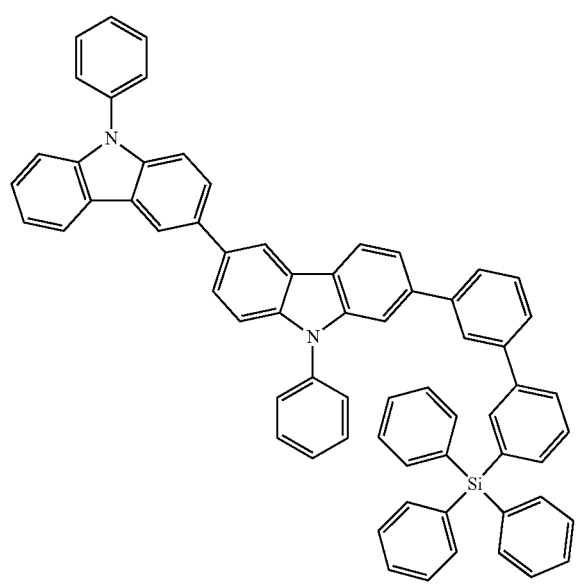
H1-272
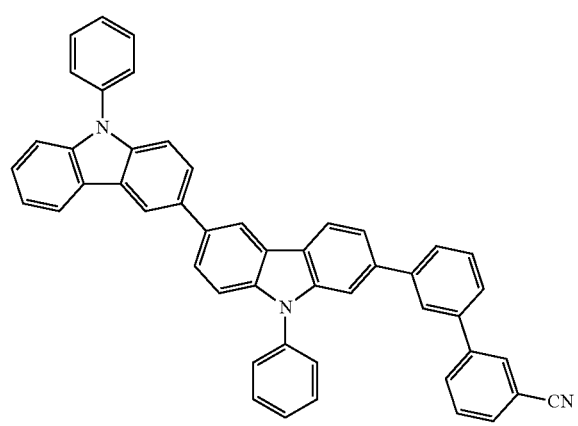

H1-273
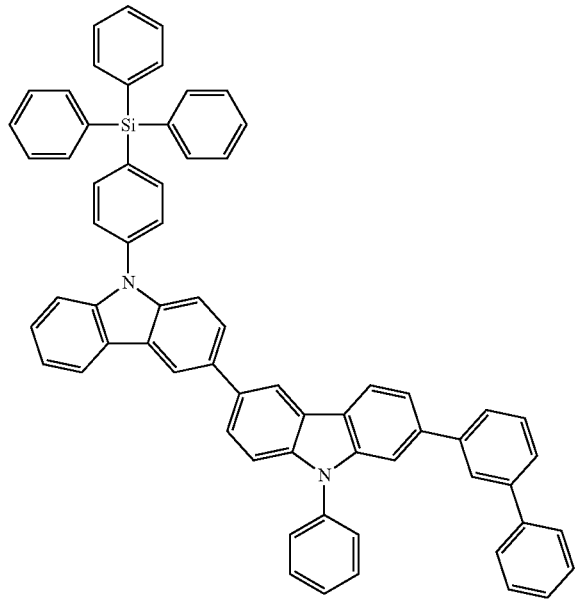
H1-274
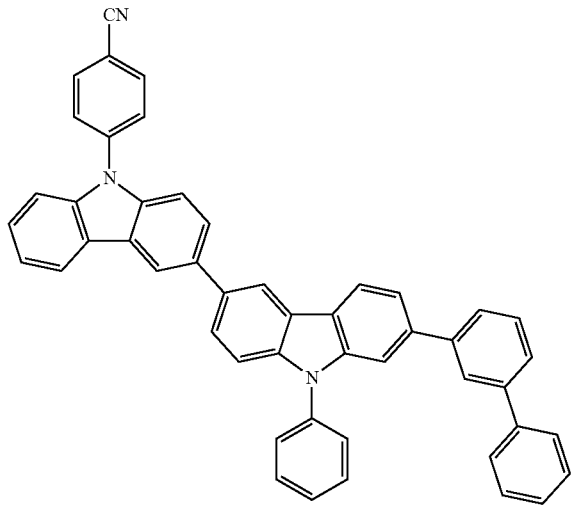
H1-275
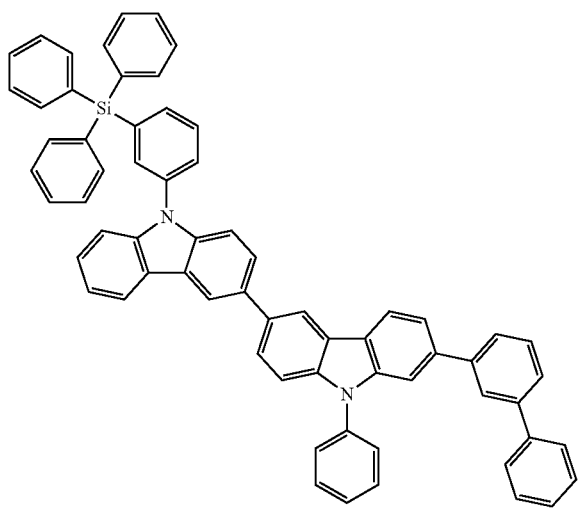
H1-276
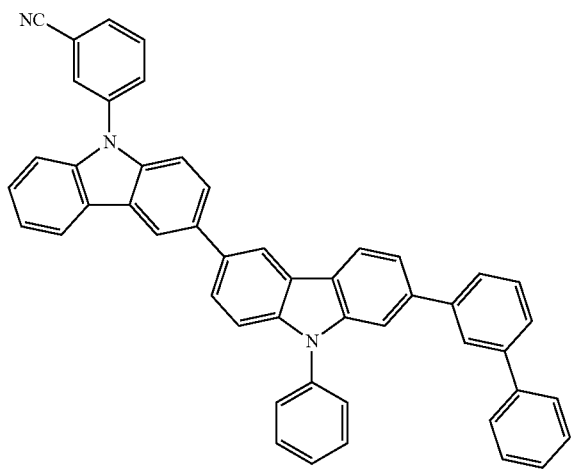
H1-277
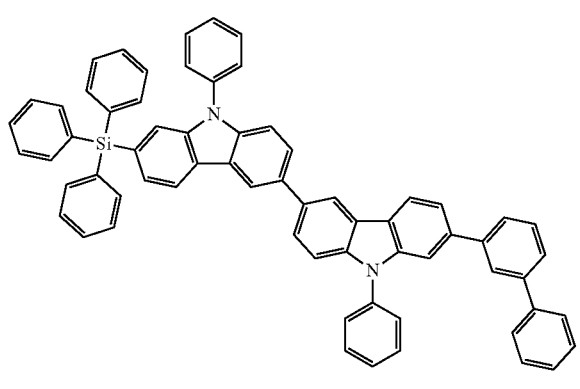
H1-278
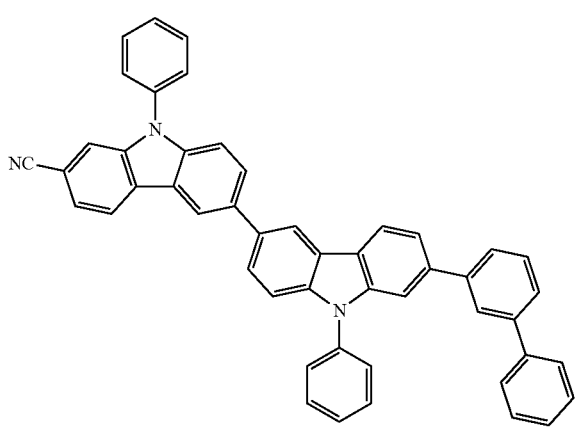

-continued
H1-279
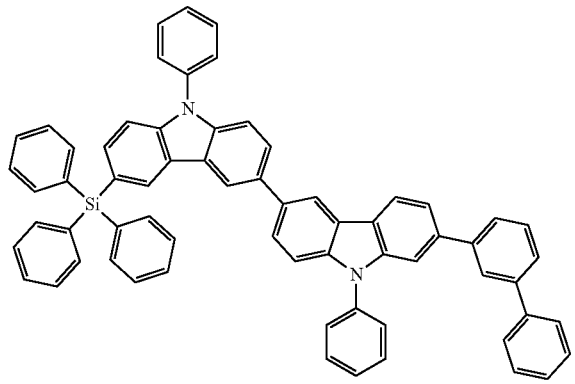
H1-280
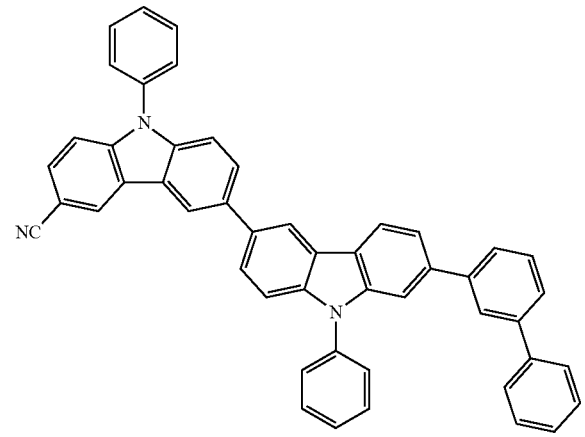
H1-281
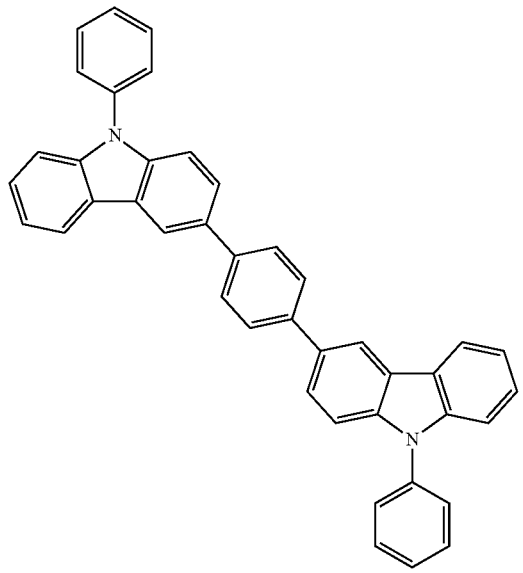
H1-282
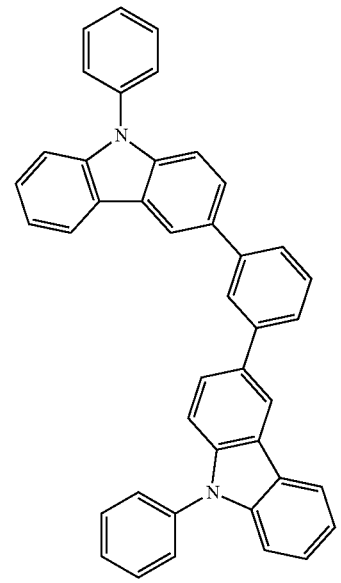
H1-283
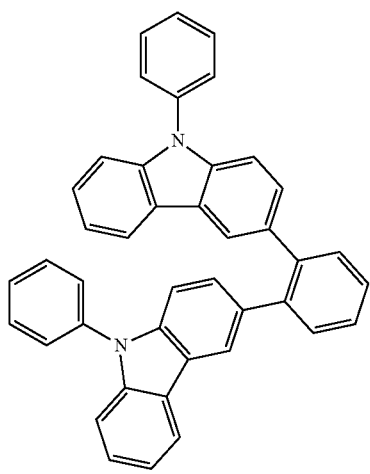
H1-284
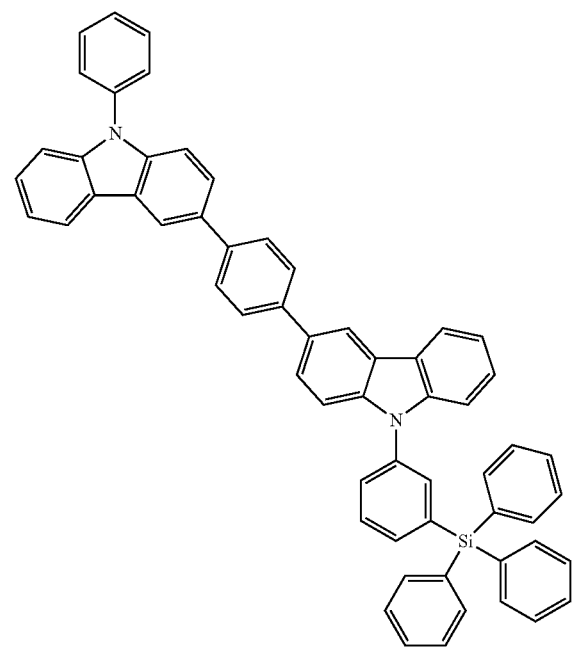

H1-285
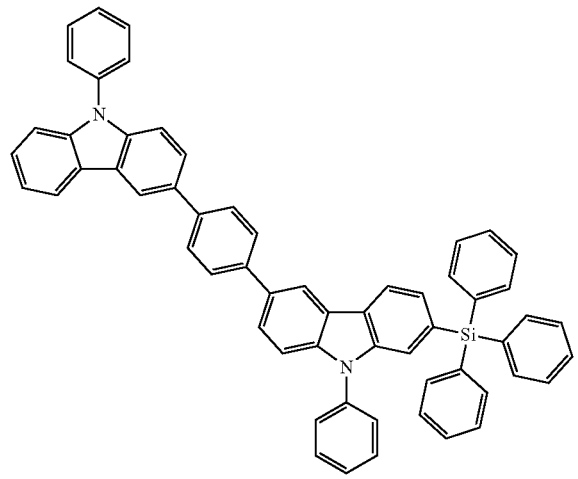
H1-286
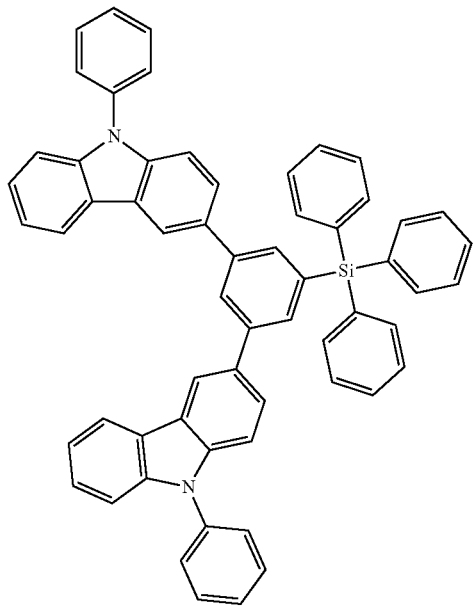
H1-287
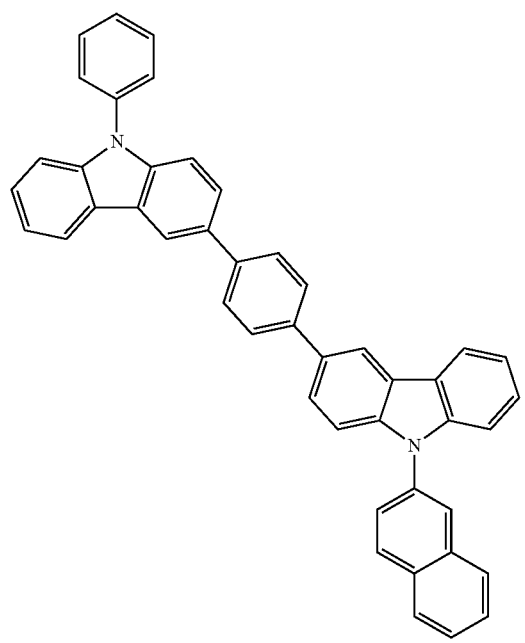
H1-288
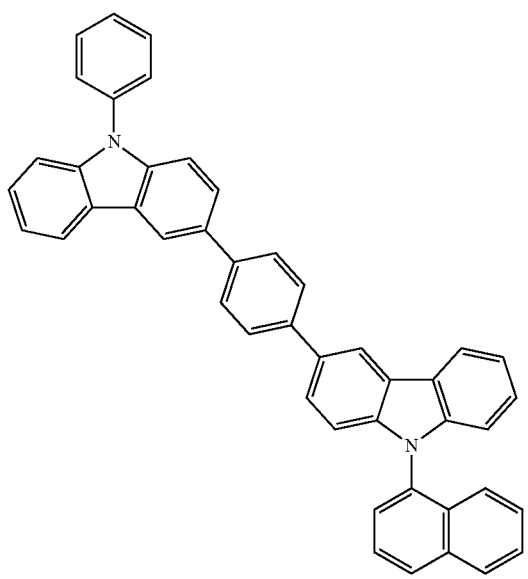

H1-289
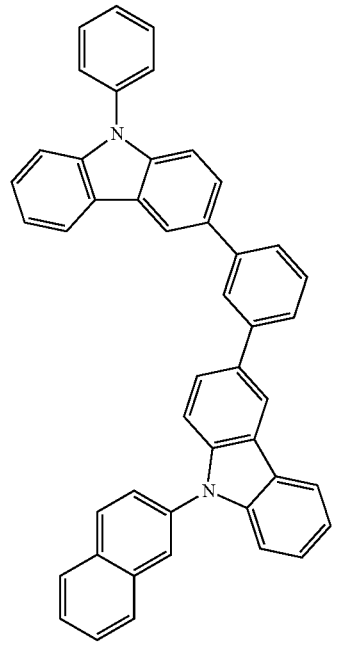
H1-290
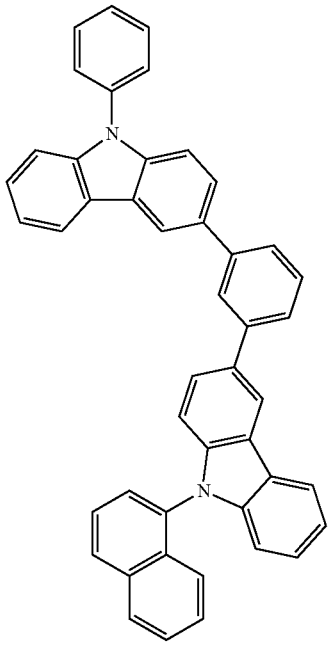
H1-291
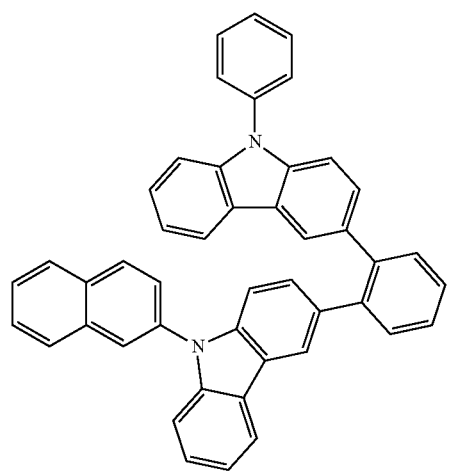
H1-292
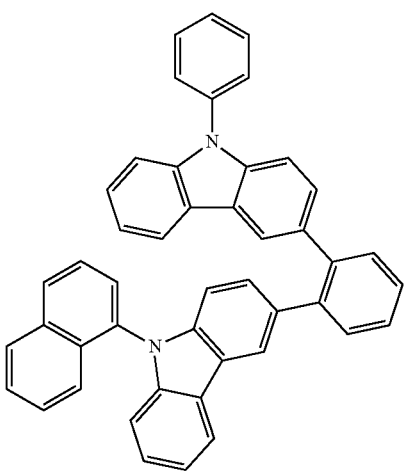

H1-293
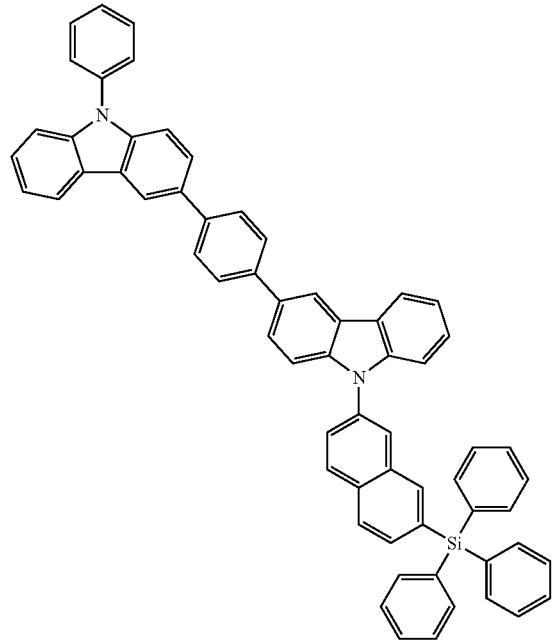
H1-294
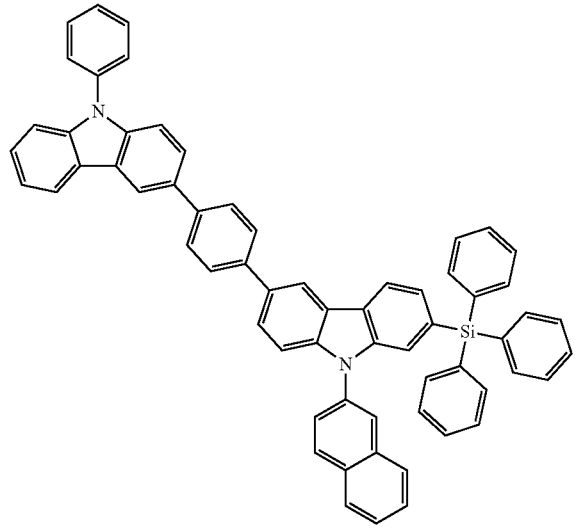
H1-295
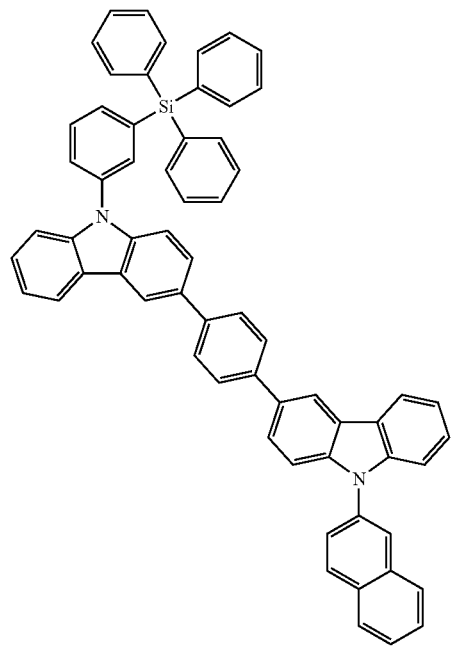
H1-296
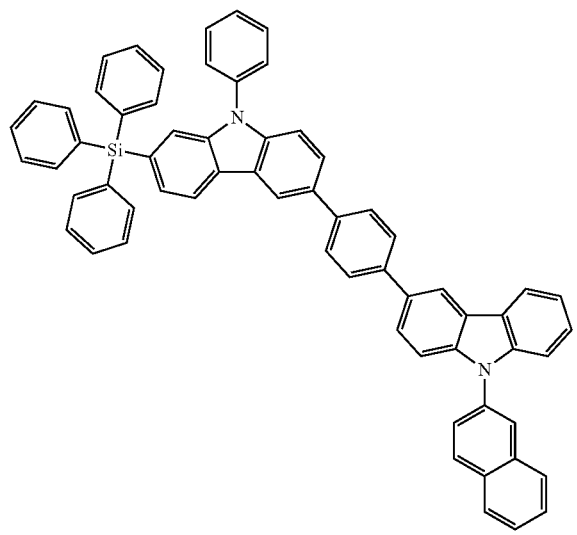

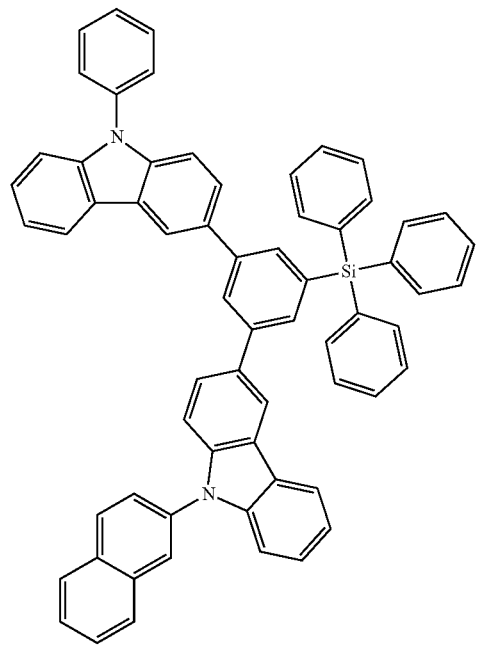
H1-297
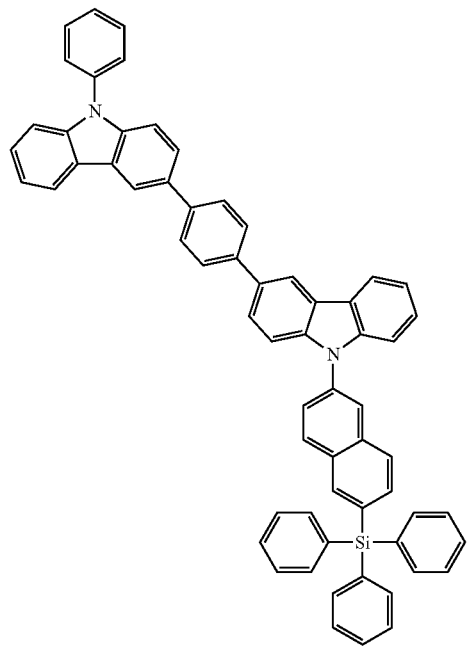
H1-298
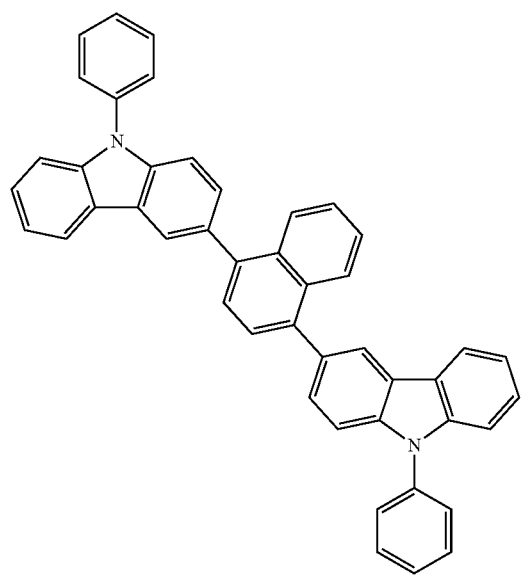
H1-299
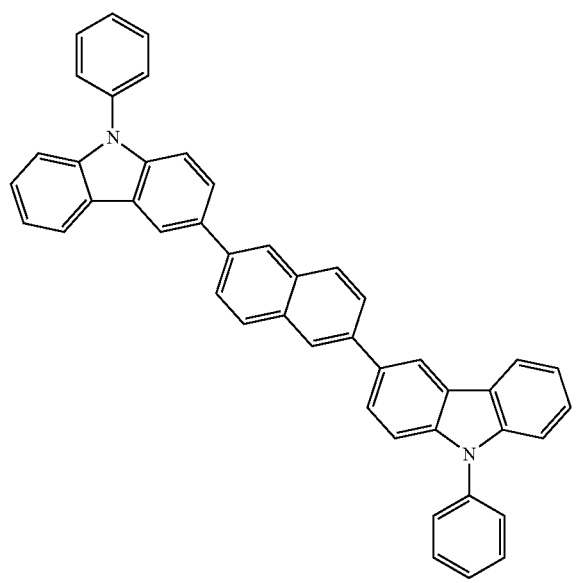
H1-300

H1-301
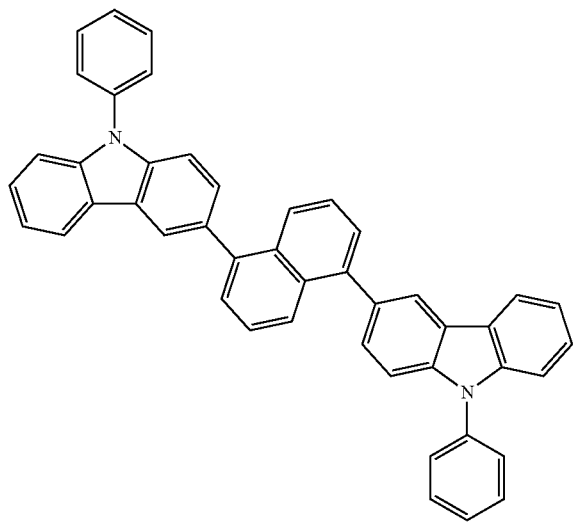
H1-302
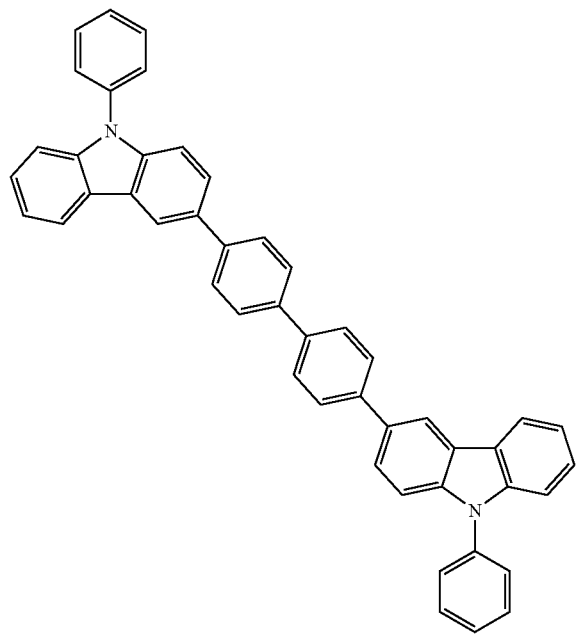
H1-303
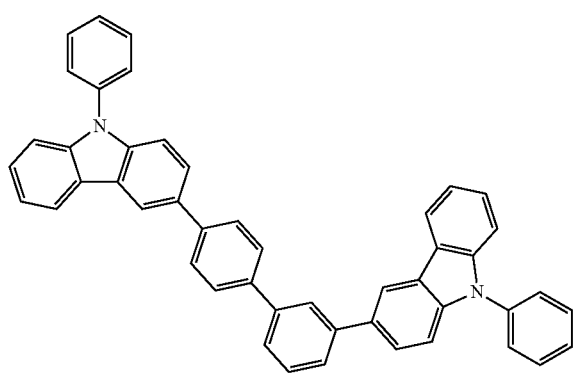
H1-304
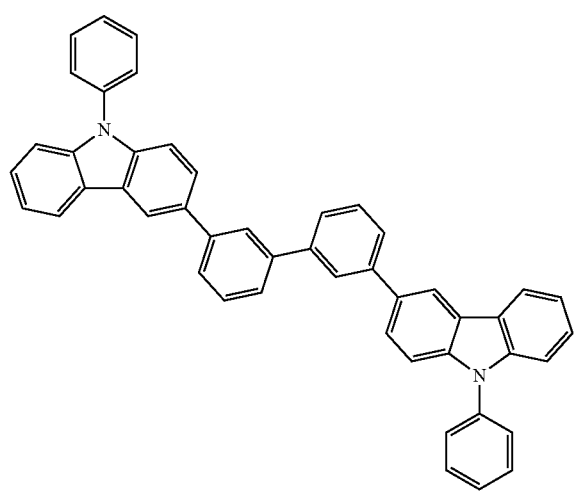

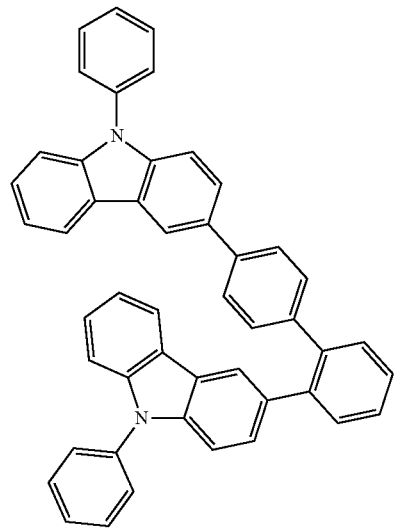
H1-305
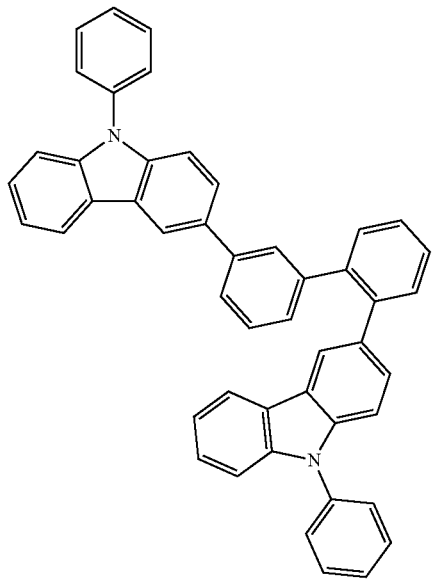
H1-306
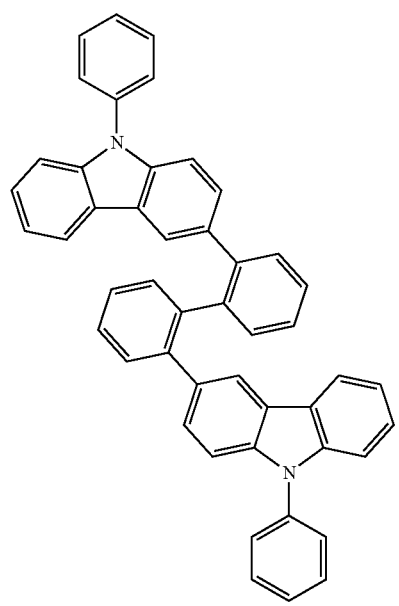
H1-307
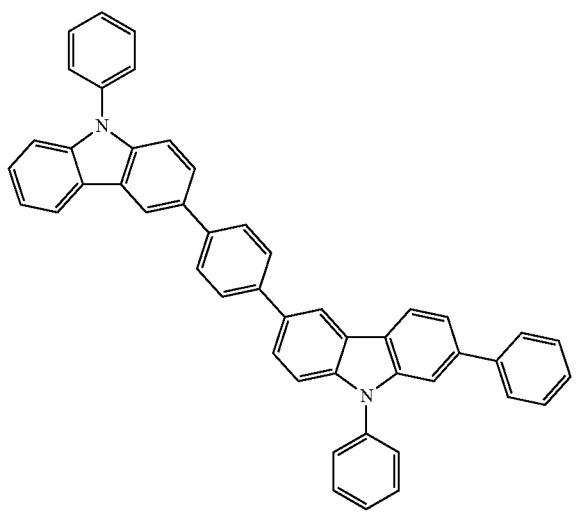
H1-308

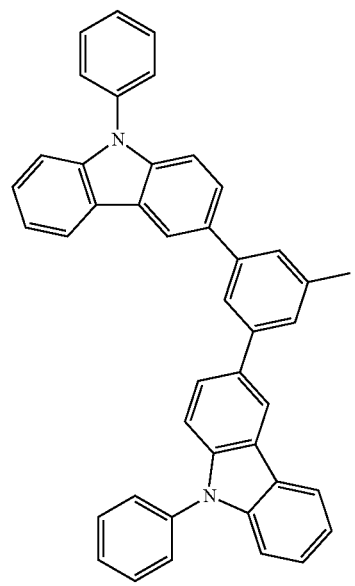
H1-309
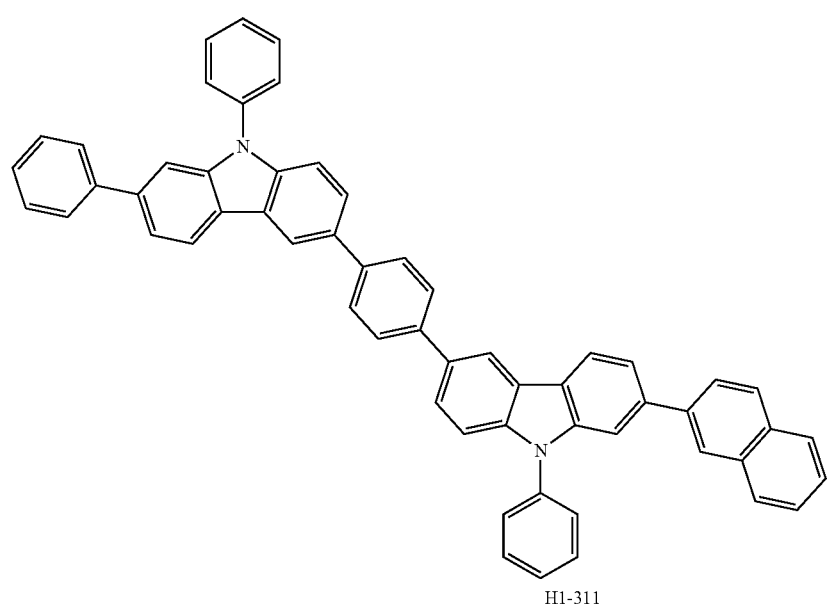
H1-310
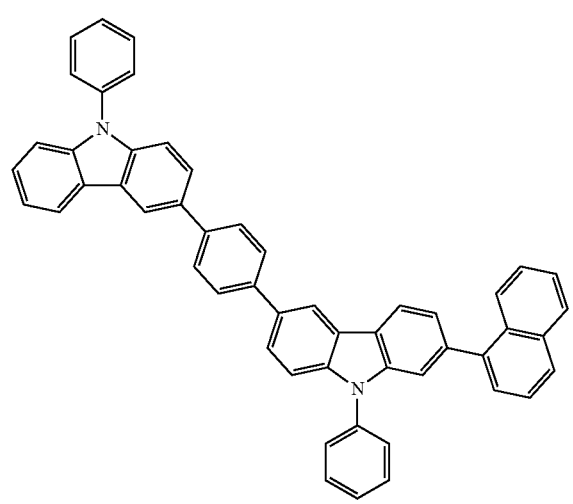
H1-311
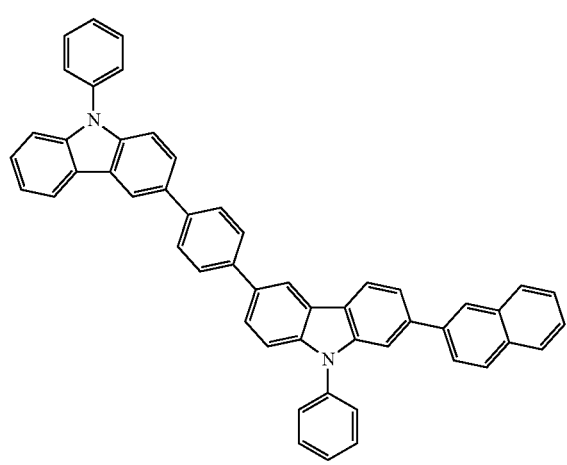
H1-312

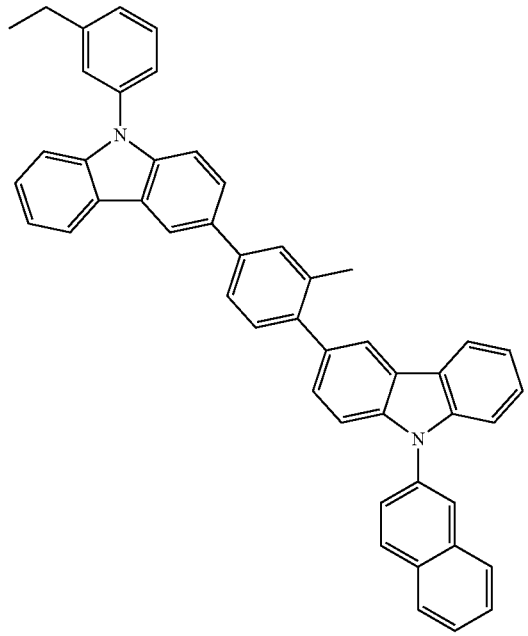
H1-313
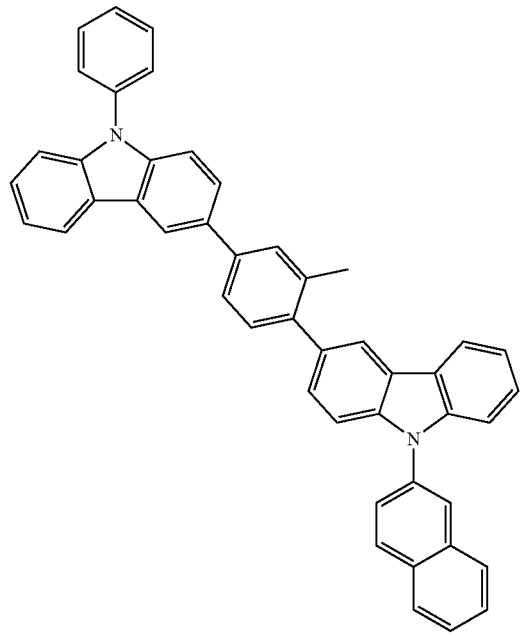
H1-314
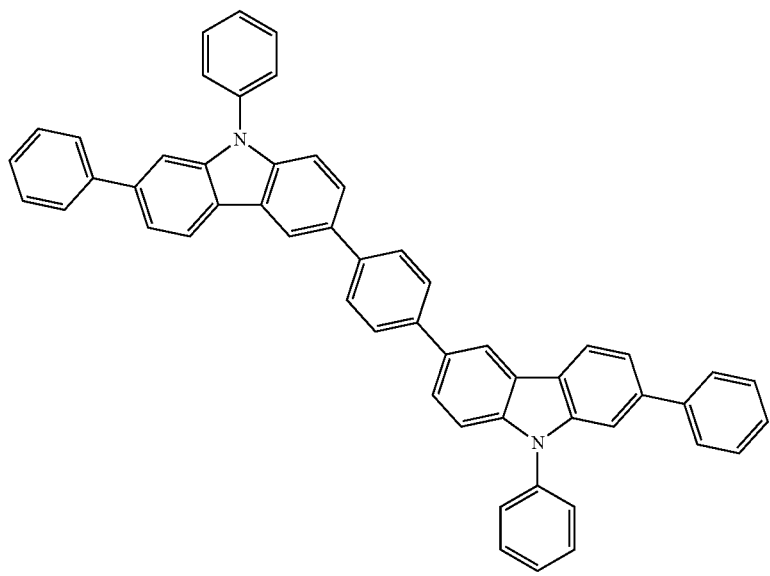
H1-315

H1-316
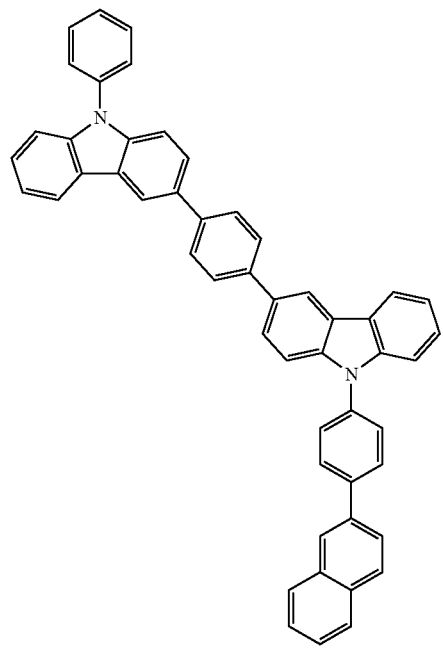
H1-317
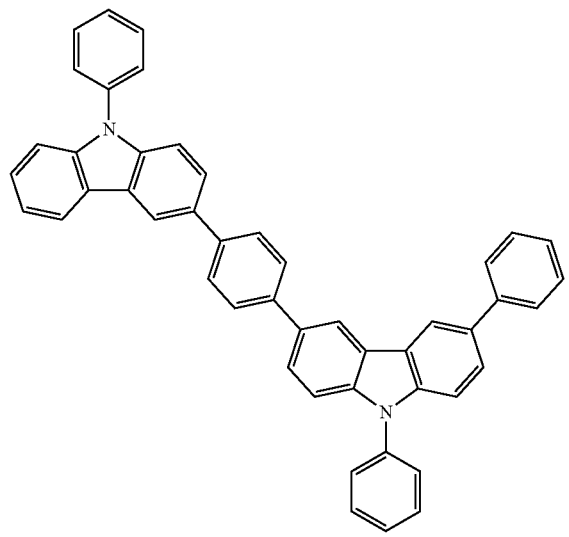
H1-318
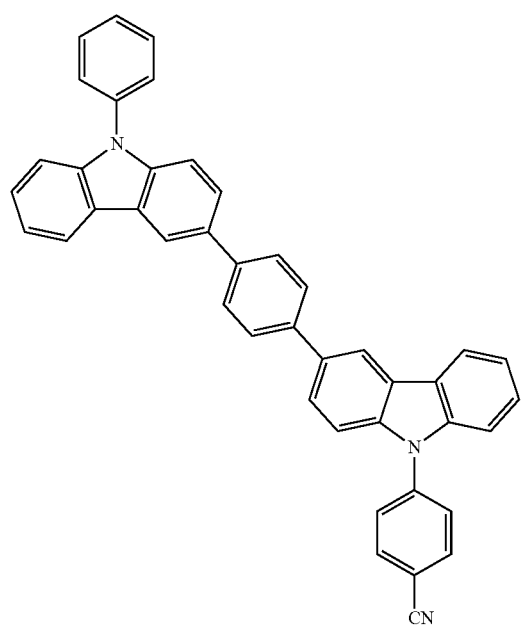
H1-319
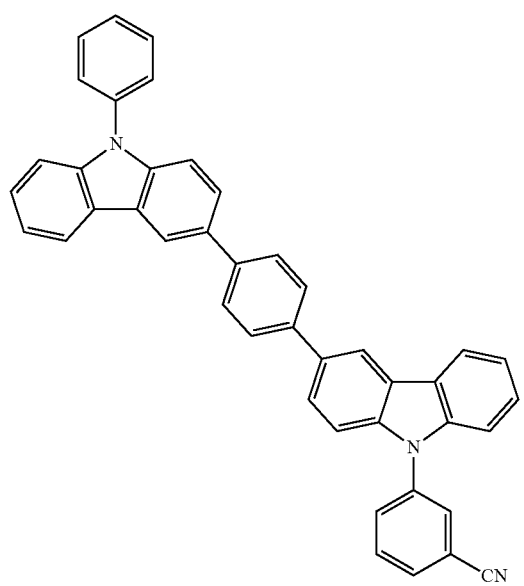

H1-320
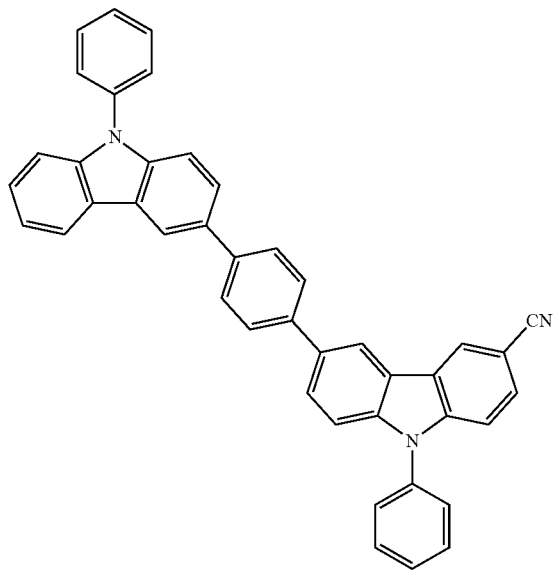
H1-321
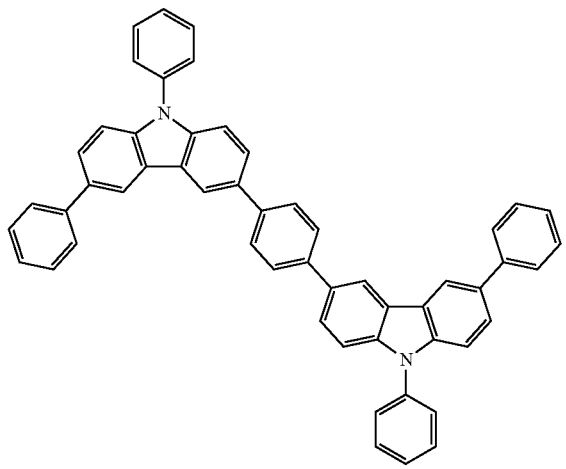
H1-322
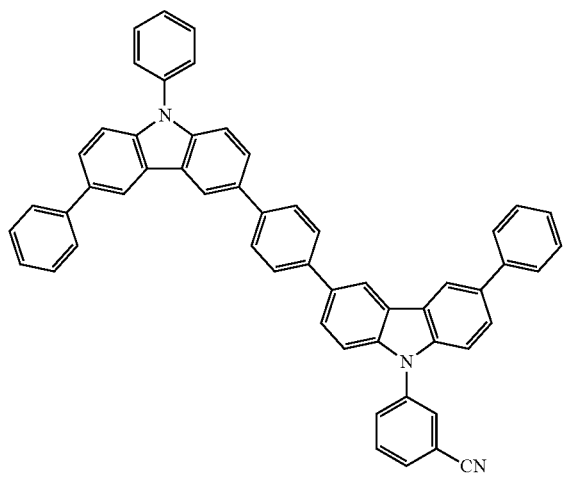
H1-323
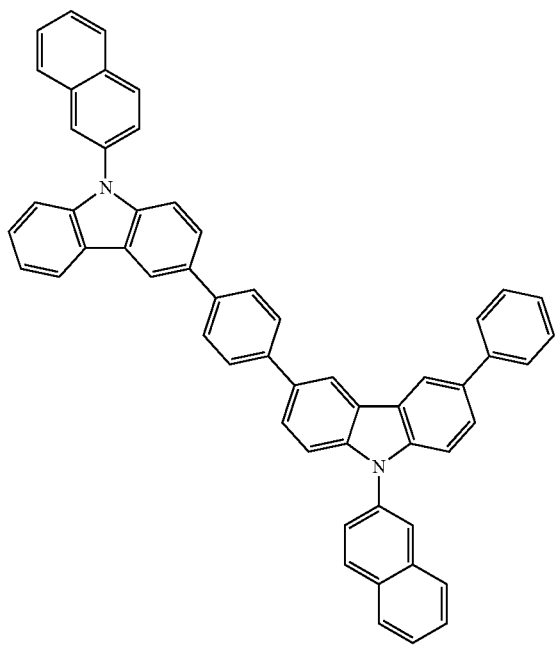

-continued
H1-324
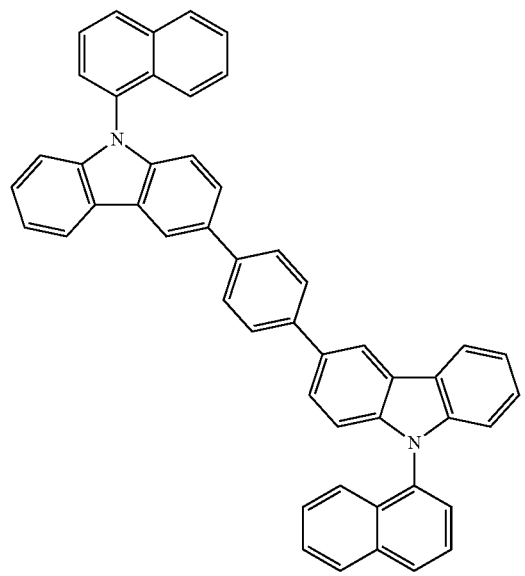
H1-325
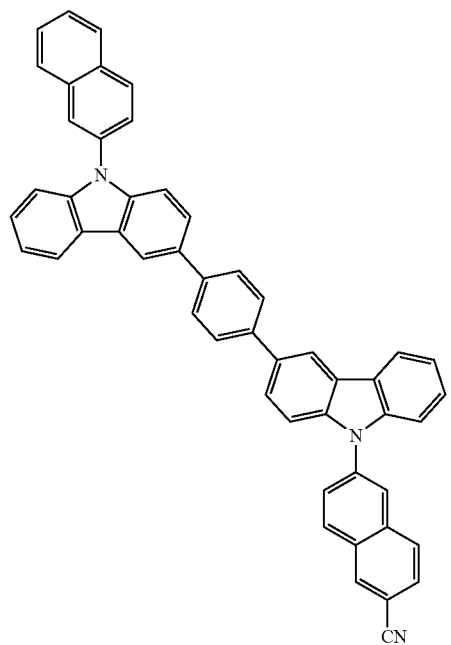
H1-326
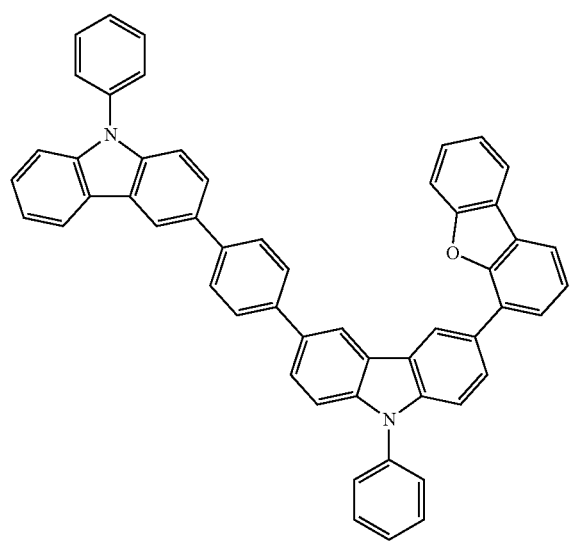
H1-327
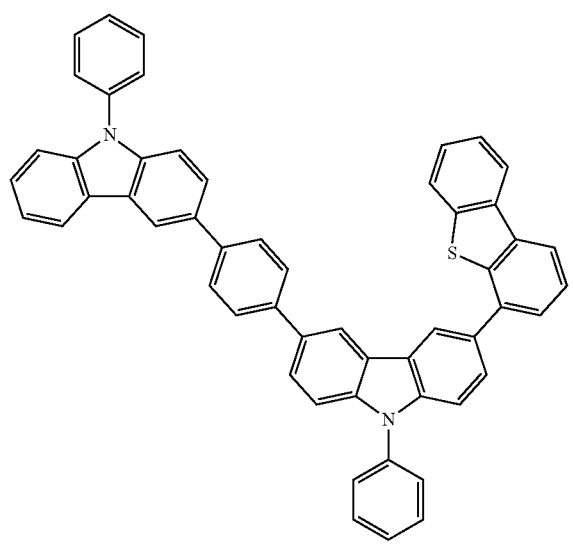

-continued
H1-328
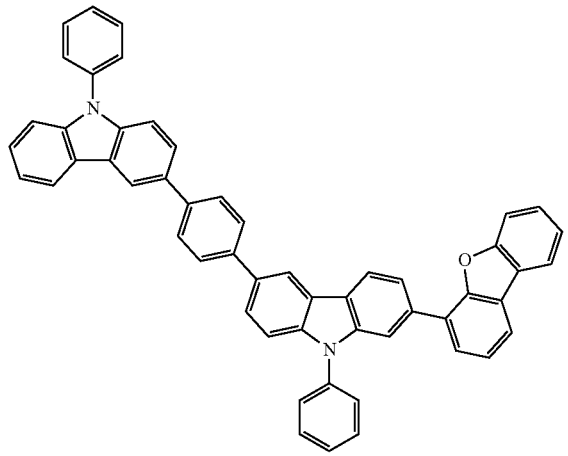
H1-329
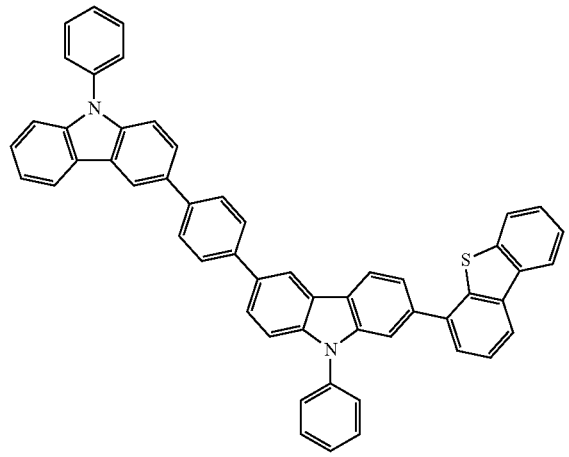
H1-330
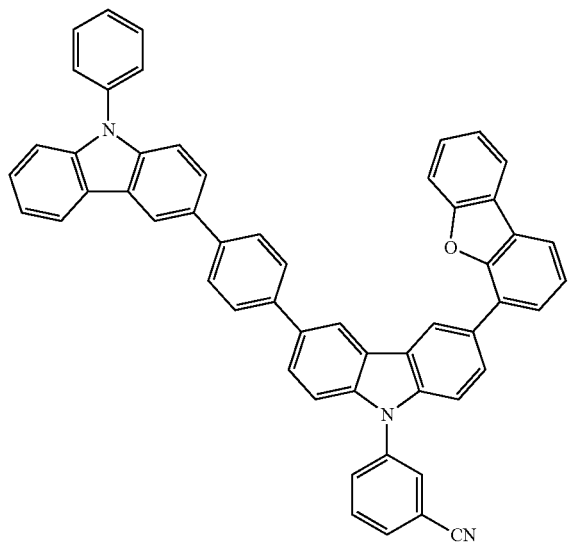
H1-331
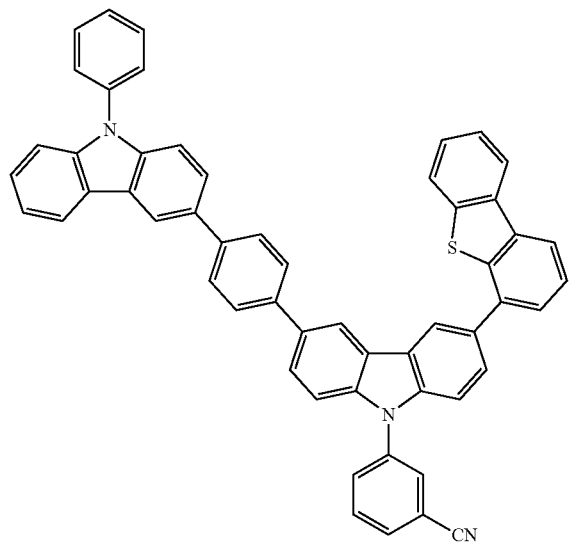
H1-332
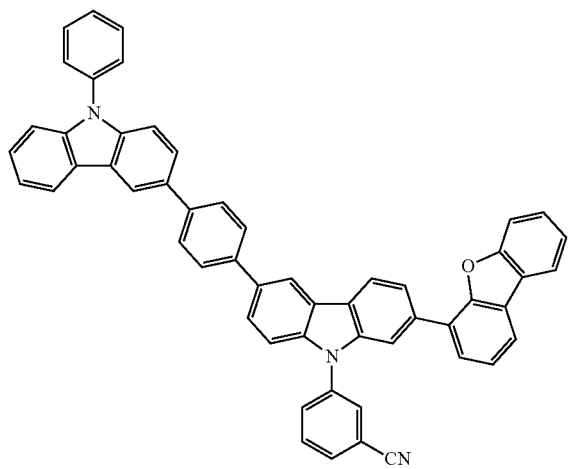
H1-333
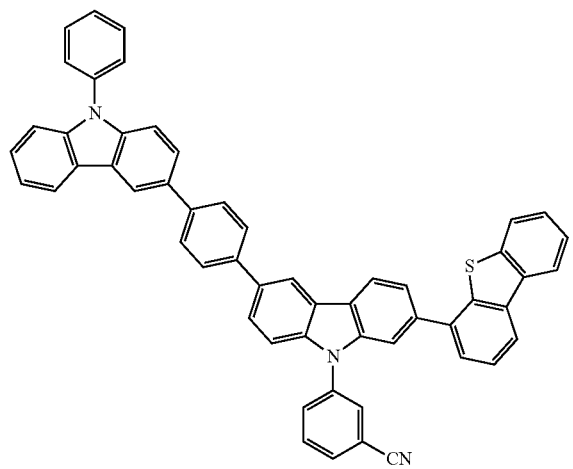

H1-334
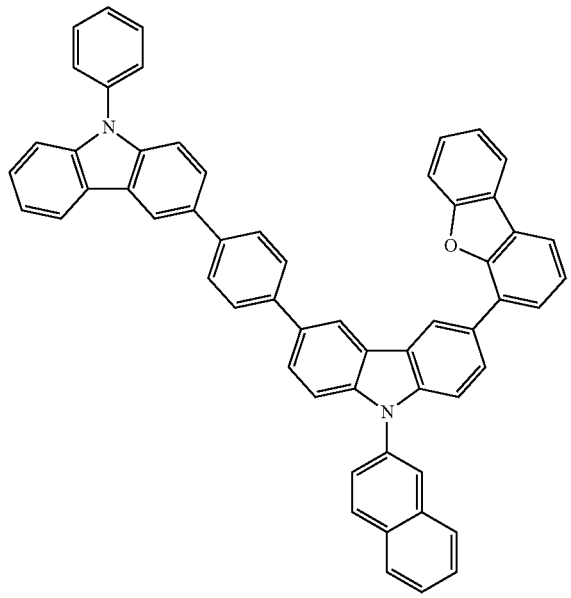
H1-335
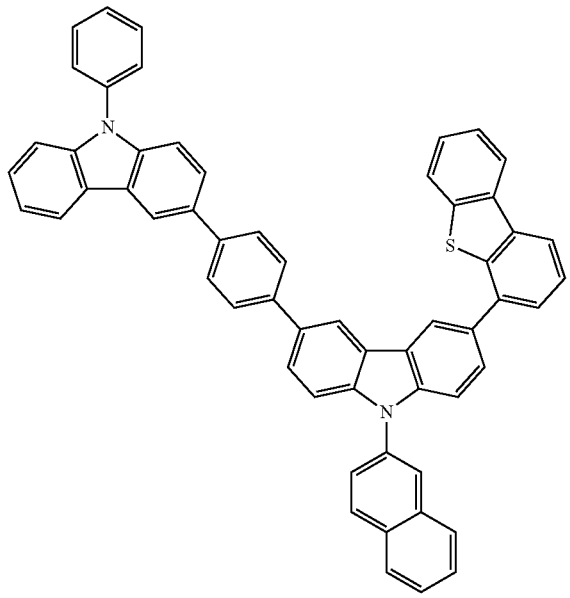
H1-336
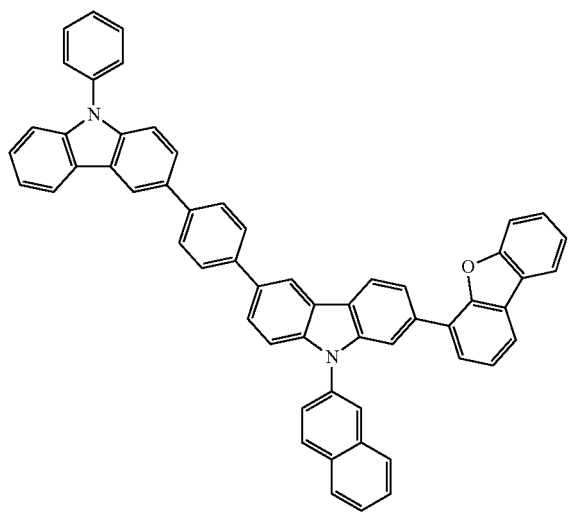
H1-337
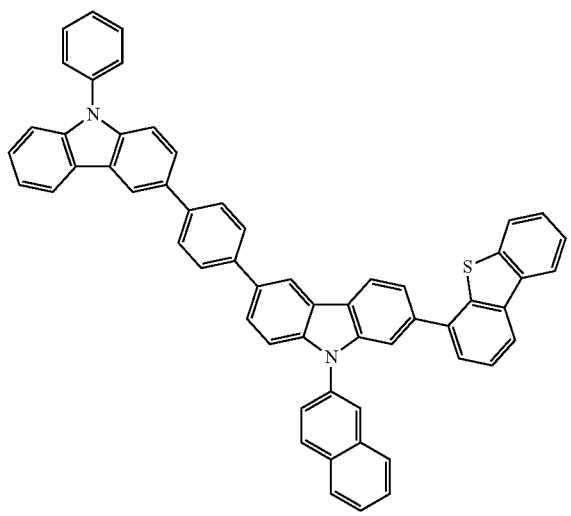

-continued
H1-338
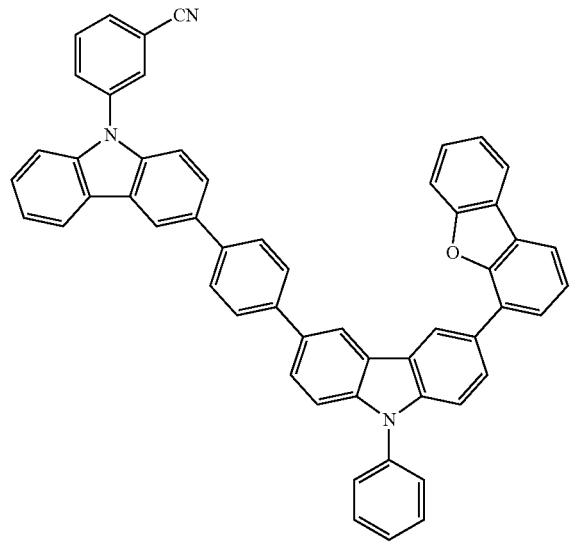
H1-339
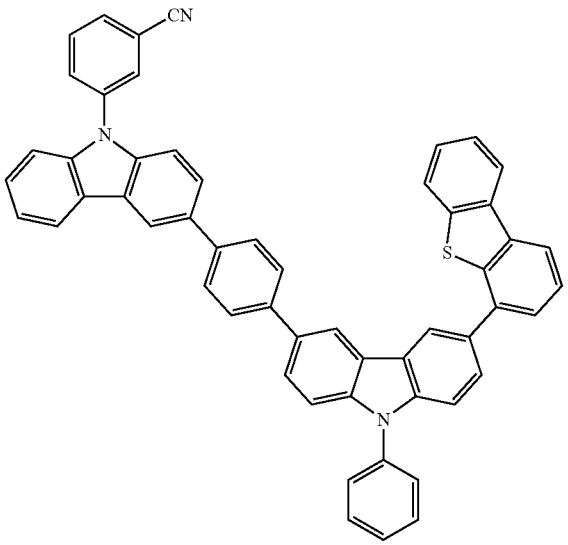
H1-340
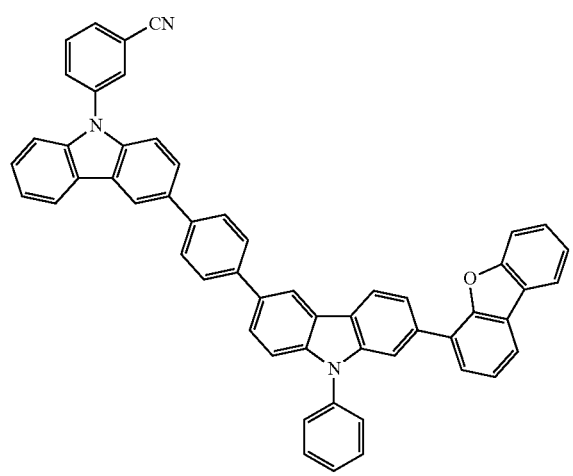
H1-341
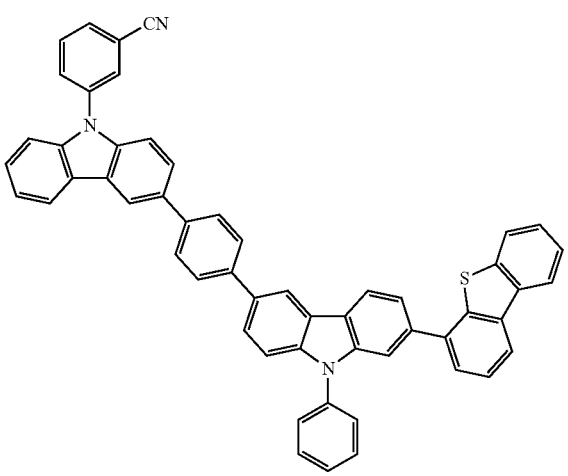
H1-342
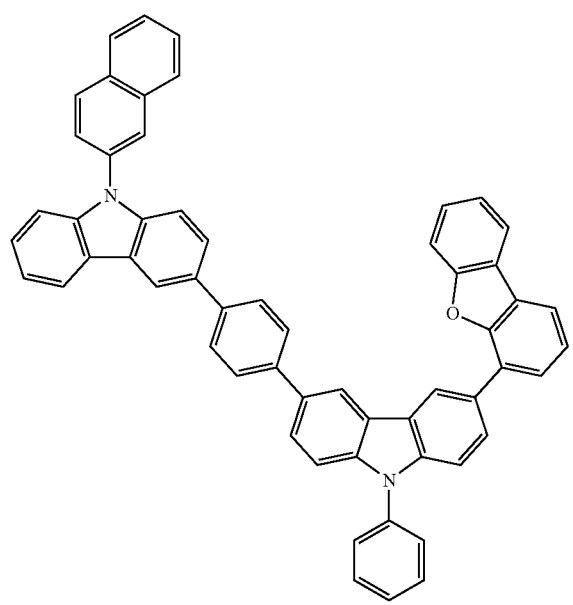
H1-343
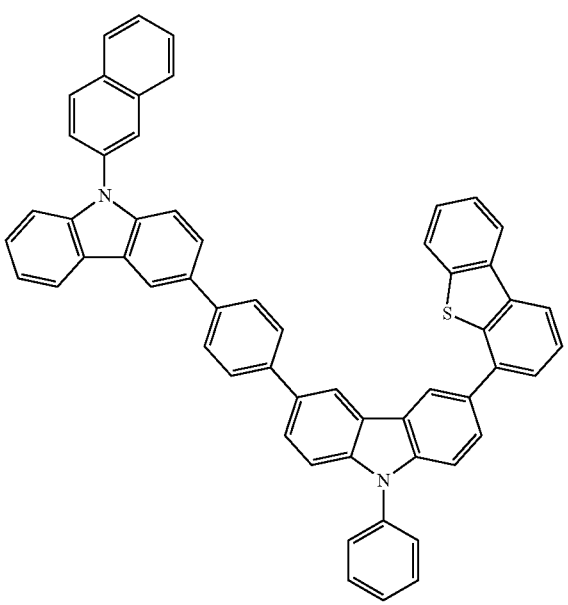

-continued
H1-344
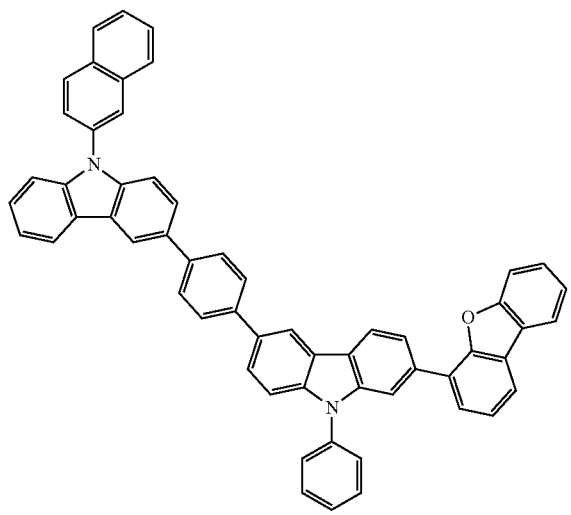
H1-345
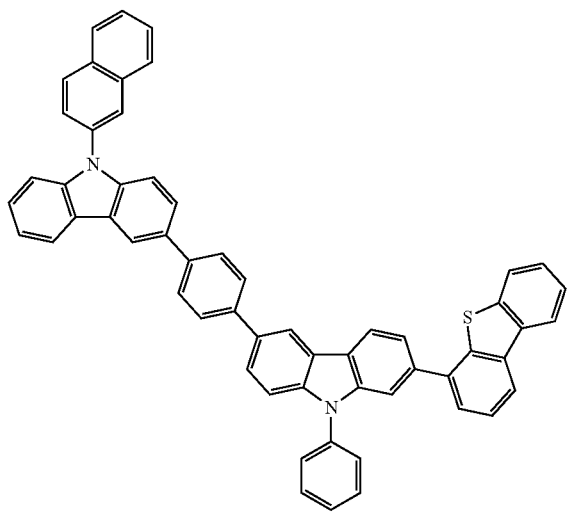
H1-346
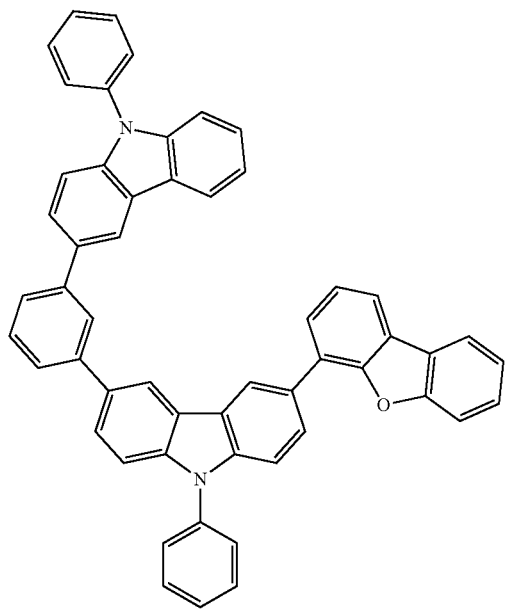
H1-347
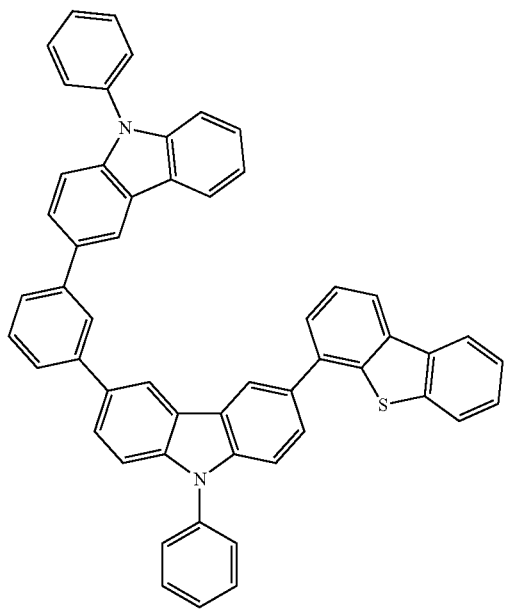

-continued
H1-348
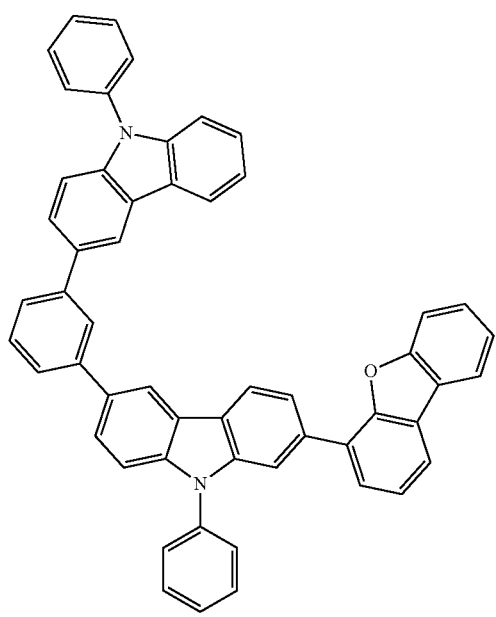
H1-349
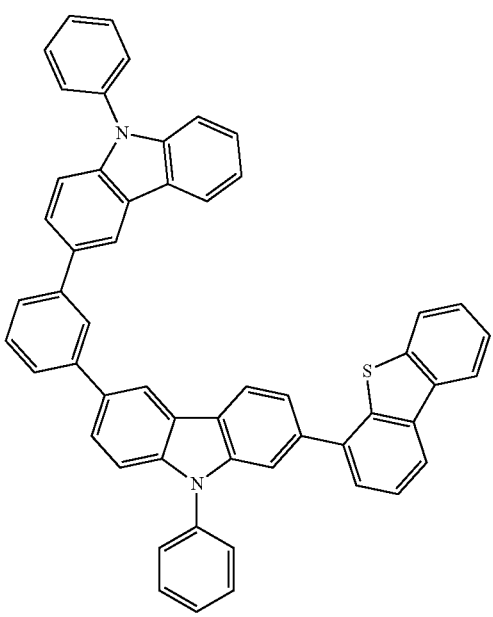
H1-350
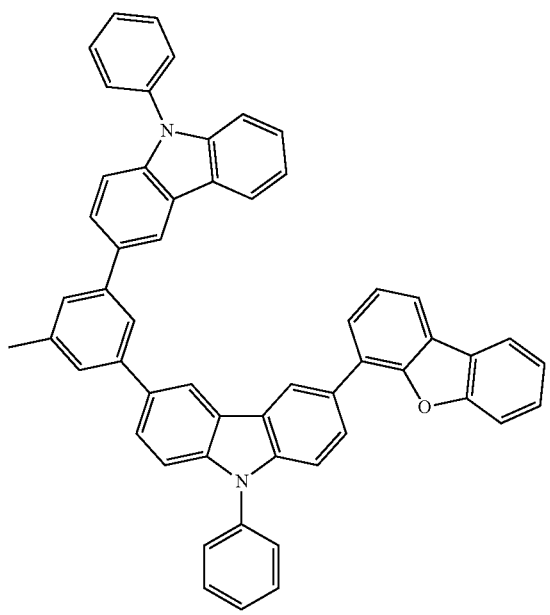
H1-351
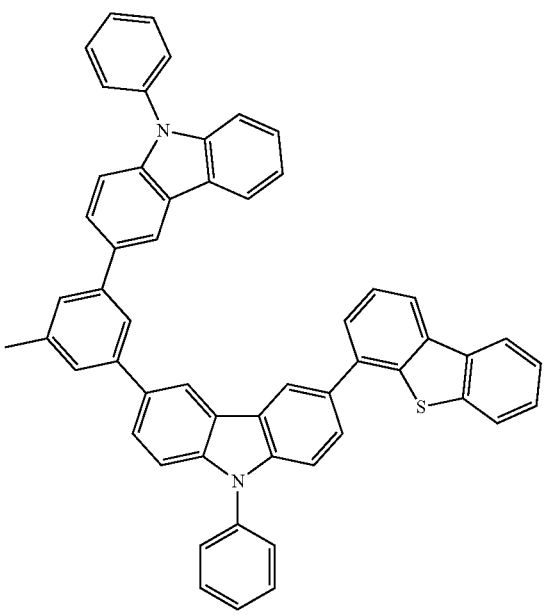

-continued
H1-352
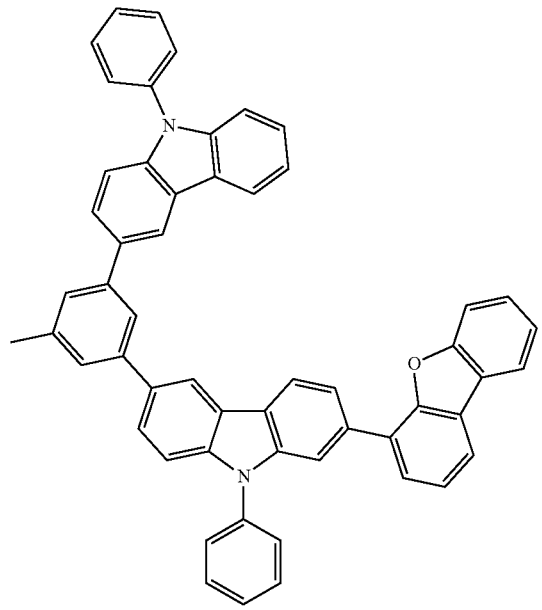
H1-353
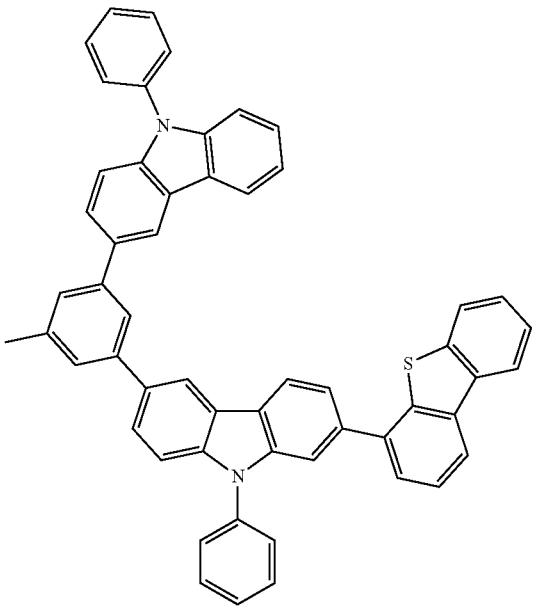
H1-354
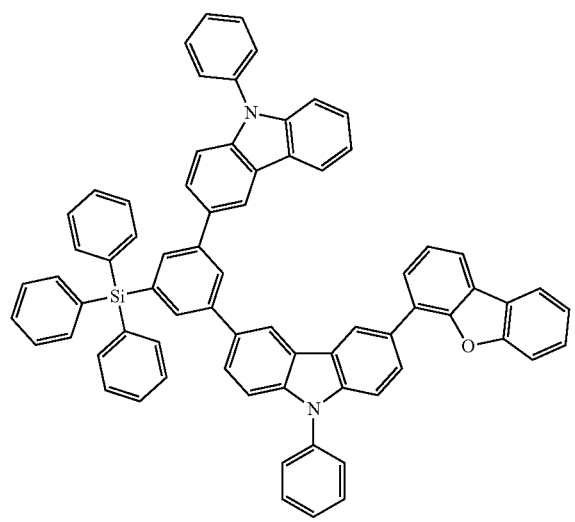
H1-355
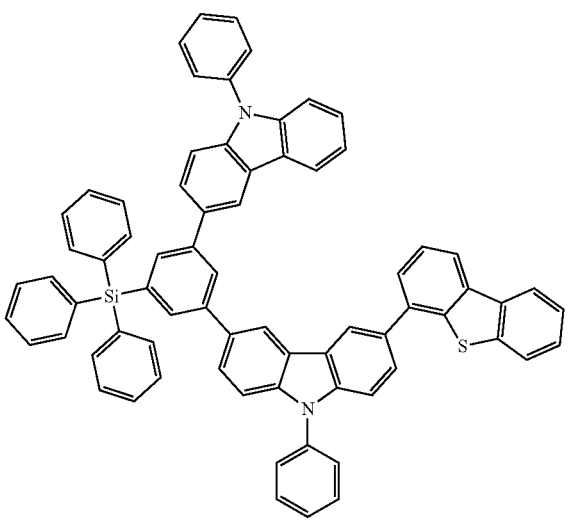

-continued
H1-356
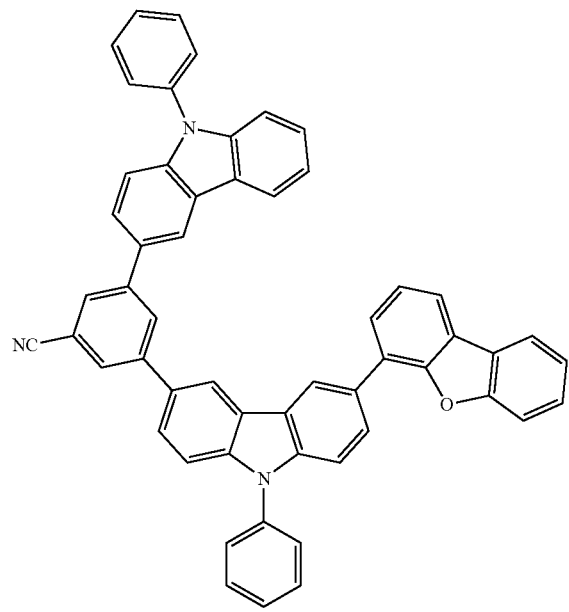
H1-357
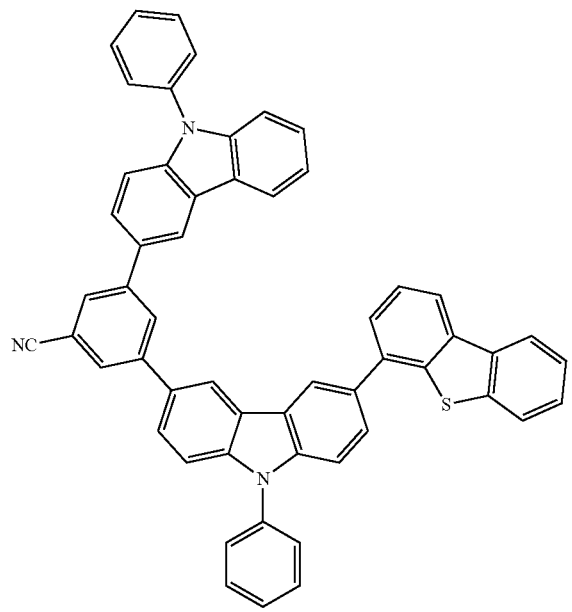
H1-358
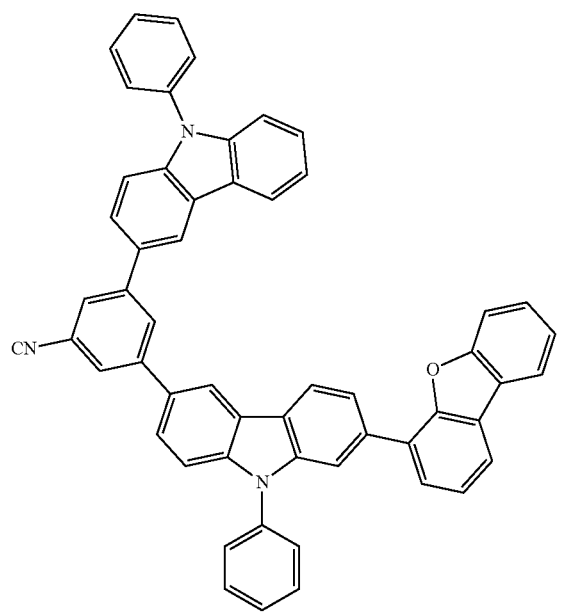
H1-359
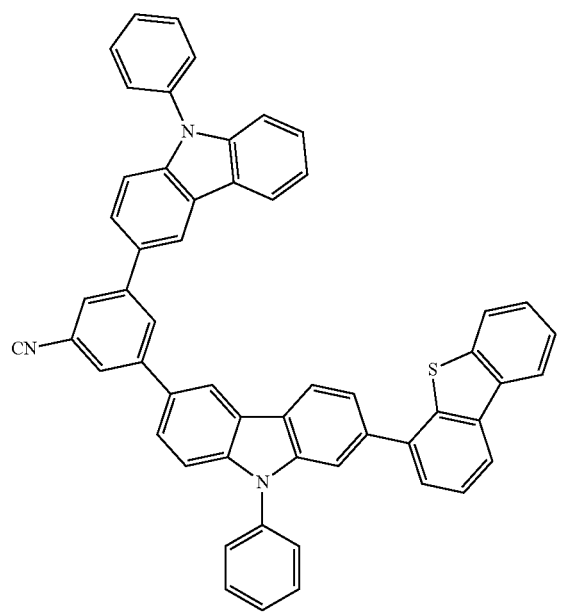

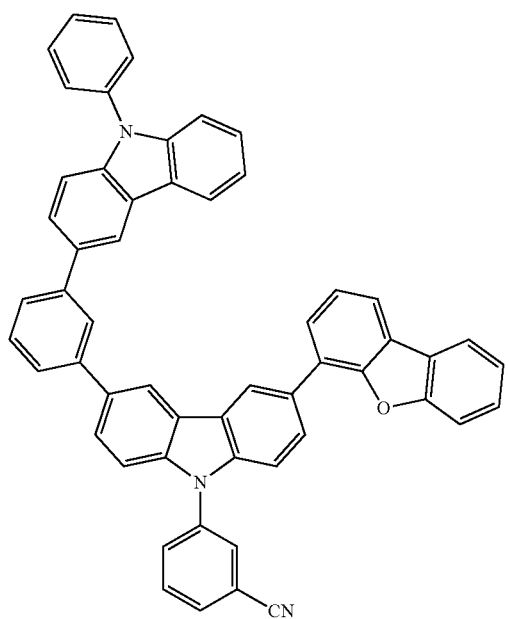
H1-360
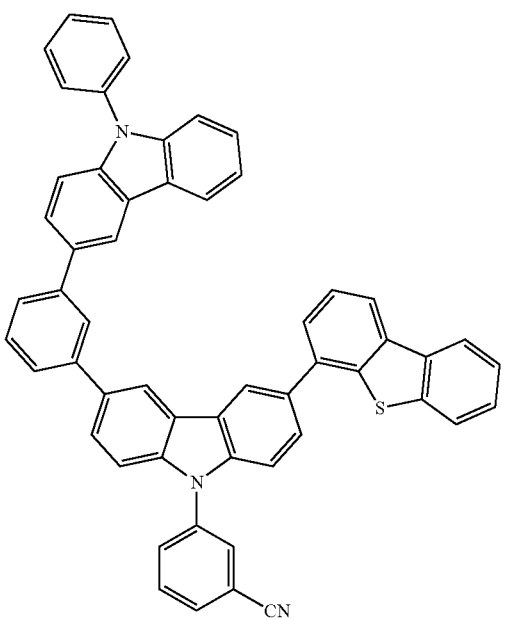
H1-361
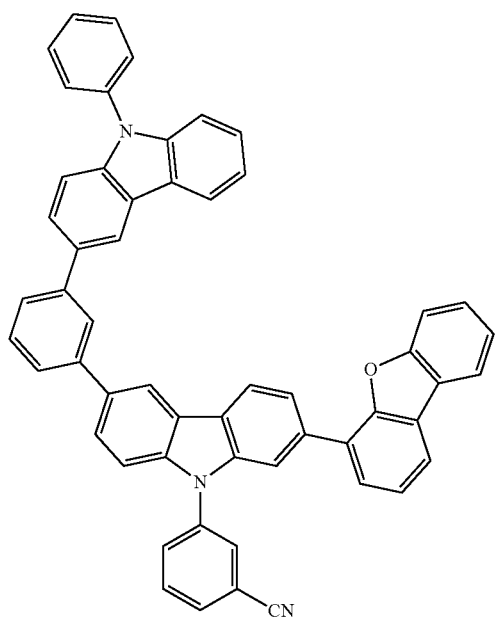
H1-362
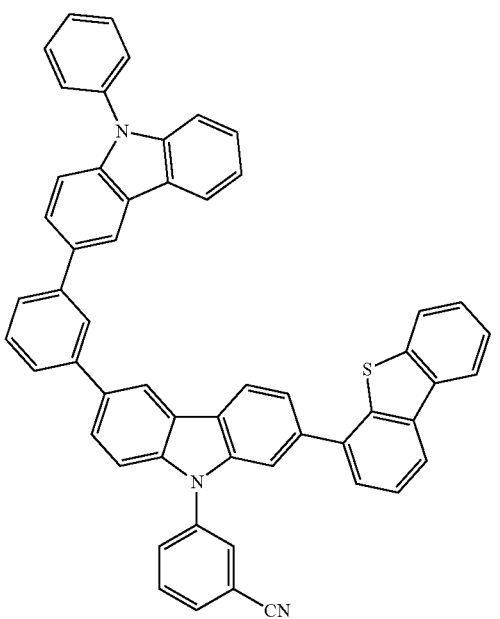
H1-363

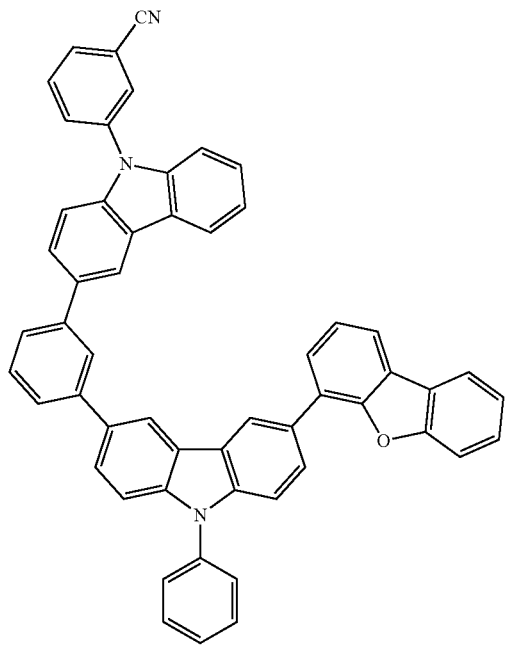
H1-364
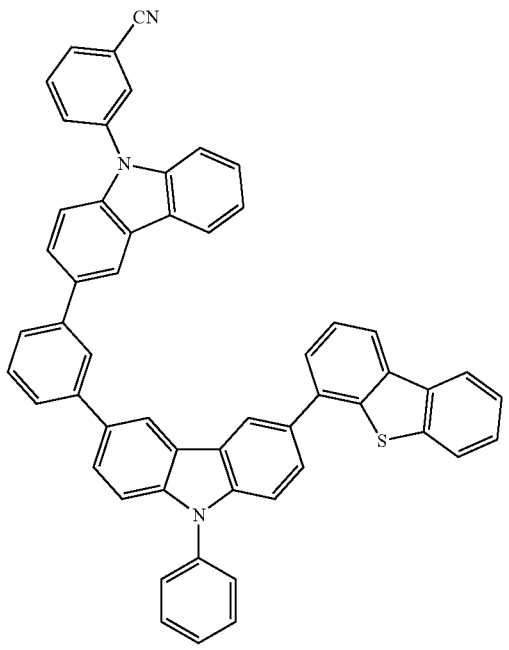
H1-365
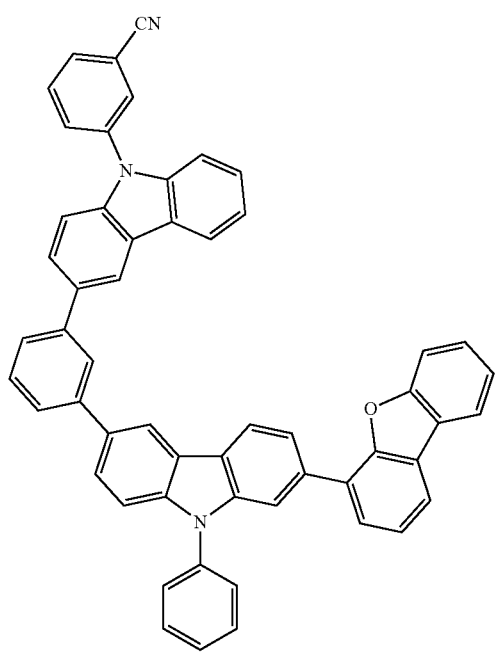
H1-366
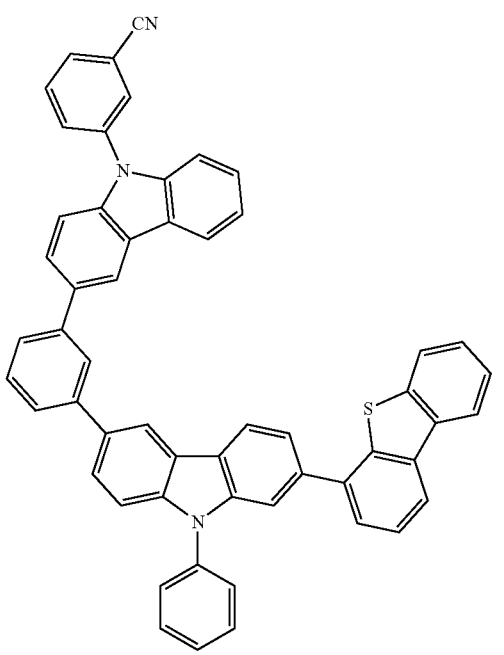
H1-367

H1-368
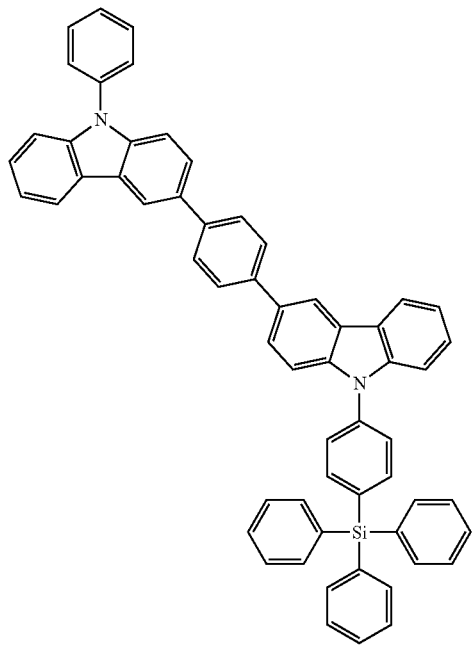
H1-369
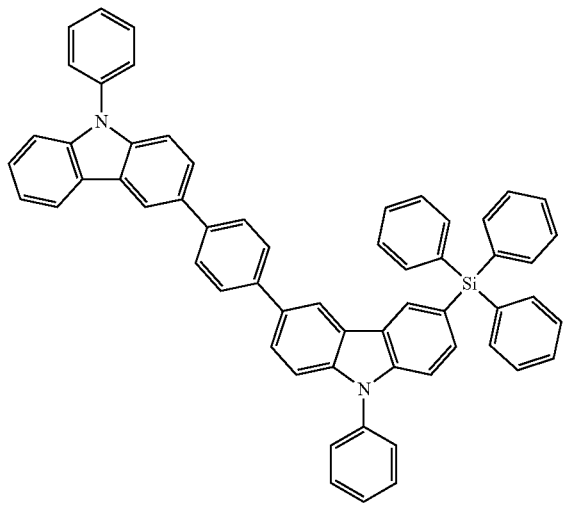
H1-370
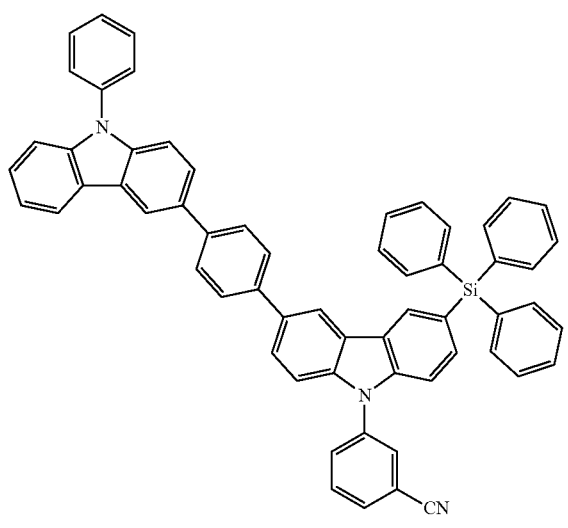
H1-371
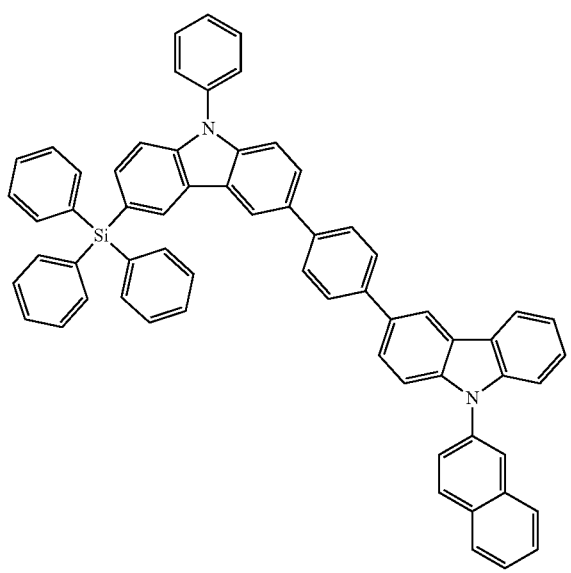

H1-372
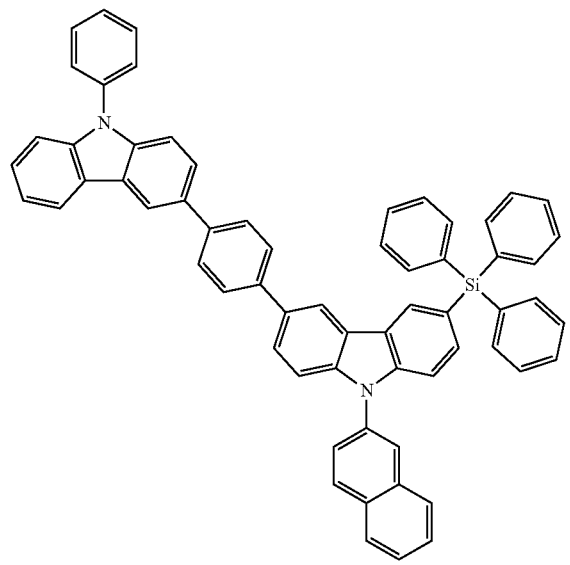
H1-373
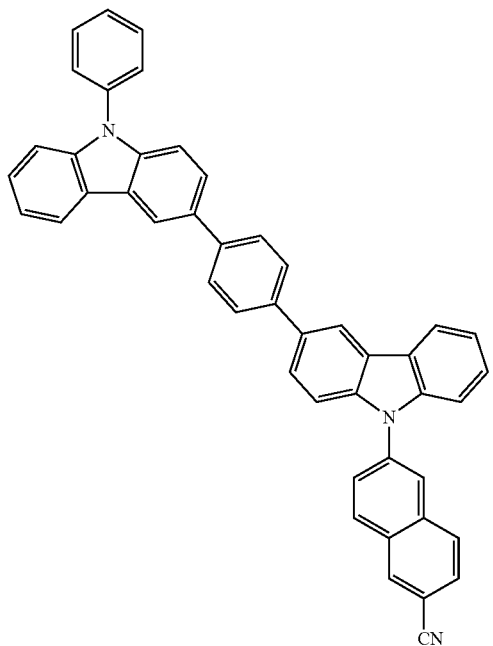
H1-374
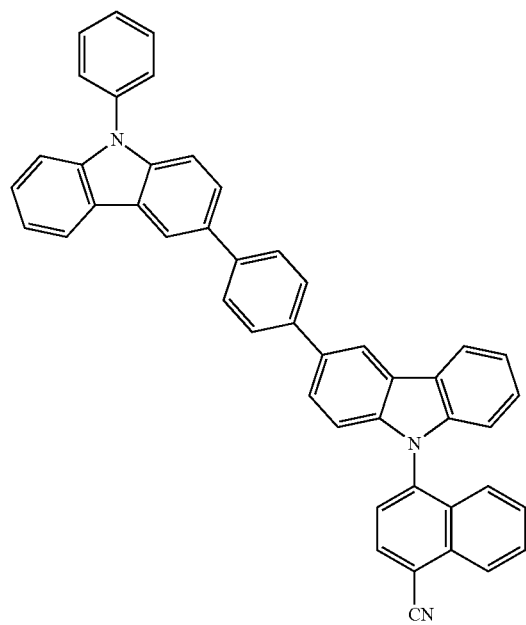
H1-375
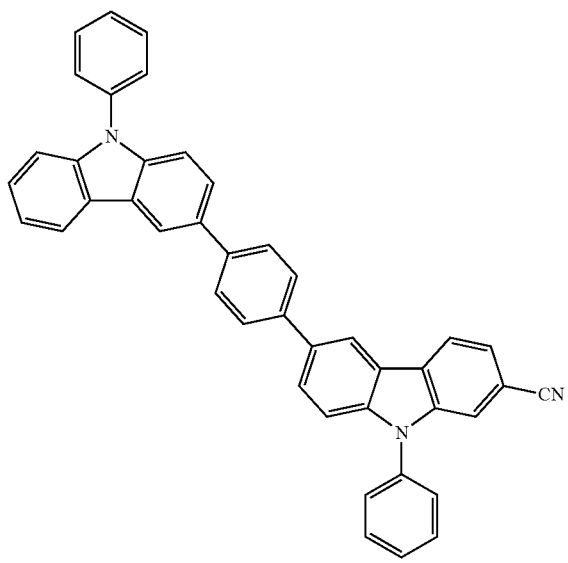

H1-376
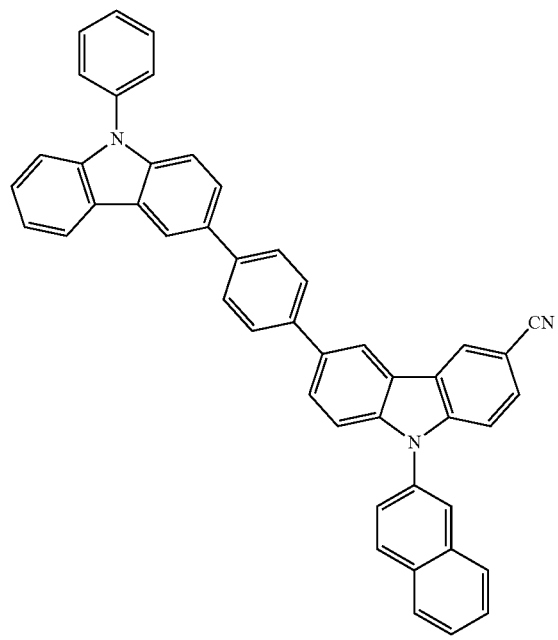
H1-377
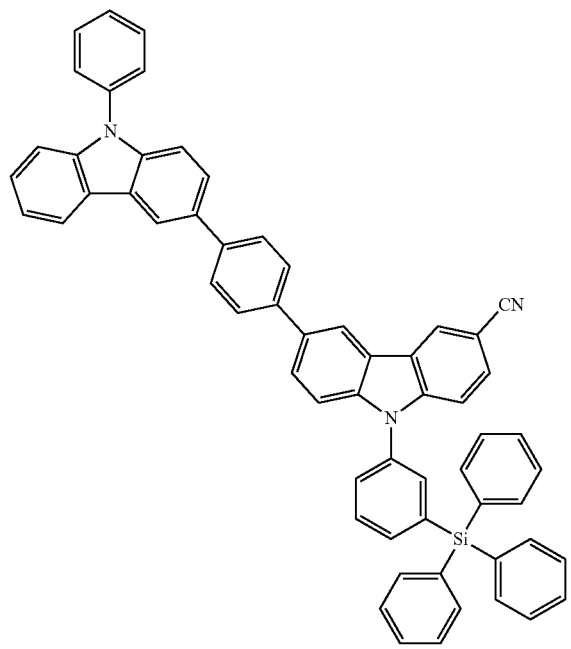
H1-378
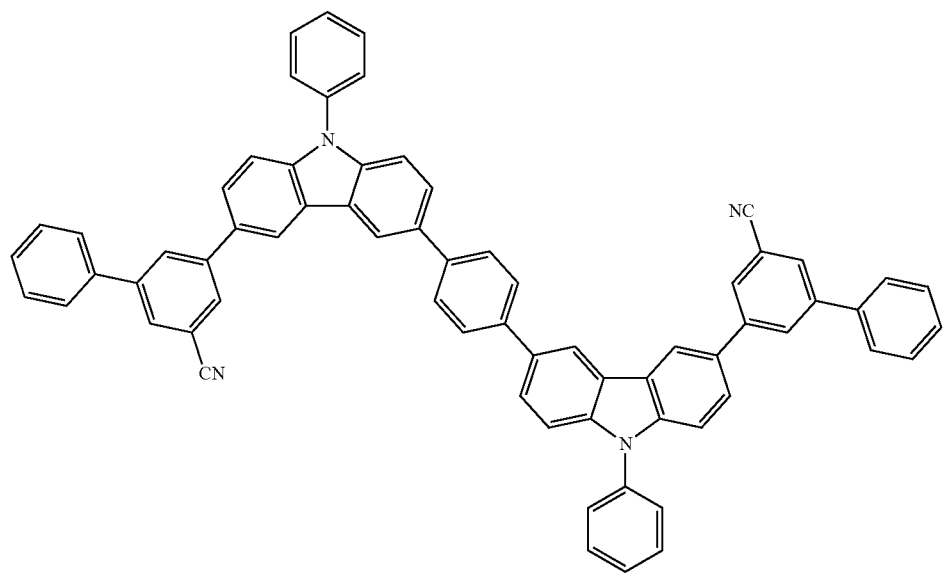

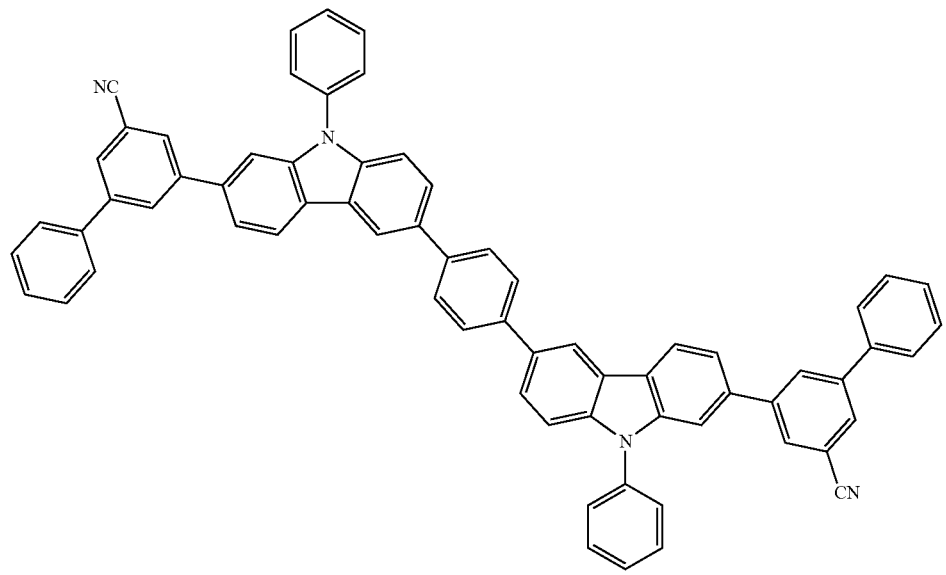
H1-379
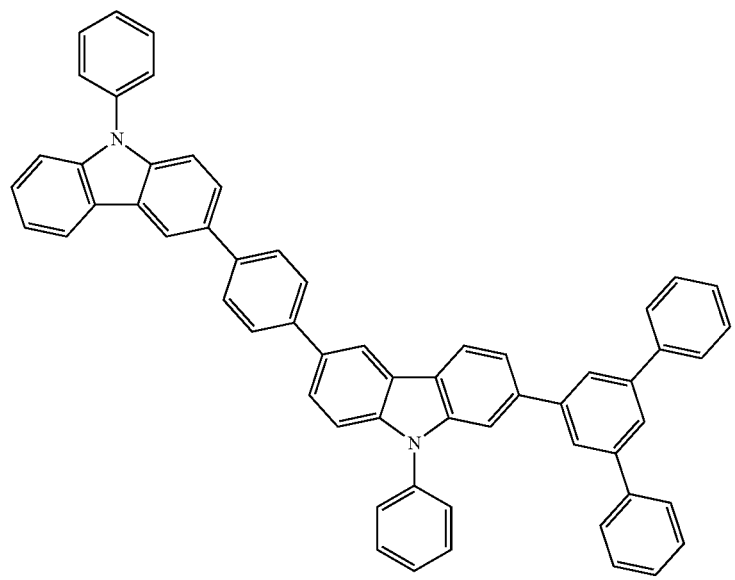
H1-380

-continued
H1-381
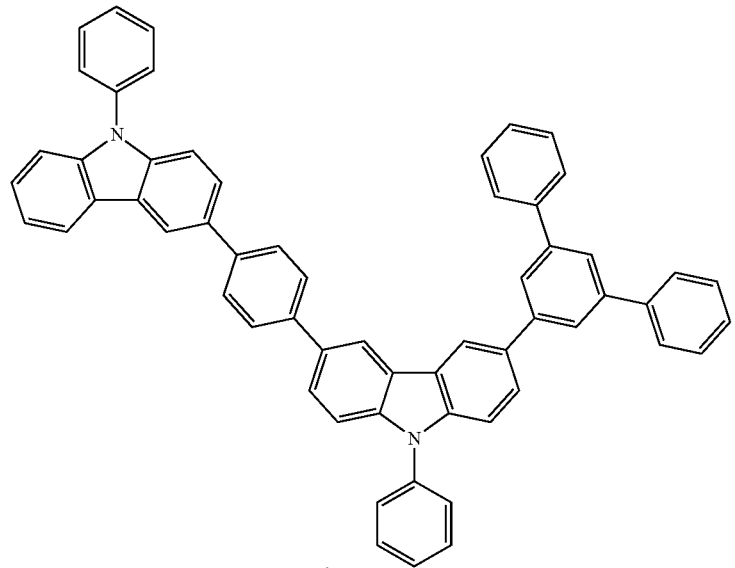
H1-382
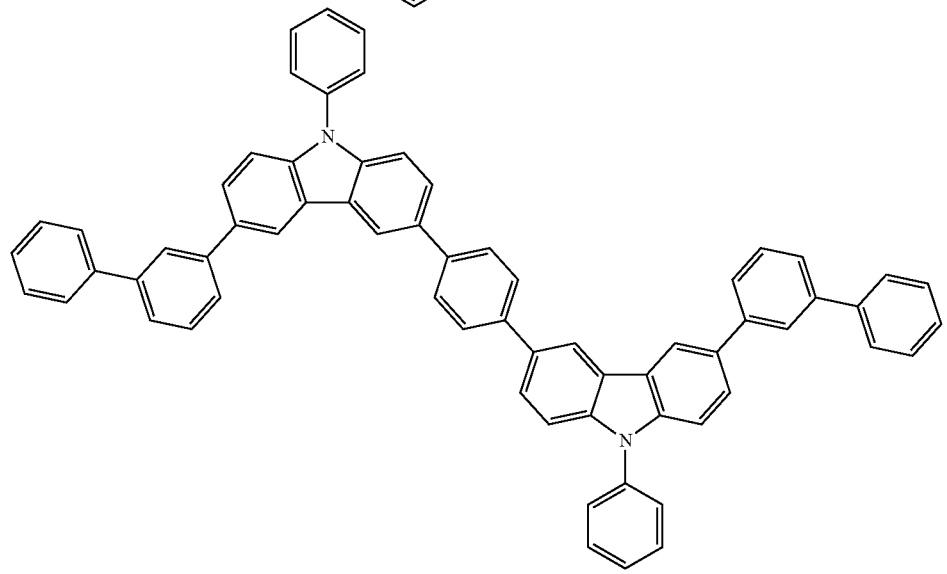
H1-383
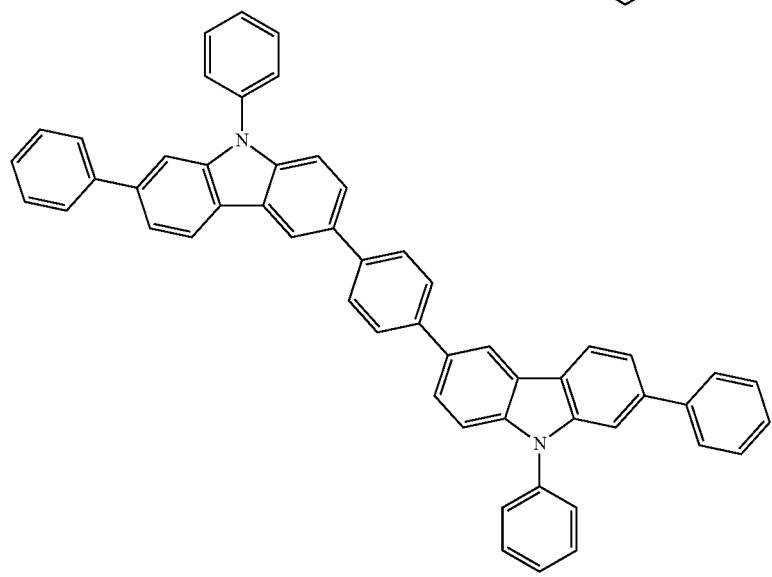

H1-384
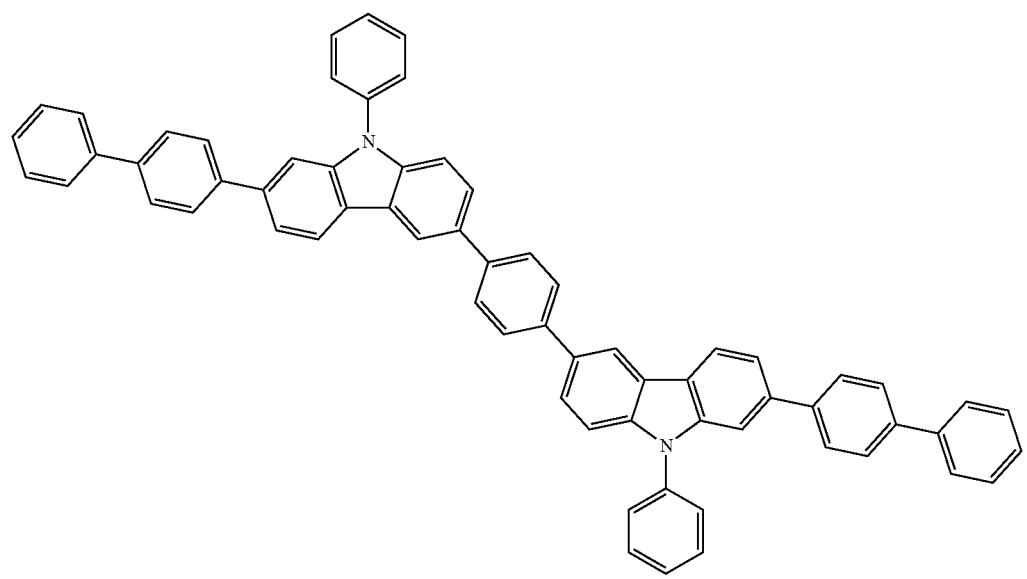
H1-385
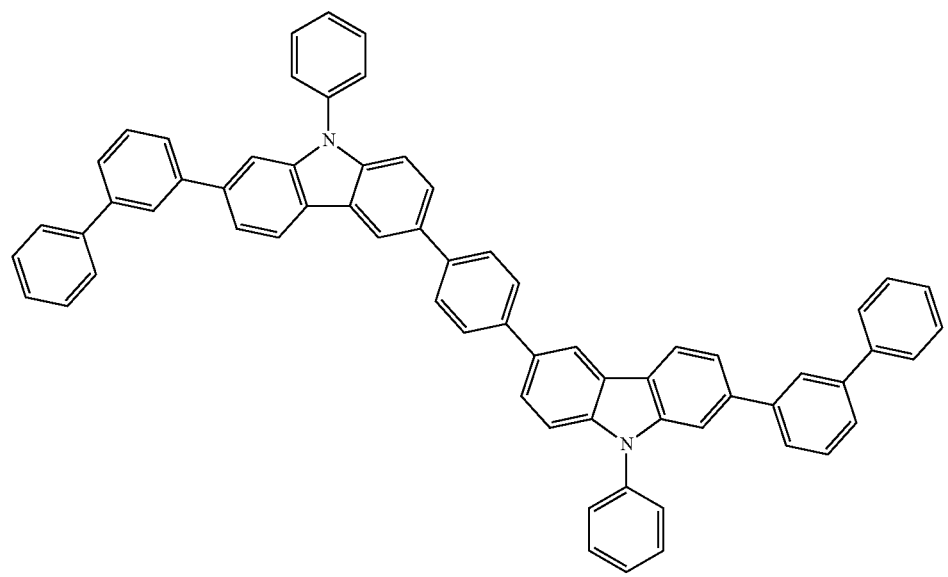
H1-386 H1-387
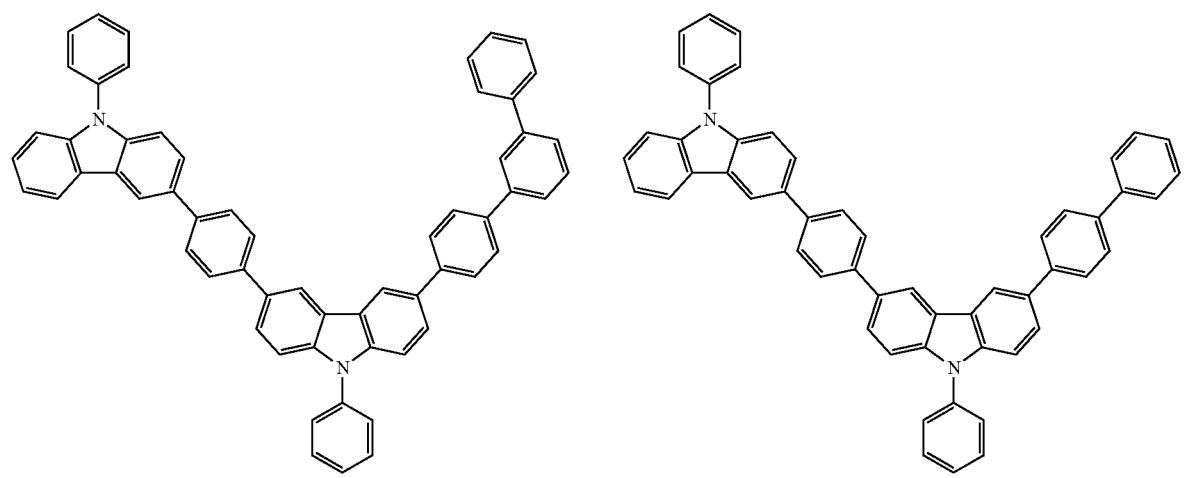

-continued
H1-388
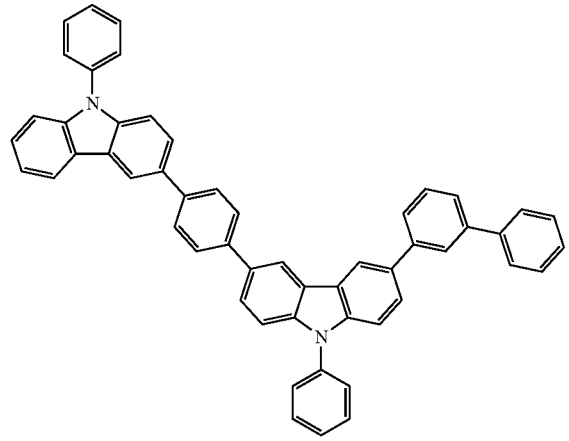
H1-389
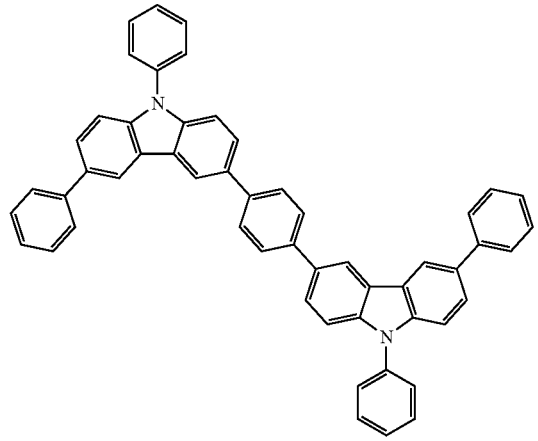
H1-390
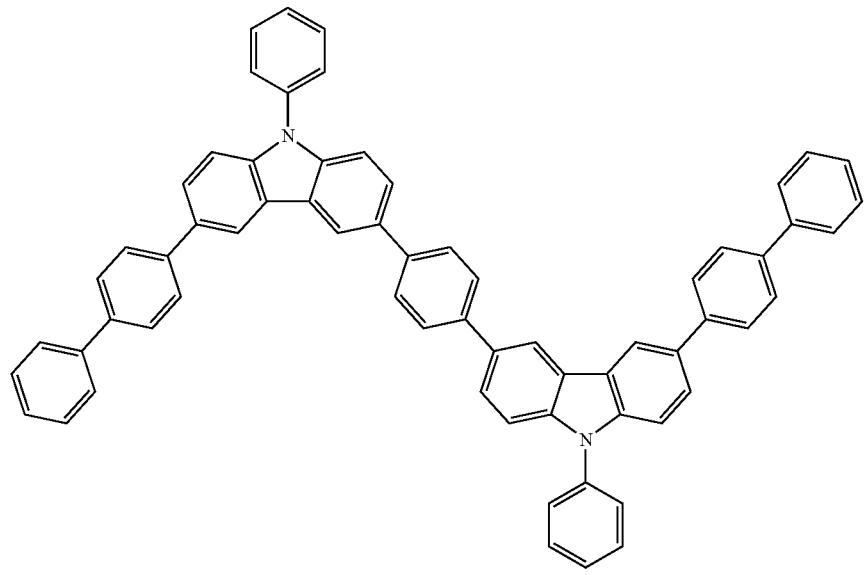
H1-391
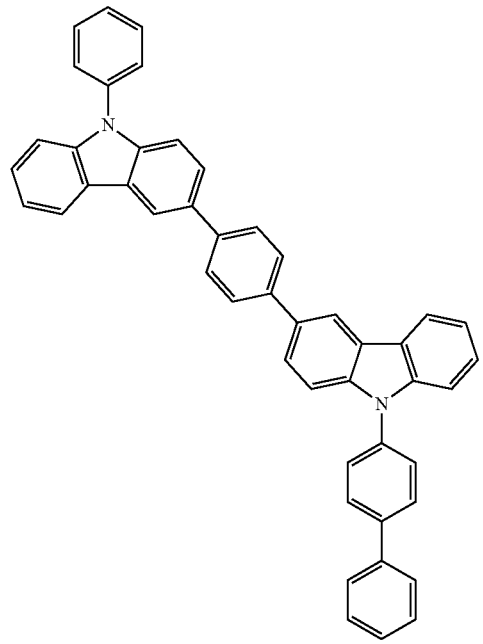
H1-392
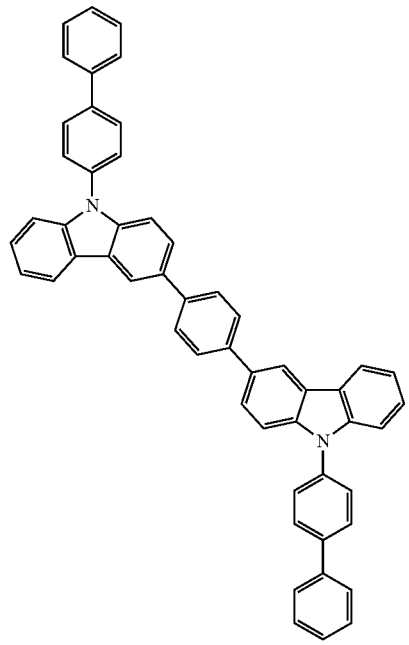

H1-393
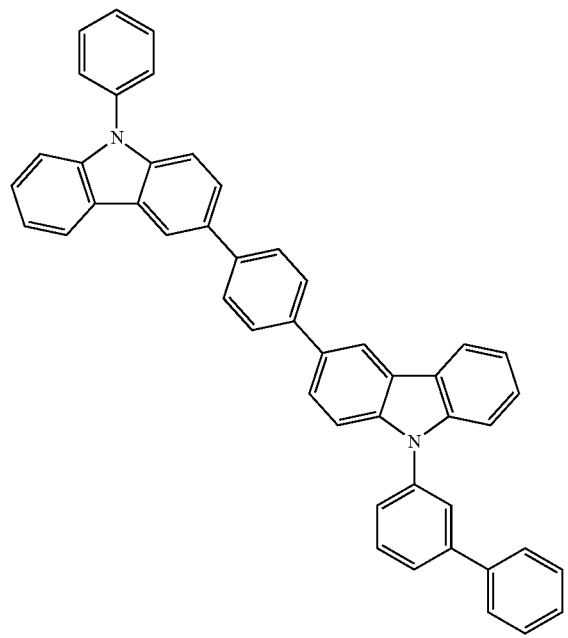
H1-394
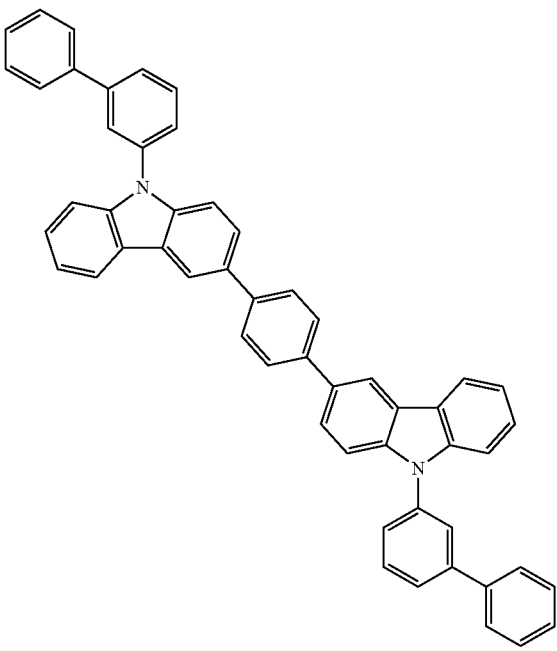
H1-395
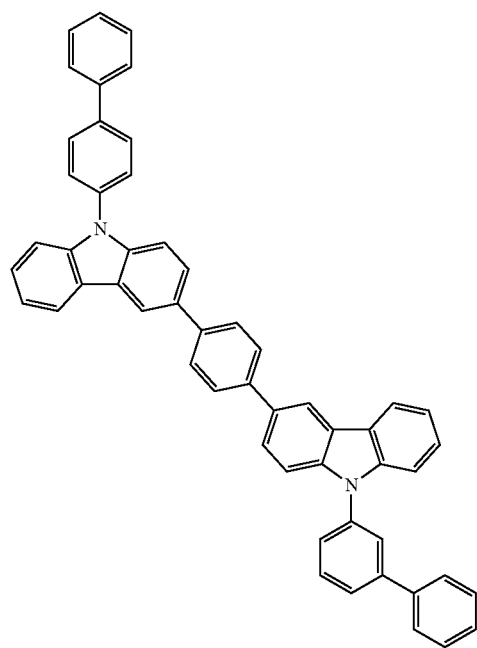
H1-396
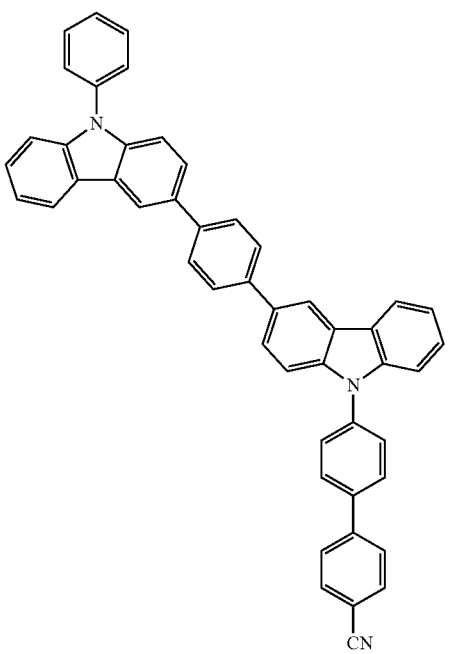

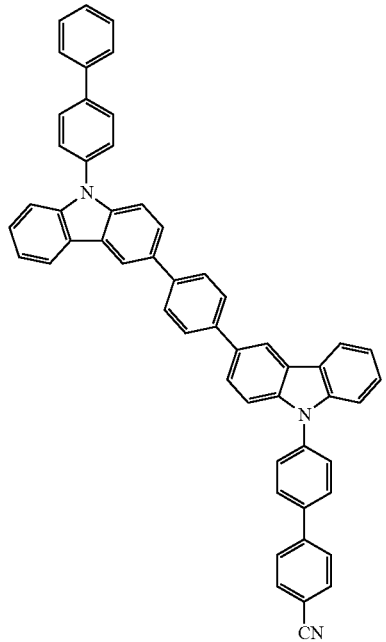
H1-397
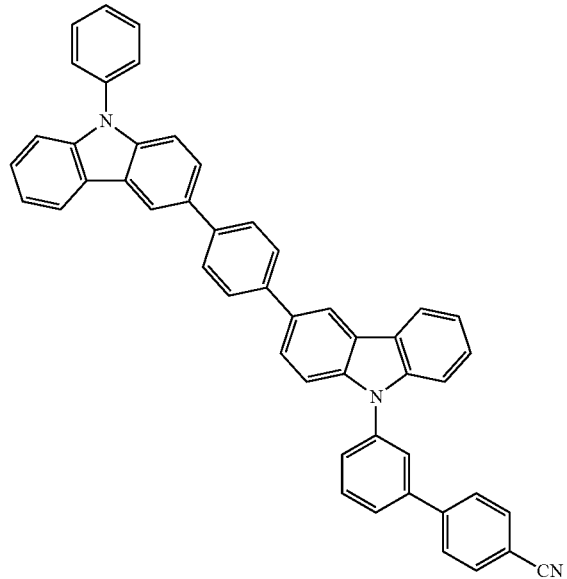
H1-398
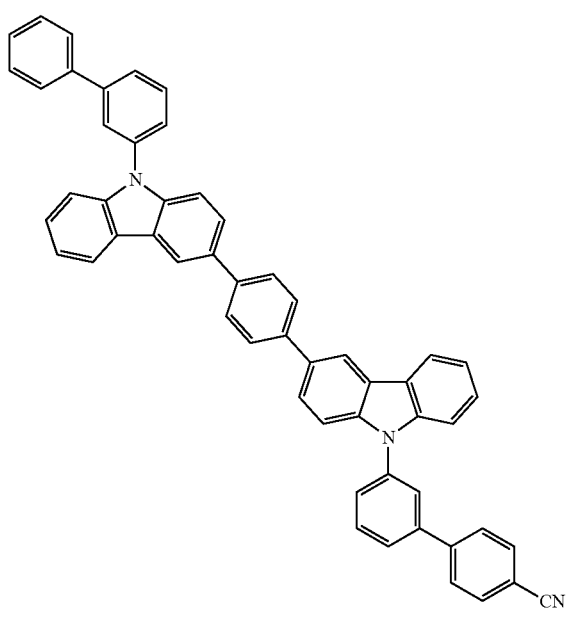
H1-399
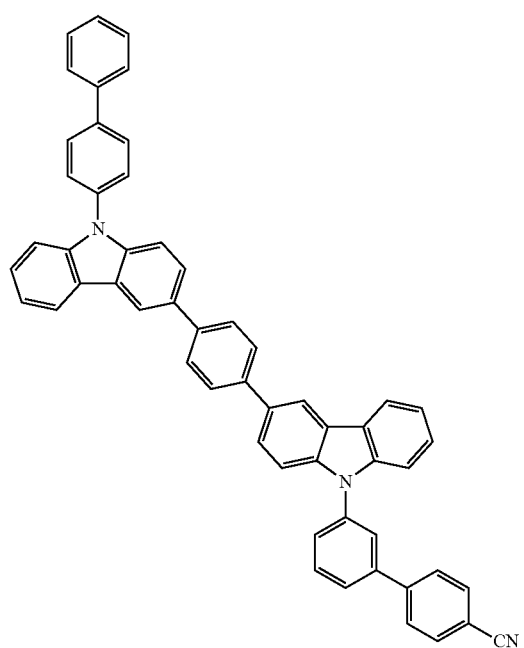
H1-400

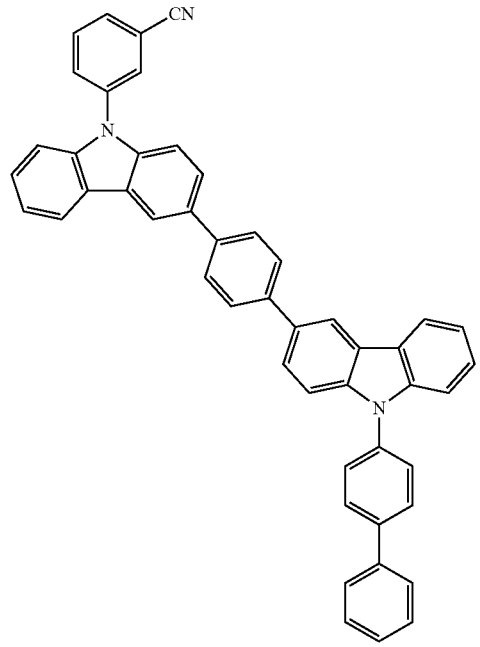
H1-401
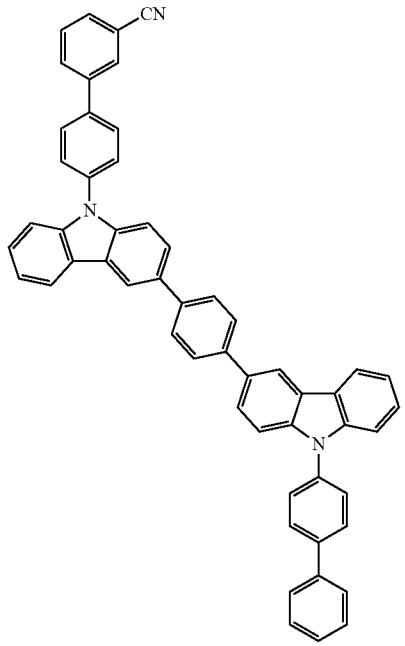
H1-402
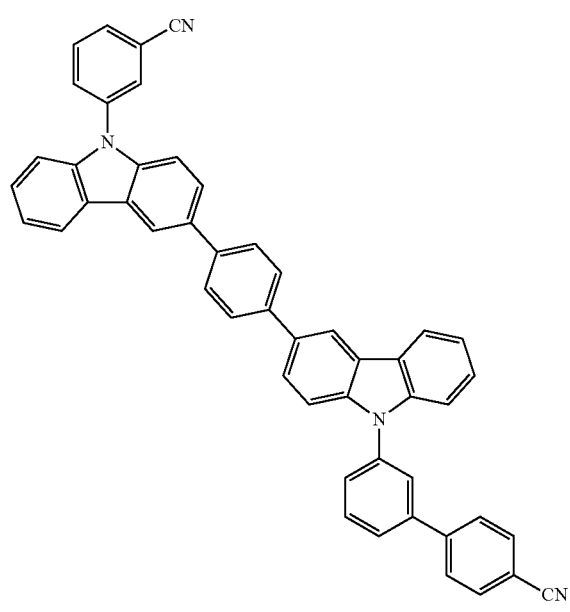
H1-403
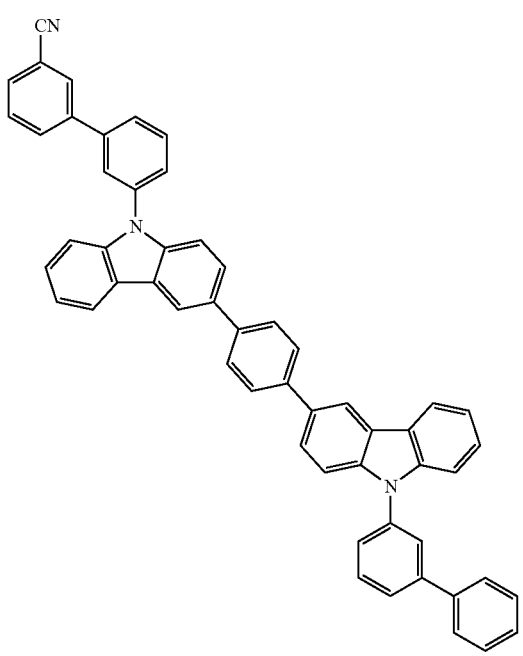
H1-404

H1-405
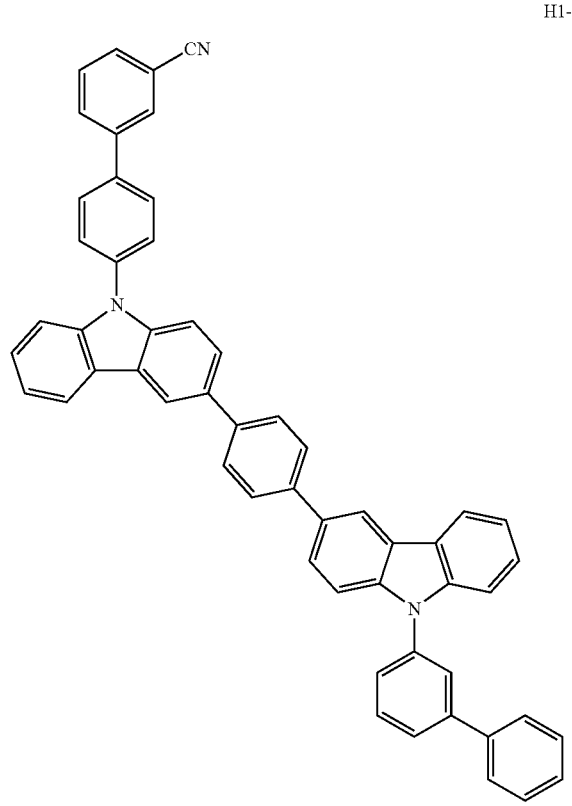
H1-406
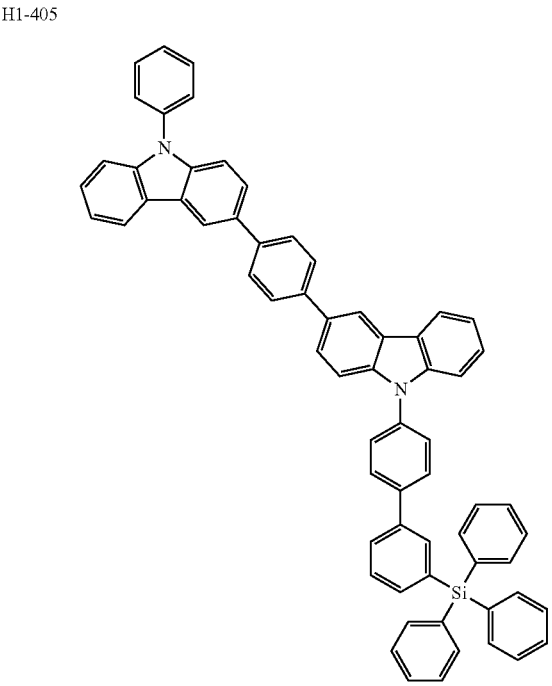
H1-407
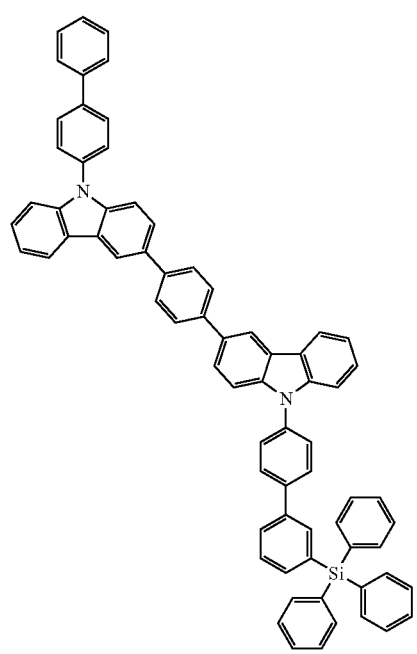
H1-408
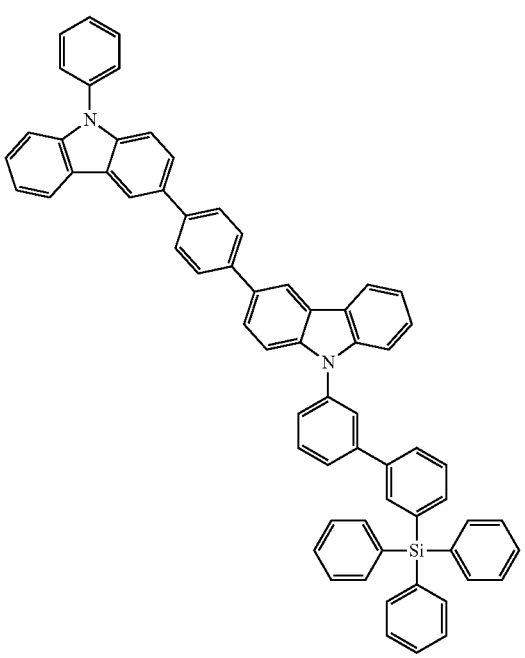

H1-409 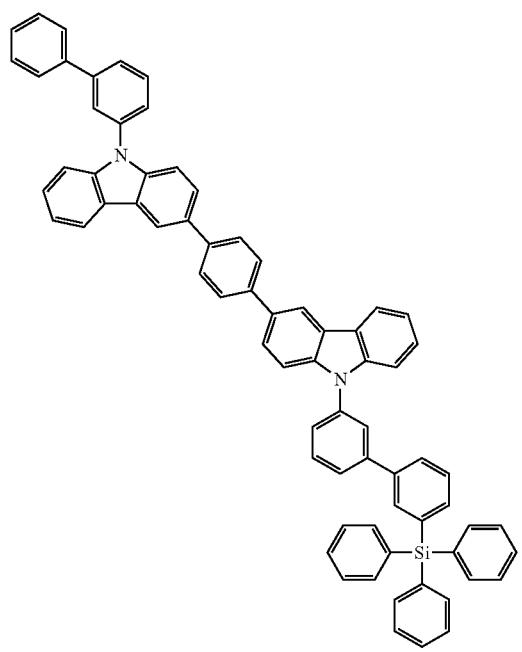
H1-410 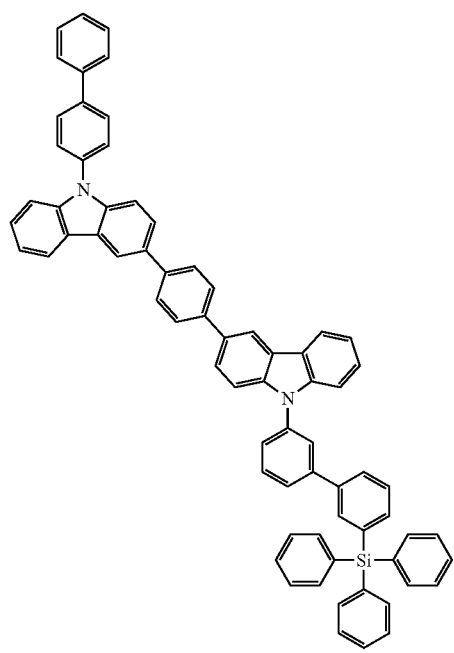
H1-411 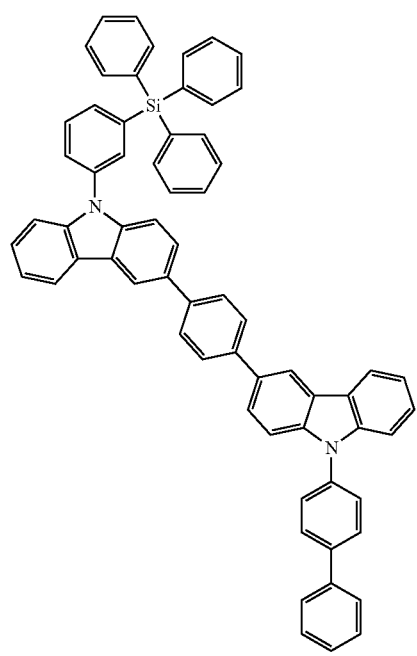
H1-412 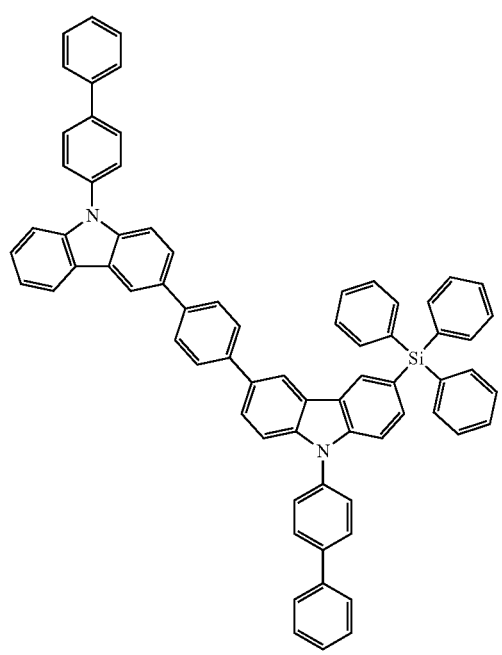

H1-413
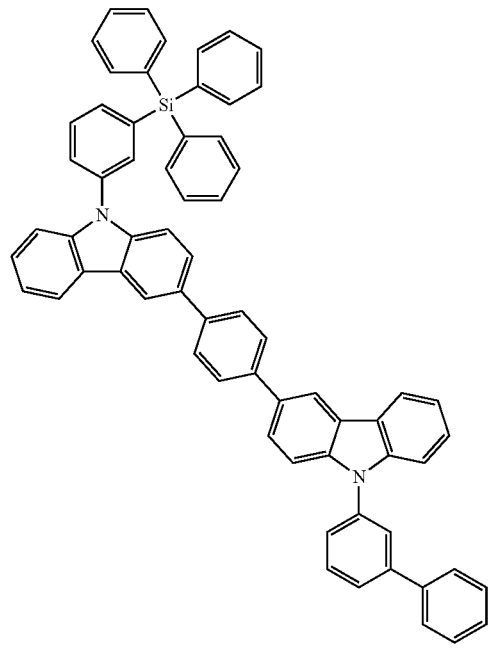
H1-414
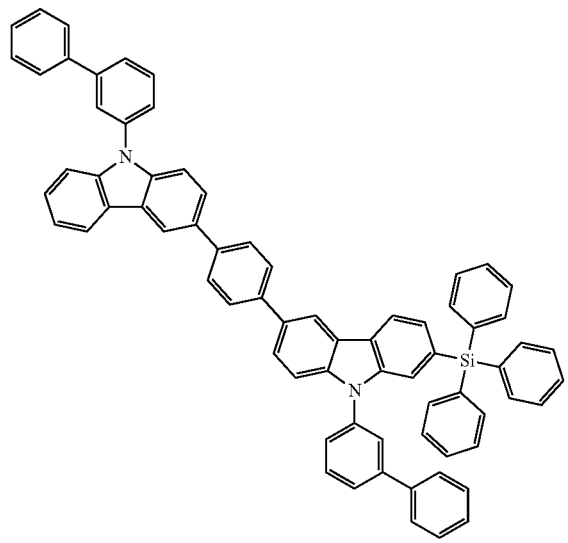
H1-415
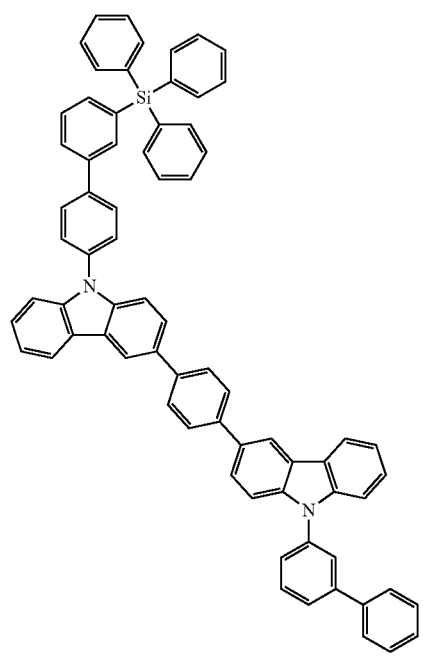
H1-416
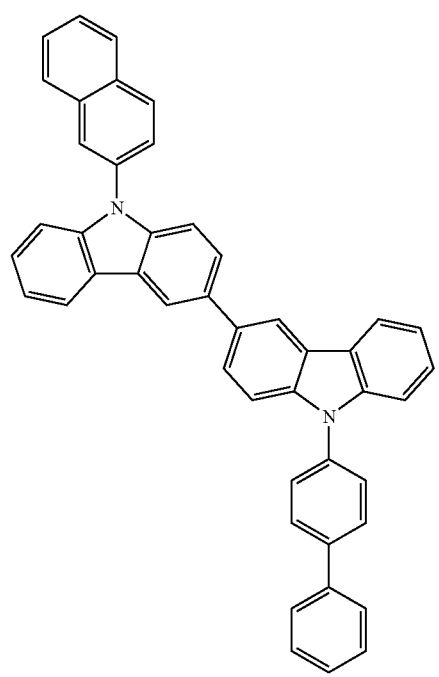

H1-417
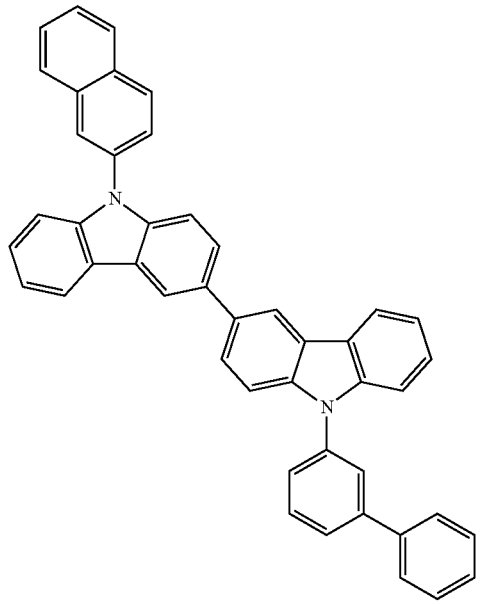
H1-418
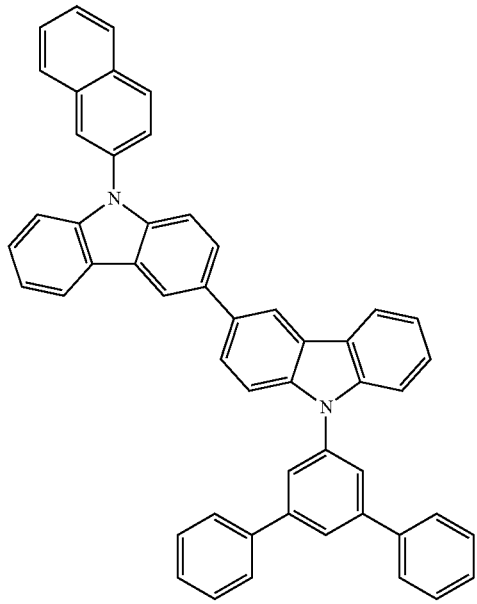
H1-419
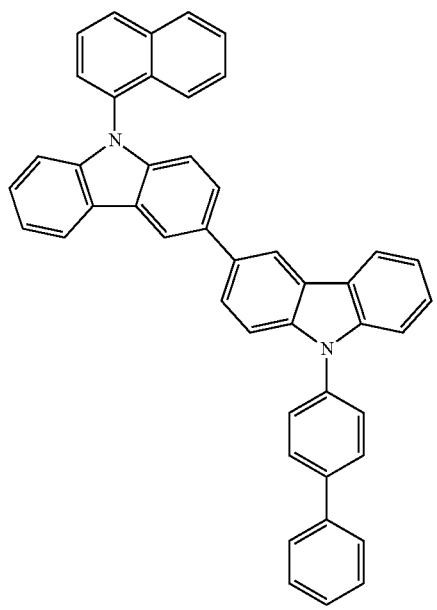
H1-420
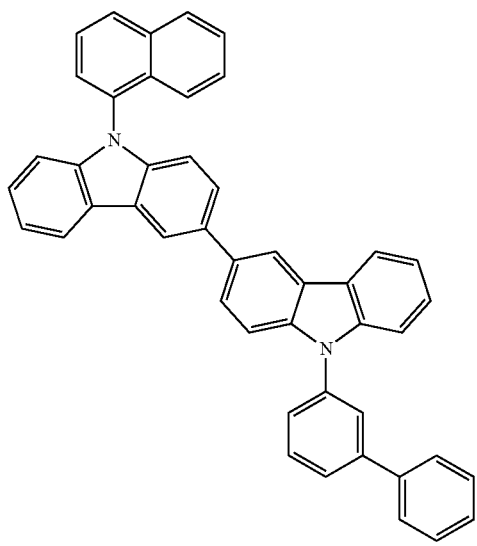

-continued
H1-421
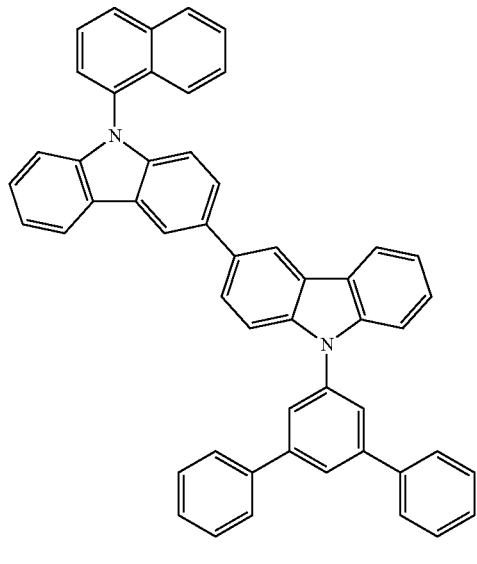
H1-422
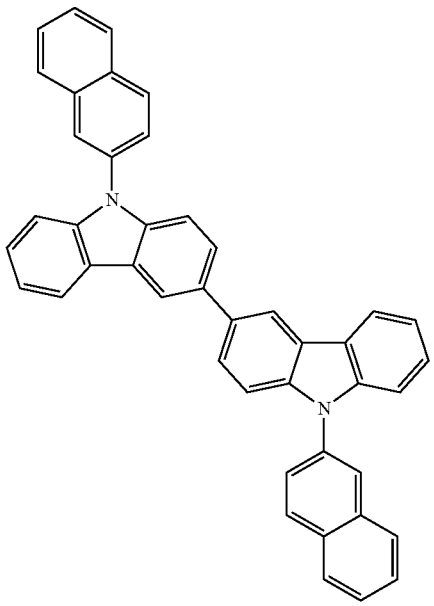
H1-423
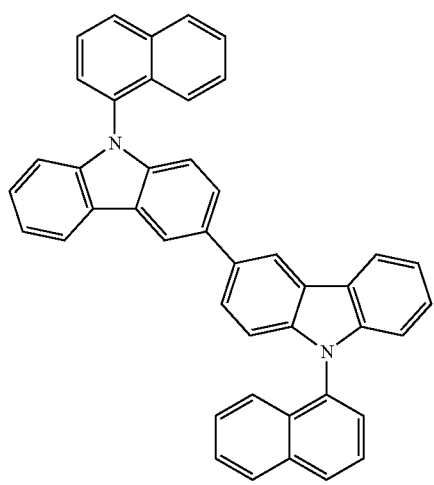
The second host compound represented by formula 2 includes the following, but is not limited thereto.
H2-1
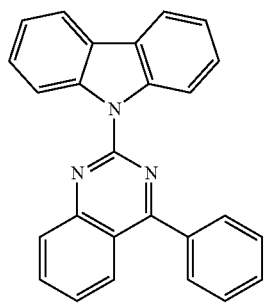
-continued
H2-2
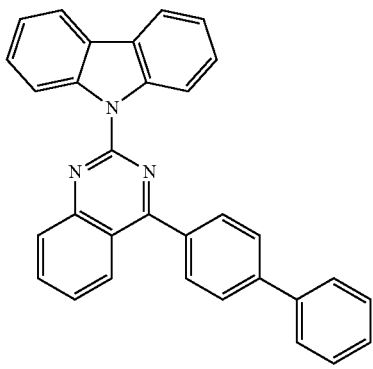

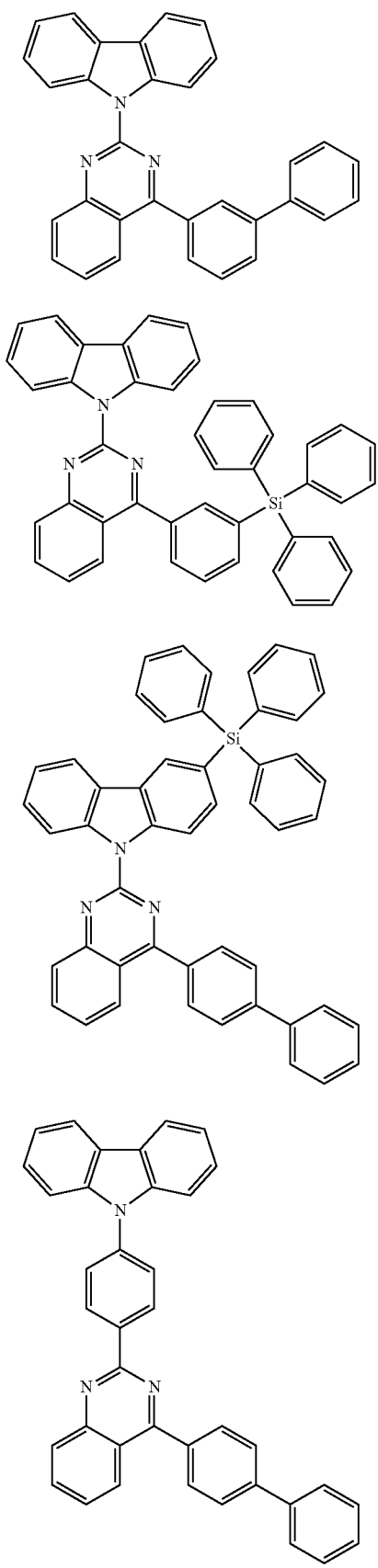
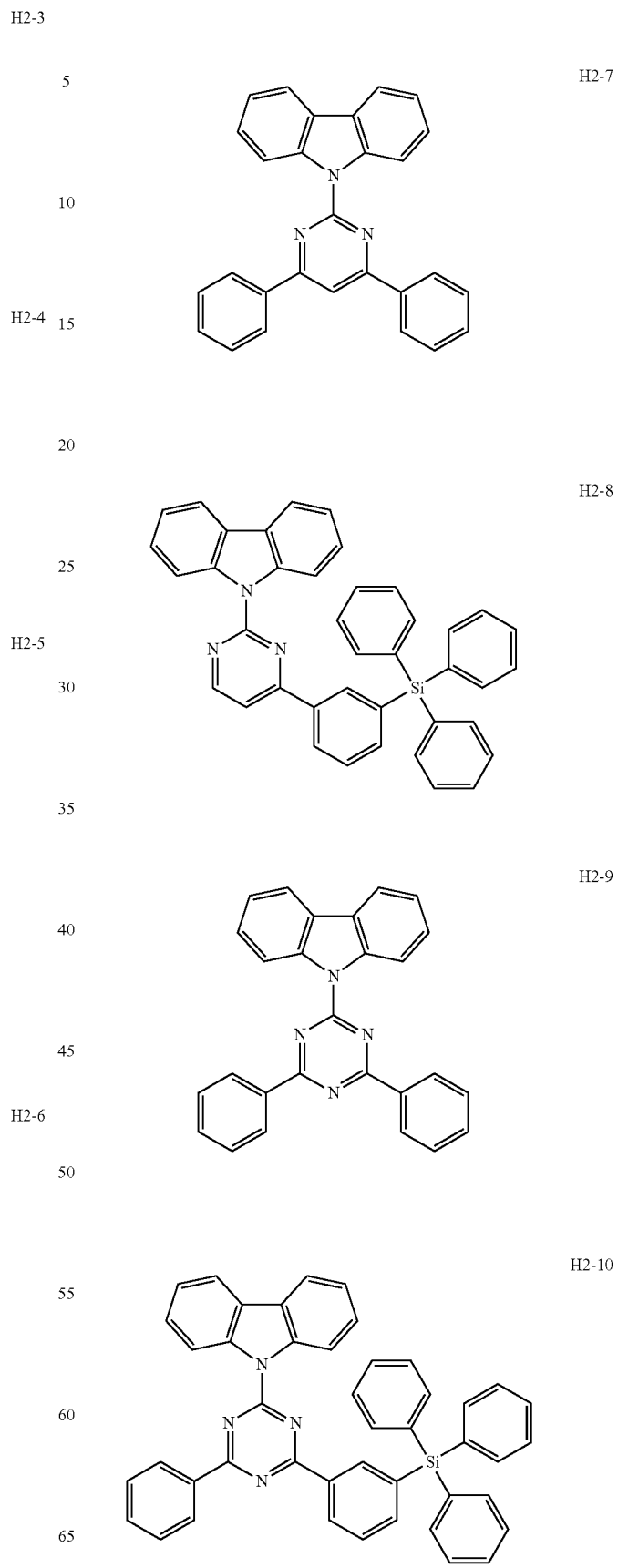

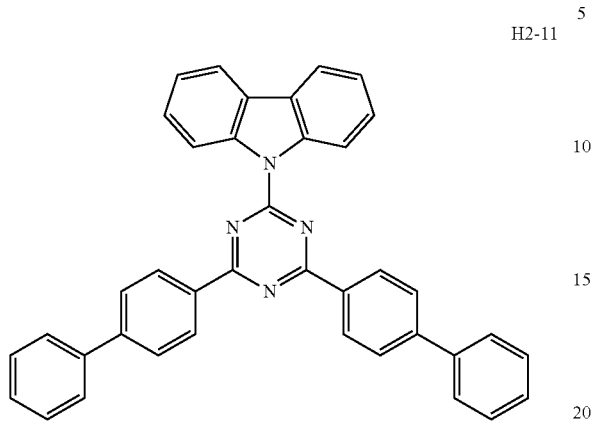
H2-11
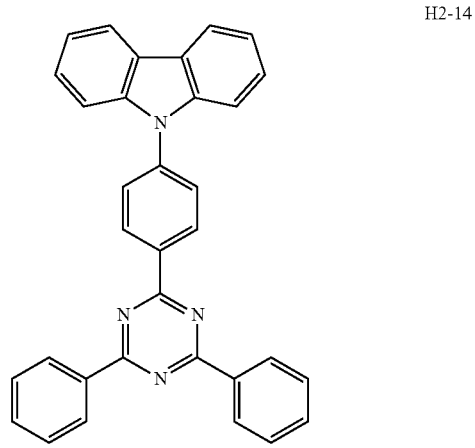
H2-14
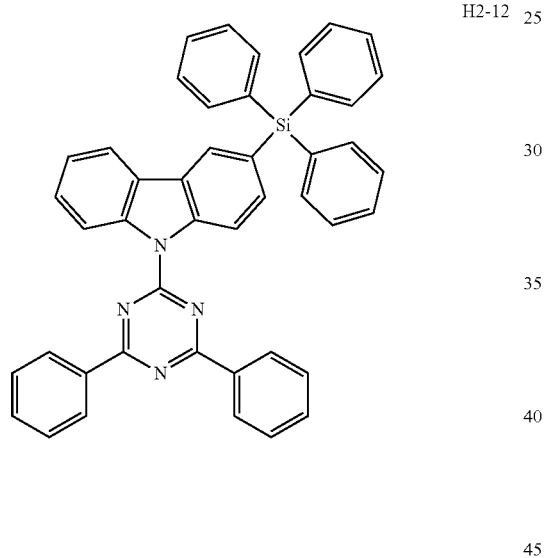
H2-12
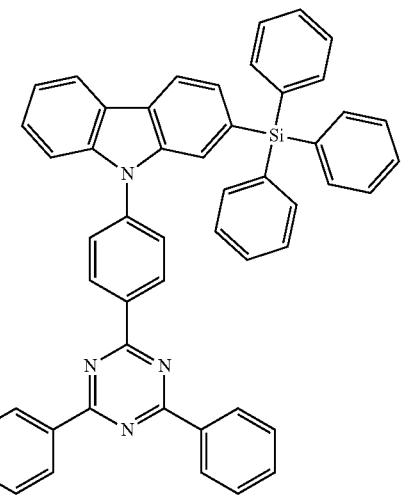
H2-15
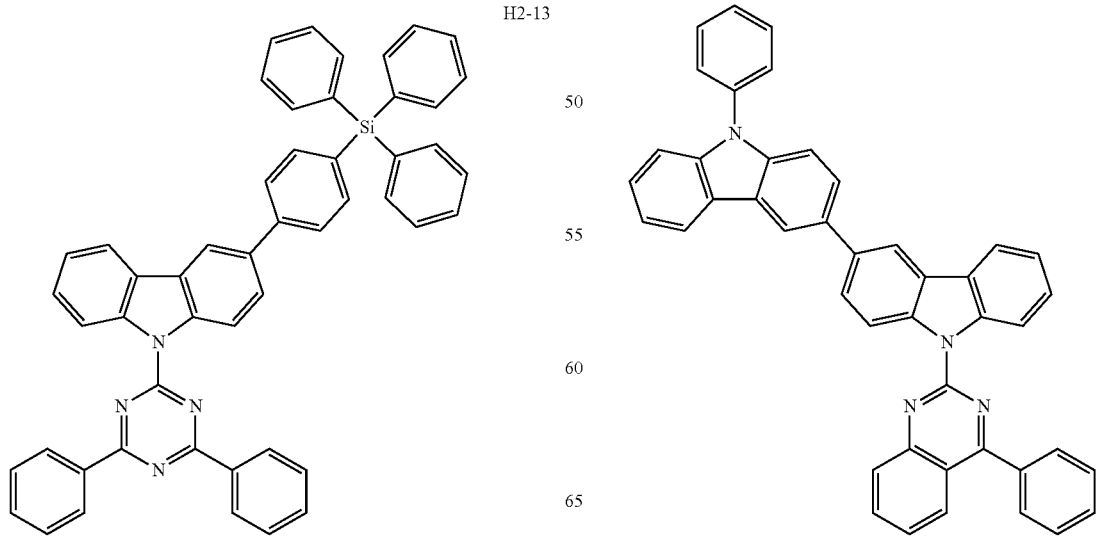
H2-13
H2-16

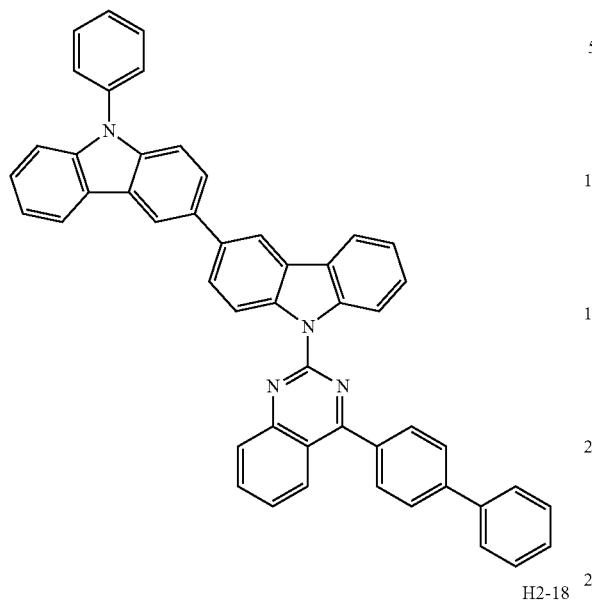
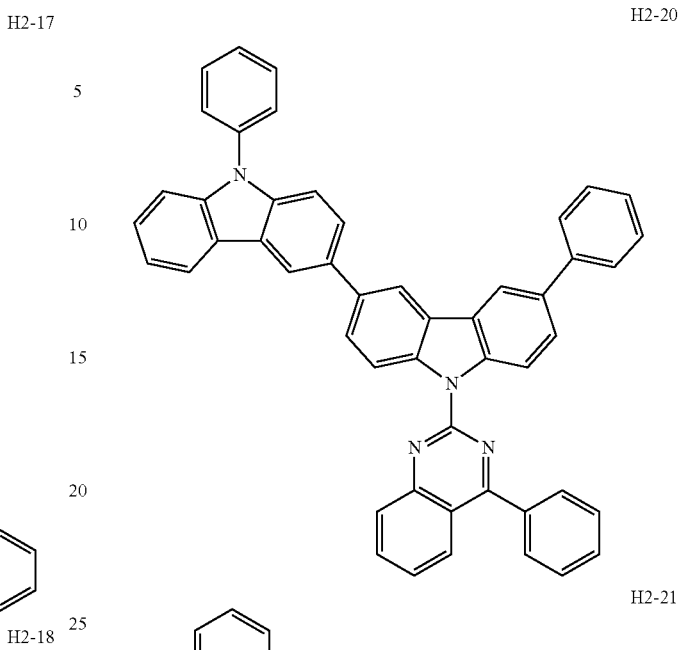

H2-23
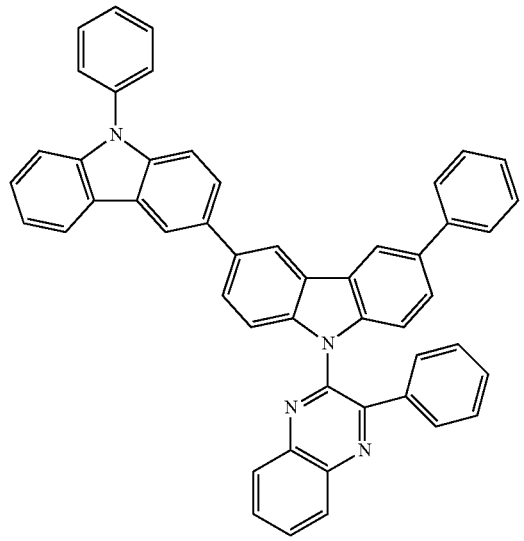
H2-24
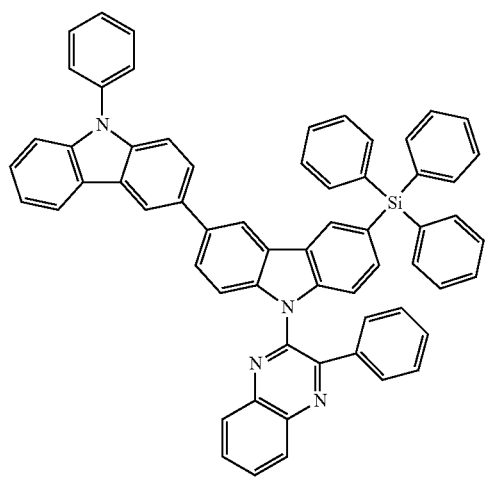
H2-25
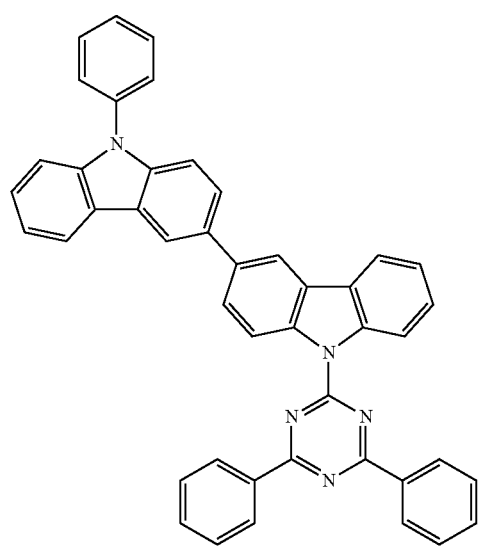
H2-26
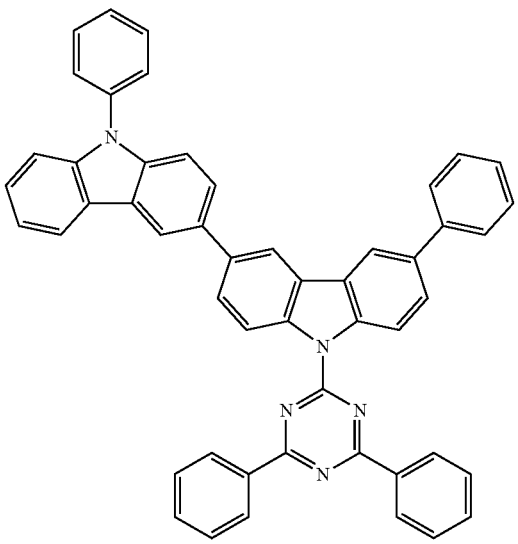
H2-27
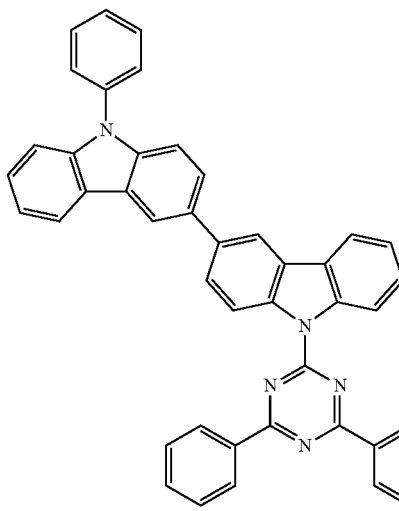
H2-28
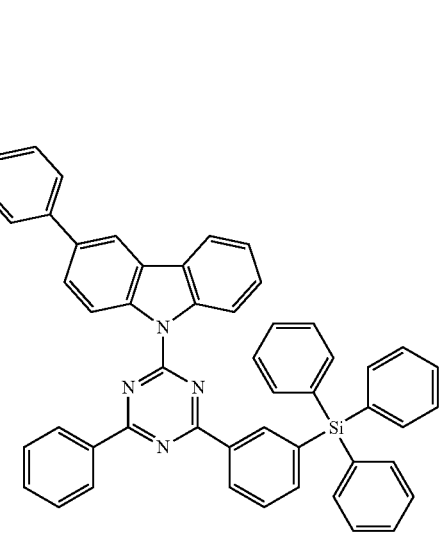

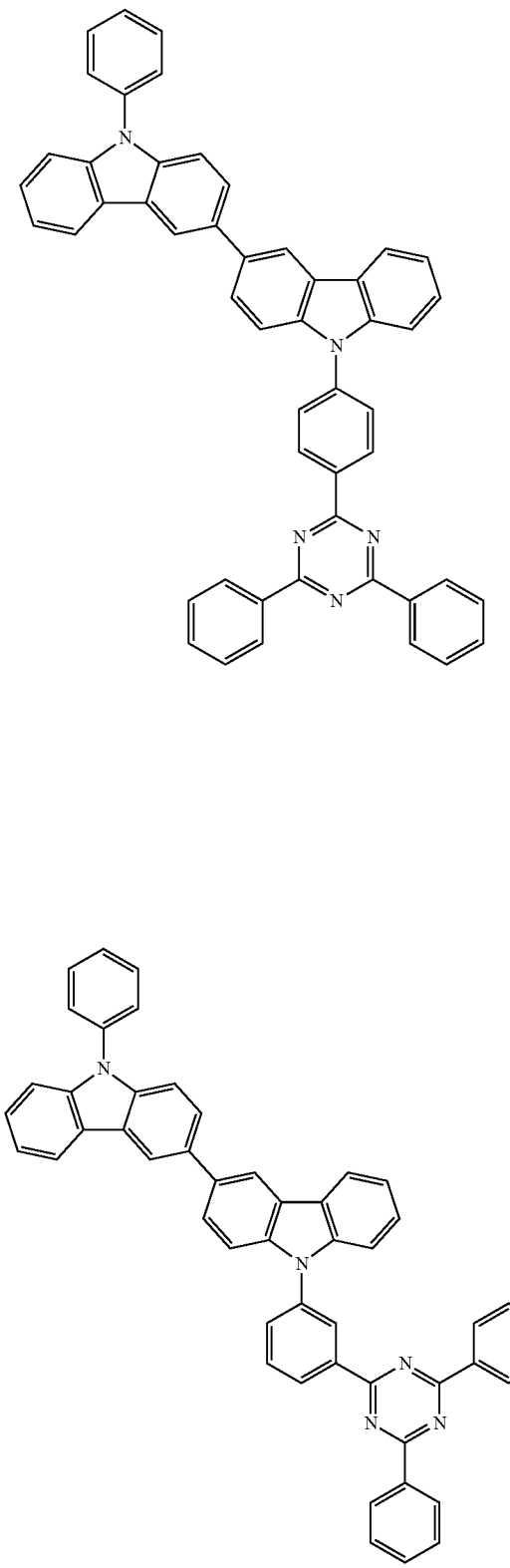
H2-29
H2-30
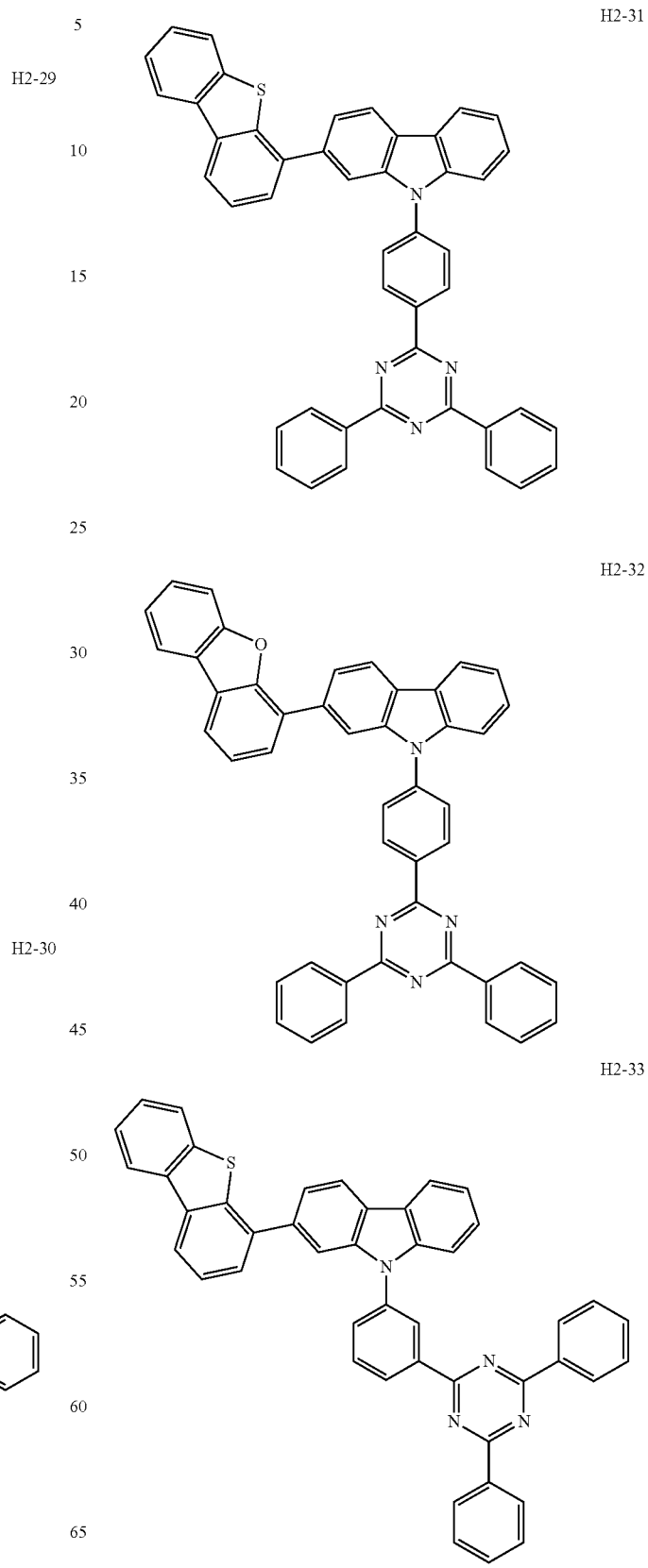
H2-31
H2-32
H2-33

H2-34
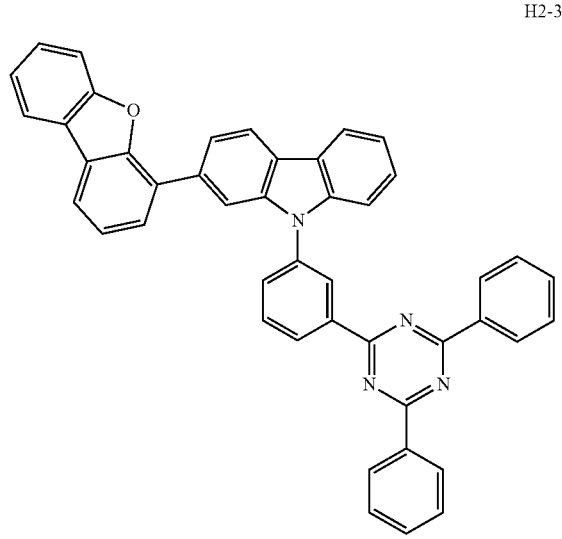
H2-35
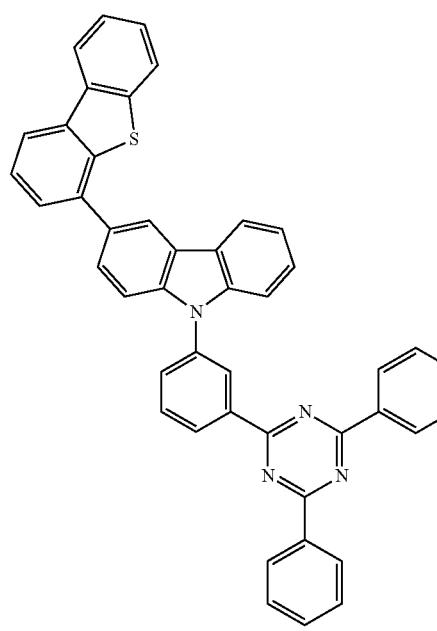
H2-36
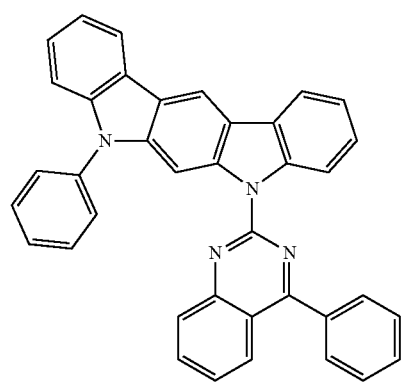
H2-37
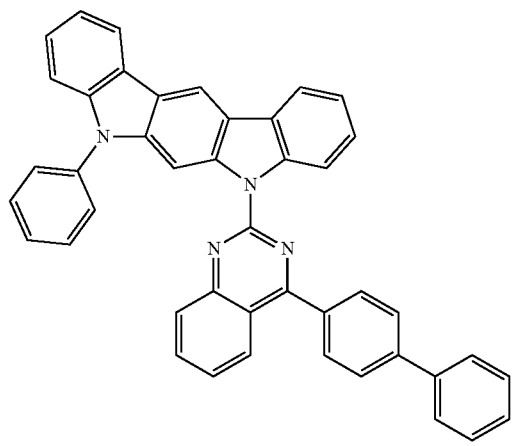
H2-38
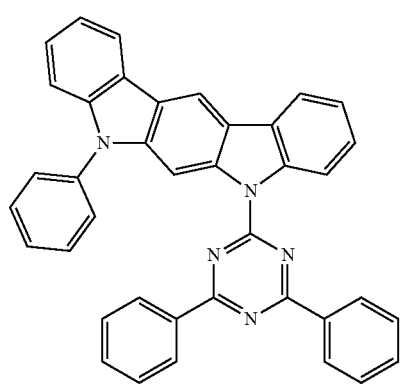
H2-39
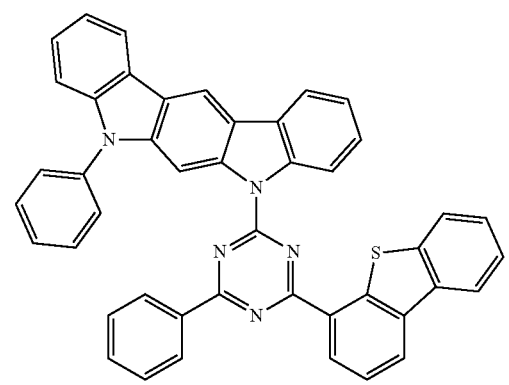

-continued
H2-40
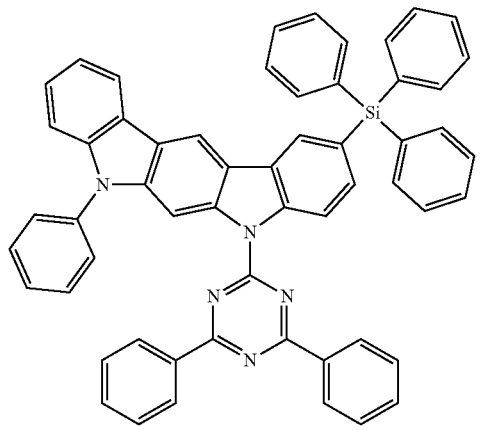
H2-41
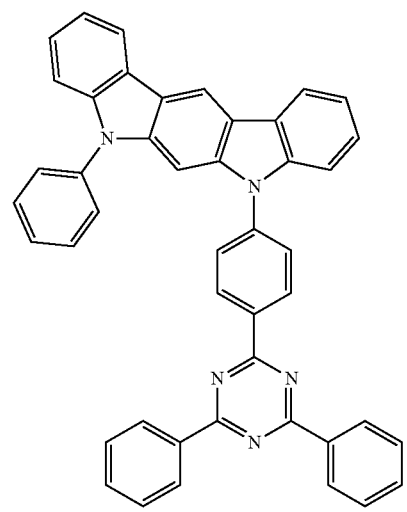
H2-42
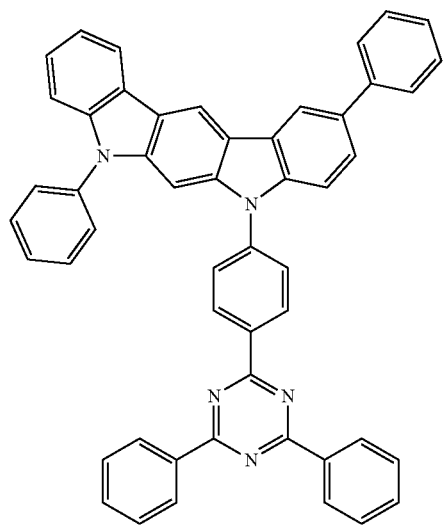
-continued
H2-43
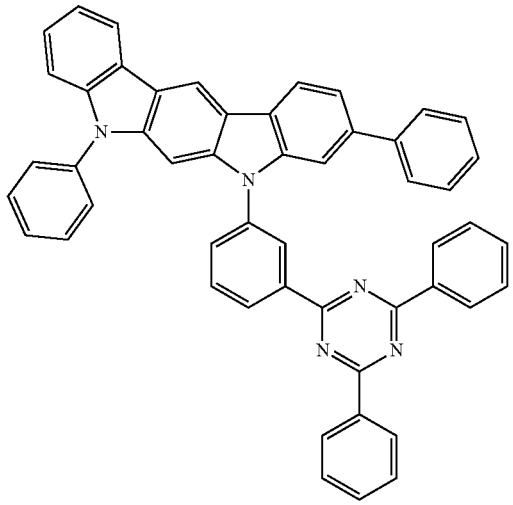
H2-44
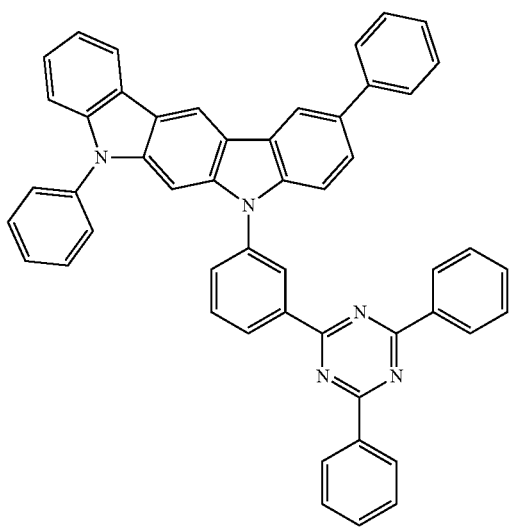
H2-45
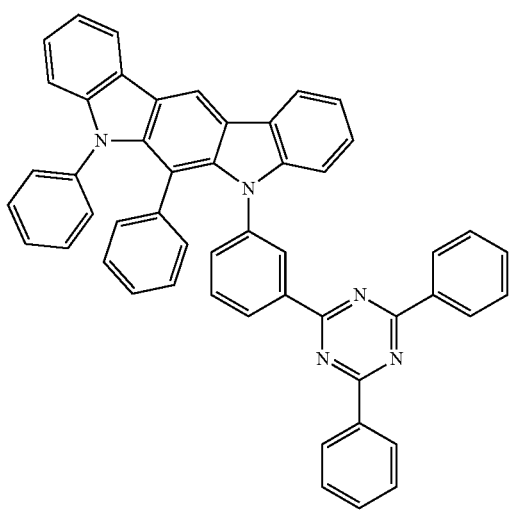

H2-46
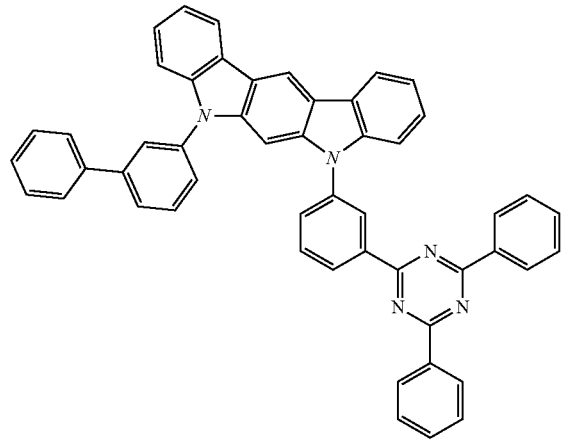
H2-47
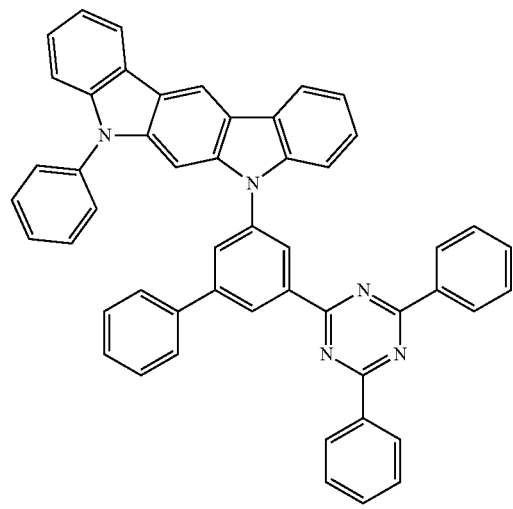
H2-48
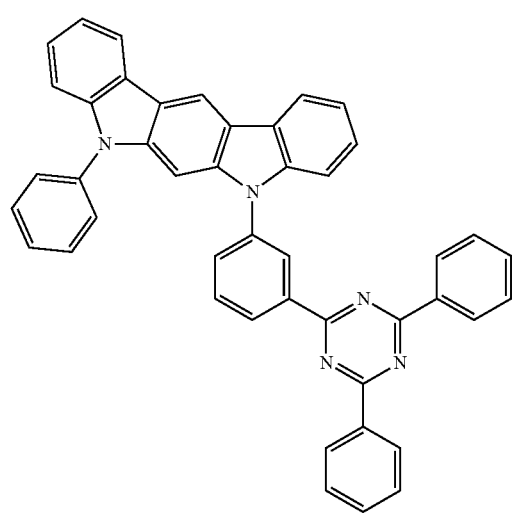
H2-49
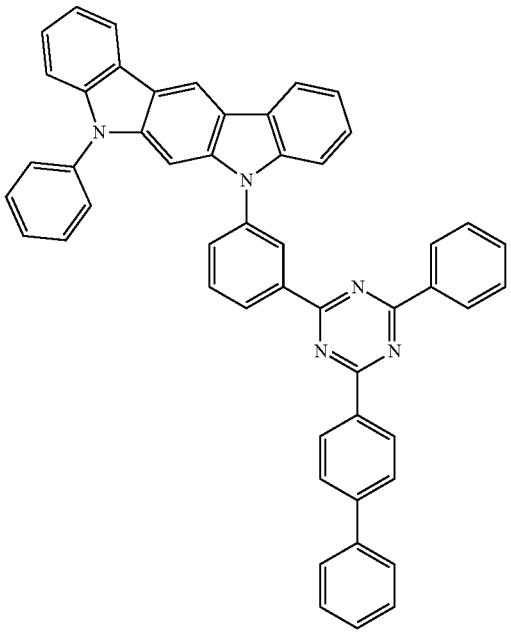
H2-50
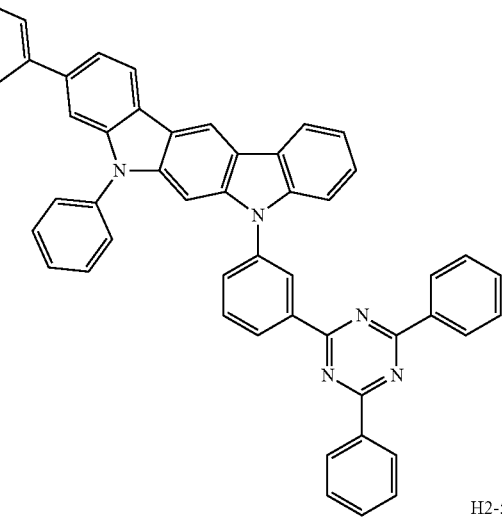
H2-51
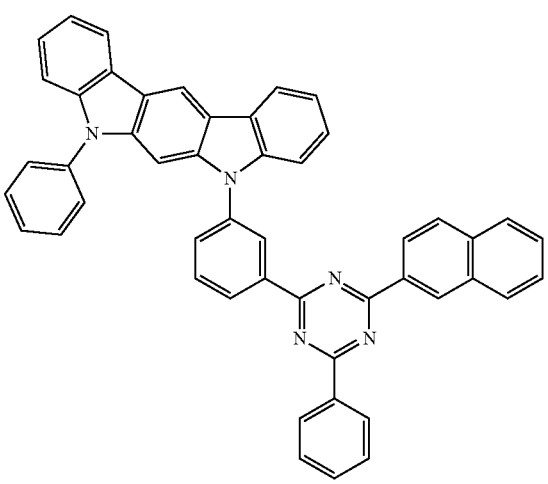

H2-52
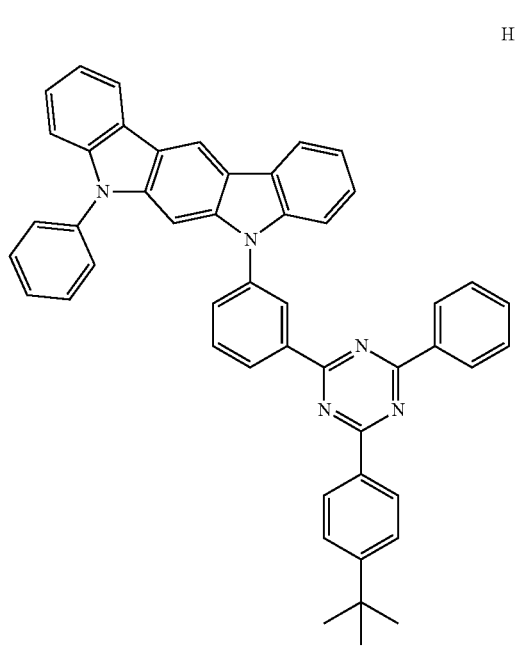
H2-53
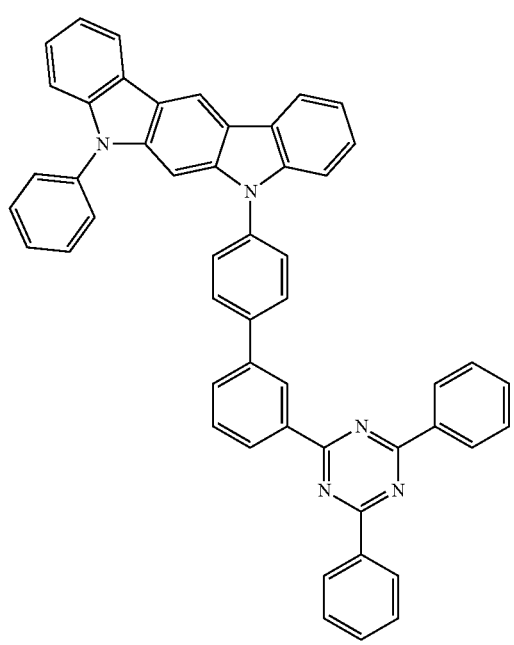
H2-54
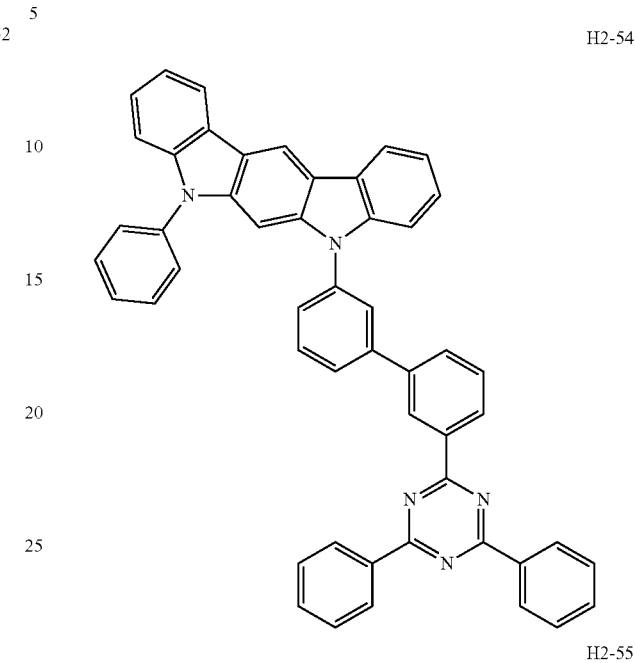
H2-55
H2-56
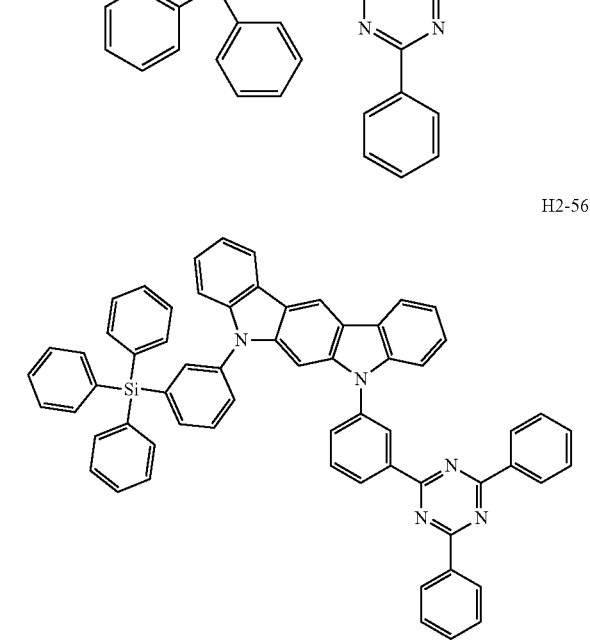

H2-57
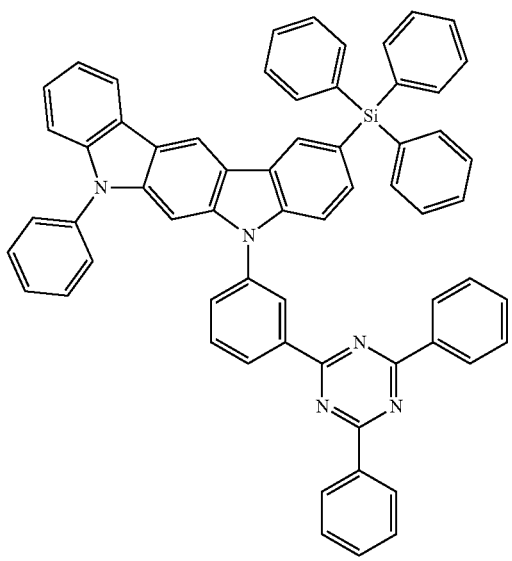
H2-58
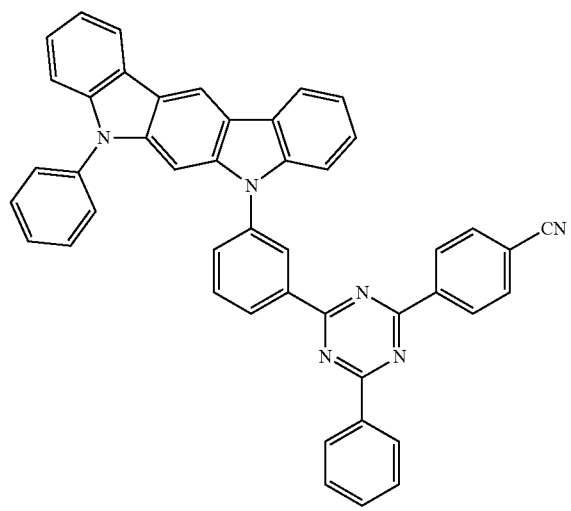
H2-59
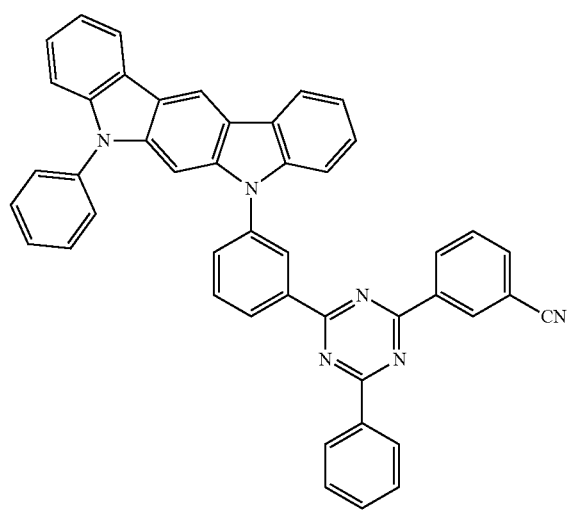
H2-60
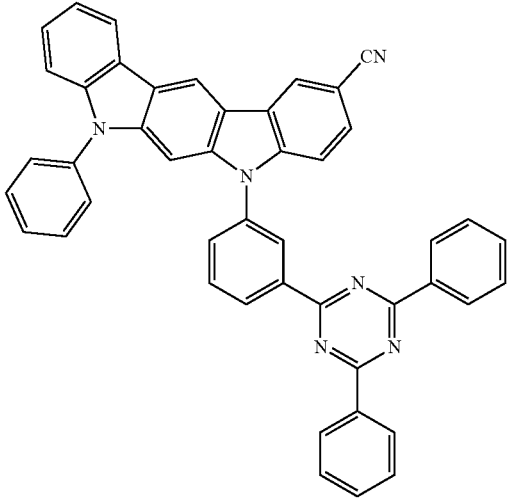
H2-61
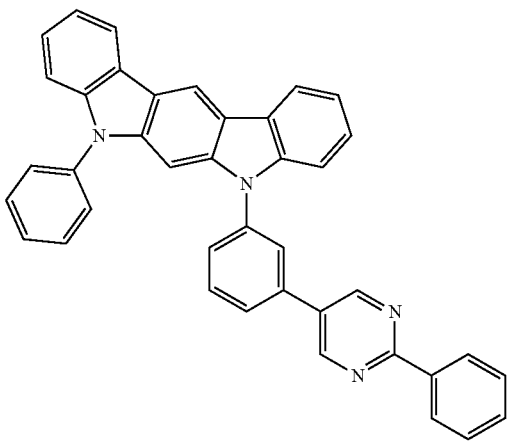
H2-62
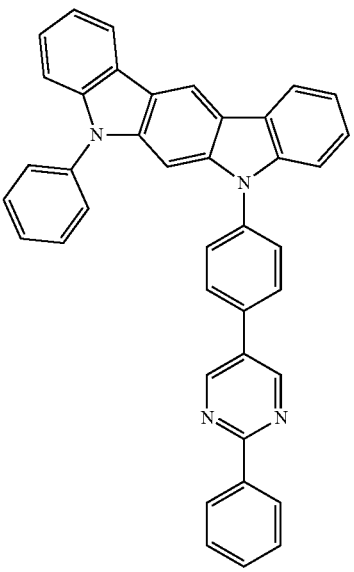

H2-63
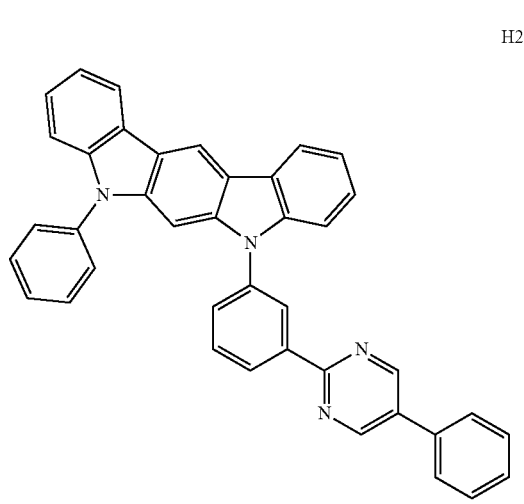
H2-66
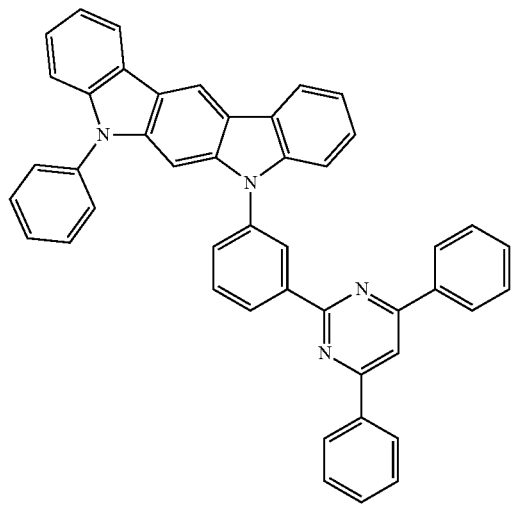
H2-64
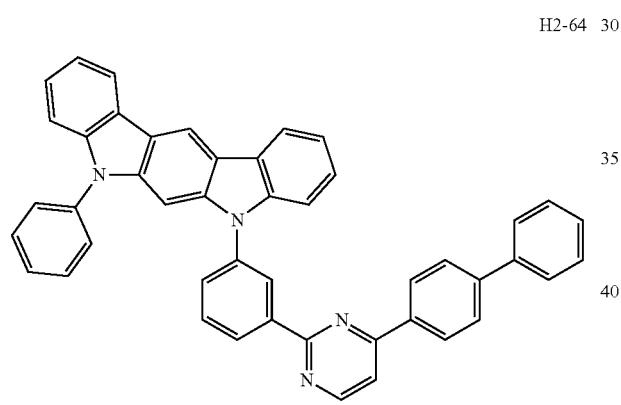
H2-67
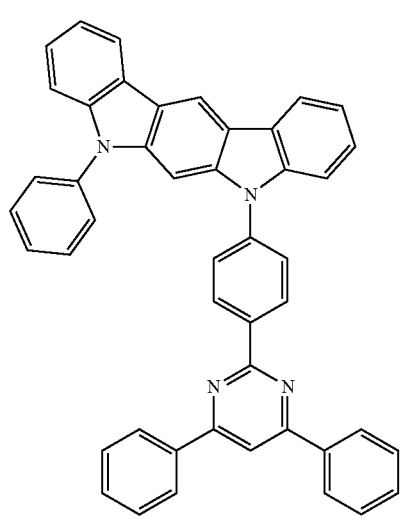
H2-65
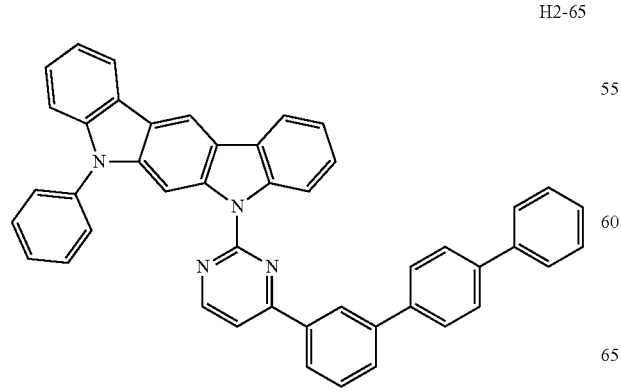
H2-68
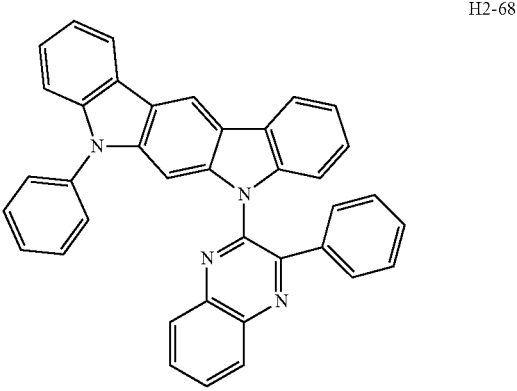

-continued
H2-69
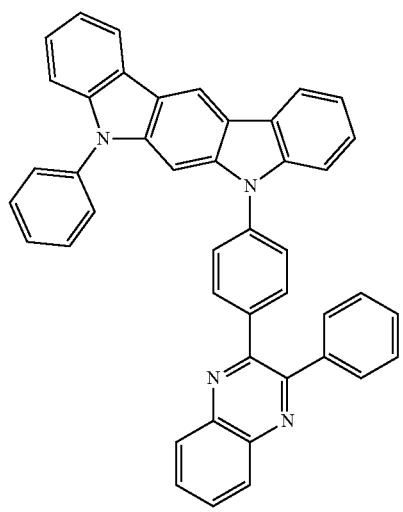
H2-70
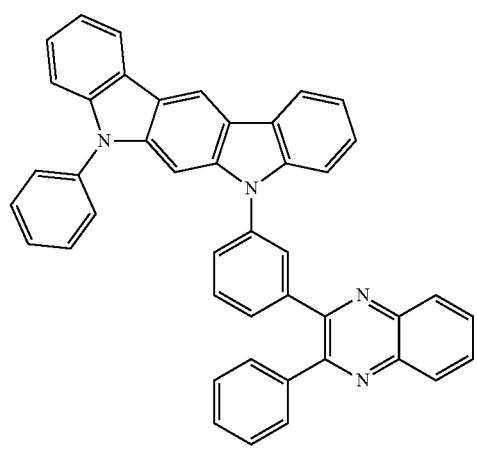
H2-71
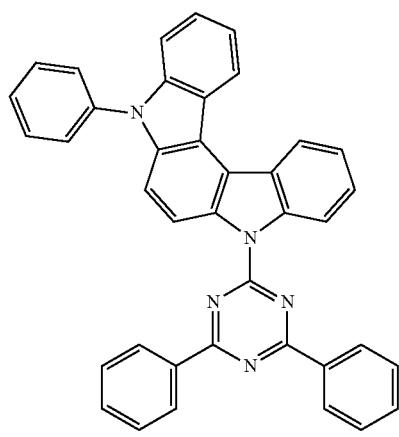
-continued
H2-72
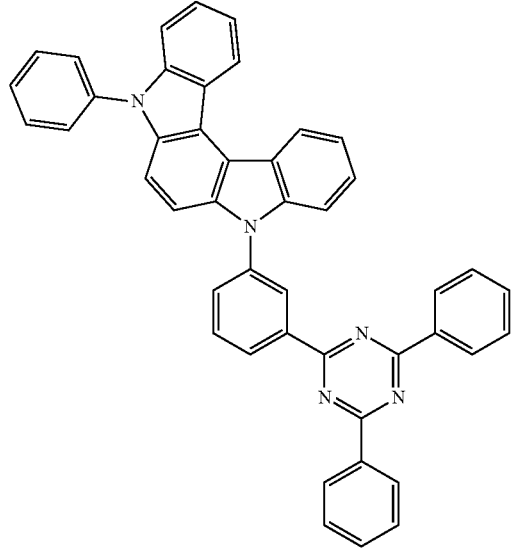
H2-73
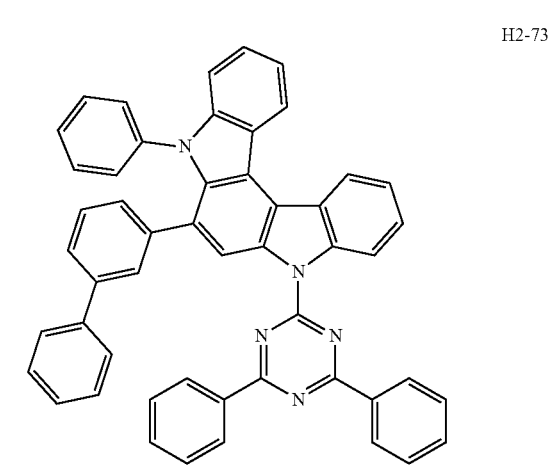
H2-74
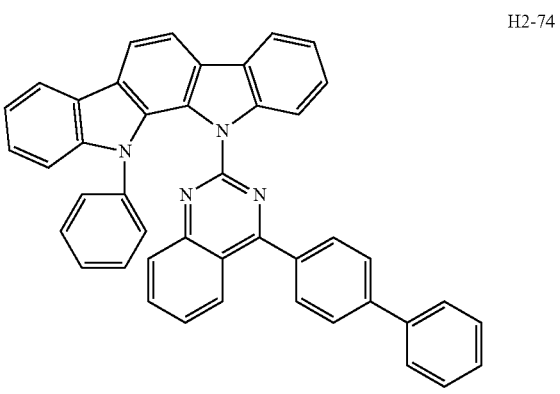

H2-75
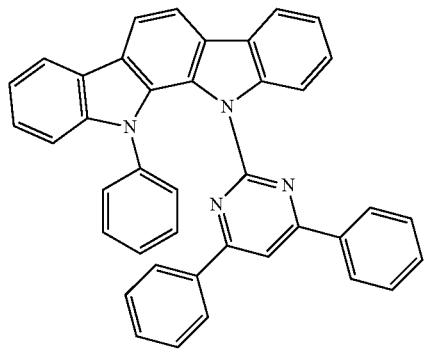
H2-76
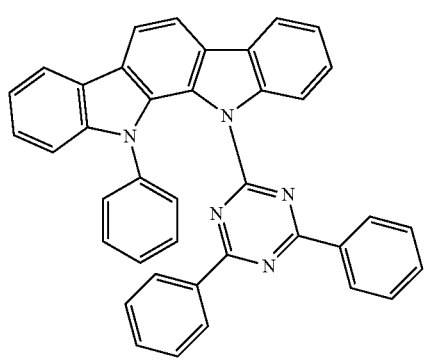
H2-77
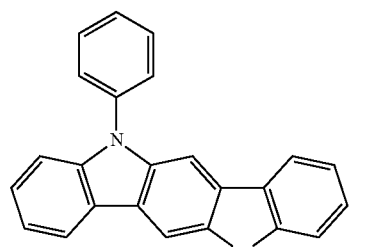
H2-78
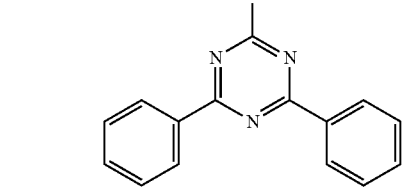
H2-79
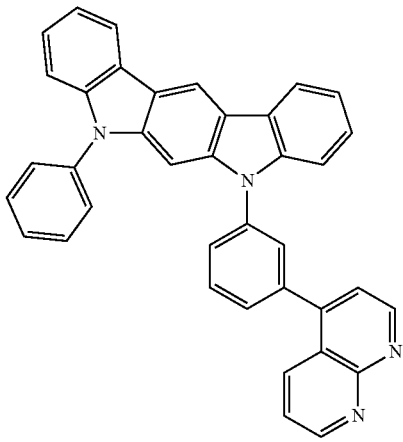
H2-80
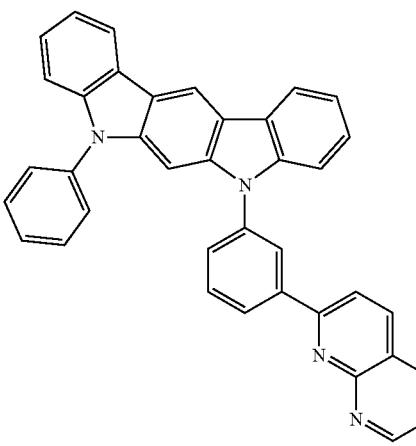
H2-81
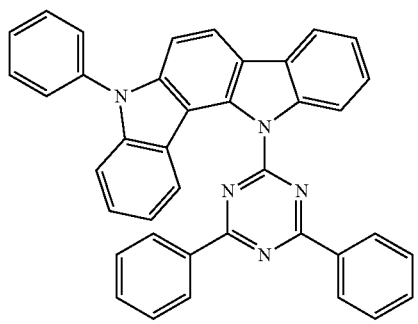

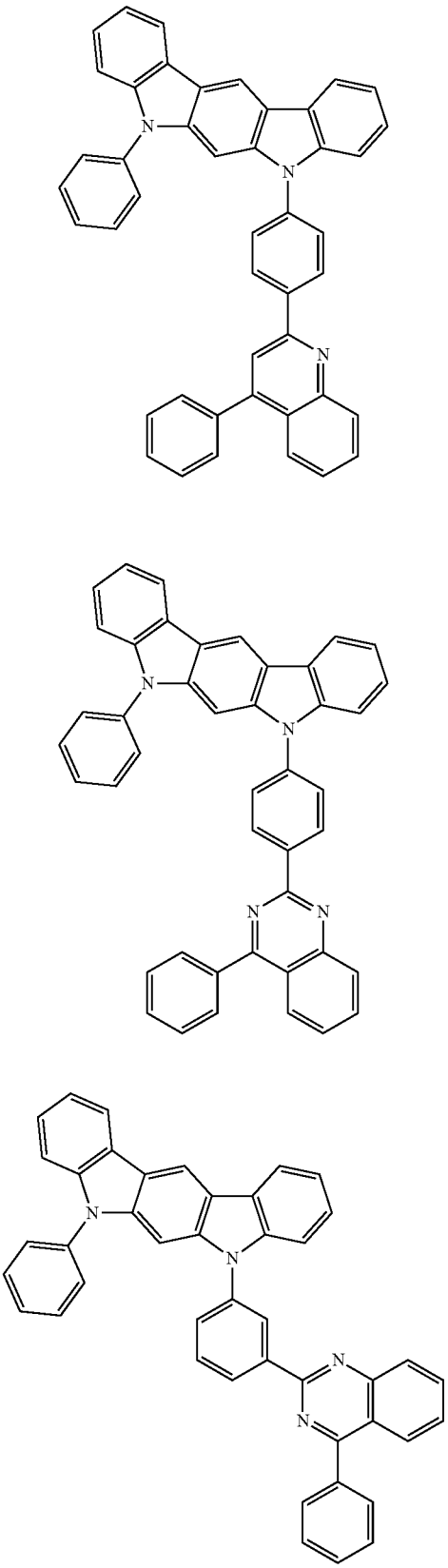
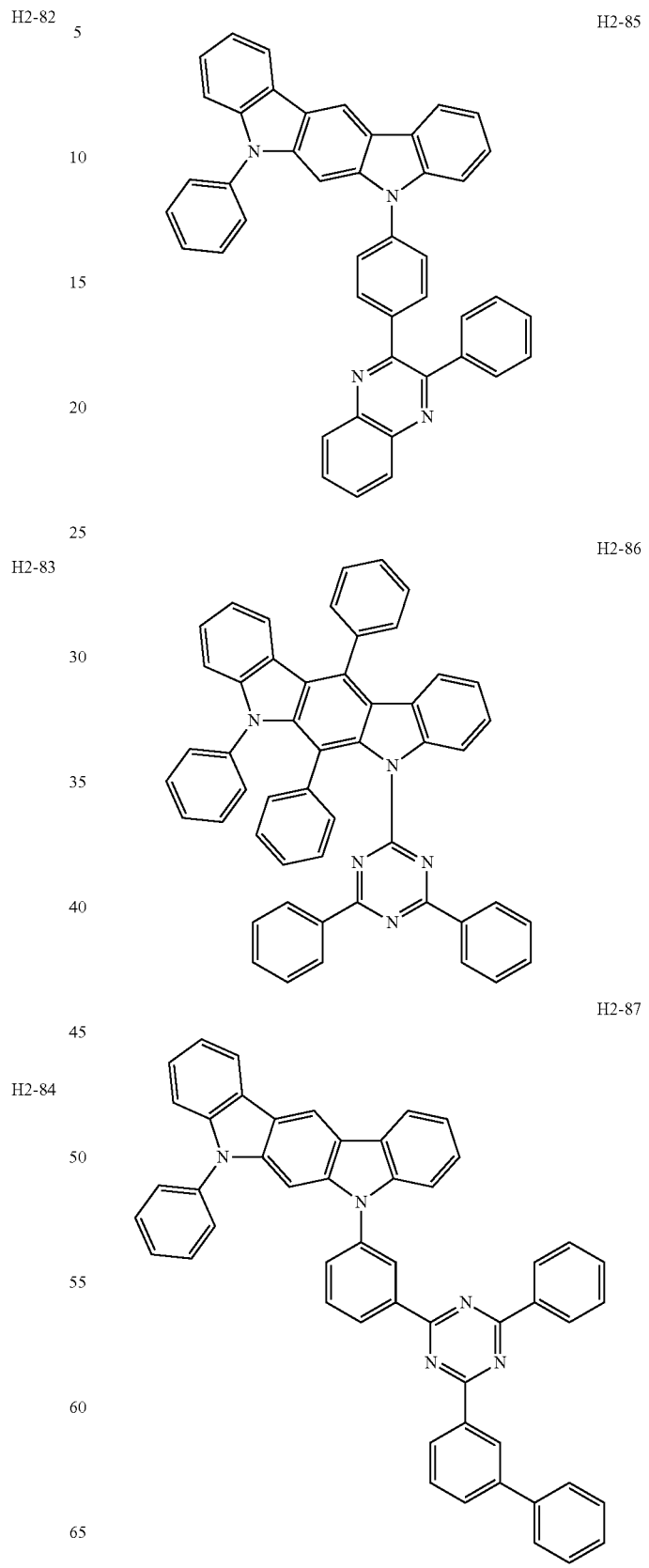

H2-88
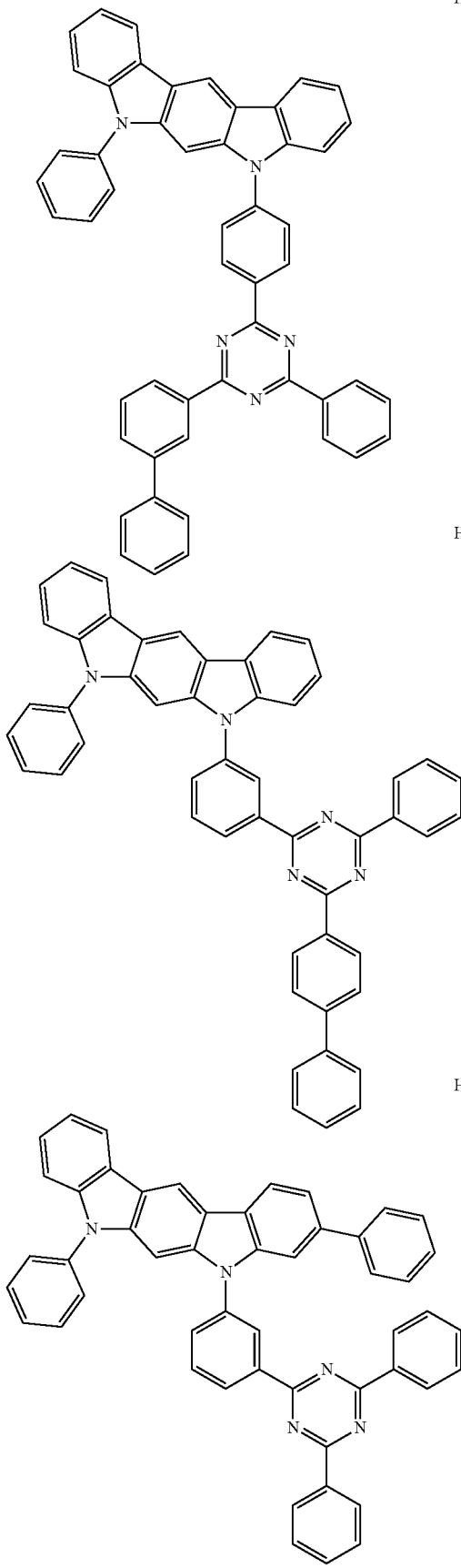
H2-89
H2-90
H2-91
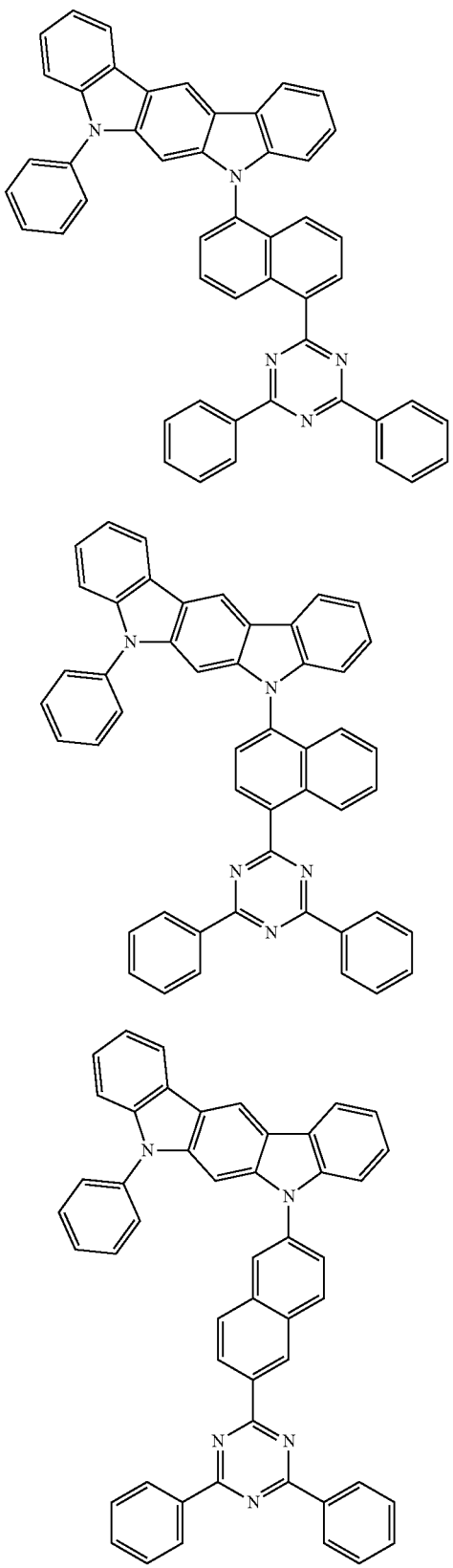
H2-92
H2-93

H2-94
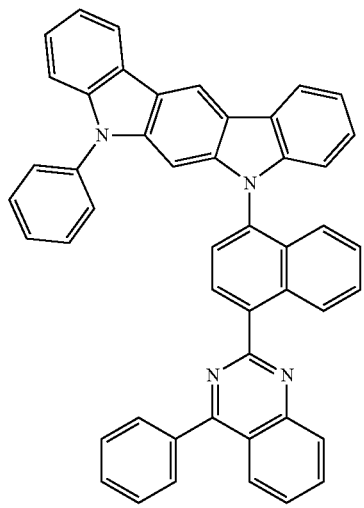
H2-95
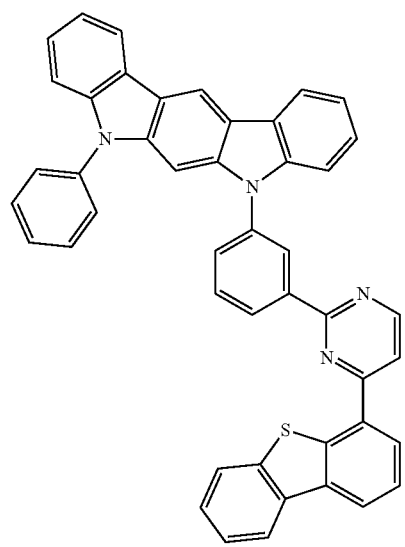
H2-96
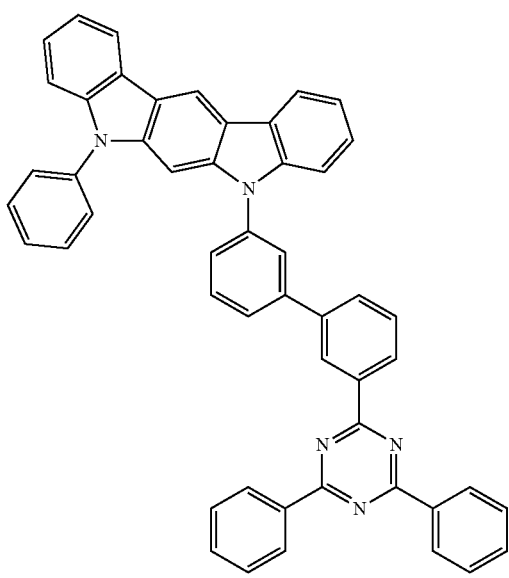
H2-97
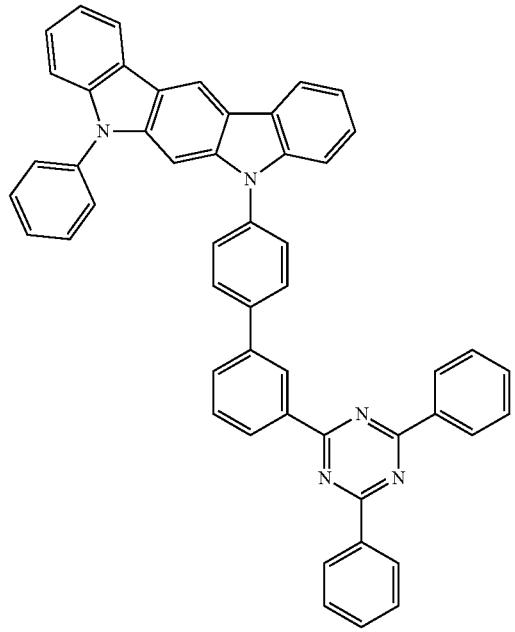
H2-98
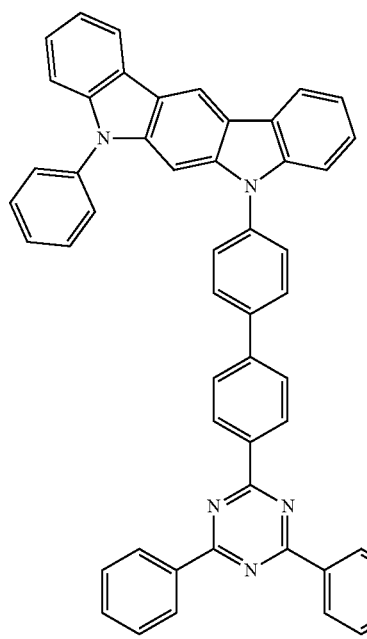

H2-99
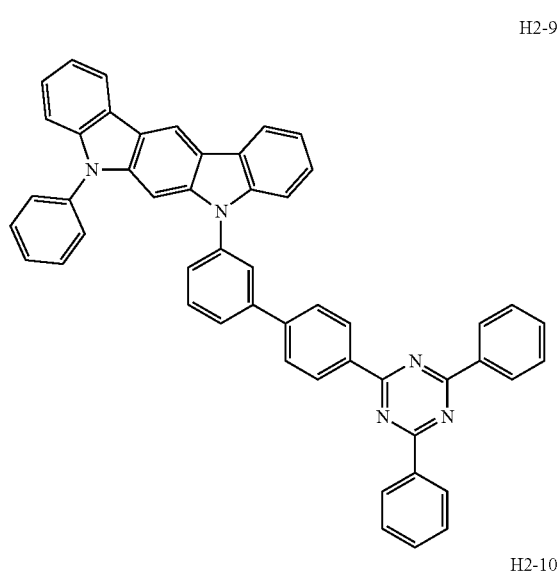
H2-100
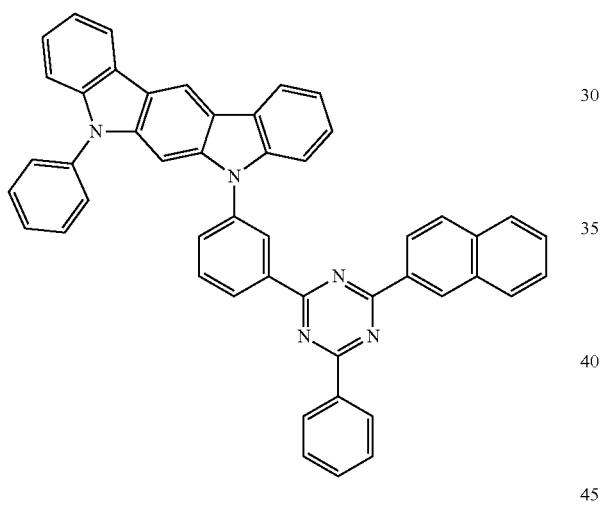
H2-101
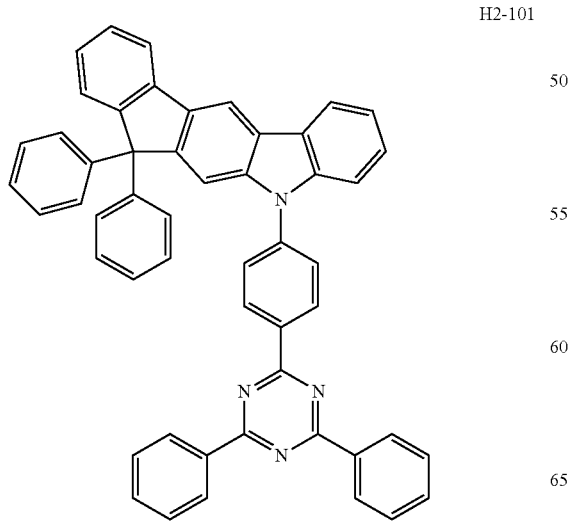
H2-102
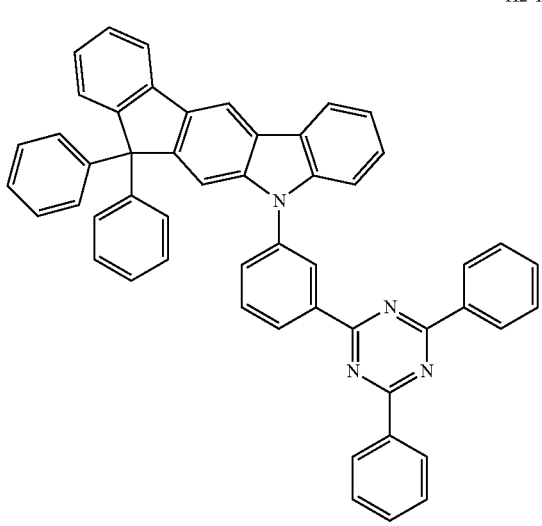
H2-103
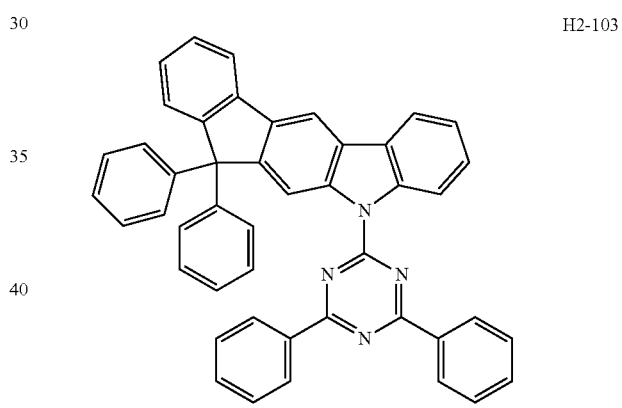
H2-104
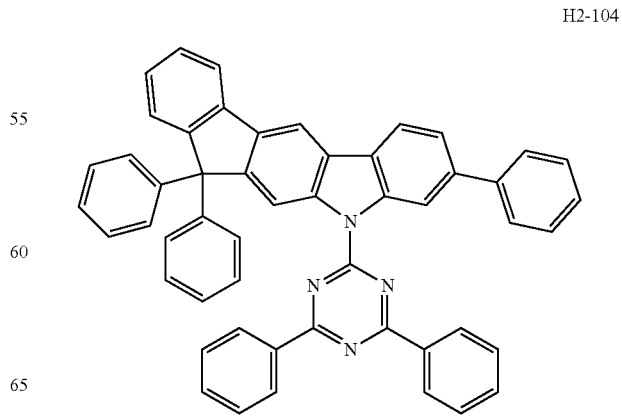

H2-105
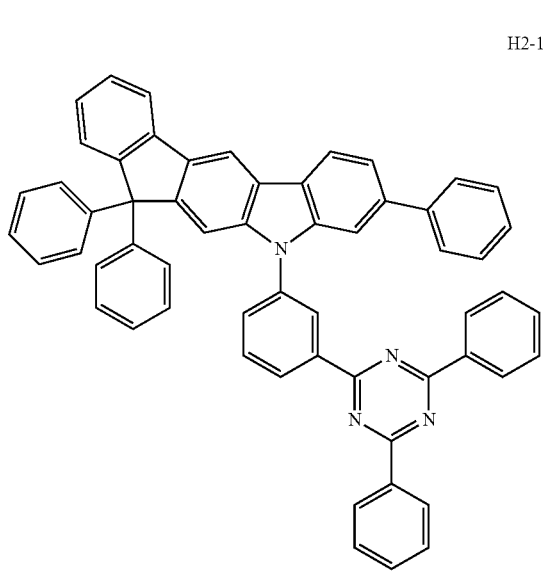
H2-108
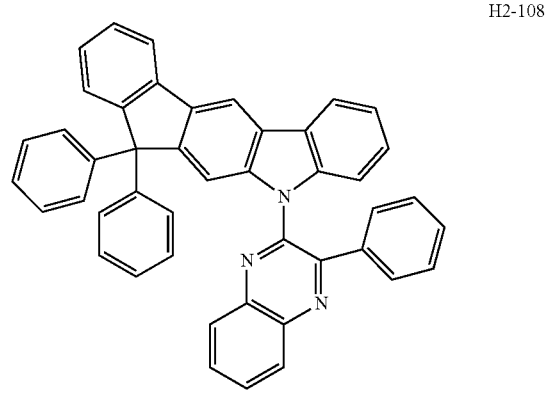
H2-106
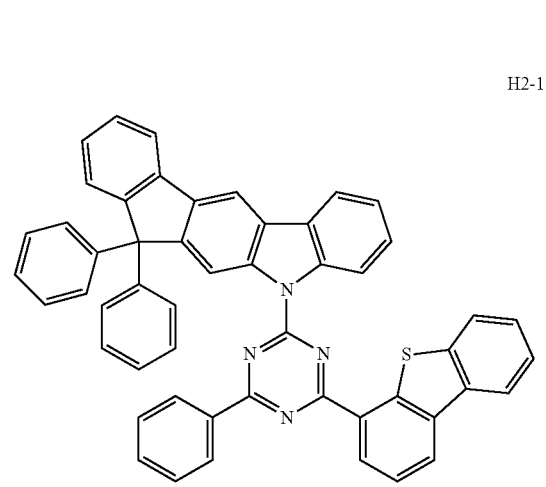
H2-109
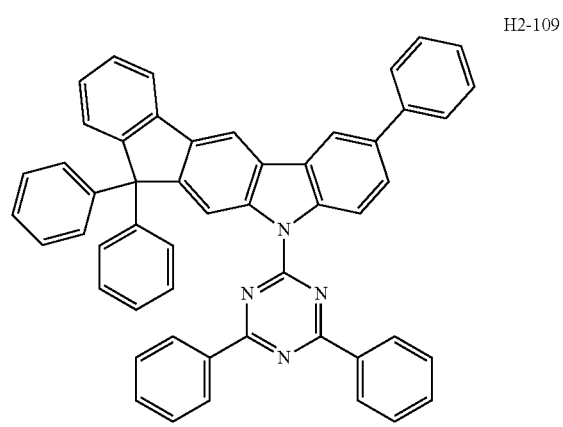
H2-107
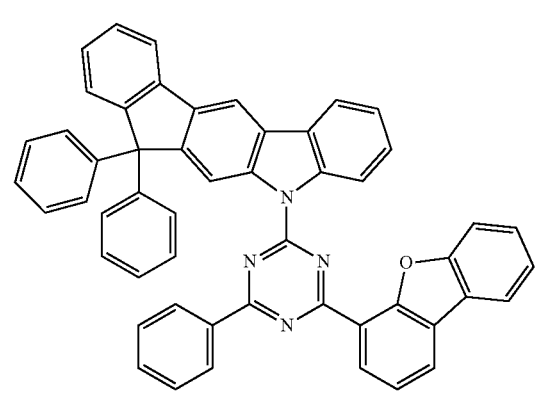
H2-110
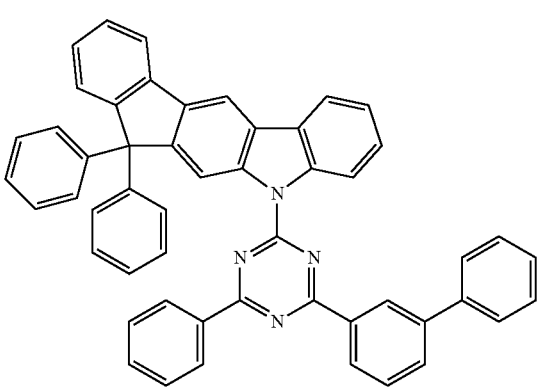

H2-111
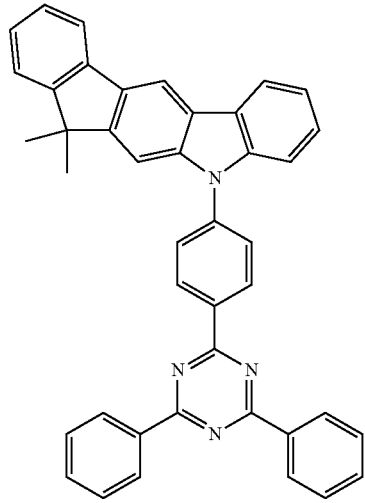
H2-112
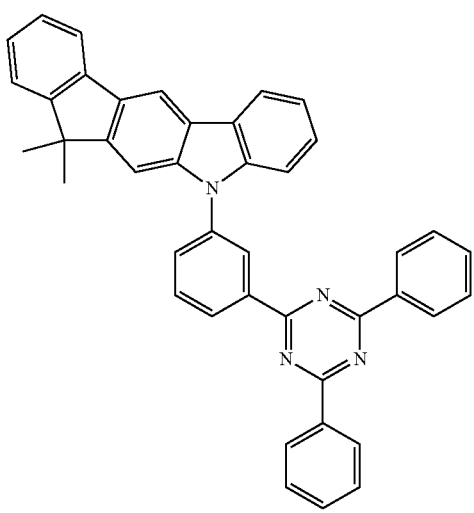
H2-113
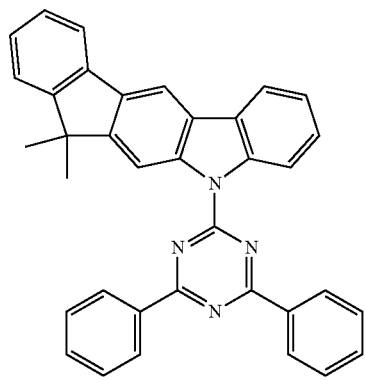
H2-114
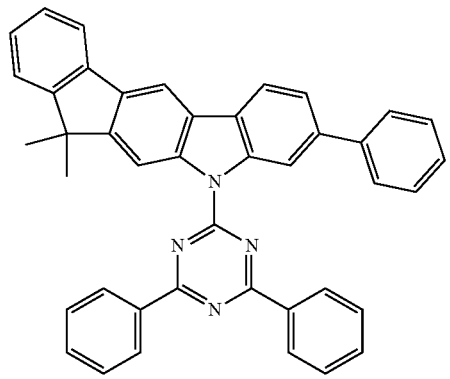
H2-115
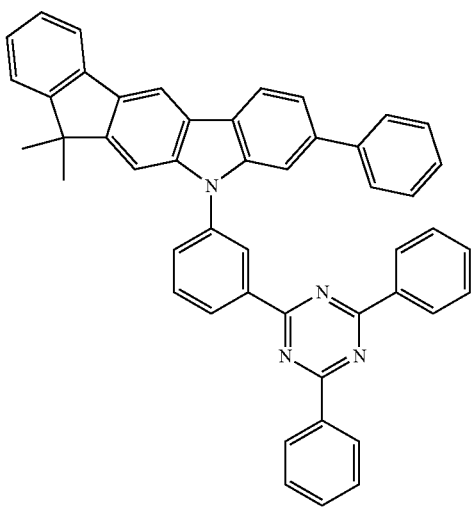
H2-116
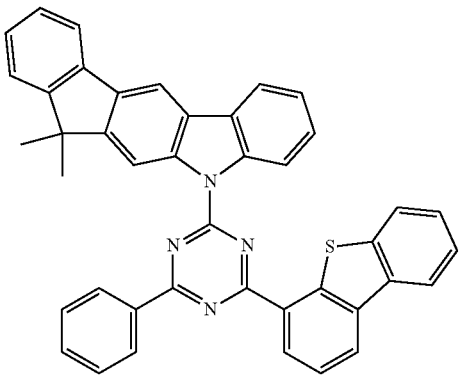
H2-117
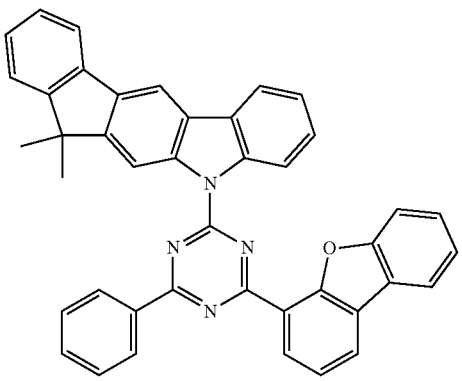

-continued
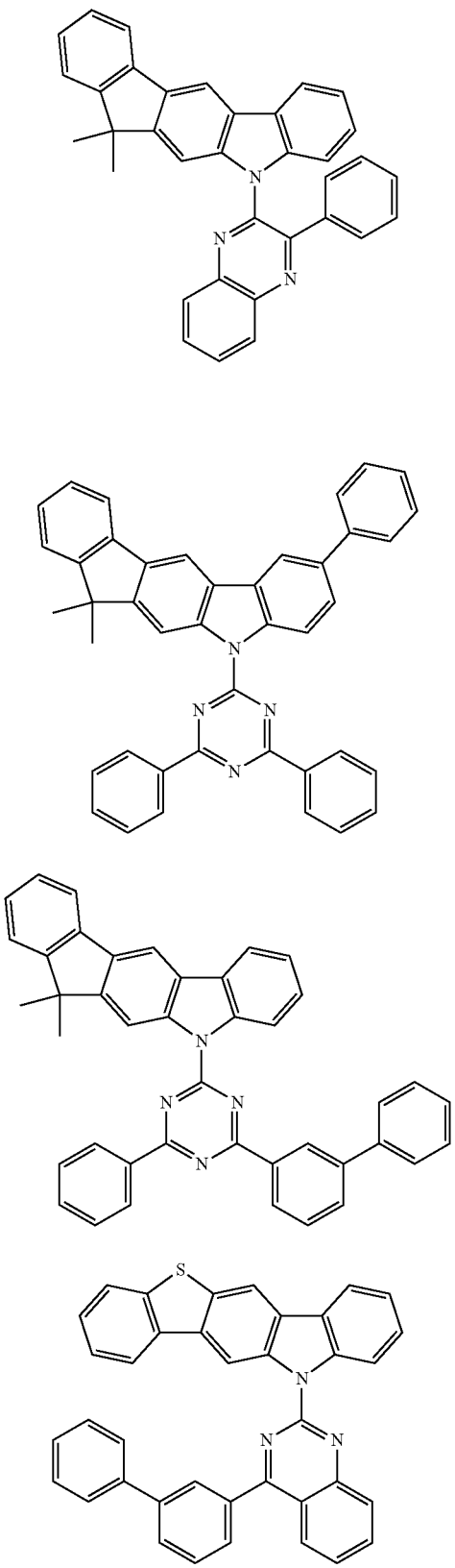
H2-118
H2-119
H2-120
H2-121
-continued
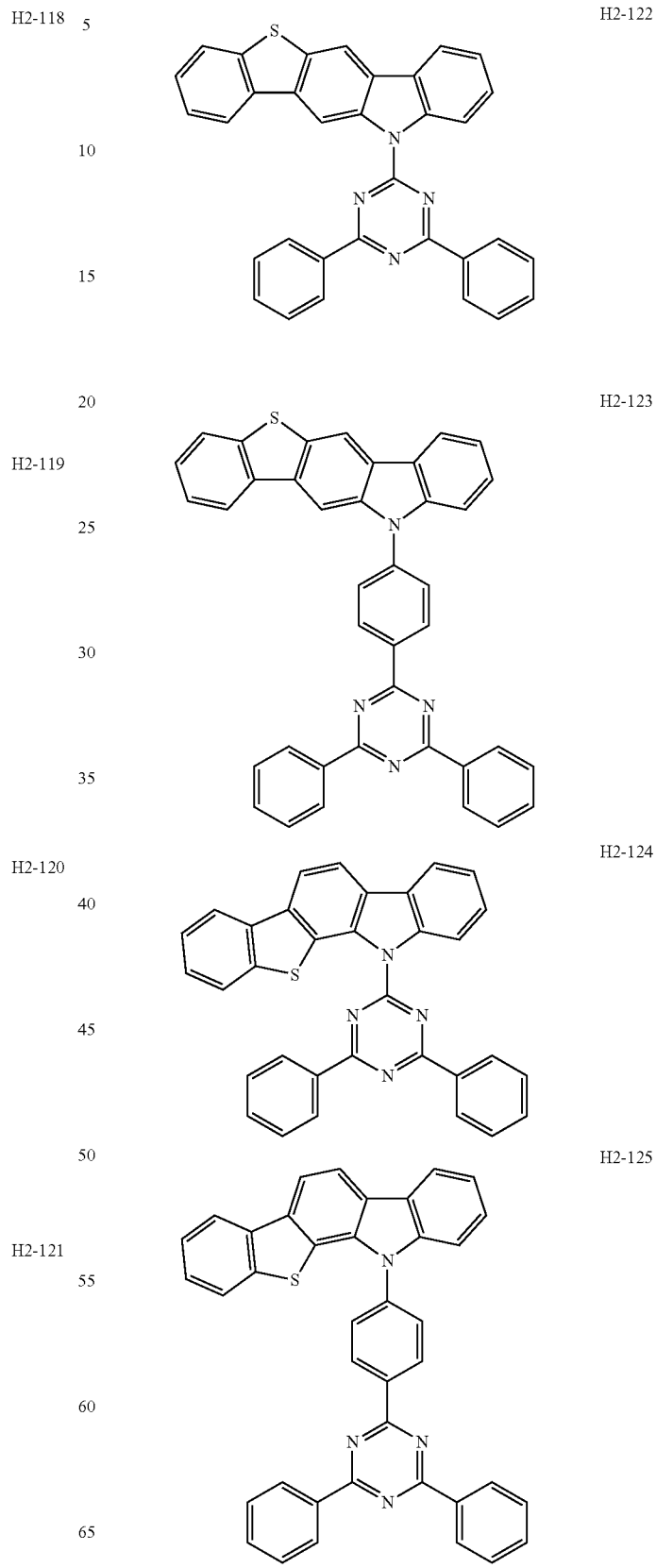
H2-122
H2-123
H2-124
H2-125

H2-126
H2-127
H2-128
H2-129
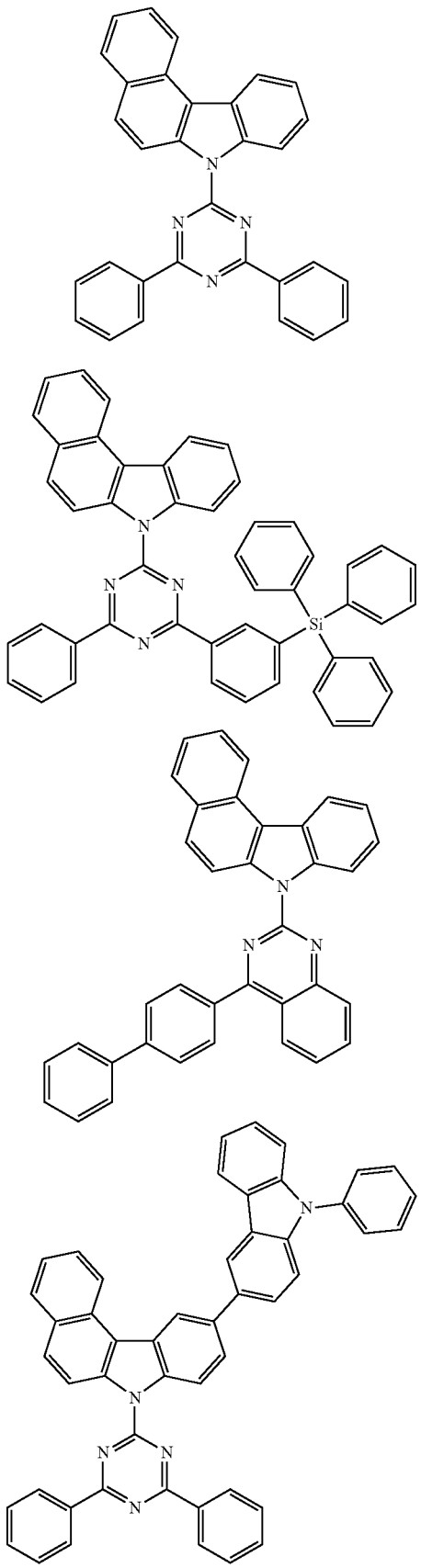
H2-130
H2-131
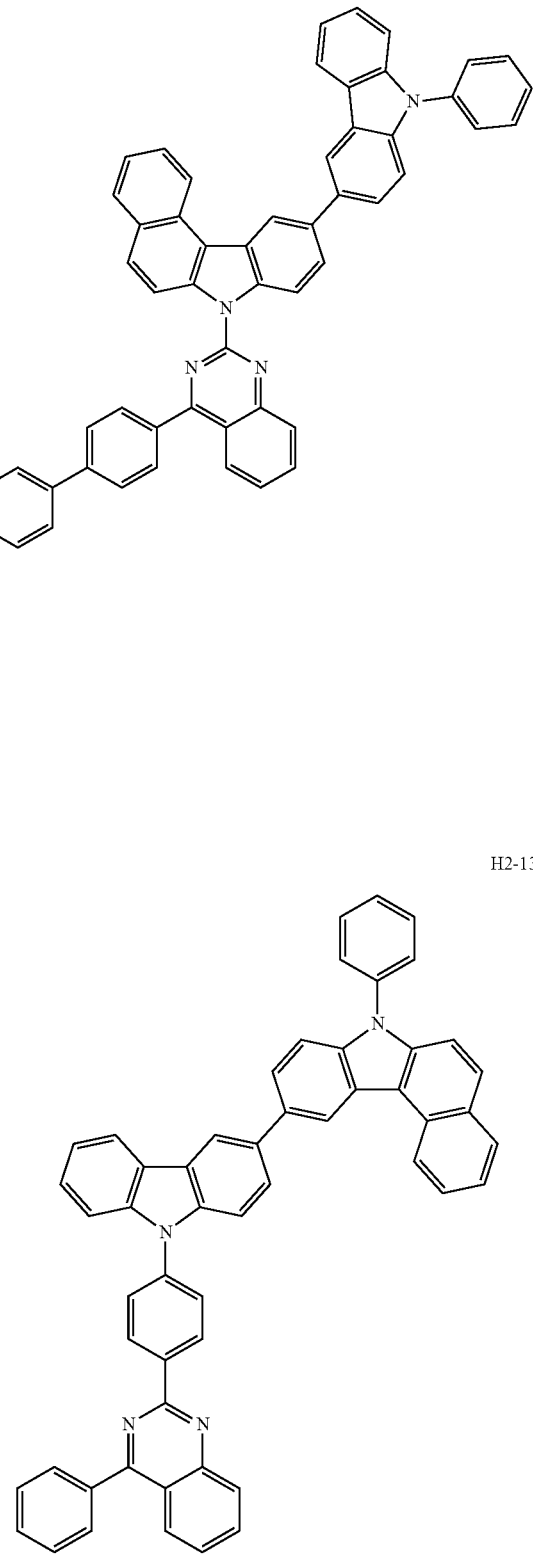

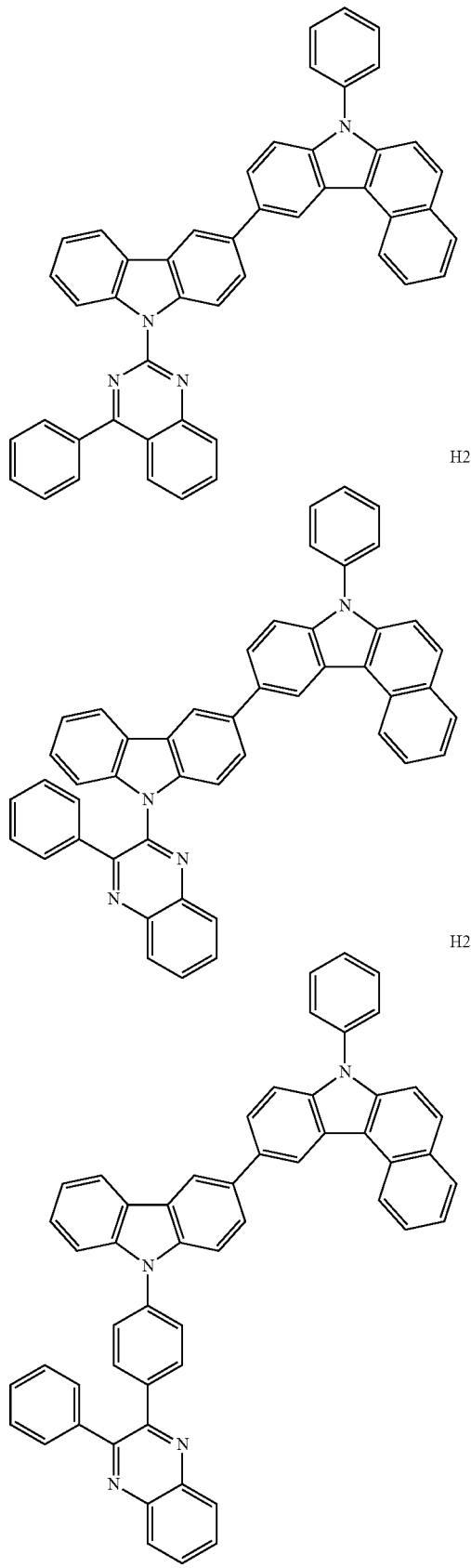
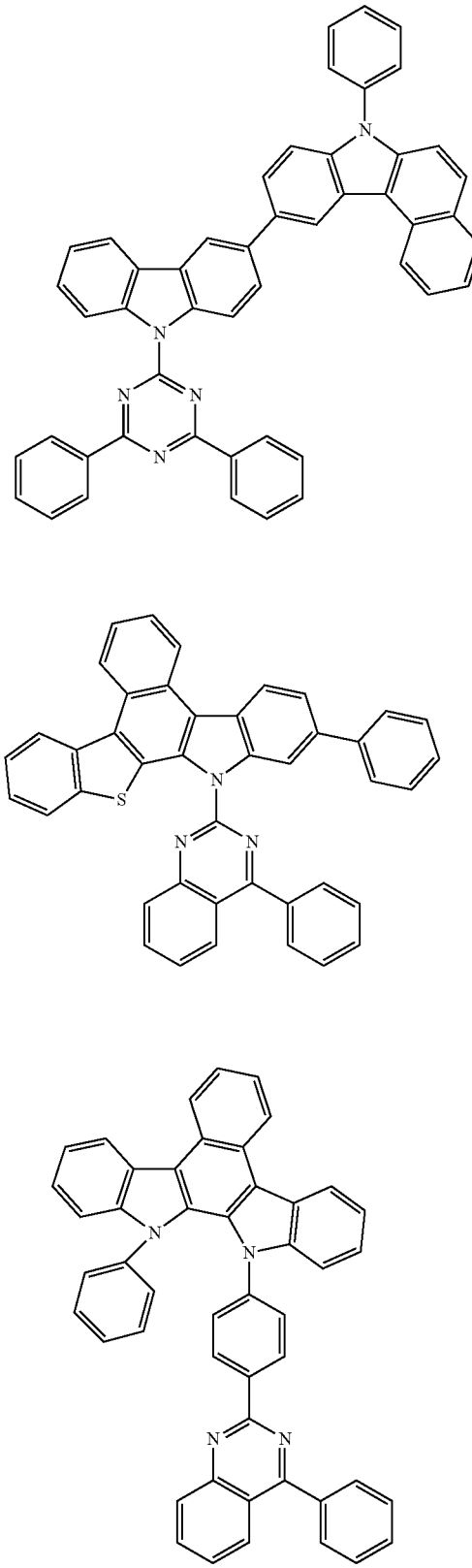

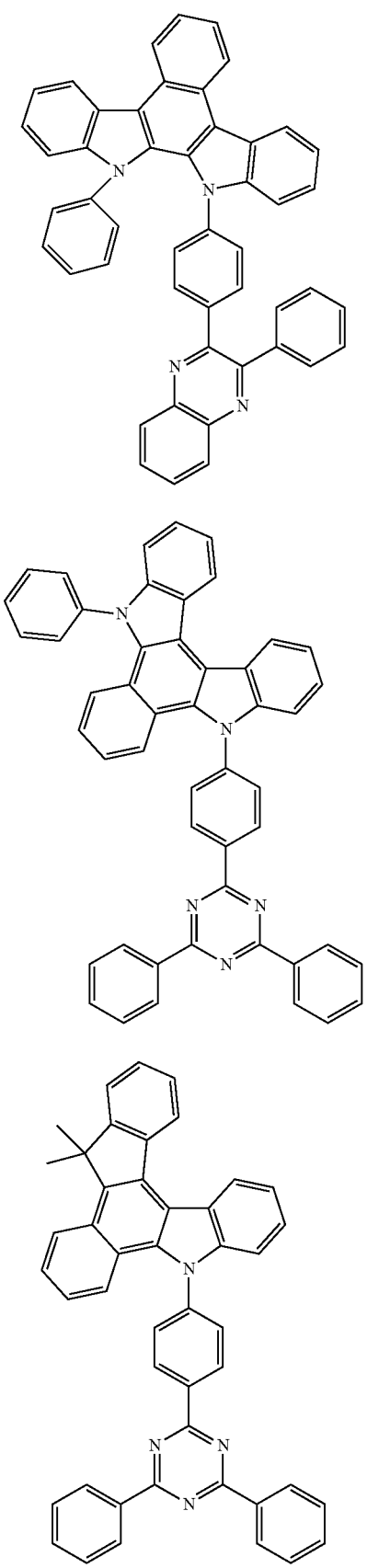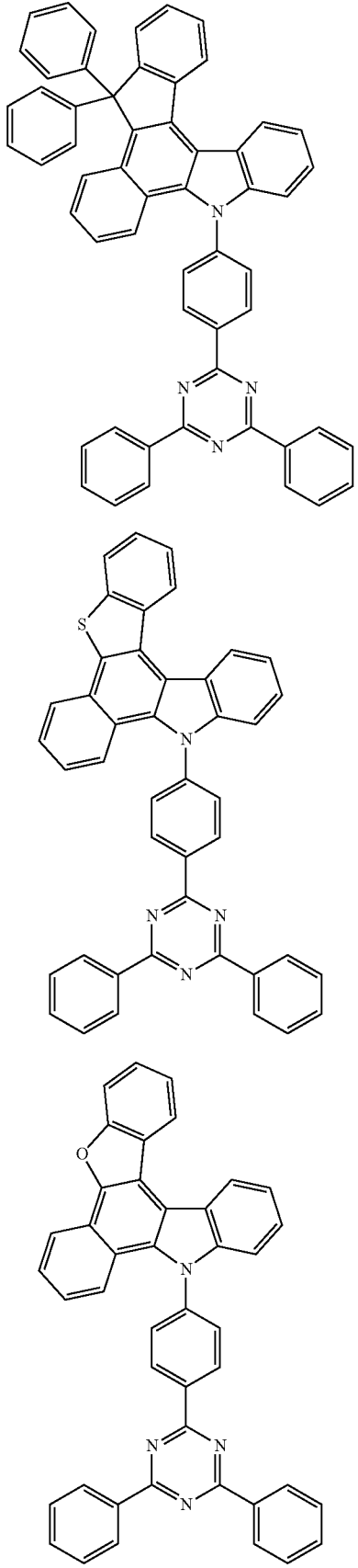

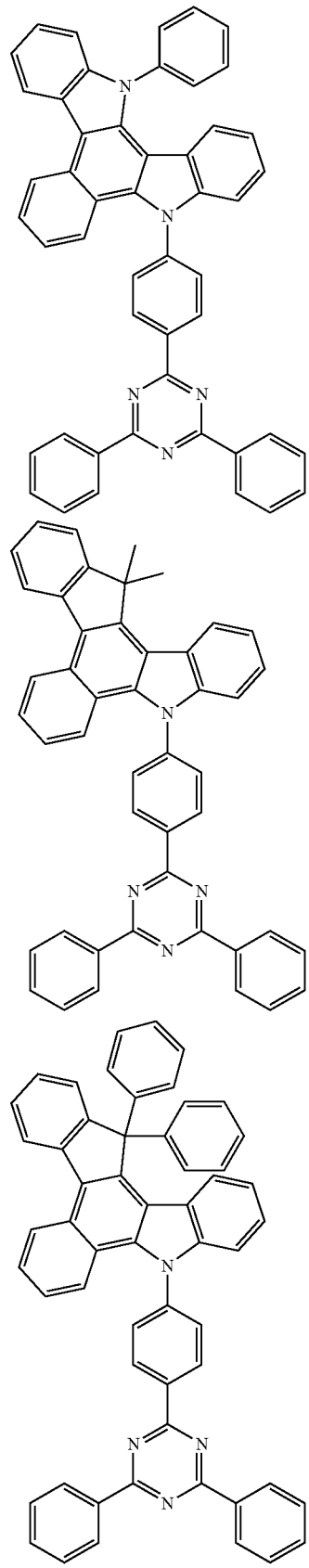
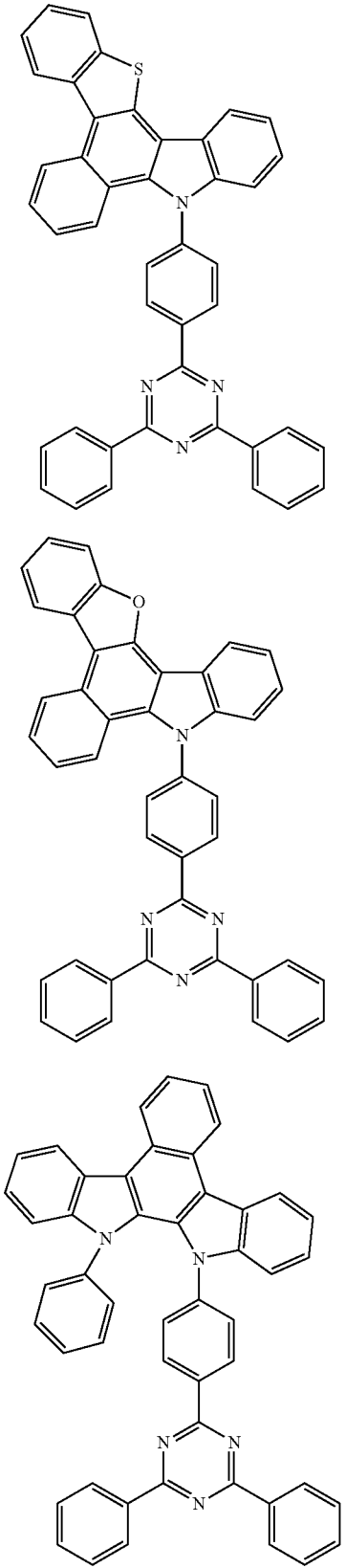

-continued
H2-150
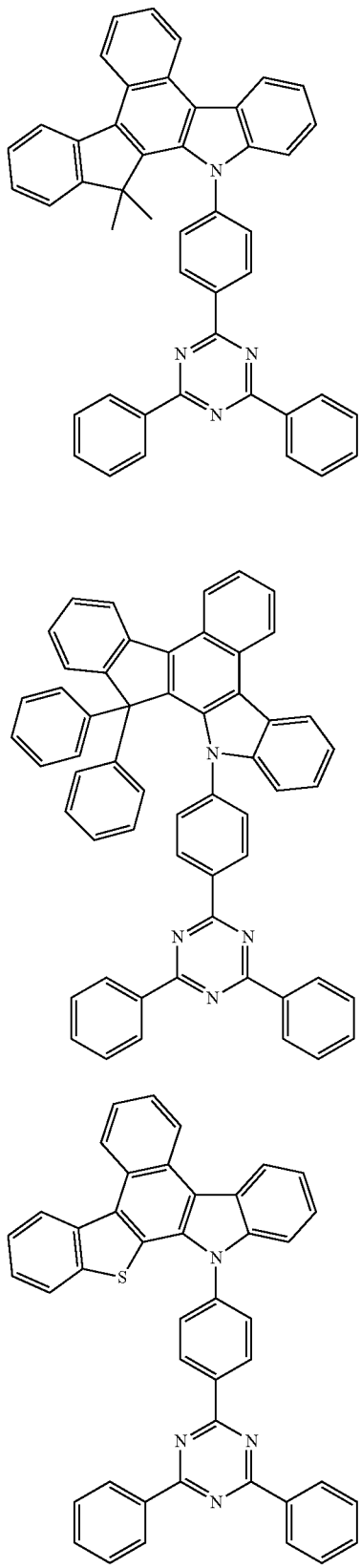
H2-153
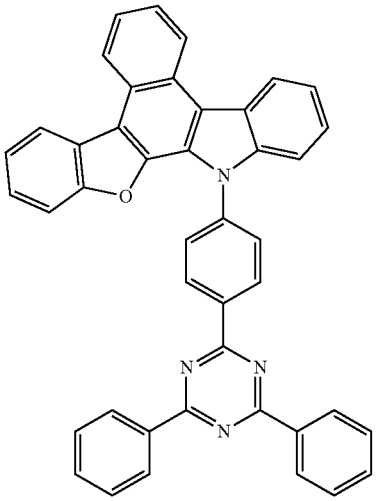
H2-151
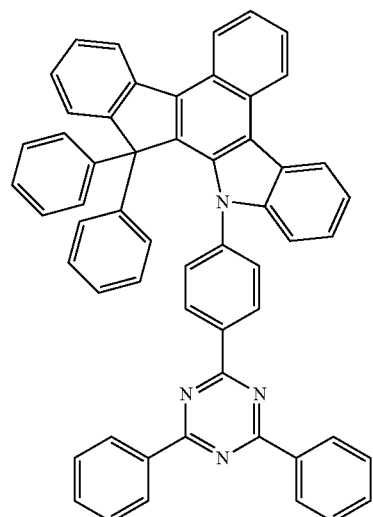
H2-154
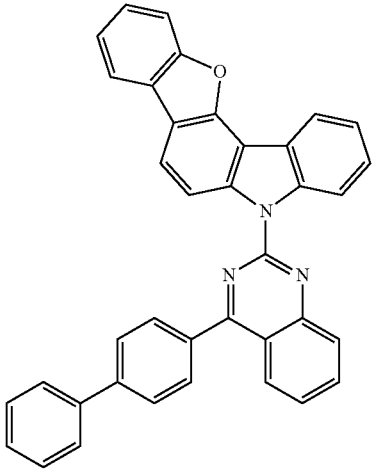
H2-152
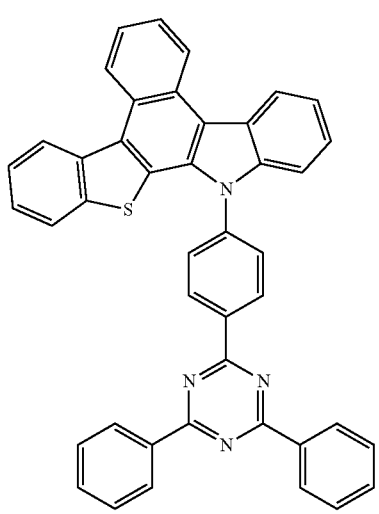
H2-155
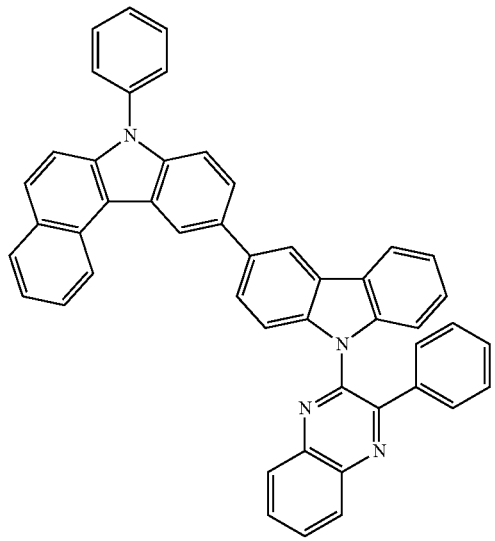

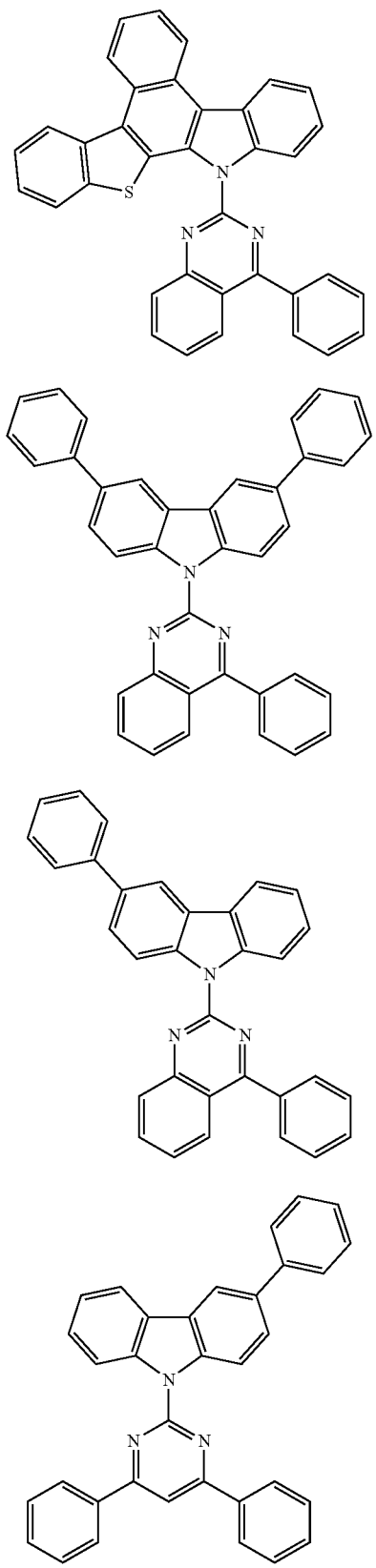
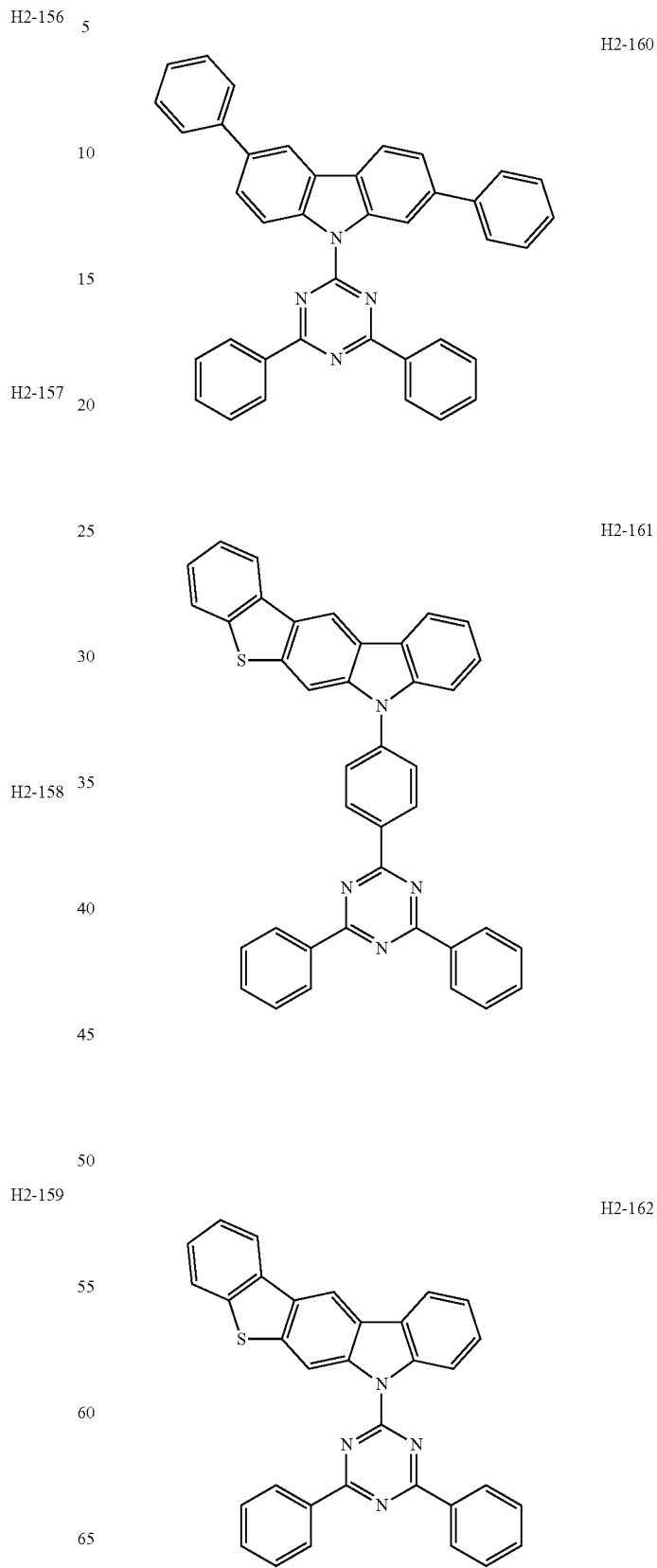

H2-163
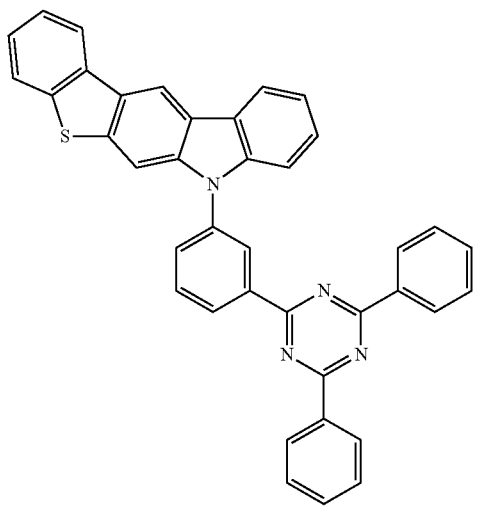
H2-164
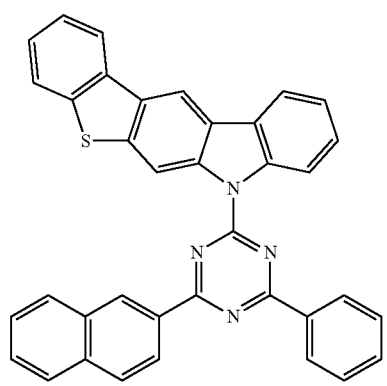
H2-165
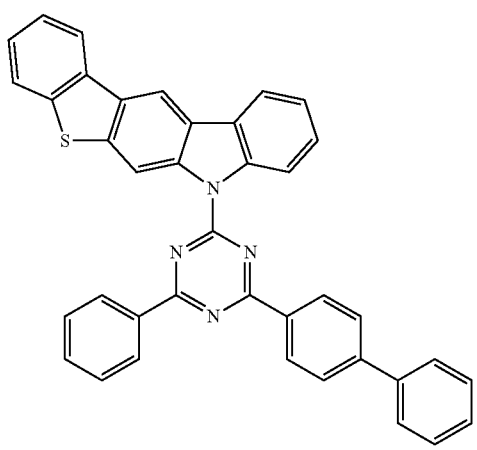
H2-166
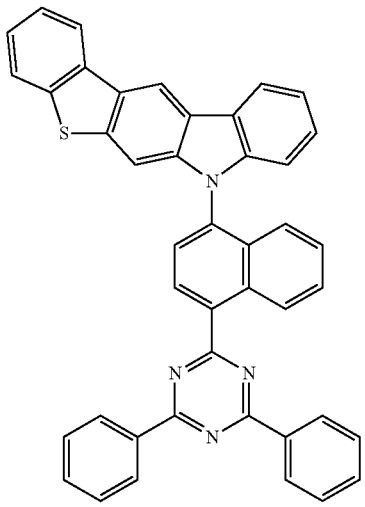
H2-167
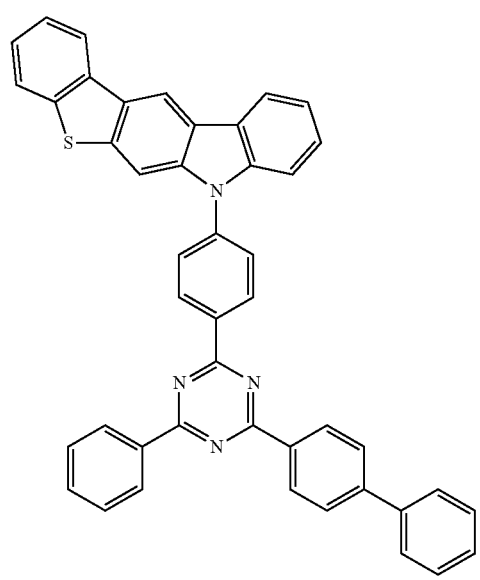
H2-168
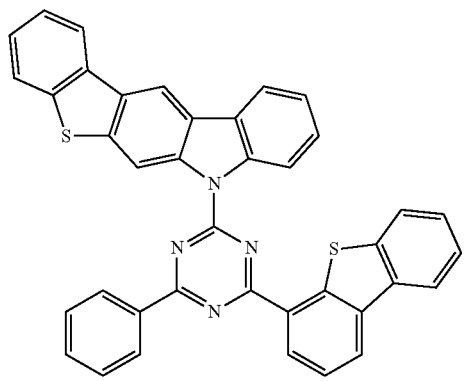

-continued
H2-169
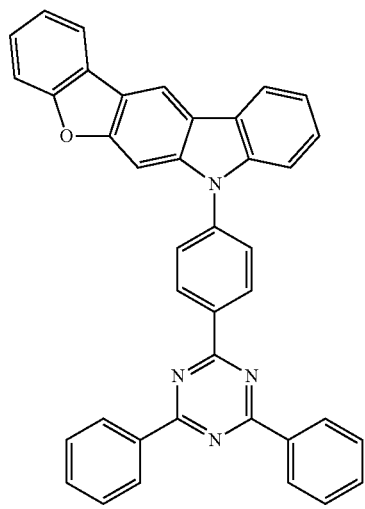
H2-170
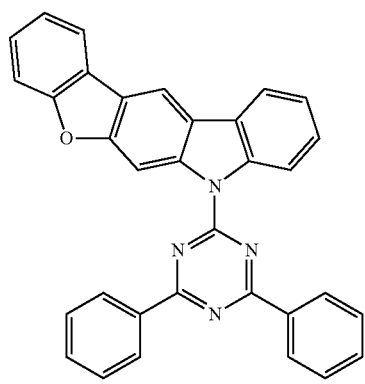
H2-171
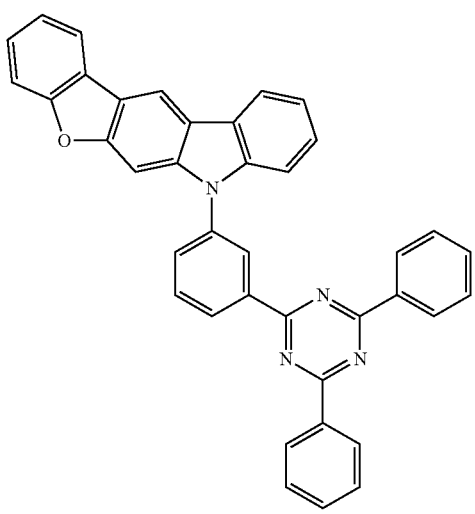
-continued
H2-172
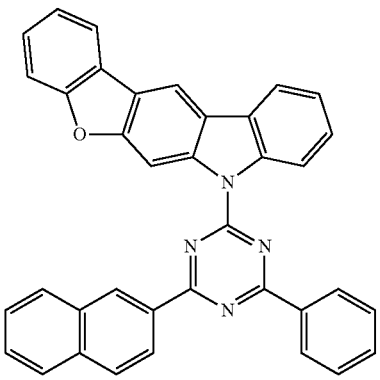
H2-173
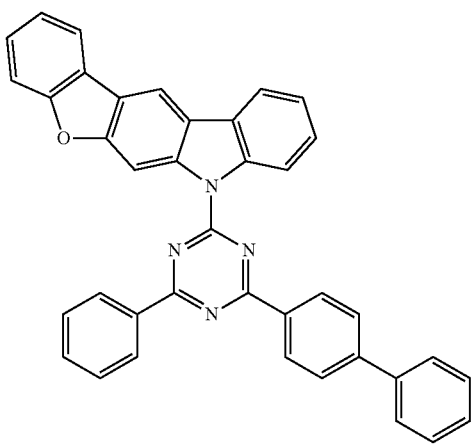
H2-174
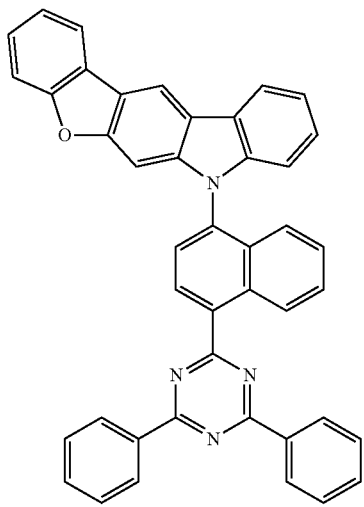

H2-175
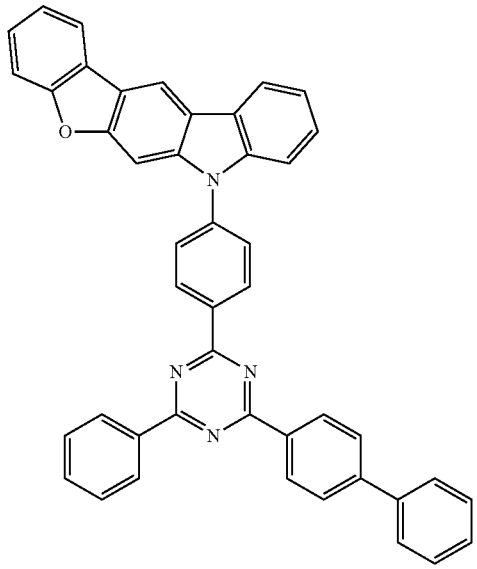
H2-176
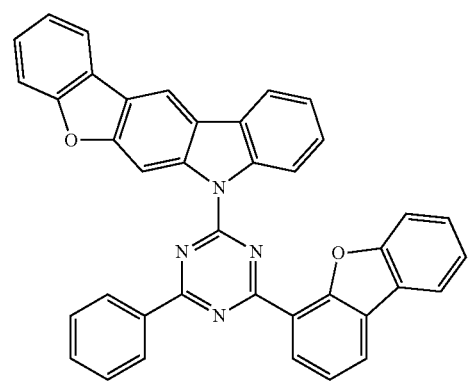
H2-177
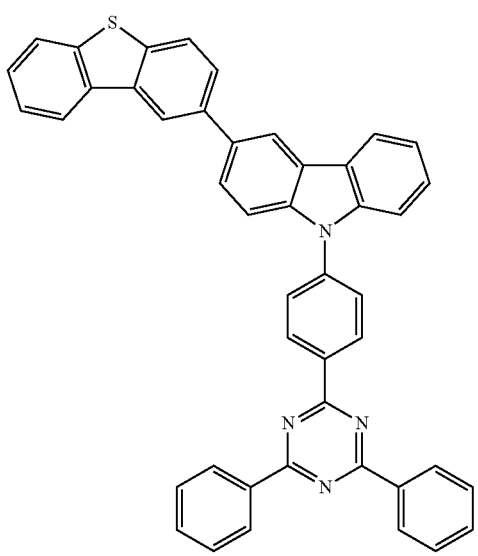
H2-178
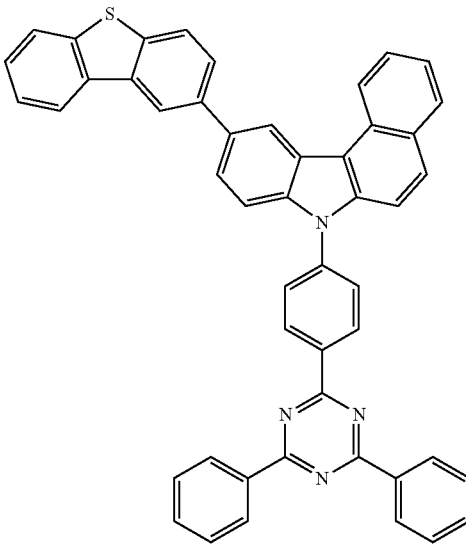
H2-179
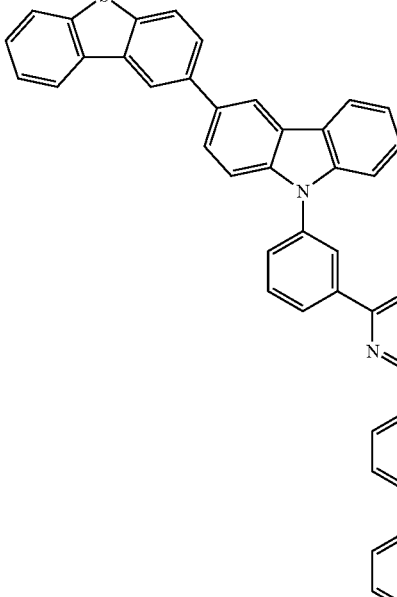
H2-180

H2-181
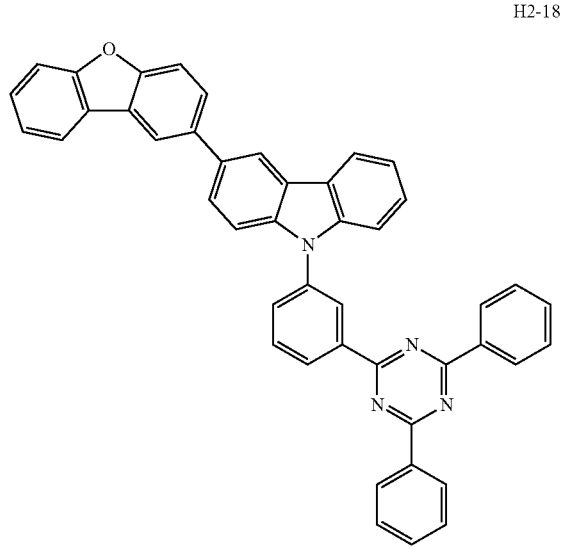
H2-182
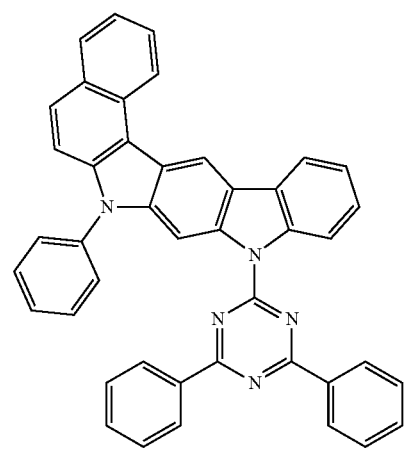
H2-183
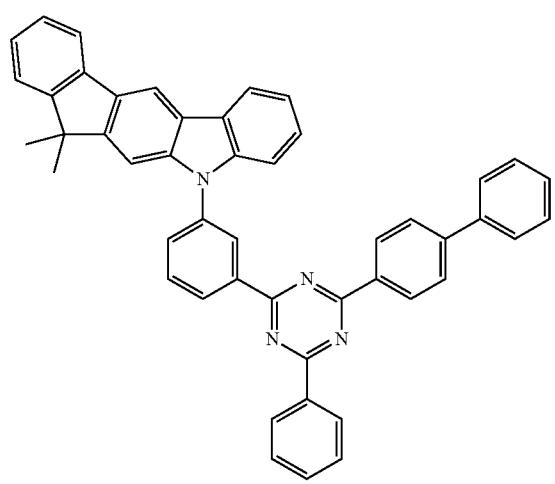
H2-184
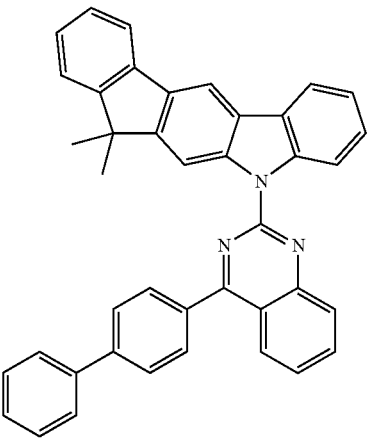
H2-185
H2-186
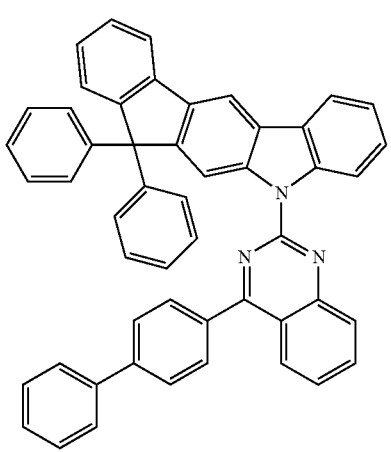

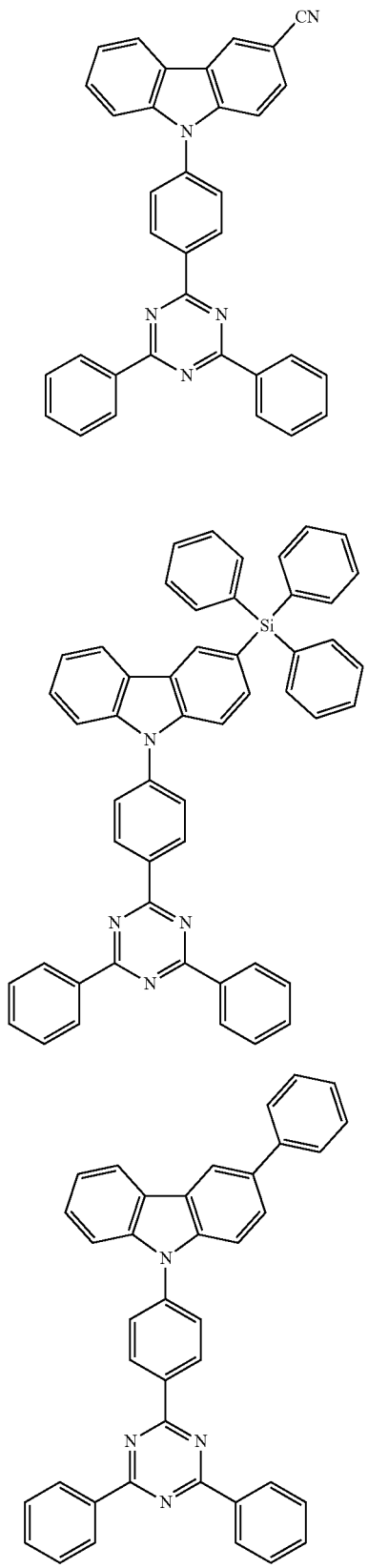
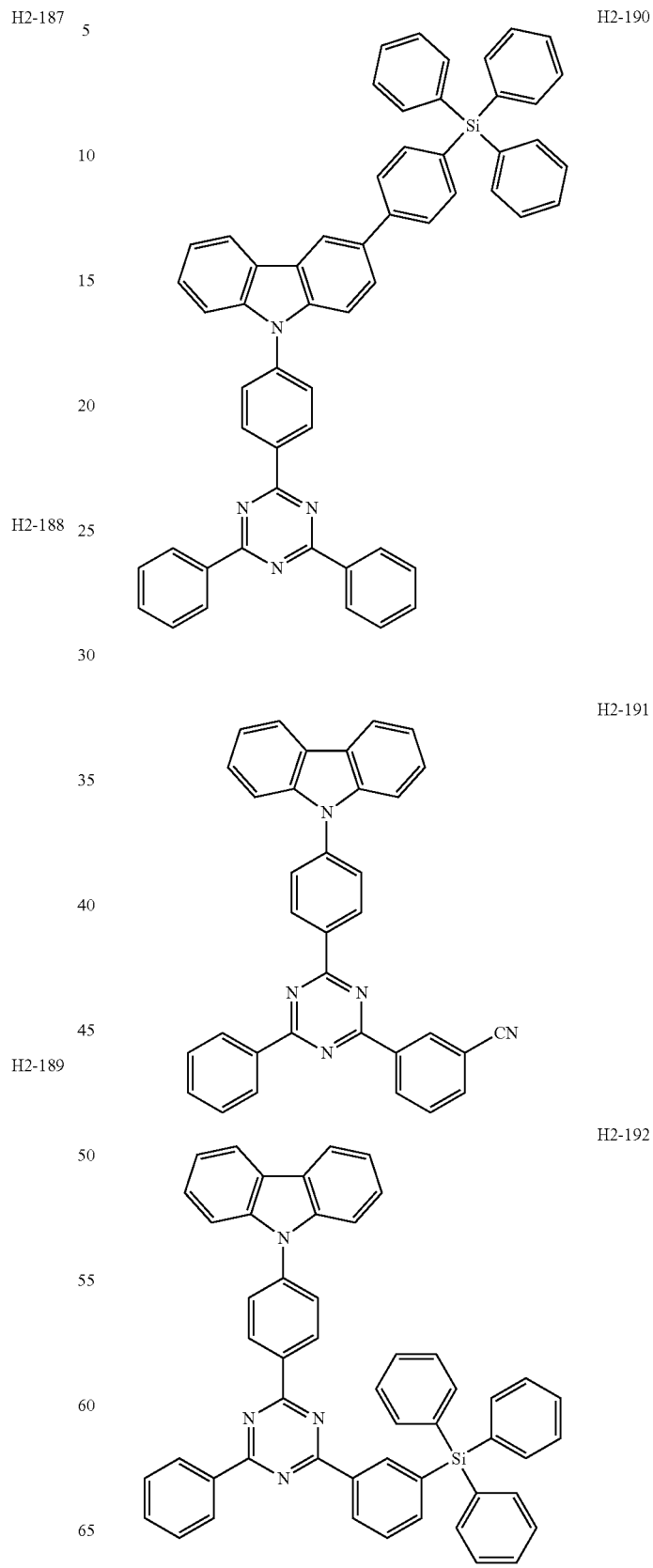

H2-193
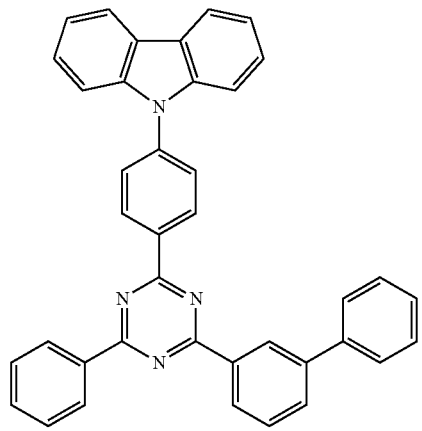
H2-194
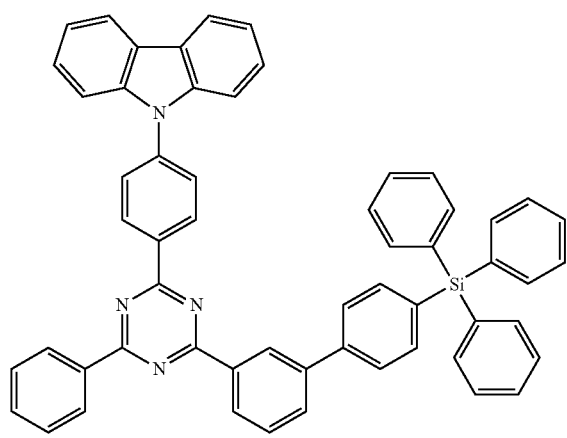
H2-195
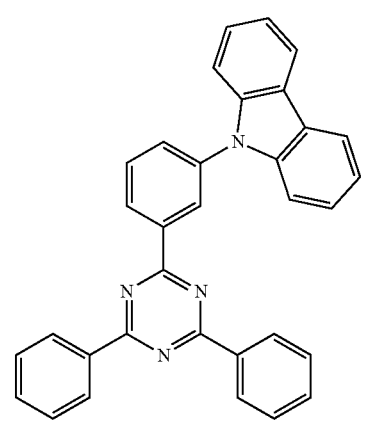
H2-196
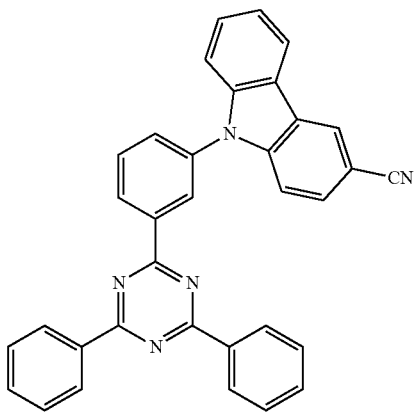
H2-197
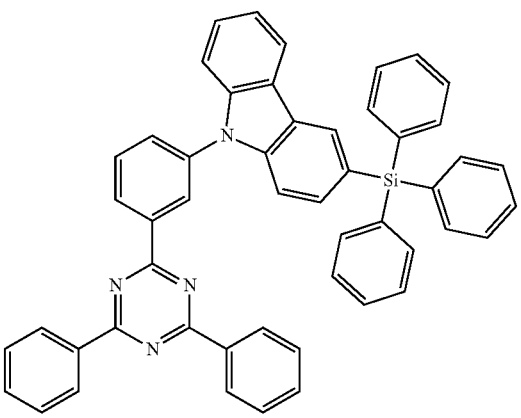
H2-198
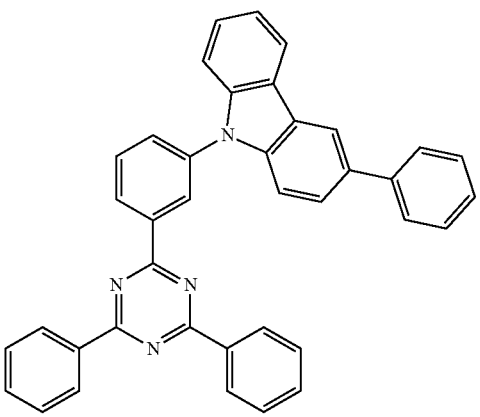
H2-199
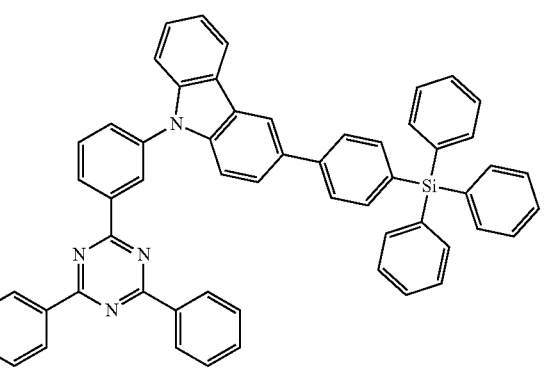

-continued
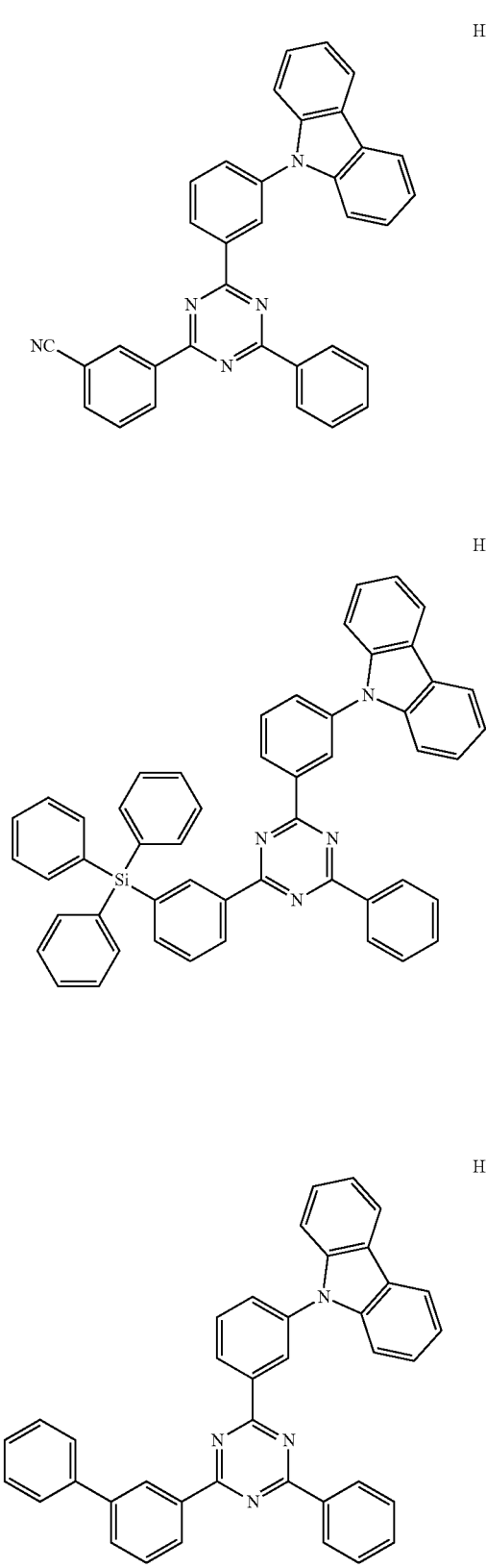
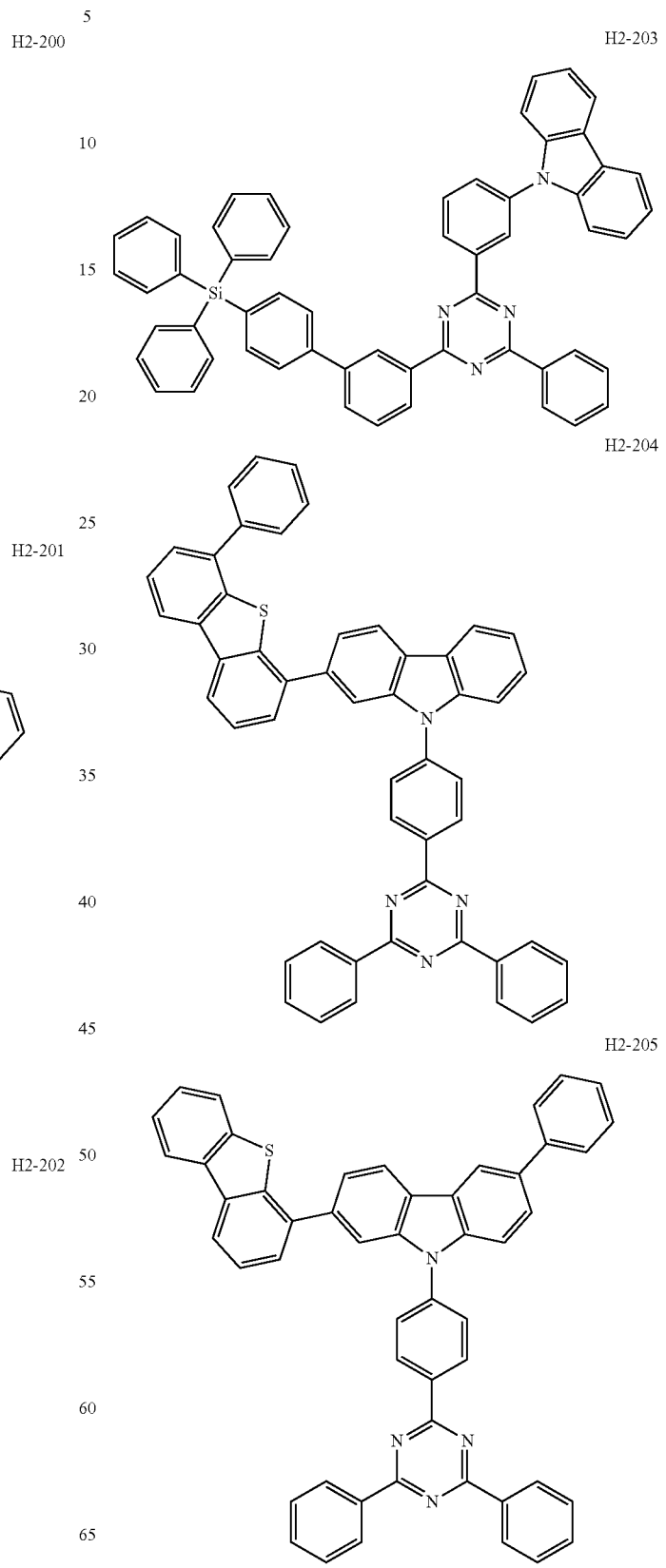

H2-206
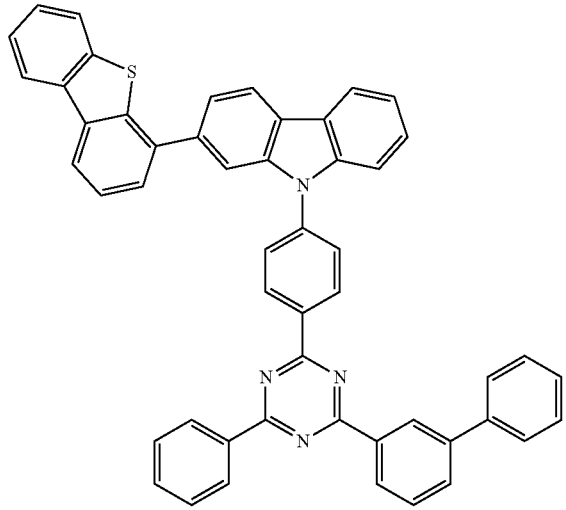
H2-207
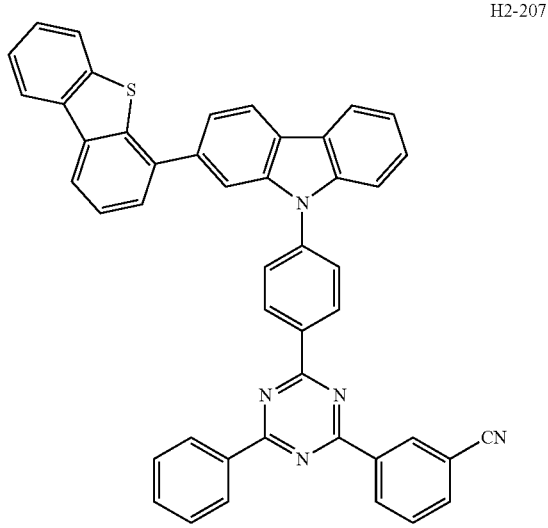
H2-208
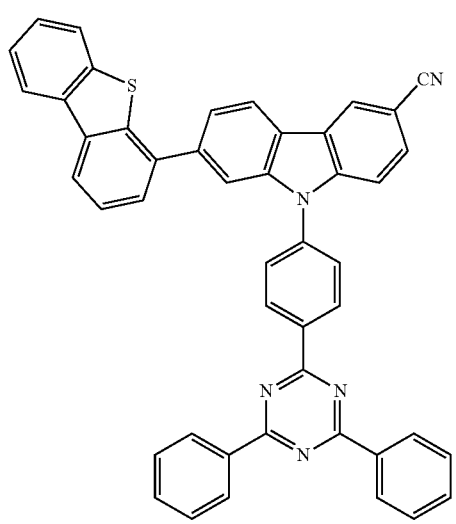
H2-209
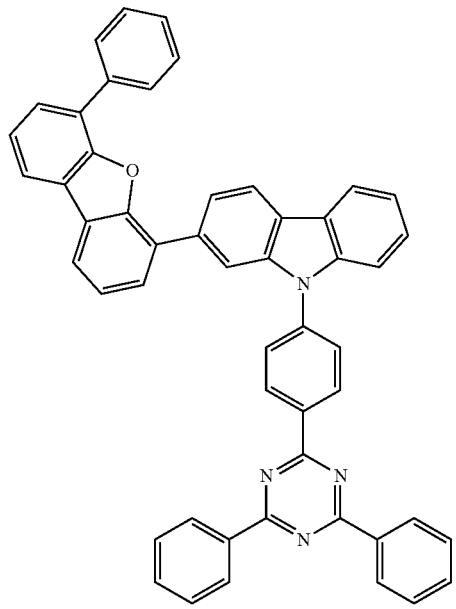
H2-210
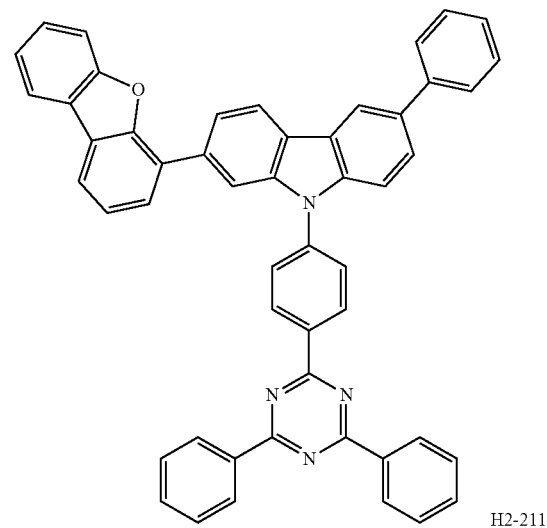
H2-211
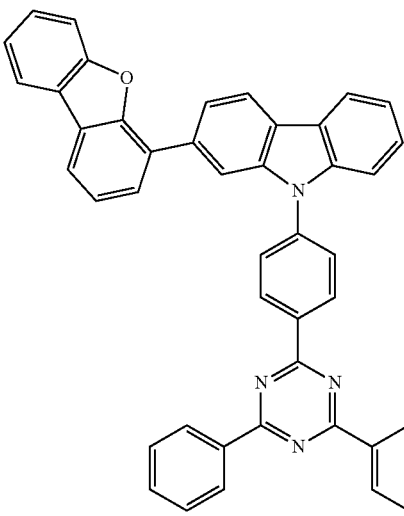

H2-212
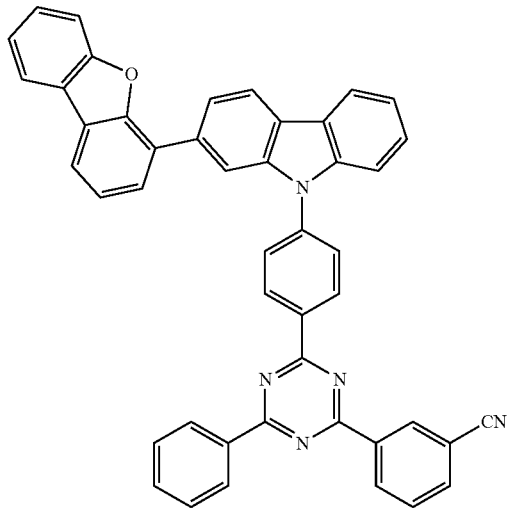
H2-213
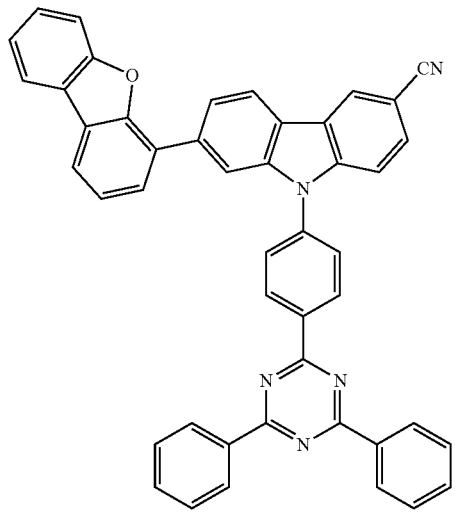
H2-214
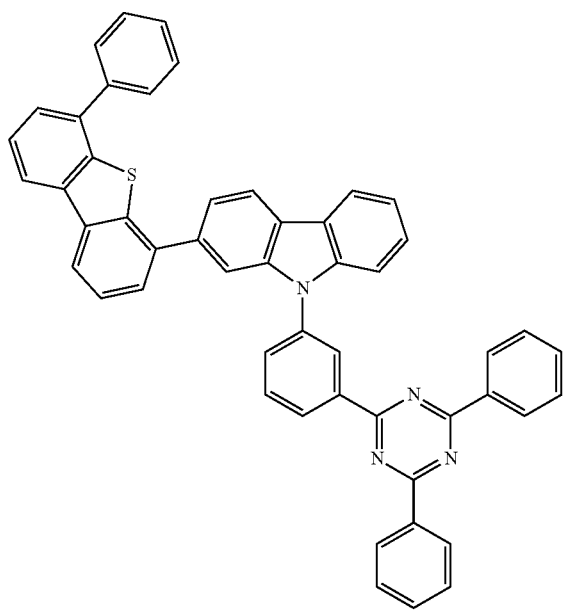
H2-215
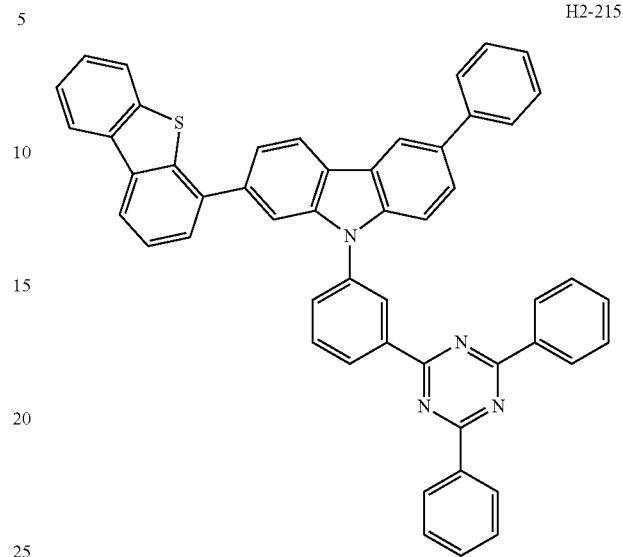
H2-216
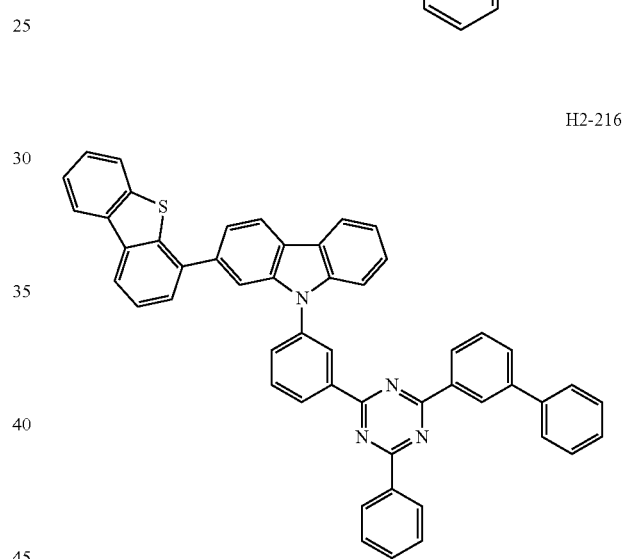
H2-217
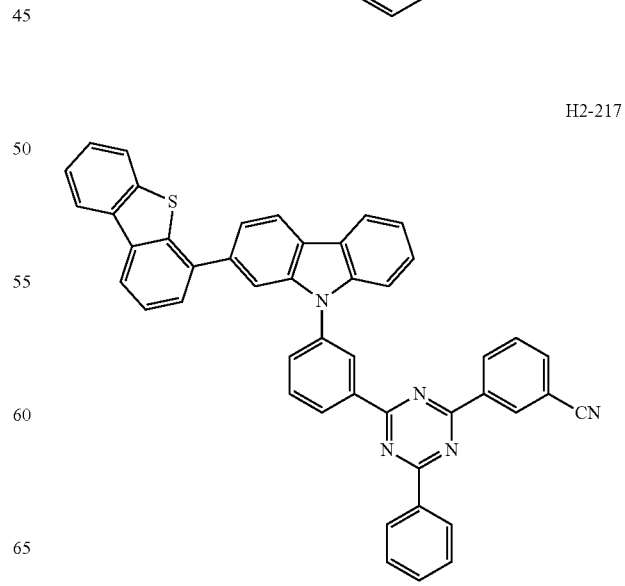

H2-218
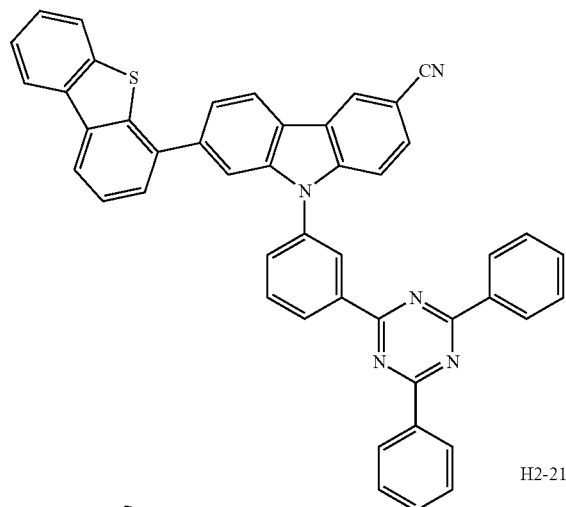
H2-219
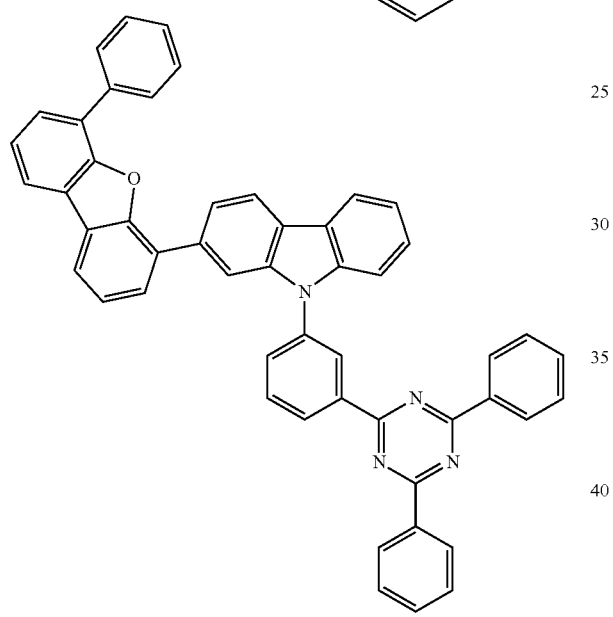
H2-220
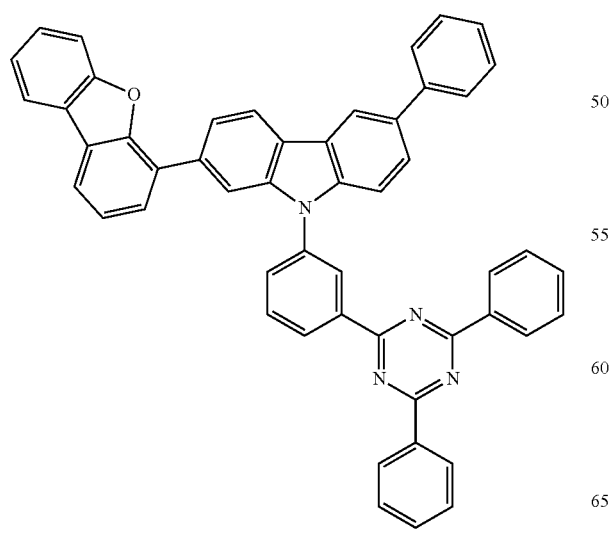
H2-221
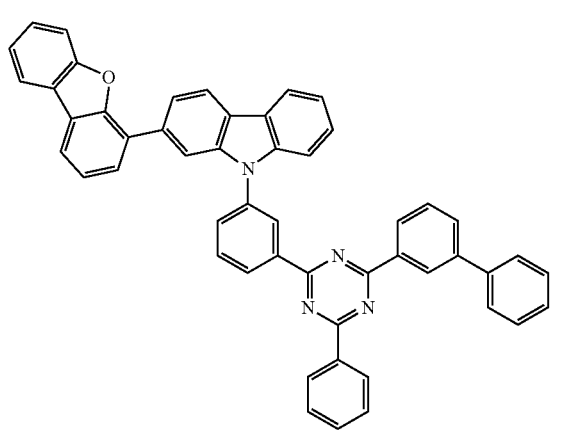
H2-222
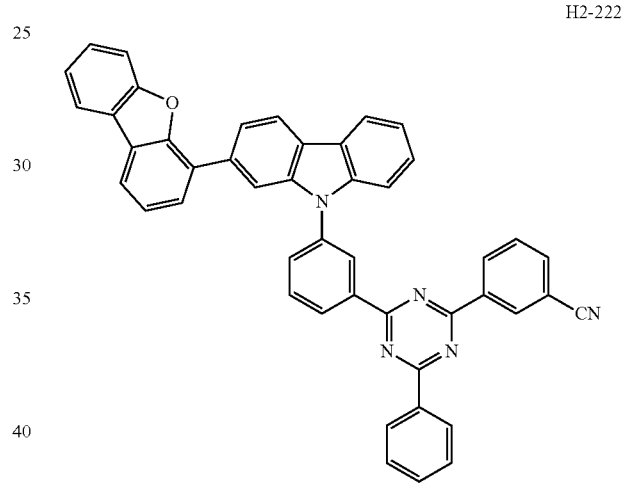
H2-223
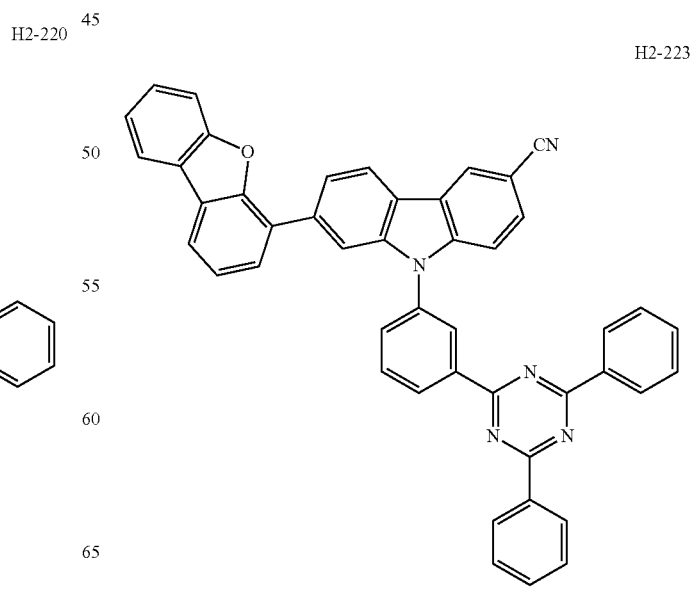

H2-224
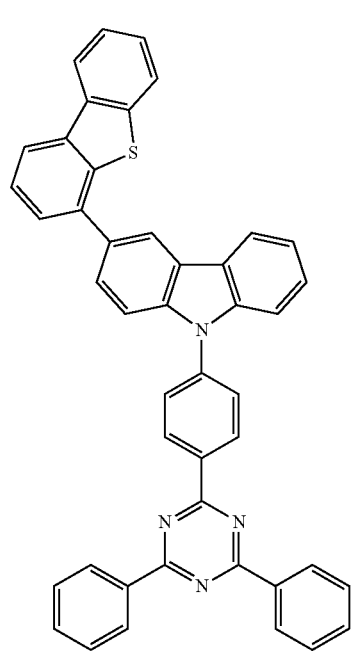
H2-226
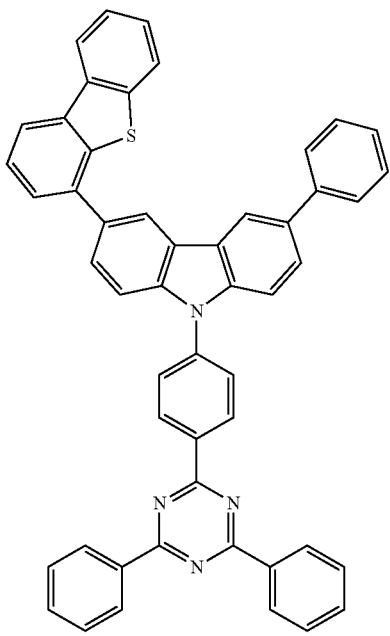
H2-225
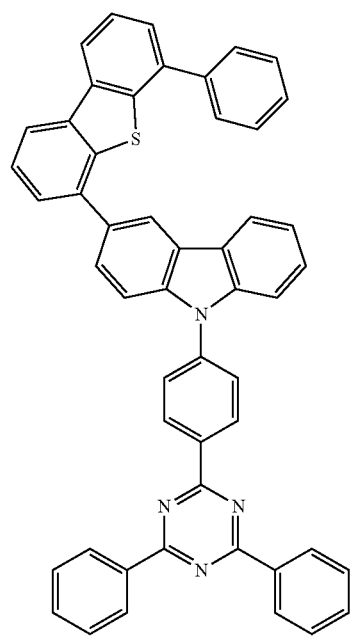
H2-227
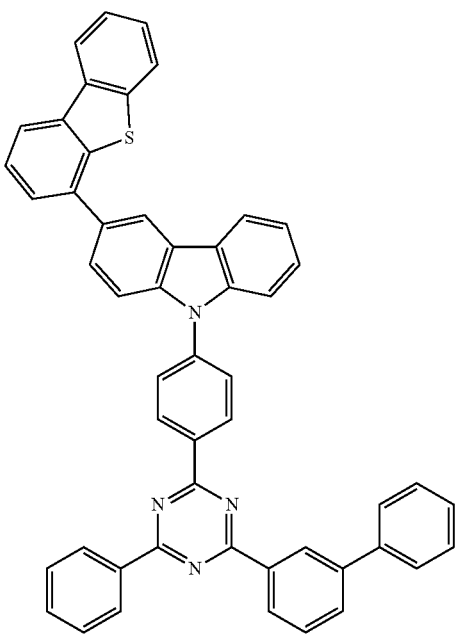

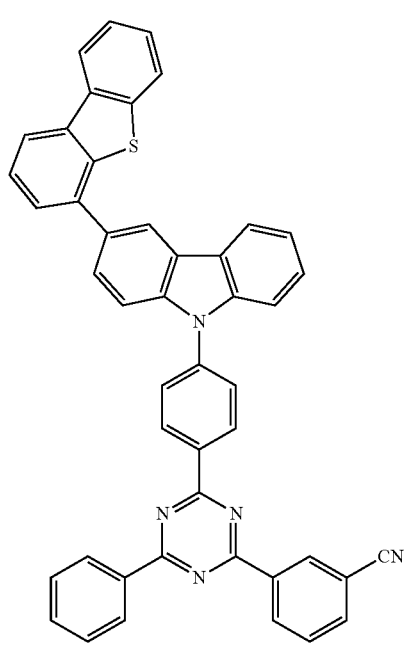
H2-228
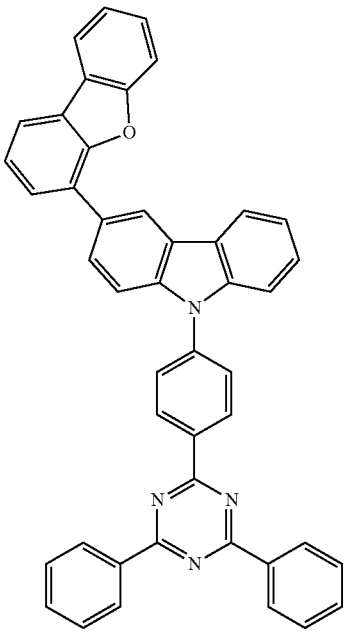
H2-230
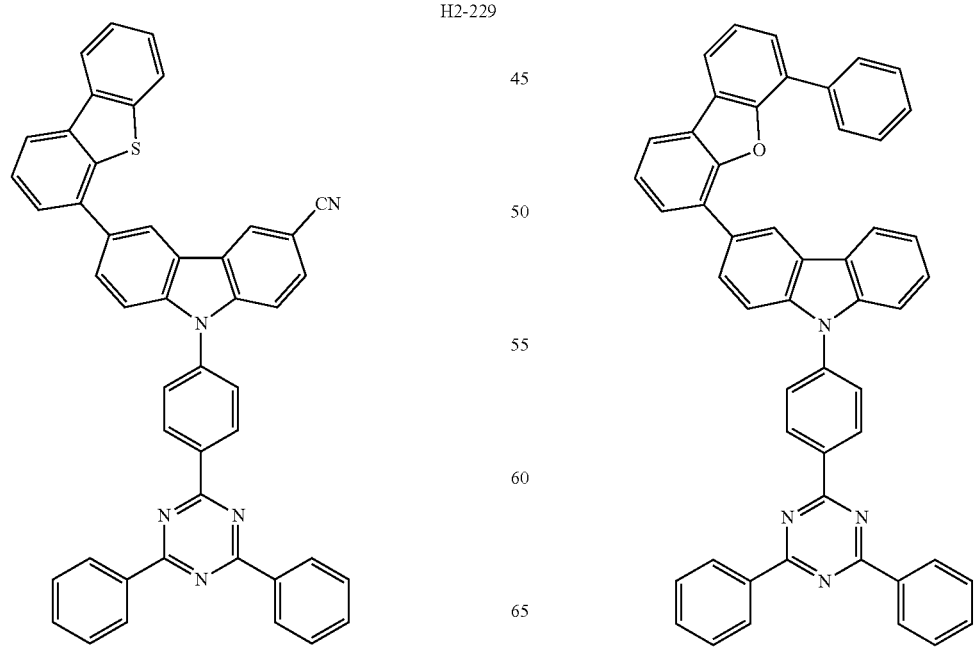
H2-229 H2-231

H2-232
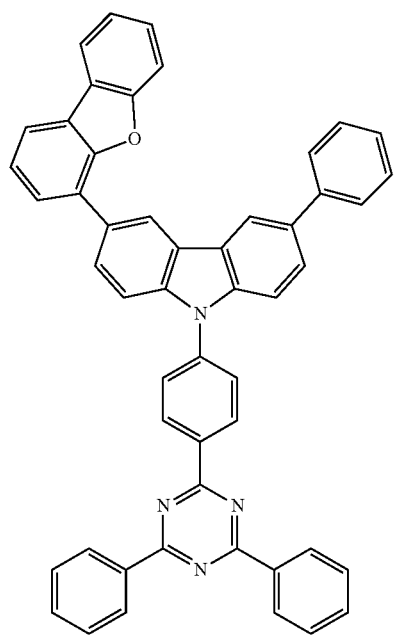
H2-234
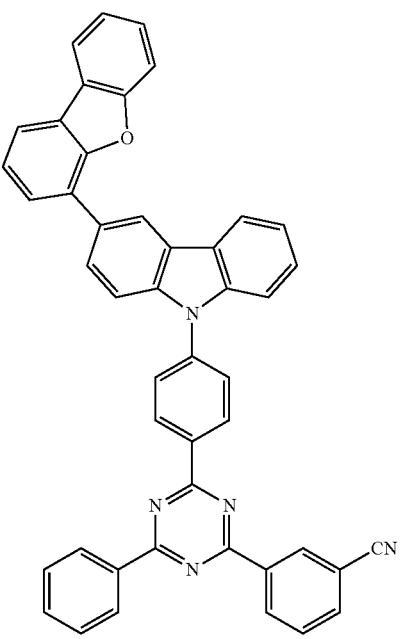
H2-233
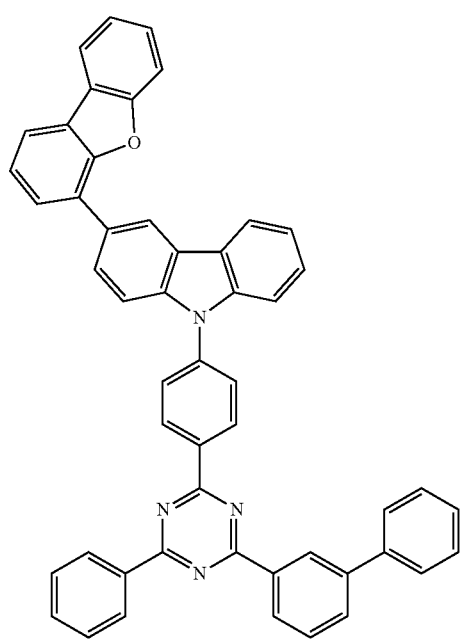
H2-235
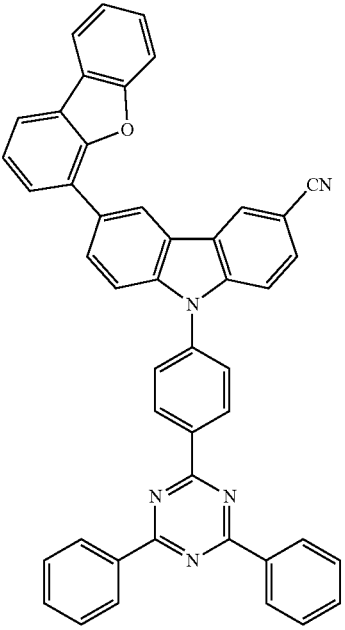

H2-236
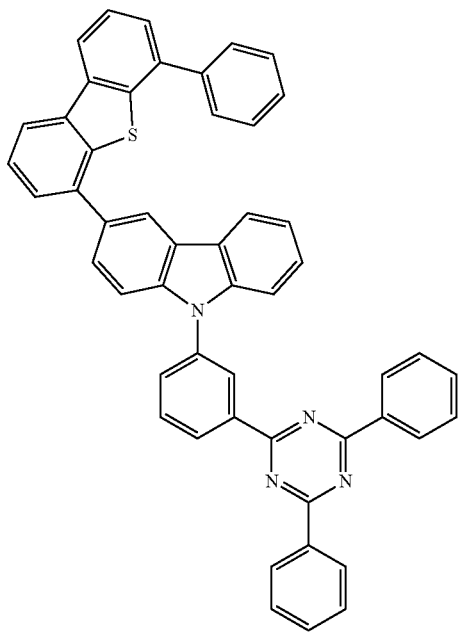
H2-238
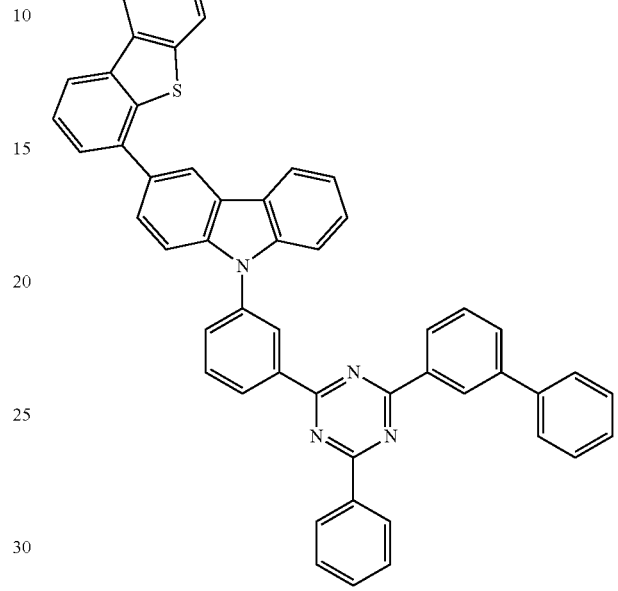
H2-237
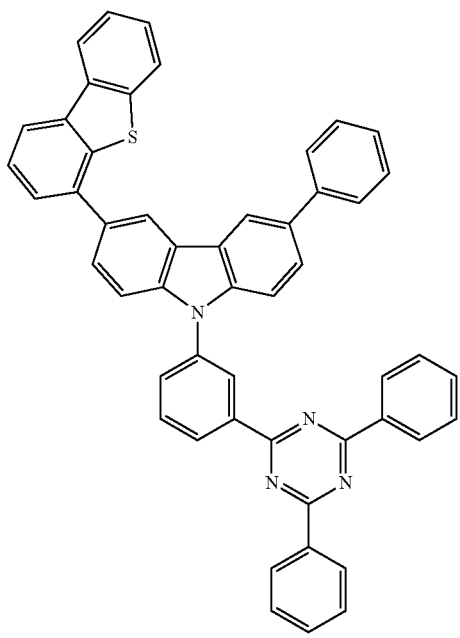
H2-239
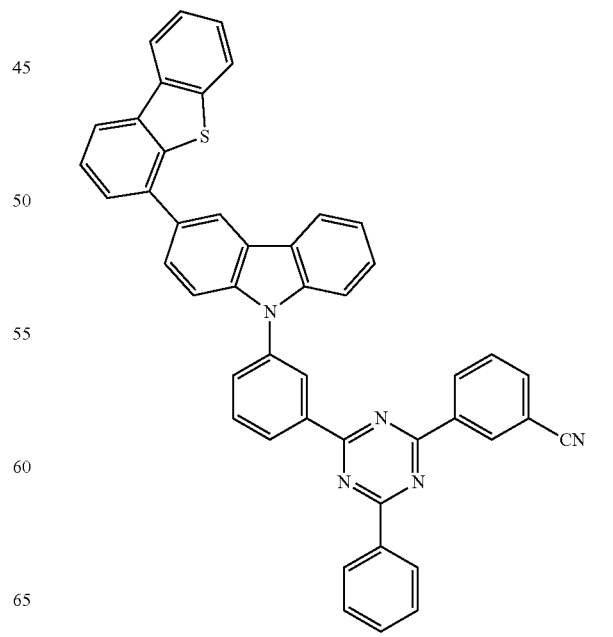

H2-240
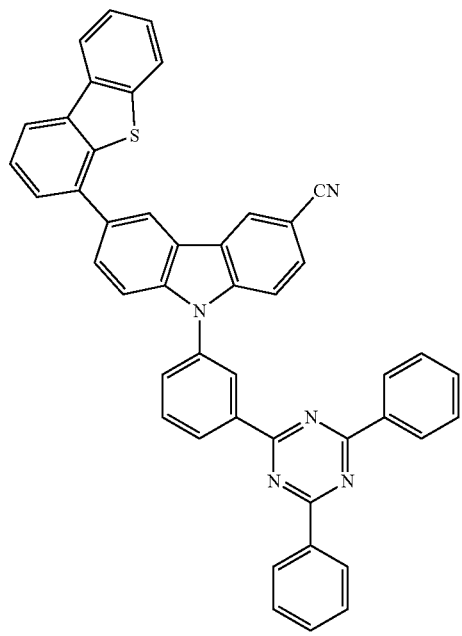
H2-241
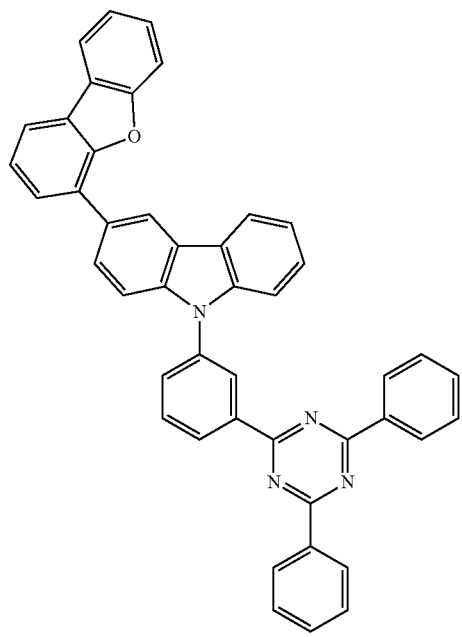
H2-242
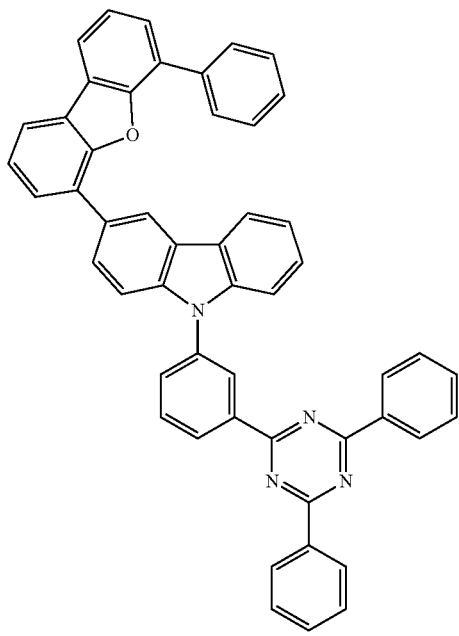
H2-243
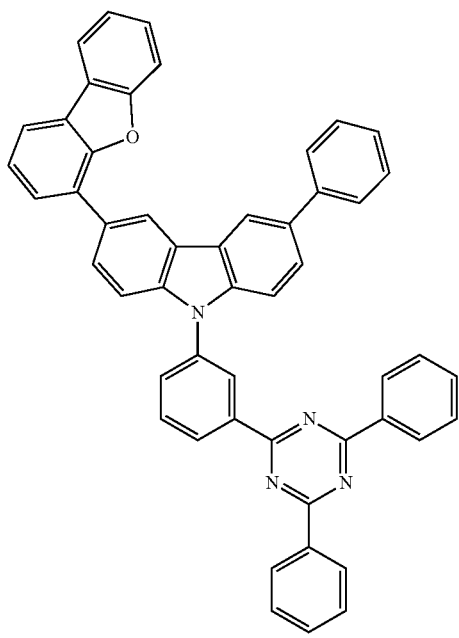

H2-244
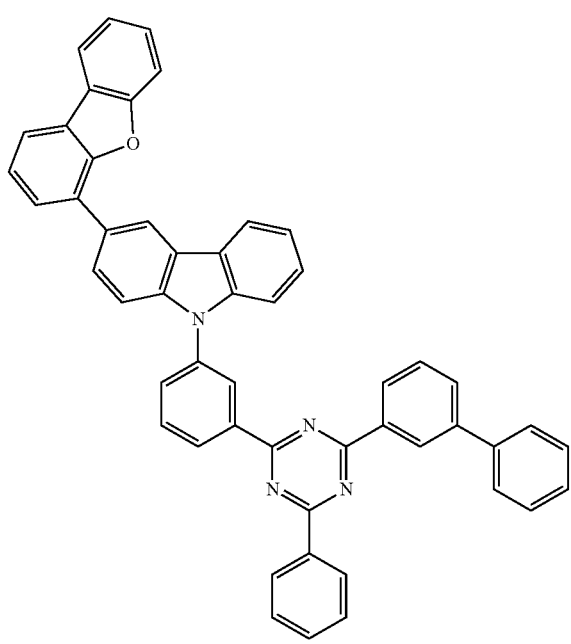
H2-246
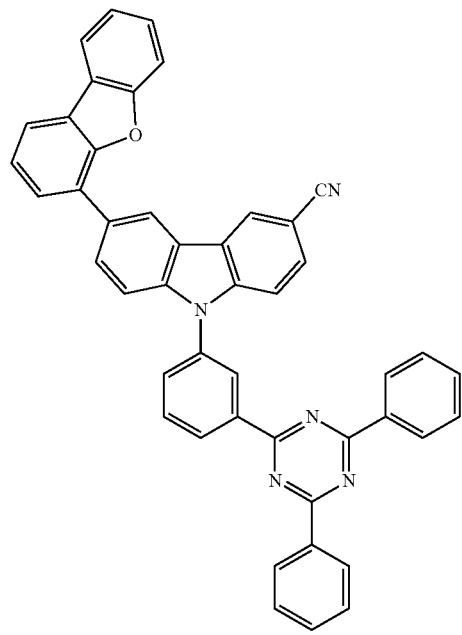
H2-247
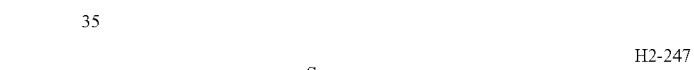
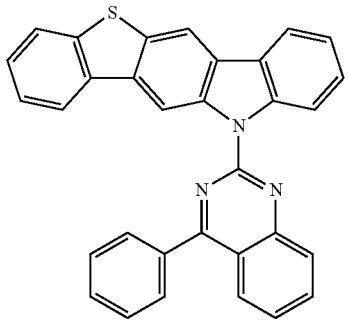
H2-245
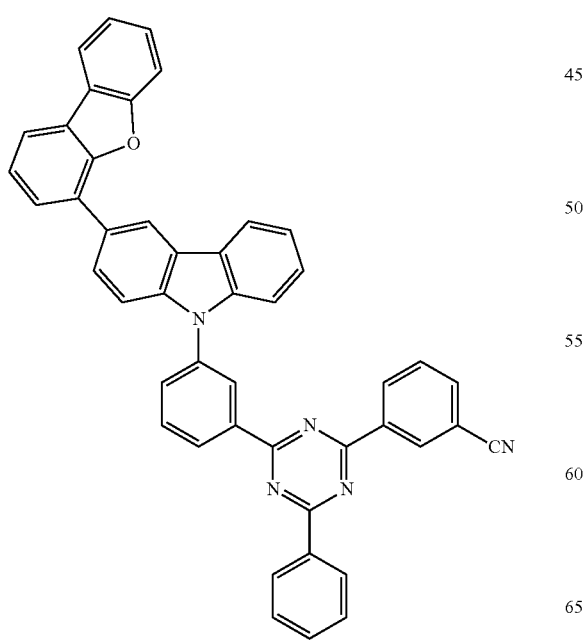
H2-248
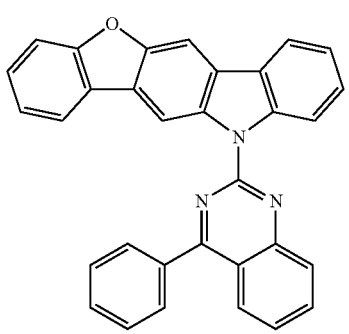

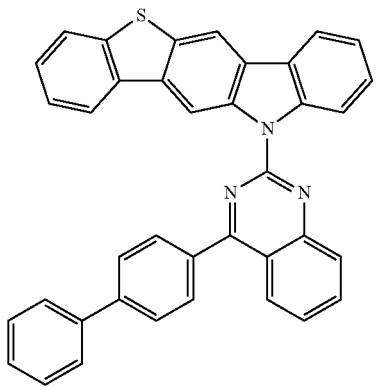
H2-249
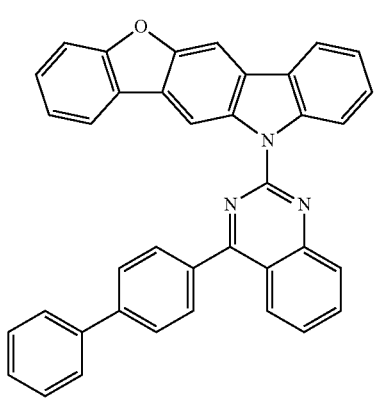
H2-250
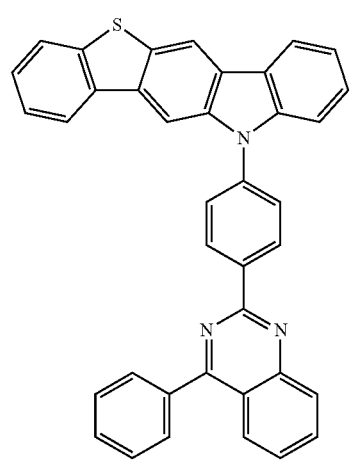
H2-251
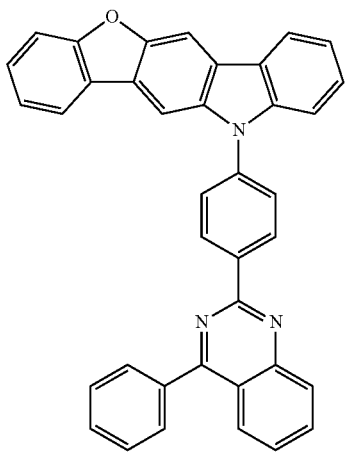
H2-252
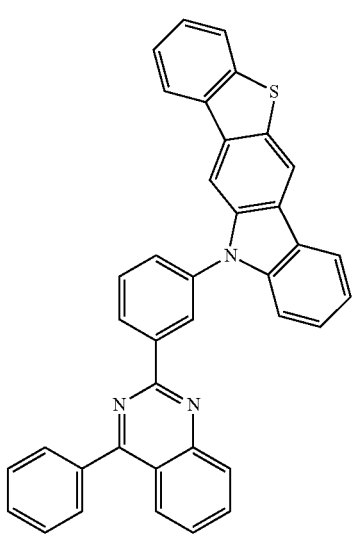
H2-253
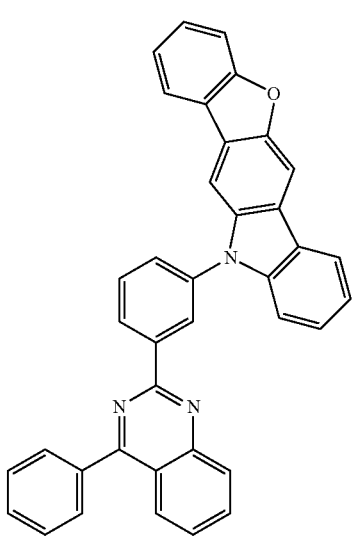
H2-254

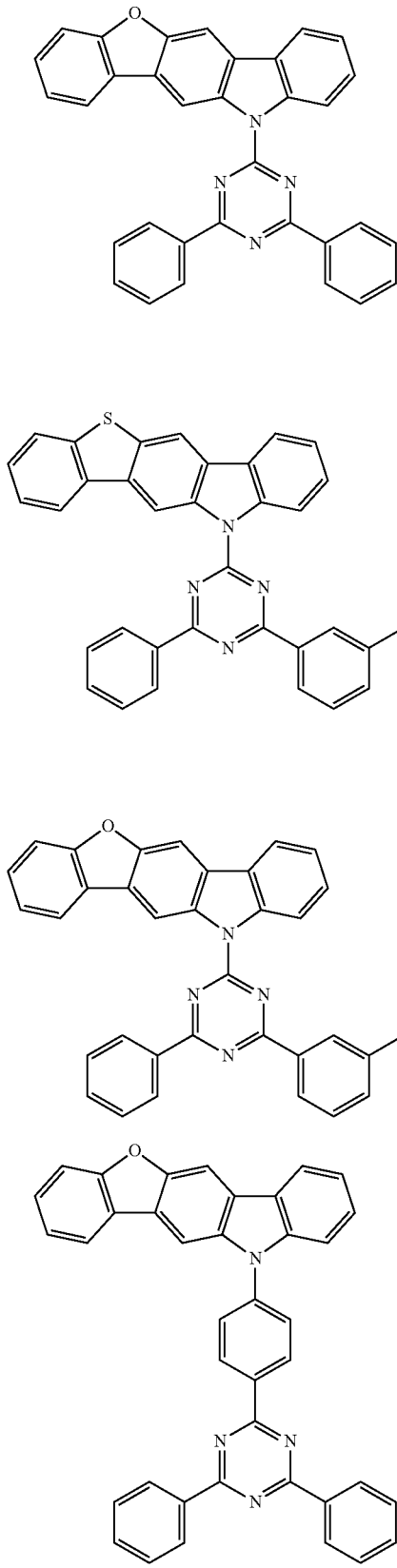
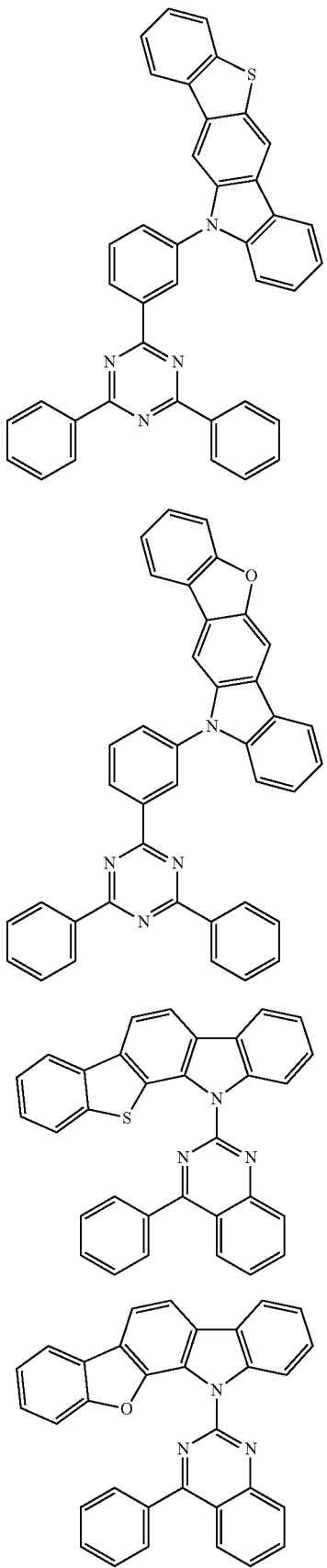

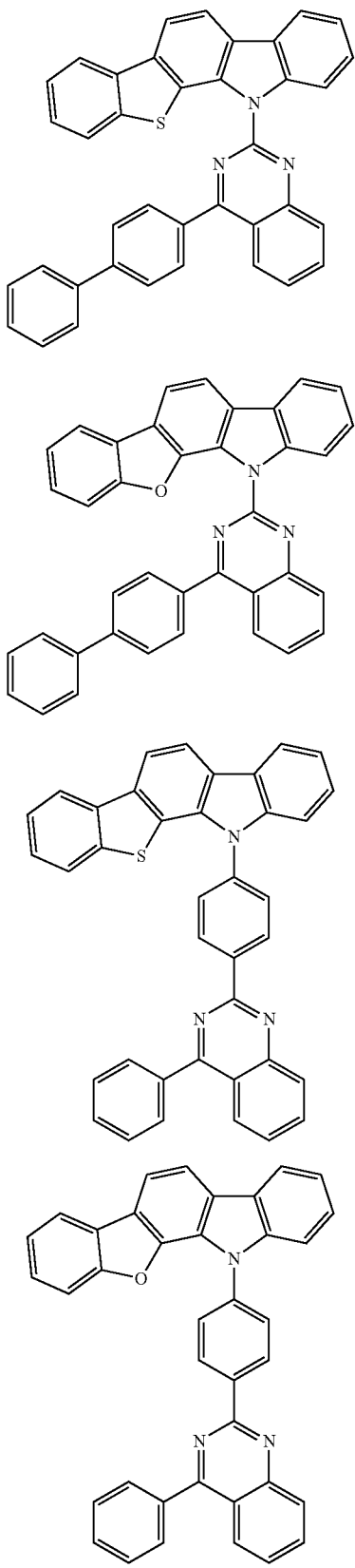
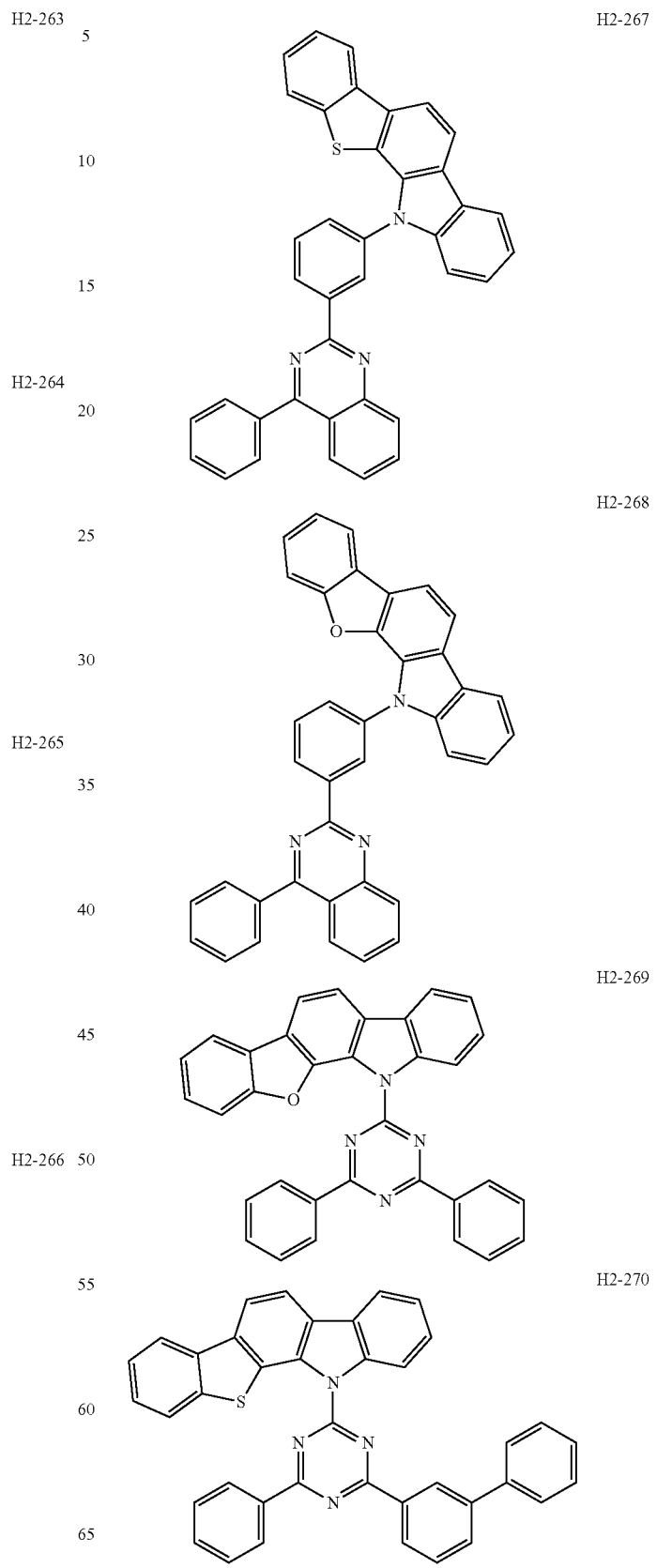

H2-271
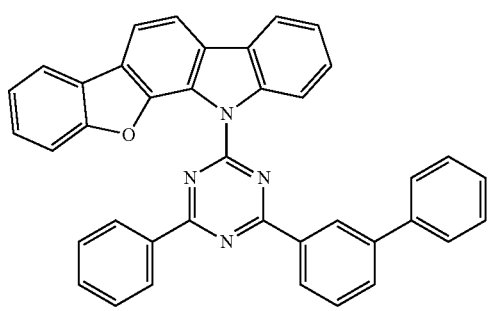
H2-272
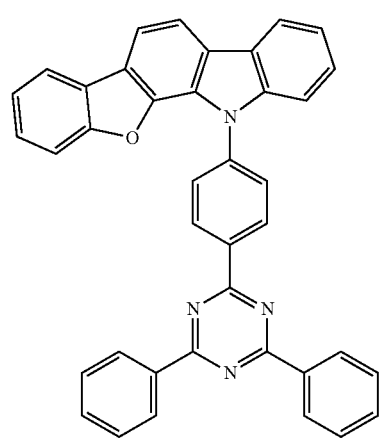
H2-273
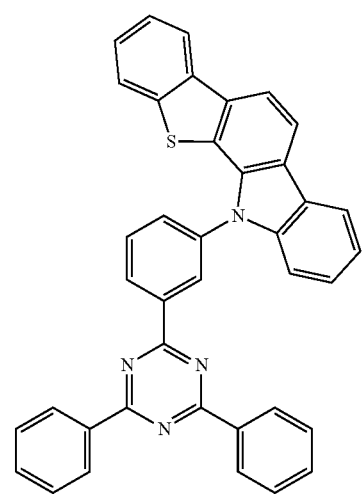
H2-274
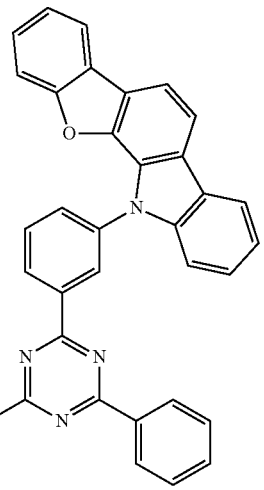
H2-275
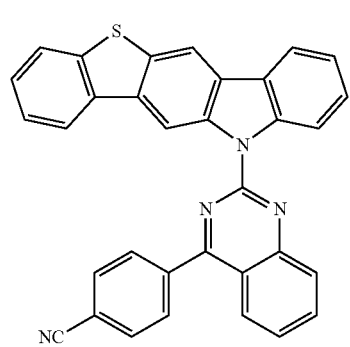
H2-276
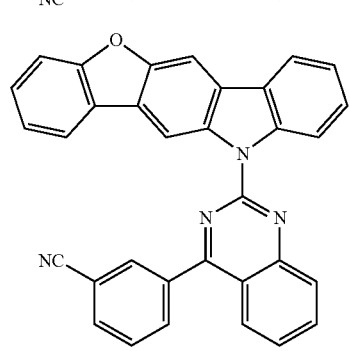
H2-277
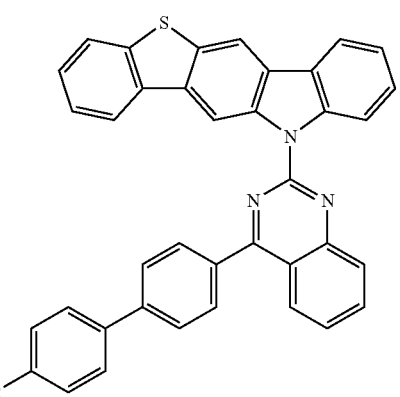

H2-278 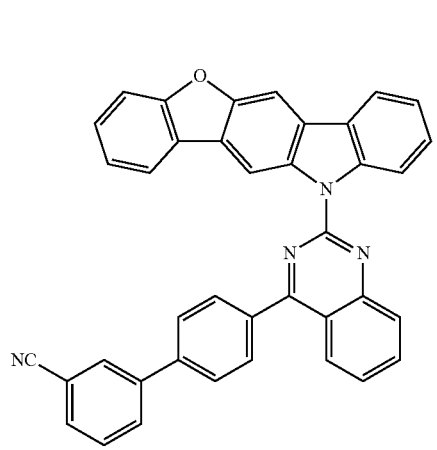
H2-279 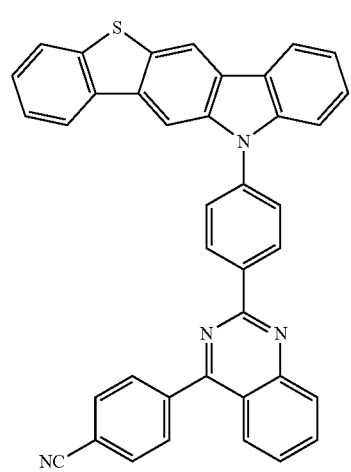
H2-280 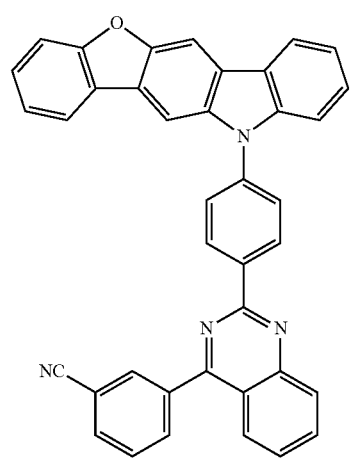
H2-281 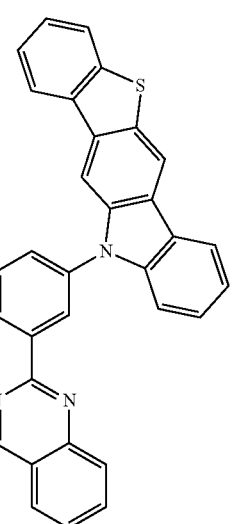
H2-282 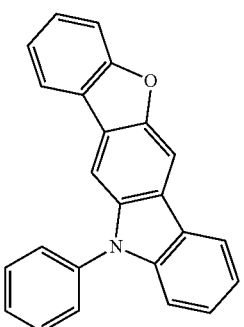
H2-283 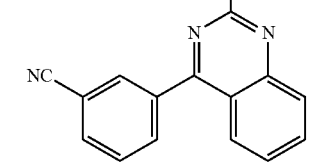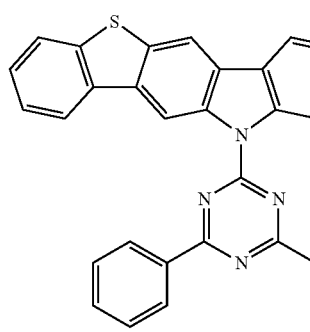

H2-284
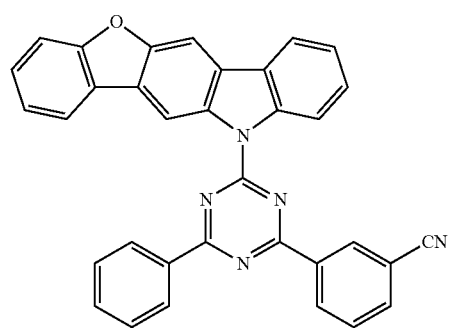
H2-285
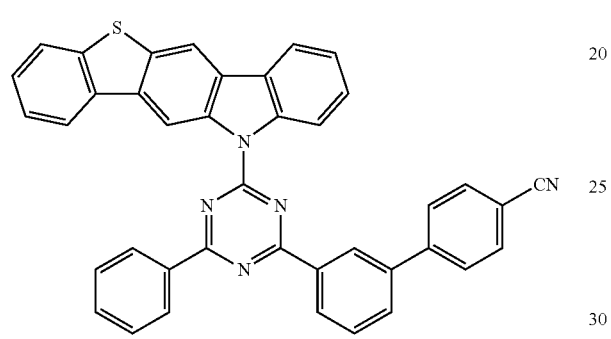
H2-286
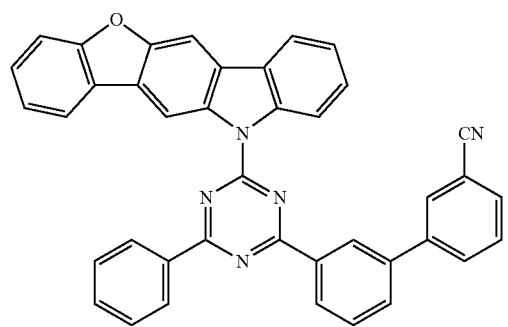
H2-287
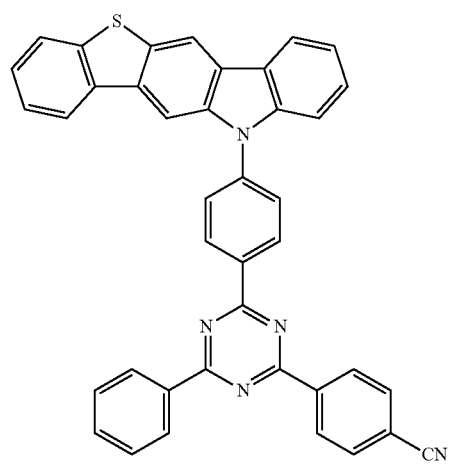
H2-288
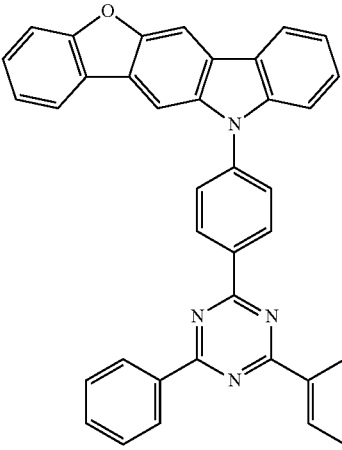
H2-289
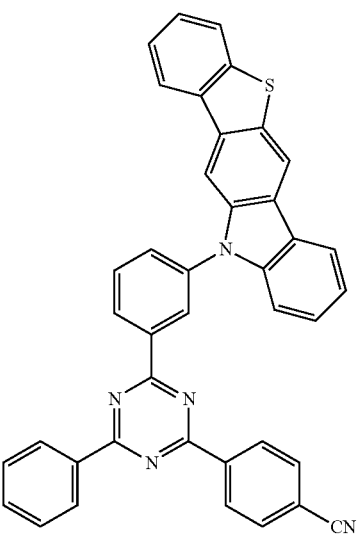
H2-290
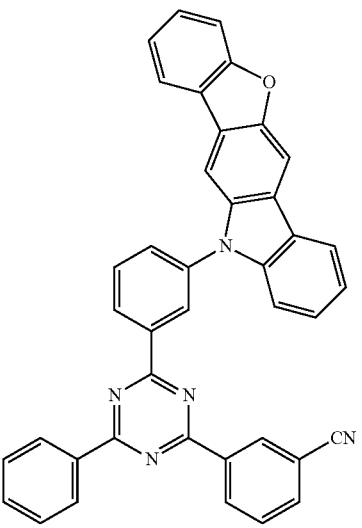

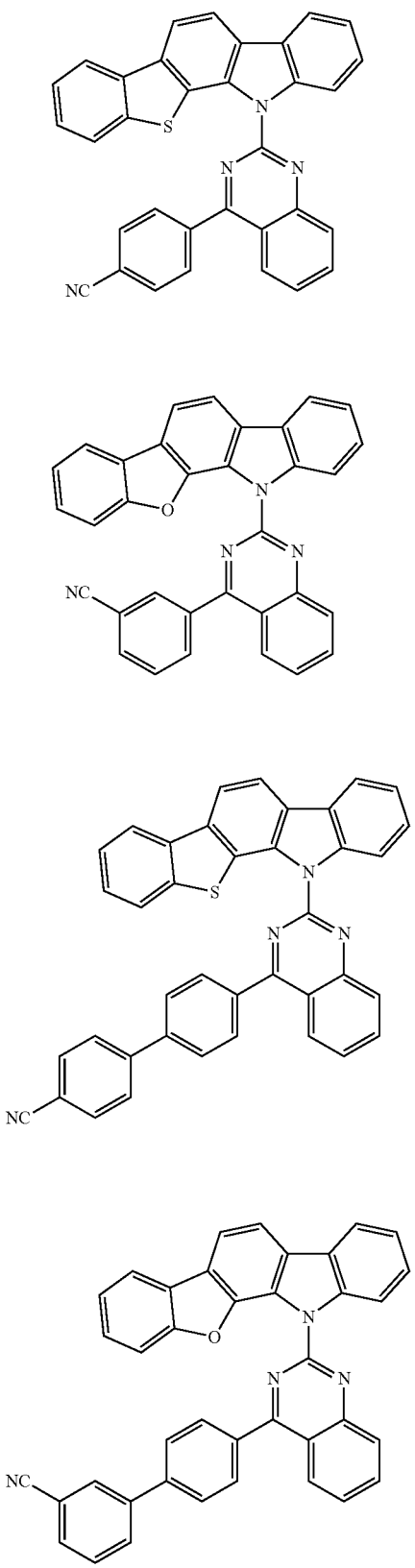
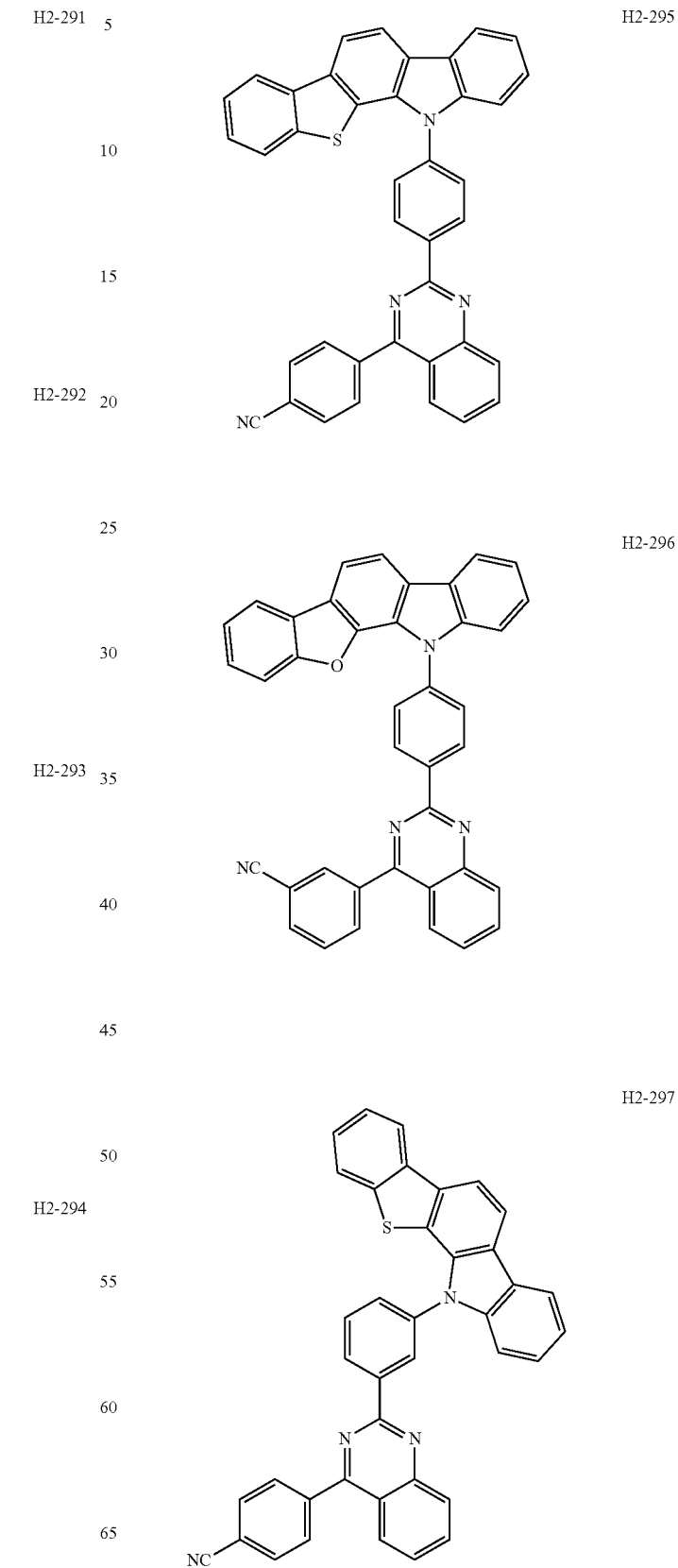

-continued
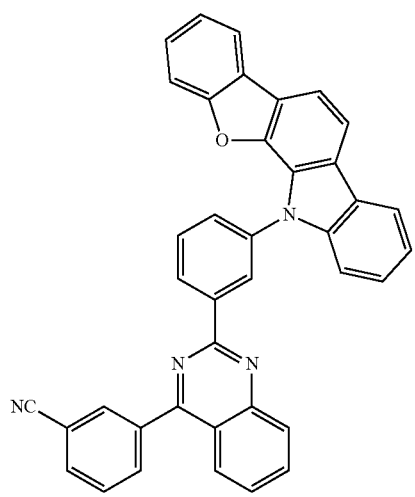
H2-298
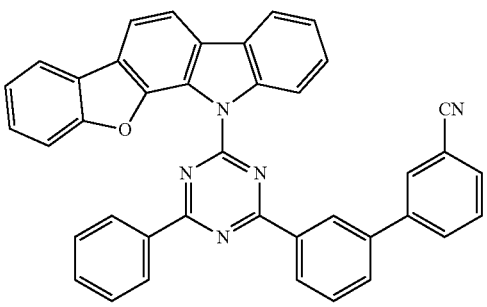
H2-302
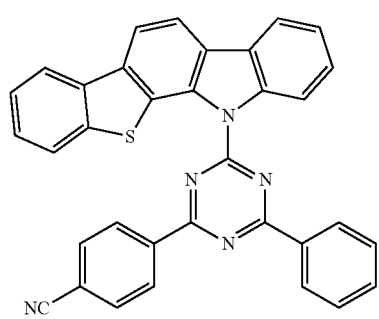
H2-299
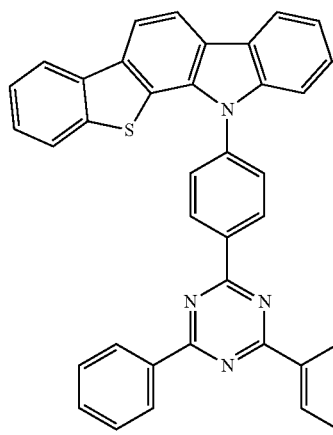
H2-303
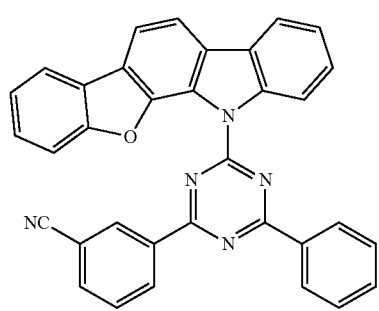
H2-300
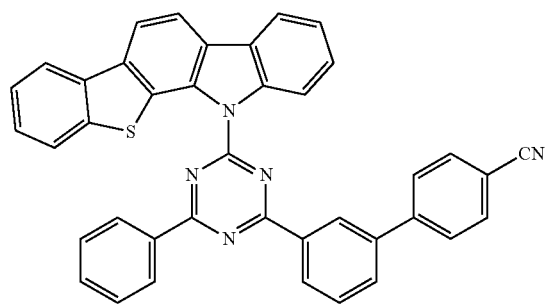
H2-301
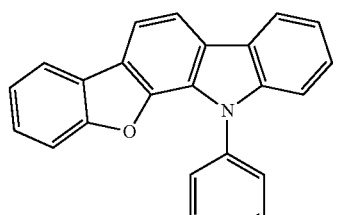
H2-304
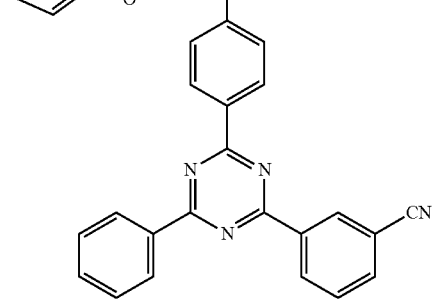

301
-continued
H2-305
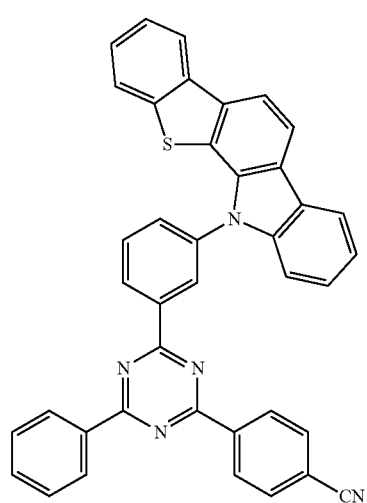
H2-306
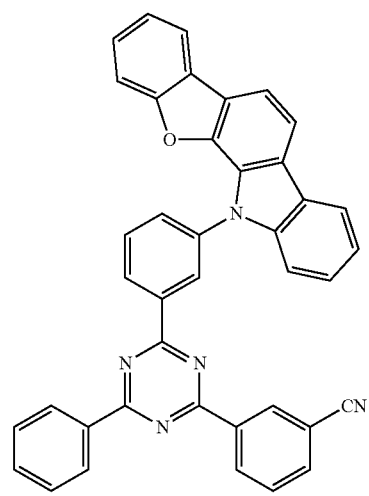
H2-307
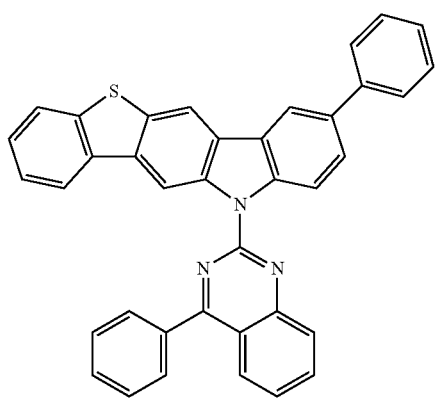
302
-continued
H2-308
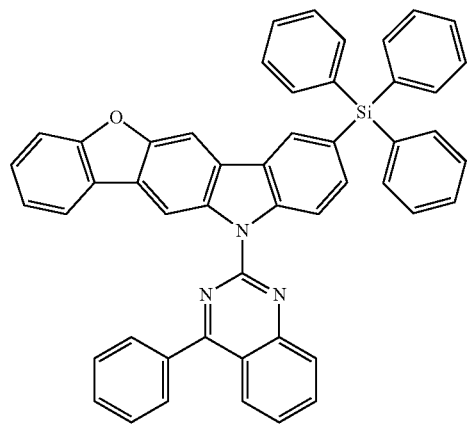
H2-309
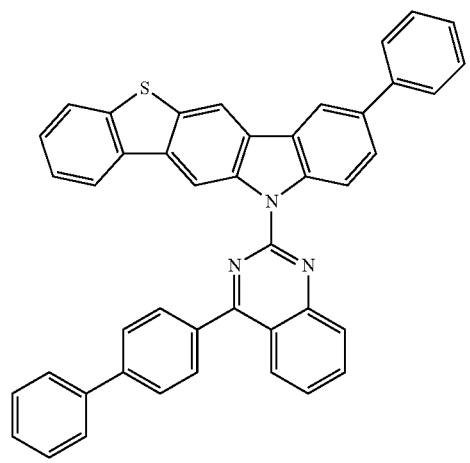
H2-310
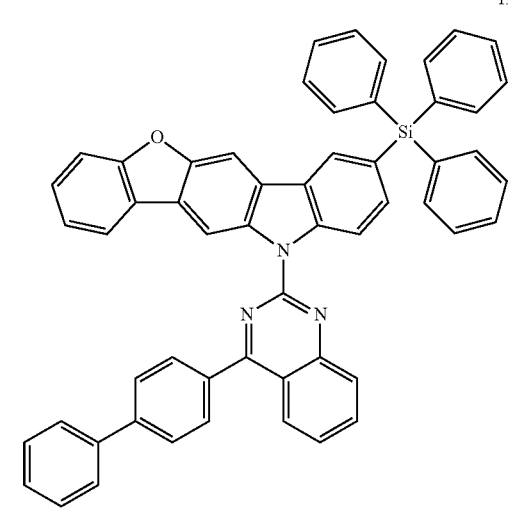

-continued
H2-311
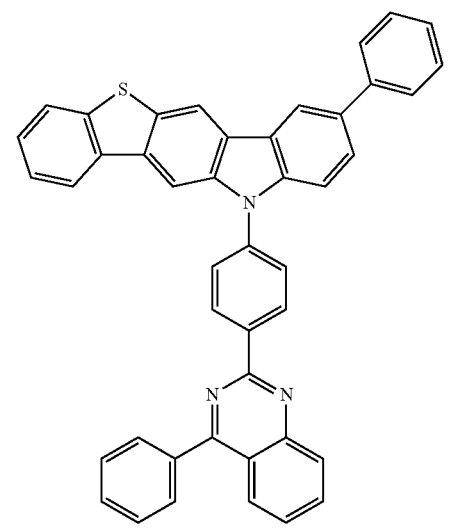
H2-312
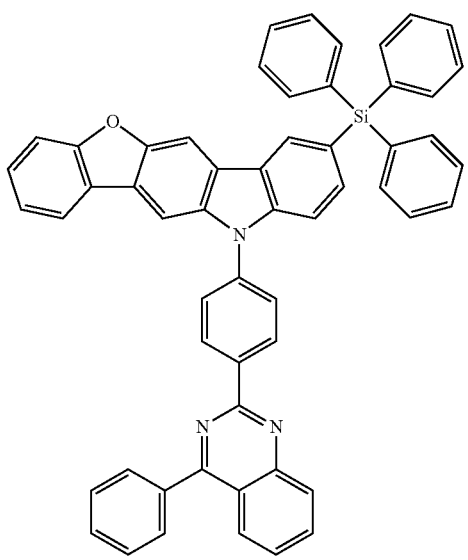
H2-313
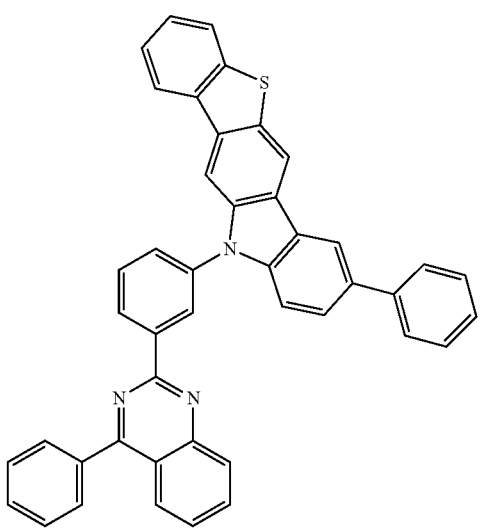
-continued
H2-314
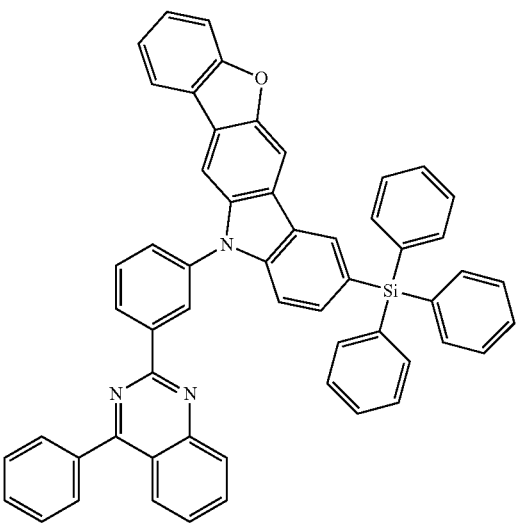
H2-315
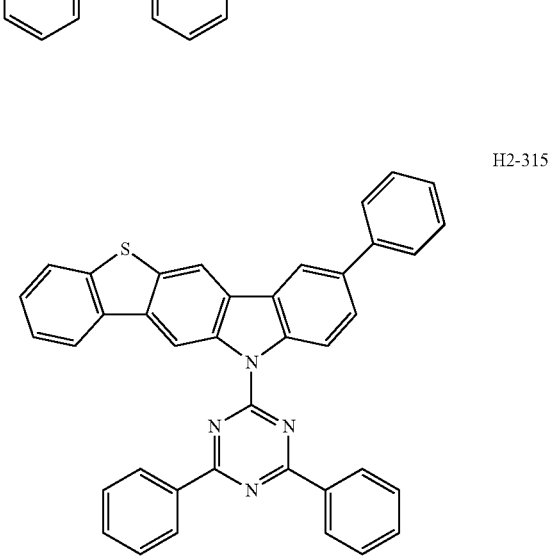
H2-316
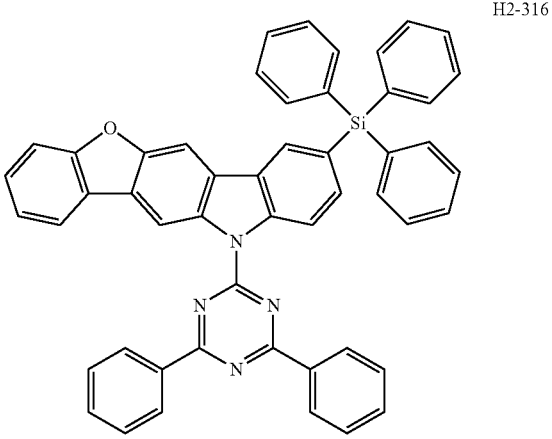

H2-317
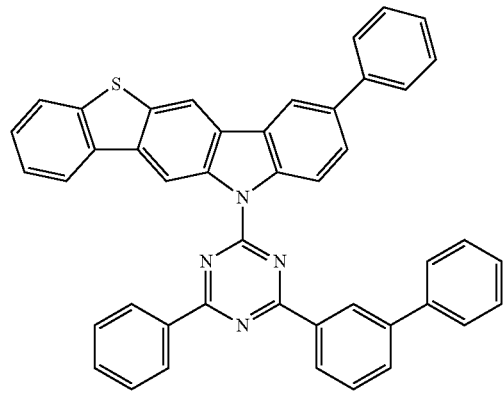
H2-318
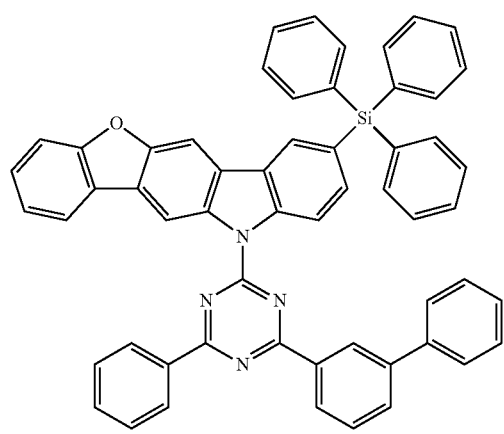
H2-319
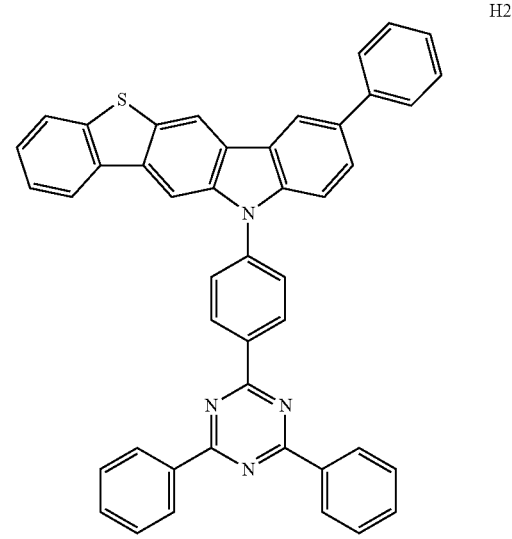
H2-320
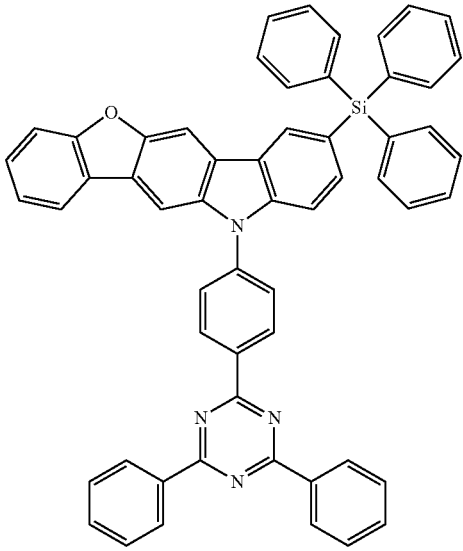
H2-321
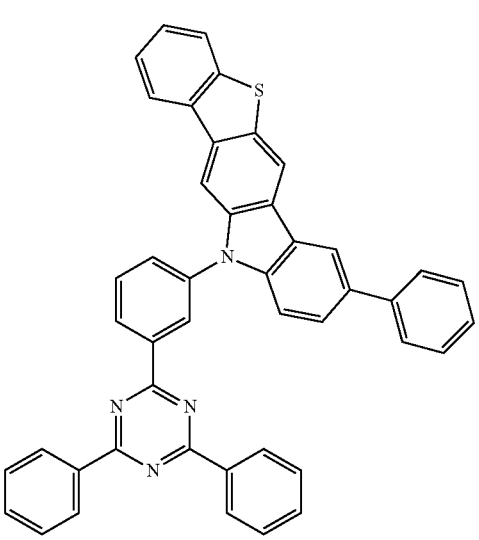
H2-322
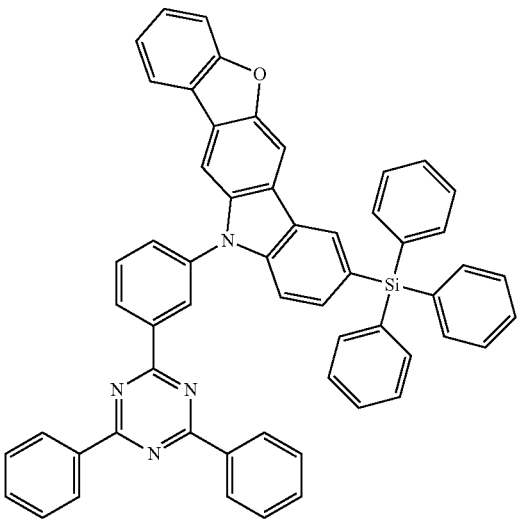

307
-continued
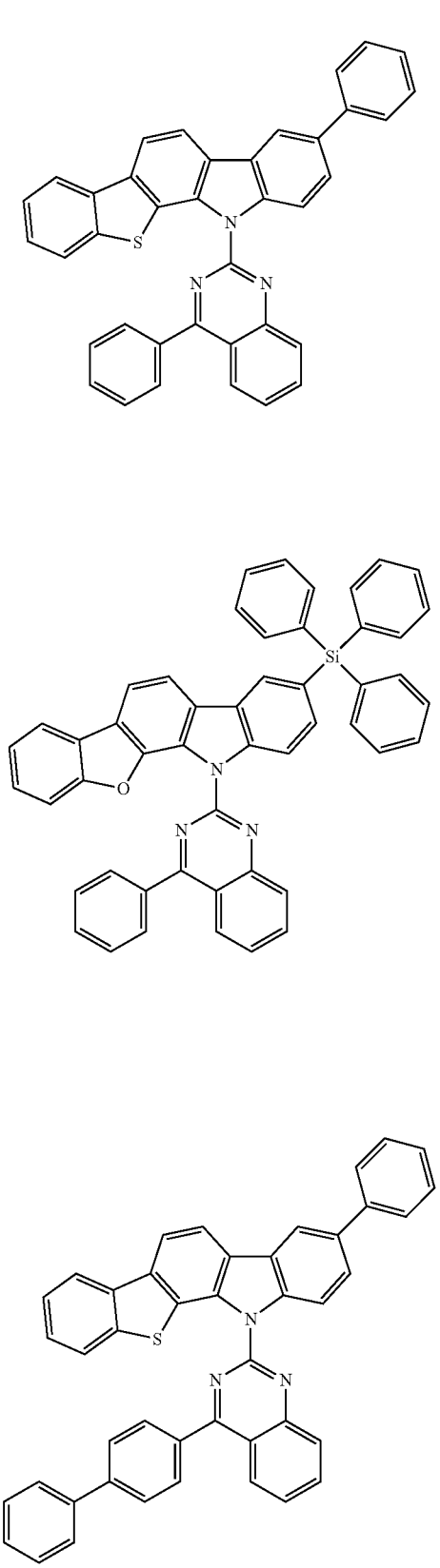
H2-323
H2-324
H2-325
308
-continued
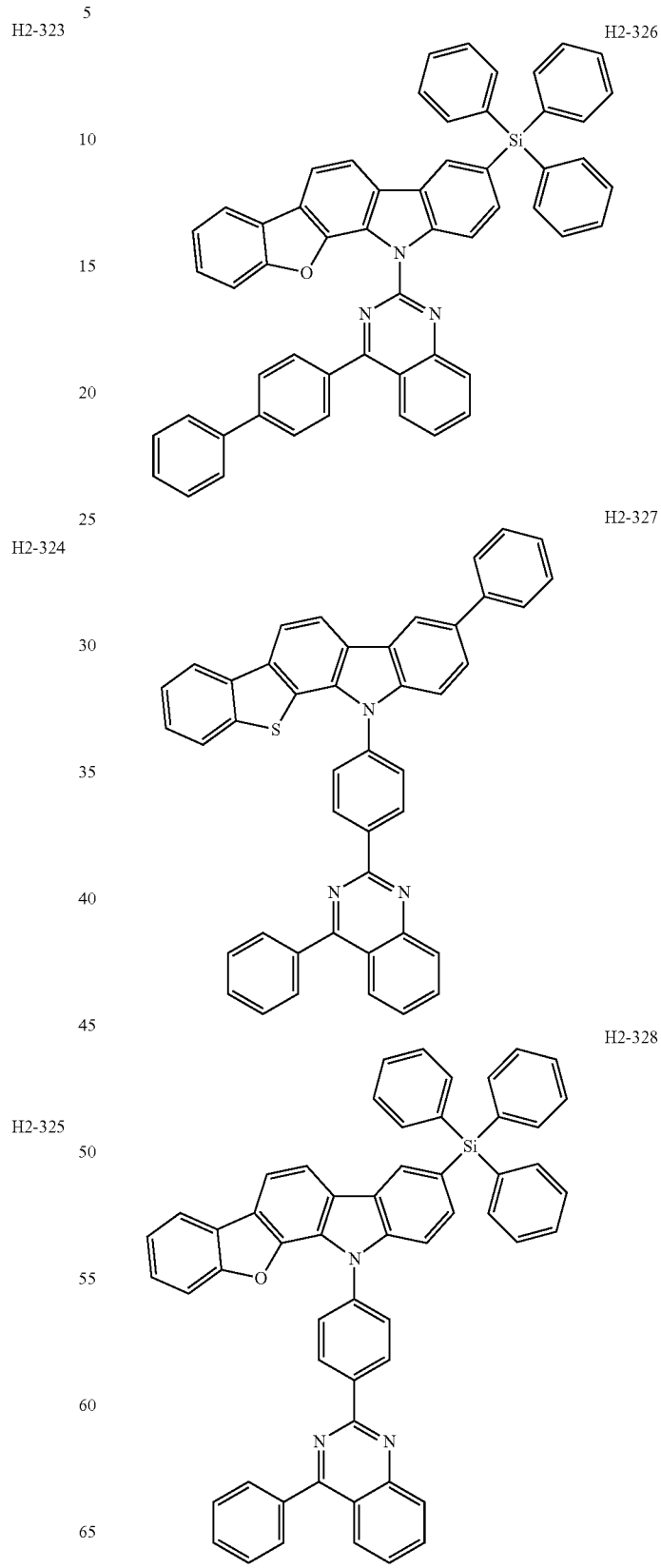
H2-326
H2-327
H2-328

H2-329
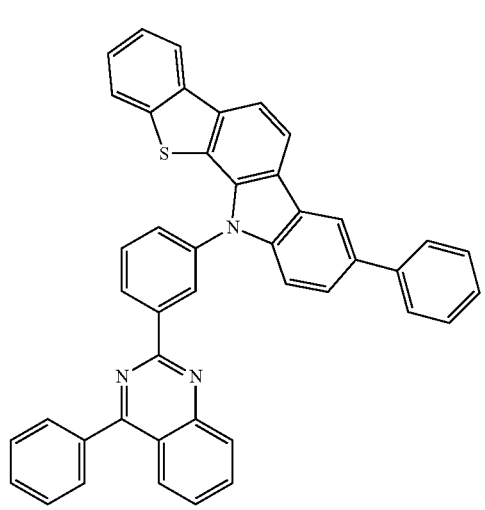
H2-330
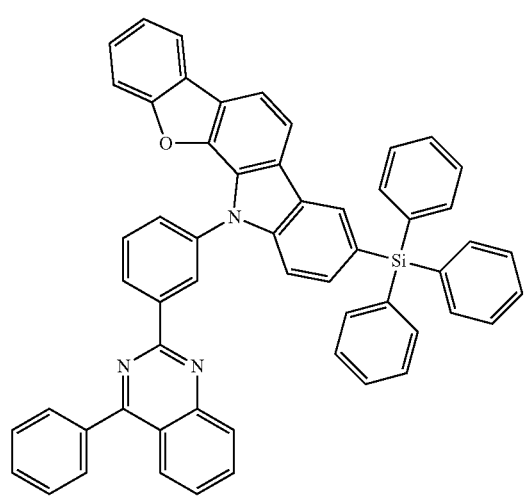
H2-331
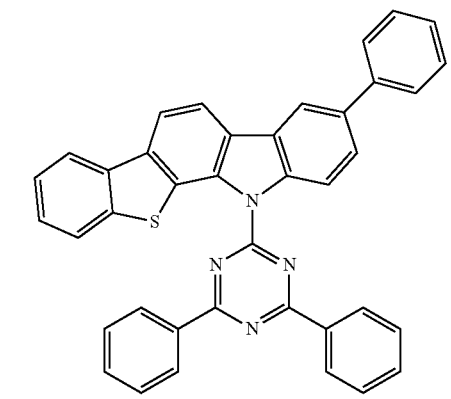
H2-332
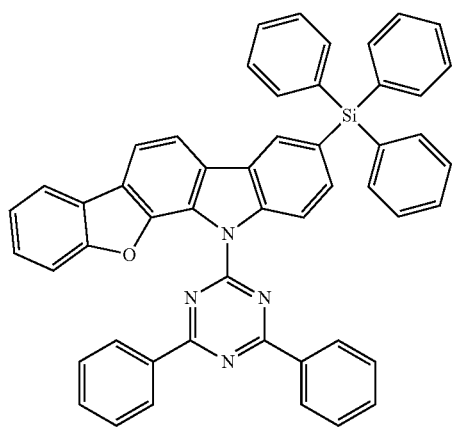
H2-333
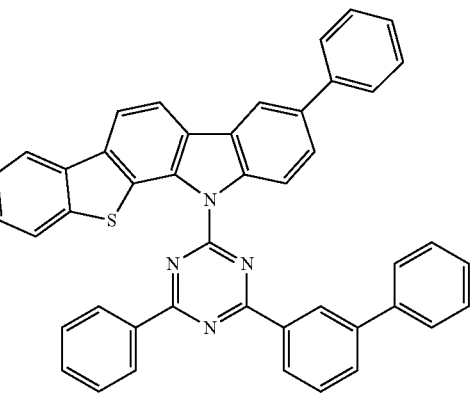
H2-334
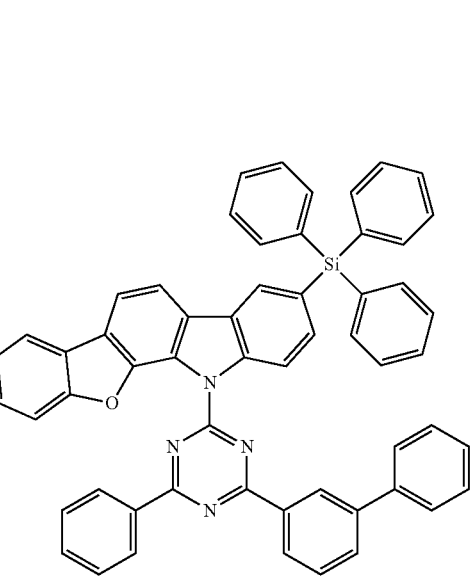

311
-continued
312
-continued
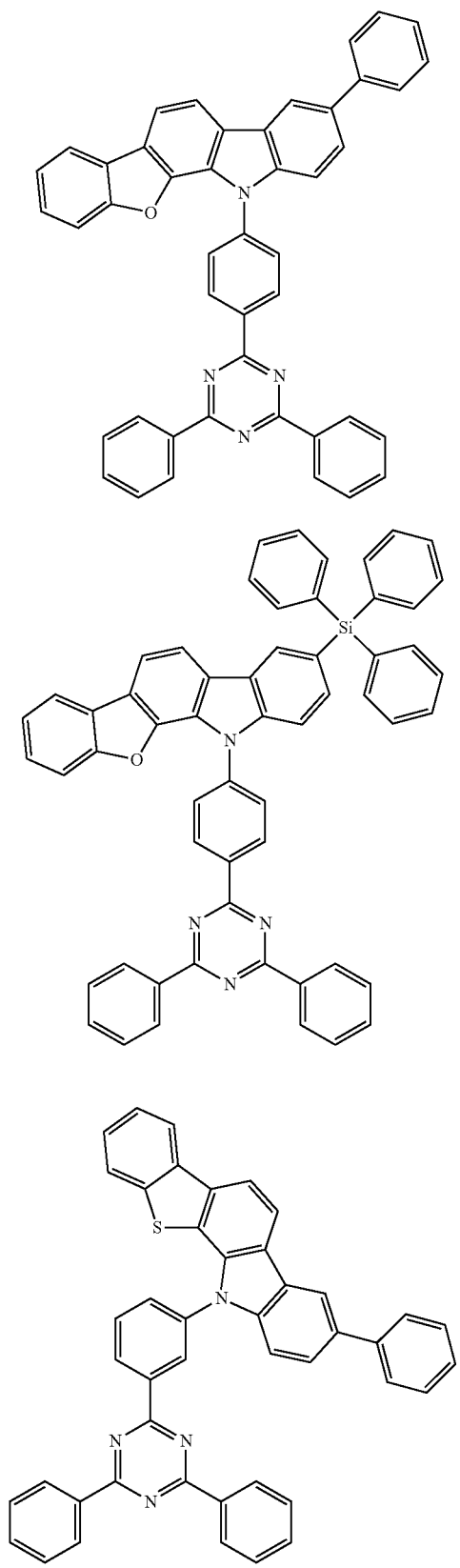
H2-335
H2-336
H2-337
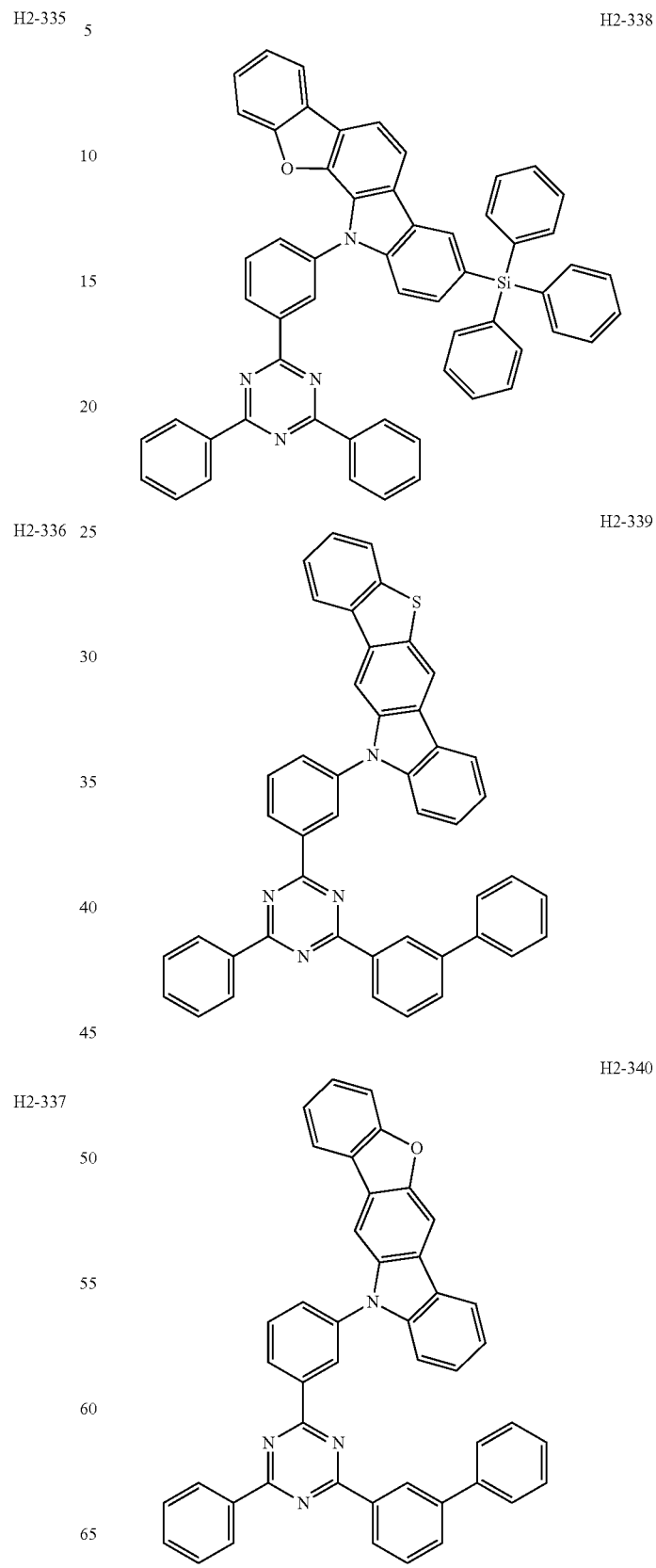
H2-338
H2-339
H2-340

H2-341
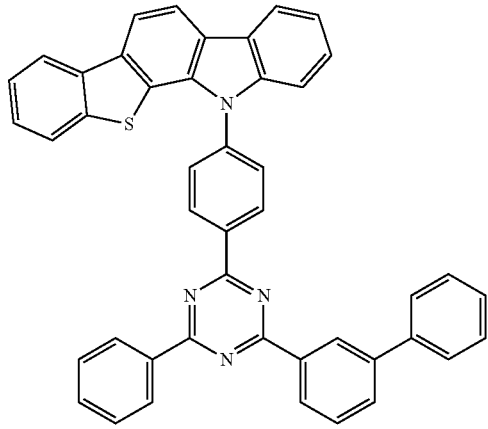
H2-344
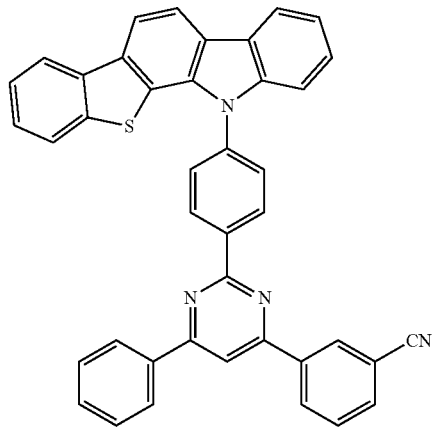
H2-342
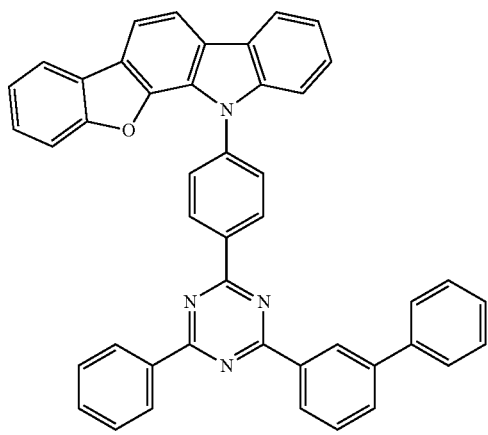
H2-345
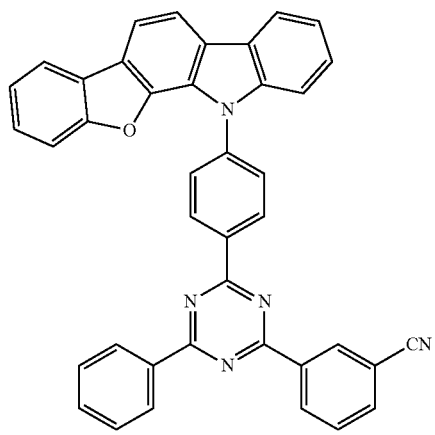
H2-343
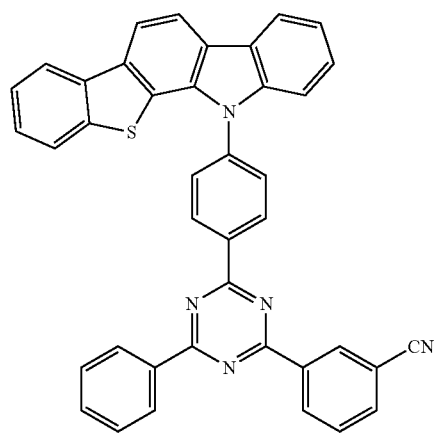
H2-346
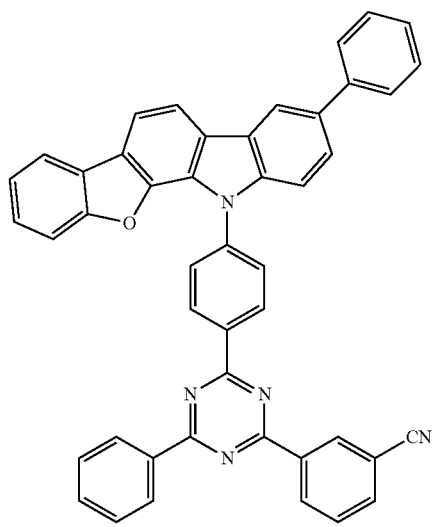

315
-continued
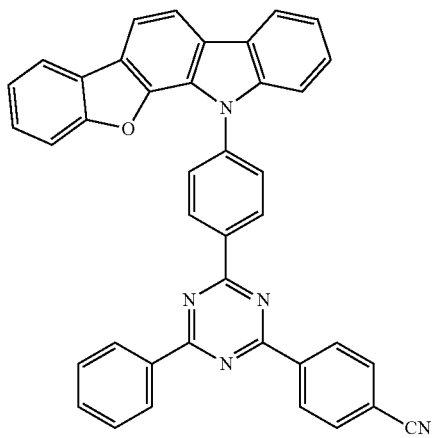
H2-347
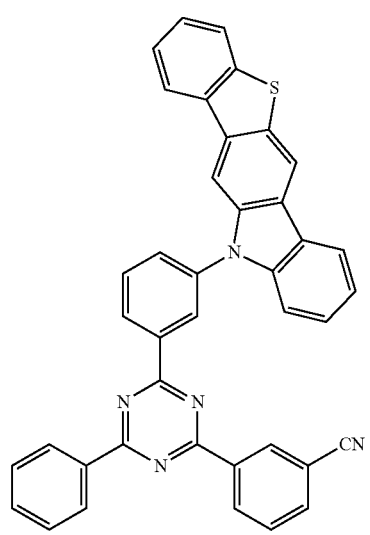
H2-348
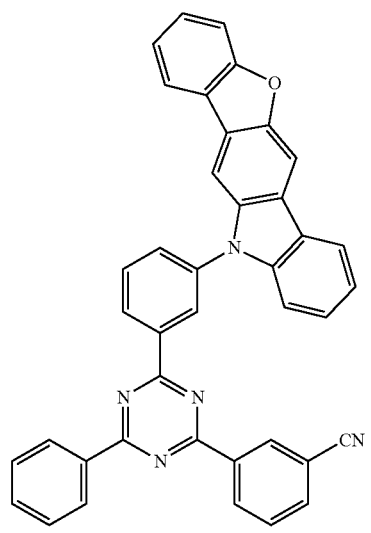
H2-349
316
-continued
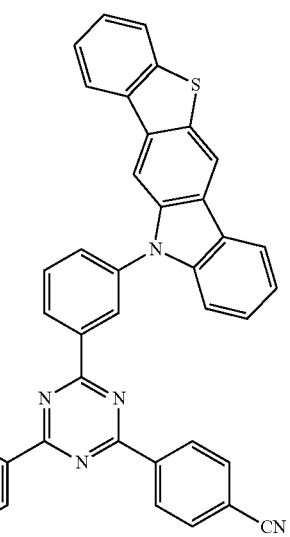
H2-350
H2-351
H2-352
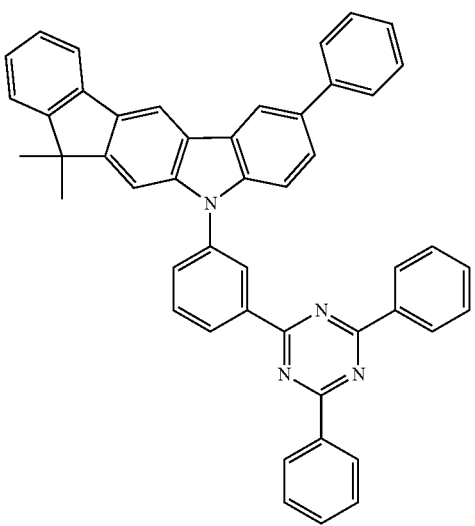

317
-continued
H2-353
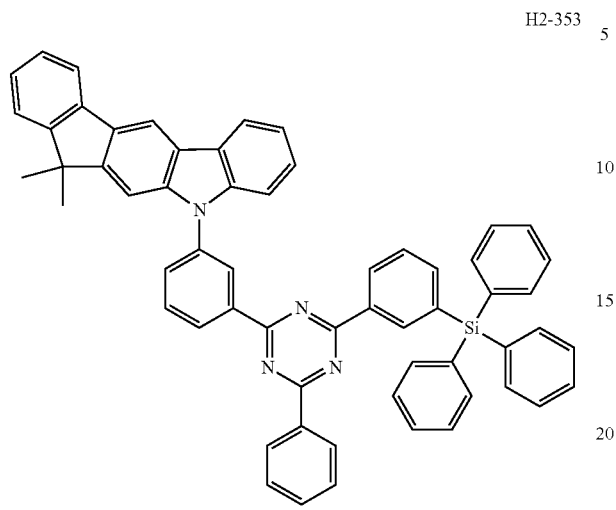
H2-354
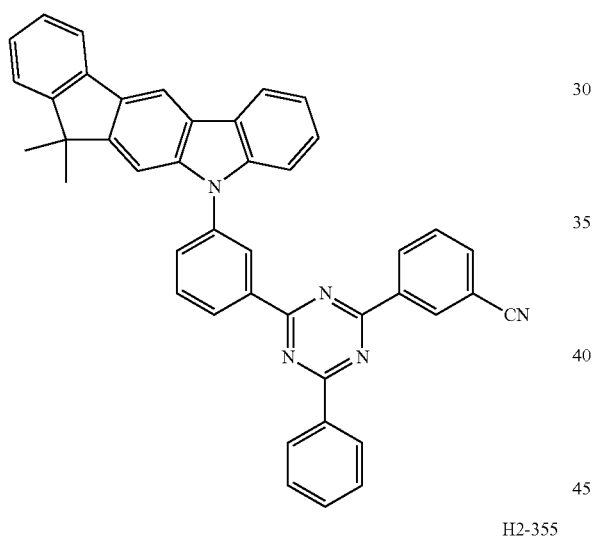
H2-355
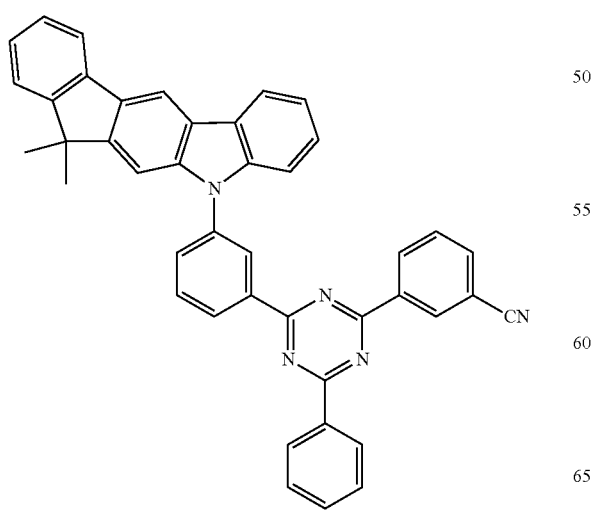
318
-continued
H2-356
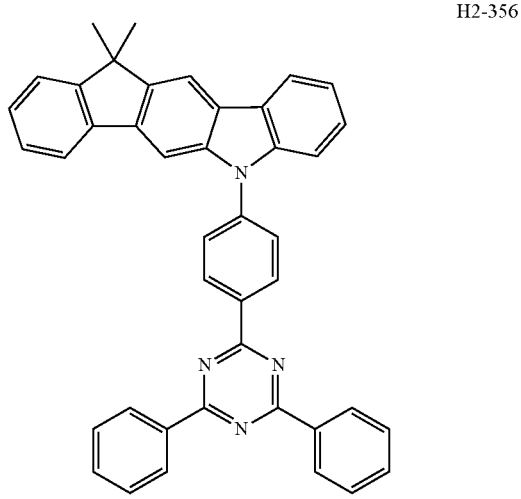
H2-357
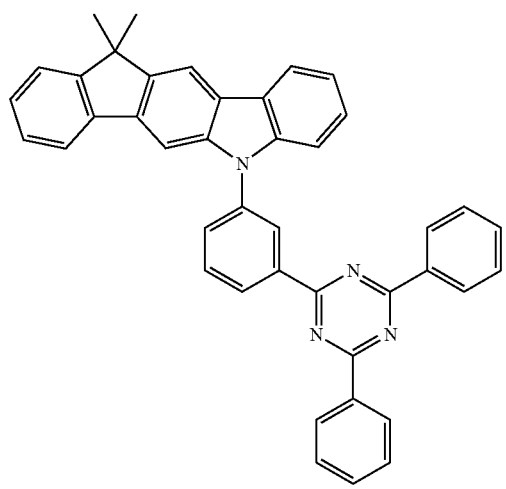
H2-358
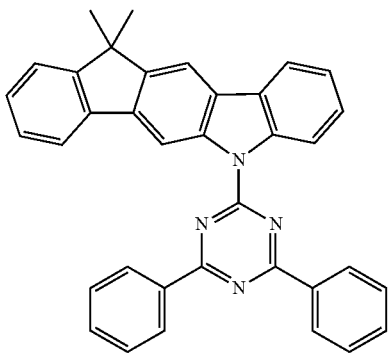

H2-359
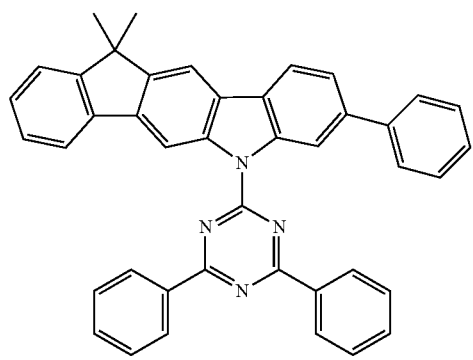
H2-360
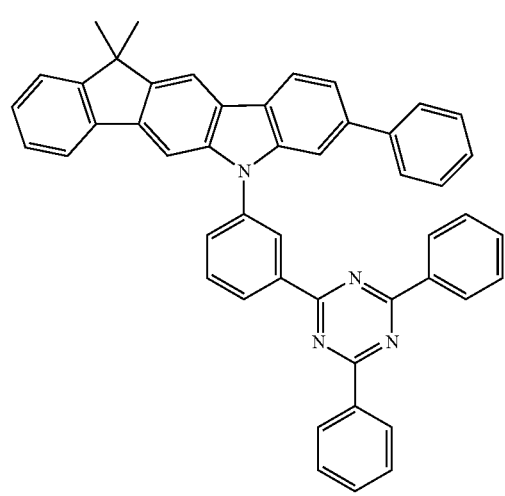
H2-361
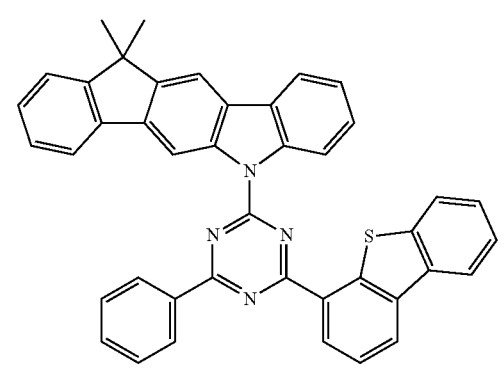
H2-362
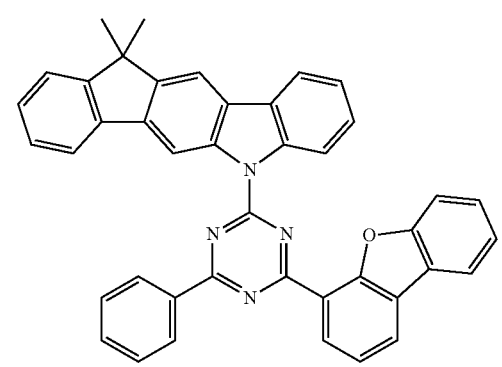
H2-363
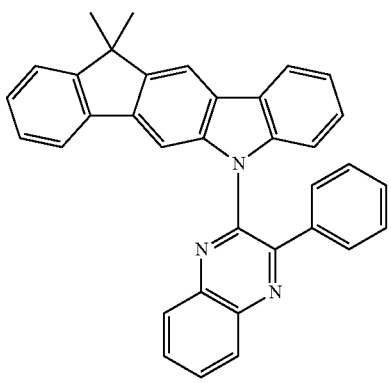
H2-364
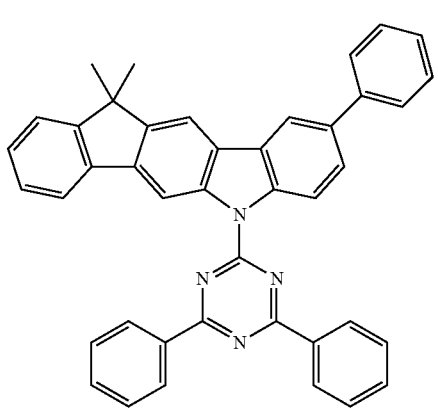
H2-365
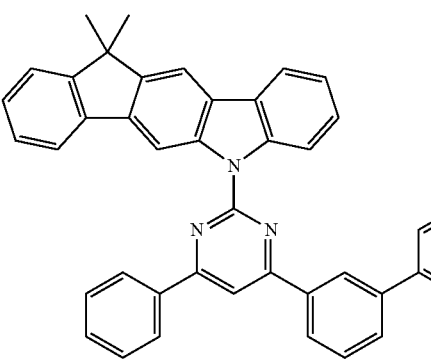
H2-366
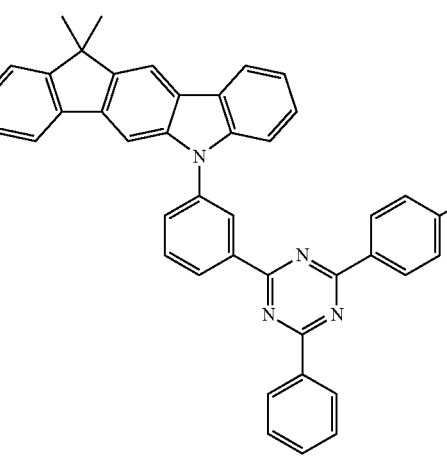

H2-367
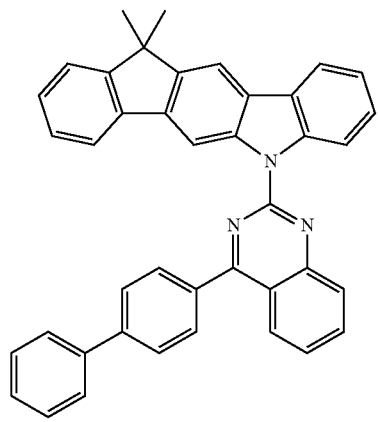
H2-368
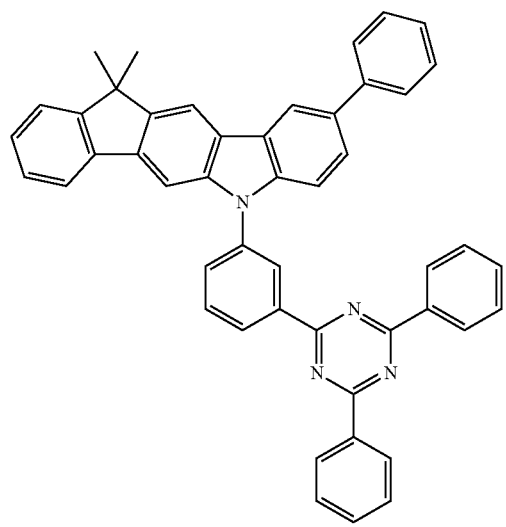
H2-369
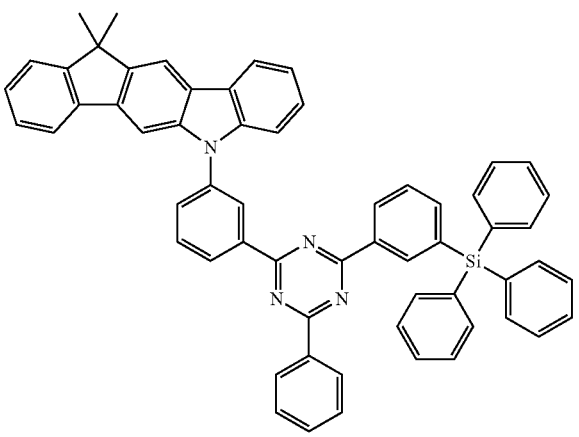
H2-370
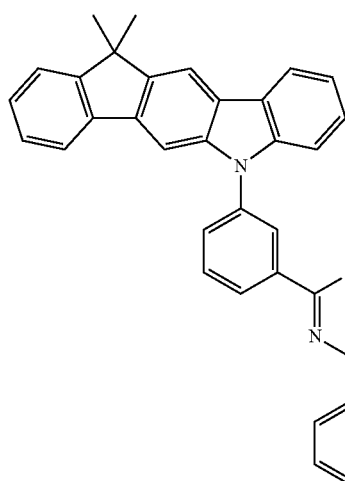
H2-371
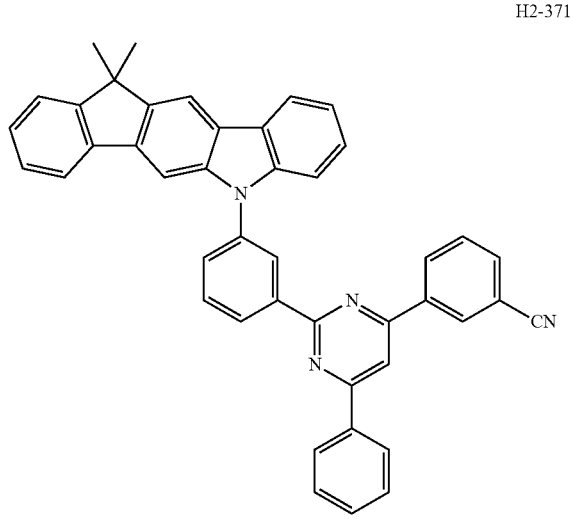
H2-372
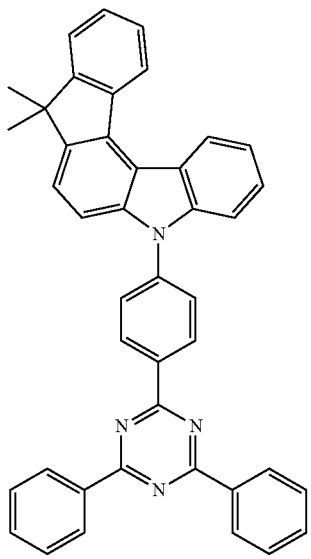

H2-373
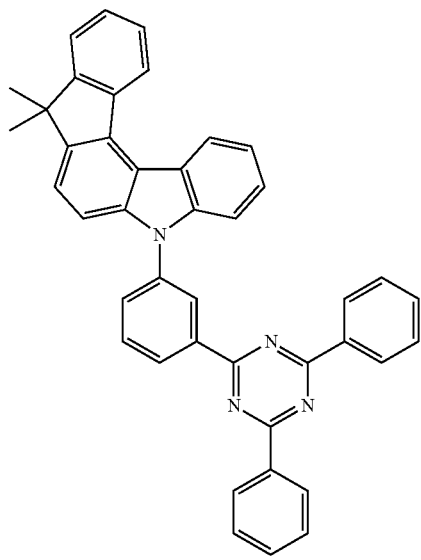
H2-376
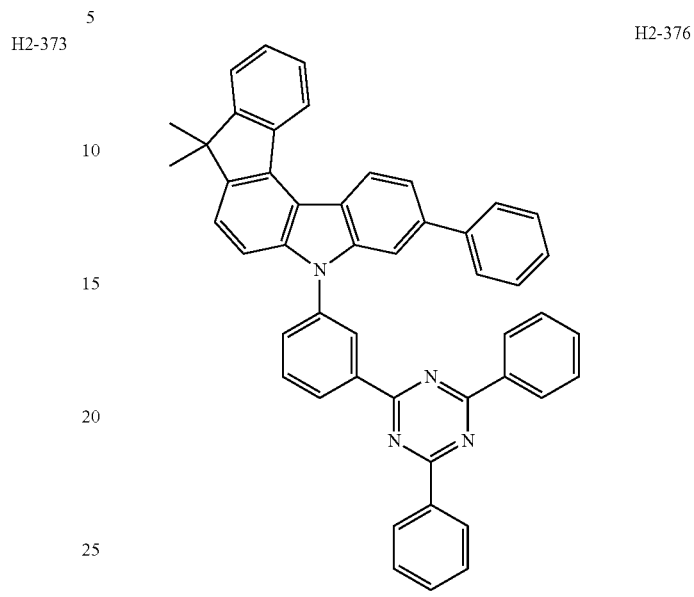
H2-374
H2-377
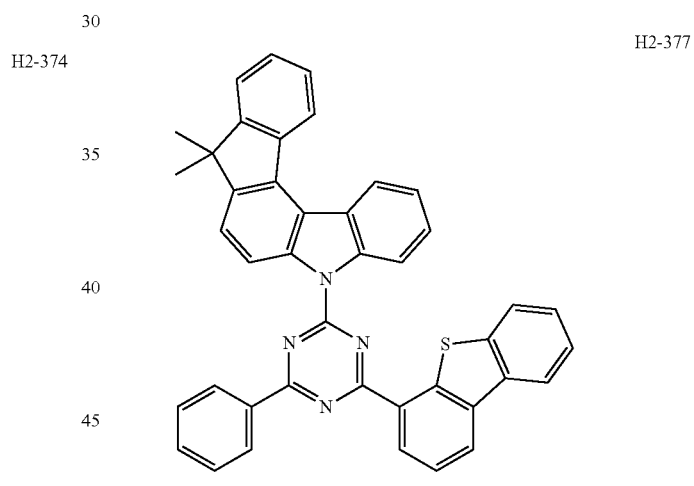
H2-375
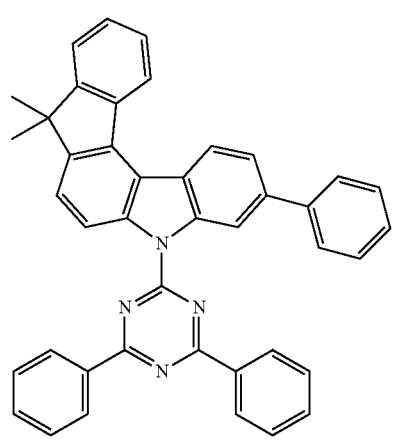
H2-378
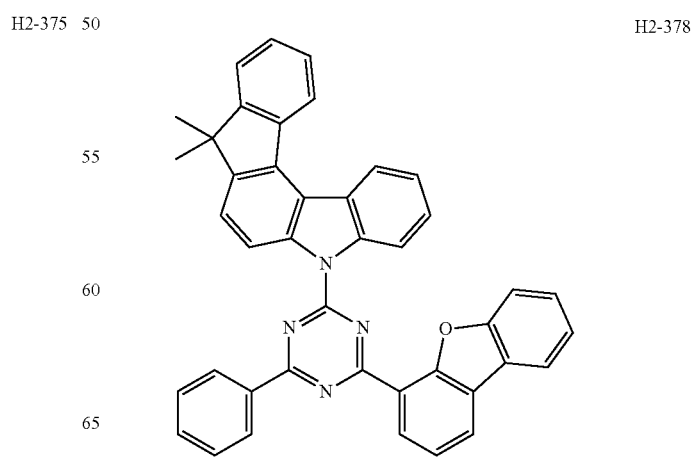

H2-379
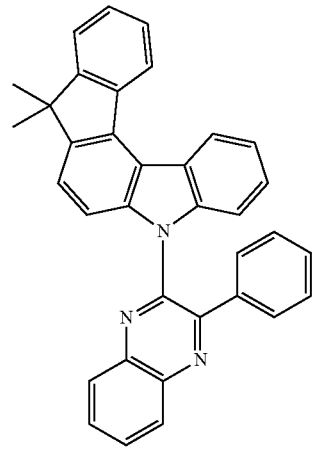
H2-380
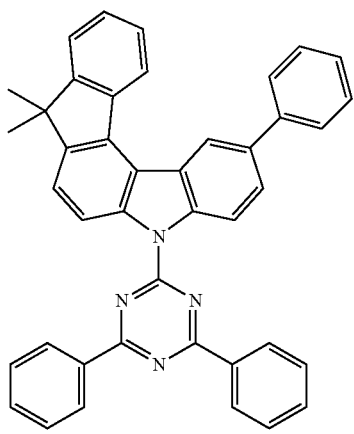
H2-381
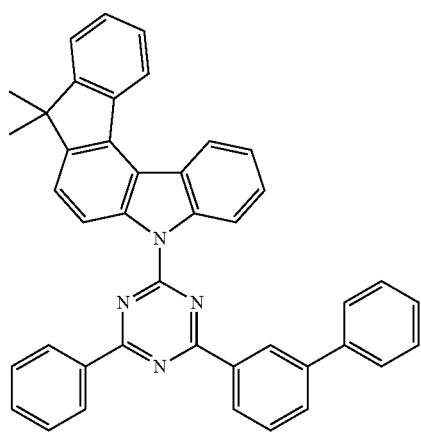
H2-382
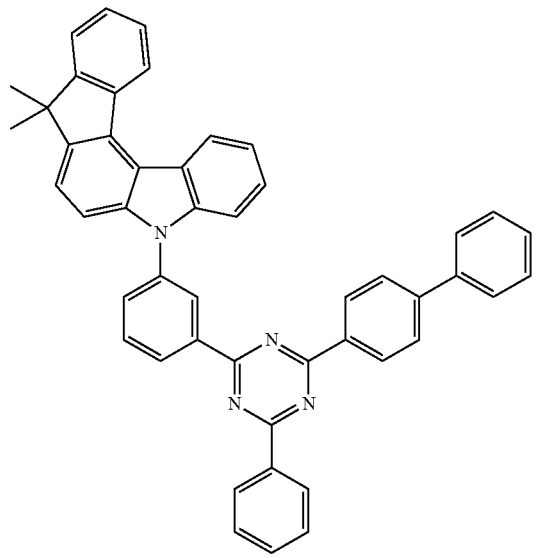
H2-383
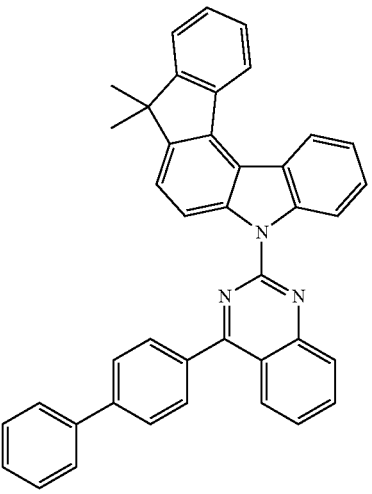
H2-384
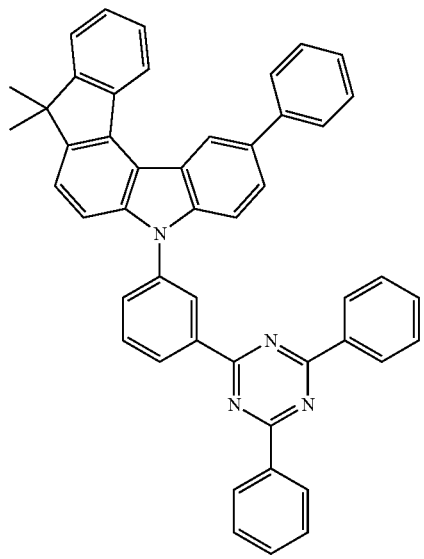

-continued
H2-385
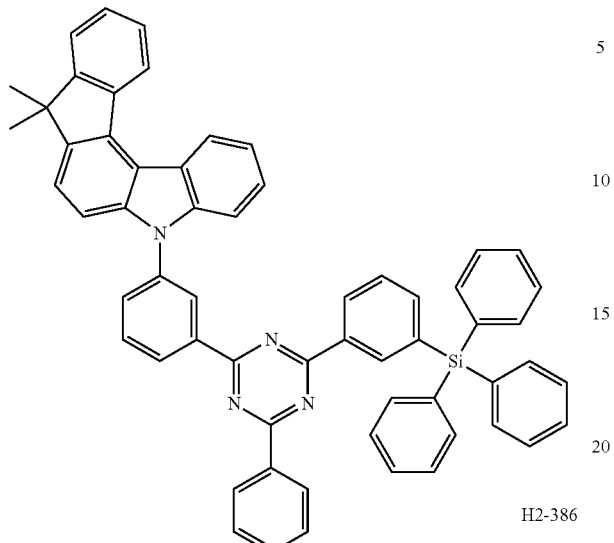
H2-386
H2-387
H2-388
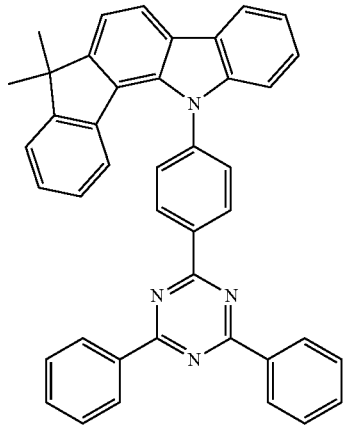
H2-389
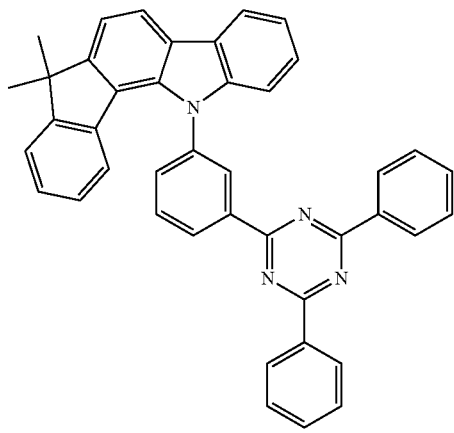
H2-390
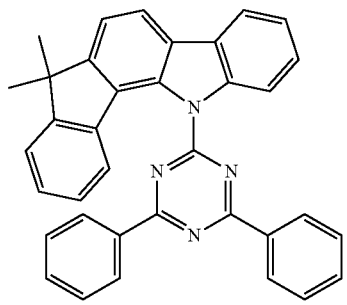
H2-391
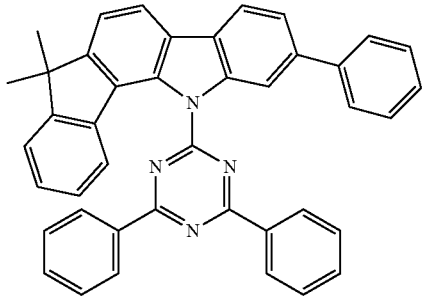

H2-392
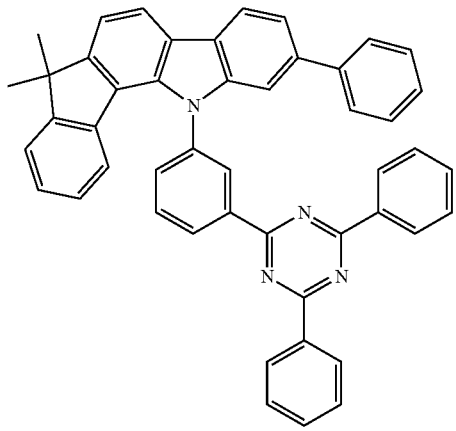
H2-393
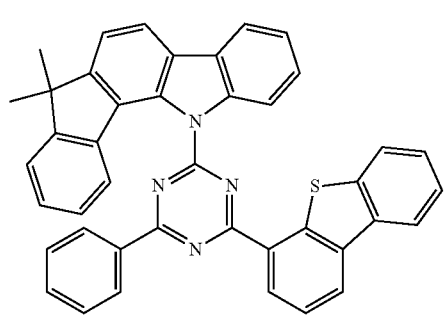
H2-394
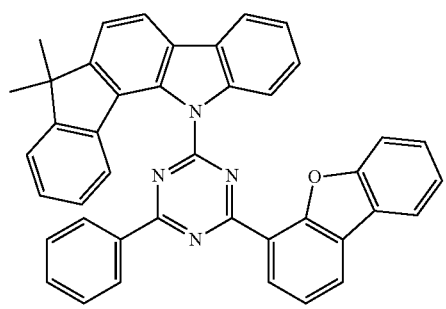
H2-395
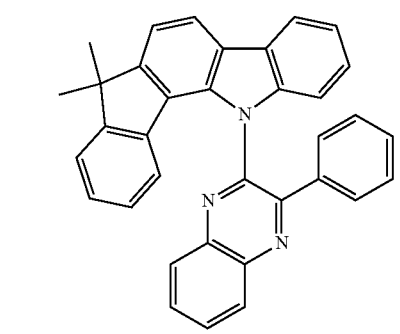
H2-396
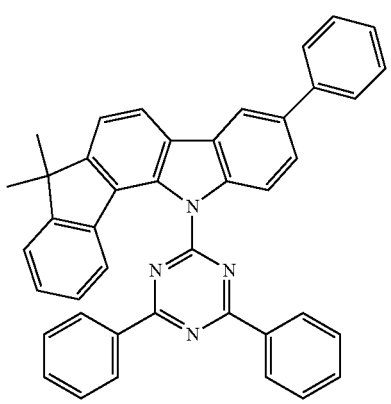
H2-397
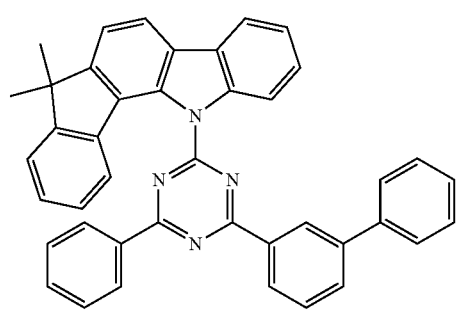
H2-398
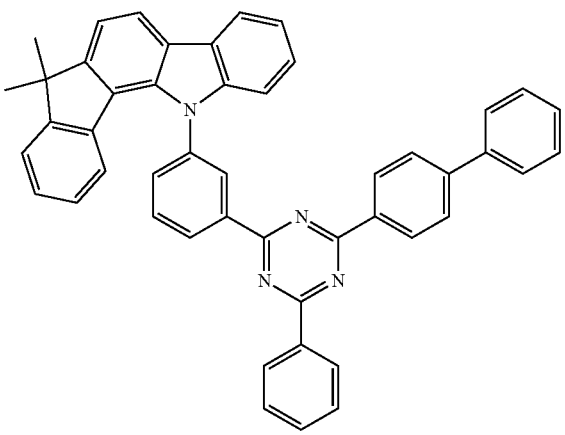
H2-399
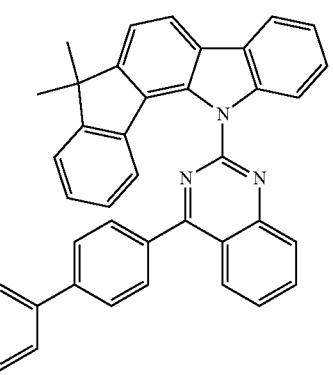

-continued
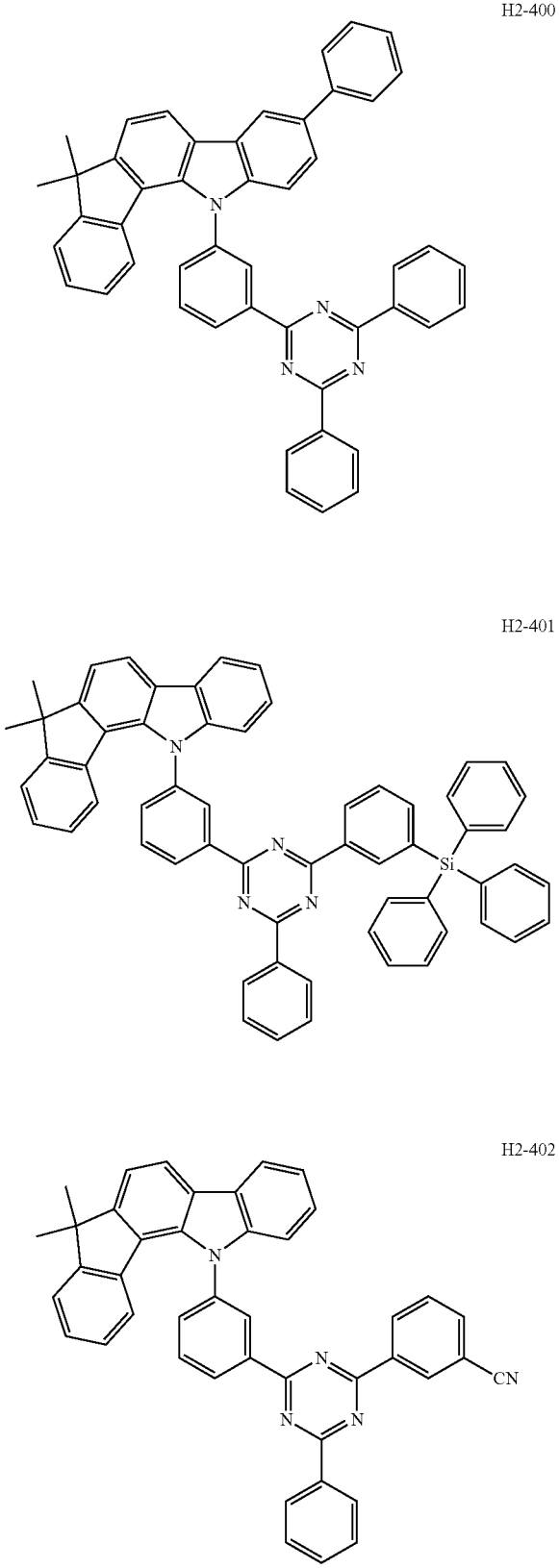
H2-400
H2-401
H2-402
-continued
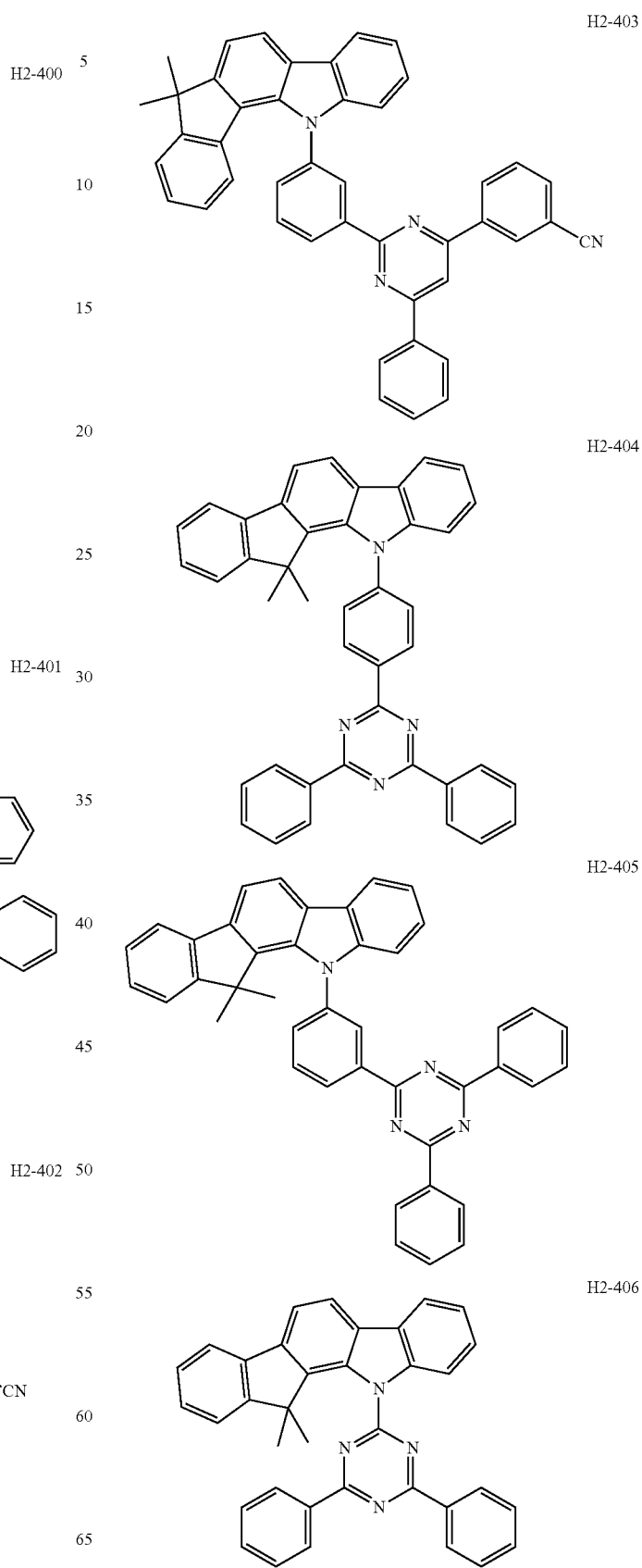
H2-403
H2-404
H2-405
H2-406

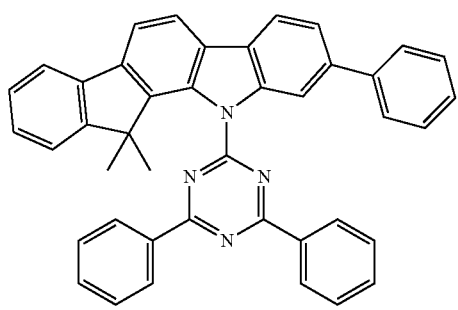
H2-407
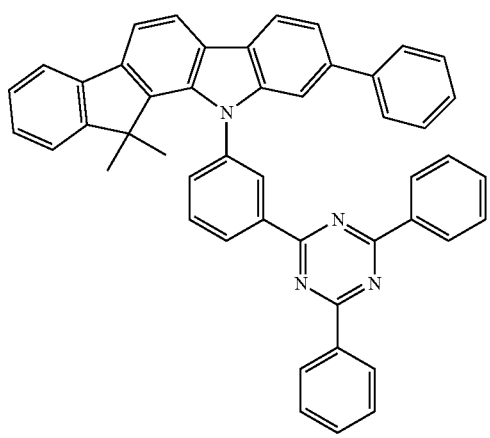
H2-408
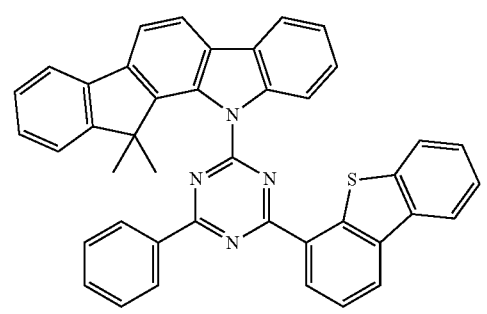
H2-409
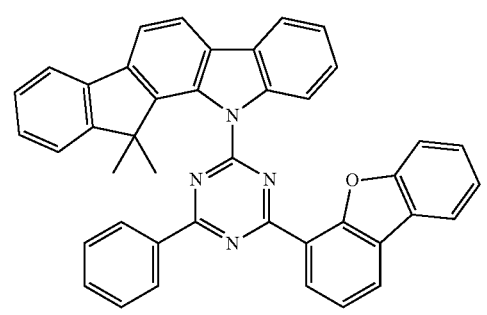
H2-410
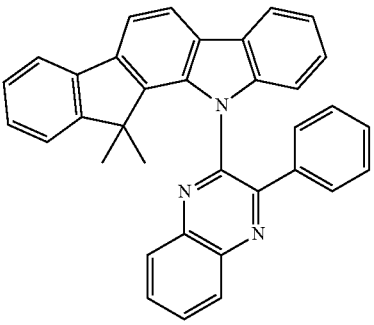
H2-411
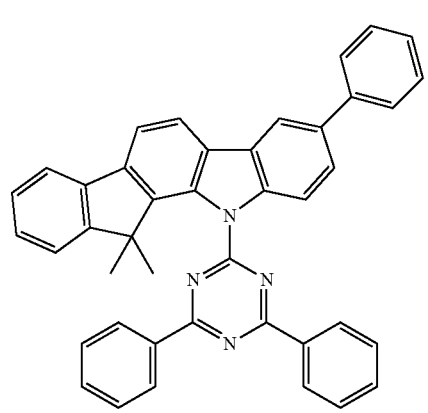
H2-412
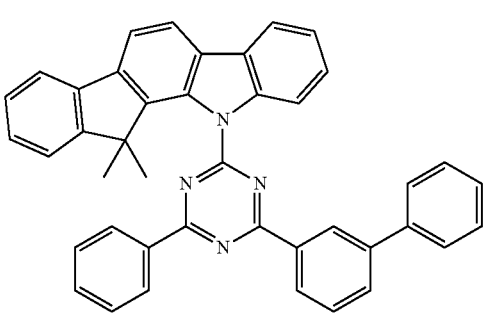
H2-413
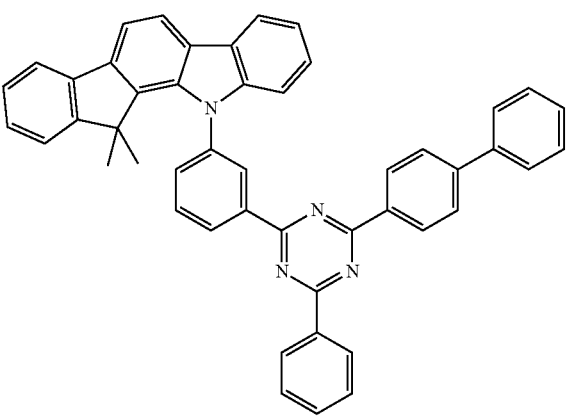
H2-414

H2-415
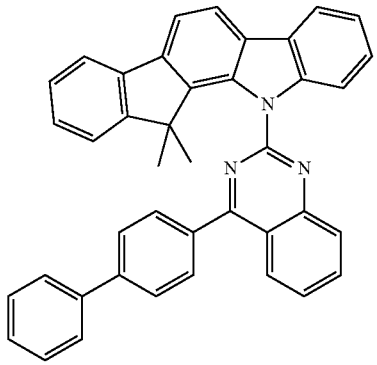
H2-418
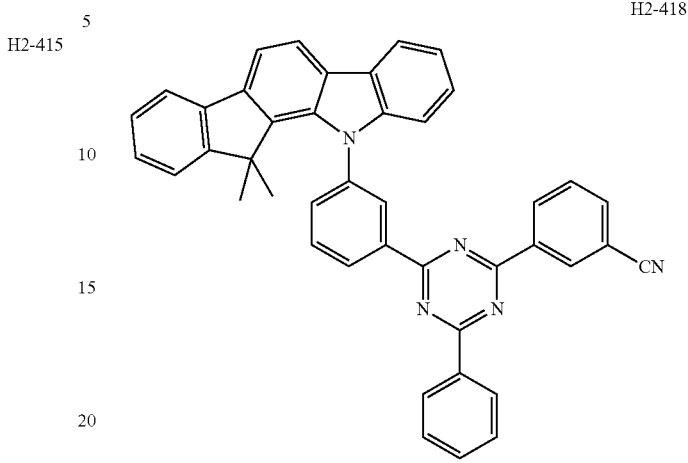
H2-416
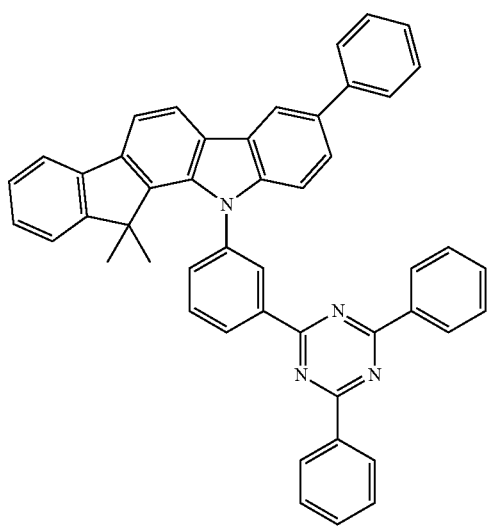
H2-419
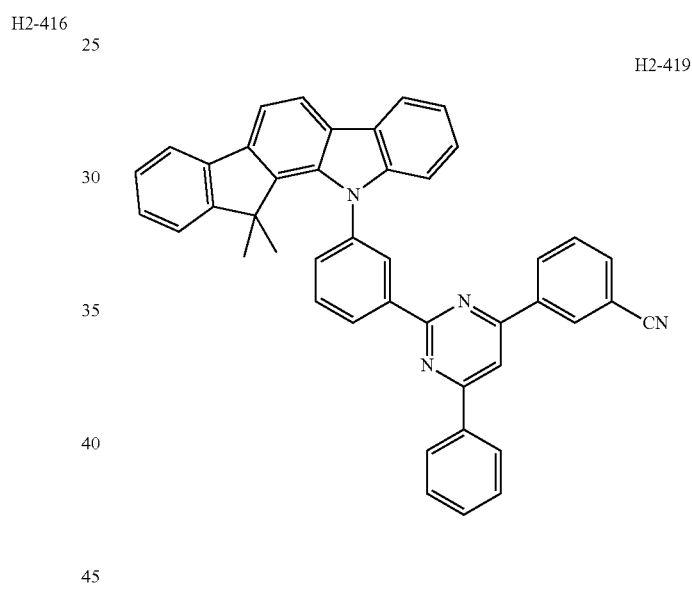
H2-417
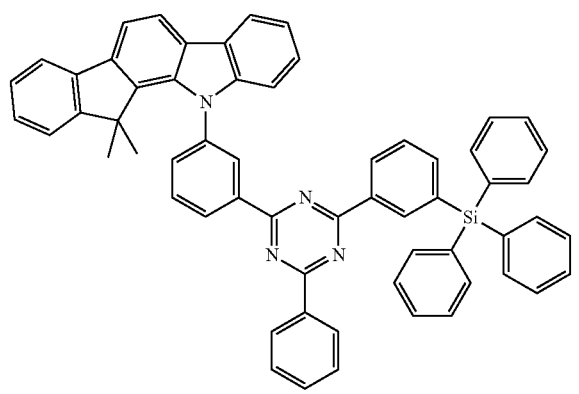
H2-420
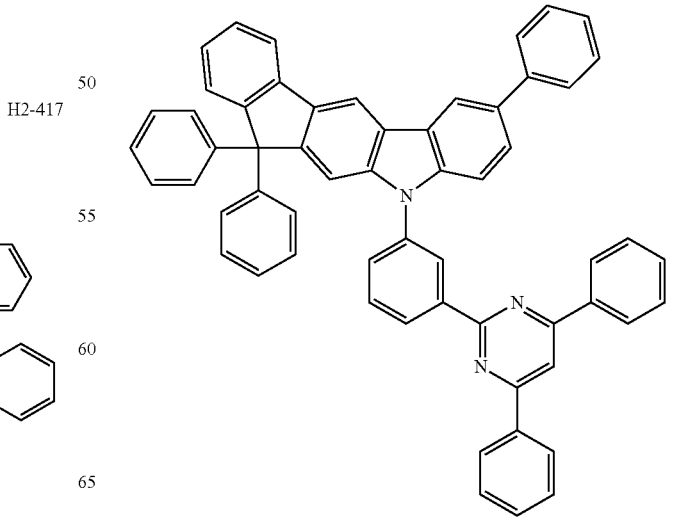

337
-continued
H2-421
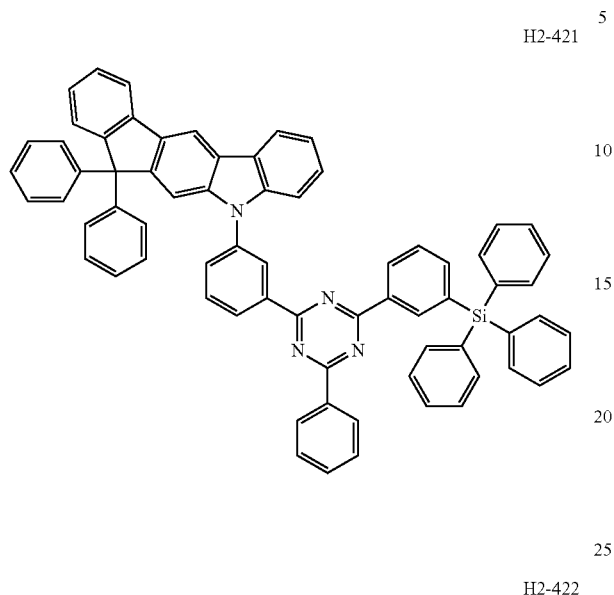
H2-422
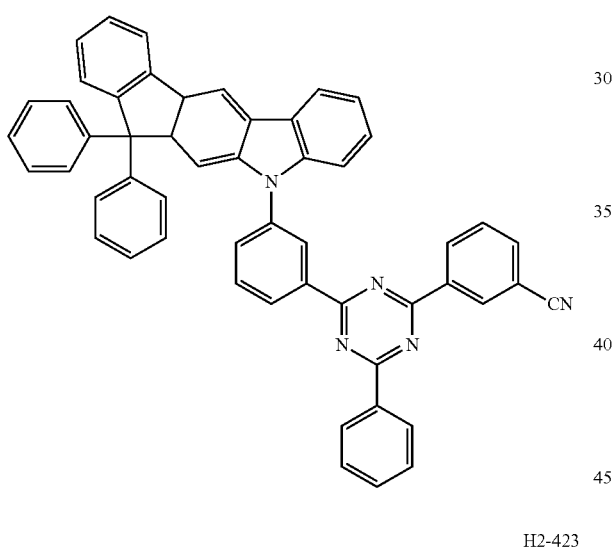
H2-423
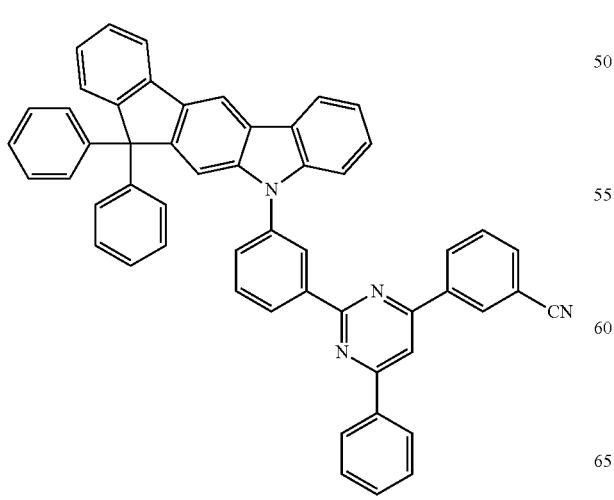
338
-continued
H2-424
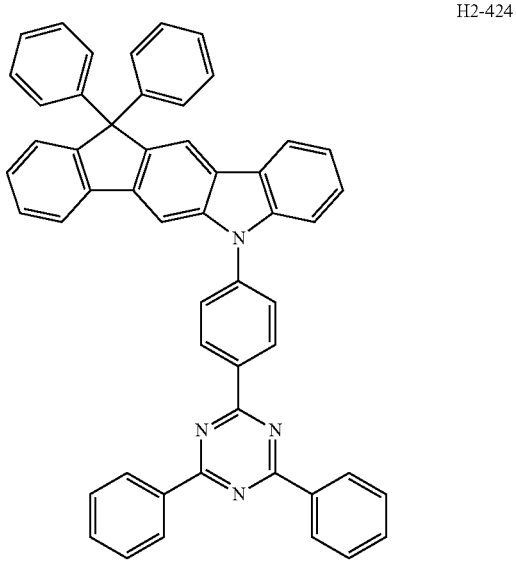
H2-425
H2-426
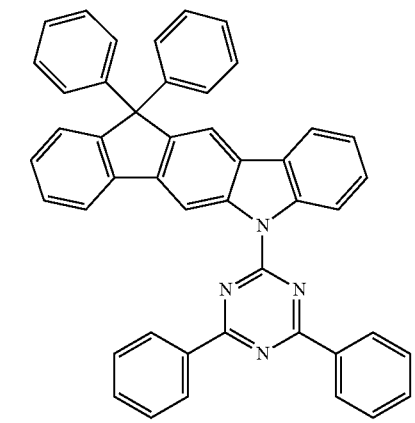

-continued
H2-427
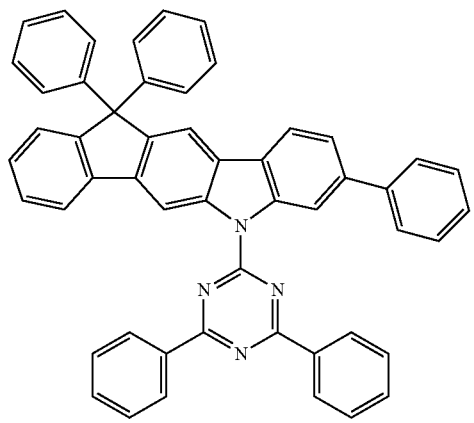
H2-428
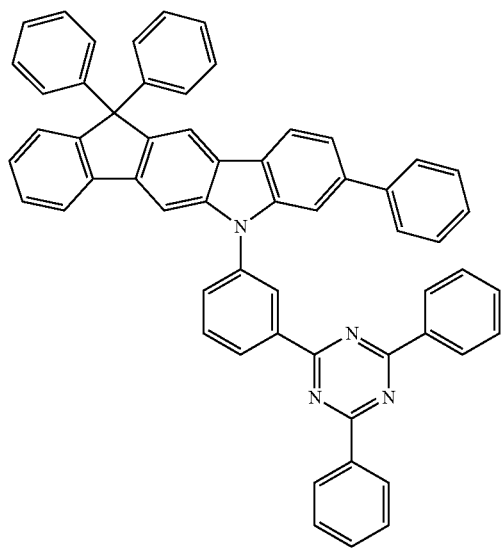
H2-429
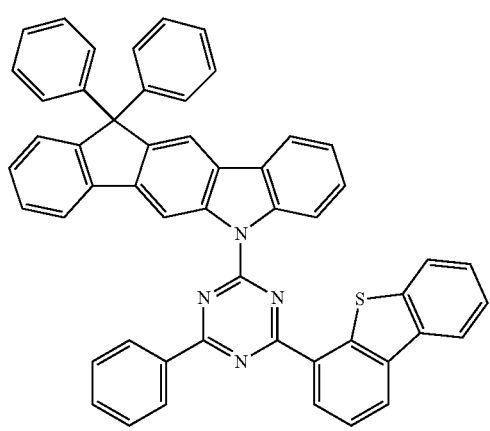
-continued
H2-430
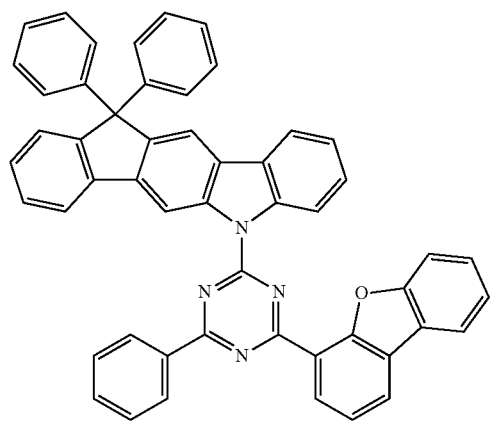
H2-431
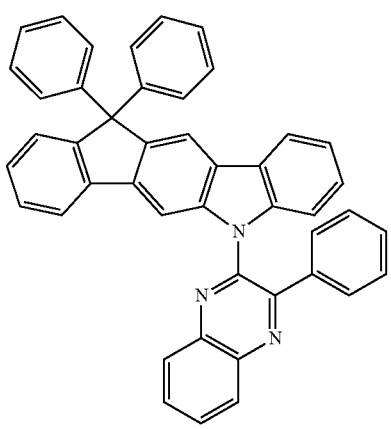
H2-432
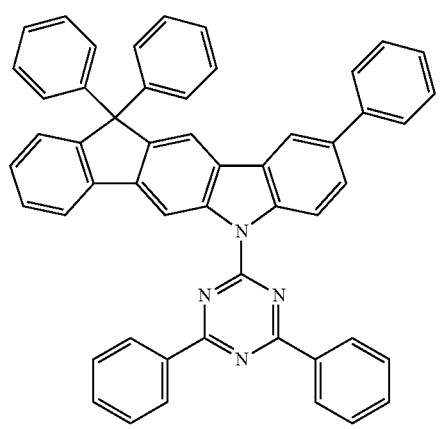

H2-433
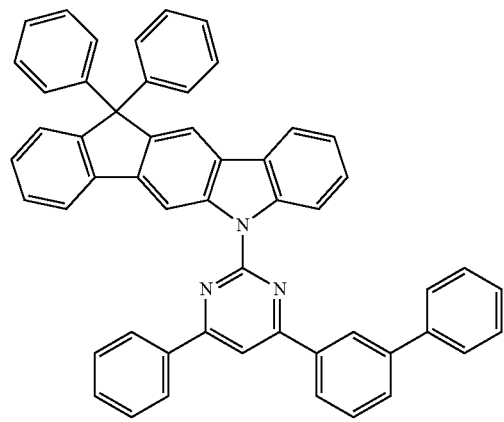
H2-434
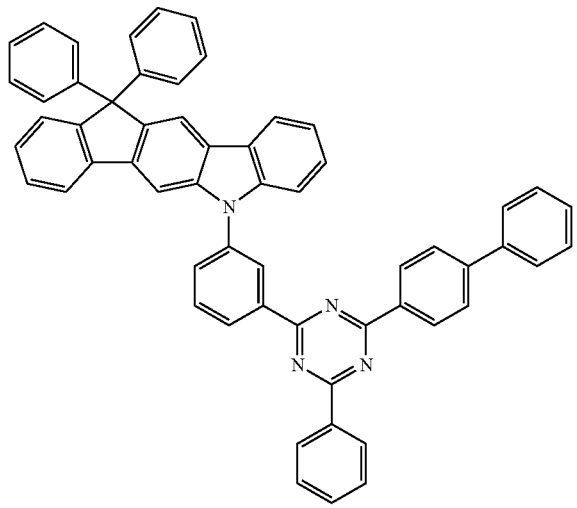
H2-435
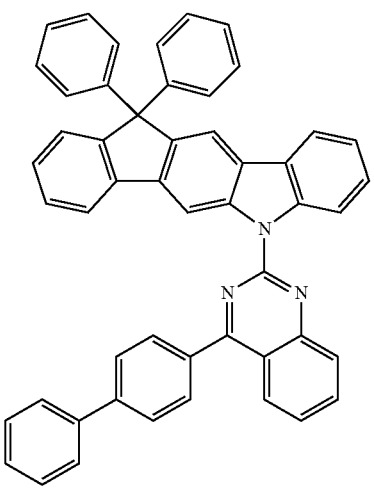
H2-436
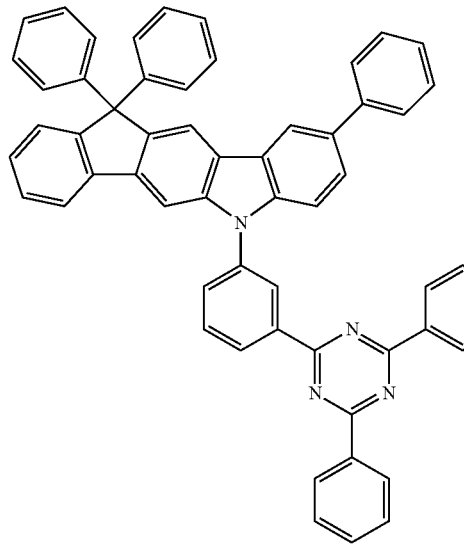
H2-437
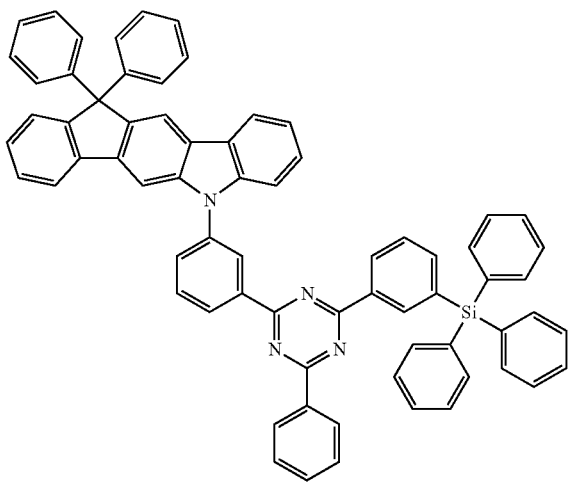
H2-438
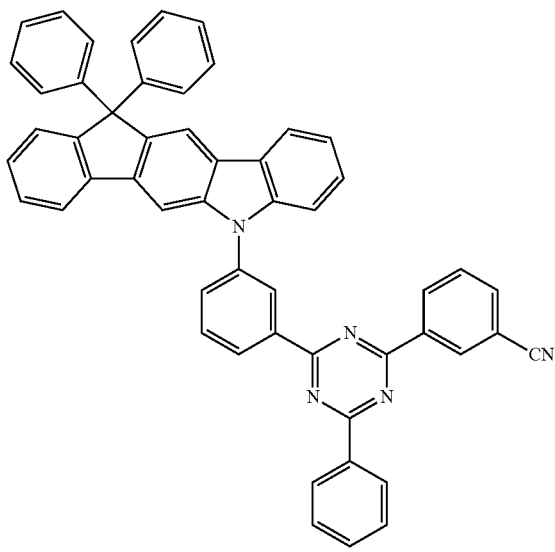

H2-439
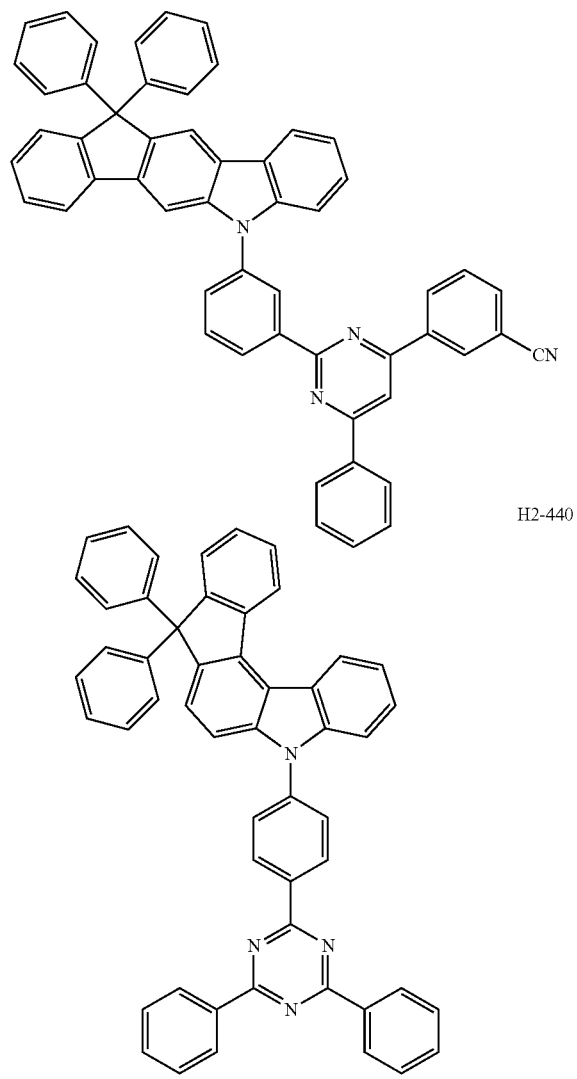
H2-440
H2-441
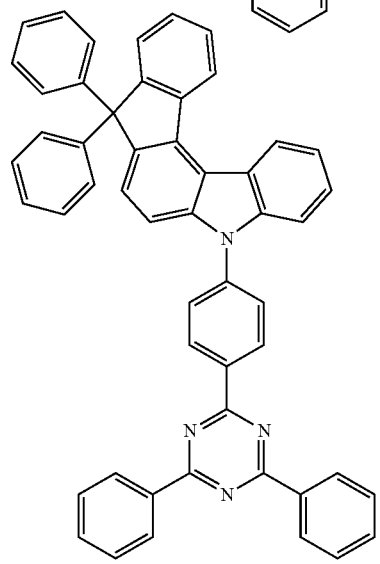
H2-442
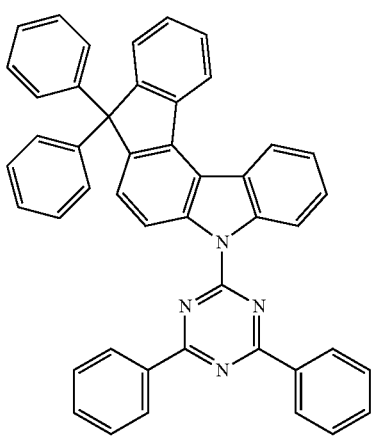
H2-443
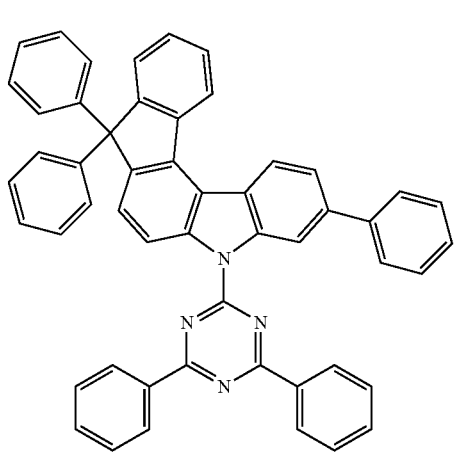
H2-444
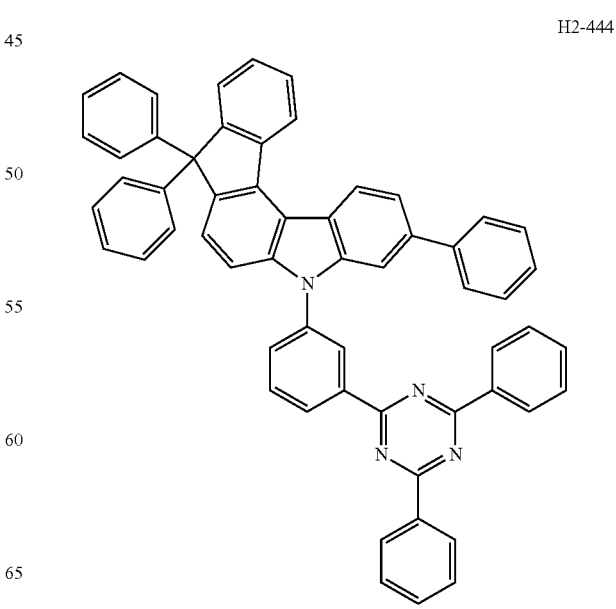

H2-445
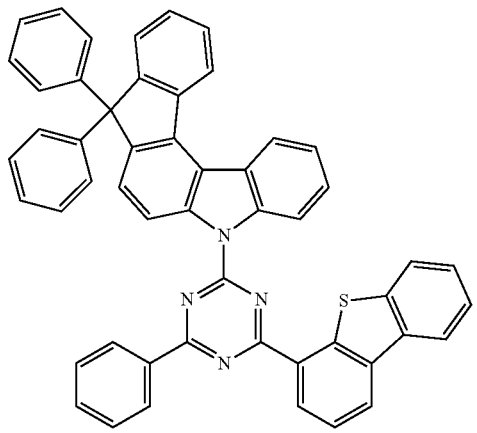
H2-446
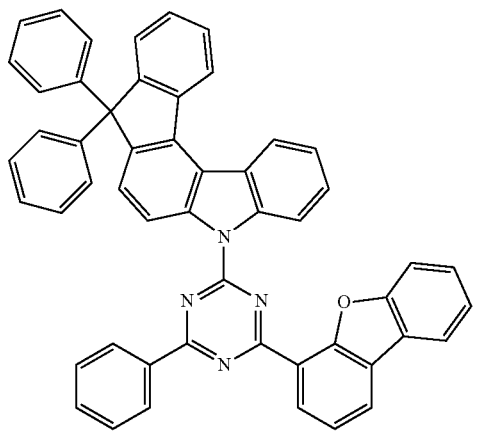
H2-447
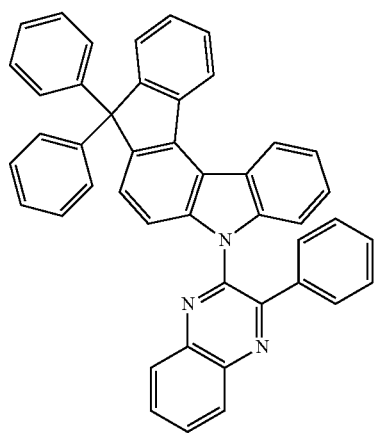
H2-448
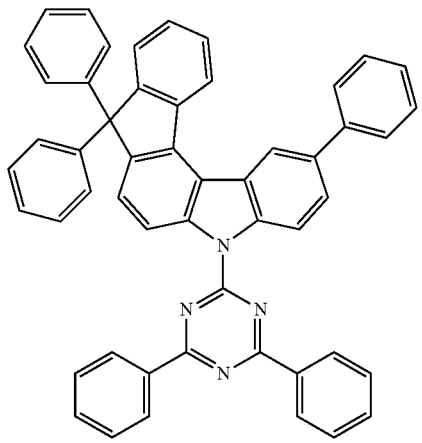
H2-449
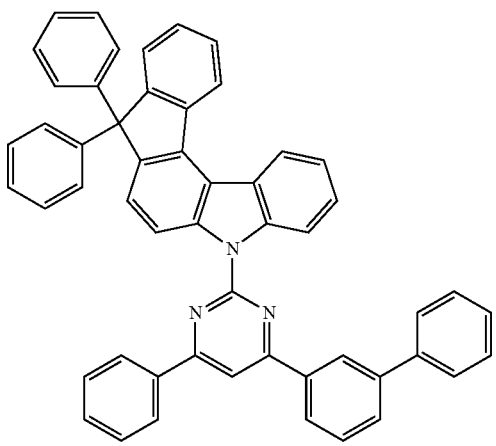
H2-450
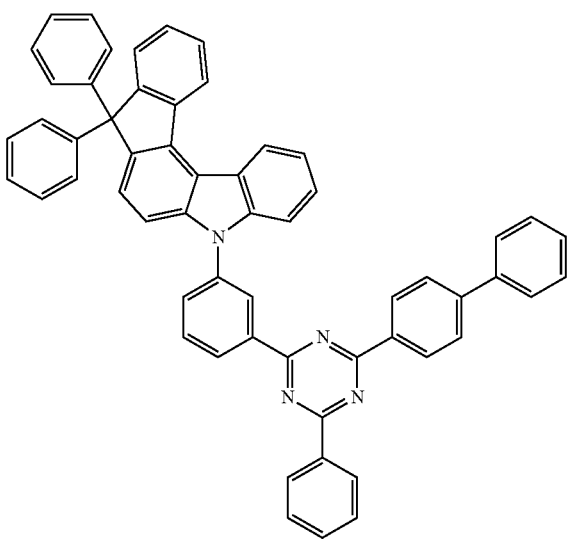

H2-451
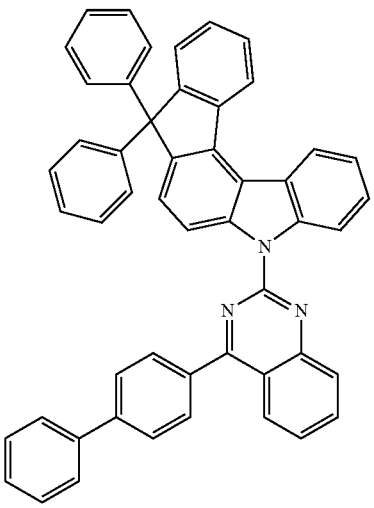
H2-454
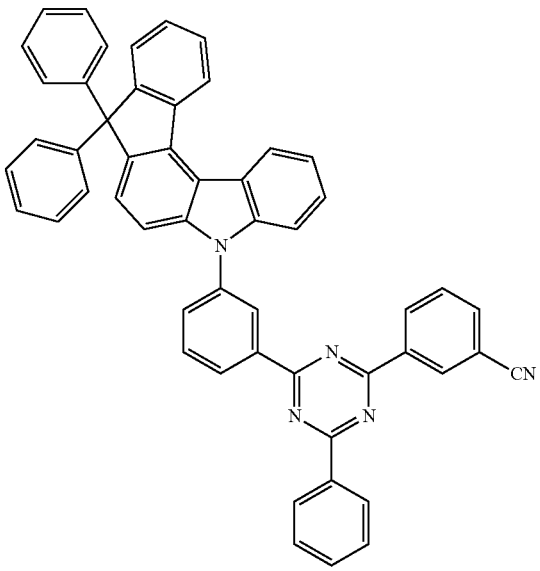
H2-452
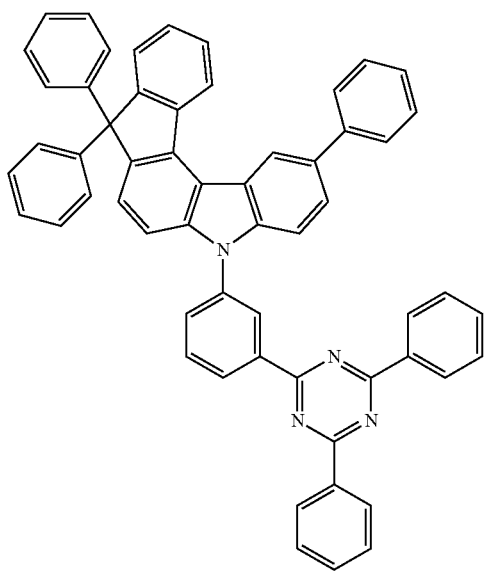
H2-455
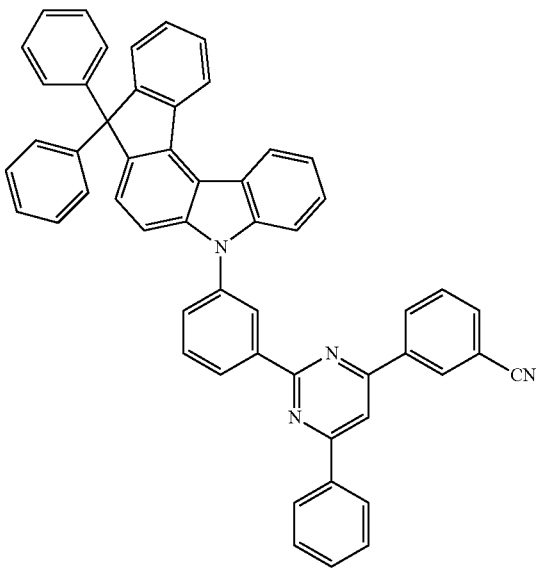
H2-453
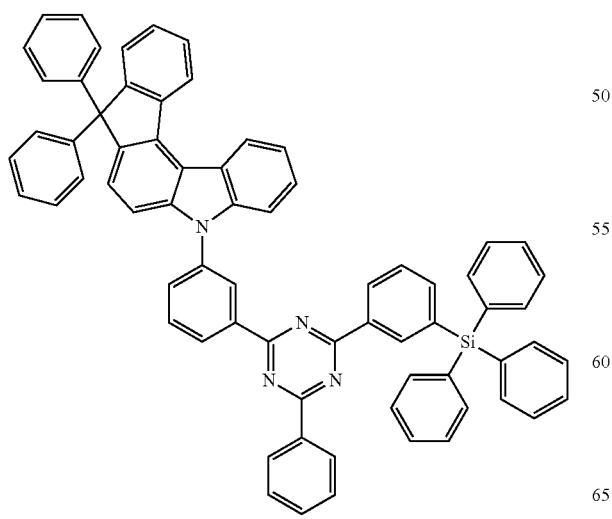
H2-456
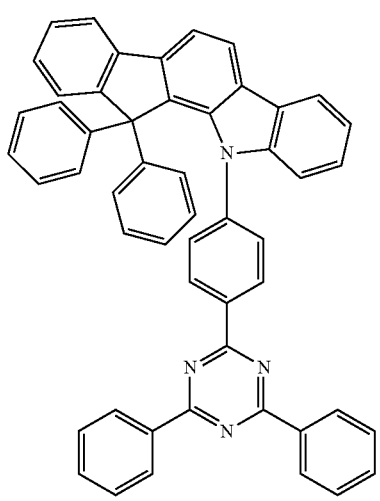

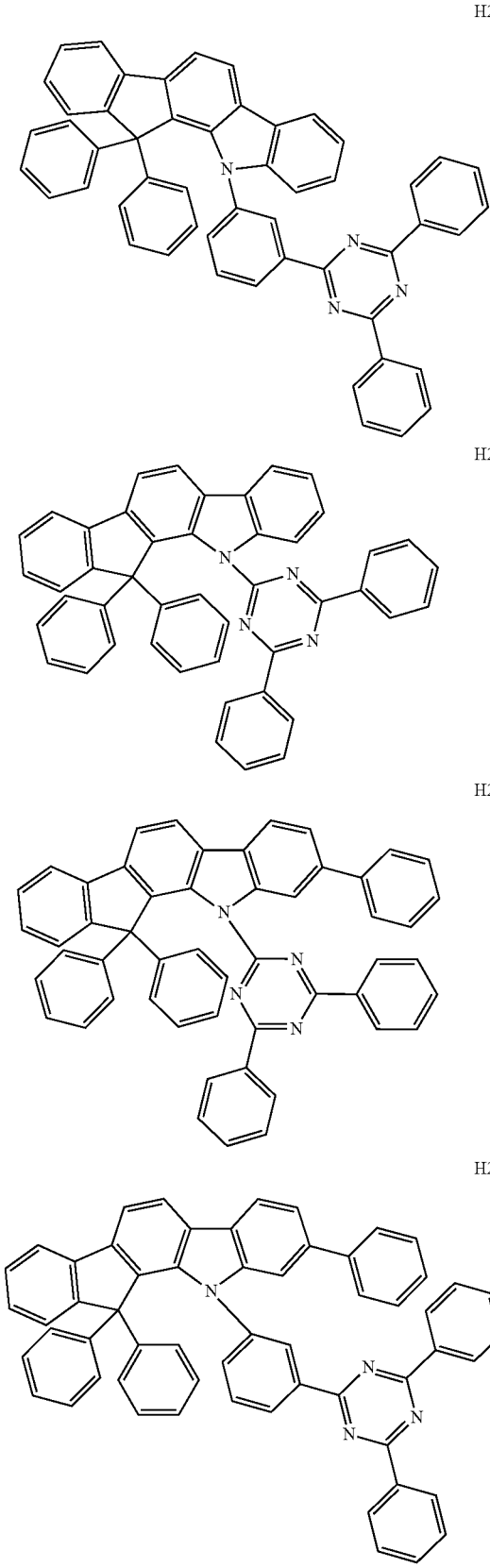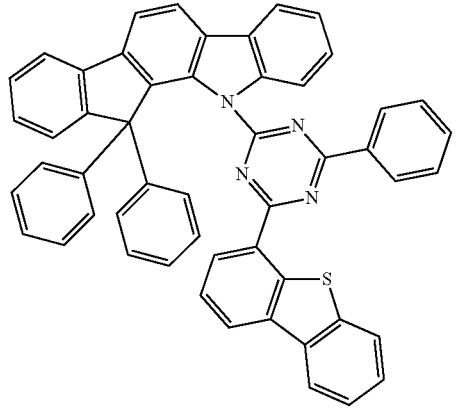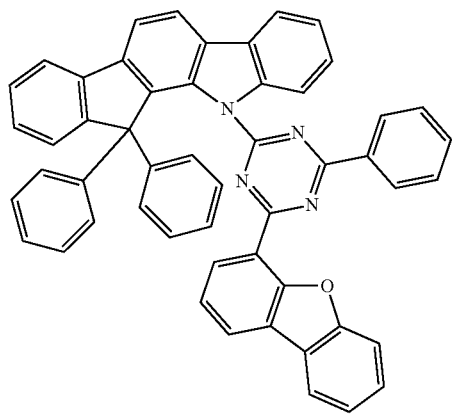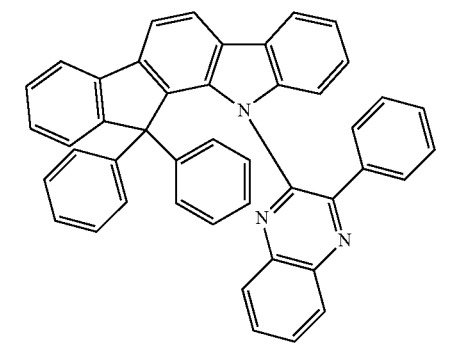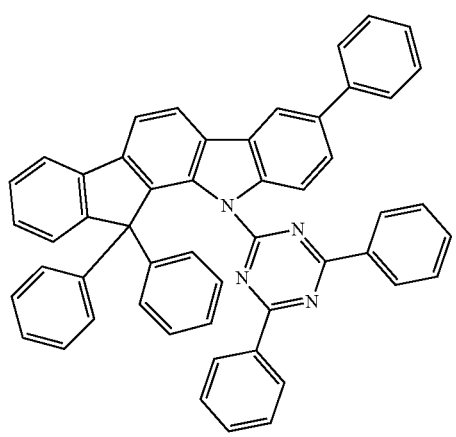

H2-465
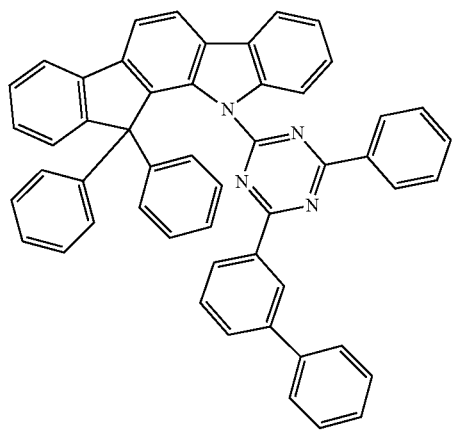
H2-466
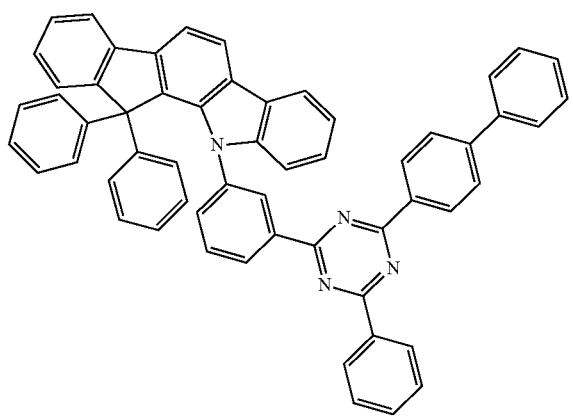
H2-467
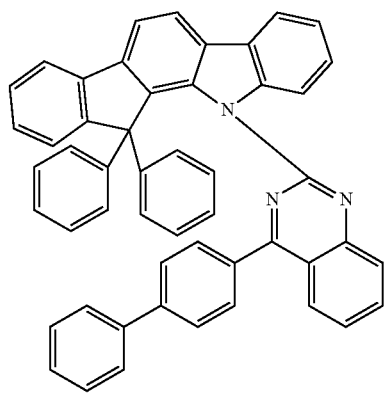
H2-468
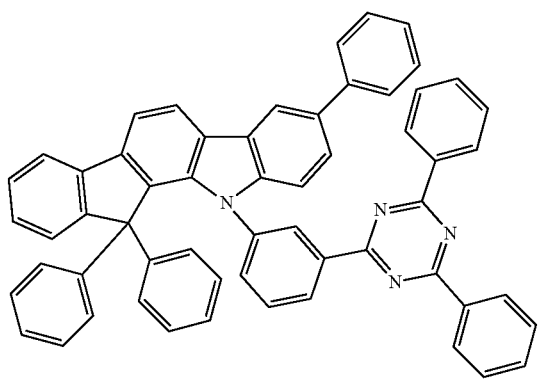
H2-469
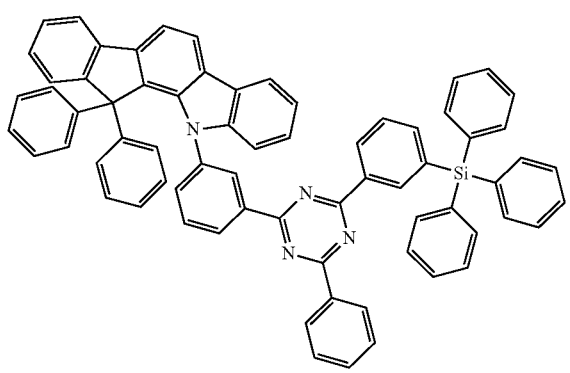
H2-470
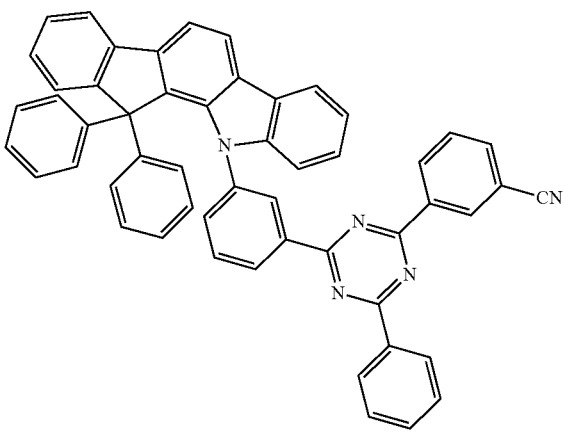
H2-471
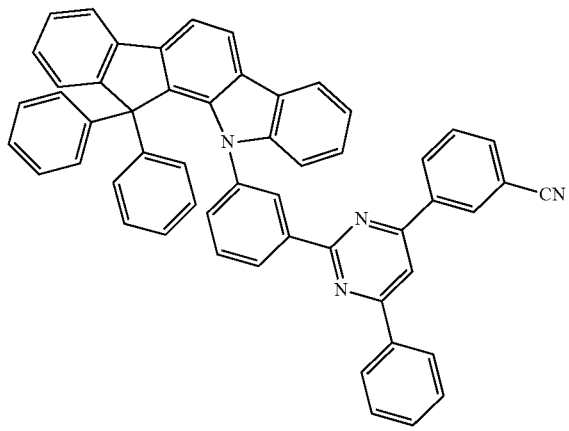
H2-472
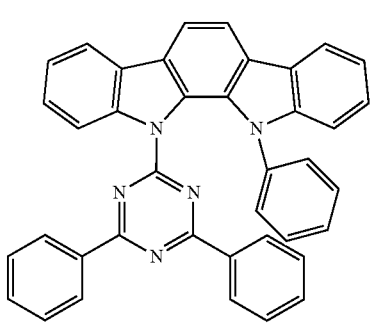

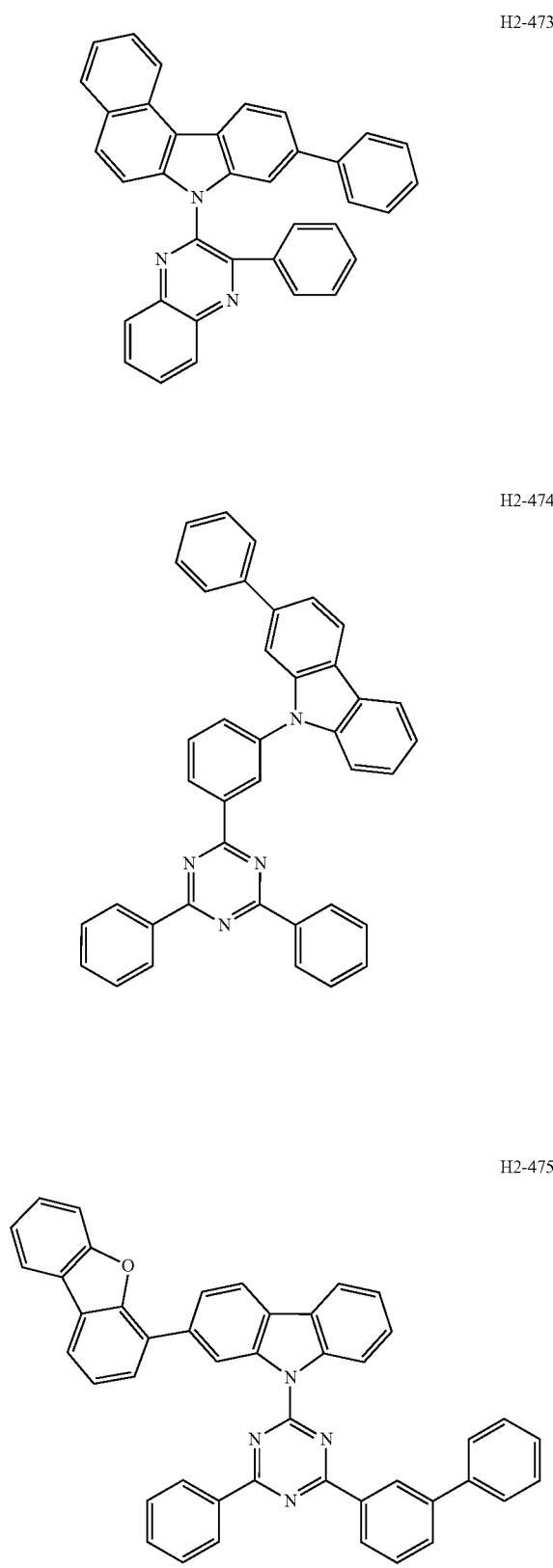
H2-473
H2-474
H2-475
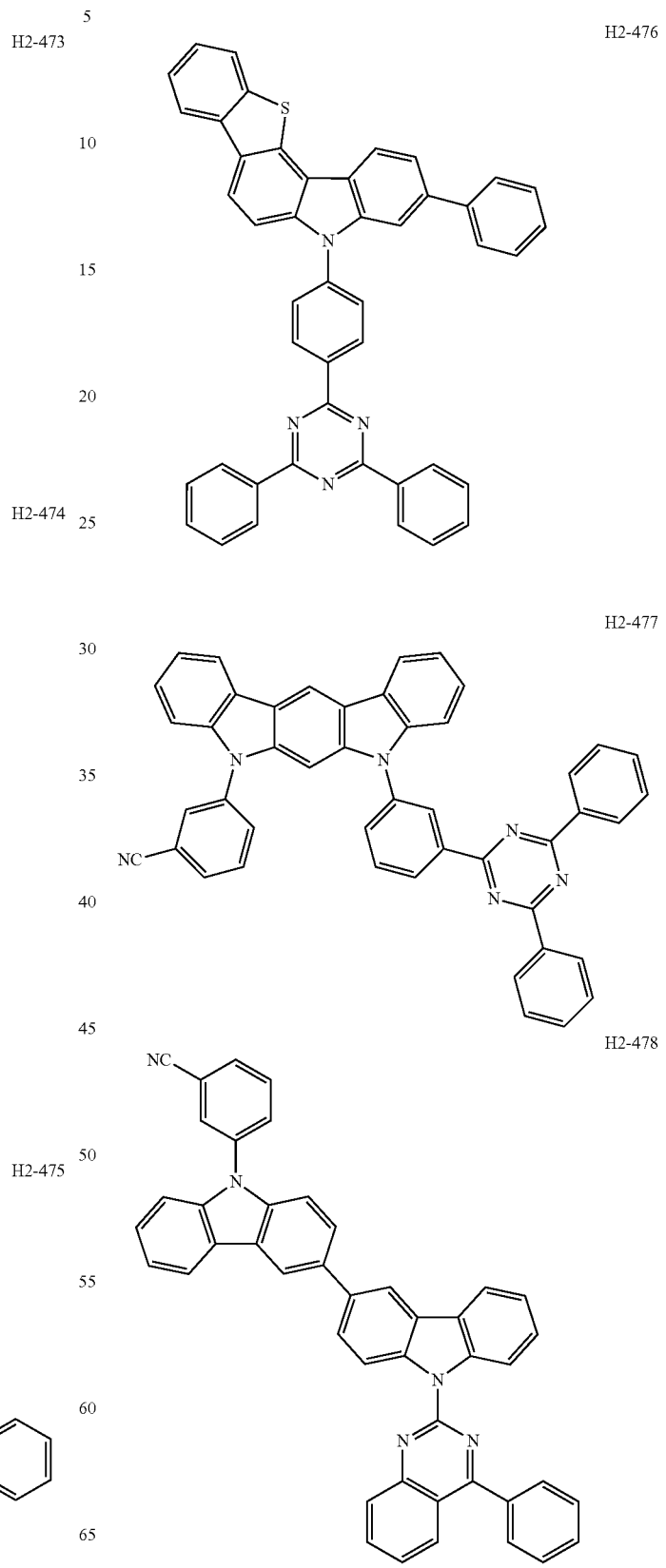
H2-476
H2-477
H2-478

H2-479
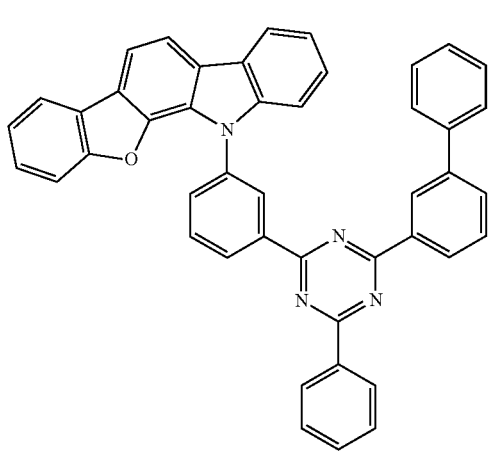
H2-480
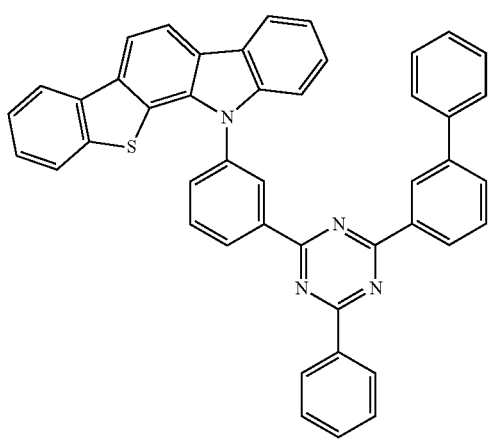
H2-481
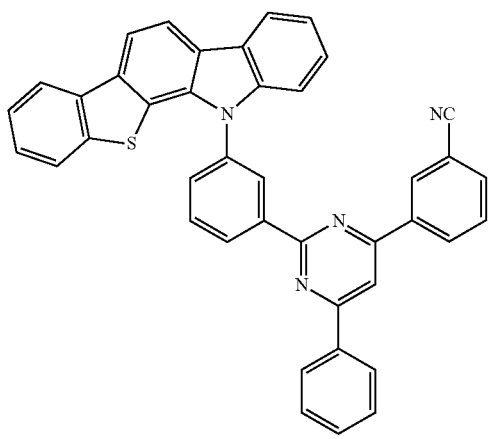
H2-482
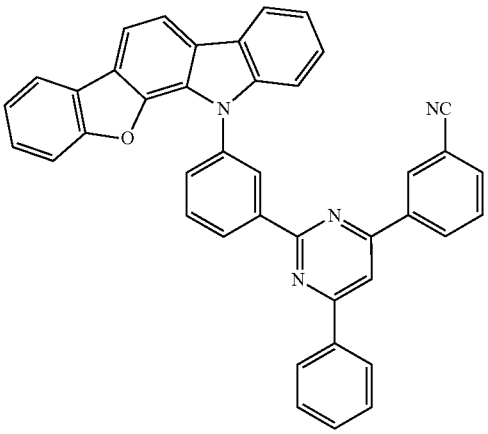
H2-483
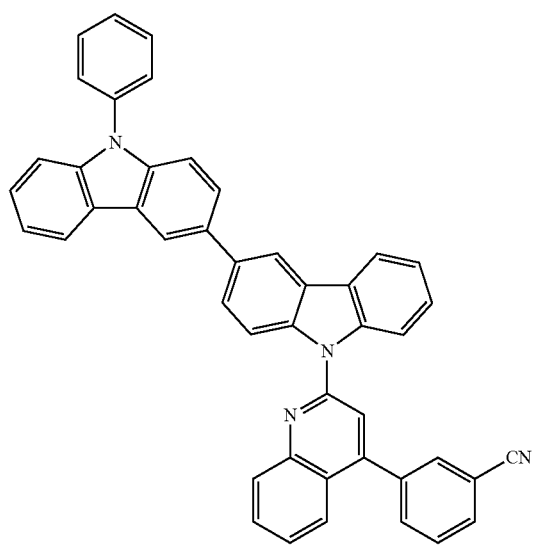
H2-484
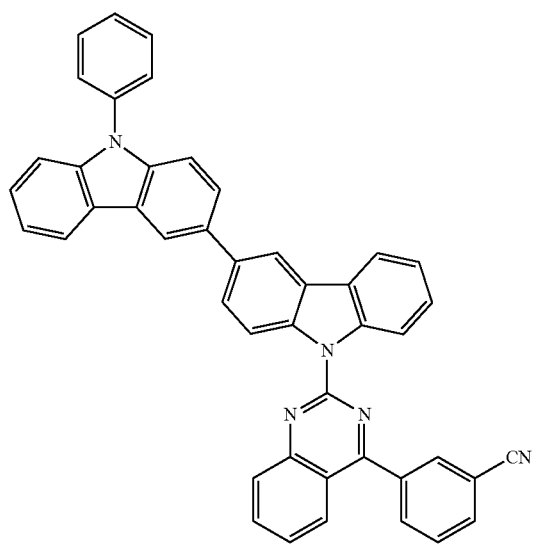

-continued
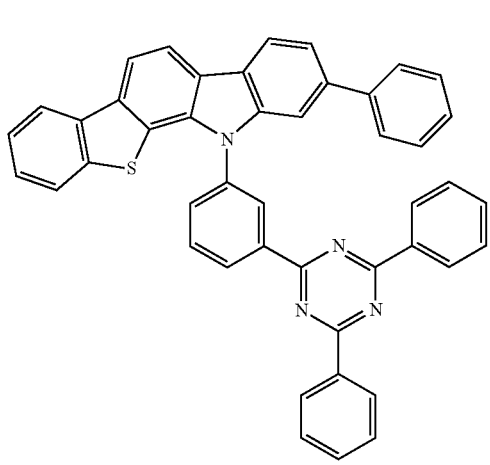
H2-485
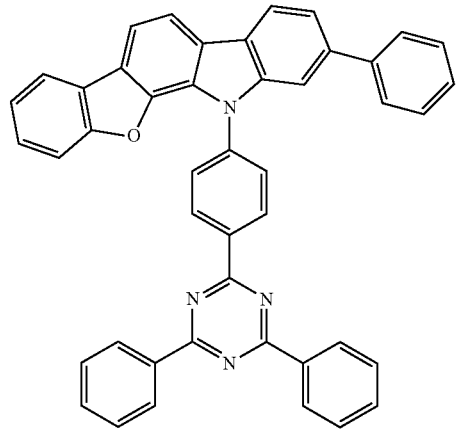
H2-488
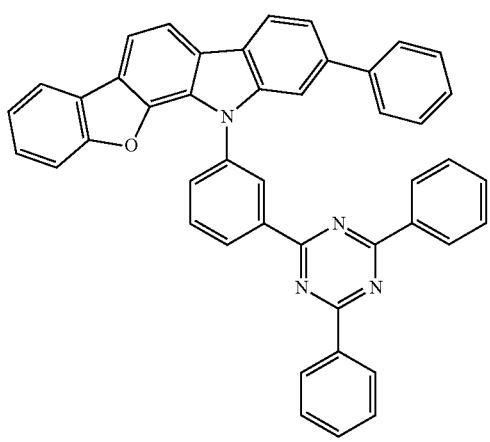
H2-486
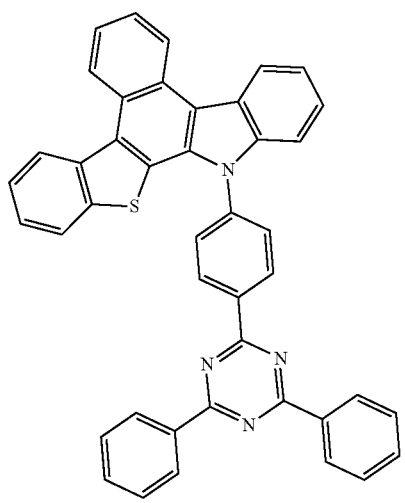
H2-489
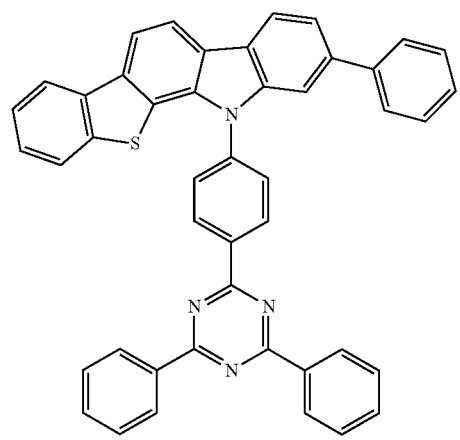
H2-487
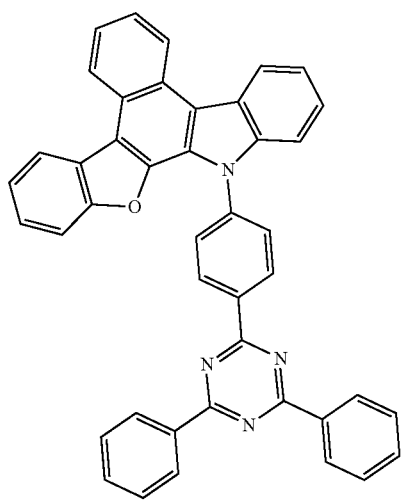
H2-490

H2-491
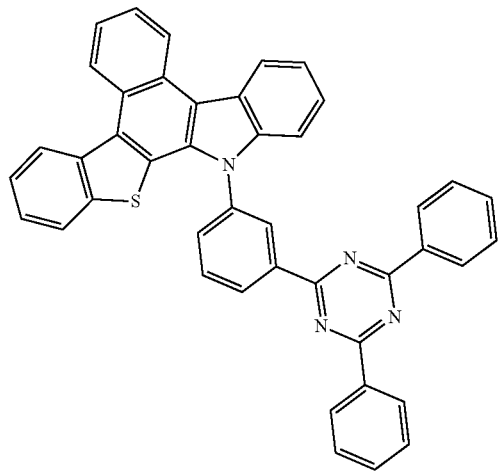
H4-2
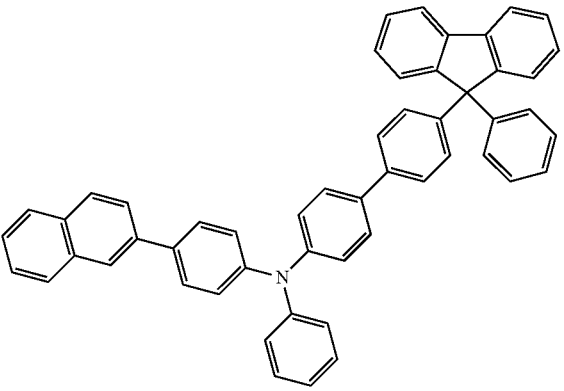
H2-492
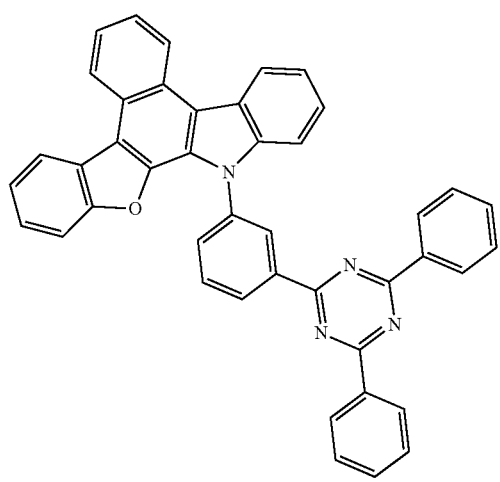
H4-3
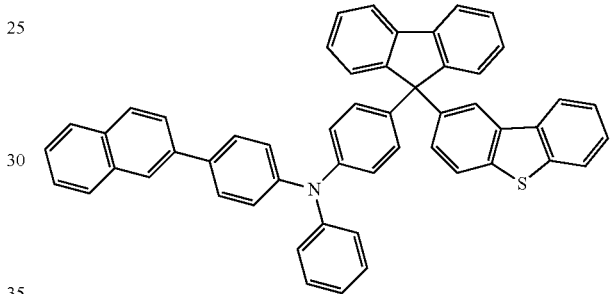
H4-4
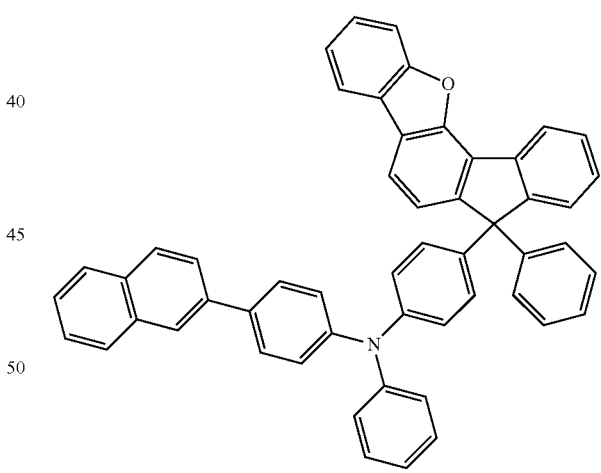
The hole transport compound represented by formula 3 includes the following, but is not limited thereto.
H4-1
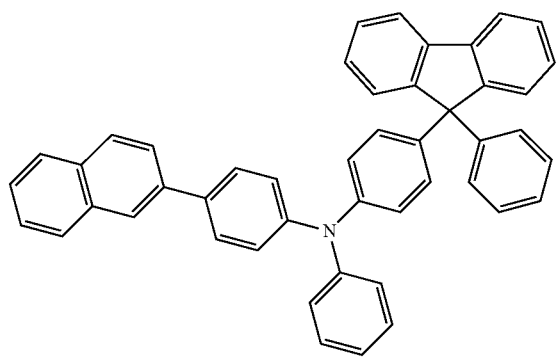
H4-5
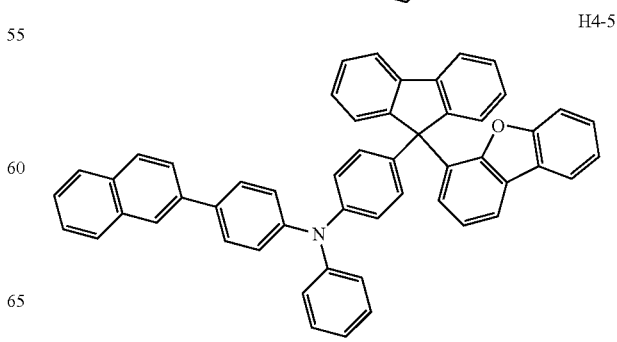

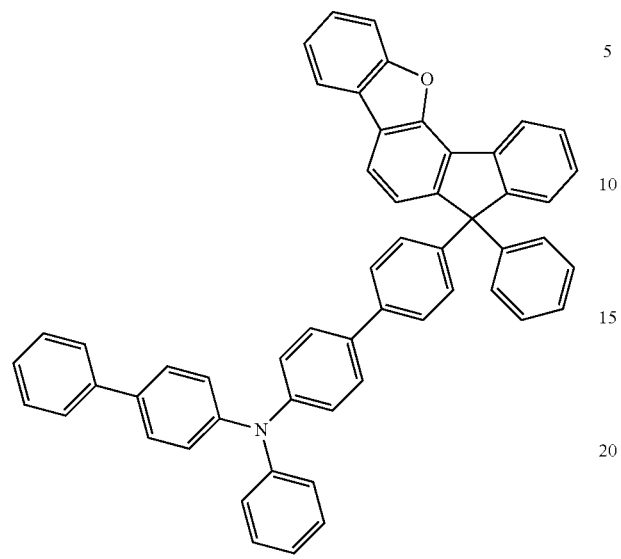
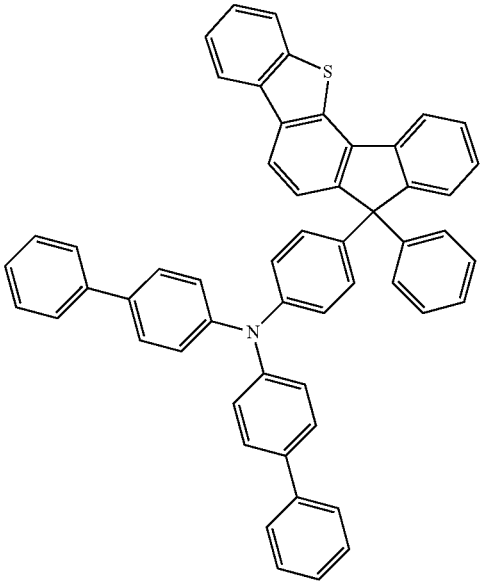
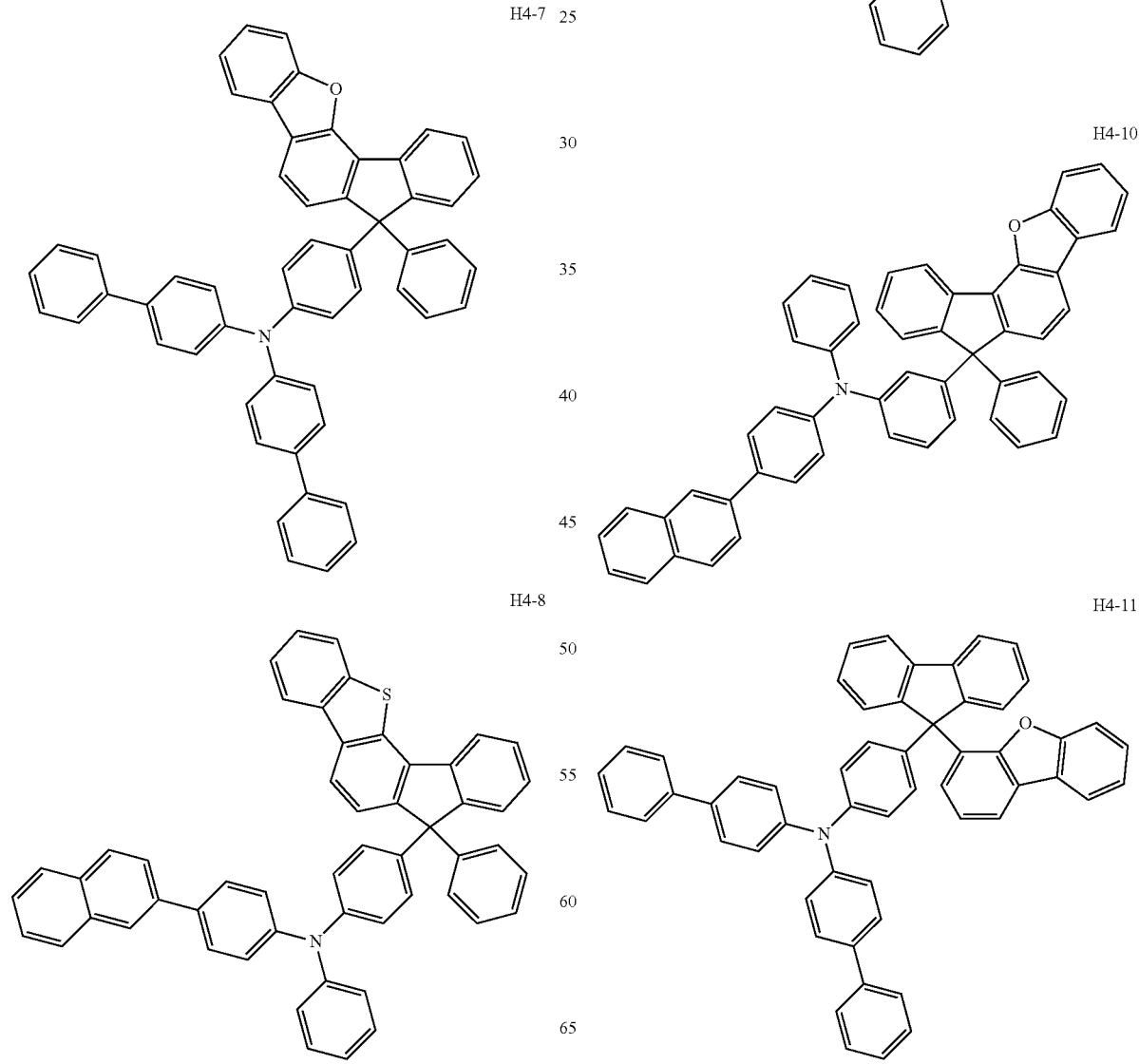

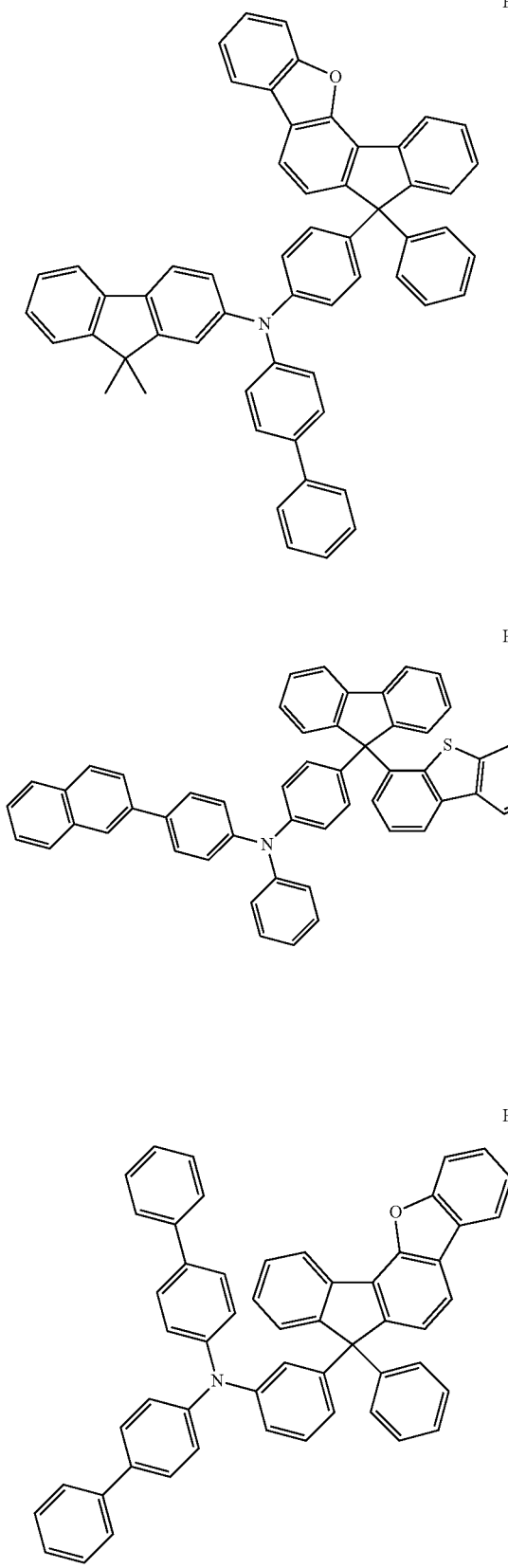
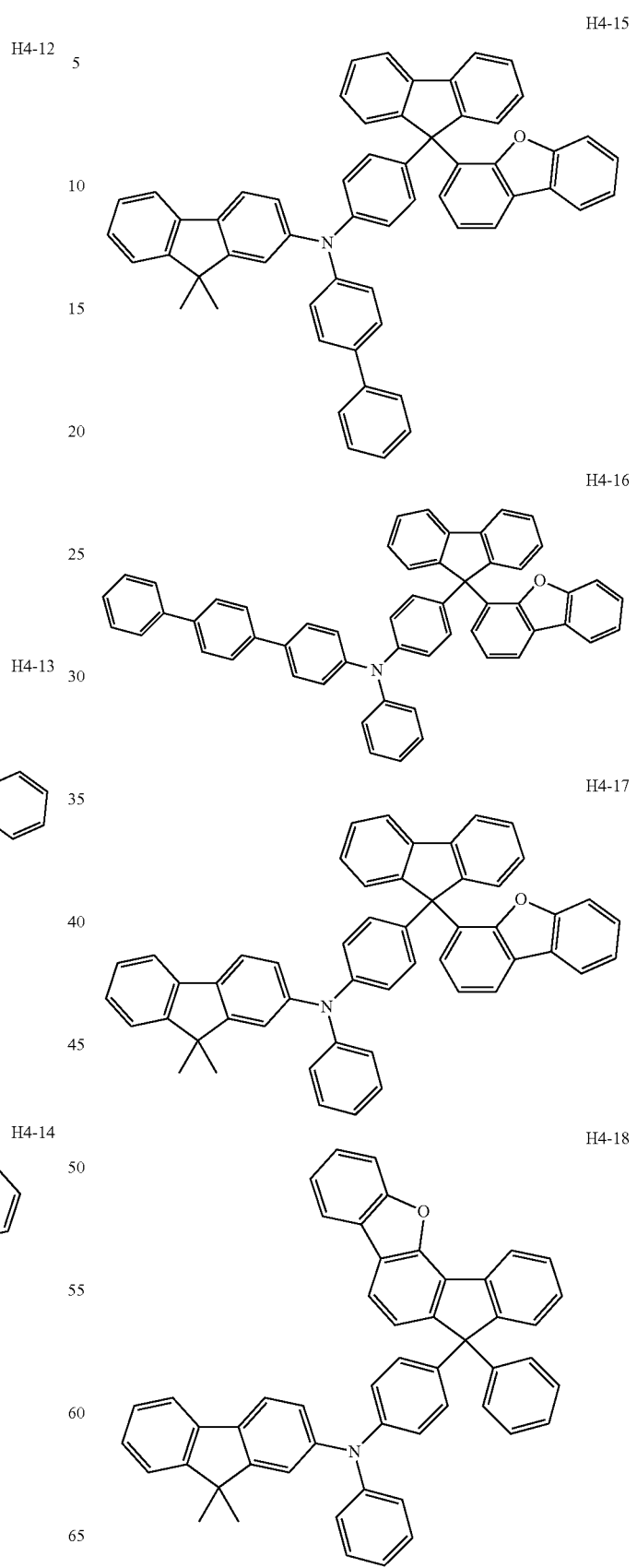

365
-continued
H4-19
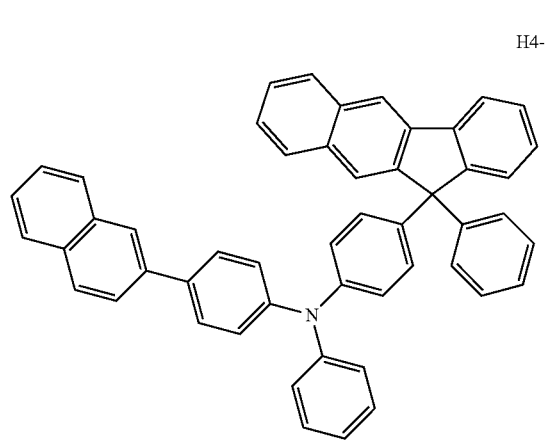
H4-20
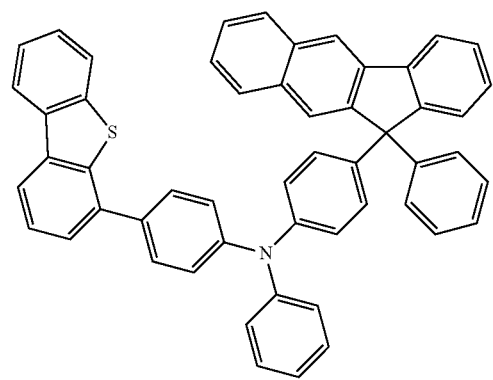
H4-21
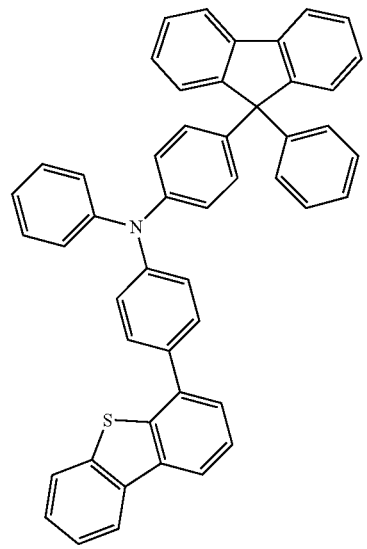
366
-continued
H4-22
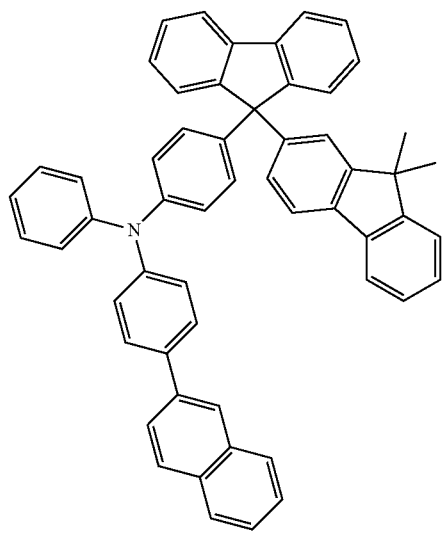
H4-23
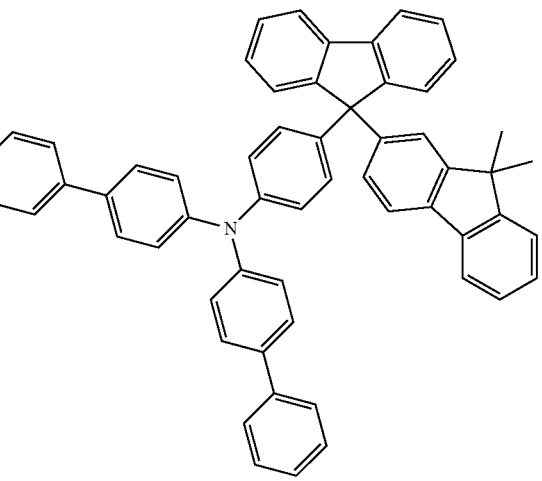
H4-24
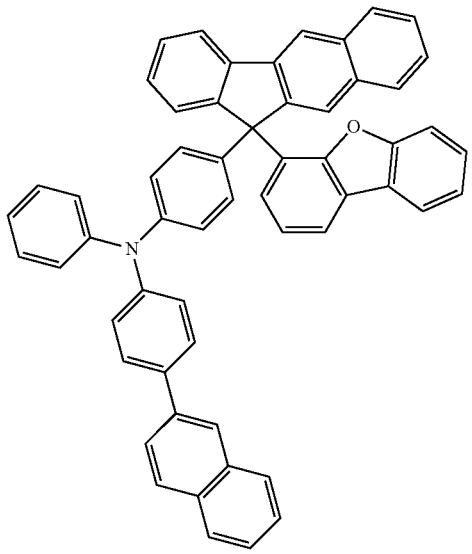

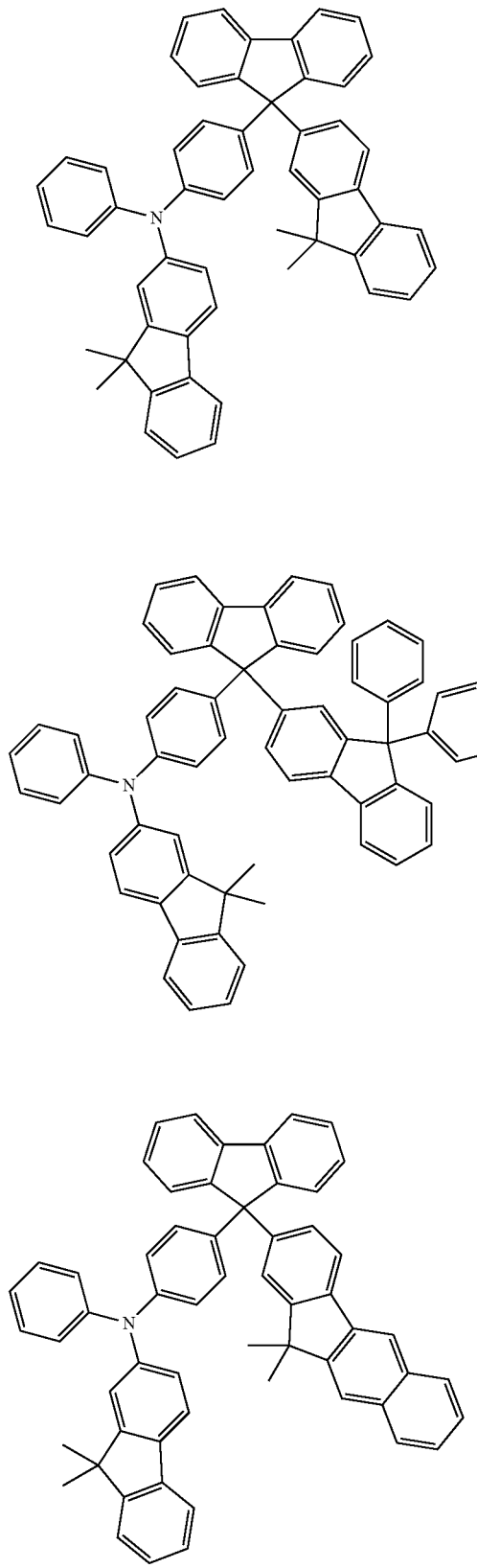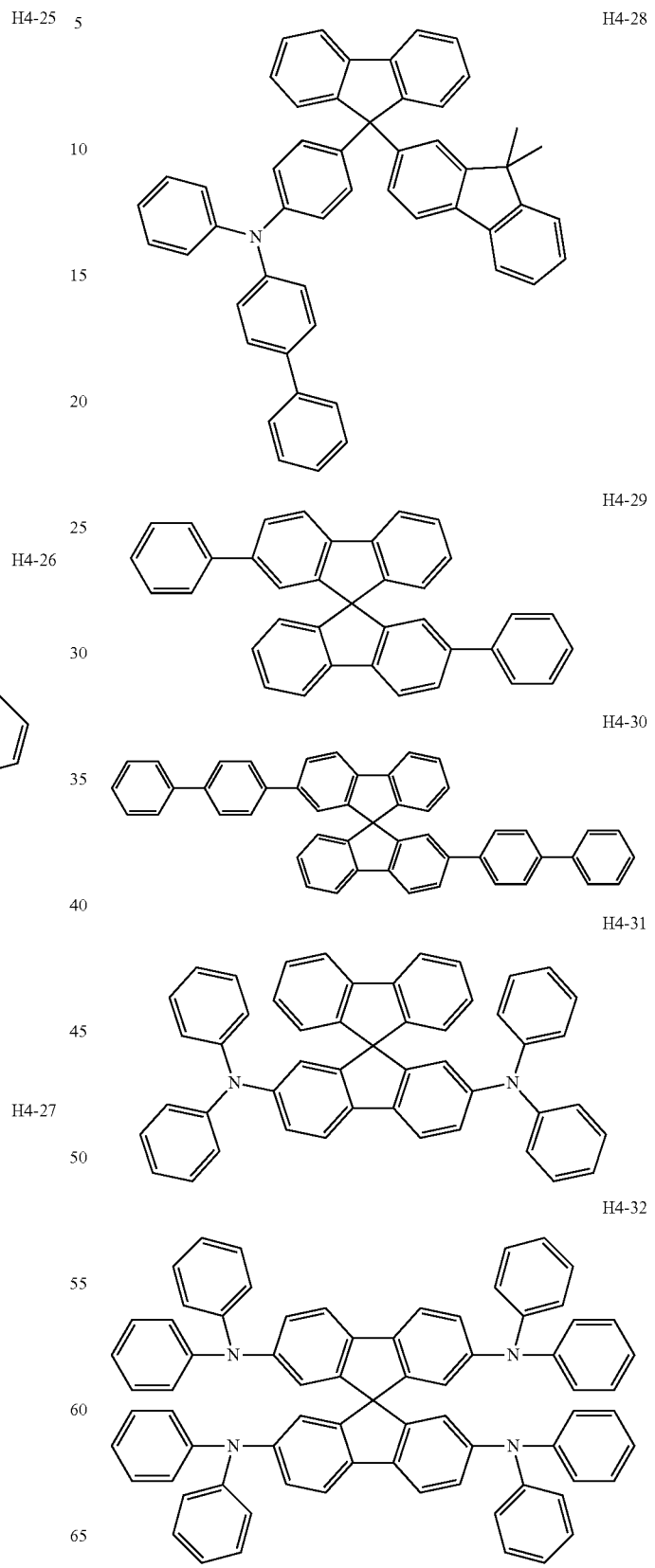

H4-33
H4-34
H4-35
H4-36
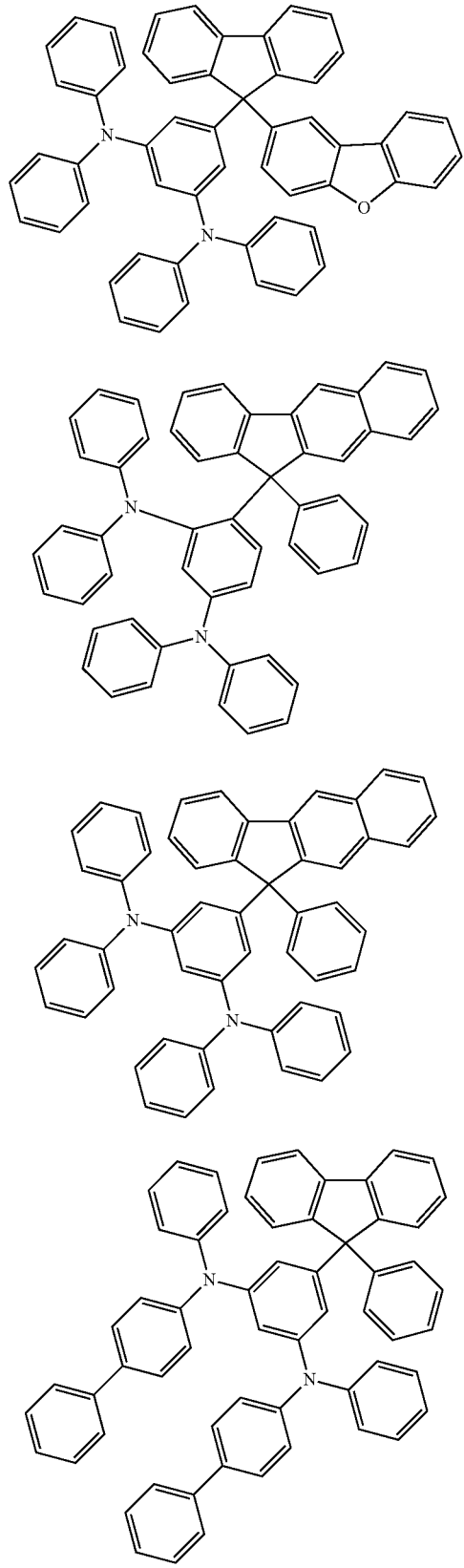
H4-37
H4-38
H4-39
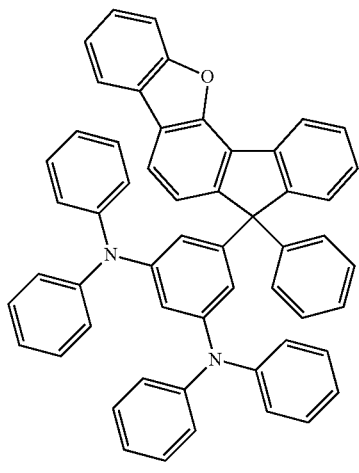
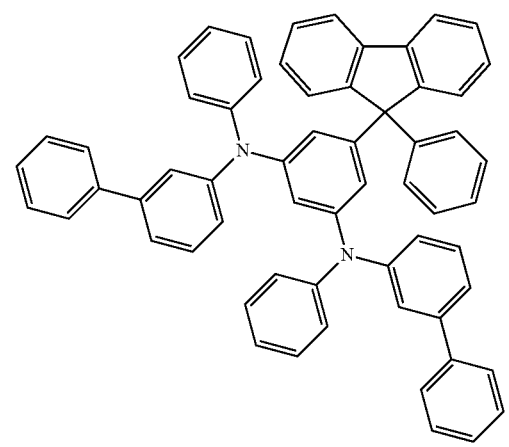
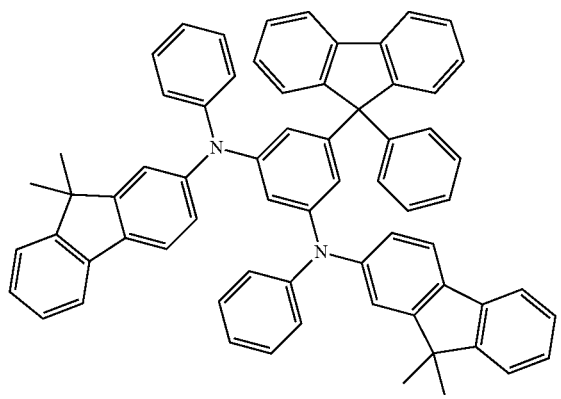

H4-40
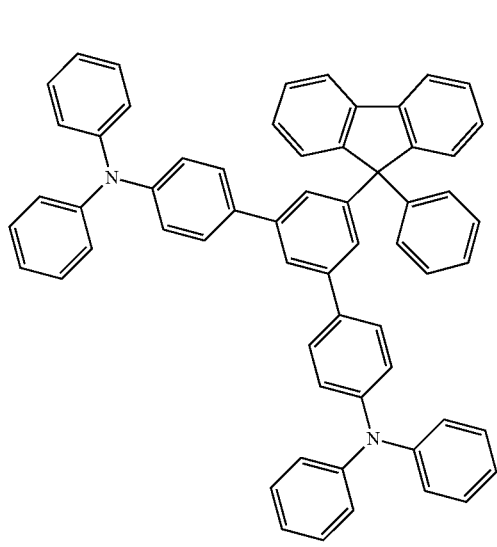
H4-43
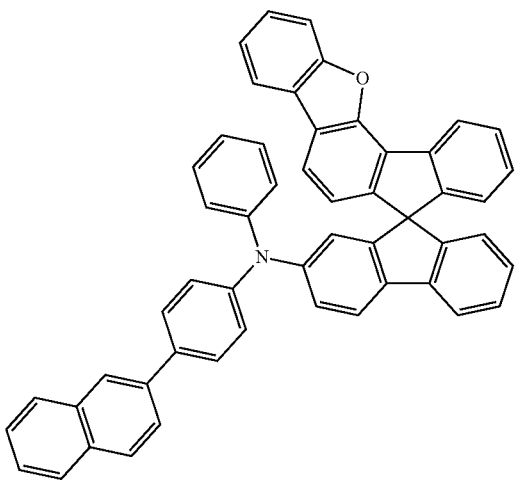
H4-41
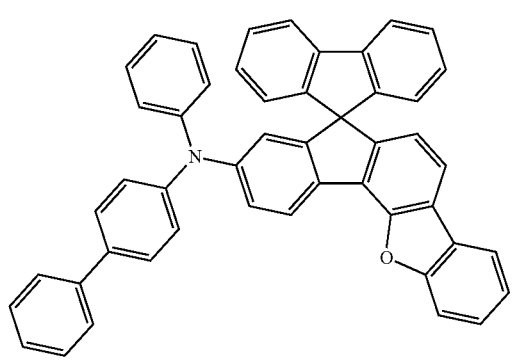
H4-44
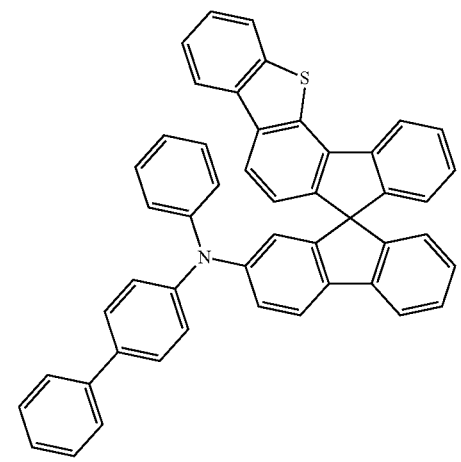
H4-42
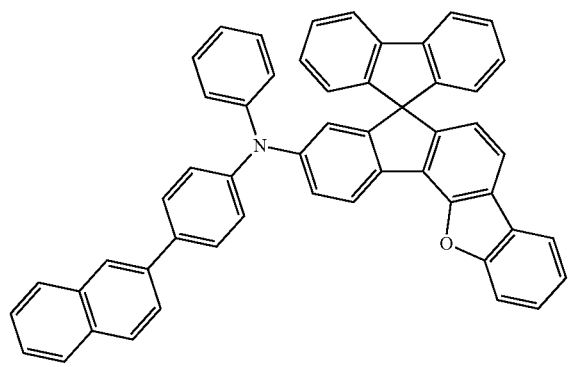
H4-45
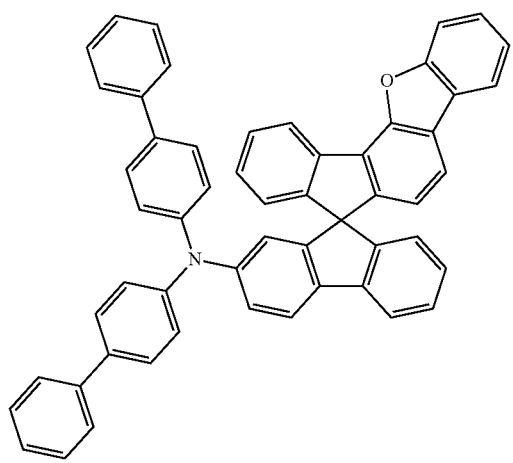

H4-46
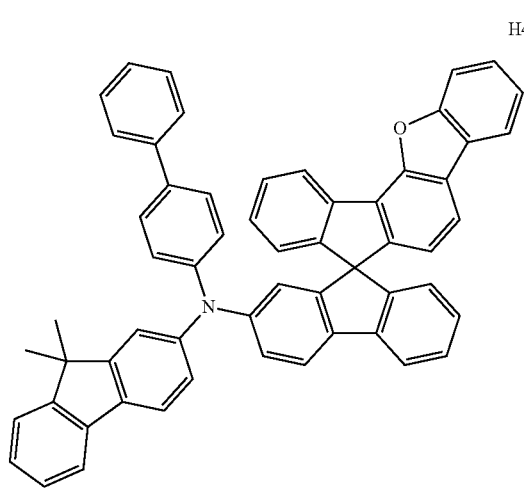
H4-47
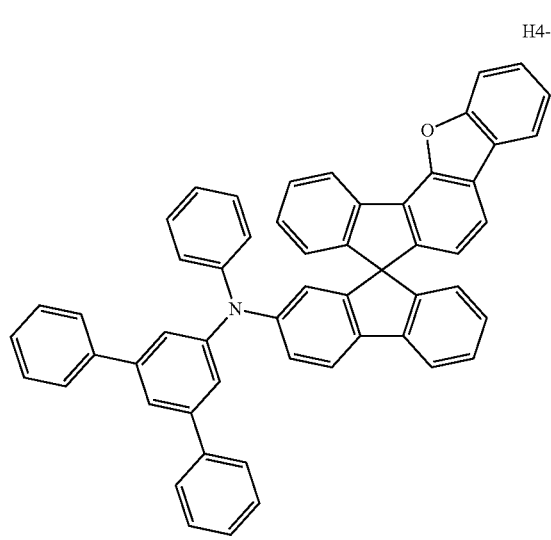
H4-48
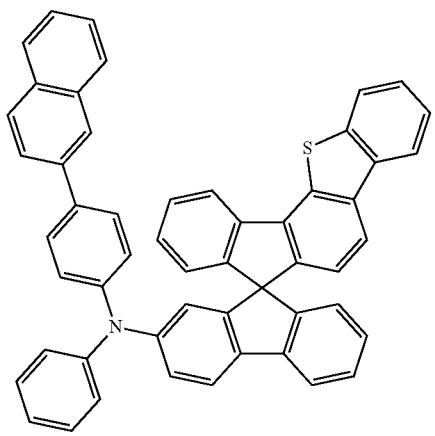
H4-49
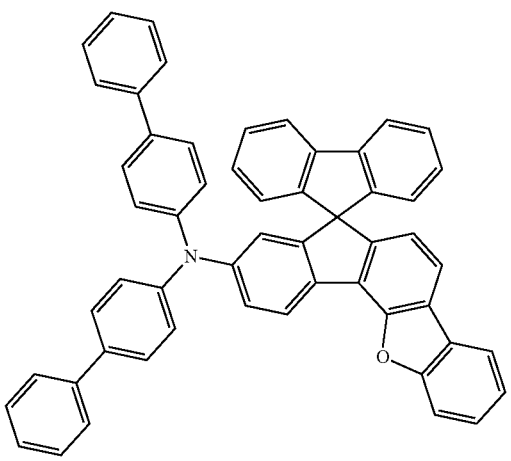
H4-50
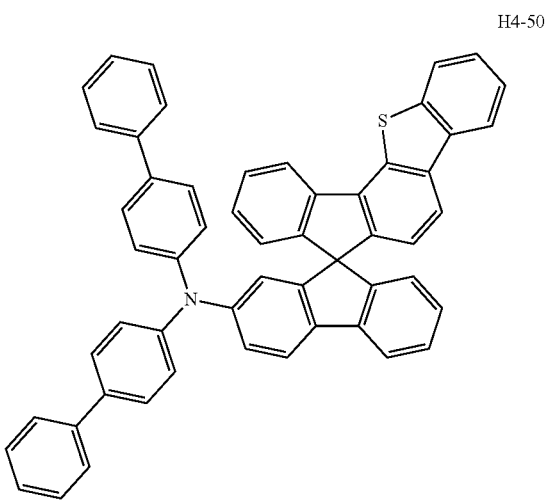
H4-51
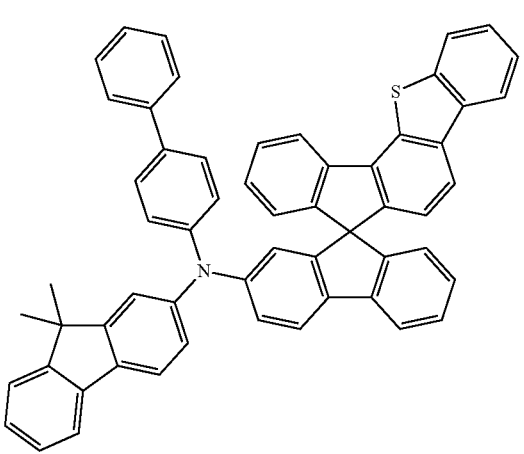

-continued
H4-52
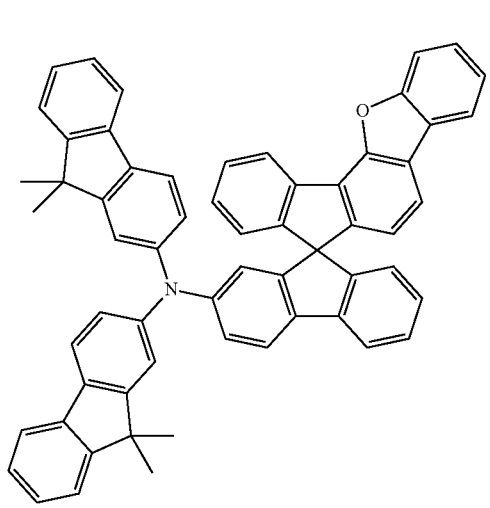
H4-53
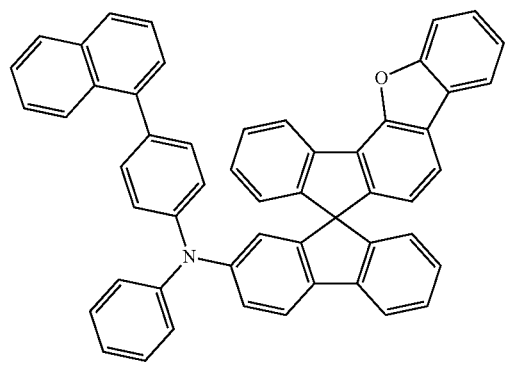
H4-54
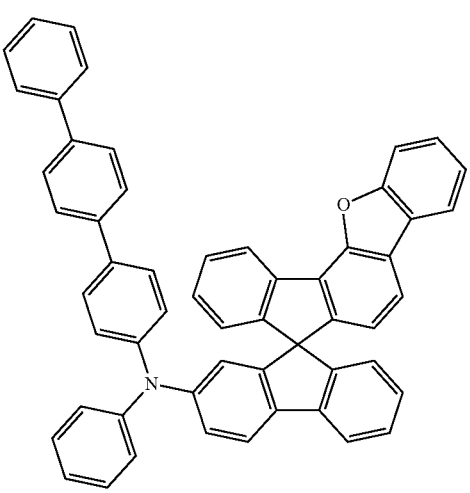
-continued
H4-55
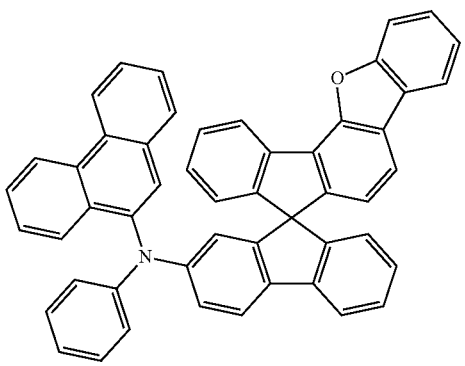
H4-56
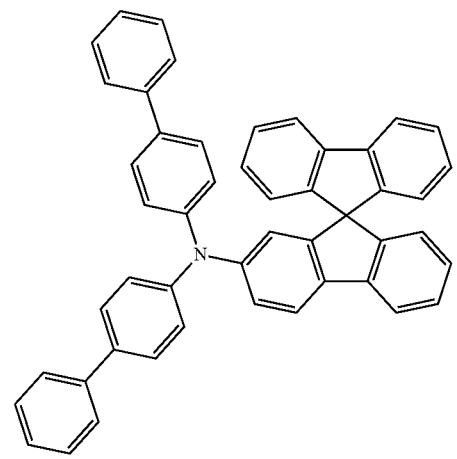
H4-57
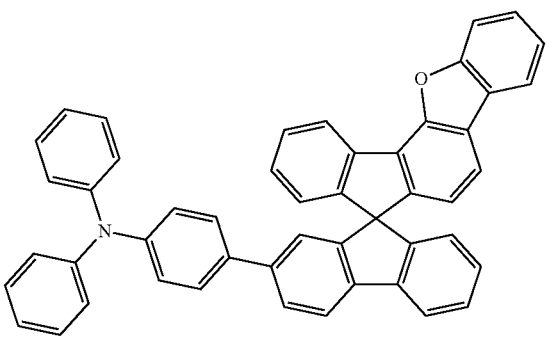

-continued
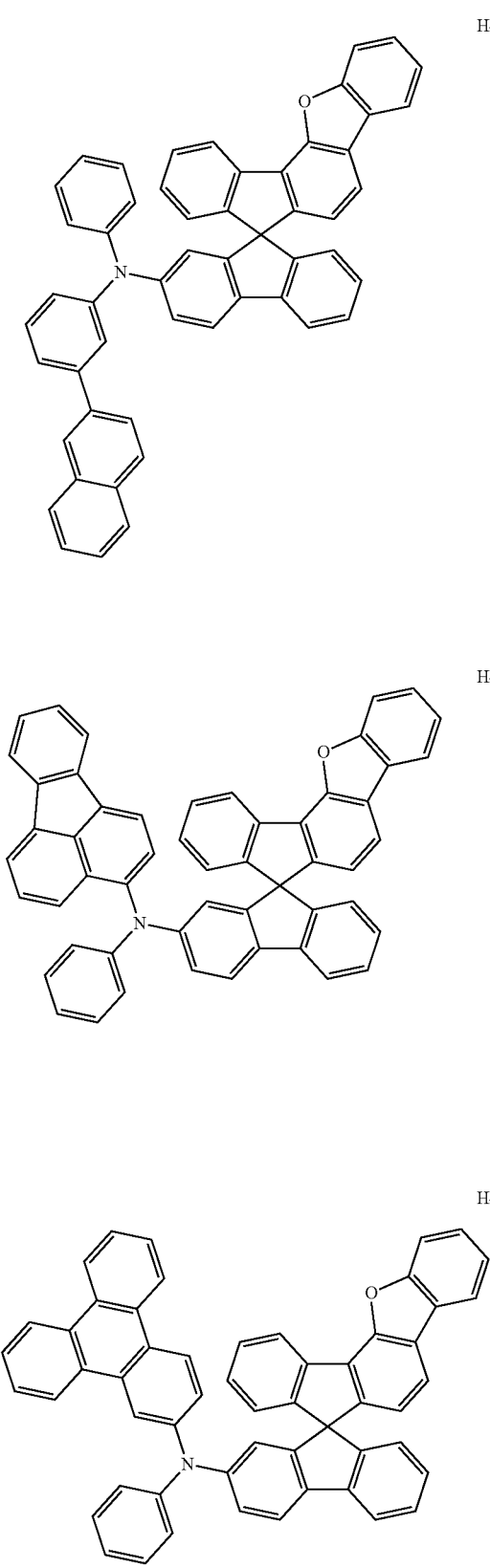
-continued
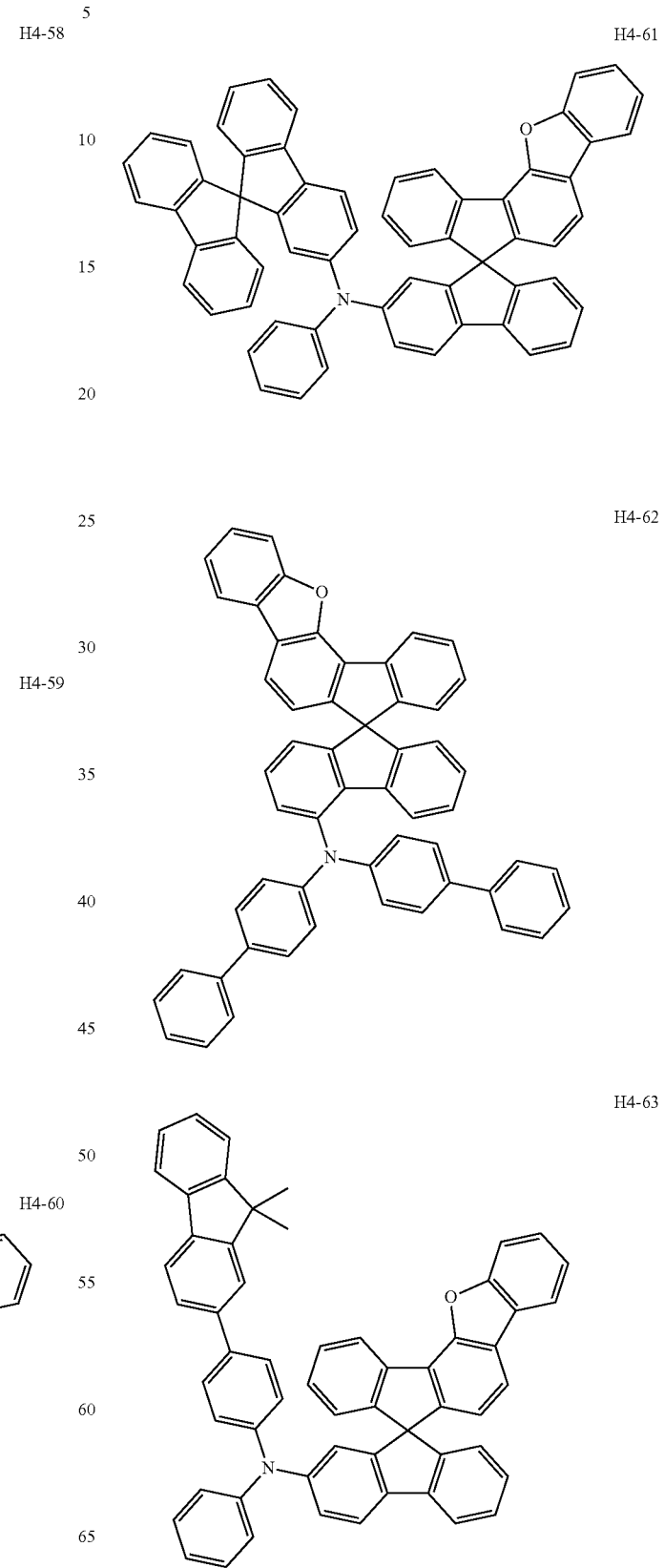

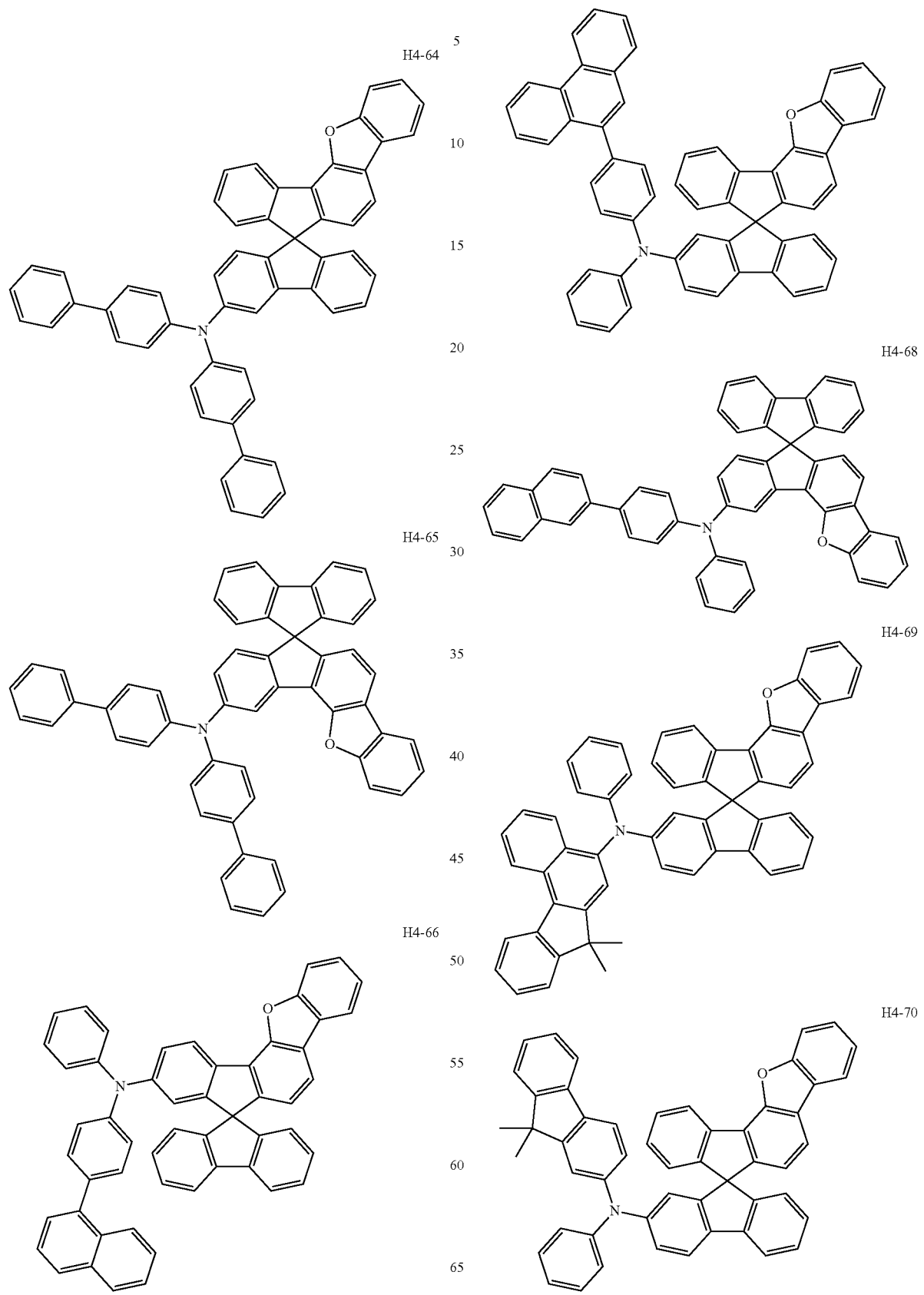

-continued
H4-71
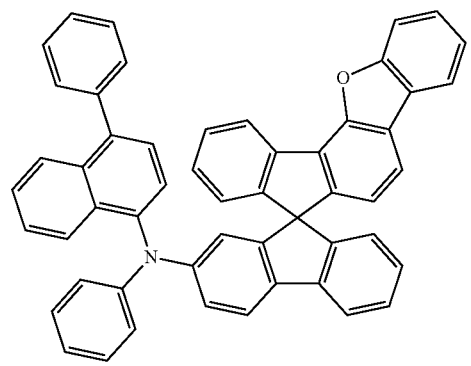
H4-72
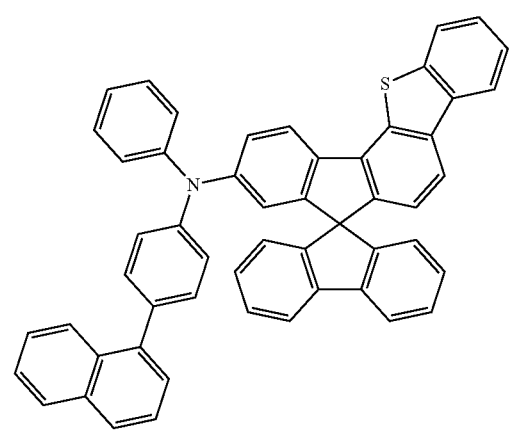
H4-73
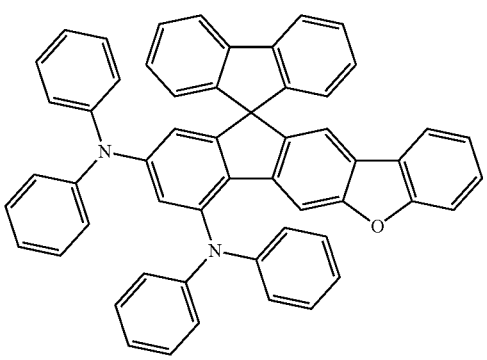
H4-74
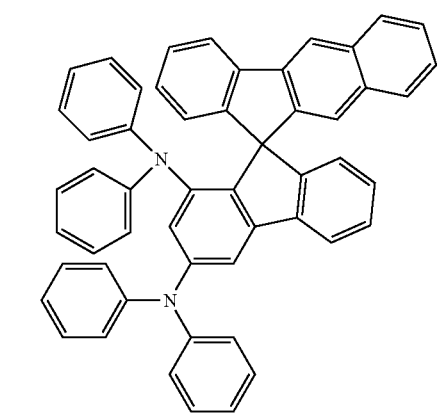
-continued
H4-75
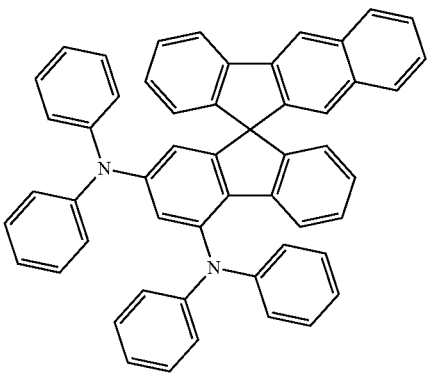
H4-76
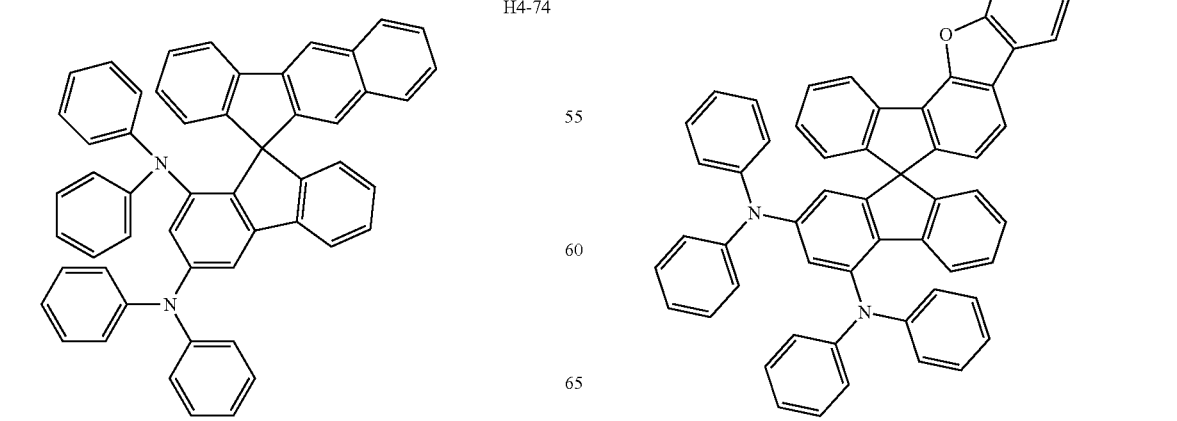
H4-77
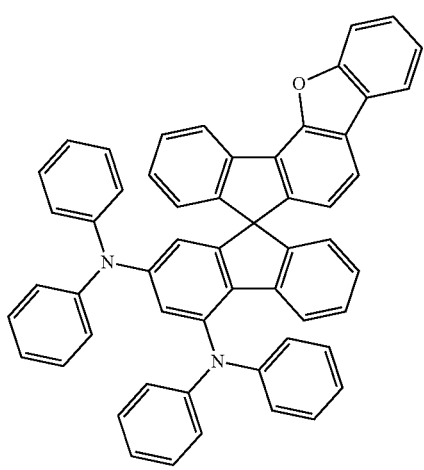

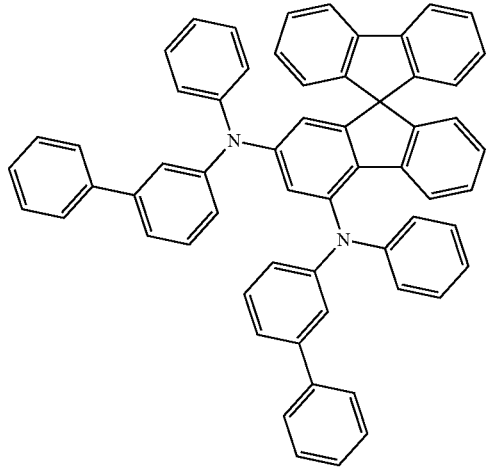

H4-78

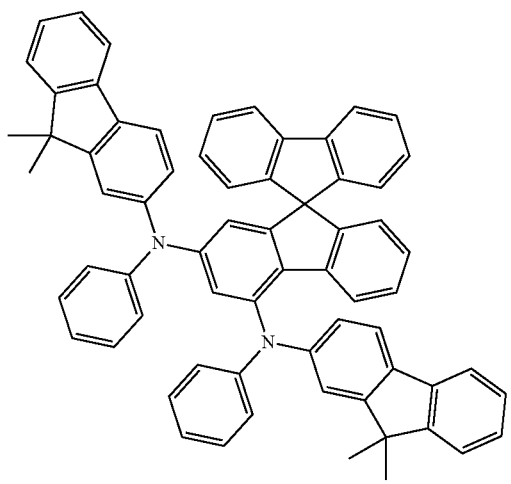

H4-79

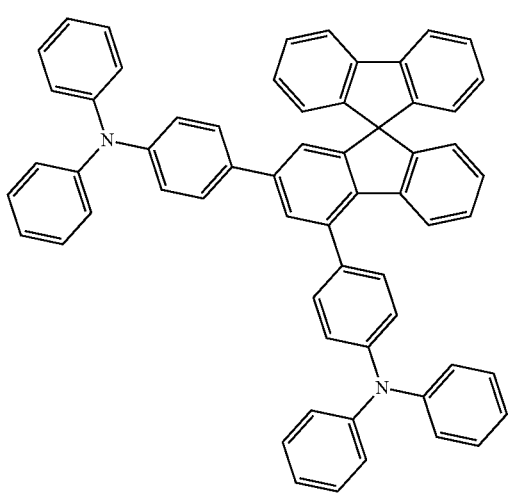

H4-80

The organic electroluminescent device of the present disclosure comprises an anode, a cathode, and an organic layer between the anode and the cathode, wherein the organic layer comprises one or more light-emitting layers and one or more hole transport layers; at least one of the one or more light-emitting layers comprises one or more dopant compounds and two or more host compounds; a first host compound of the two or more host compounds is represented by formula 1; a second host compound is represented by formula 2; and at least one of the one or more hole transport layers comprises the compound represented by formula 3.

The light-emitting layer indicates a layer from which light is emitted. It is preferable that a doping amount of the dopant compound is less than 20 wt % based on the total amount of the host compound and the dopant compound. In the organic electroluminescent device of the present disclosure, the weight ratio between the first host material and the second host material may be in the range of 1:99 to 99:1, and specifically 30:70 to 70:30.

In addition to the light-emitting layer and the hole transport layer, the organic layer may further comprise at least one layer selected from a hole injection layer, an electron transport layer, an electron injection layer, an electron buffering layer, an interlayer, a hole blocking layer, and an electron blocking layer.

The dopant to be comprised in the organic electroluminescent device of the present disclosure is preferably at least one phosphorescent dopant. The phosphorescent dopant material for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds. Preferably, the phosphorescent dopant may be selected from the group consisting of compounds represented by the following formulae 101 to 103.

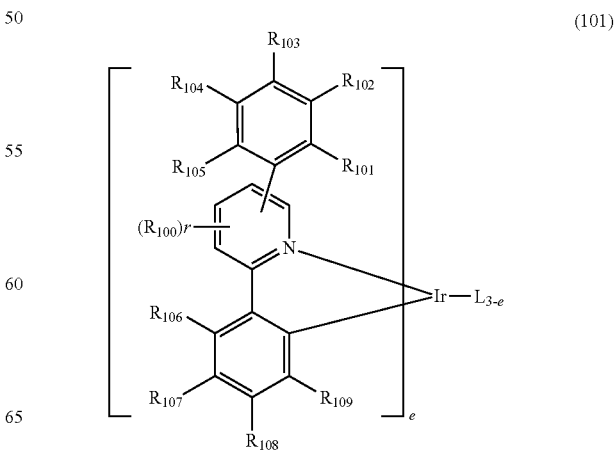

(101)

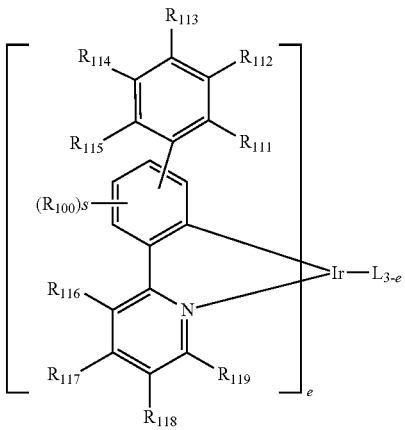

(102)

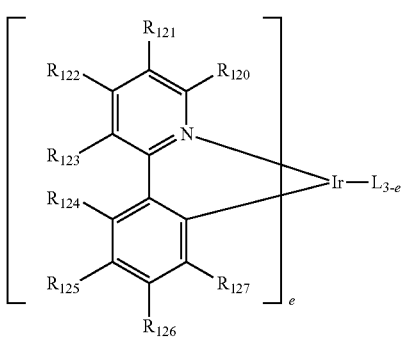

(103)

wherein L is selected from the following structures:

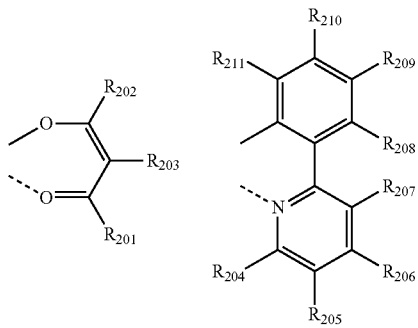

R₁₀₀ represents hydrogen, a substituted or unsubstituted (C1-C30)alkyl, or a substituted or unsubstituted (C3-C30)cycloalkyl; R₁₀₁ to R₁₀₉ and R₁₁₁ to R₁₂₃, each independently, represent hydrogen, deuterium, a halogen, a (C1-C30)alkyl unsubstituted or substituted with a halogen, a cyano, a substituted or unsubstituted (C1-C30)alkoxy or a substituted or unsubstituted (C3-C30)cycloalkyl; R₁₀₆ to R₁₀₉, each independently, may be linked to an adjacent substituent(s) to form a substituted or unsubstituted 3- to 30-membered, mono- or polycyclic, alicyclic or aromatic ring (e.g., a substituted or unsubstituted fluorene, a substituted or unsubstituted dibenzothiophene, or a substituted or unsubstituted dibenzofuran); R₁₂₀ to R₁₂₃, each independently, may be linked to an adjacent substituent(s) to form a substituted or unsubstituted 3- to 30-membered, mono- or polycyclic, alicyclic or aromatic ring (e.g., a substituted or unsubstituted quinoline); R₁₂₄ to R₁₂₇, each independently, represent hydrogen, deuterium, a halogen, a substituted or unsubstituted (C1-C30)alkyl, or a substituted or unsubstituted (C6-C30)aryl; where R₁₂₄, R₁₂₅, R₁₂₆, or R₁₂₇ is aryl, it may be linked to an adjacent substituent(s) to form a substituted or unsubstituted 3- to 30-membered, mono- or polycyclic, alicyclic or aromatic ring (e.g., a substituted or unsubstituted fluorene, a substituted or unsubstituted dibenzothiophene, or a substituted or unsubstituted dibenzofuran); R₂₀₁ to R₂₁₁, each independently, represent hydrogen, deuterium, a halogen, a (C1-C30)alkyl unsubstituted or substituted with a halogen, a substituted or unsubstituted (C3-C30)cycloalkyl, or a substituted or unsubstituted (C6-C30)aryl; R₂₀₈, R₂₀₉, R₂₁₀, or R₂₁₁ may be linked to an adjacent substituent(s) to form a substituted or unsubstituted 3- to 30-membered, mono- or polycyclic, alicyclic or aromatic ring (e.g., a substituted or unsubstituted fluorene, a substituted or unsubstituted dibenzothiophene, or a substituted or unsubstituted dibenzofuran); r and s, each independently, represent an integer of 1 to 3; when r or s is an integer of 2 or more, each of R₁₀₀ may be the same or different; and e represents an integer of 1 to 3.

Specifically, the phosphorescent dopant material includes the following:

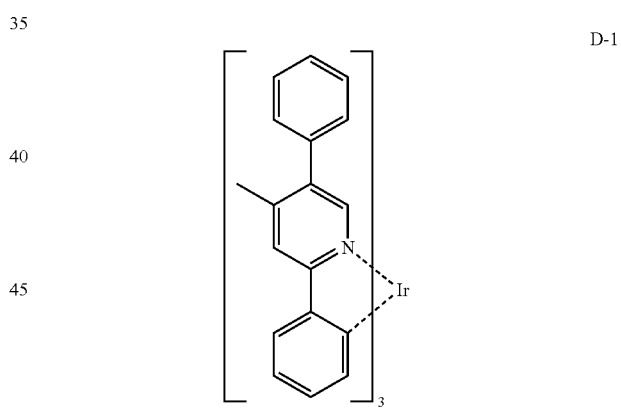

D-1

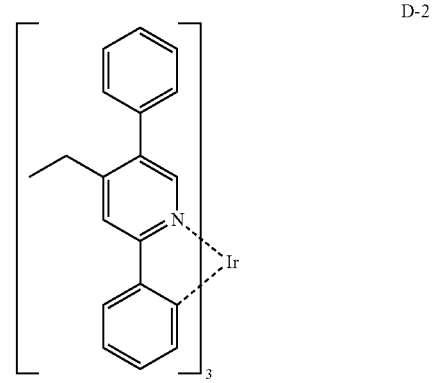

D-2

D-3
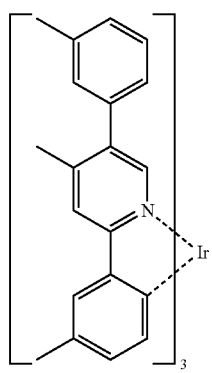
D-4
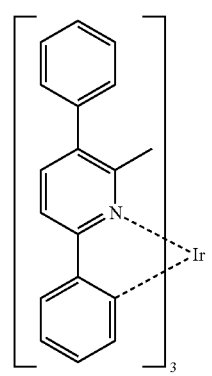
D-5
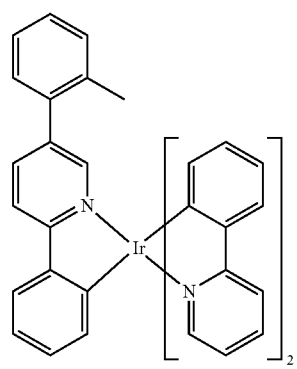
D-6
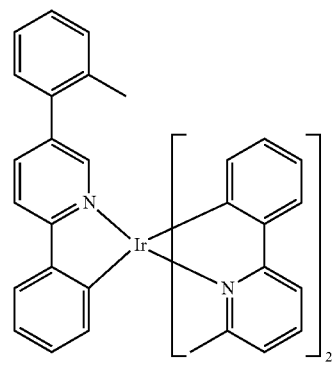
D-7
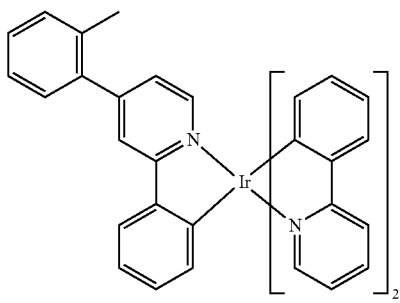
D-8
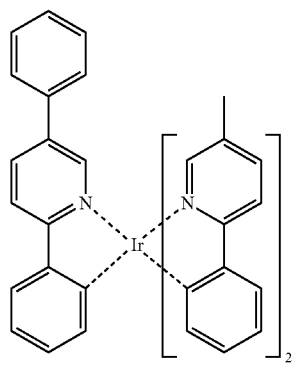
D-9
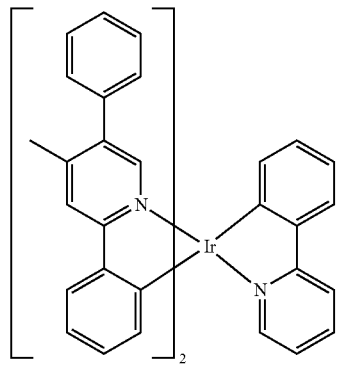
D-10
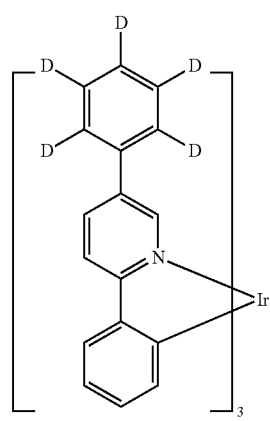

-continued
D-11
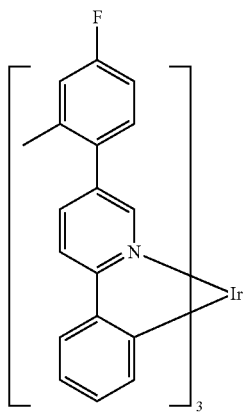
D-12
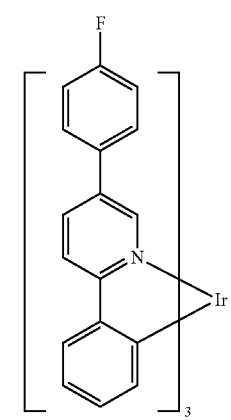
D-13
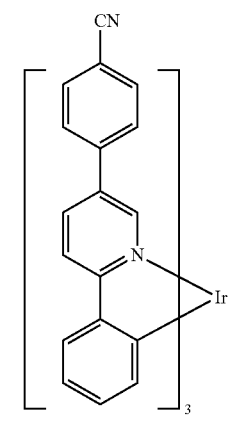
D-14
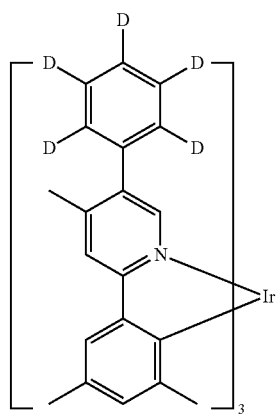
-continued
D-15
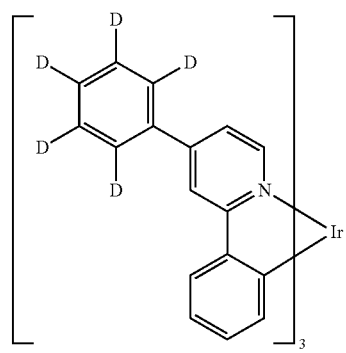
D-16
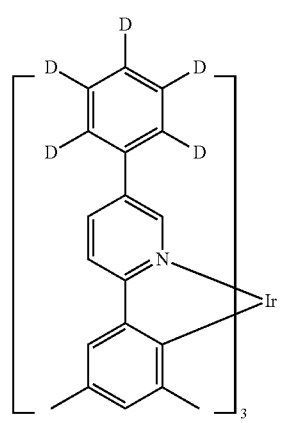
D-17
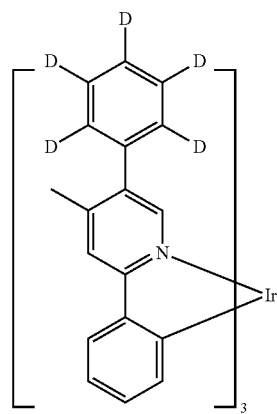
D-18
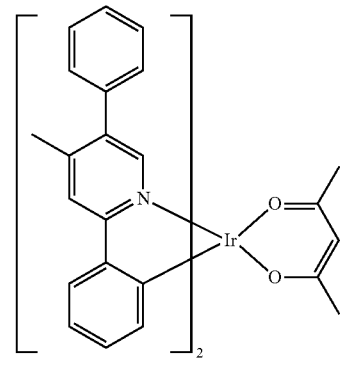

D-19
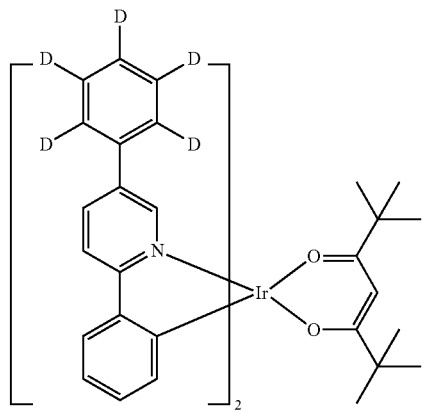
D-20
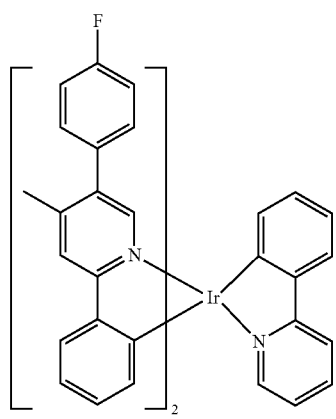
D-21
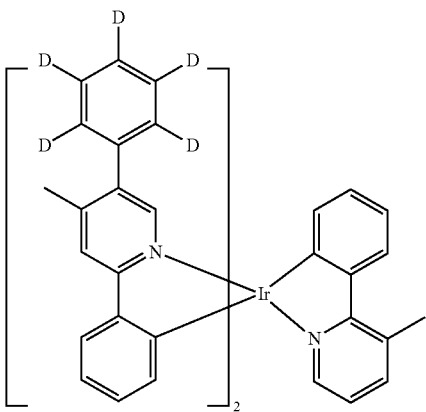
D-22
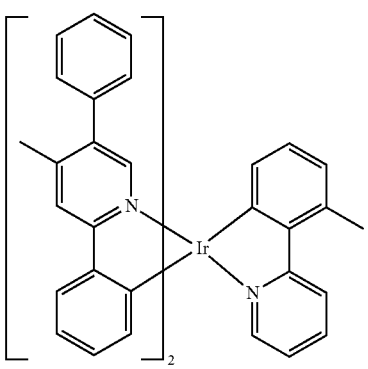
D-23
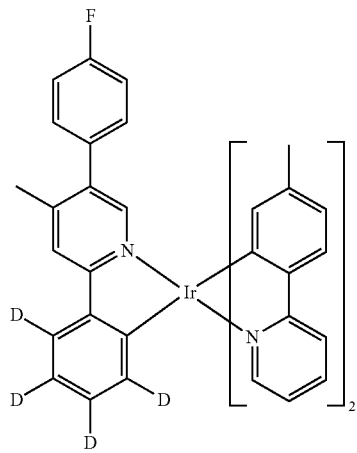
D-24
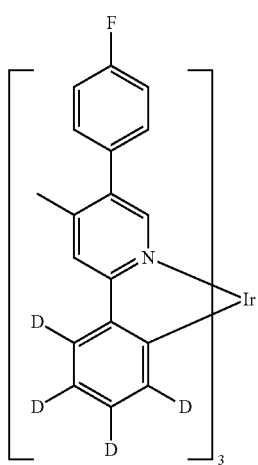
D-25
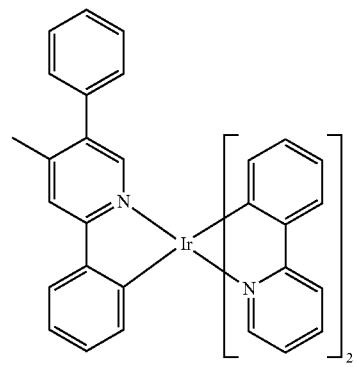
D-26
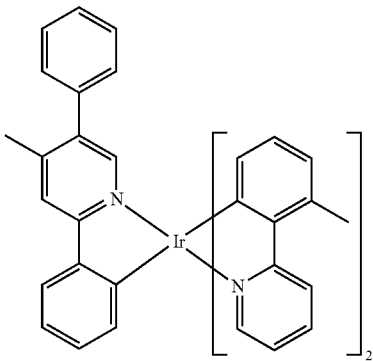

-continued
D-27
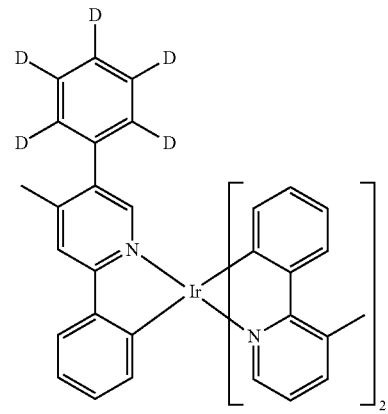
D-28
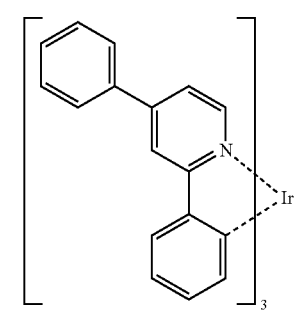
D-29
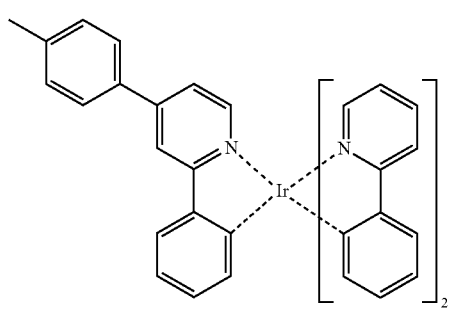
D-30
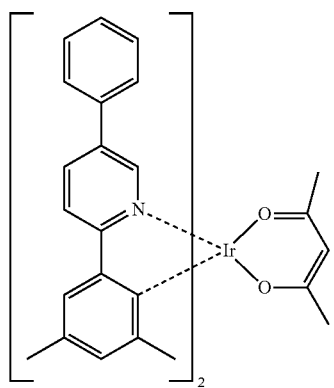
-continued
D-31
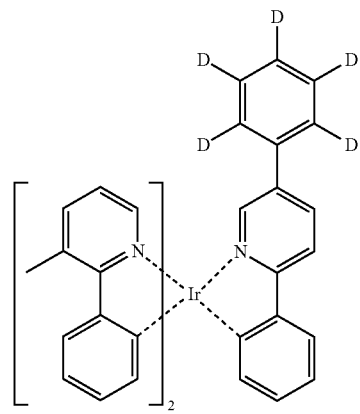
D-32
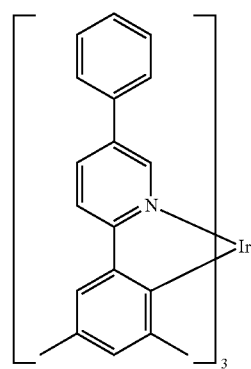
D-33
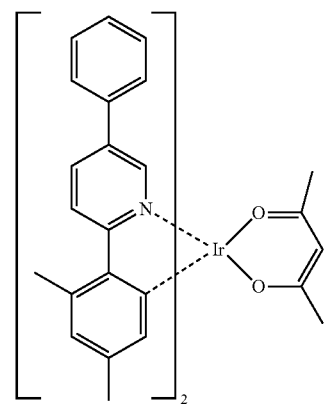
D-34
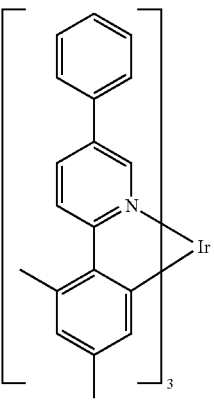

D-35 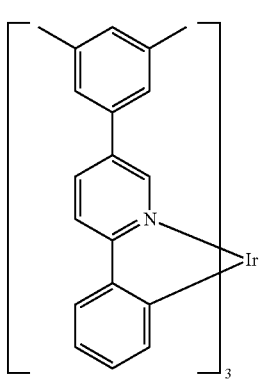
D-36 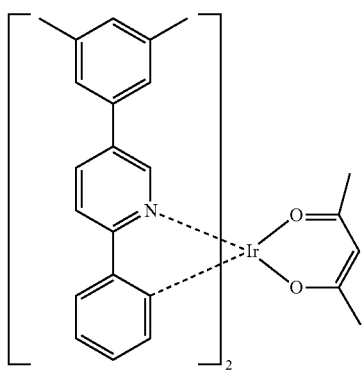
D-37 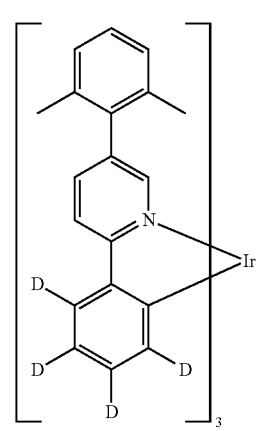
D-38 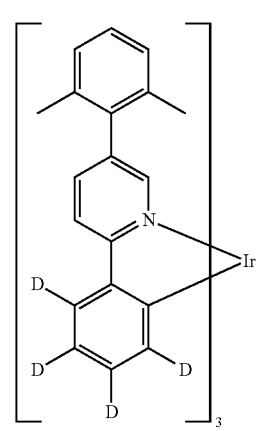
D-39 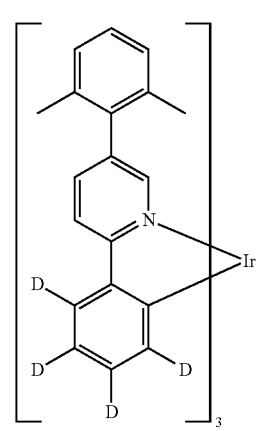
D-40 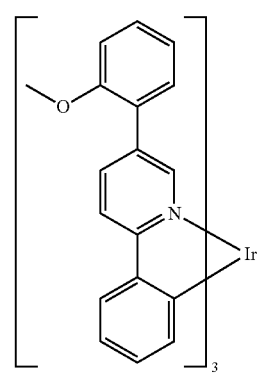
D-41 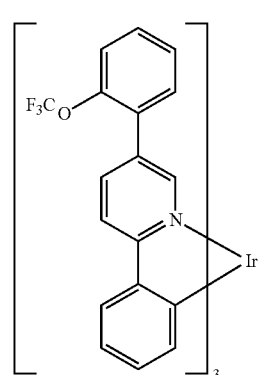
D-42 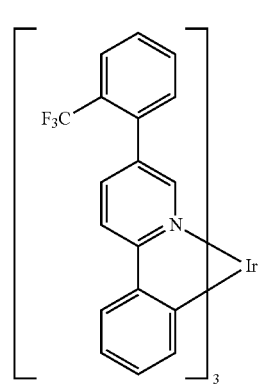

D-43 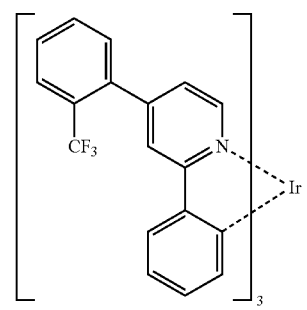
D-44 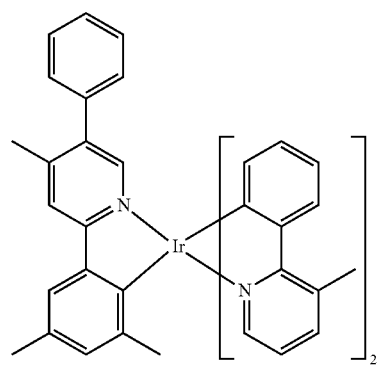
D-45 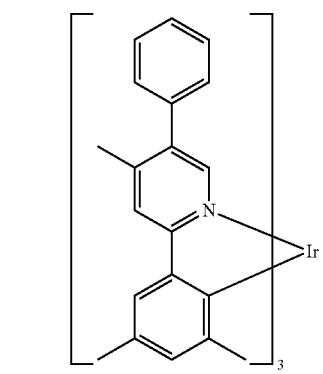
D-46 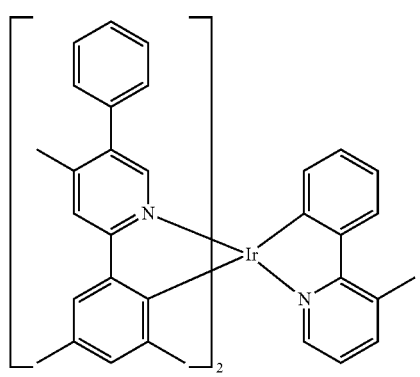
D-47 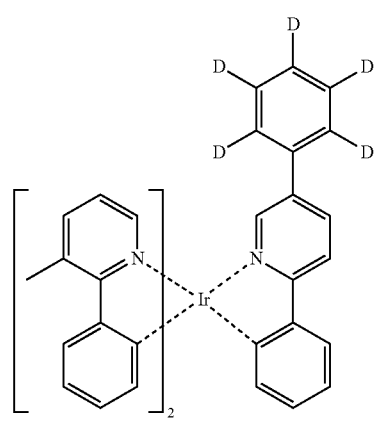
D-48 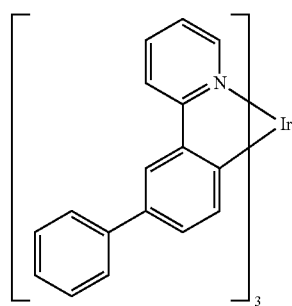
D-49 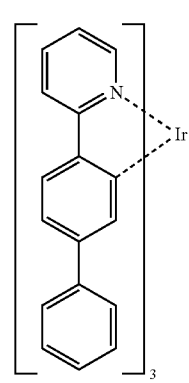
D-50 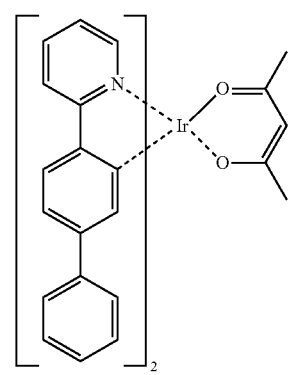

-continued
D-51
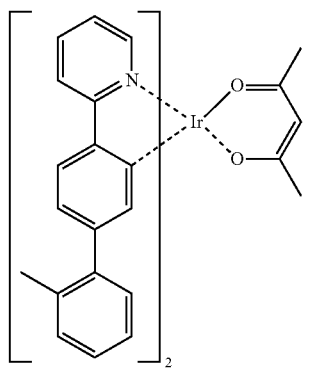
D-52
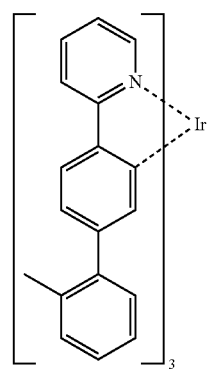
D-53
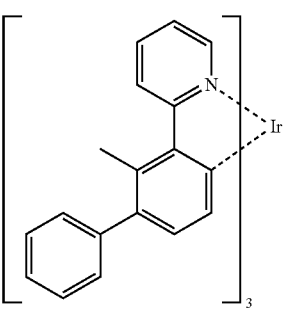
D-54
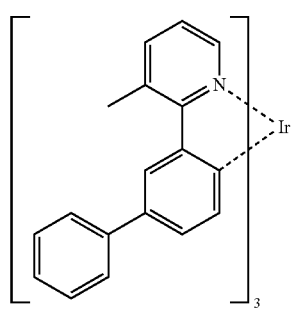
-continued
D-55
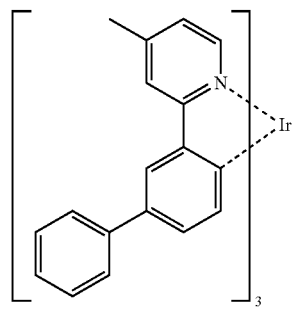
D-56
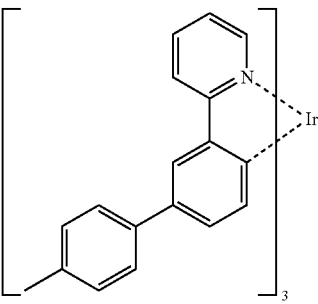
D-57
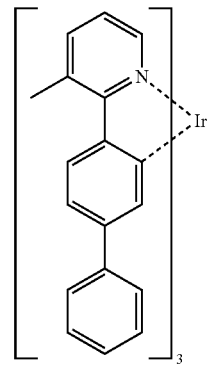
D-58
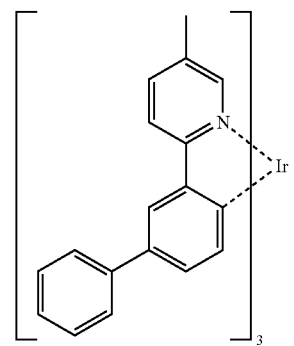
D-59
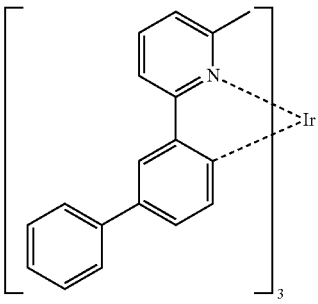

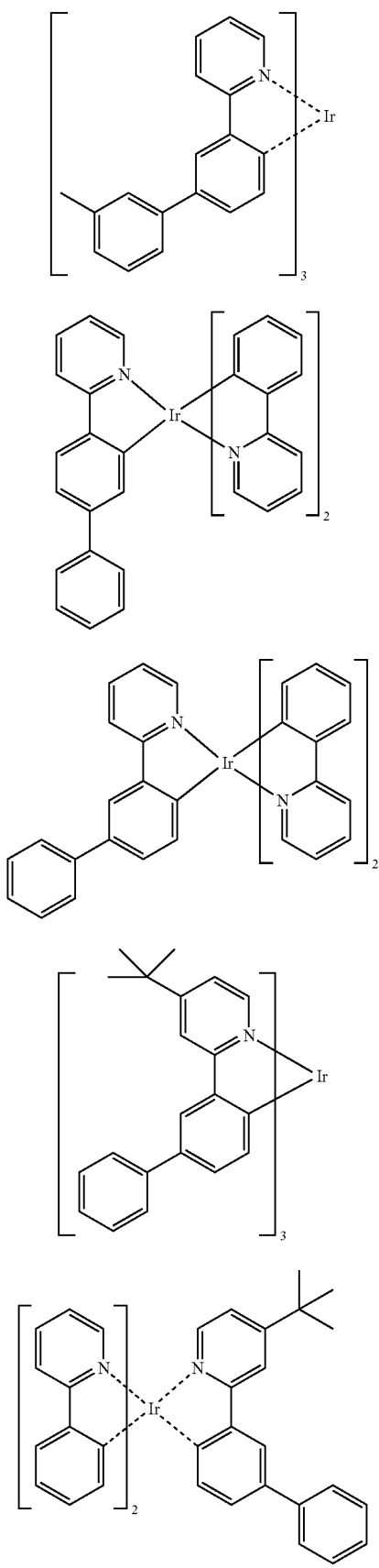

D-69
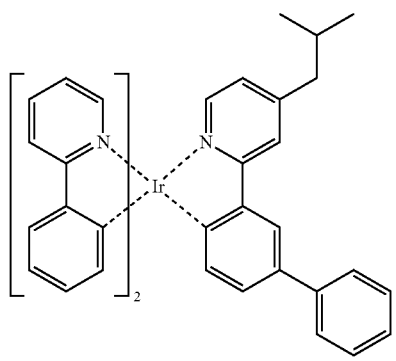
D-70
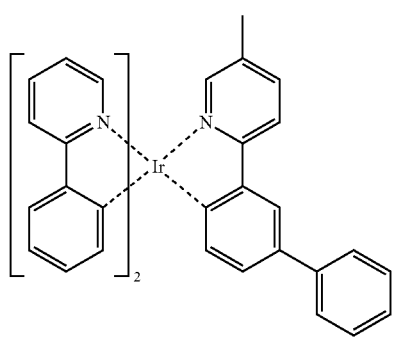
D-71
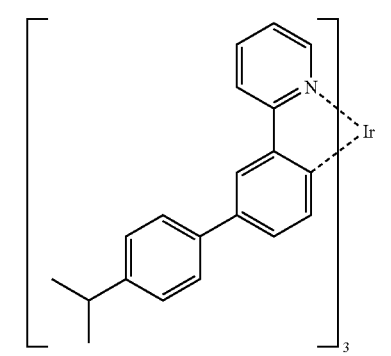
D-72
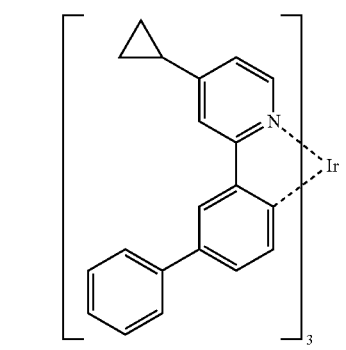
D-73
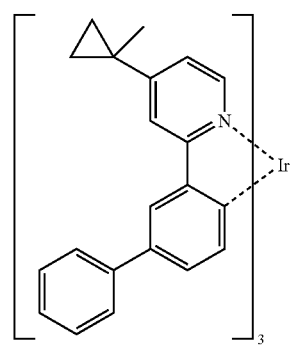
D-74
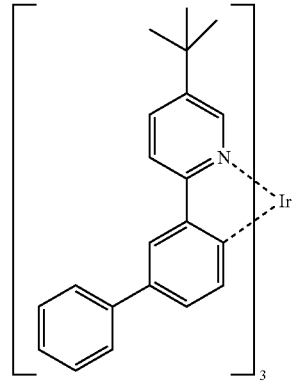
D-75
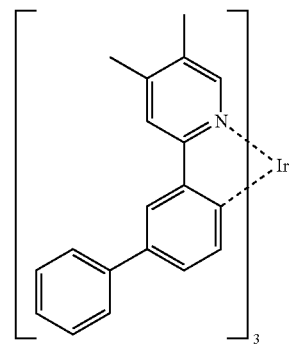
D-76
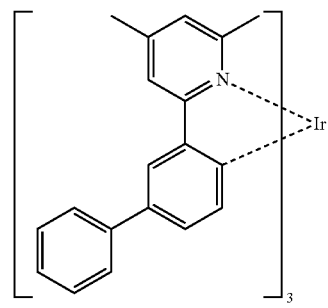

D-77 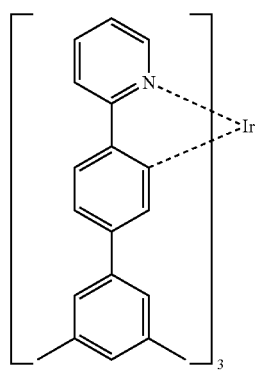
D-78 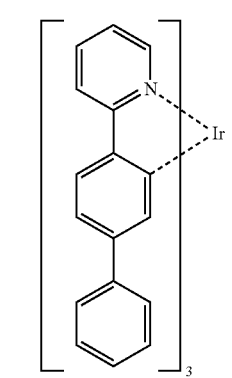
D-79 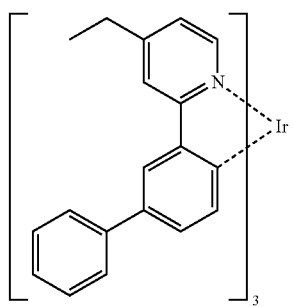
D-80 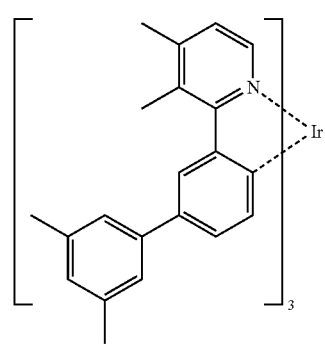
D-81 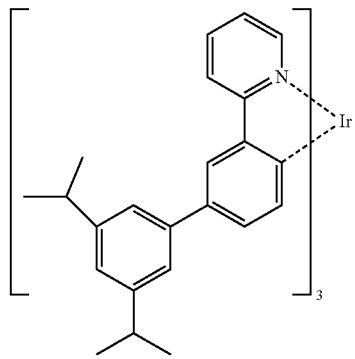
D-82 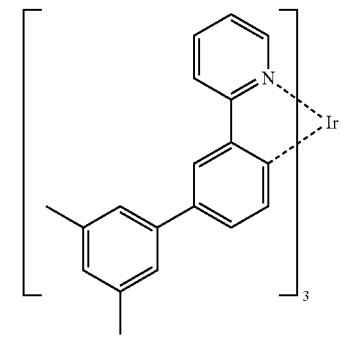
D-83 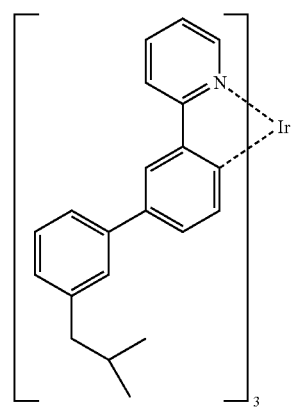
D-84 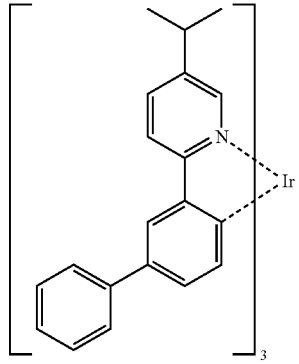

407
-continued
D-85
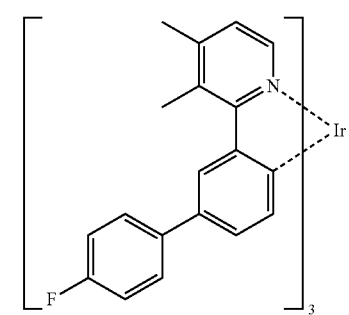
D-86
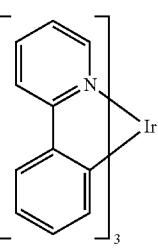
D-87
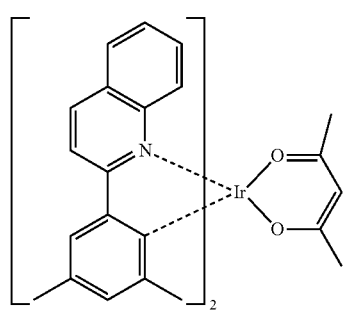
D-88
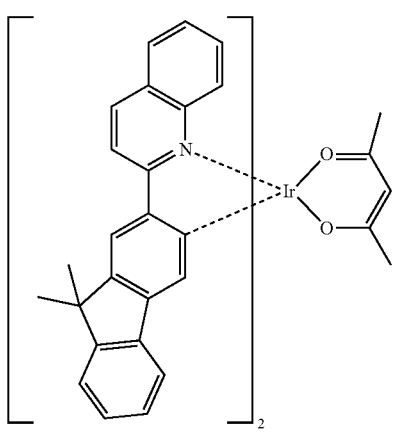
D-89
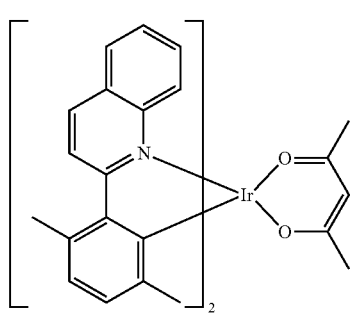
408
-continued
D-90
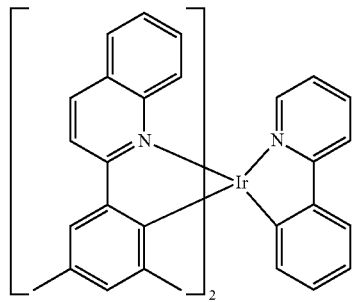
D-91
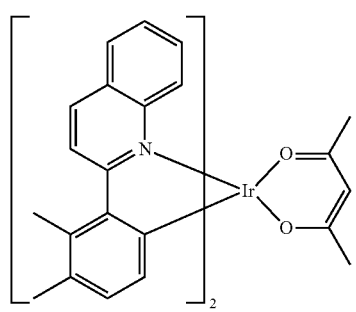
D-92
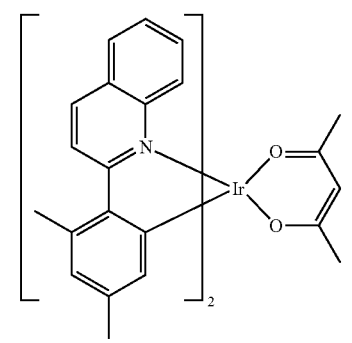
D-93
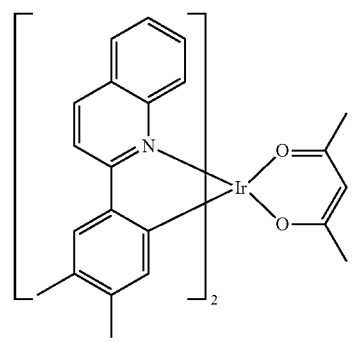

D-94
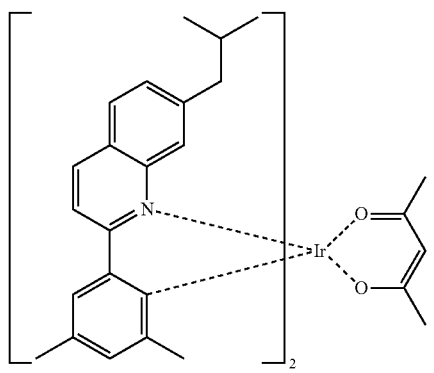
D-95
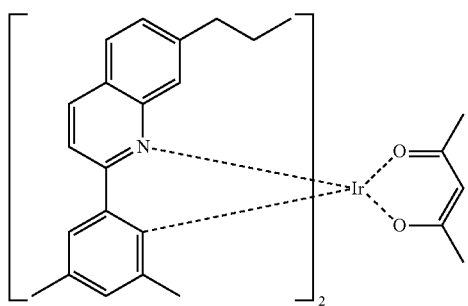
D-96
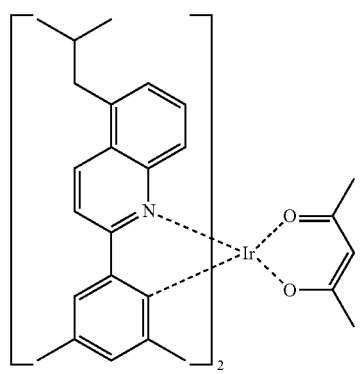
D-97
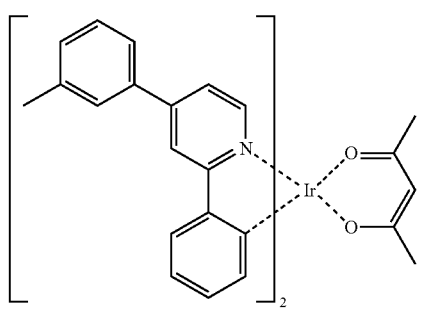
D-98
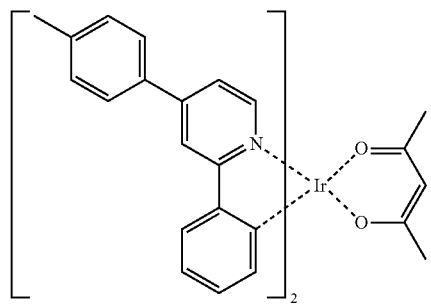
D-99
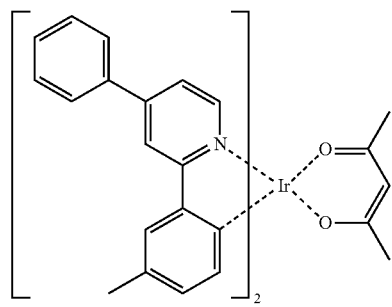
D-100
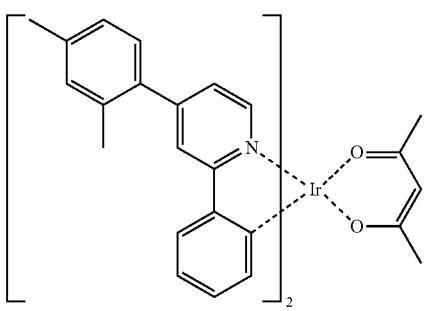
D-101
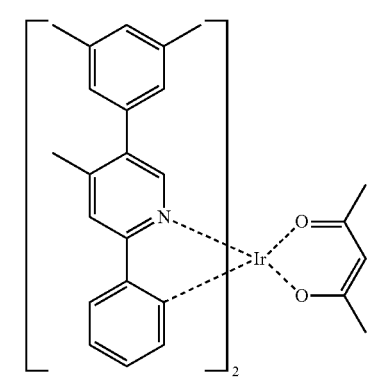
D-102
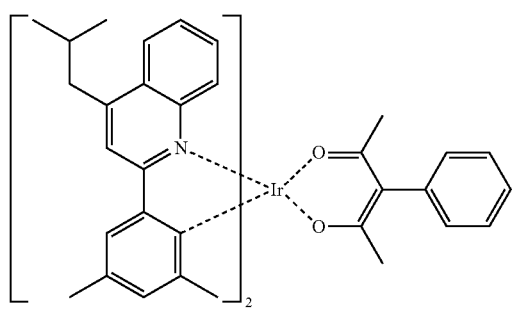

D-103 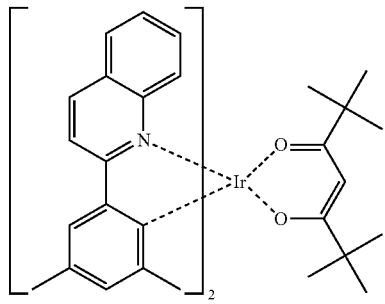
D-104 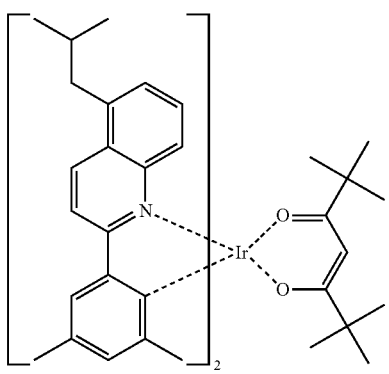
D-105 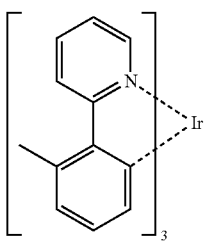
D-106 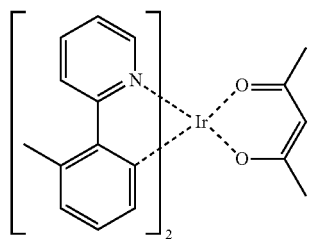
D-107 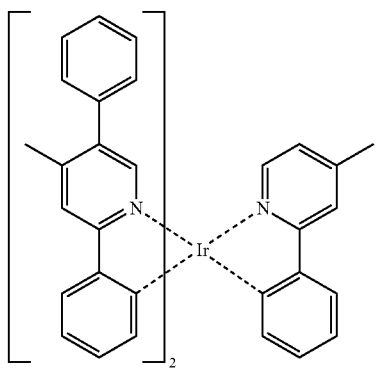
D-108 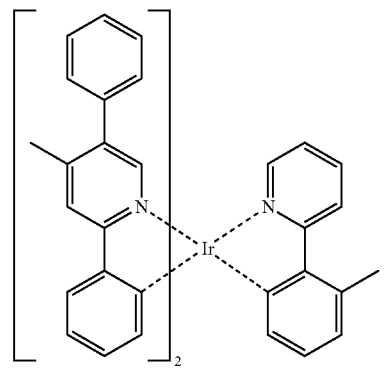
D-109 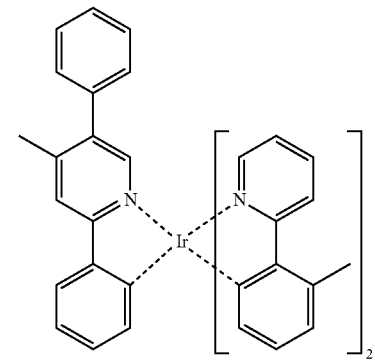
D-110 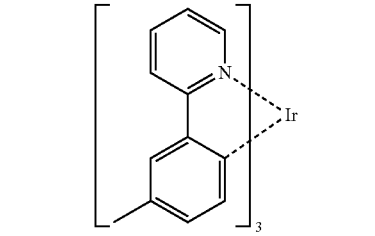
D-111 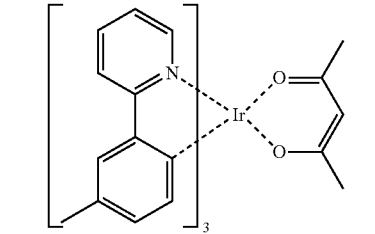
D-112 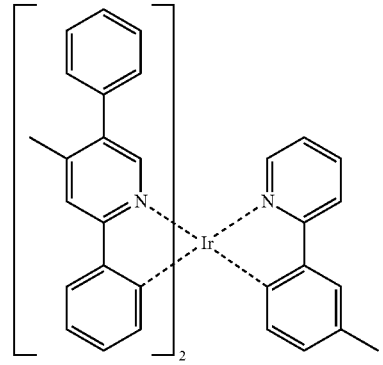

D-113
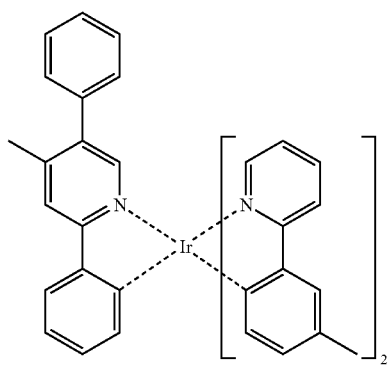
D-114
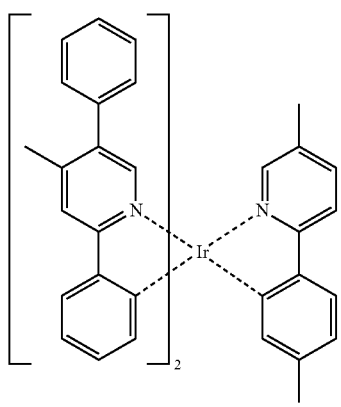
D-115
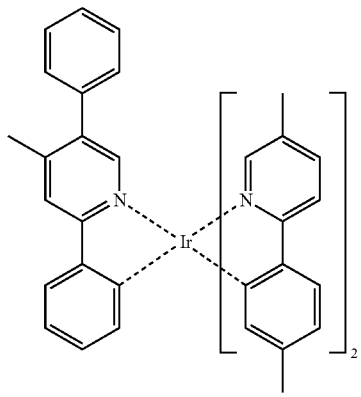
D-116
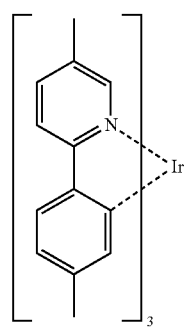
D-117
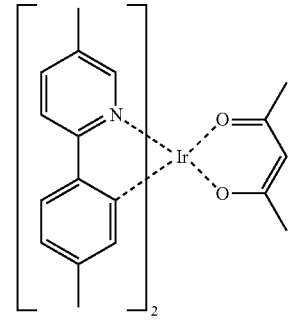
D-118
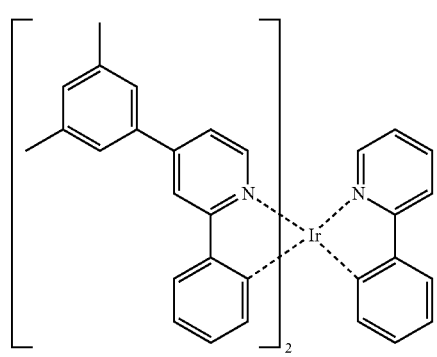
D-119
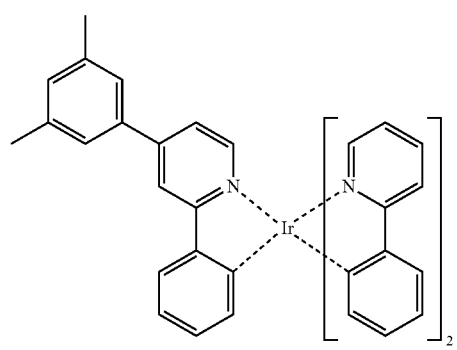
D-120
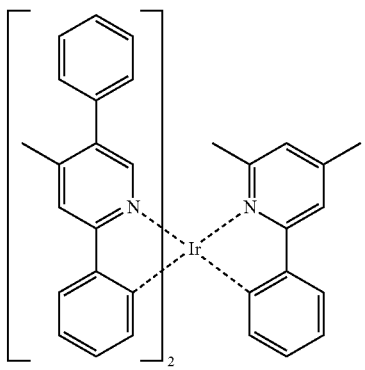

D-121 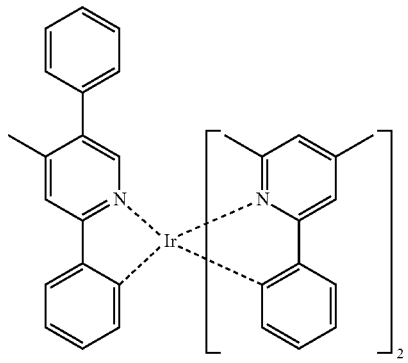
D-122 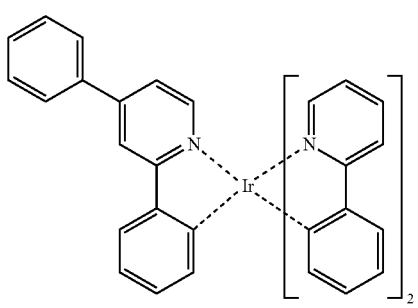
D-123 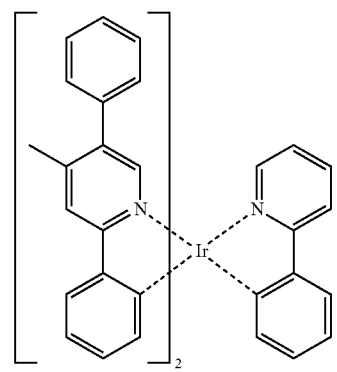
D-124 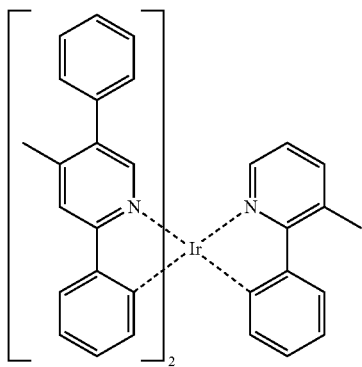
D-125 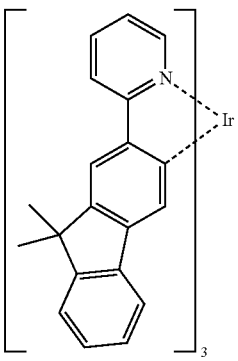
D-126 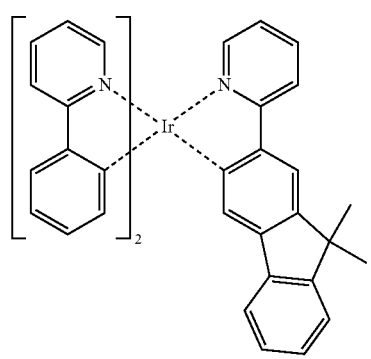
D-127 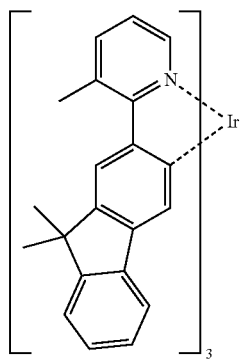
D-128 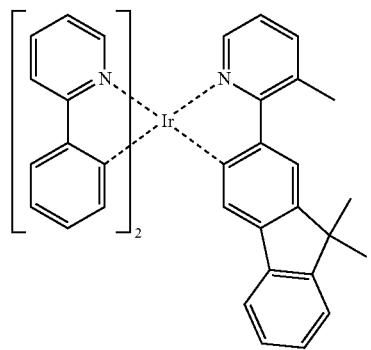

D-129 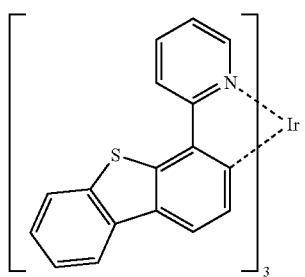
D-130 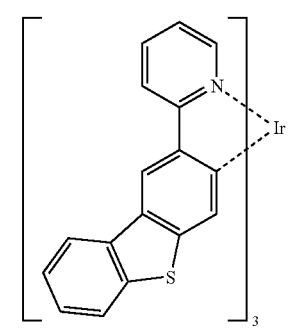
D-131 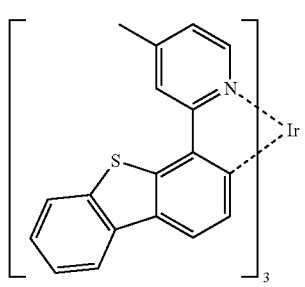
D-132 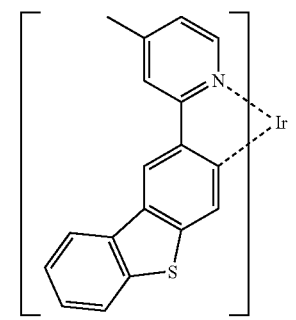
D-133 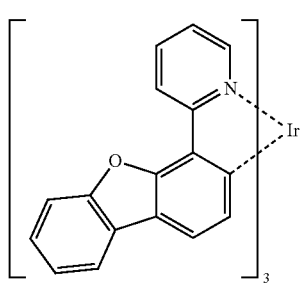
D-134 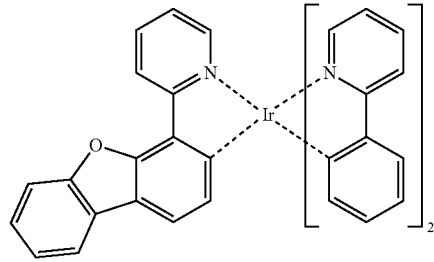
D-135 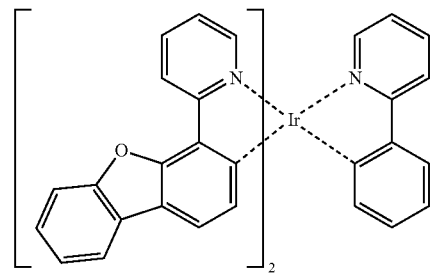
D-136 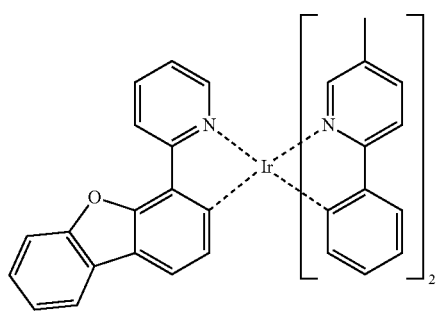
D-137 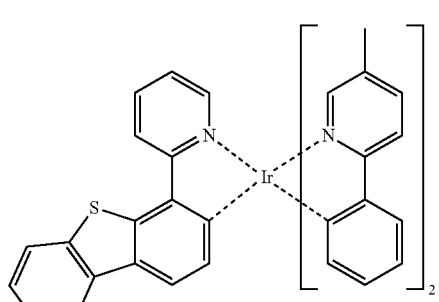
D-138 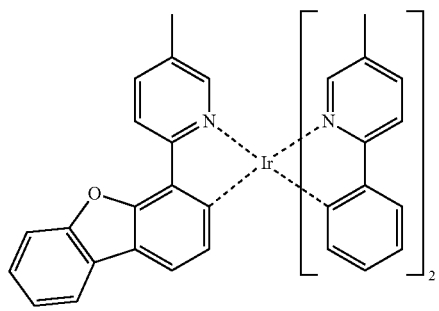

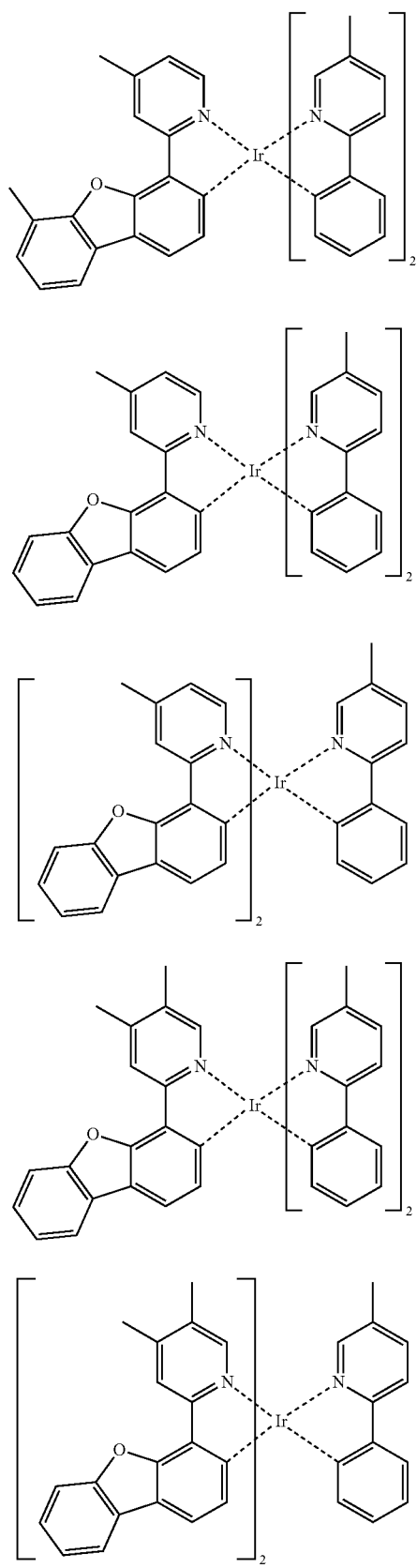
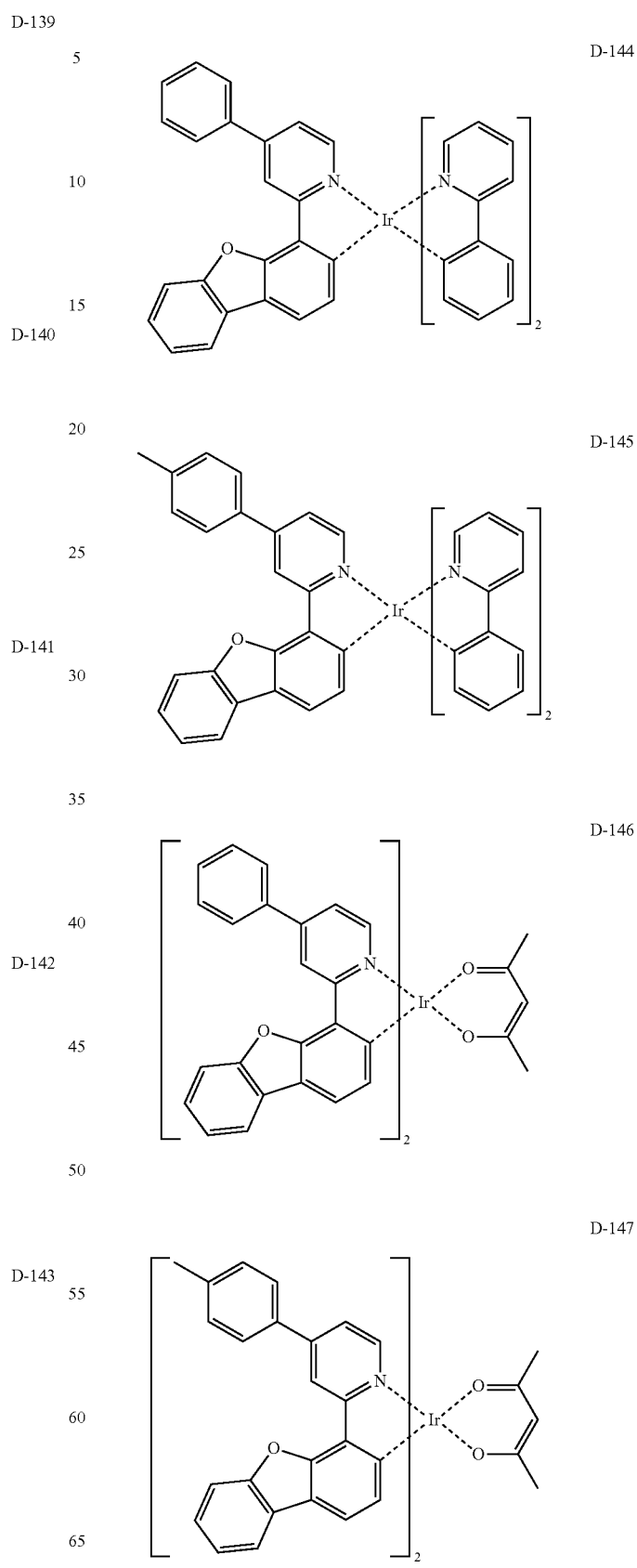

D-148
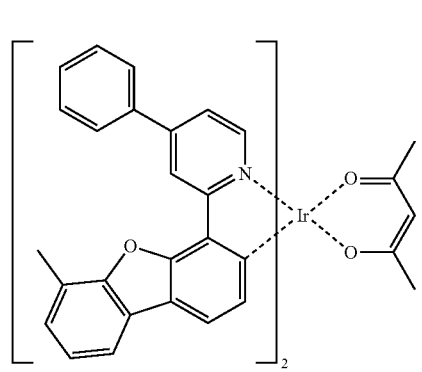
D-149
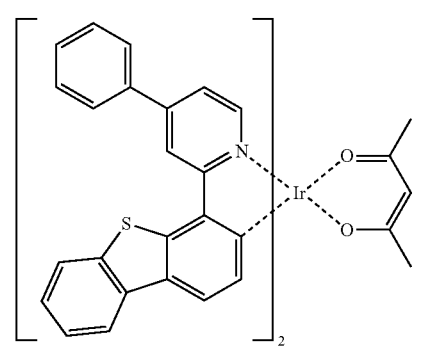
D-150
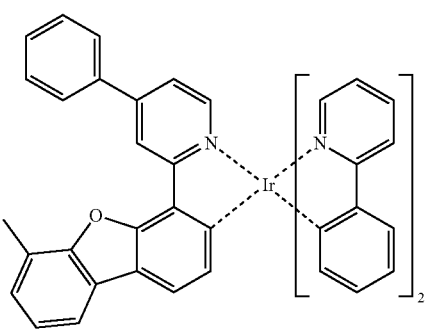
D-151
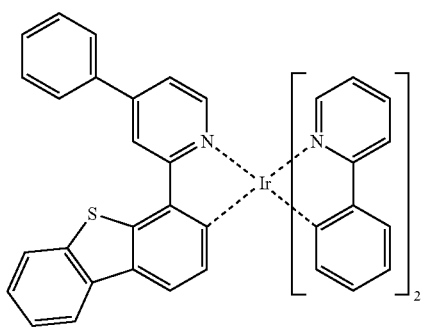
D-152
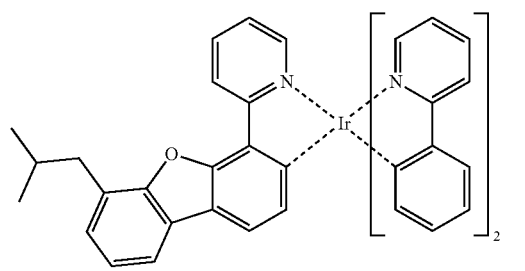
D-153
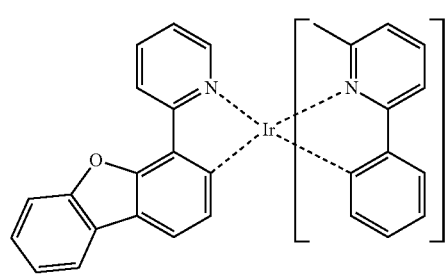
D-154
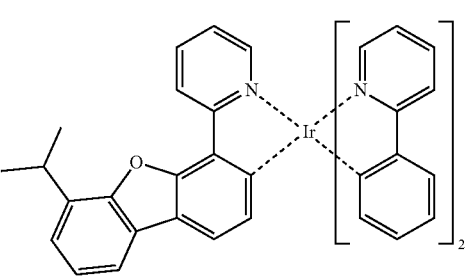
D-155
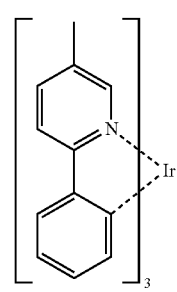
D-156
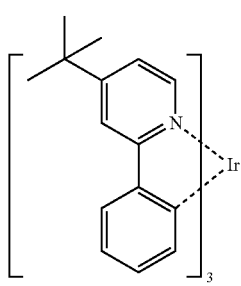

D-157
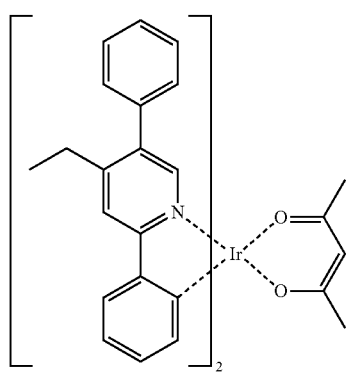
D-162
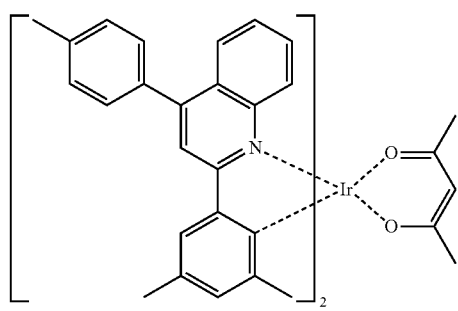
D-158
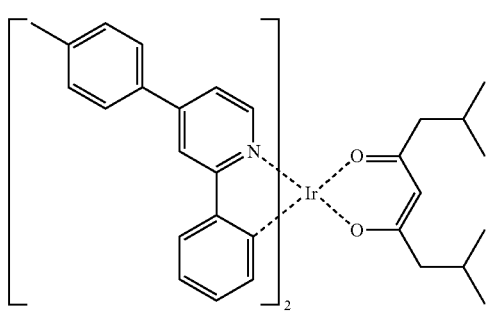
D-163
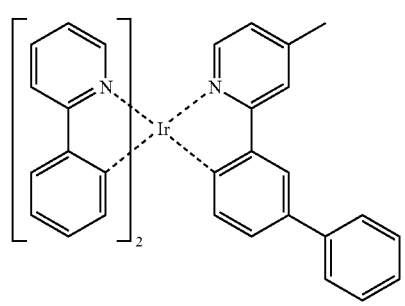
D-159
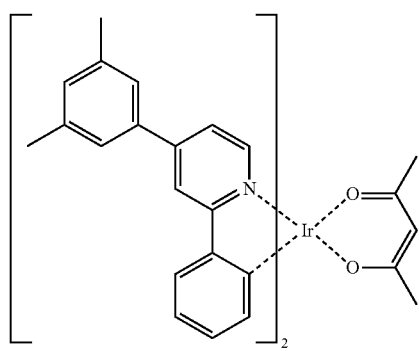
D-164
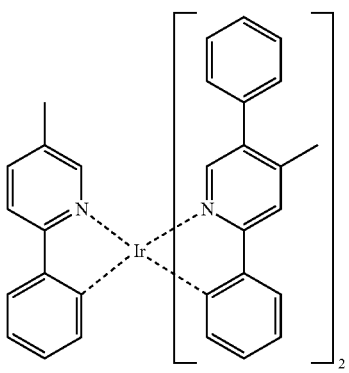
D-160
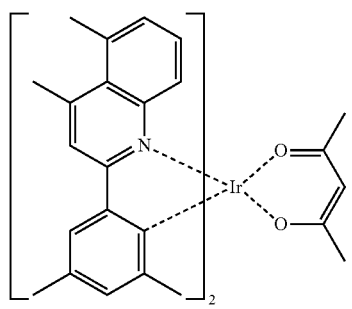
D-161
D-165
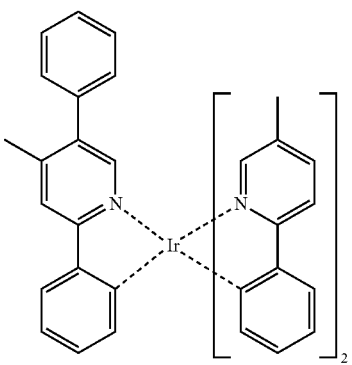

D-166
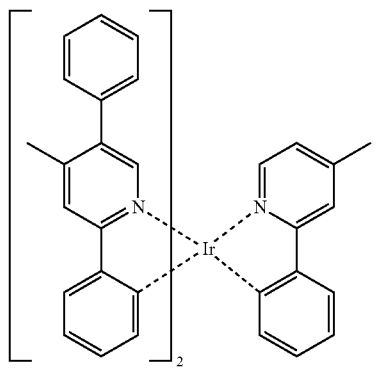
D-167
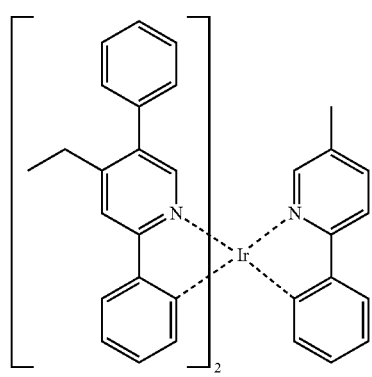
D-168
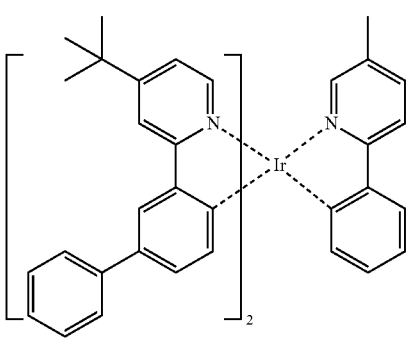
D-169
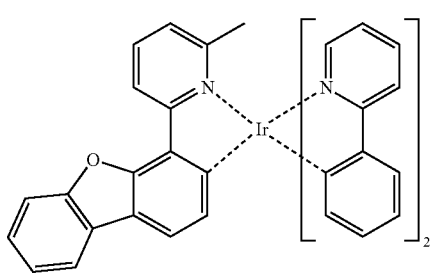
D-170
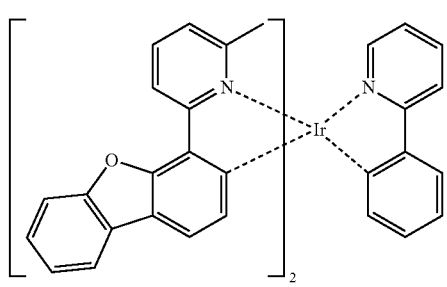
D-171
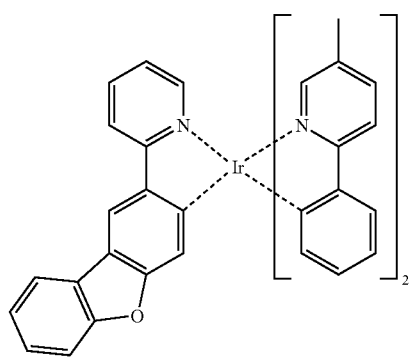
D-172
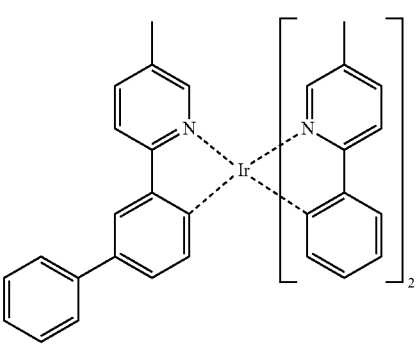
D-173
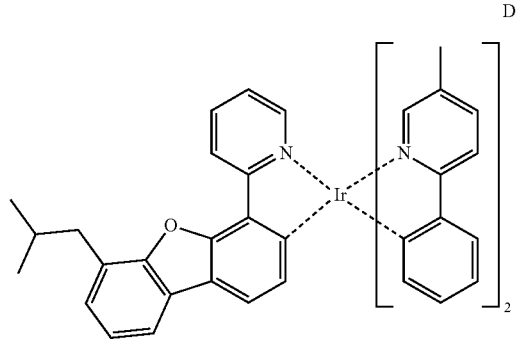
D-174
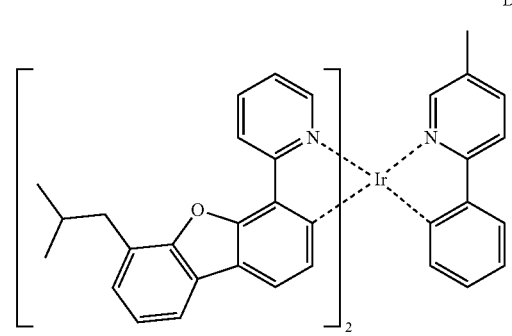

-continued
D-175
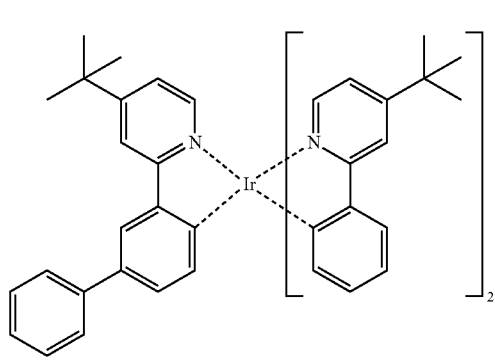
D-179
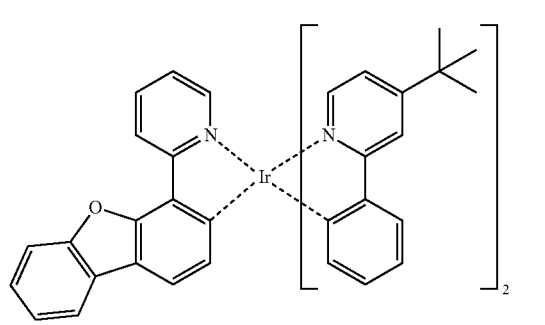
D-176
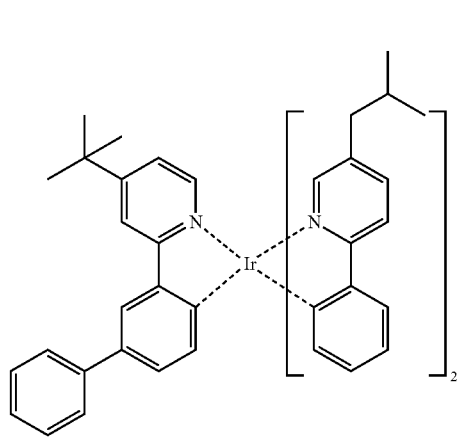
D-180
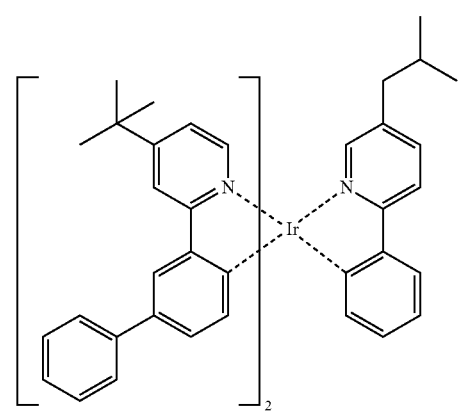
D-177
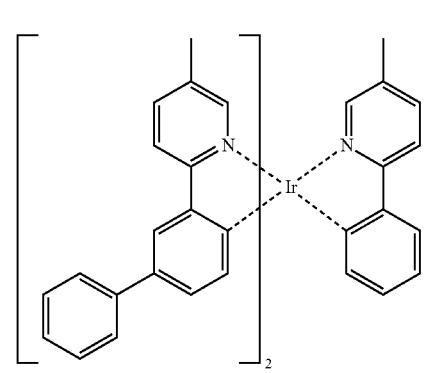
D-181
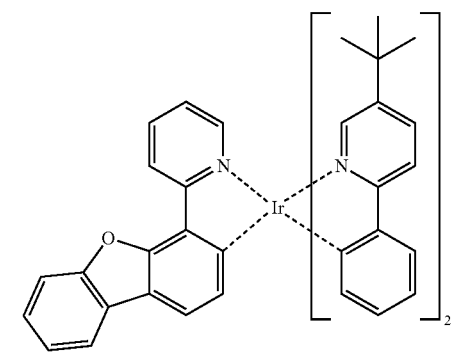
D-178
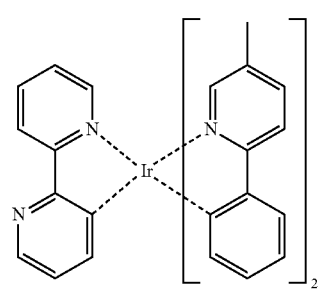
D-182
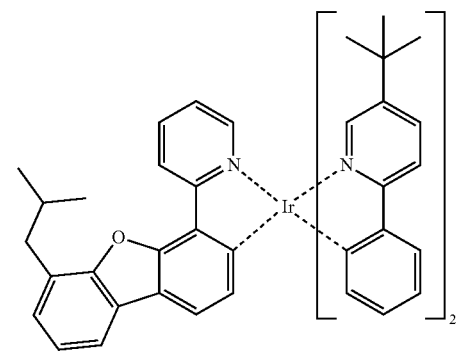

D-183 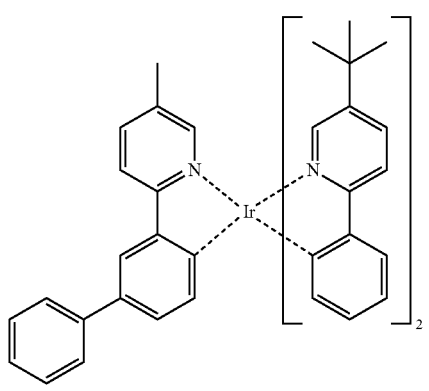
D-184 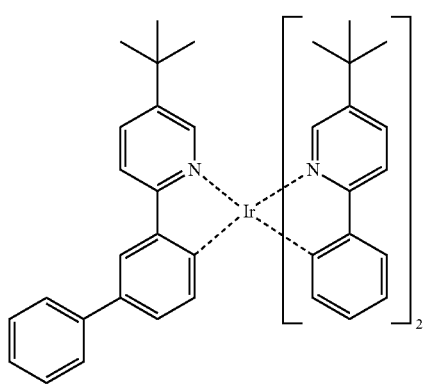
D-185 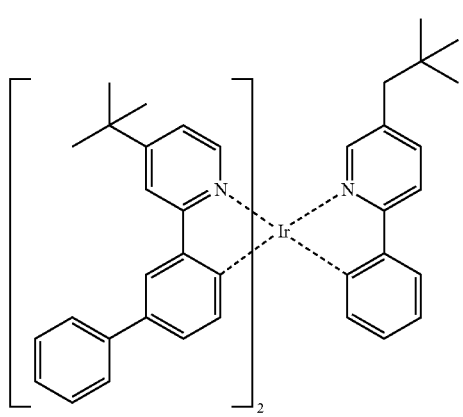
D-186 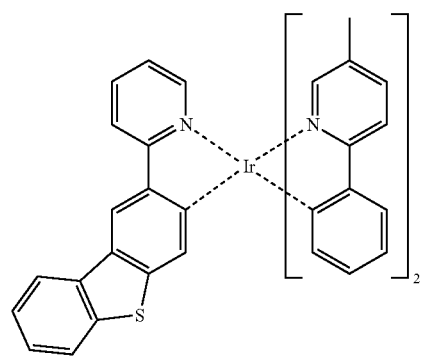
D-187 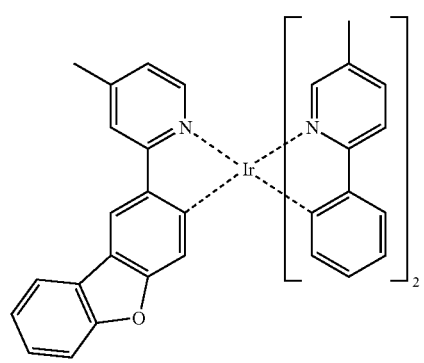
D-188 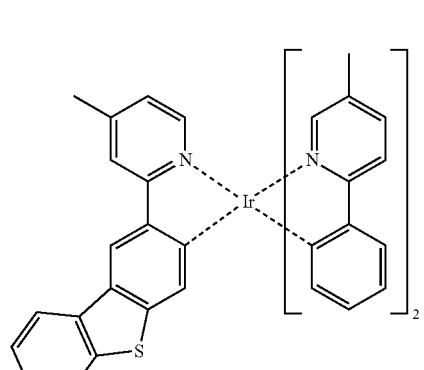
D-189 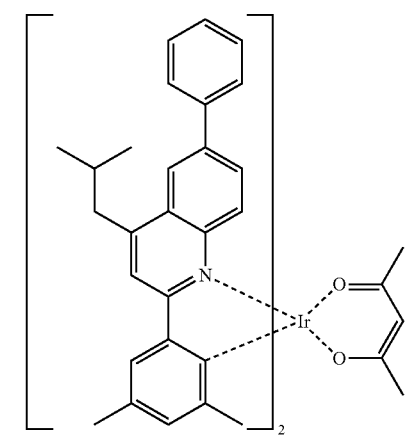
D-190 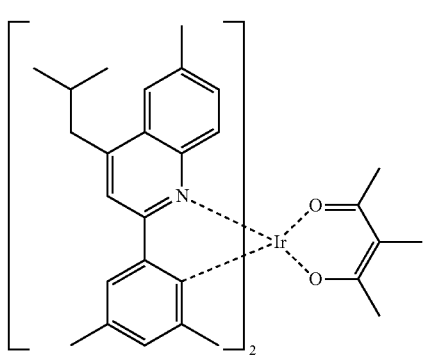

D-191
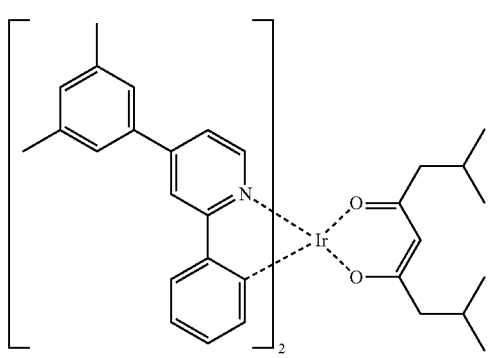
D-192
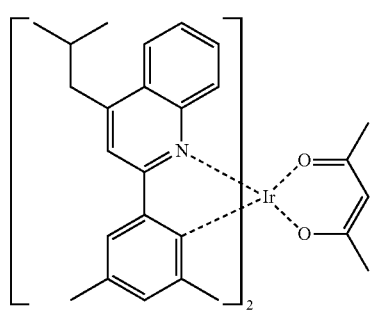
D-193
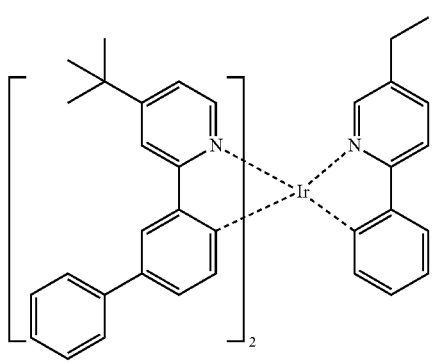
D-194
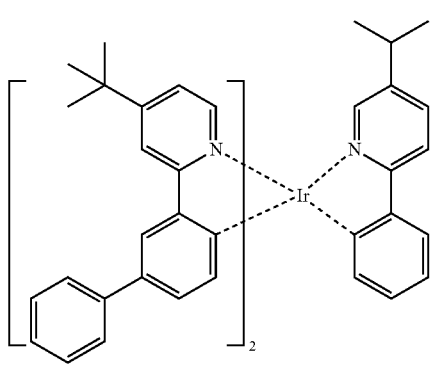
D-195
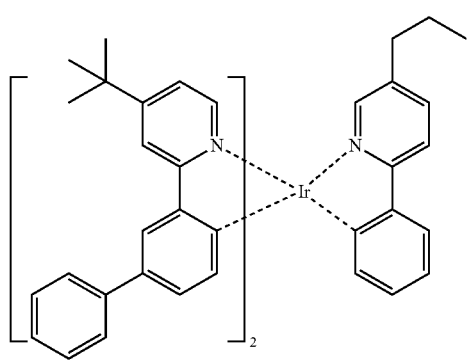
D-196
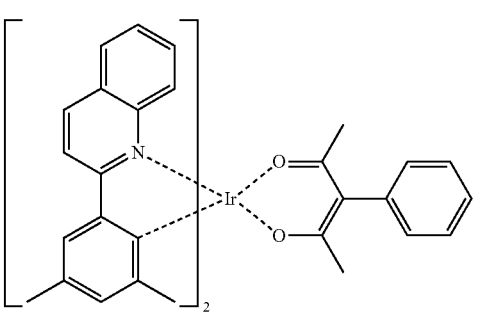
D-197
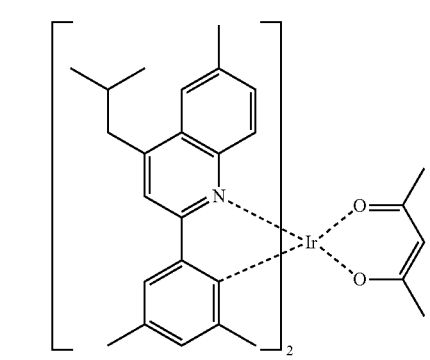
D-198
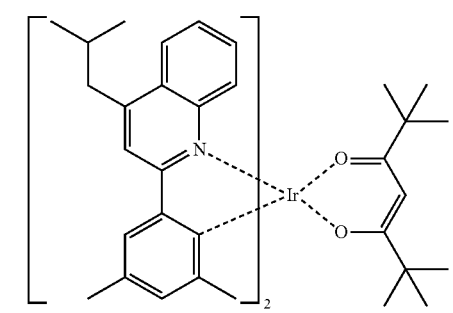

-continued
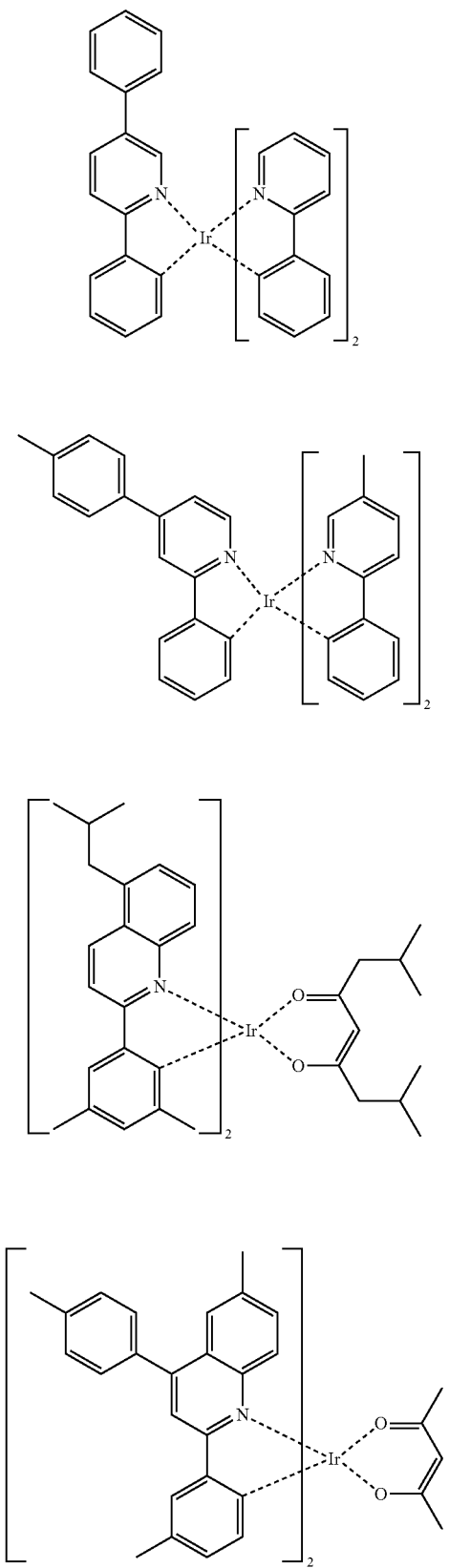
D-199
D-200
D-201
D-202
-continued
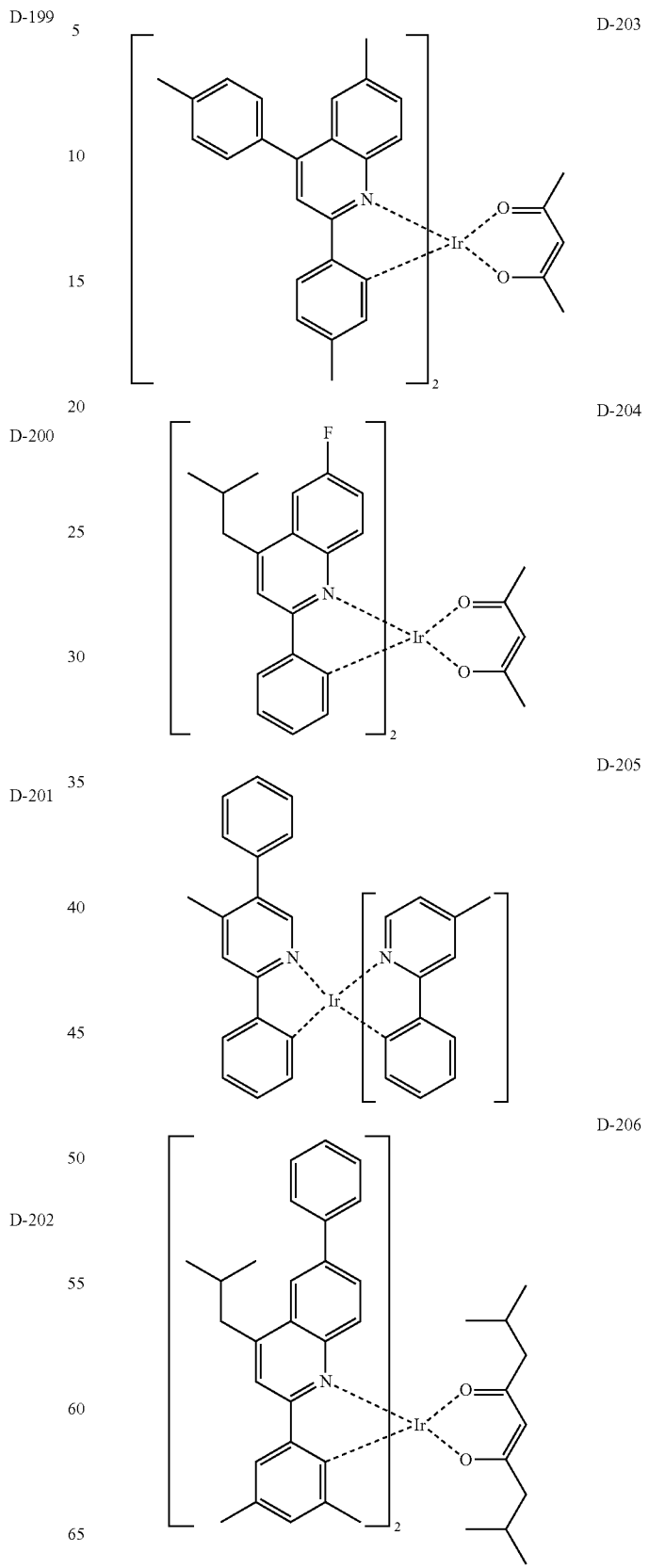
D-203
D-204
D-205
D-206

D-207
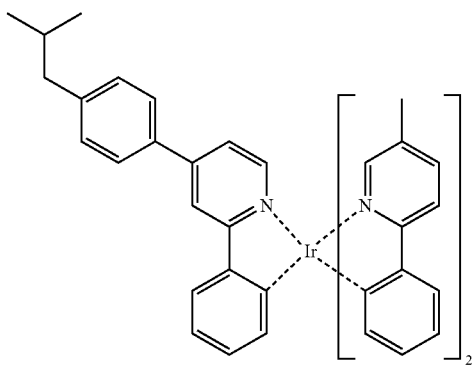

D-208
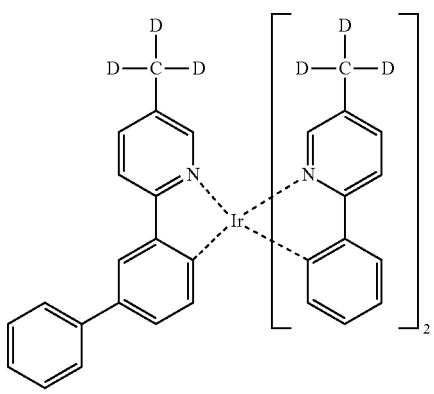

D-209
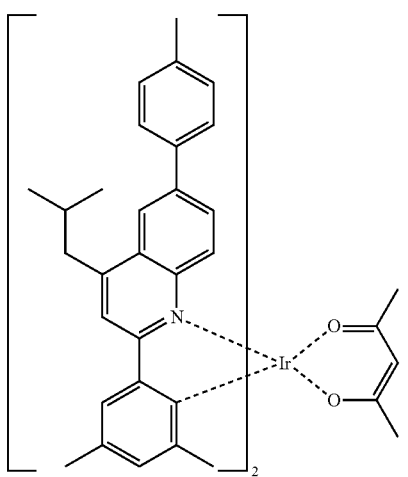

D-210
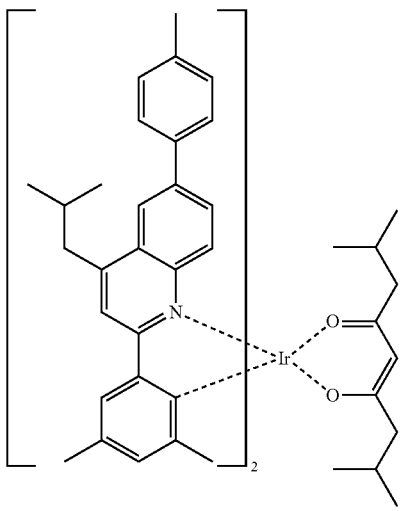

D-211

D-212
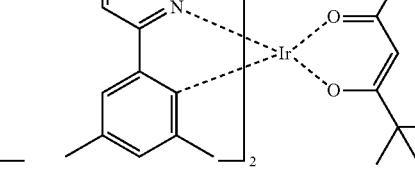

In the organic electroluminescent device of the present disclosure, the organic layer may further comprise at least one compound selected from the group consisting of arylamine-based compounds and styrylarylamine-based compounds.

In the organic electroluminescent device of the present disclosure, the organic layer may further comprise at least one metal selected from the group consisting of metals of Group 1, metals of Group 2, transition metals of the 4th period, transition metals of the 5th period, lanthanides and organic metals of the d-transition elements of the Periodic Table, or at least one complex compound comprising the metal.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x$ ($1 \leq X \leq 2$), $AlO_x$ ($1 \leq x \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In addition to the hole transport layer, a hole injection layer, an electron blocking layer, or a combination thereof may be disposed between the anode and the light-emitting layer. The hole injection layer may be composed of two or more layers in order to lower an energy barrier for injecting holes from the anode to a hole transport layer or an electron blocking layer (or a voltage for injecting a hole). Each of the layers may comprise two or more compounds. The electron blocking layer may be composed of two or more layers.

An electron buffering layer, a hole blocking layer, an electron transport layer, an electron injection layer, or a combination thereof may be disposed between the light-emitting layer and the cathode. The electron buffering layer may be composed of two or more layers in order to control the electron injection and improve characteristics of interface between the light-emitting layer and the electron injection layer. Each of the layers may comprise two or more compounds. The hole blocking layer or electron transport layer may be composed of two or more layers, and each of the layers may comprise two or more compounds.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as inkjet printing, nozzle printing, slot coating, spin coating, dip coating, and flow coating methods can be used. Where a layer is formed with the first host compound and the second host compound of the present disclosure, they may be co-evaporated or mixture-evaporated.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

In the organic electroluminescent device of the present disclosure, two or more host compounds for a light-emitting layer may be co-evaporated or mixture-evaporated. Herein, a co-evaporation indicates a process for two or more materials to be deposited as a mixture, by introducing each of the two or more materials into respective crucible cells, and applying electric current to the cells for each of the materials to be evaporated. Herein, a mixture-evaporation indicates a process for two or more materials to be deposited as a mixture, by mixing the two or more materials in one crucible cell before the deposition, and applying electric current to the cell for the mixture to be evaporated.

The organic electroluminescent device of the present disclosure can be used for the manufacture of a display system or a lighting system.

Hereinafter, the preparation method of the device comprising a host compound and a hole transport compound of the present disclosure, and the luminescent properties of the device will be explained in detail with reference to the following examples.

Device Examples 1-1 to 1-81 OLED Produced by an Evaporation of the Hole Transport Compound of the Present Disclosure and a Co-Evaporation of a First Host Compound and a Second Host Compound of the Present Disclosure An organic electroluminescent device (OLED) was produced using the light-emitting material of the present disclosure as follows. A transparent electrode indium tin oxide (ITO) thin film (10 Ω/sq) on a glass substrate for an OLED (Geomatec) was subjected to an ultrasonic washing with acetone, ethanol, and distilled water sequentially, and was then stored in isopropanol. The ITO substrate was then mounted on a substrate holder of a vacuum vapor depositing apparatus. N4,N4'-biphenyl-N4,N4'-bis(9-phenyl-9H-carbazol-3-yl)-[1,1'-biphenyl]-4,4'-diamine (HI-1) was introduced into a cell of the vacuum vapor depositing apparatus, and then the pressure in the chamber of the apparatus was controlled to $10^{-6}$ torr. Thereafter, an electric current was applied to the cell to evaporate HI-1, thereby forming a first hole injection layer having a thickness of 80 nm on the ITO substrate. 1,4,5,8,9,12-hexa-azatriphenylene-hexacarbonitrile (HI-2) was then introduced into another cell of the vacuum vapor depositing apparatus, and evaporated by applying electric current to the cell, thereby forming a second hole injection layer having a thickness of 3 nm on the first hole injection layer. N-([1,1'-biphenyl]-4-yl)-9,9-dimethyl-N-(4-(9-phenyl-9H-carbazol-3-yl)phenyl)-9H-fluoren-2-amine was introduced into one cell of the vacuum vapor depositing apparatus, and evaporated by applying electric current to the cell, thereby forming a first hole transport layer having a thickness of 10 nm on the second hole injection layer. A second hole transport compound shown in Table 1 below was then introduced into another cell of the vacuum vapor depositing apparatus, and evaporated by applying electric current to the cell, thereby forming a second hole transport layer having a thickness of 30 nm on the first hole transport layer. As a host material, H1-34 or H1-35, and H2-31 were introduced into two cells of the vacuum vapor depositing apparatus, respectively. A dopant compound D-25 was introduced into another cell. The two host compounds were evaporated at the same rate of 1:1, while the dopant was evaporated at a different rate from the host compounds, so that the dopant was deposited in a doping amount of 15 wt % based on the total amount of the host and dopant to form a light-emitting layer having a thickness of 40 nm on the hole transport layer. 2,4-bis(9,9-dimethyl-9H-fluoren-2-yl)-6-(naphthalen-2-yl)-1,3,5-triazine (ET-1) and lithuim quinolate (EI-1) were introduced into two cells of the vacuum vapor depositing apparatus, respectively, and evaporated at the rate of 4:6, thereby forming an electron transport layer having a thickness of 35 nm on the light-emitting layer. After depositing lithium quinolate (EI-1) as an electron injection layer having a thickness of 2 nm on the electron transport layer, an Al cathode having a thickness of 80 nm was then deposited by another vacuum vapor deposition apparatus on the electron injection layer.

HI-1

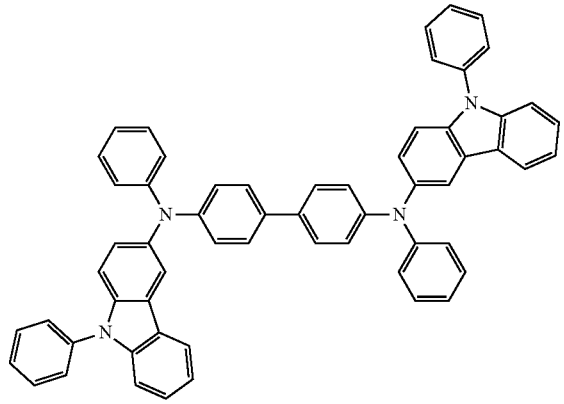

HI-2

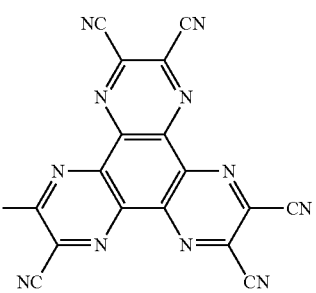

ET-1

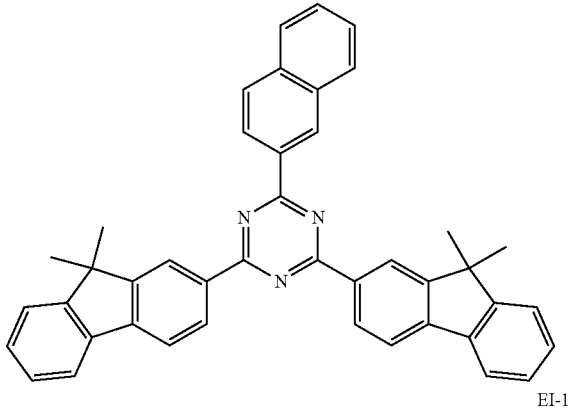

EI-1

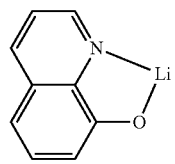

Comparative Examples 1-1 and 1-21 OLED Using HTL-A as a Second Hole Transport Compound OLEDs were produced in the same manner as in Device Examples 1-1 to 1-8, except that
HTL-A shown below was used as a second hole transport compound.

HTL-A

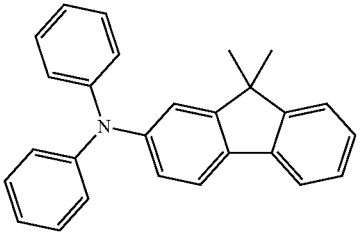

A luminous efficiency, CIE color coordinate, a driving voltage at 1,000 nit, and time taken to be reduced from 100% to 85% of the luminance at 15,000 nit and a constant current (T85 lifespan) of OLEDs produced above were measured. The luminous characteristics of the organic electroluminescent devices produced in Device Examples 1-1 to 1-8 and Comparative Examples 1-1 to 1-2 are shown in Table 1 below.

TABLE 1

| Device Example No. | The second hole transport layer | Host | Voltage [V] | Efficiency [cd/A] | Color coordinate (x, y) | T85 Lifespan [hr] |
|---|---|---|---|---|---|---|
| 1-1 | H4-11 | H1-34:H2-31 | 3.2 | 60.0 | 0.297, 0.658 | 250 |
| 1-2 | H4-49 | H1-34:H2-31 | 3.1 | 56.6 | 0.298, 0.658 | 230 |
| 1-3 | H4-56 | H1-35:H2-31 | 3.2 | 58.4 | 0.299, 0.659 | 220 |
| 1-4 | H4-1 | H1-35:H2-31 | 3.4 | 57.6 | 0.298, 0.658 | 220 |
| 1-5 | H4-76 | H1-35:H2-31 | 3.2 | 60.4 | 0.297, 0.659 | 240 |
| 1-6 | H4-17 | H1-35:H2-31 | 3.0 | 61.4 | 0.295, 0.660 | 260 |

TABLE 1-continued

| Device Example No. | The second hole transport layer | Host | Voltage [V] | Efficiency [cd/A] | Color coordinate (x, y) | T85 Lifespan [hr] |
|---|---|---|---|---|---|---|
| 1-7 | H4-9 | H1-35:H2-31 | 3.1 | 61.2 | 0.296, 0.660 | 240 |
| 1-8 | H4-23 | H1-35:H2-31 | 3.1 | 63.6 | 0.295, 0.660 | 230 |
| Comparative Example 1-1 | HTL-A | H1-34:H2-31 | 3.5 | 51.6 | 0.301, 0.660 | 40 |
| Comparative Example 1-2 | HTL-A | H1-35:H2-31 | 3.5 | 62.8 | 0.297, 0.657 | 50 |

As confirmed in the Device Examples, the organic electroluminescent device of the present disclosure has better lifespan than conventional devices by comprising a specific hole transport compound and a plurality of hosts.

The invention claimed is:

1. An organic electroluminescent device comprising an anode, a cathode, and an organic layer between the anode and the cathode, wherein the organic layer comprises one or more light-emitting layers and one or more hole transport layers; at least one of the one or more light-emitting layers comprises one or more dopant compounds and two or more host compounds; a first host compound of the two or more host compounds is represented by the following formula 1; a second host compound is represented by the following formula 2; and at least one of the one or more hole transport layers comprises the compound represented by the following formula 3:

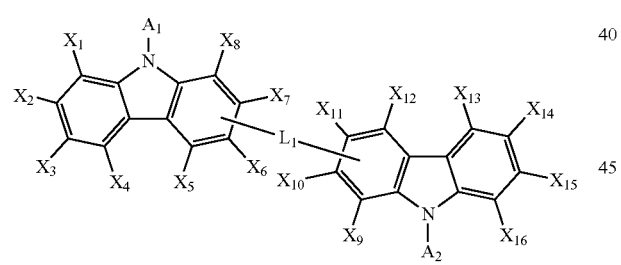

(1)

wherein $A_1$ and $A_2$, each independently, represent a deuterium-substituted or unsubstituted (C6-C18)aryl;

$L_1$ represents a single bond or a substituted or unsubstituted (C6-C30)arylene;

$X_1$ to $X_{16}$, each independently, represent hydrogen, deuterium, a substituted or unsubstituted (C1-C30)alkyl, a substituted or unsubstituted (C3-C30)cycloalkyl, a substituted or unsubstituted (C6-C60)aryl, a substituted or unsubstituted 3- to 30-membered heteroaryl containing at least one hetero atom selected from B, N, O, S, Si, and P, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted (C1-C30)alkyldi(C6-C30)arylsilyl;

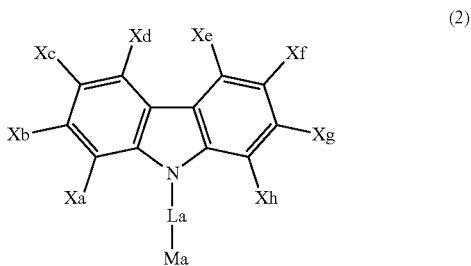

(2)

wherein

Ma represents a substituted or unsubstituted nitrogen-containing 5- to 11-membered heteroaryl;
La represents a substituted or unsubstituted (C6-C30) arylene;
Xa to Xh, each independently, represent hydrogen, deuterium, a cyano, a substituted or unsubstituted (C1-C30)alkyl, a substituted or unsubstituted (C2-C30) alkenyl, a substituted or unsubstituted (C2-C30) alkynyl, a substituted or unsubstituted (C3-C30) cycloalkyl, a substituted or unsubstituted (C6-C60)aryl, a substituted or unsubstituted 3- to 30-membered heteroaryl containing at least one heteroatom selected from O and S, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino; or may be linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur, with the proviso that at least one of Xa to Xh is not hydrogen;

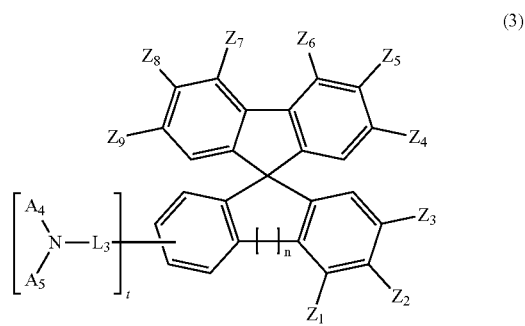

(3)

wherein
- $A_4$ and $A_5$, each independently, represent a substituted or unsubstituted (C6-C30)aryl;
- $L_3$ represents a single bond or a substituted or unsubstituted (C6-C30)arylene;
- $Z_1$ to $Z_9$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted mono- or di-(C6-C30)arylamino provided that at least one of $Z_1$ to $Z_9$ is linked to an adjacent substituent(s) to form a substituted or unsubstituted (C3-C30), mono- or polycyclic, alicyclic or aromatic ring, whose carbon atom(s) may be replaced with at least one hetero atom selected from nitrogen, oxygen, and sulfur;
- n represents an integer of 0;
- t represents an integer of 0, 1, or 2; and
- the heteroaryl contains at least one hetero atom selected from B, N, O, S, Si, and P.

2. The organic electroluminescent device according to claim 1, wherein in formula 1, $A_1$ and $A_2$, each independently, represent a deuterium-substituted or unsubstituted (C6-C18)aryl wherein the (C6-C18)aryl is selected from the group consisting of a phenyl, a biphenyl, a terphenyl, a naphthyl, a fluorenyl, a benzofluorenyl, a phenanthrenyl, a anthracenyl, a indenyl, a triphenylenyl, a pyrenyl, a tetracenyl, a perylenyl, a chrysenyl, a phenylnaphthyl, a naphthylphenyl, and a fluoranthenyl.

3. The organic electroluminescent device according to claim 1, wherein in formula 1, Li represents a single bond, or one selected from the following formulae 9 to 21

(9)
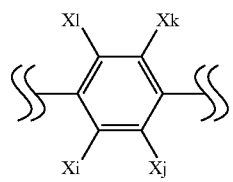

(10)
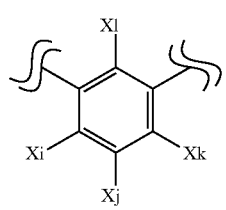

(11)
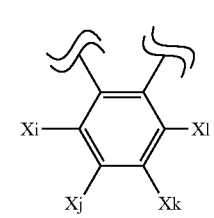

(12)
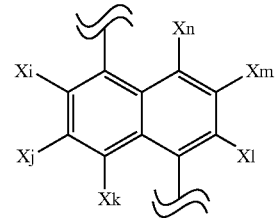

(13)
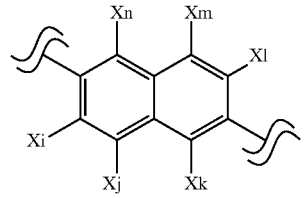

(14)
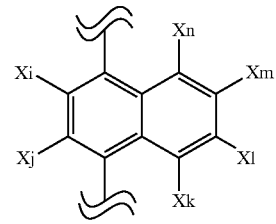

(15)
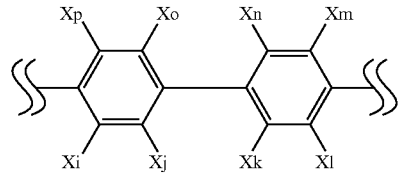

(16)
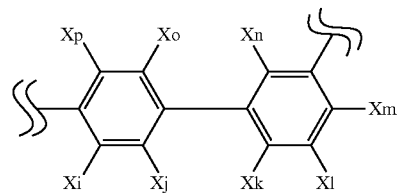

(17)
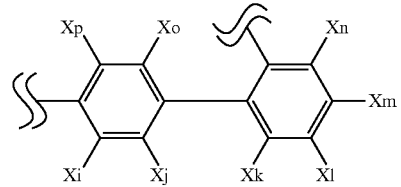

(18)
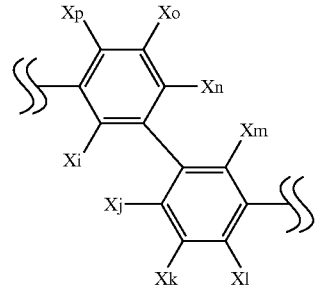

-continued

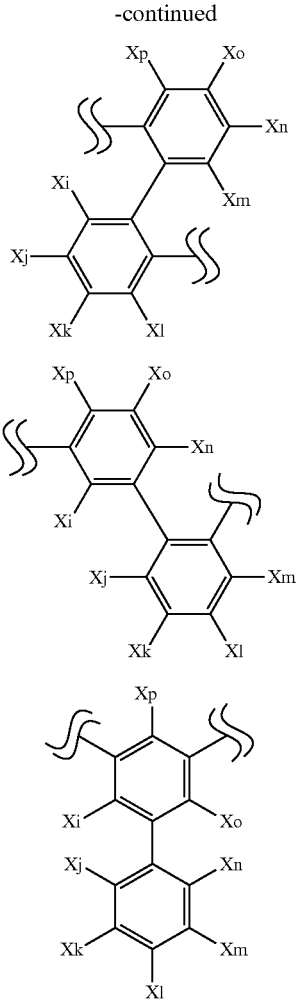

wherein
Xi to Xp, each independently, represent hydrogen, deuterium a substituted or unsubstituted (C3-C30)cycloalkyl, a substituted or unsubstituted (C6-C60)aryl, or a substituted or unsubstituted 3- to 30-membered heteroaryl; and  represents a bonding site.

4. The organic electroluminescent device according to claim 1, wherein in formula 2, Ma represents a substituted or unsubstituted monocyclic ring-type heteroaryl selected from the group consisting of a substituted or unsubstituted pyrrolyl, a substituted or unsubstituted imidazolyl, a substituted or unsubstituted pyrazolyl, a substituted or unsubstituted triazinyl, a substituted or unsubstituted tetrazinyl, a substituted or unsubstituted triazolyl, a substituted or unsubstituted tetrazolyl, a substituted or unsubstituted pyridyl, a substituted or unsubstituted pyrazinyl, a substituted or unsubstituted pyrimidinyl, and a substituted or unsubstituted pyridazinyl, or a substituted or unsubstituted fused ring-type heteroaryl selected from the group consisting of a substituted or unsubstituted benzimidazolyl, a substituted or unsubstituted isoindolyl, a substituted or unsubstituted indolyl, a substituted or unsubstituted indazolyl, a substituted or unsubstituted benzothiadiazolyl, a substituted or unsubstituted quinolyl, a substituted or unsubstituted isoquinolyl, a substituted or unsubstituted cinnolinyl, a substituted or unsubstituted quinazolinyl, a substituted or unsubstituted naphthyridinyl, and a substituted or unsubstituted quinoxalinyl.

5. The organic electroluminescent device according to claim 1, wherein in formula 2, La represents a single bond, or one selected from the following formulae 9 to 21

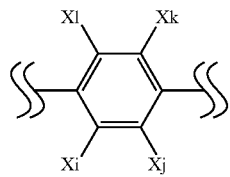

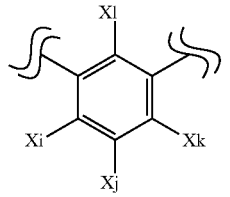

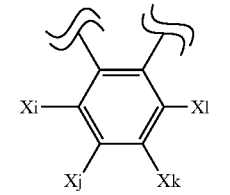

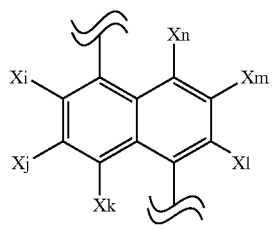

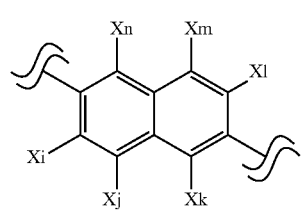

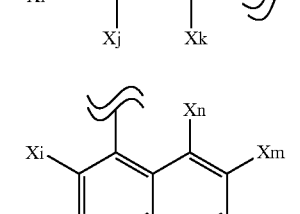

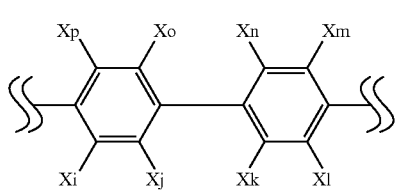

447
-continued

(16)
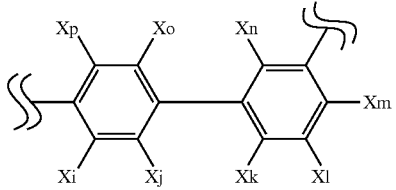

(17)
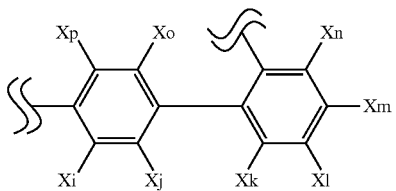

(18)
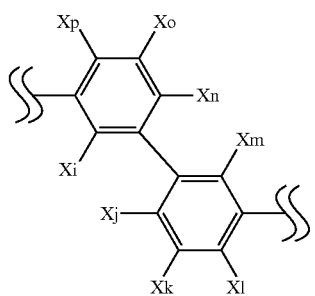

(19)
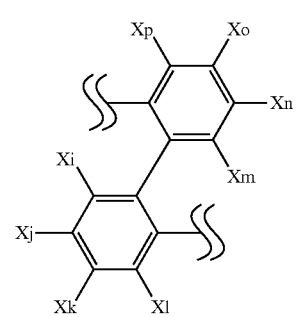

(20)
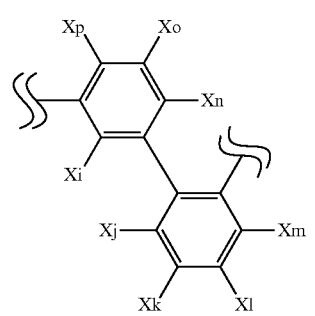

448
-continued

(21)
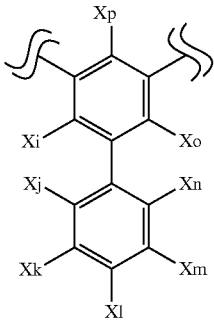

Wherein

Xi to Xp, each independently, represent hydrogen, deuterium, a substituted or unsubstituted (C1-C30)alkyl, a substituted or unsubstituted (C3-C30)cycloalkyl, a substituted or unsubstituted (C6-C60)aryl, or a substituted or unsubstituted 3- to 30-membered heteroaryl; and sulfur; and ⟩⟩ represents a bonding site.

6. The organic electroluminescent device according to claim 1, wherein in formula 2, Xa to Xh, each independently, represent hydrogen, a cyano, a (C6-C15)aryl unsubstituted or substituted with a tri(C6-C10)arylsilyl, or a 10- to 20-membered heteroaryl containing at least one heteroatom selected from O and S unsubstituted or substituted with a (C6-C12)aryl; or may be linked to an adjacent substituent(s) to form a substituted or unsubstituted benzene, a substituted or unsubstituted indole, a substituted or unsubstituted benzindole, a substituted or unsubstituted indene, a substituted or unsubstituted benzofuran, or a substituted or unsubstituted benzothiophene, with the proviso that at least one of Xa to Xh is not hydrogen.

7. The organic electroluminescent device according to claim 1, wherein in formula 3, $A_4$ and $A_5$, each independently, represent a substituted or unsubstituted (C6-C30)aryl; $L_3$ represents a single bond or a substituted or unsubstituted (C6-C18)arylene; $Z_1$ to $Z_9$, each independently, represent hydrogen, deuterium, a halogen, a cyano, a substituted or unsubstituted (C1-C30)alkyl, a substituted or unsubstituted (C6-C30)aryl, or a substituted or unsubstituted 6- to 30-membered heteroaryl, provided that one to three pairs selected from $Z_1$ and $Z_2$, $Z_2$ and $Z_3$, $Z_4$ and $Z_5$, $Z_5$ and $Z_6$, $Z_7$ and $Z_8$, and $Z_8$ and $Z_9$, as a pair of adjacent substituents, may form a substituted or unsubstituted (C3-C30), mono- or polycyclic aromatic ring, whose carbon atom(s) may be replaced with one to three hetero atoms selected from nitrogen, oxygen, and sulfur; n represents an integer of 0 or 1; and t represents an integer of 1 or 2.

8. The organic electroluminescent device according to claim 1, wherein in formula 3, $A_4$ and $A_5$, each independently, is selected from the group consisting of a substituted or unsubstituted phenyl, a substituted or unsubstituted biphenyl, a substituted or unsubstituted terphenyl, a substituted or unsubstituted naphthyl, a substituted or unsubstituted phenanthrenyl, a substituted or unsubstituted anthracenyl, a substituted or unsubstituted pyrenyl, a substituted or unsubstituted tetracenyl, a substituted or unsubstituted chrysenyl, a substituted or unsubstituted fluorenyl, a substituted or unsubstituted benzofluorenyl, a substituted or unsubstituted fluoranthenyl, a substituted or unsubstituted triphenylenyl, and a substituted or unsubstituted spirobifluorenyl; and t represents an integer of 1 or 2.

9. The organic electroluminescent device according to claim 1, wherein the compound of formula 1 is selected from the group consisting of:
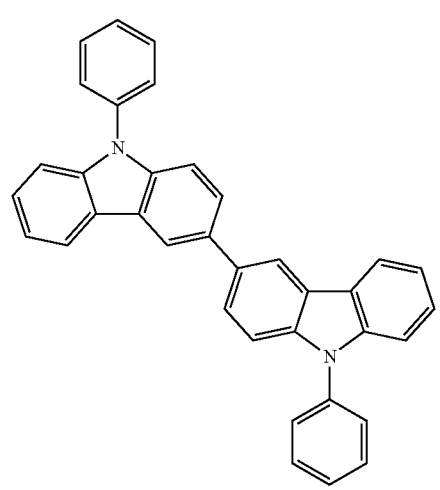
H1-1
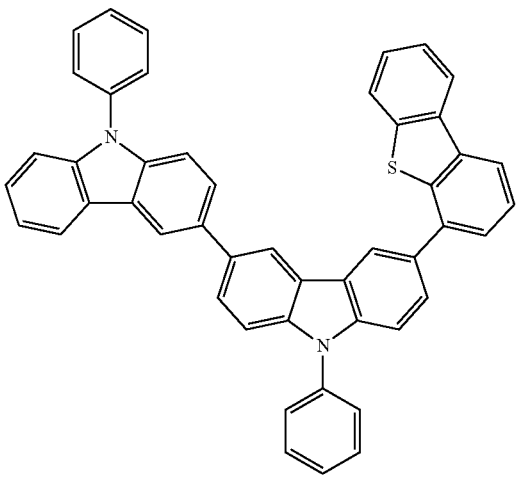
H1-2
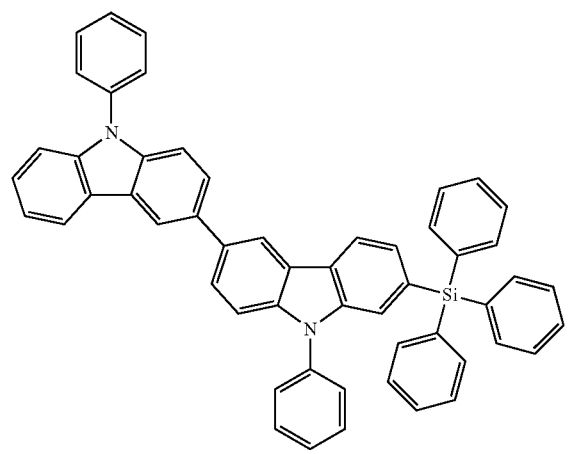
H1-5
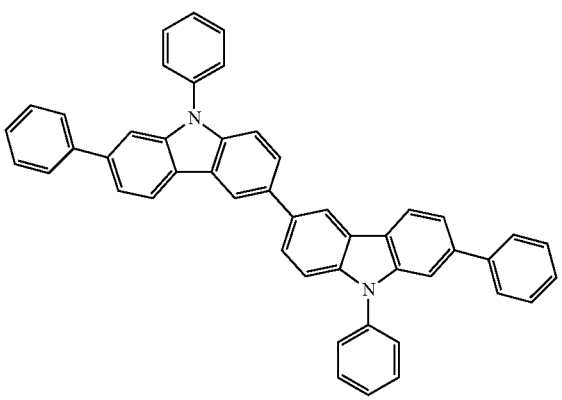
H1-7
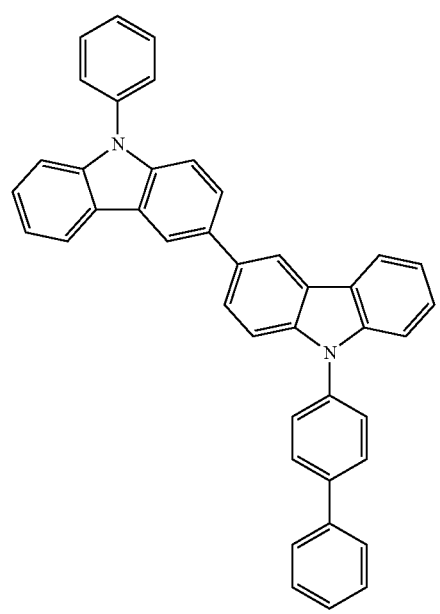
H1-8
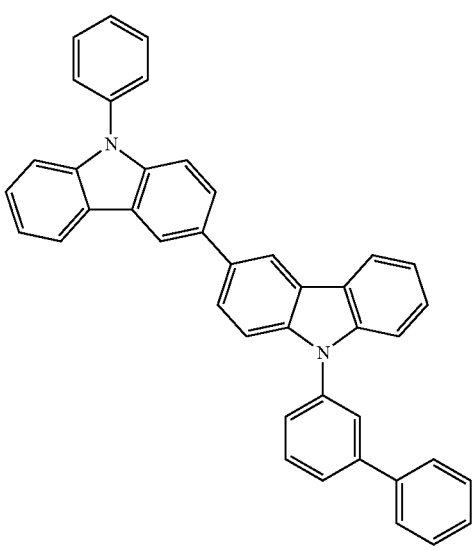
H1-9

-continued
H1-10
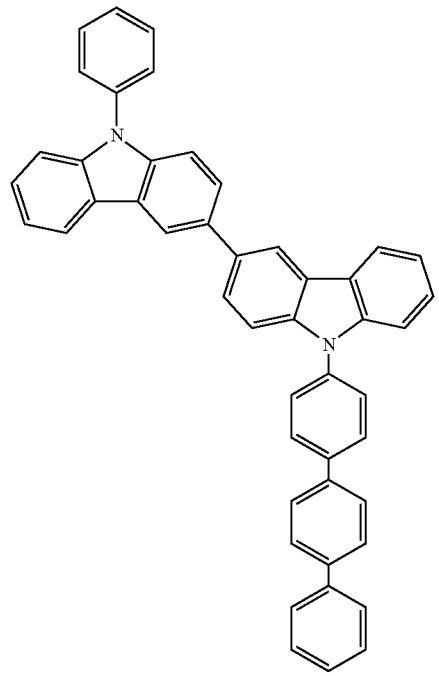
H1-11
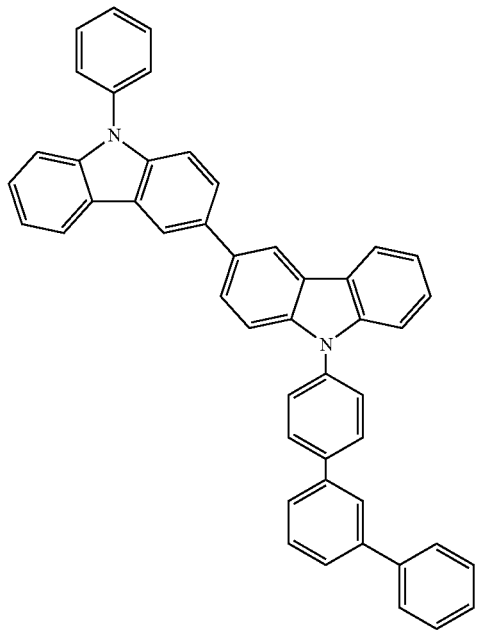
H1-12
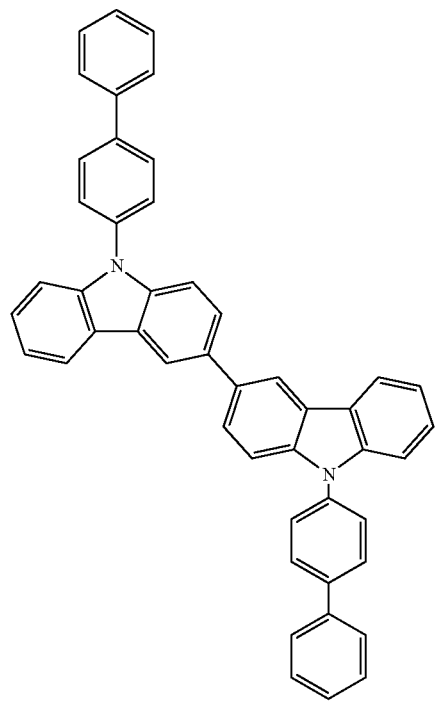
H1-13
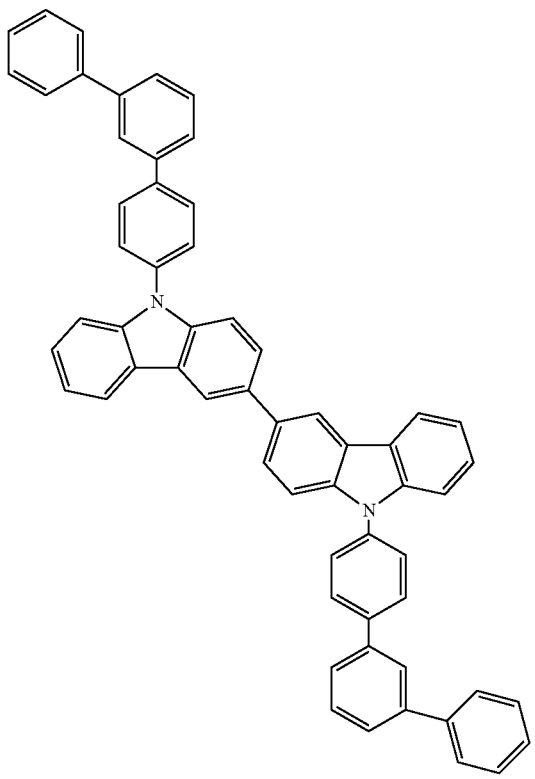

-continued
H1-14
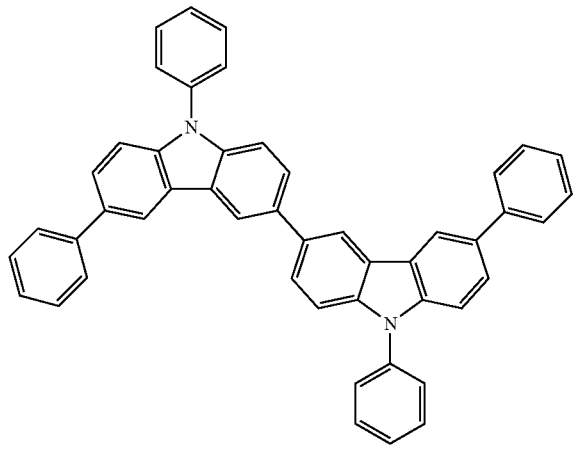
H1-15
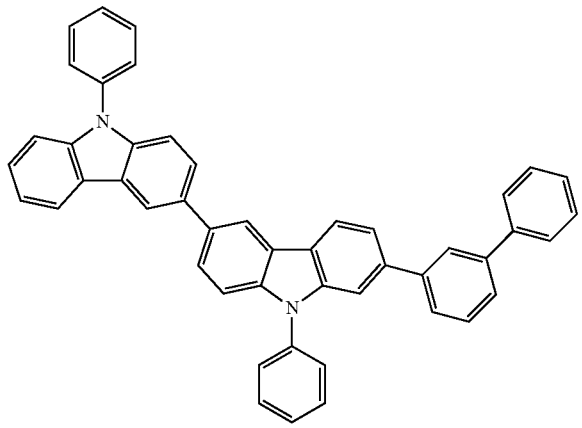
H1-16
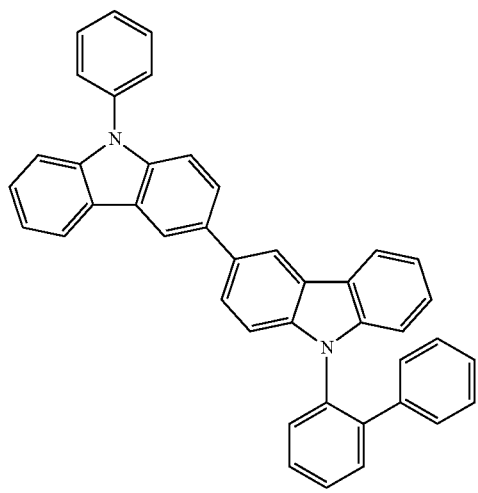
H1-17
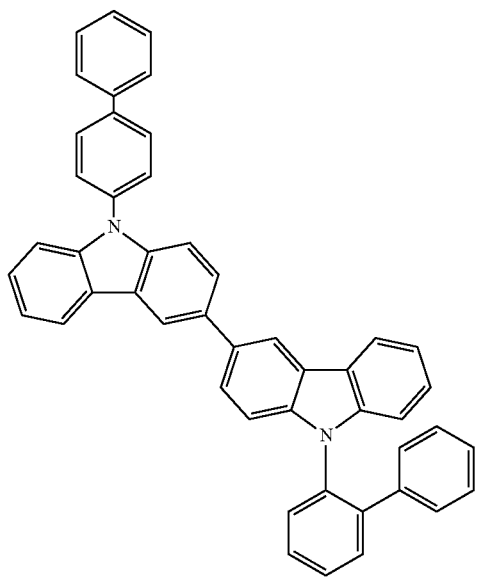
H1-18
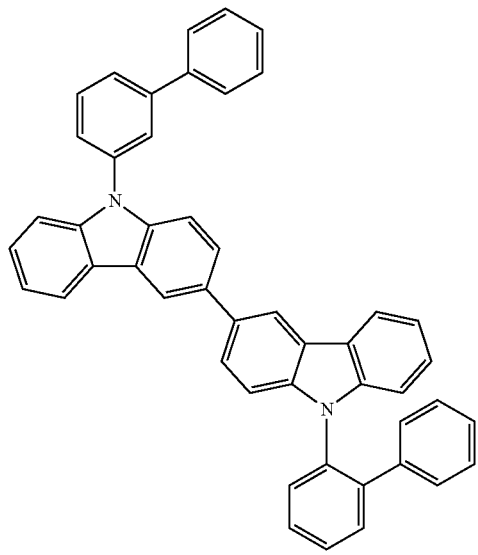
H1-19
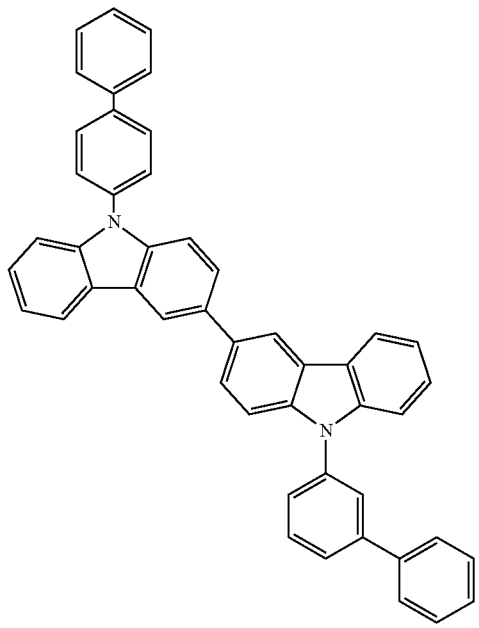

-continued
H1-20
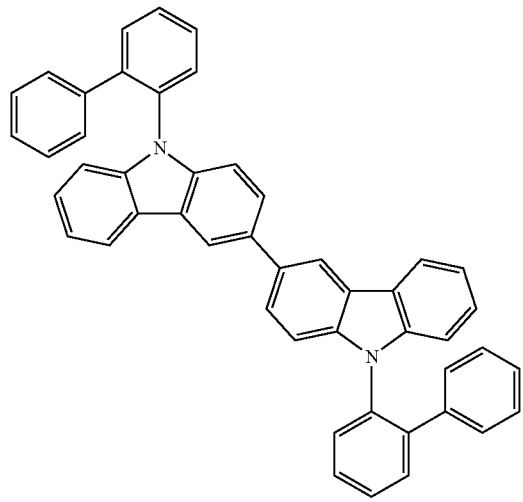
H1-21
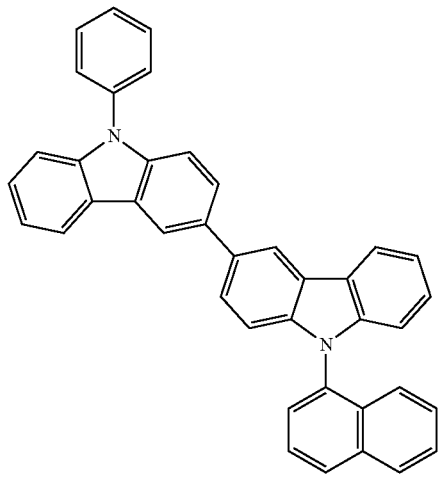
H1-22
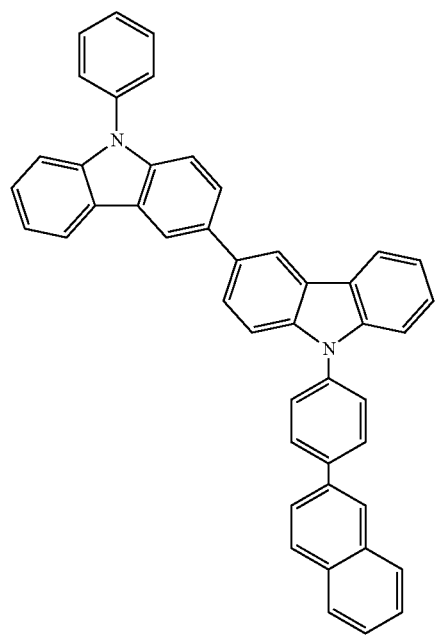
H1-24
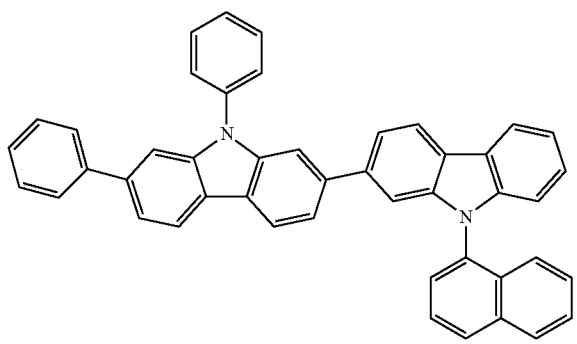

-continued
H1-25
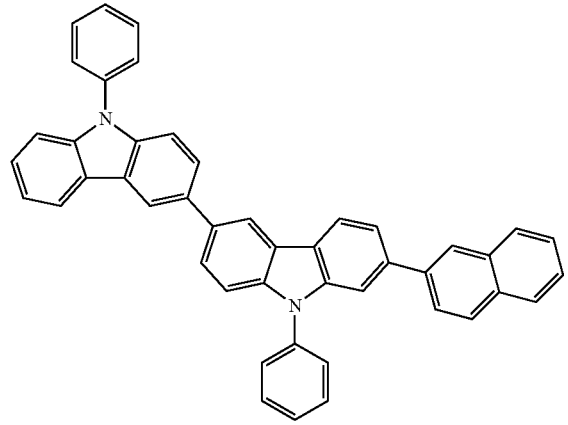
H1-26
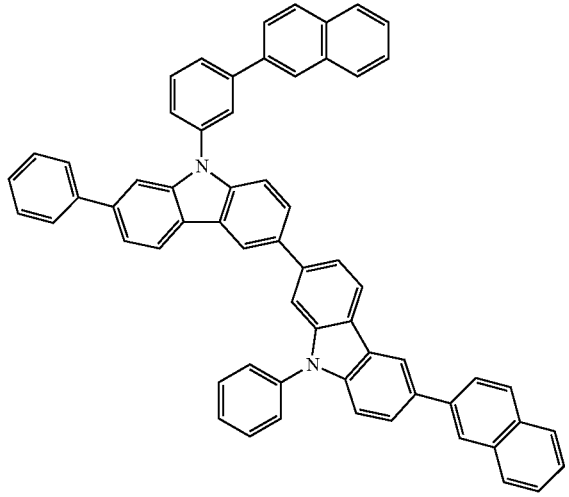
H1-27
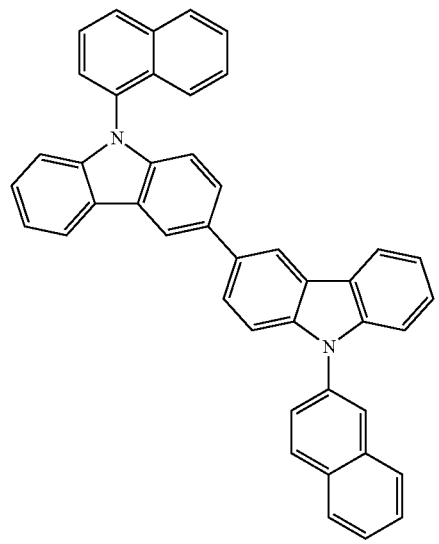
H1-28
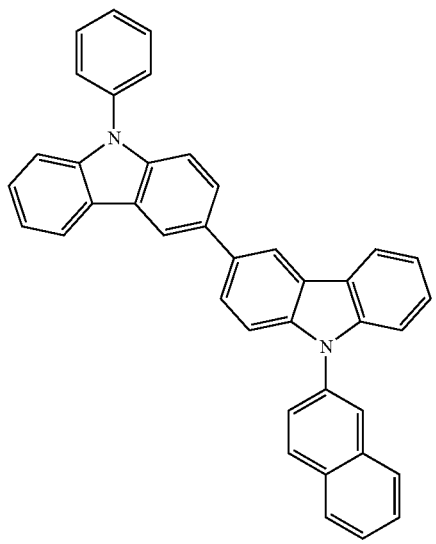

H1-29
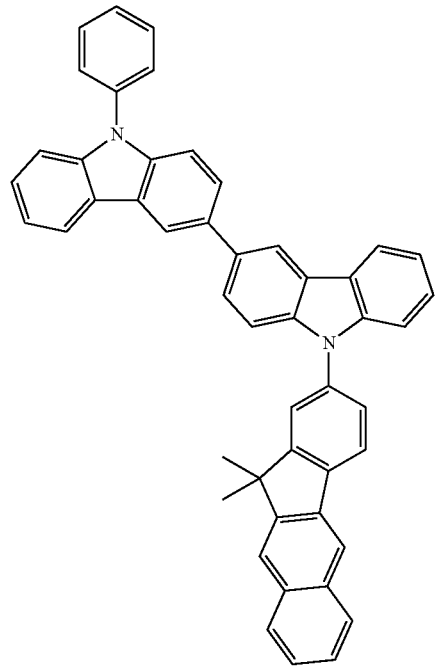
H1-30
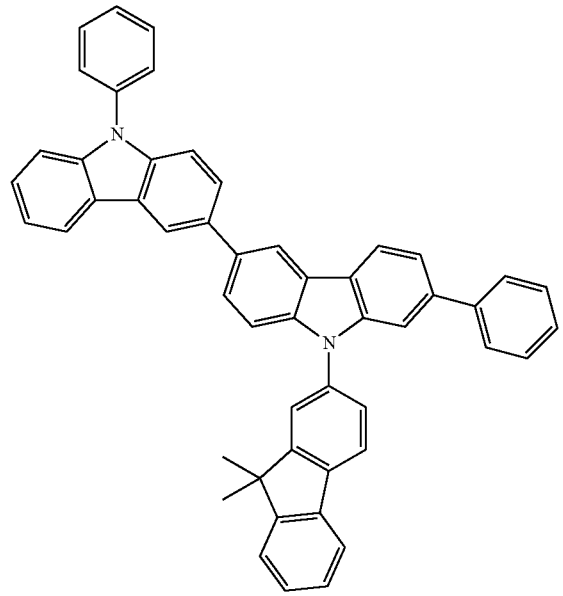
H1-31
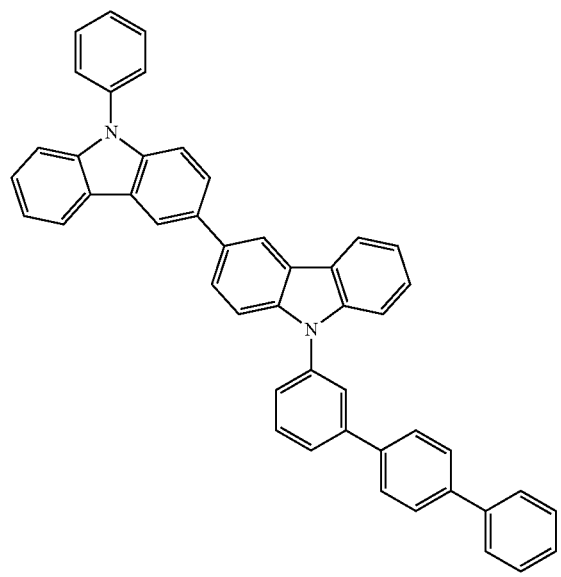
H1-32
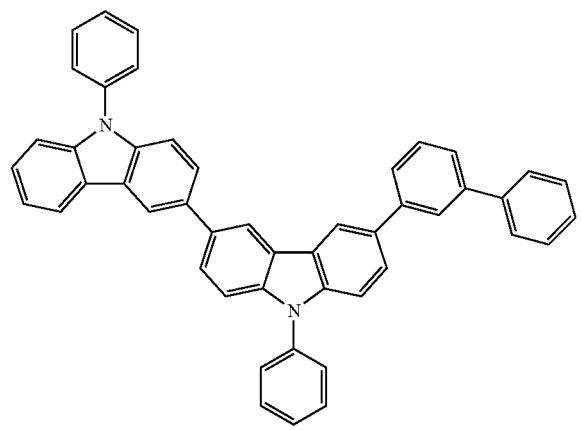

H1-33
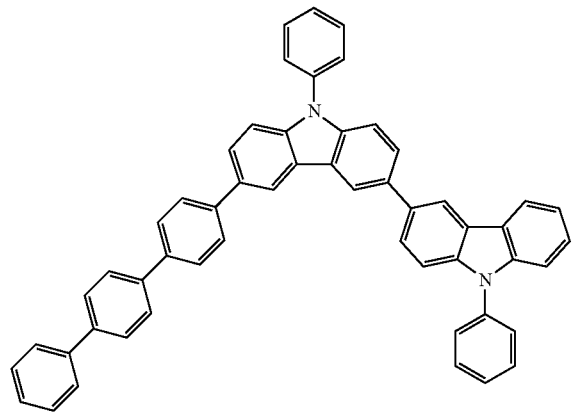
H1-34
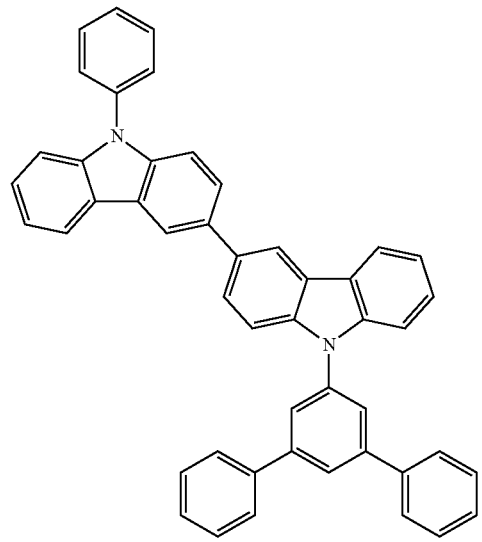
H1-35
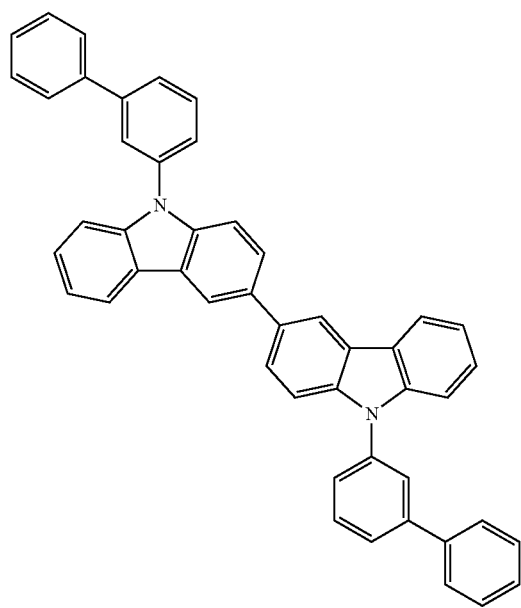
H1-36
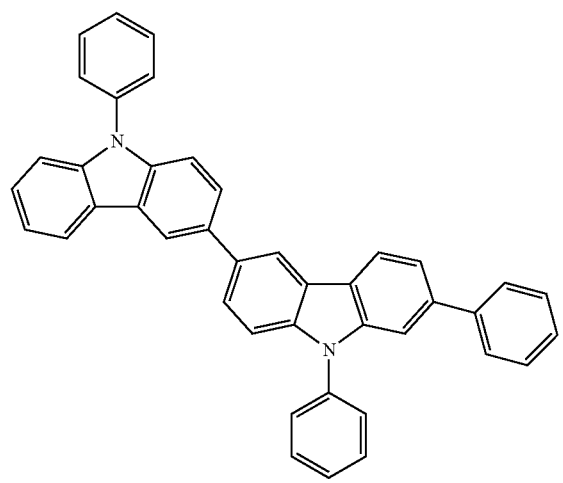

H1-37
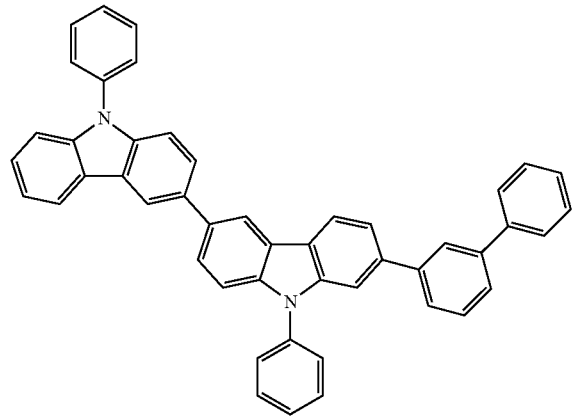
H1-38
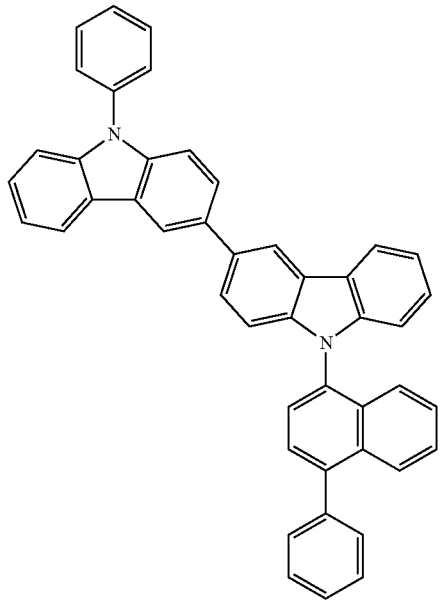
H1-39
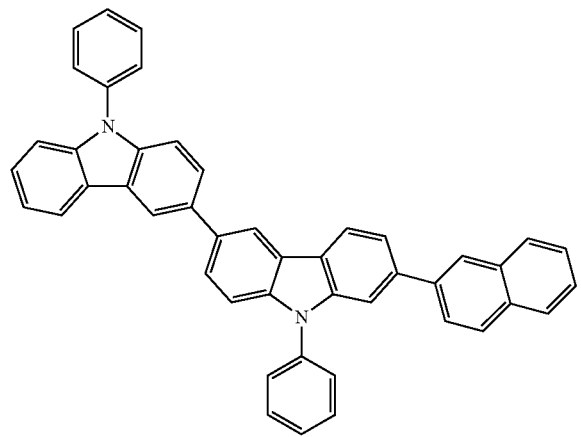
H1-40
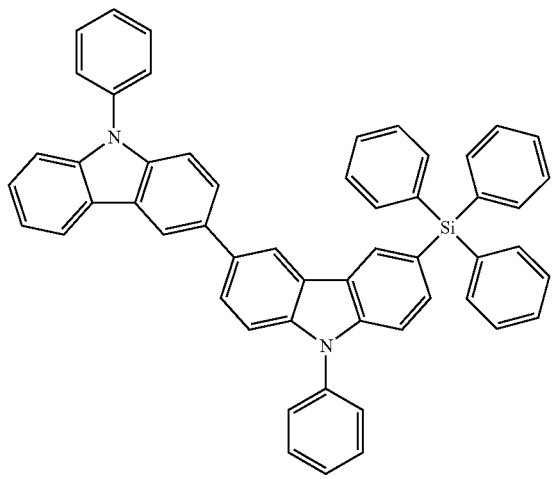

-continued
H1-41 H1-42
H1-43 H1-44
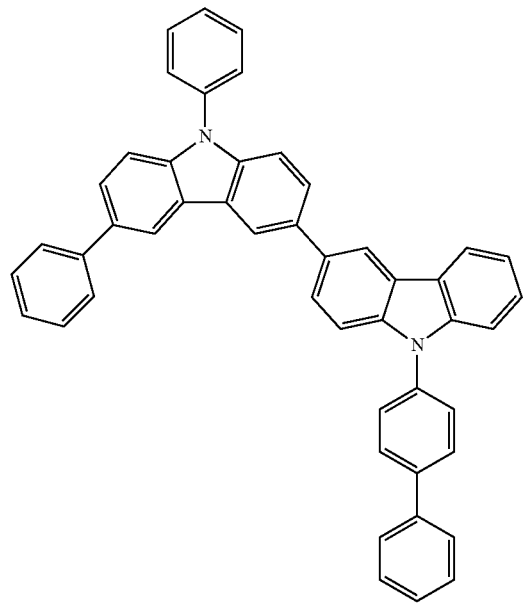

H1-45
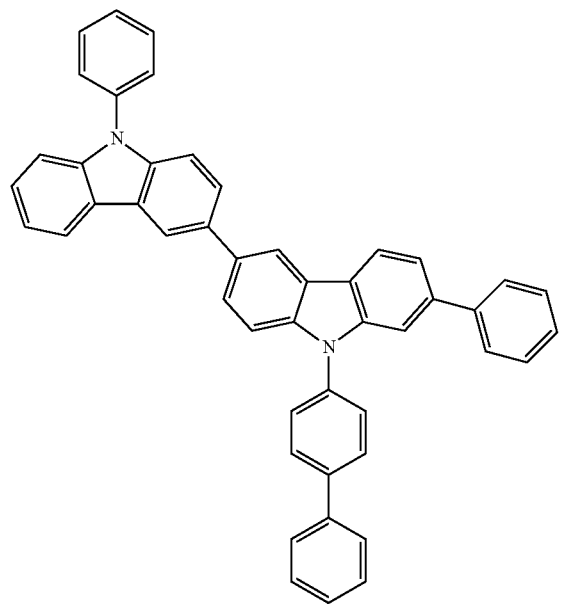
H1-46
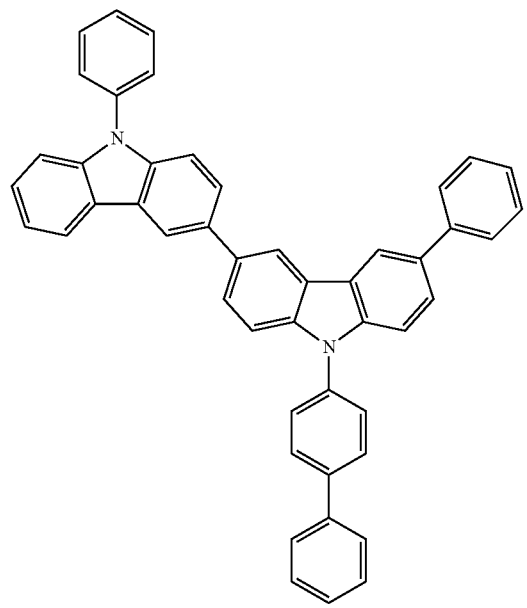
H1-47
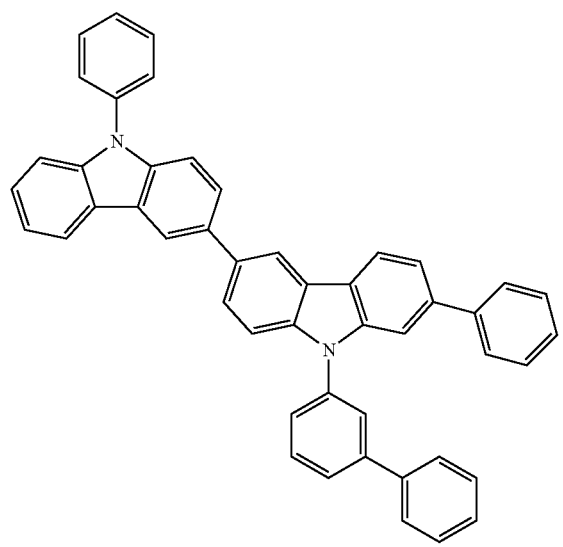
H1-48
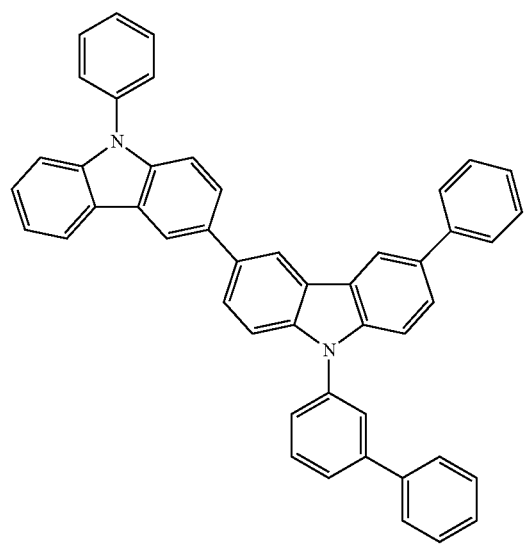

-continued
H1-50 H1-51
H1-52 H1-53
H1-54 H1-55
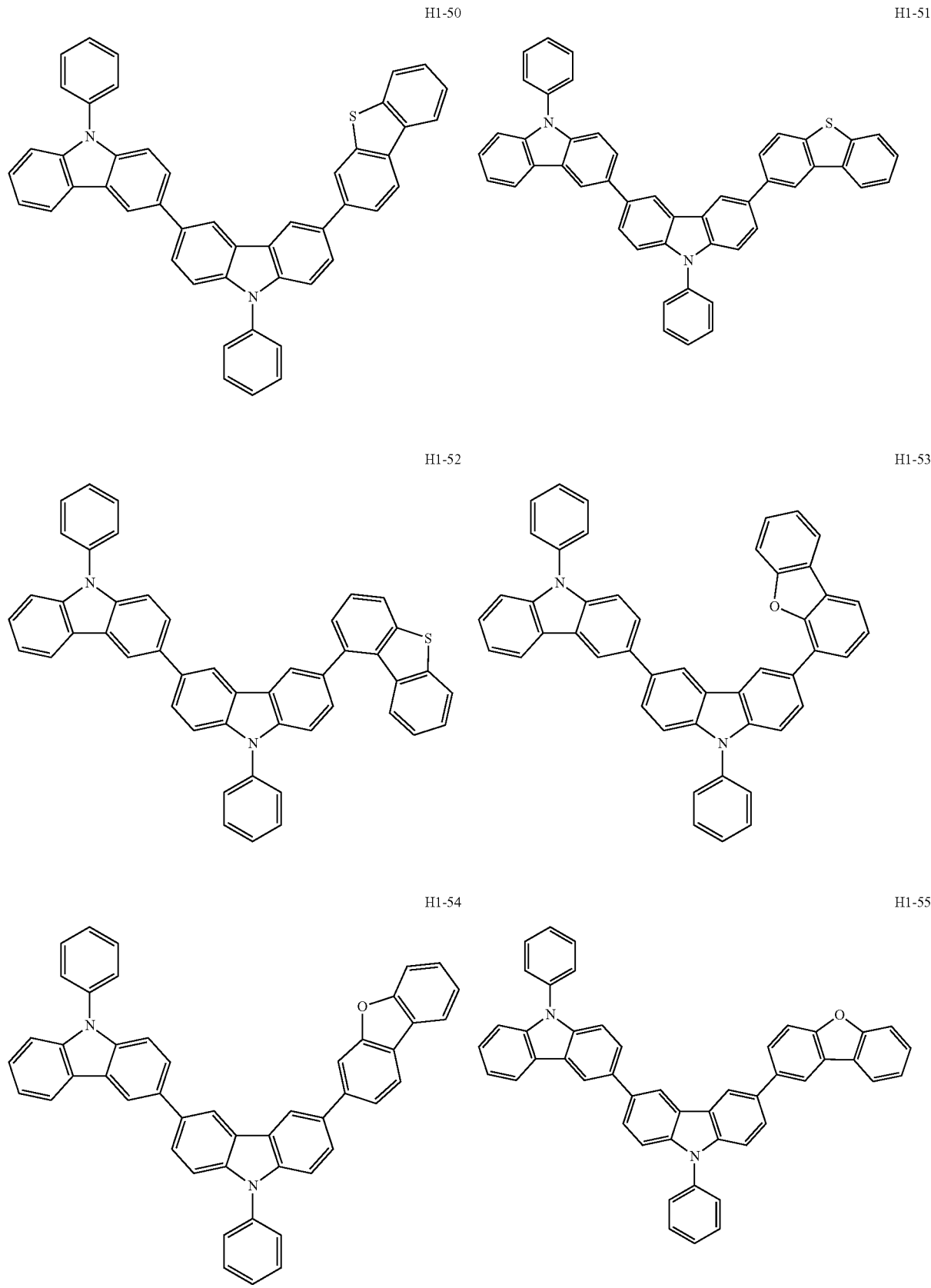

-continued
H1-56
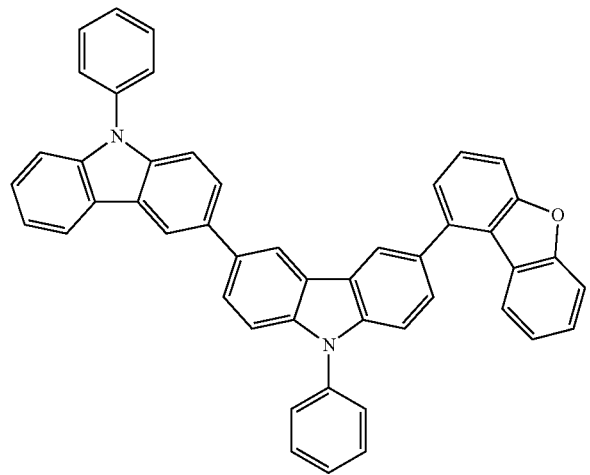
H1-57
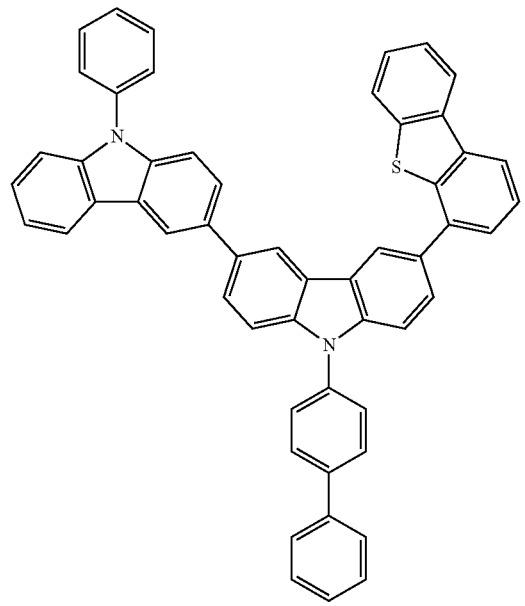
H1-58
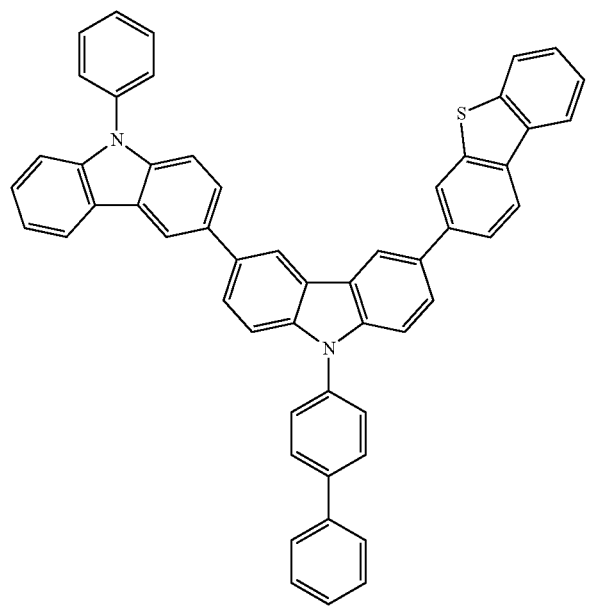
H1-59
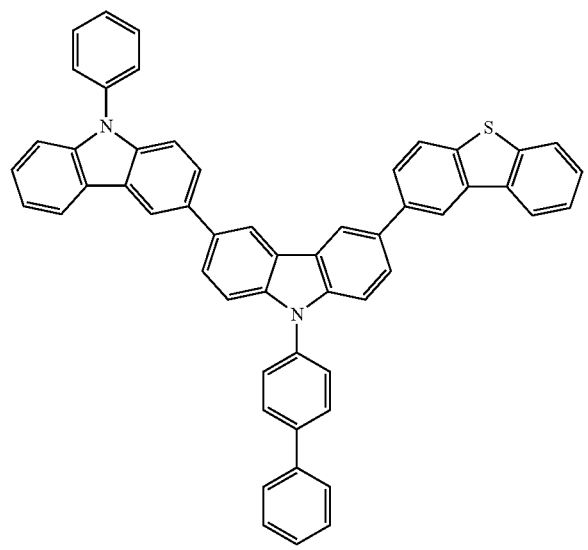

H1-60
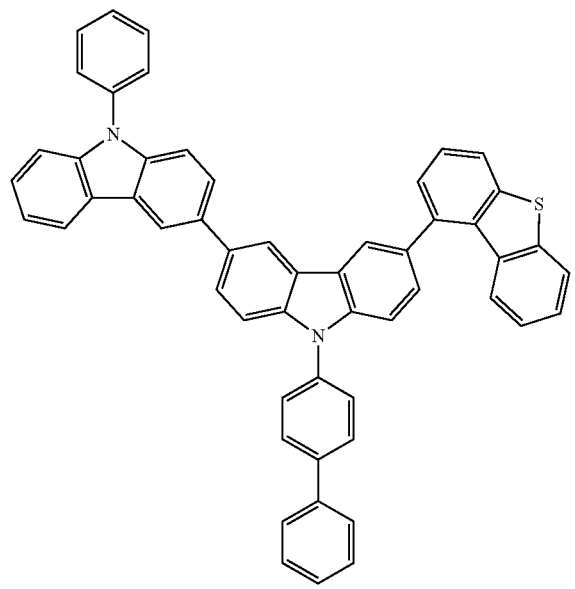
H1-61
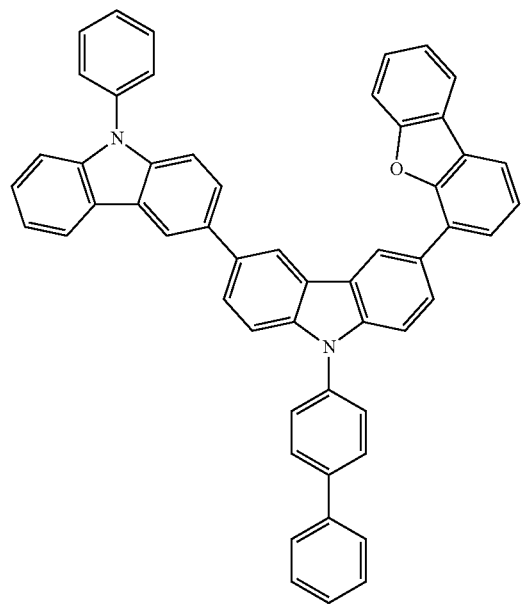
H1-62
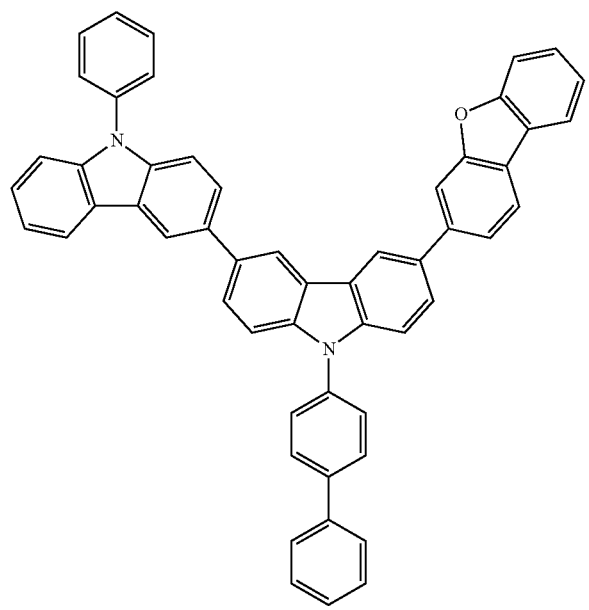
H1-63
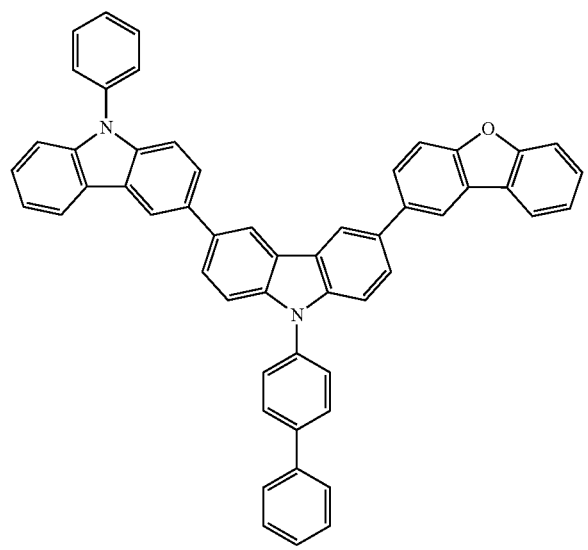

H1-64
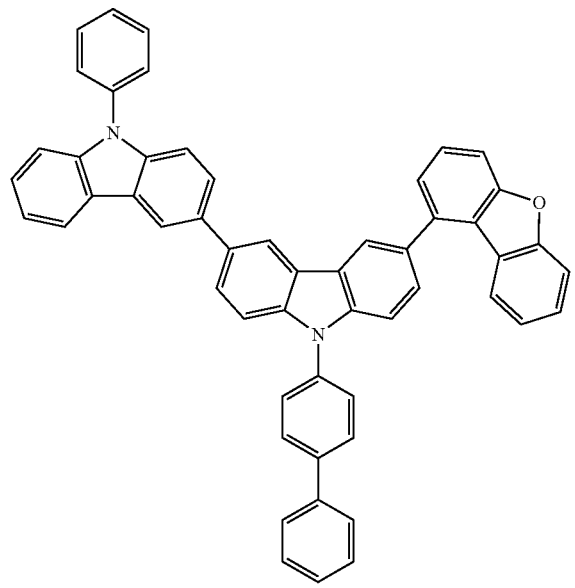
H1-65
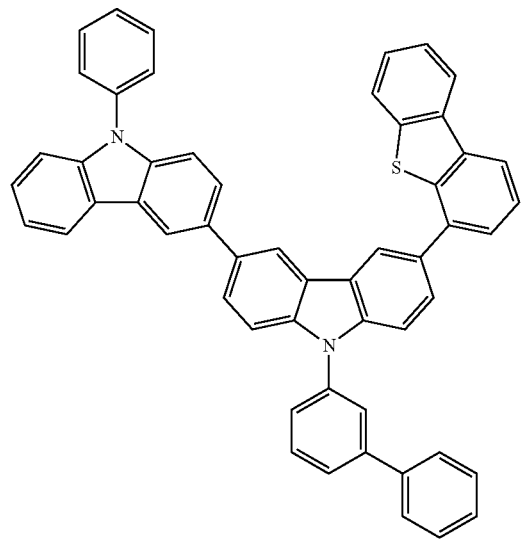
H1-66
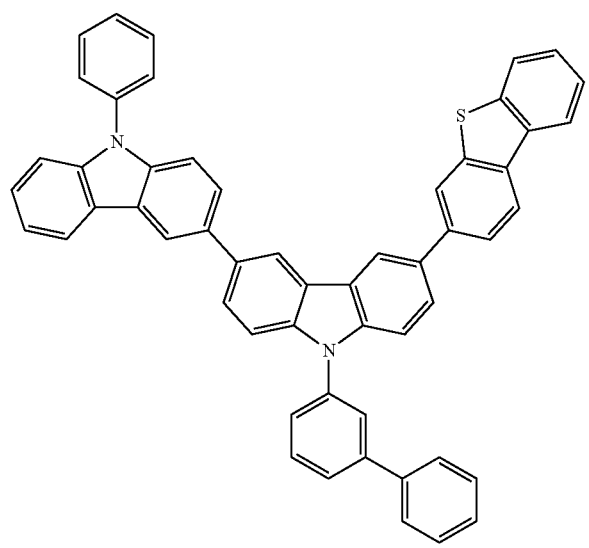
H1-67
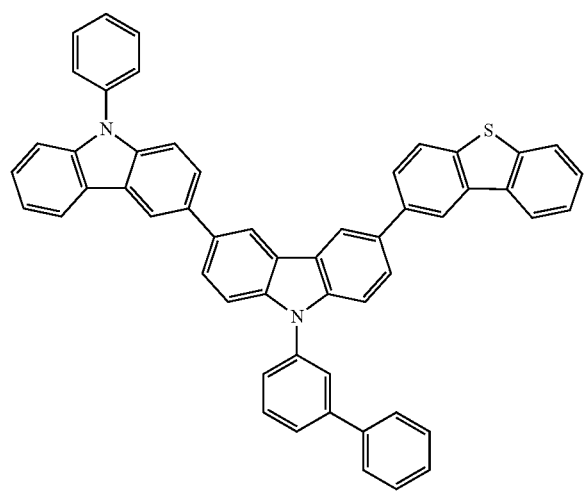

-continued
H1-68
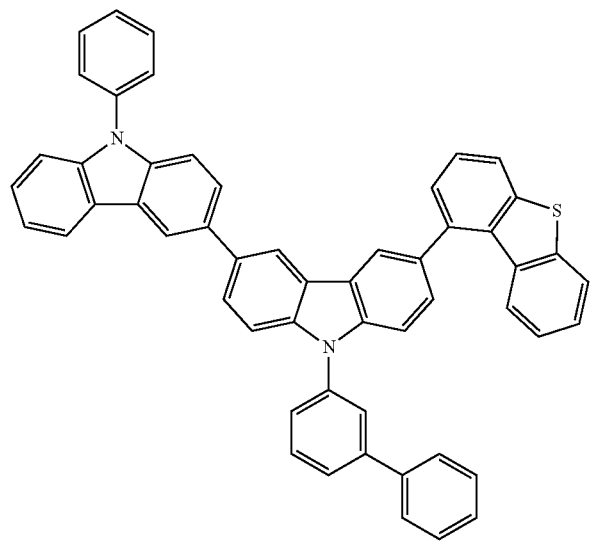
H1-69
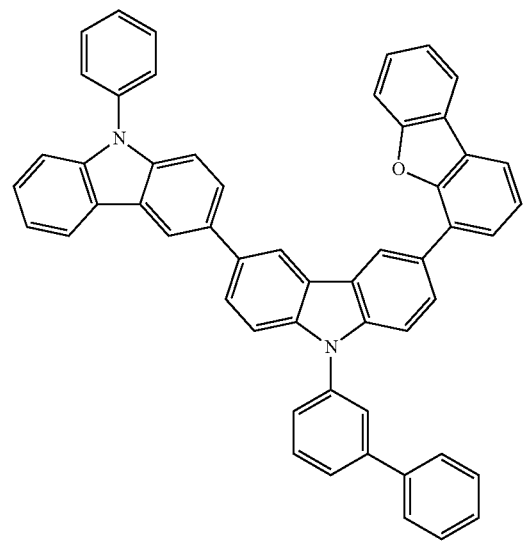
H1-70
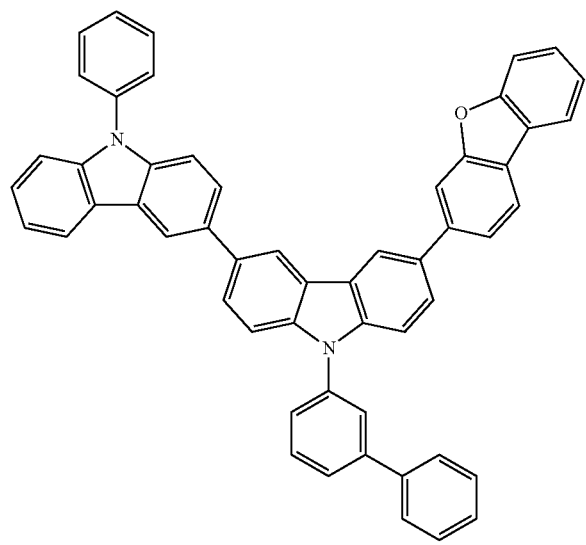
H1-71
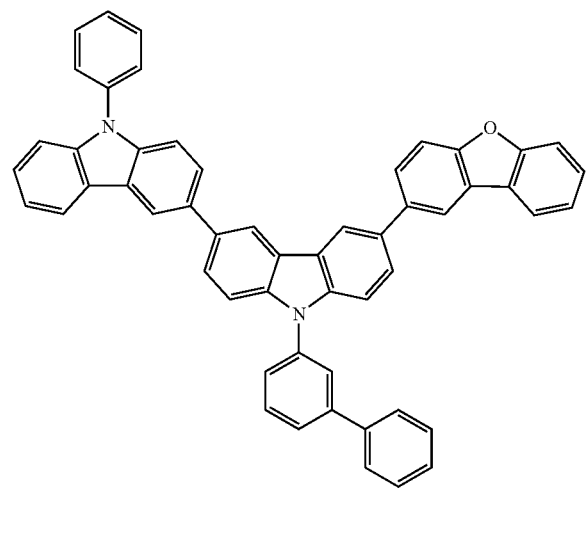

-continued
H1-72
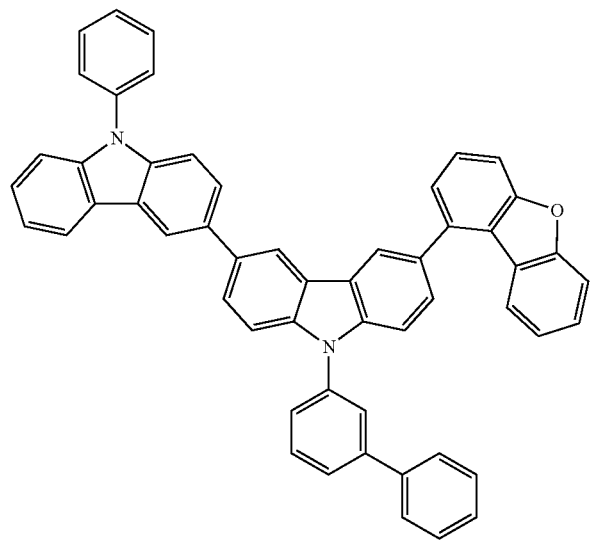
H1-73
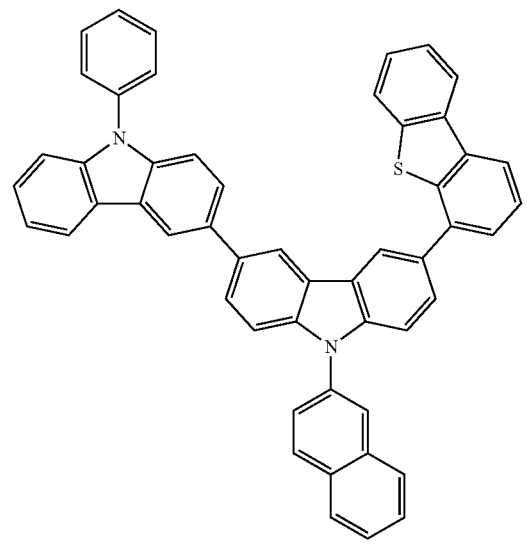
H1-74
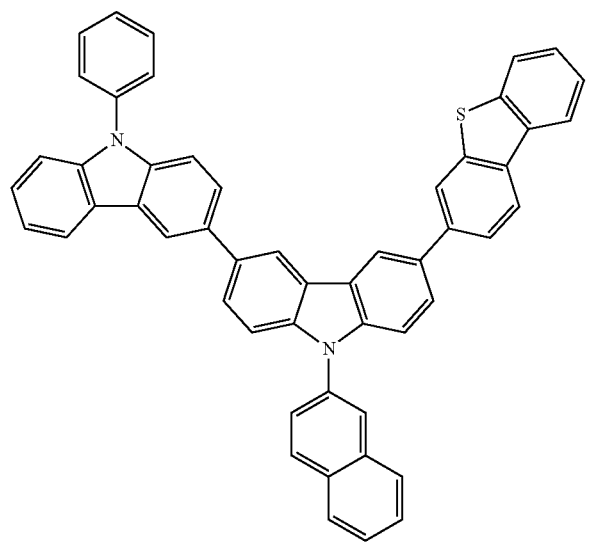
H1-75
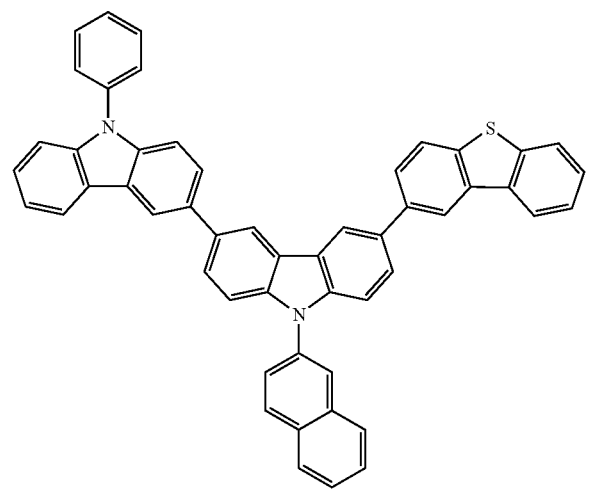

-continued
H1-76
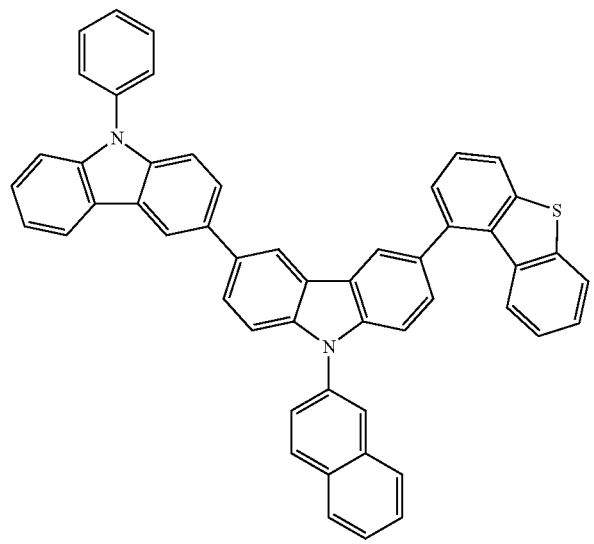
H1-77
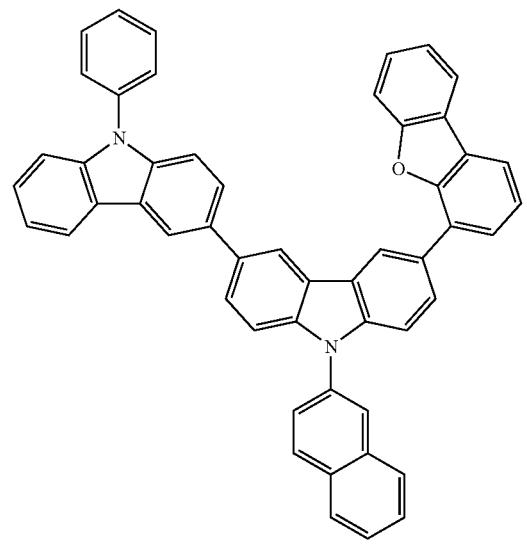
H1-78
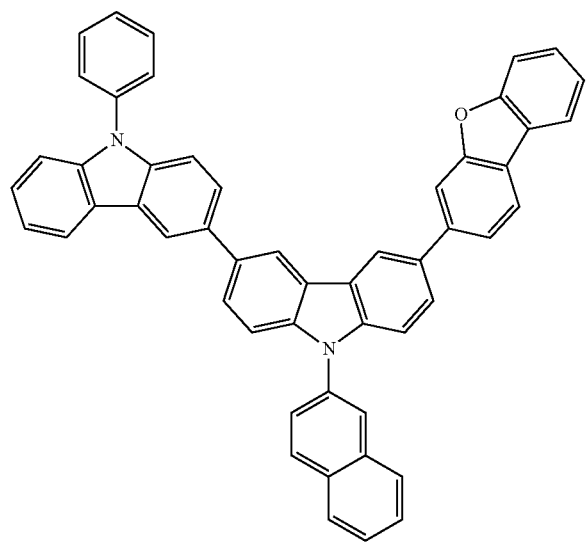
H1-79
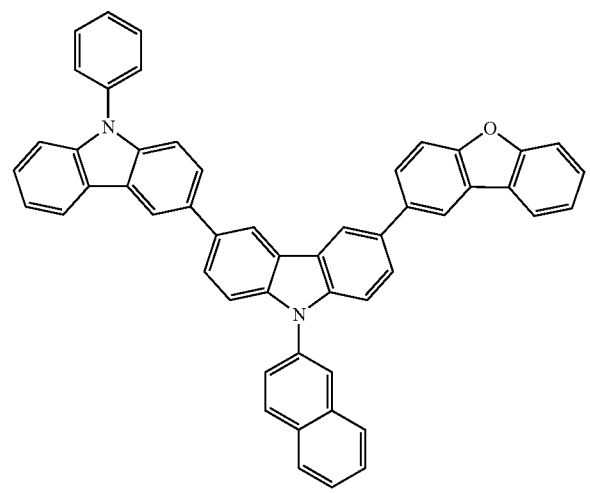

-continued
H1-80
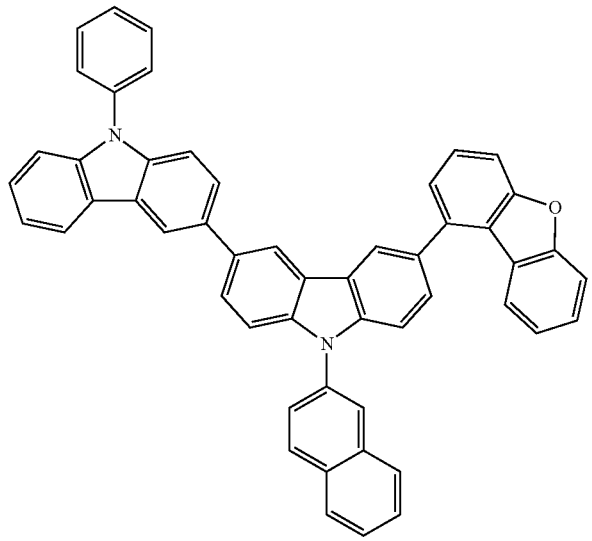
H1-81
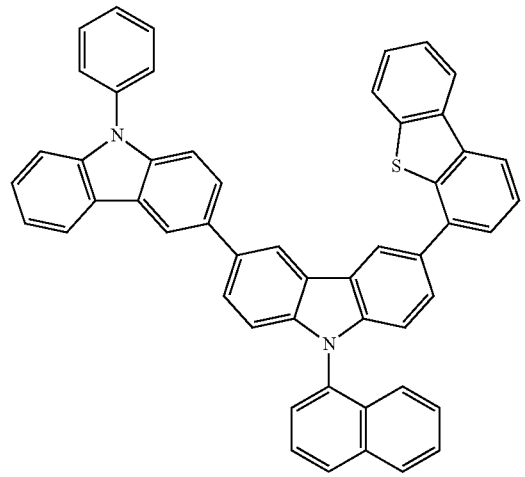
H1-82
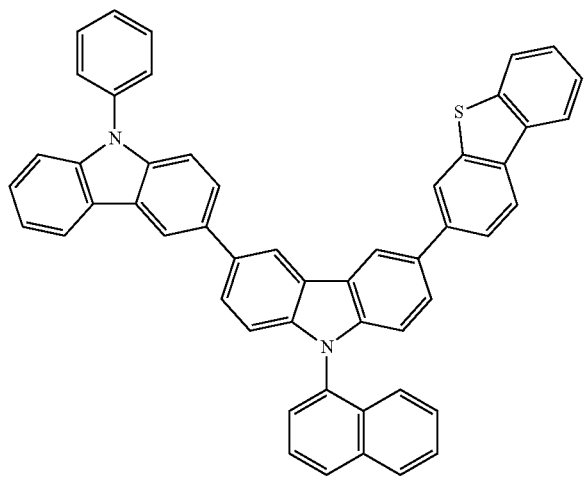
H1-83
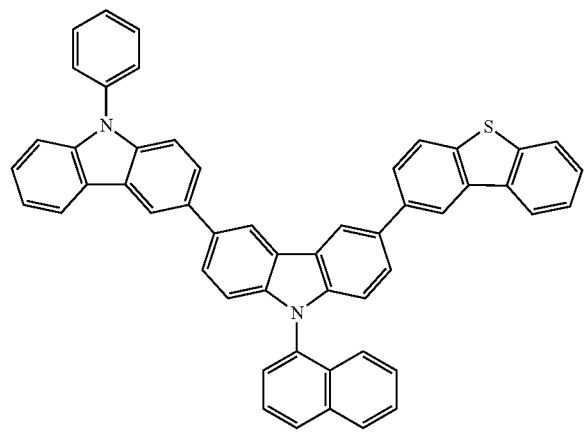
H1-84
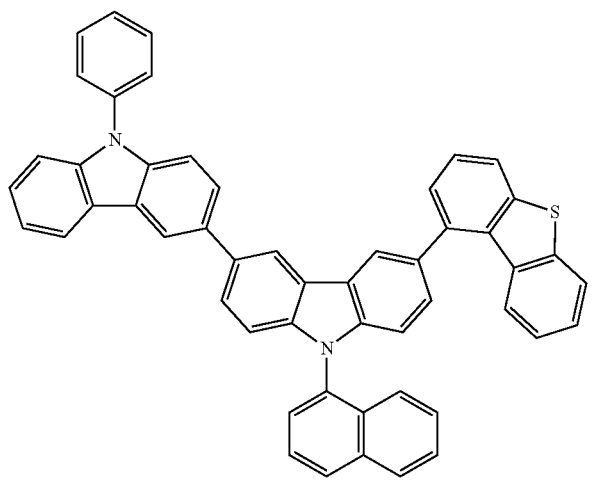
H1-85
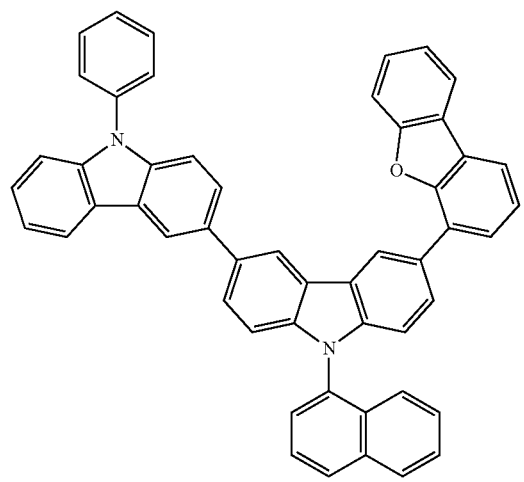

-continued
H1-86
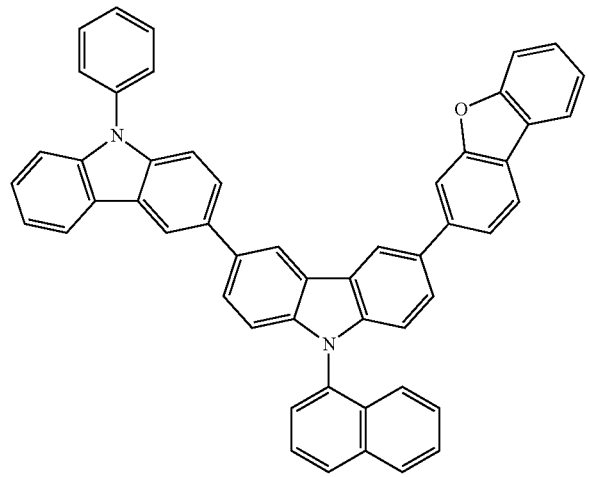
H1-87
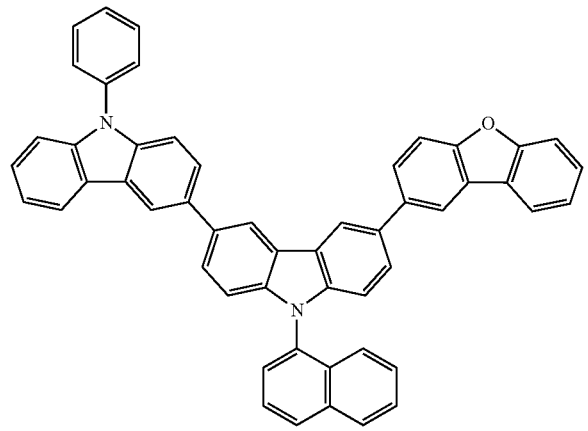
H1-88
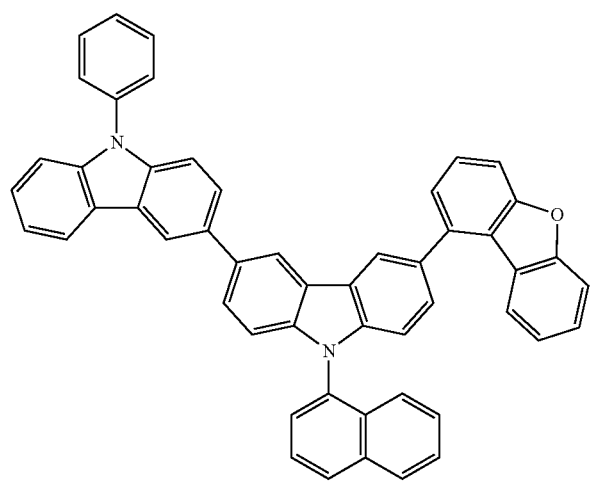
H1-89
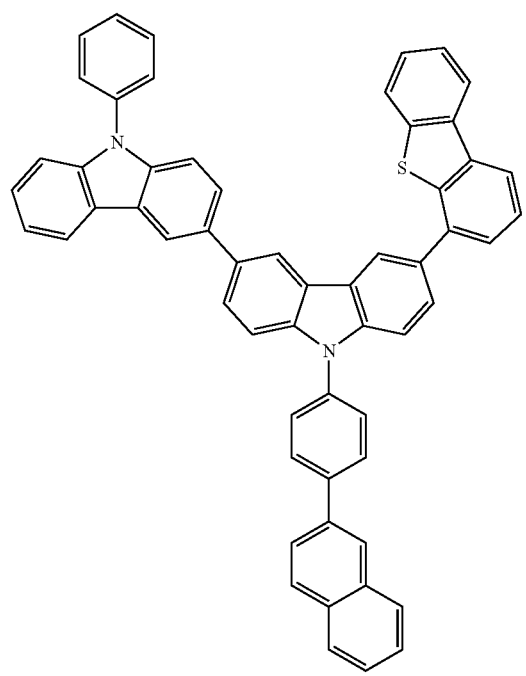

H1-90
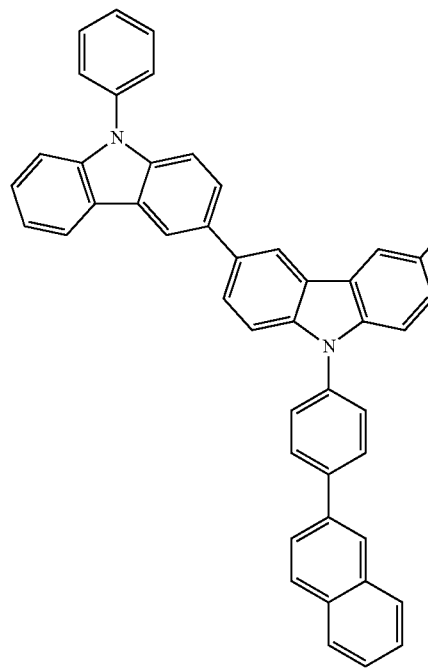
H1-91
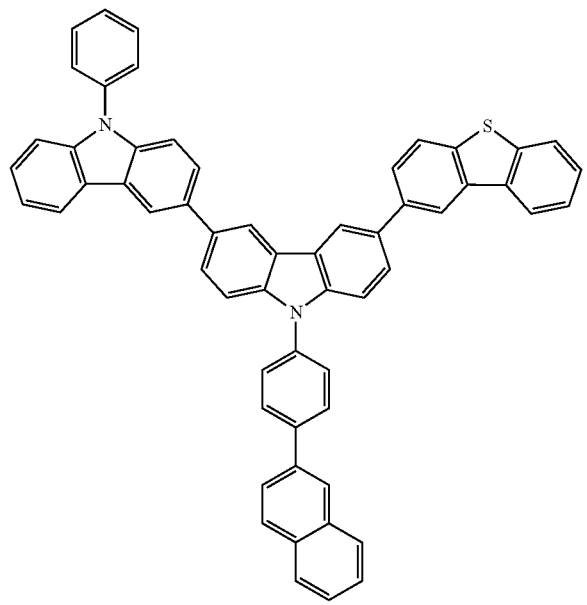
H1-92
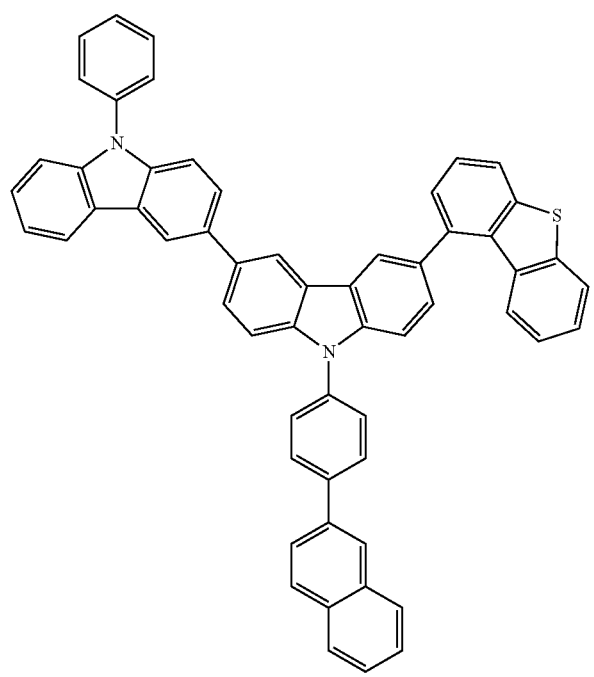
H1-93
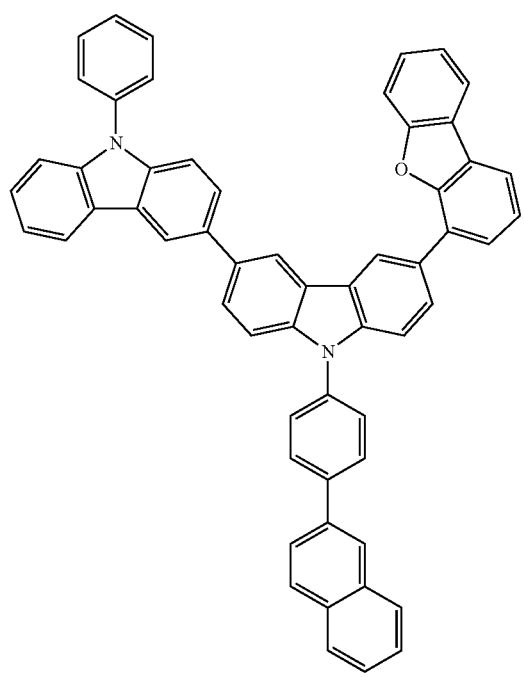

-continued
H1-94
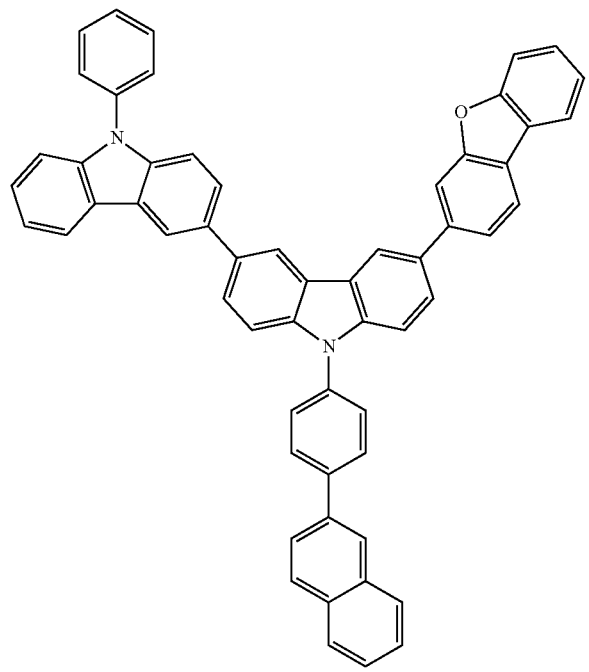
H1-95
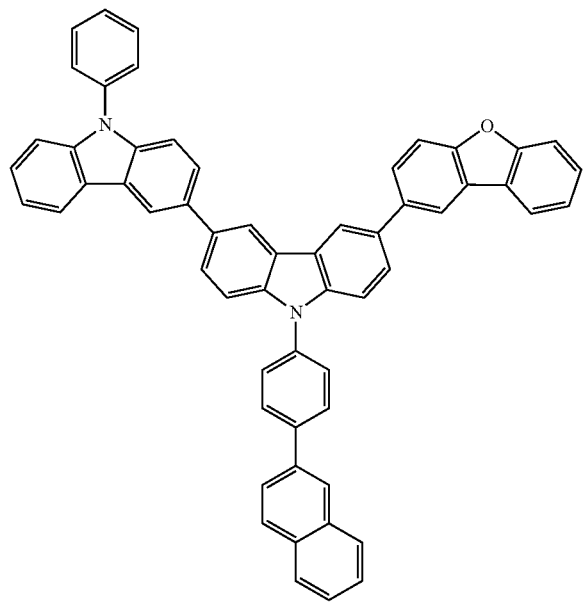
H1-96
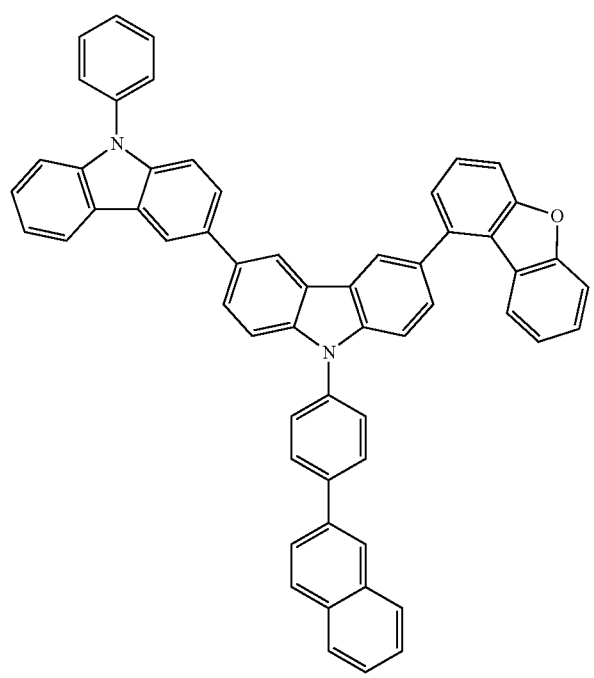
H1-97
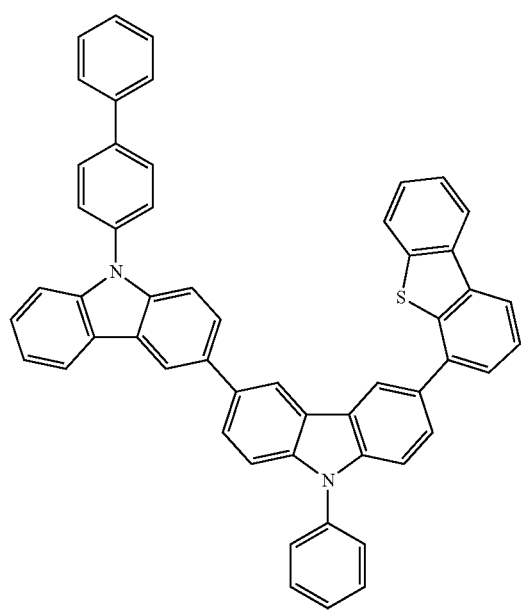

-continued
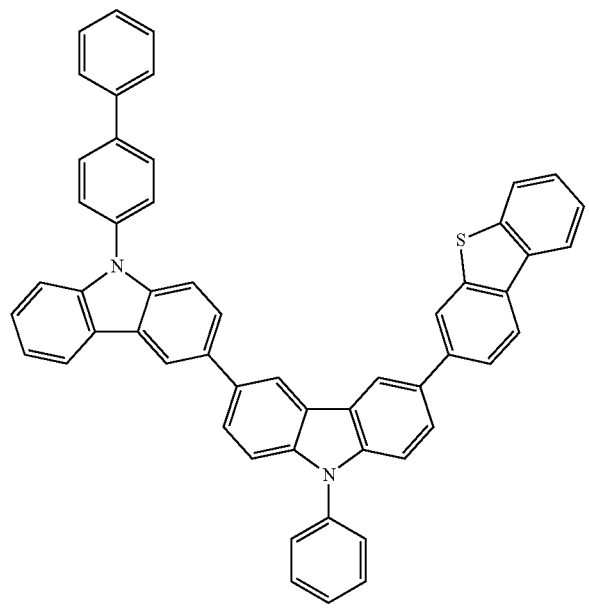
H1-98
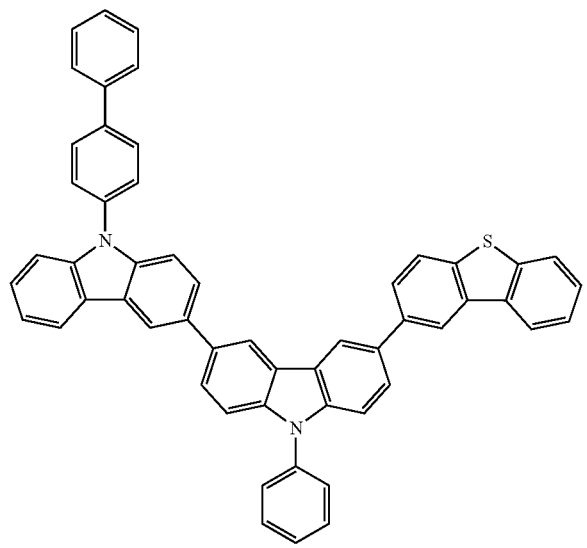
H1-99
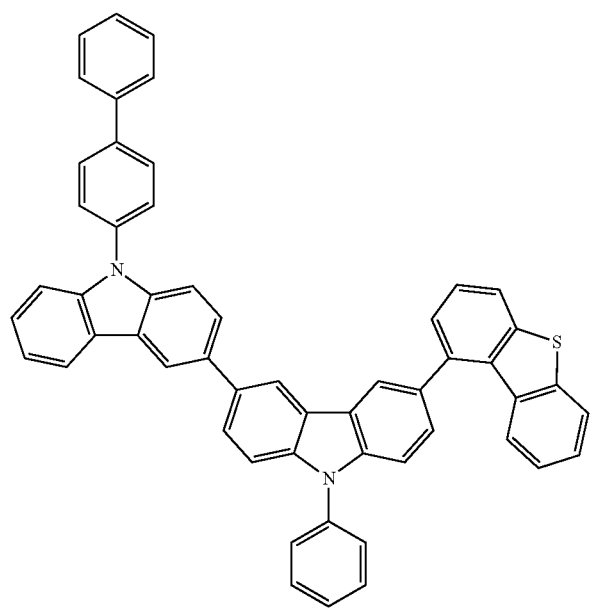
H1-100
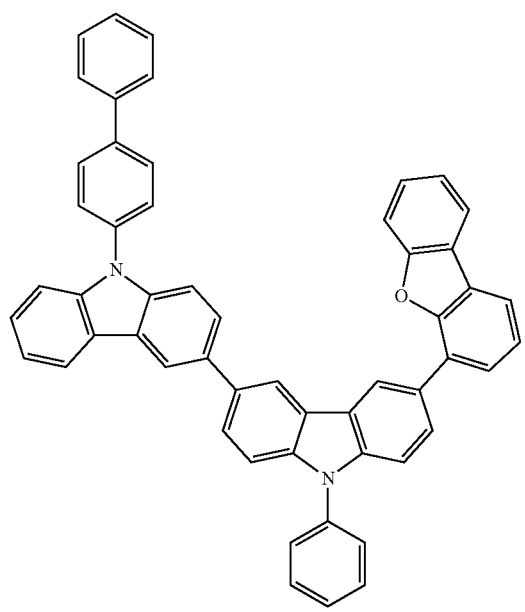
H1-101

-continued
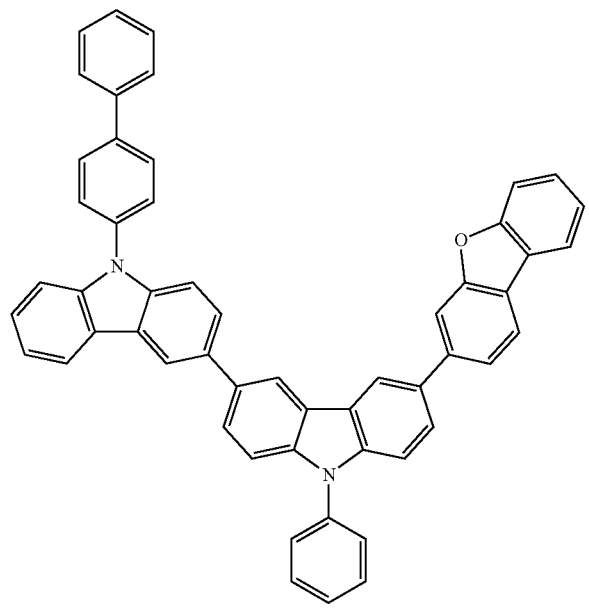
H1-102
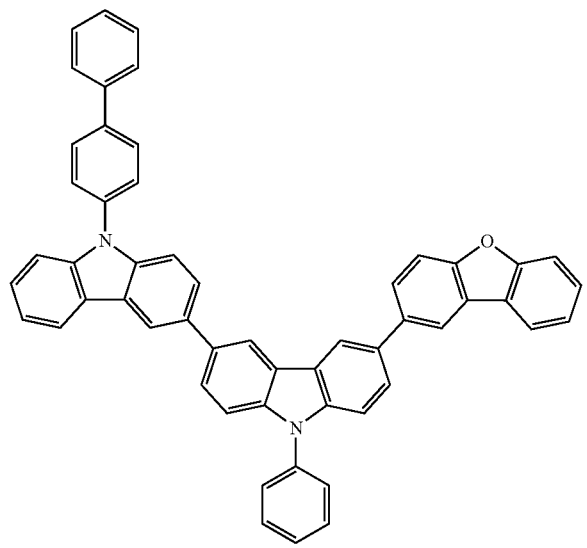
H1-103
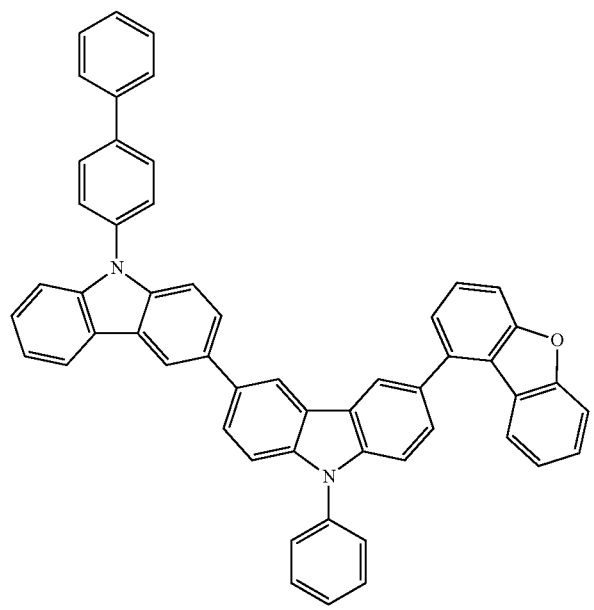
H1-104
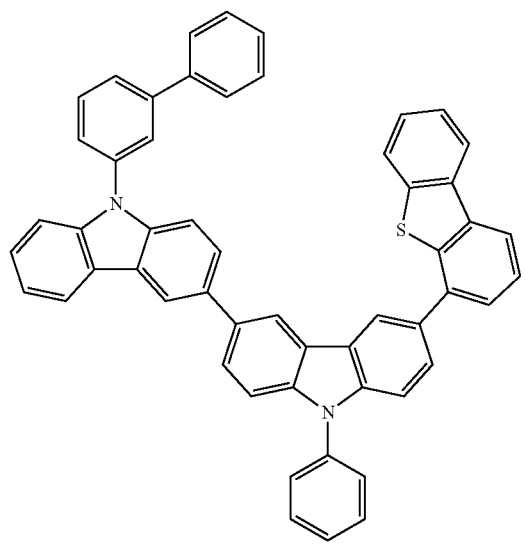
H1-105

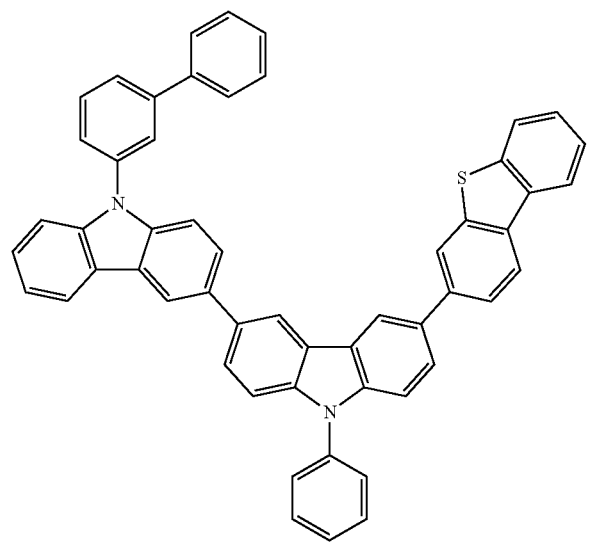
H1-106
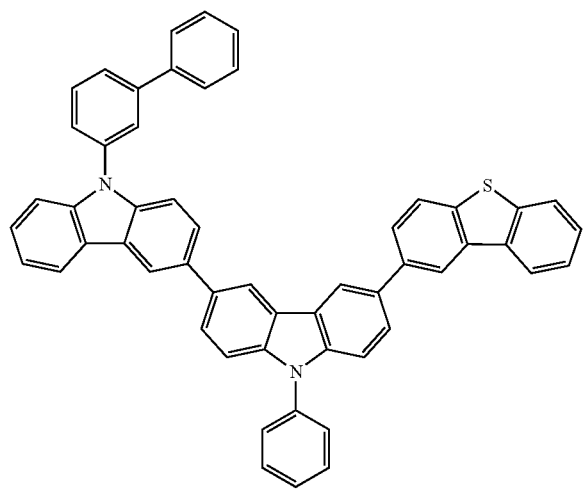
H1-107
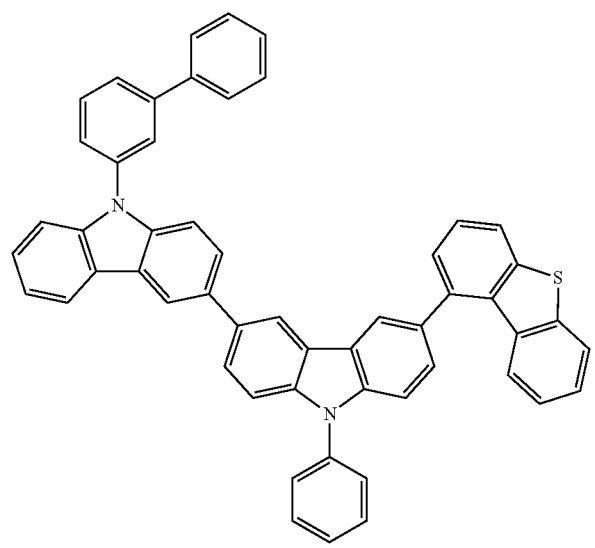
H1-108
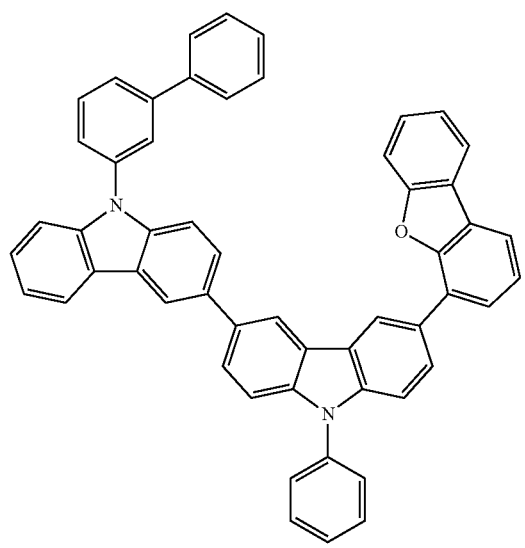
H1-109

H1-110
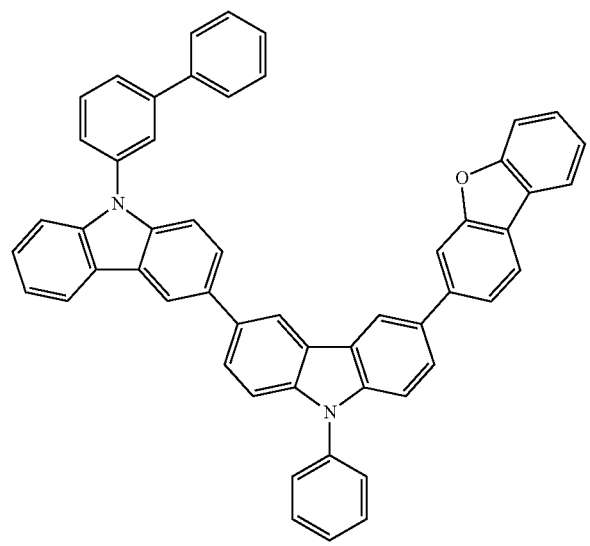
H1-111
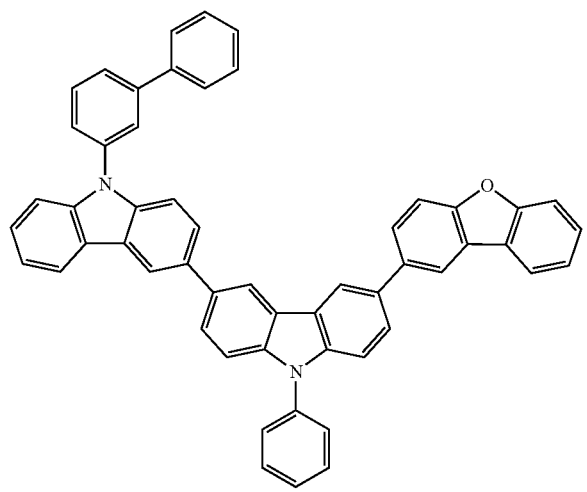
H1-112
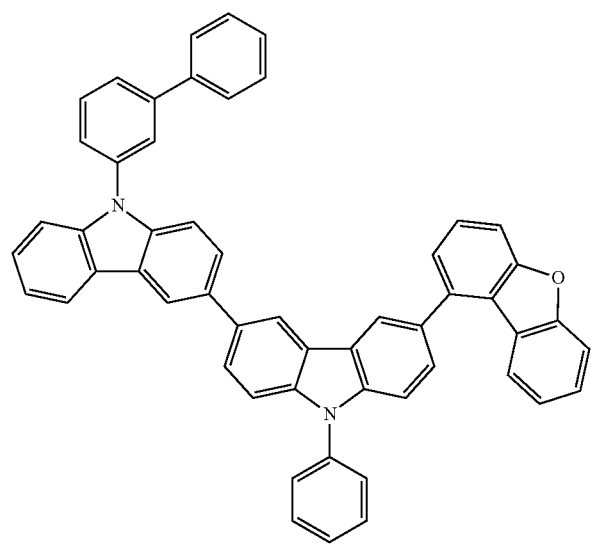
H1-113
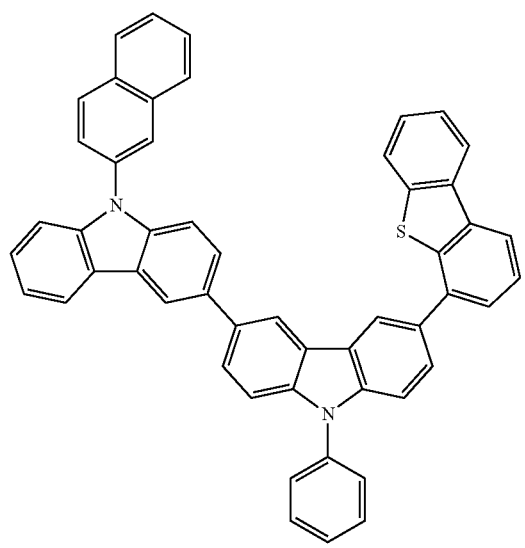

-continued
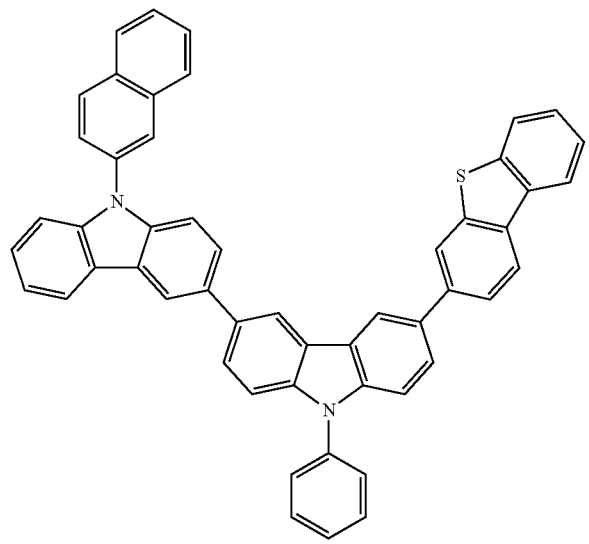
H1-114
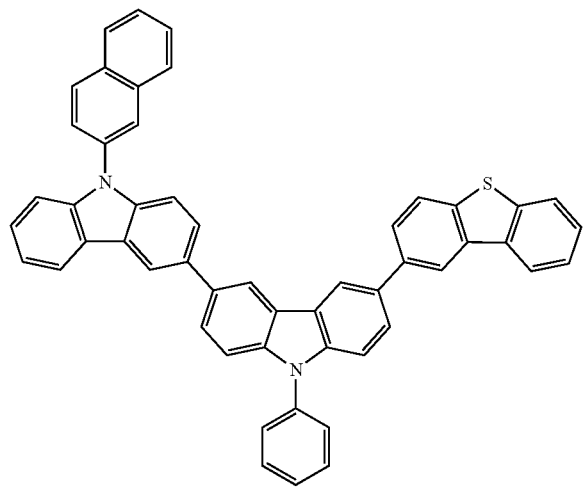
H1-115
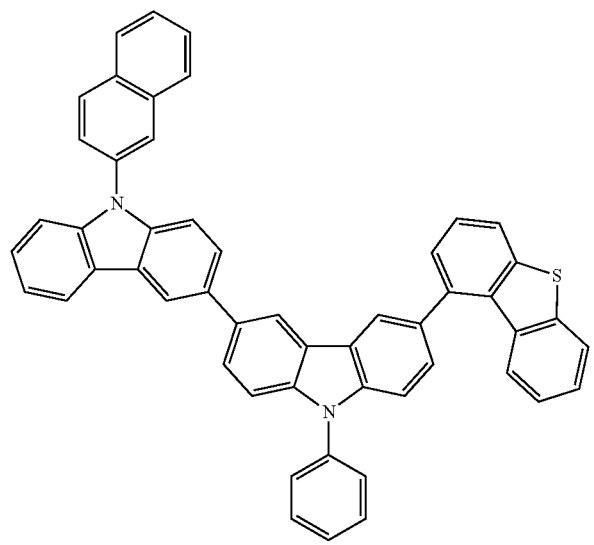
H1-116
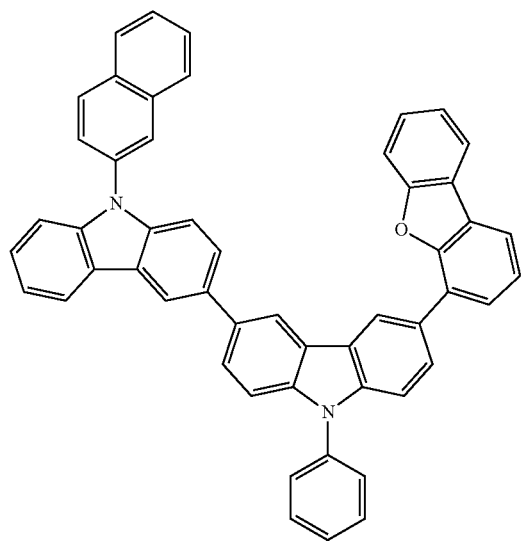
H1-117

-continued
H1-118
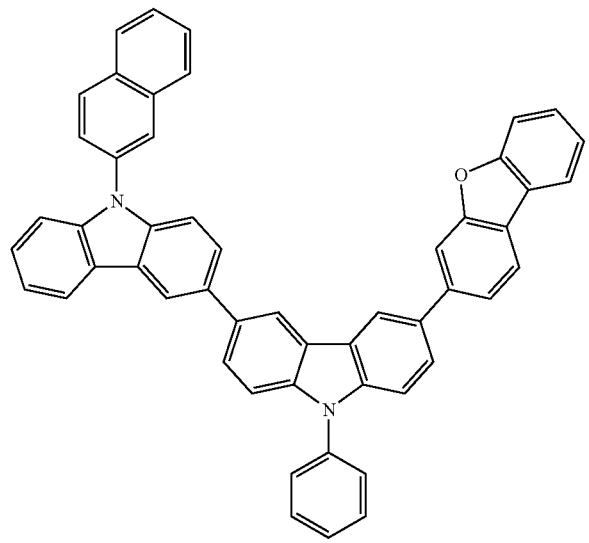
H1-119
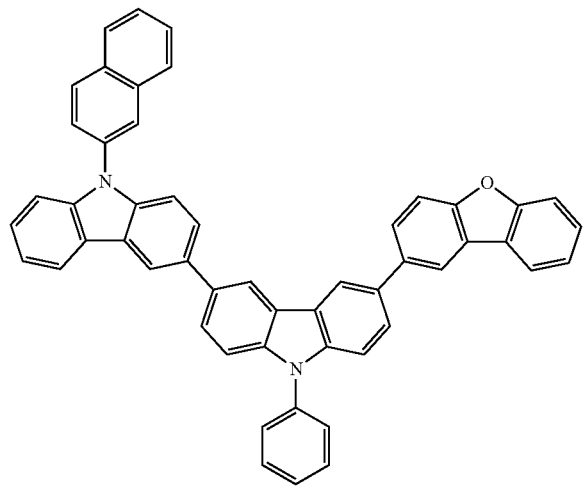
H1-120
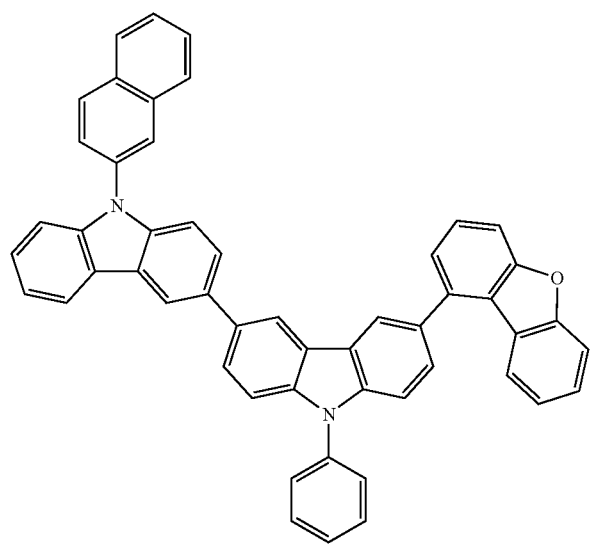
H1-121
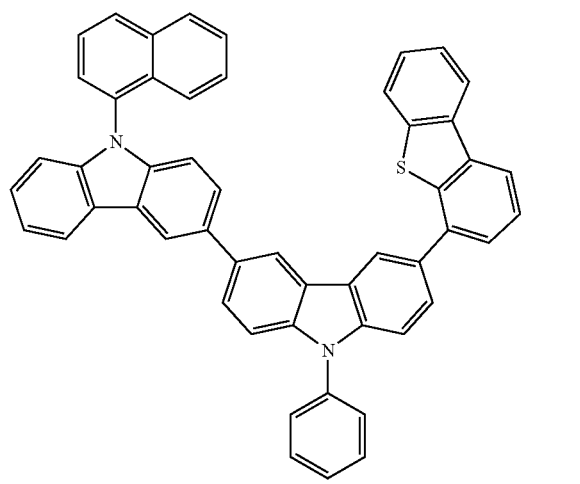
H1-122
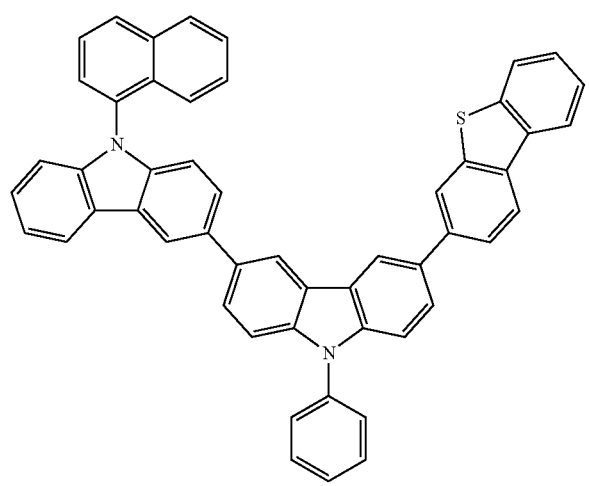
H1-123
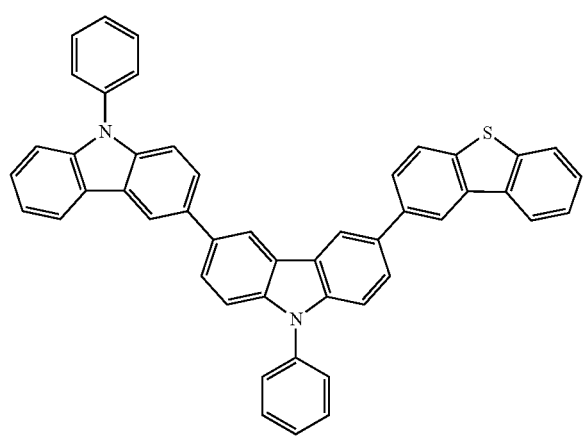

-continued
H1-124
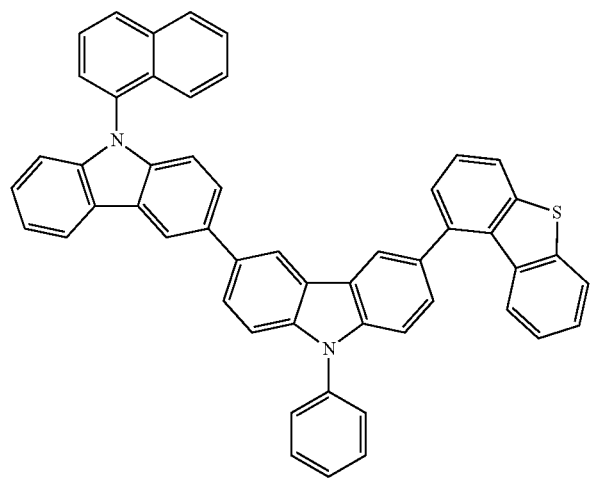
H1-125
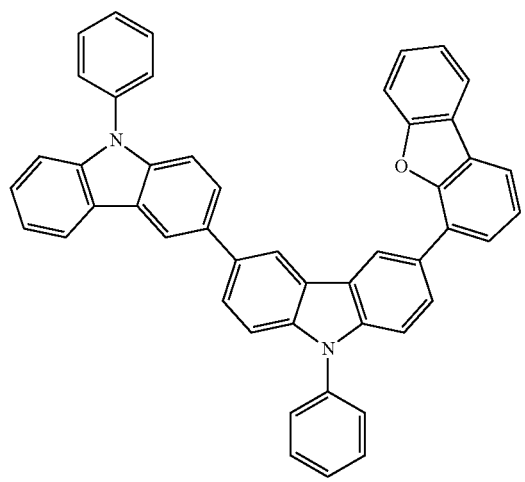
H1-126
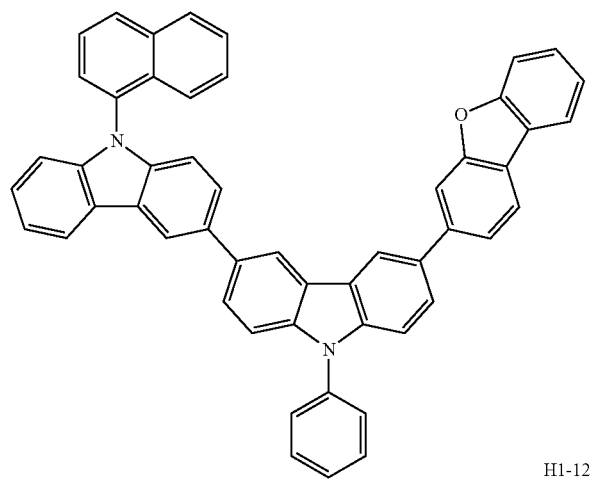
H1-127
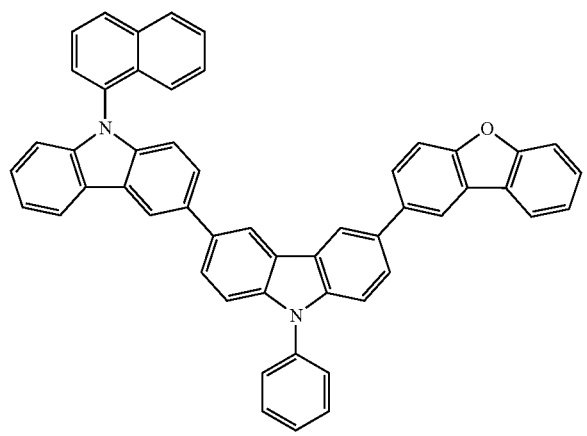
H1-128
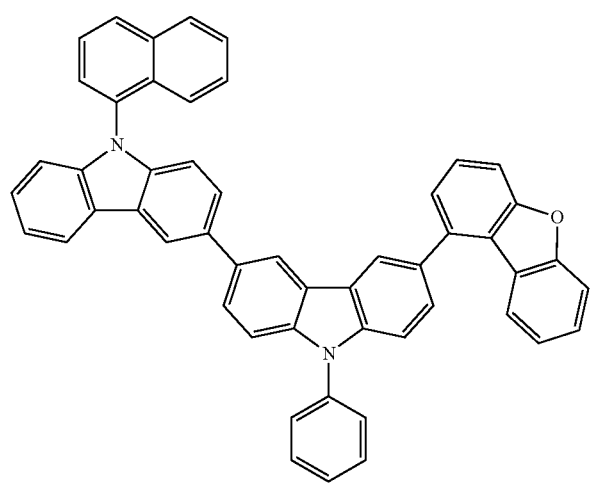
H1-129
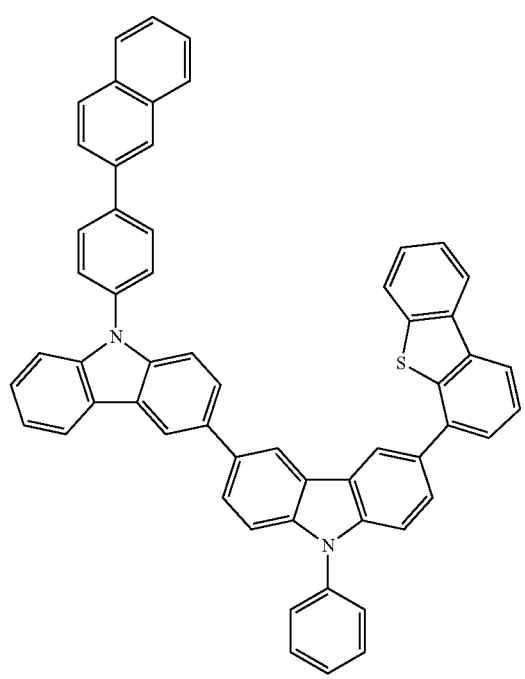

-continued
H1-130
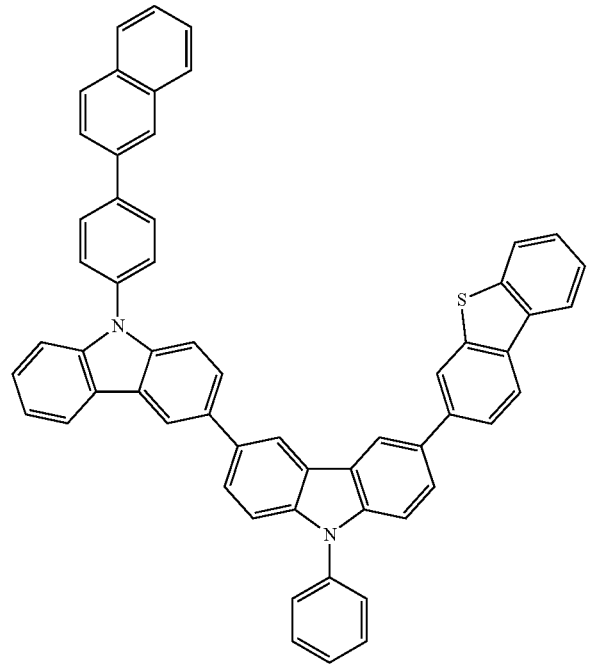
H1-131
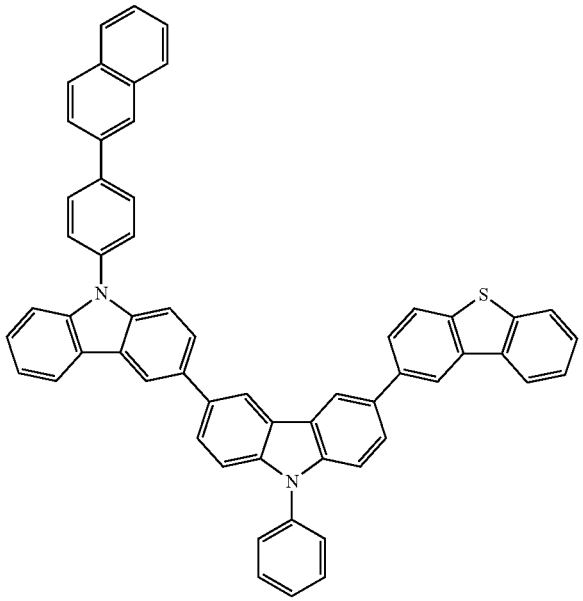
H1-132
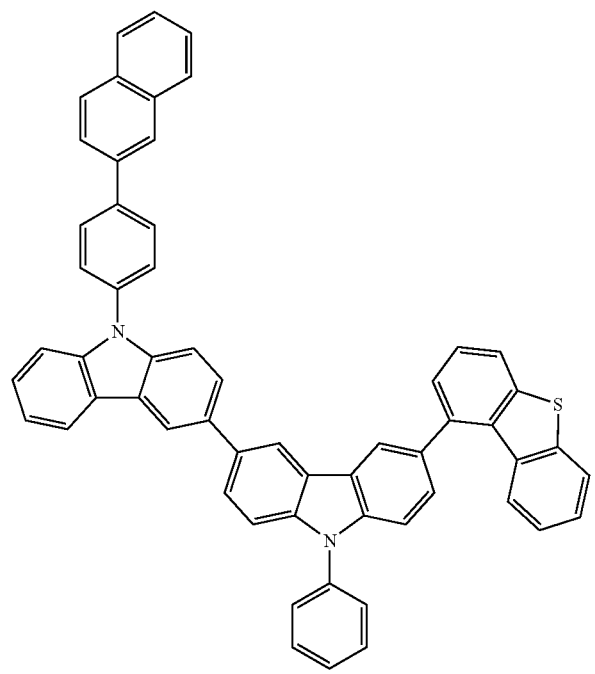
H1-133
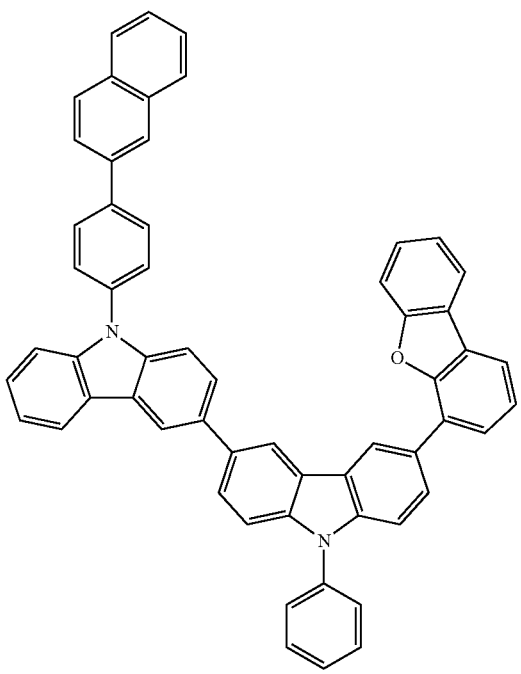

H1-134
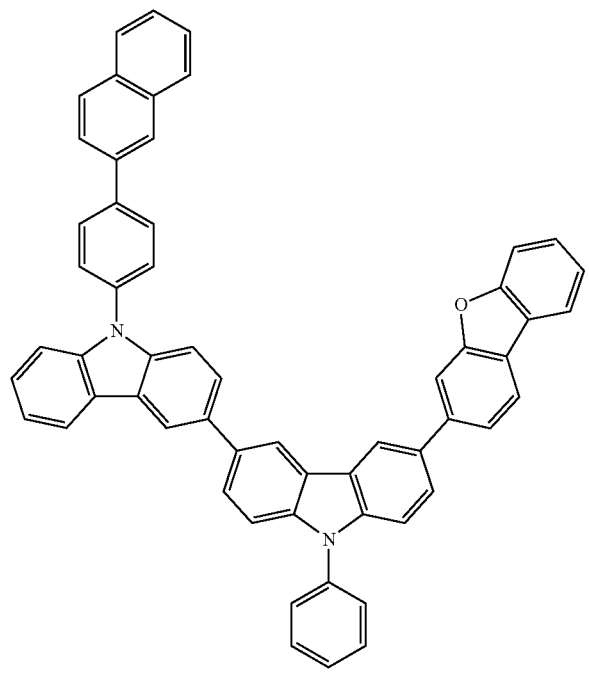
H1-135
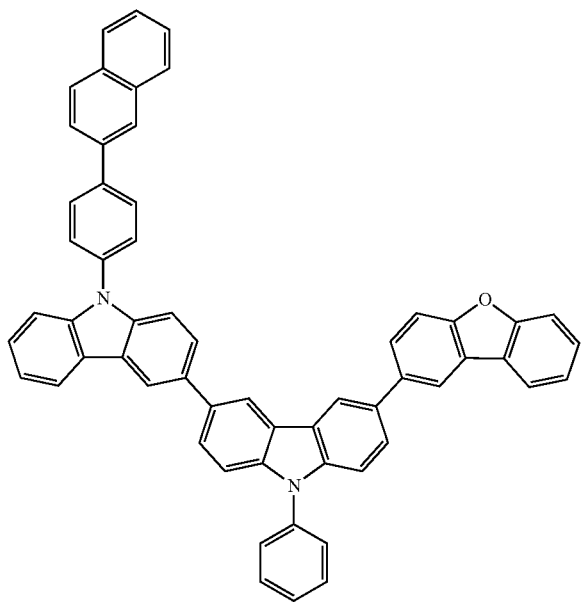
H1-136
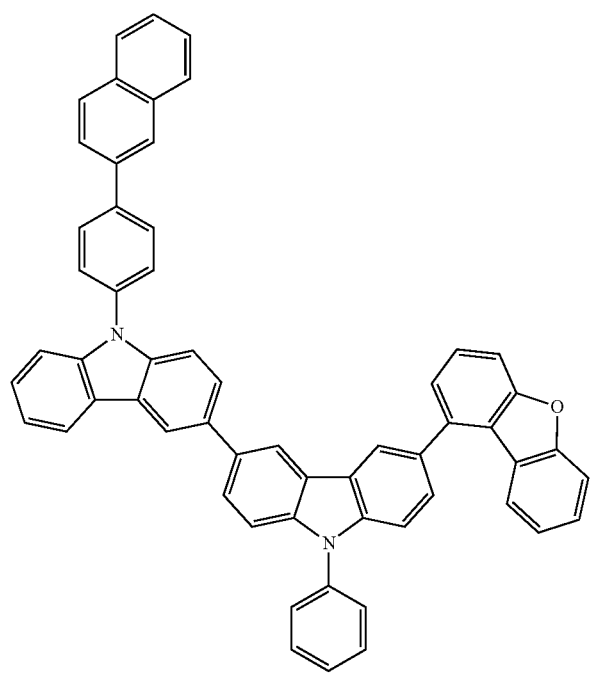
H1-141
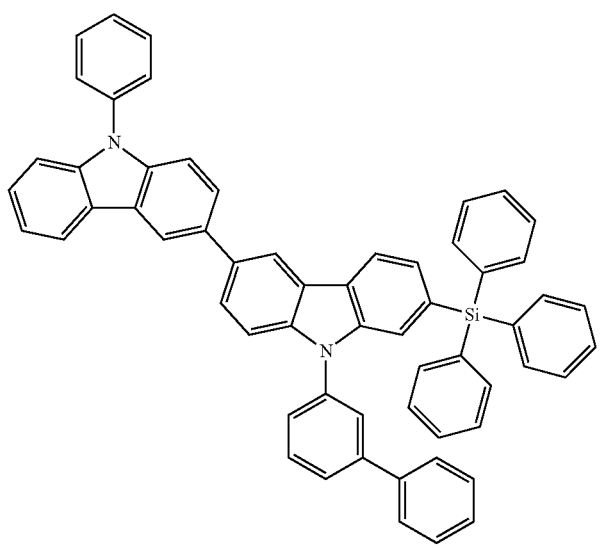

H1-143
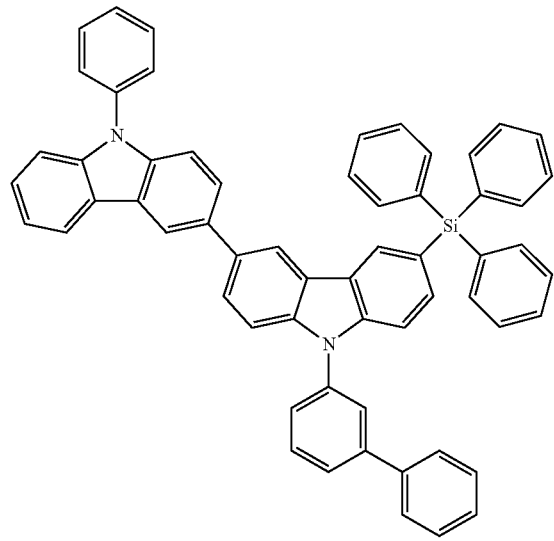
H1-149
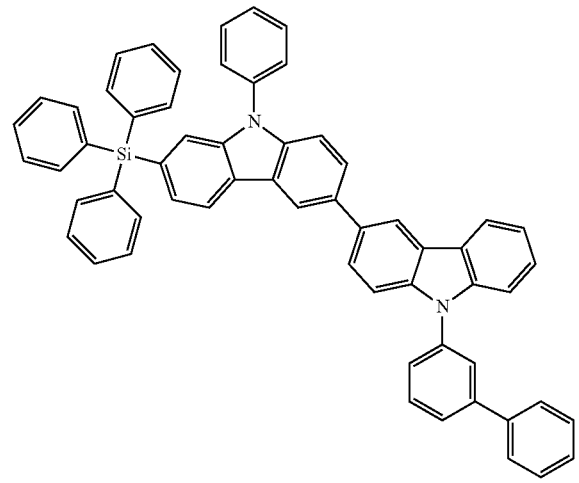
H1-151
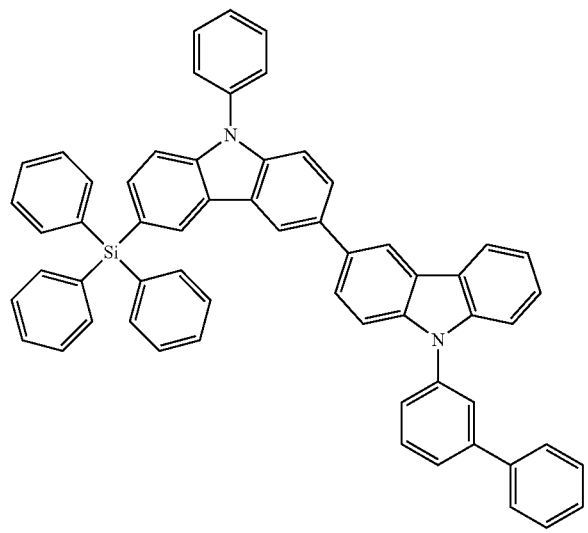
H1-155
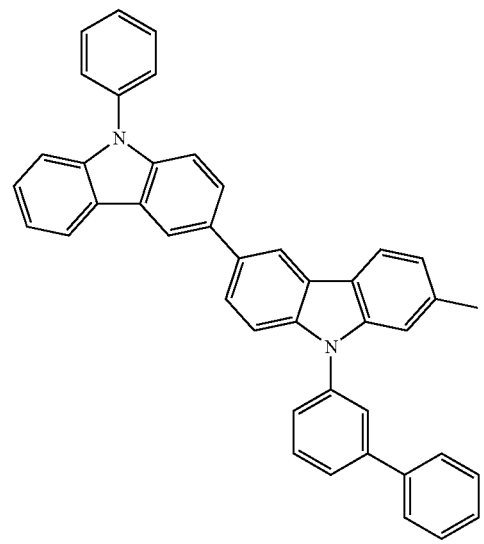
H1-156
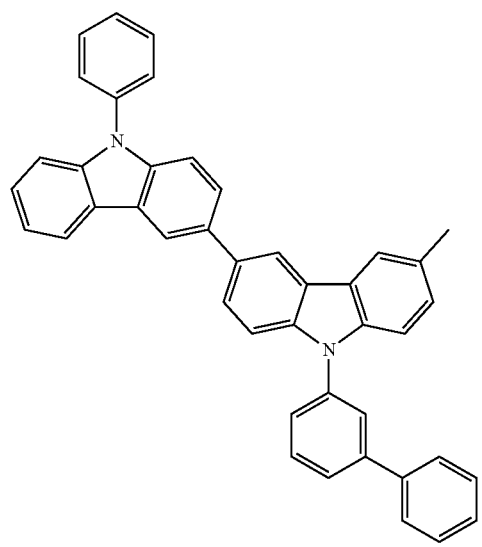
H1-159
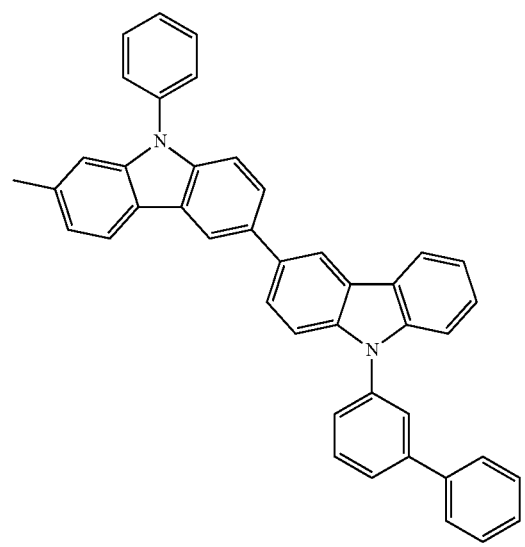

-continued
H1-160
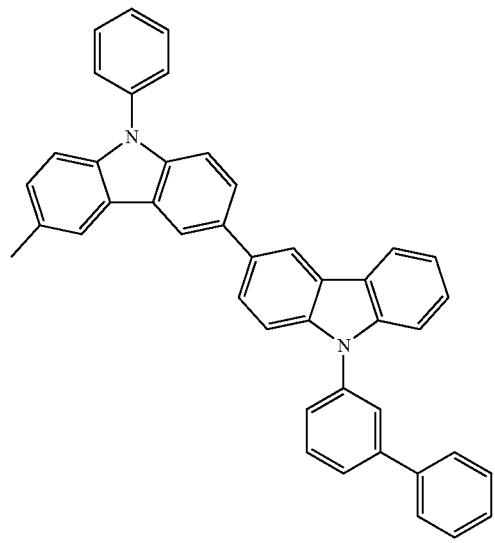
H1-161
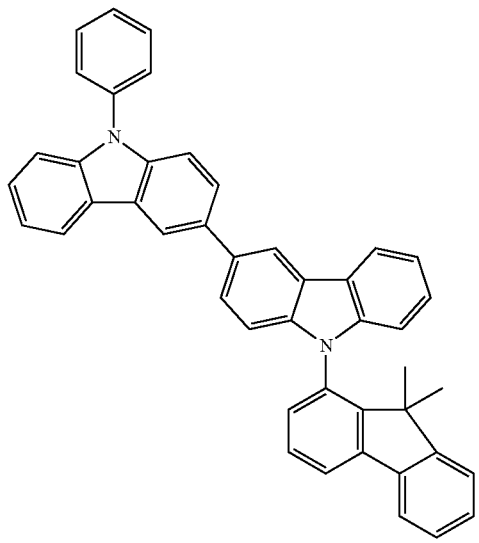
H1-162
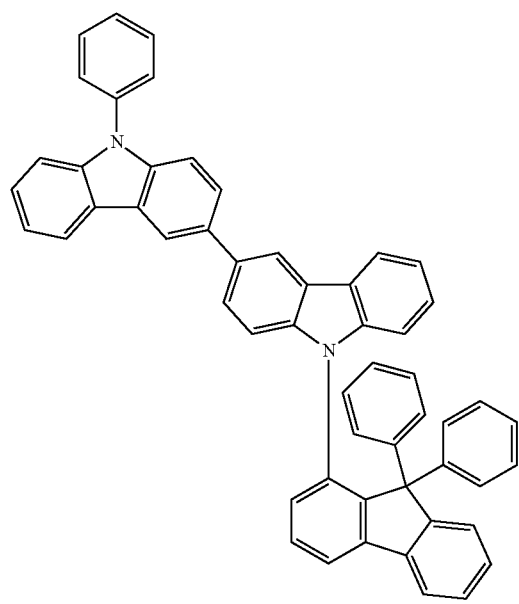
H1-163
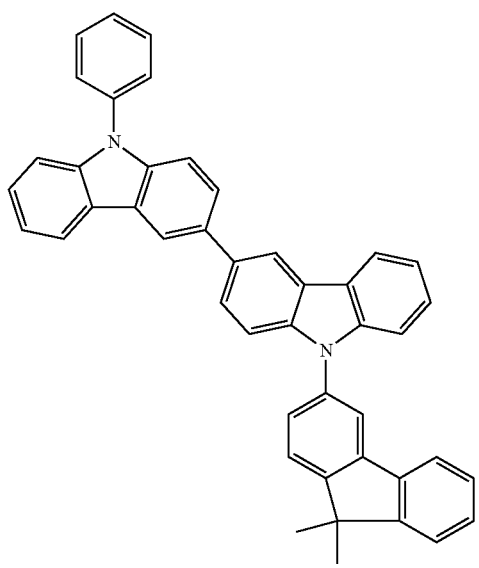

H1-164
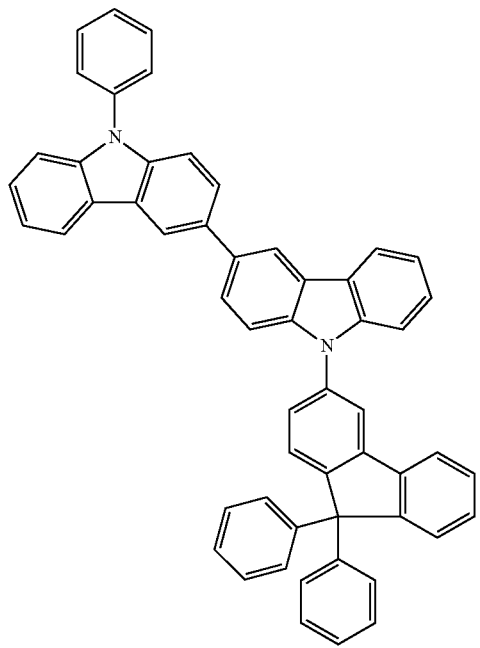
H1-173
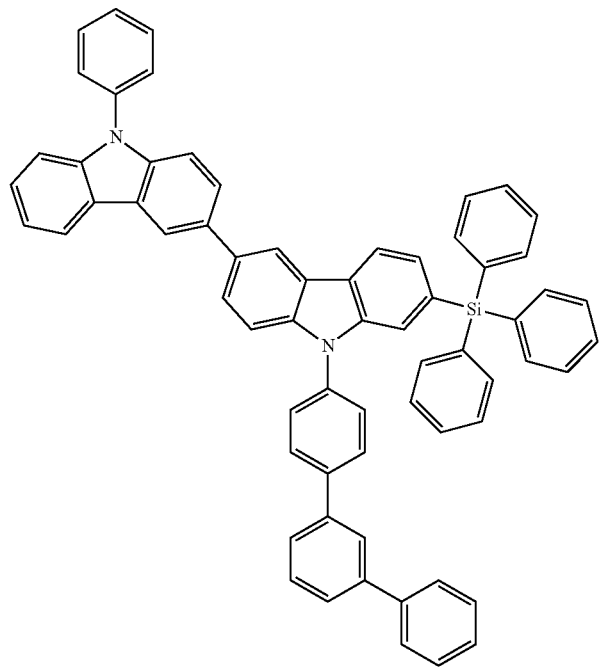
H1-175
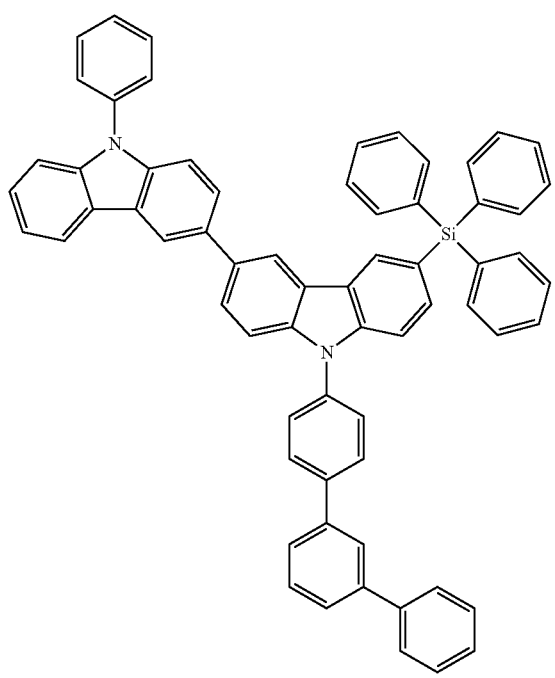
H1-181
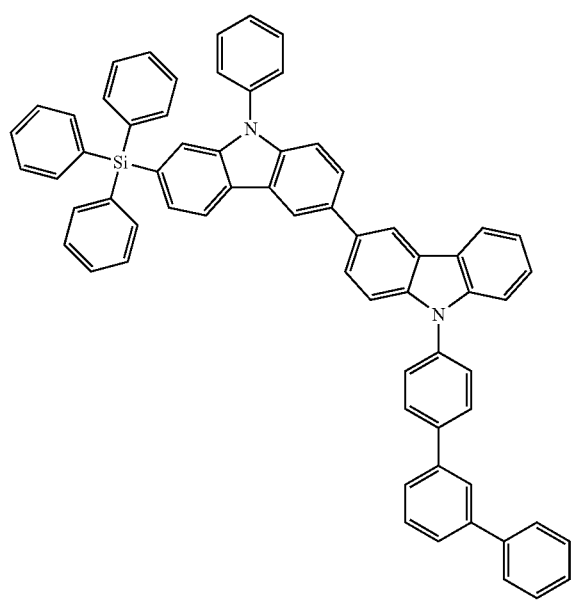

-continued
H1-183
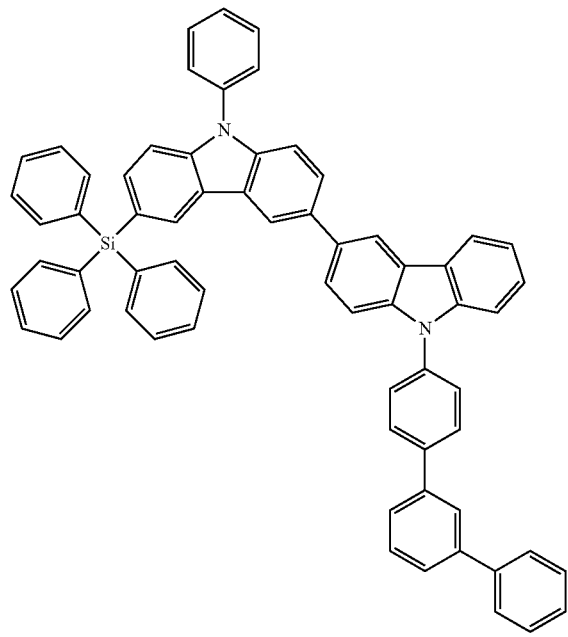
H1-189
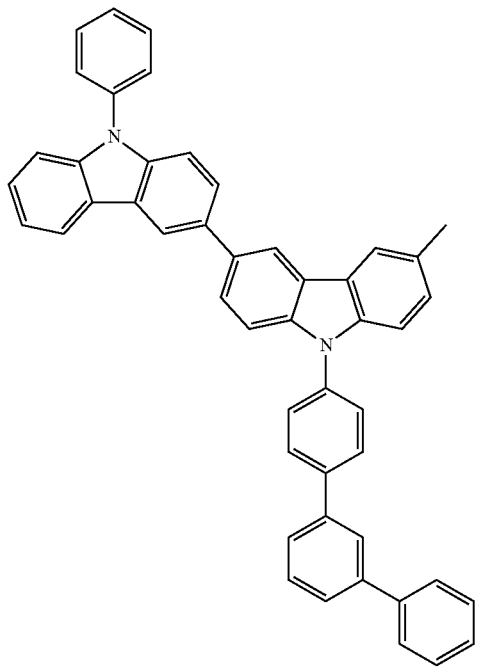
H1-191
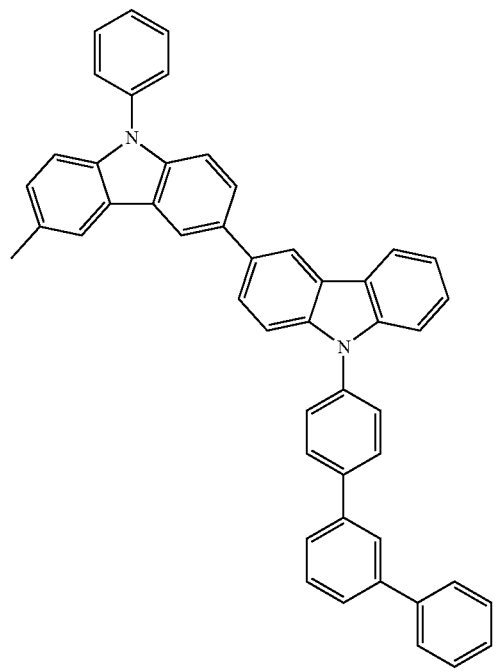
H1-193
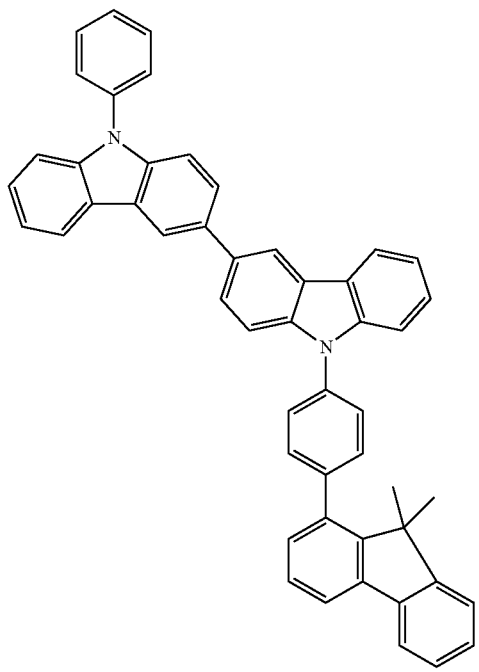

H1-194
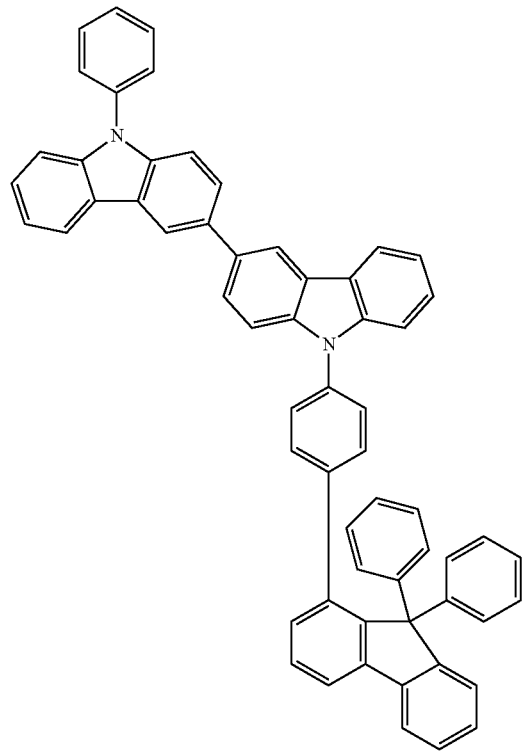
H1-195
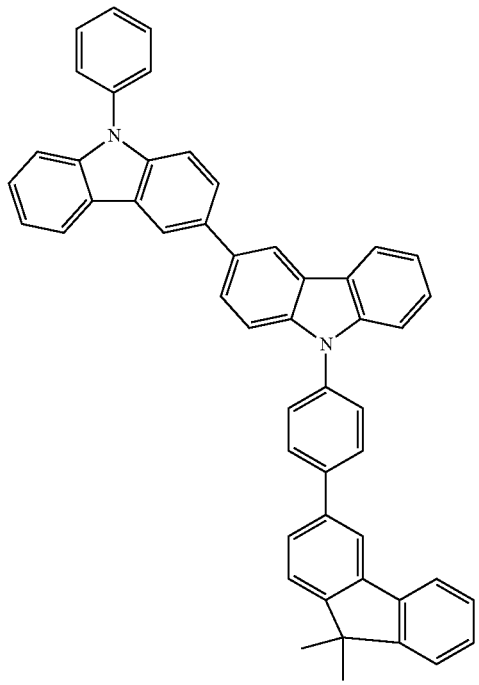
H1-196
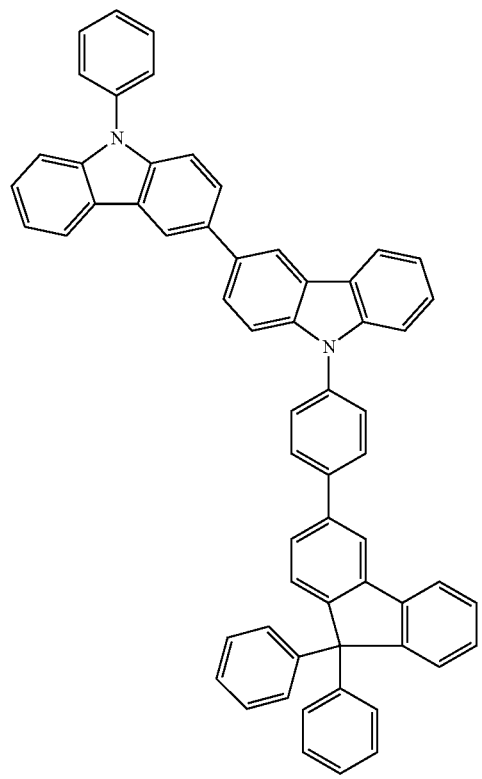
H1-205
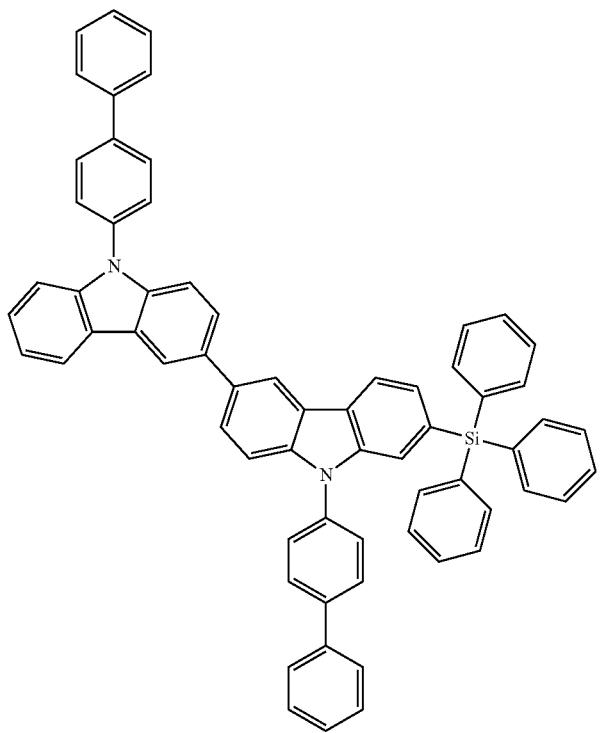

H1-207
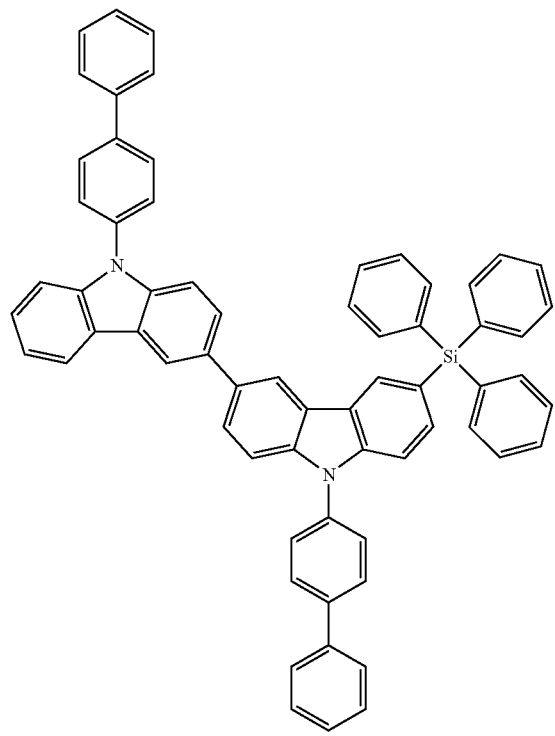
H1-211
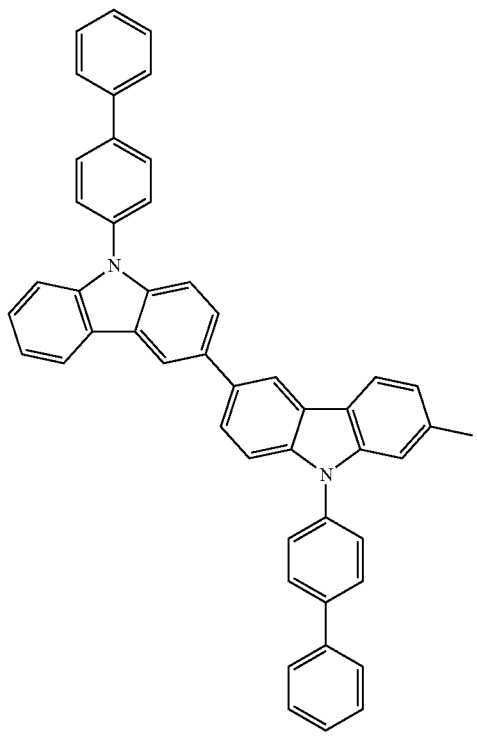
H1-212
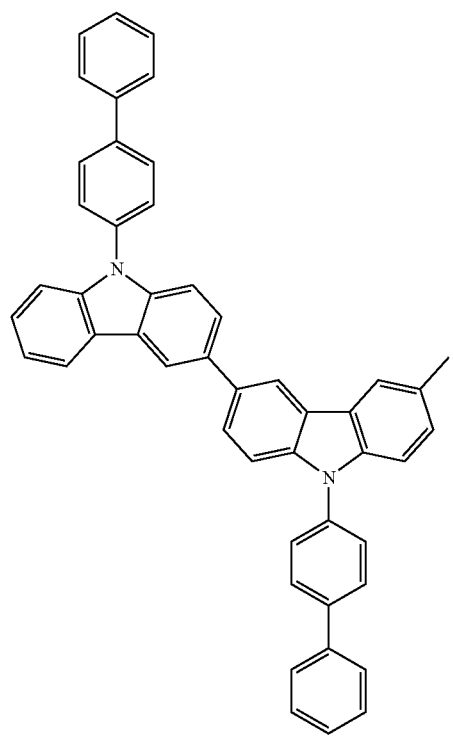
H1-215
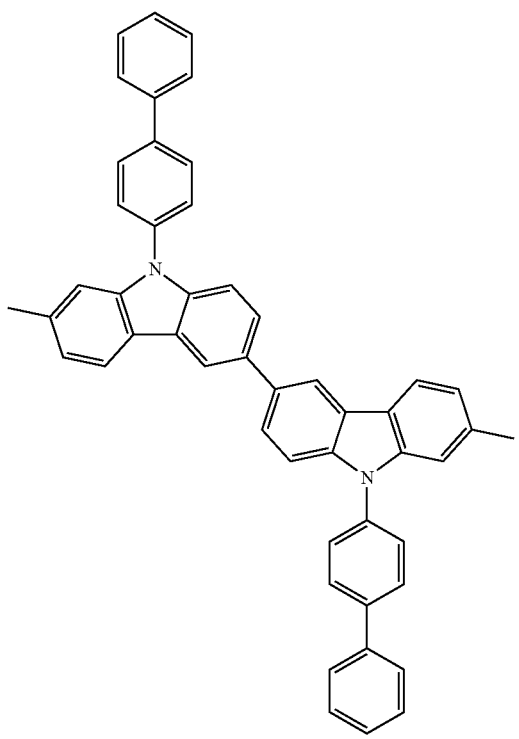

-continued
H1-216
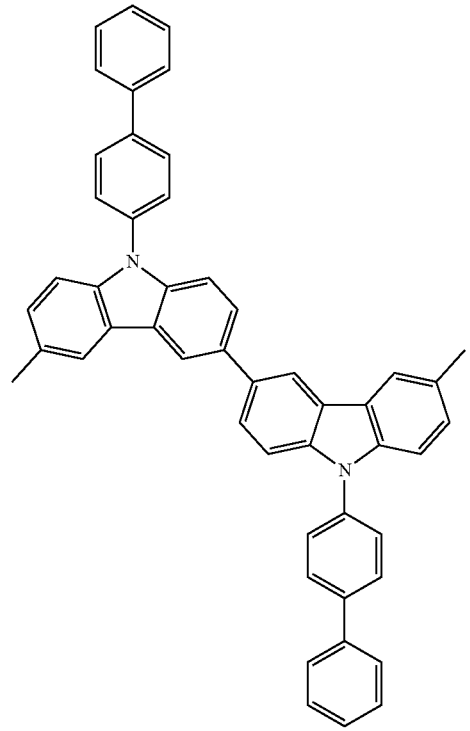
H1-217
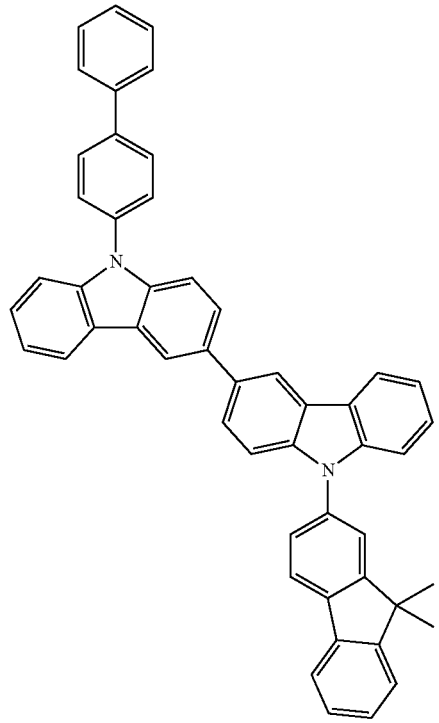
H1-218
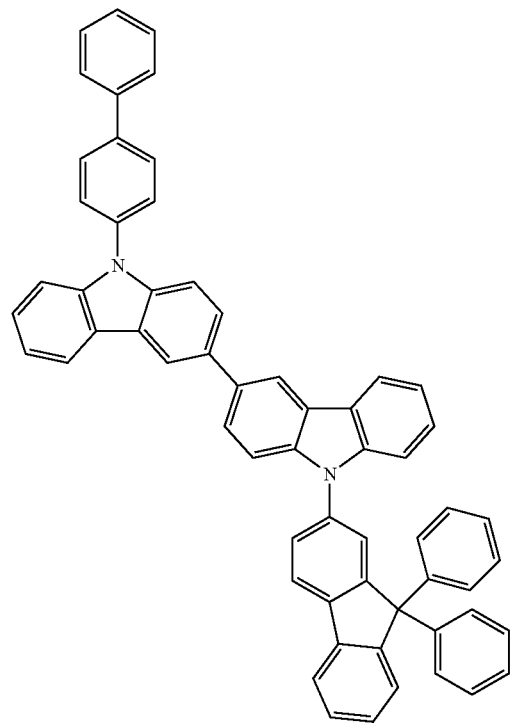
H1-219
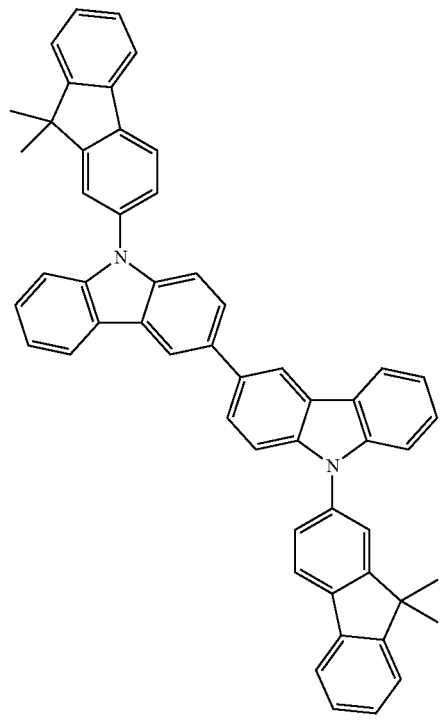

H1-220
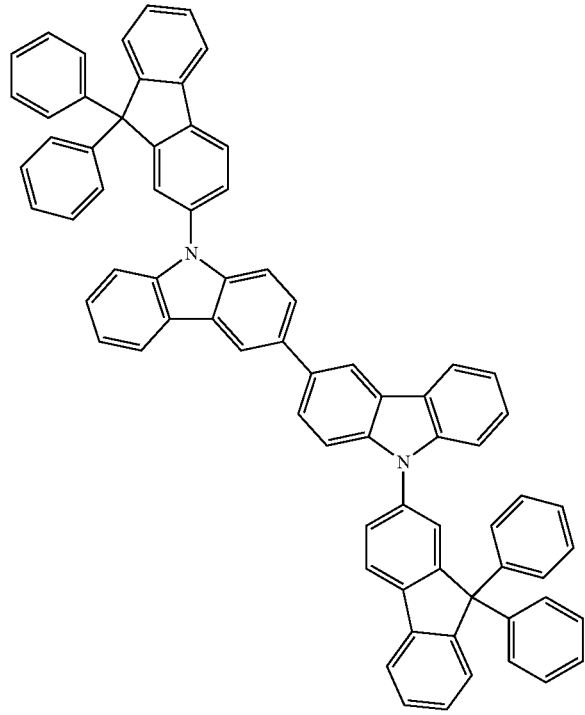
H1-221
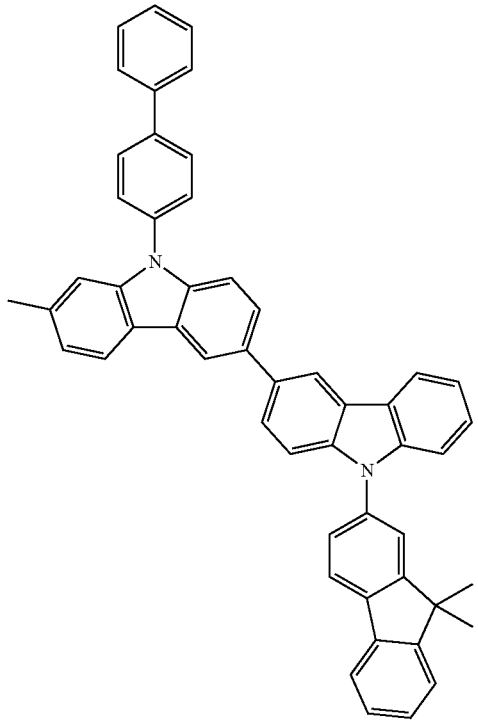
H1-223
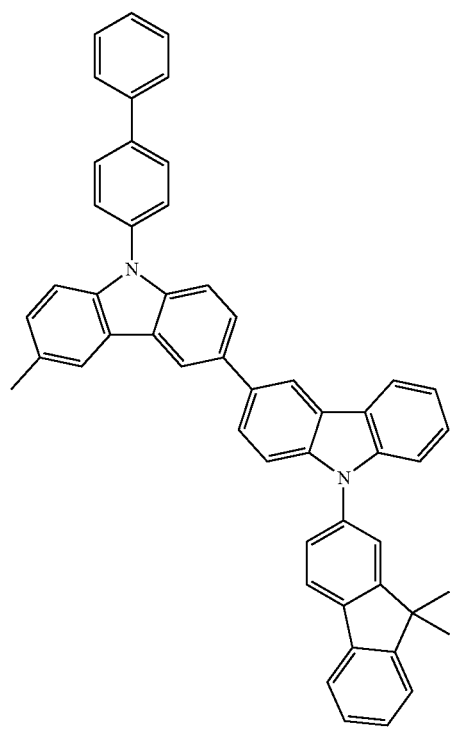

525					526
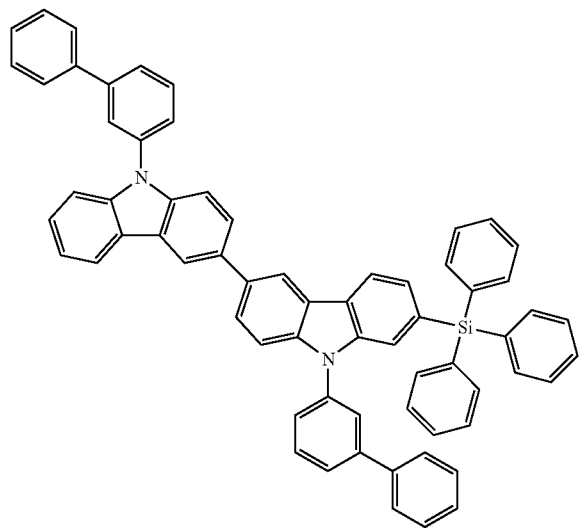
H1-237
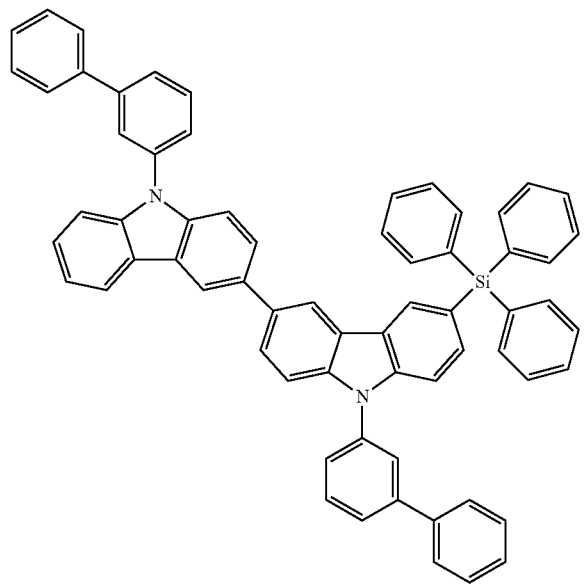
H1-239
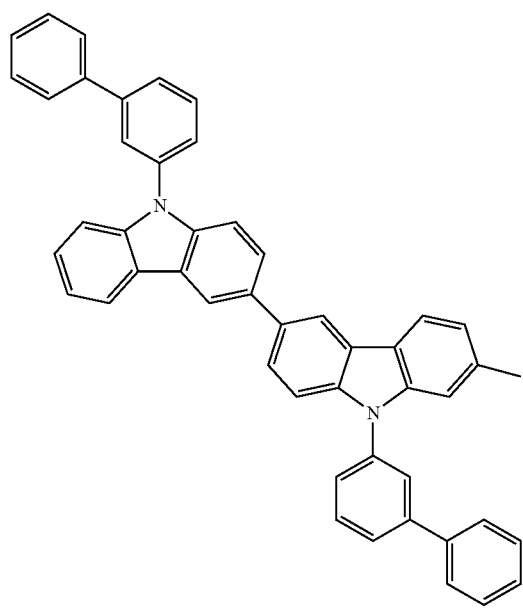
H1-243
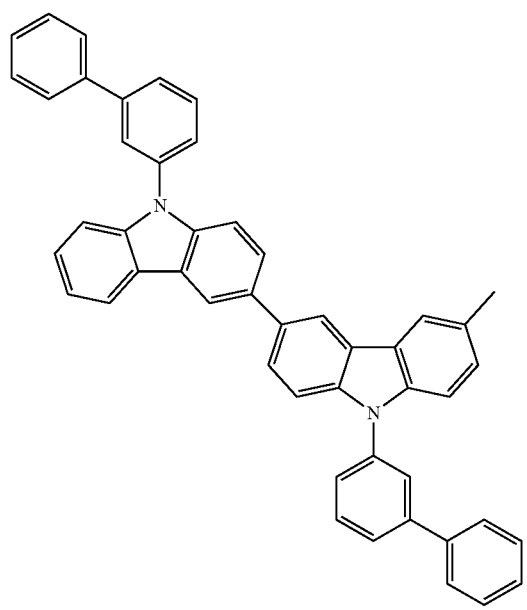
H1-244

-continued
H1-247
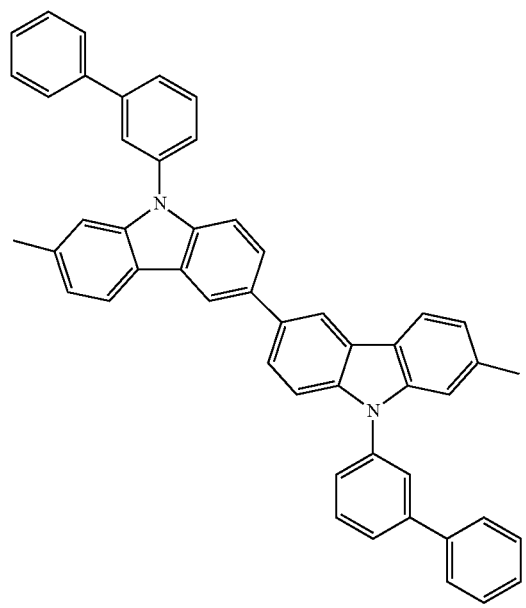
H1-248
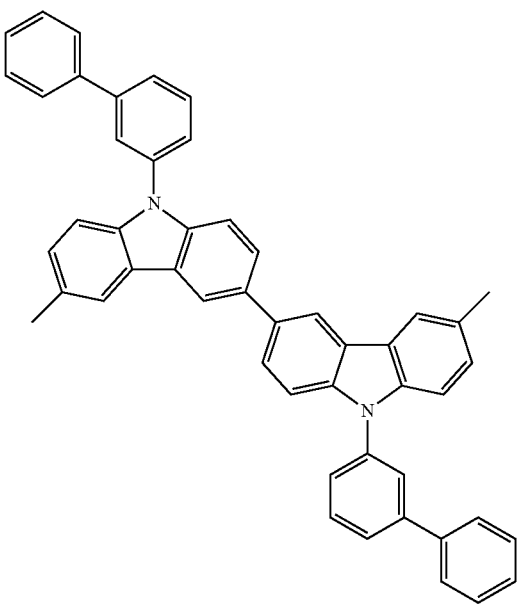
H1-249
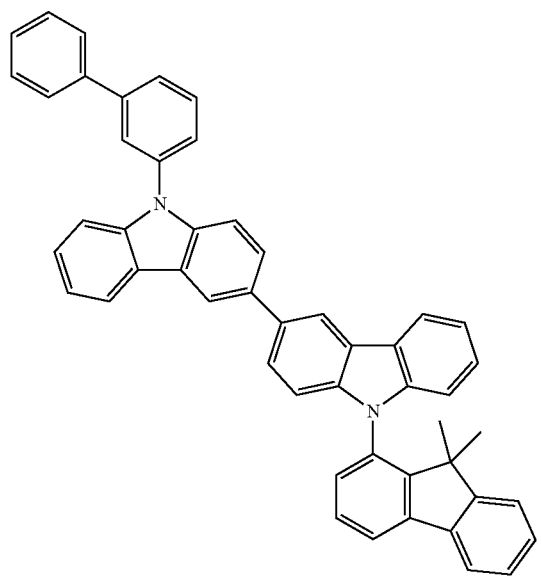
H1-250
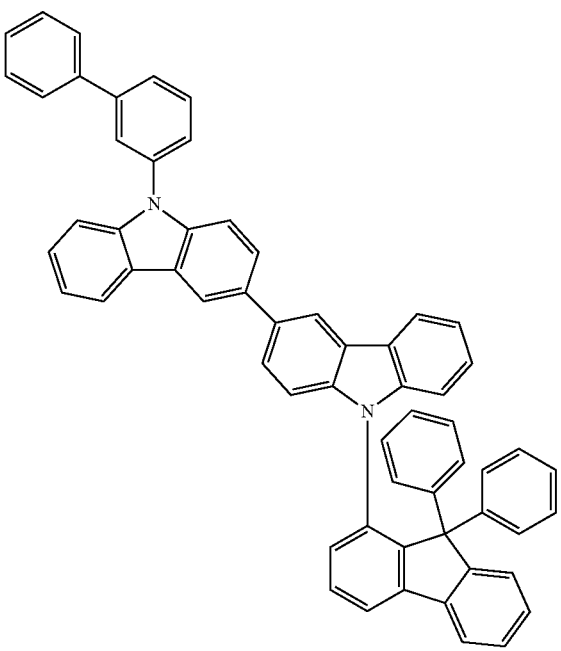

H1-251
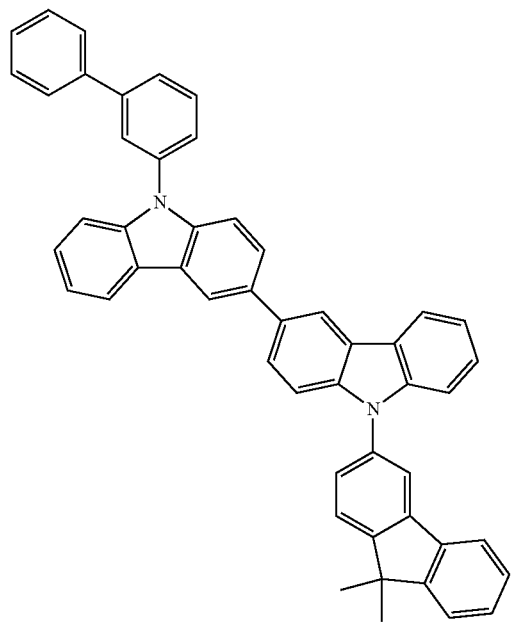
H1-252
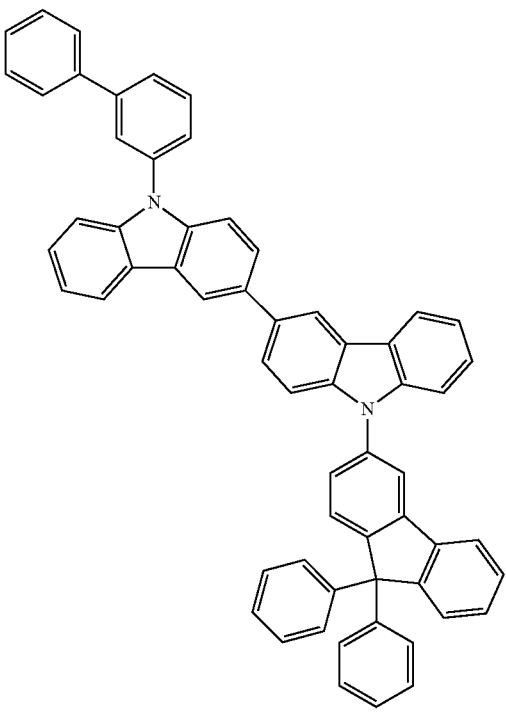
H1-253
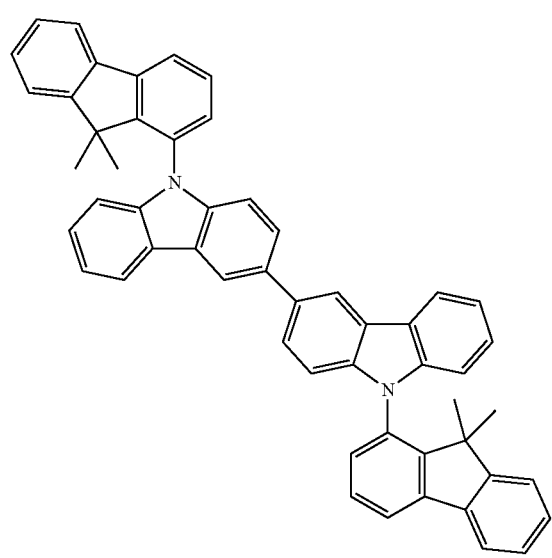
H1-254
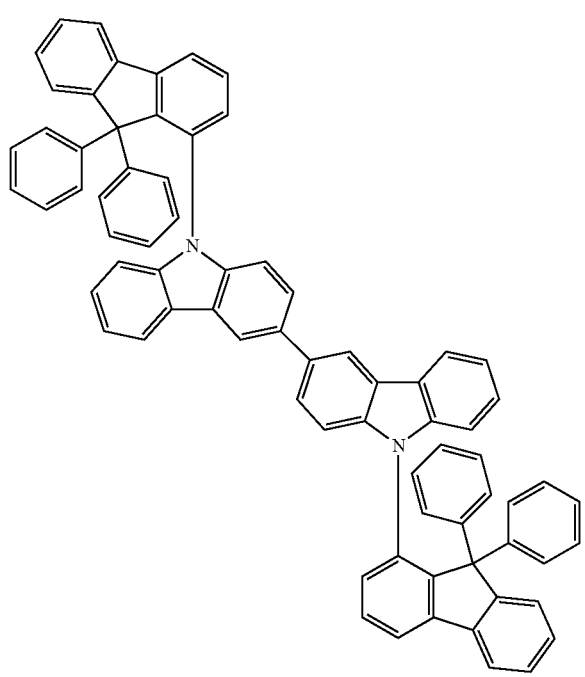

H1-255
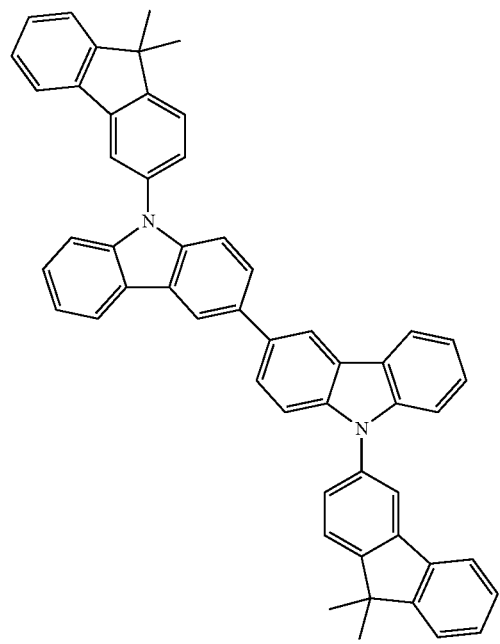
H1-256
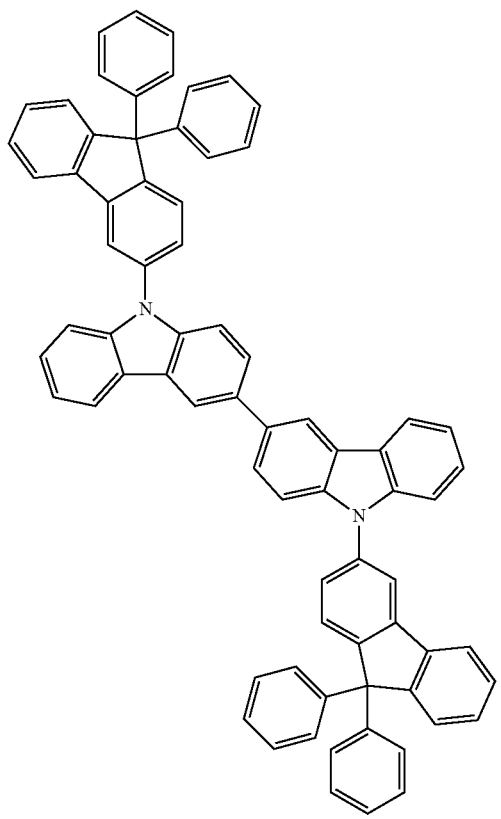
H1-269
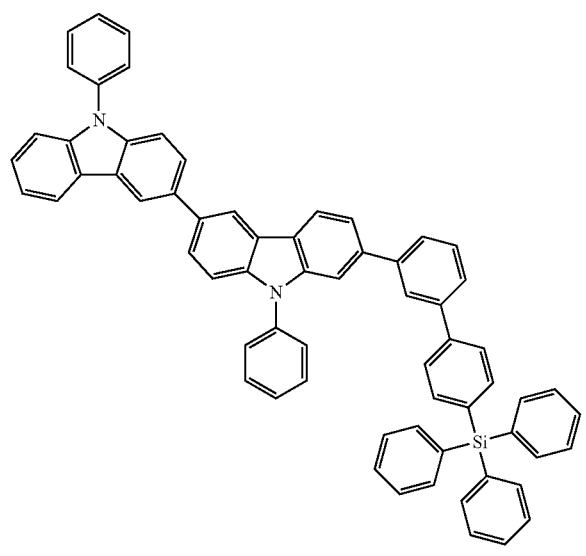
H1-271
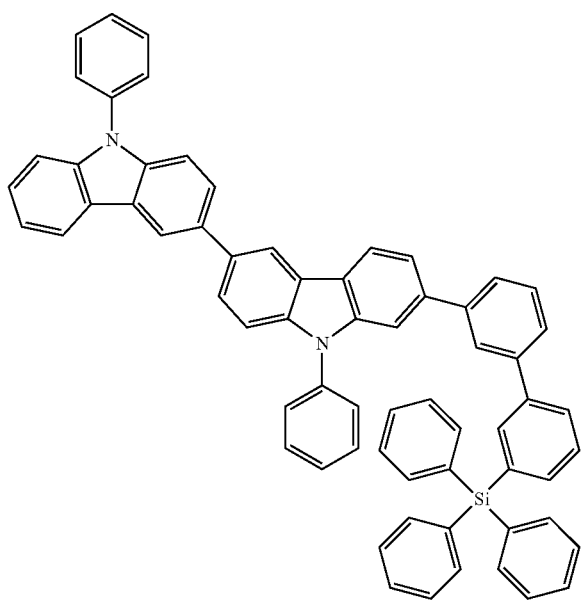

-continued
H1-277
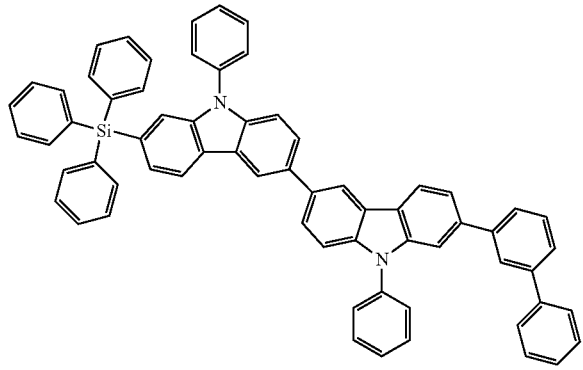
H1-279
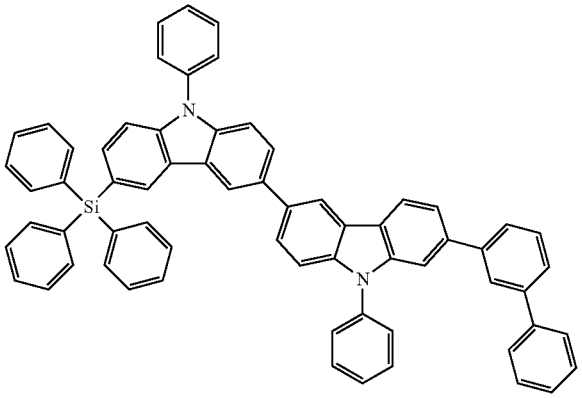
H1-281
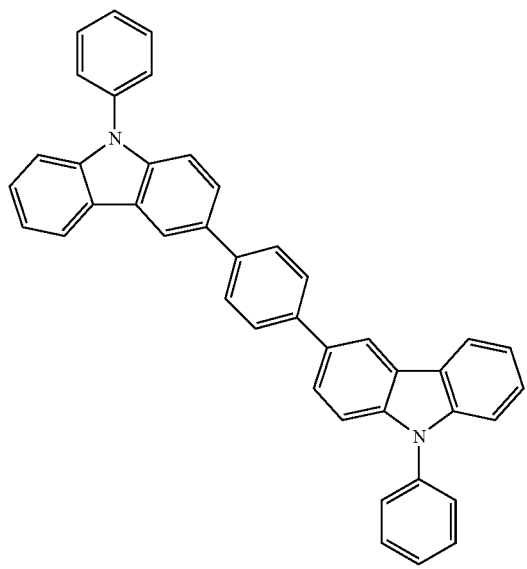
H1-282
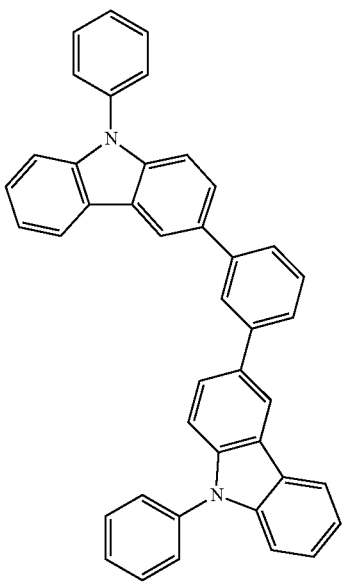
H1-283
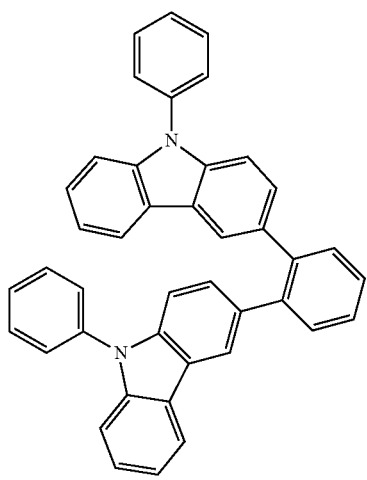
H1-285
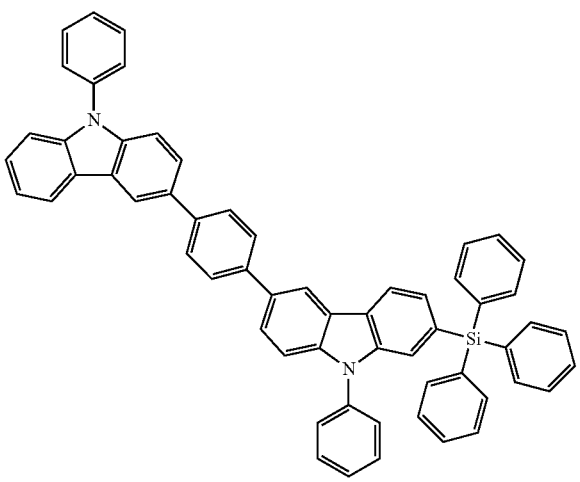

H1-287
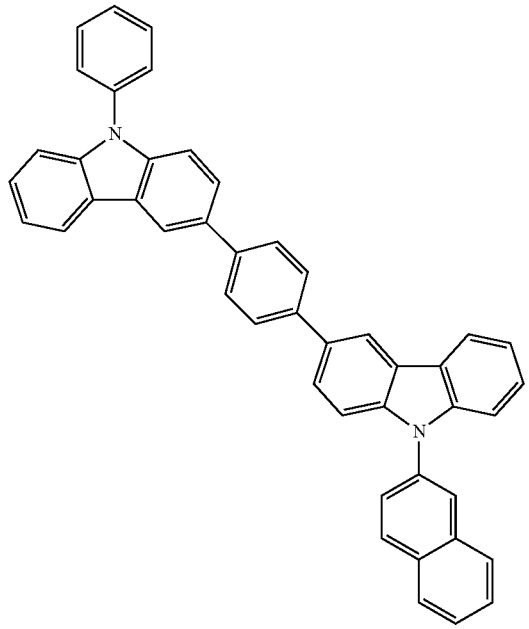
H1-288
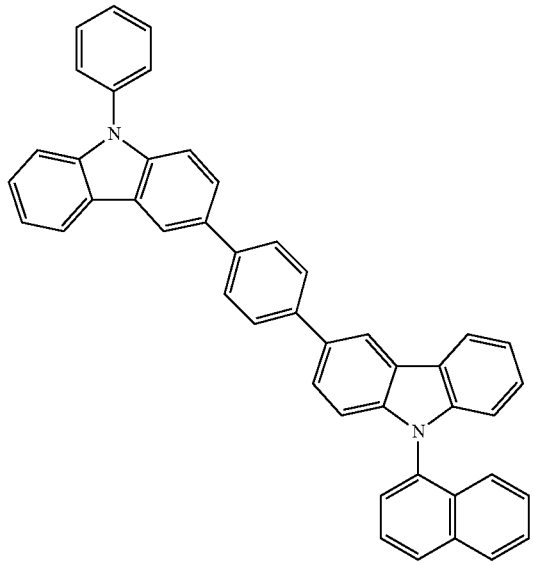
H1-289
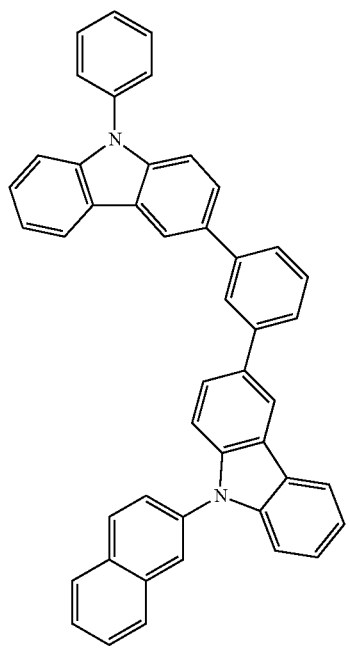
H1-290
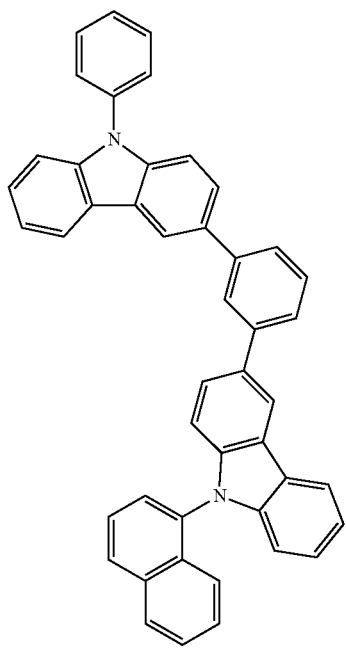

-continued
H1-291
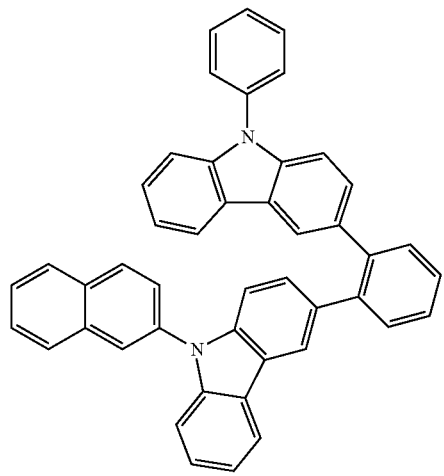
H1-292
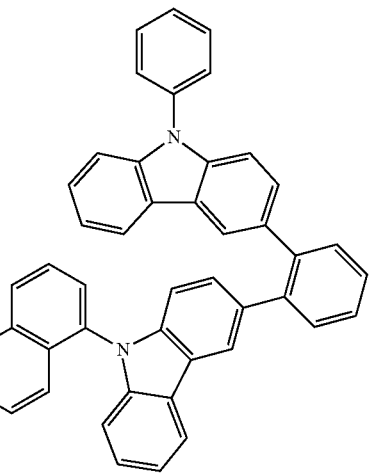
H1-294
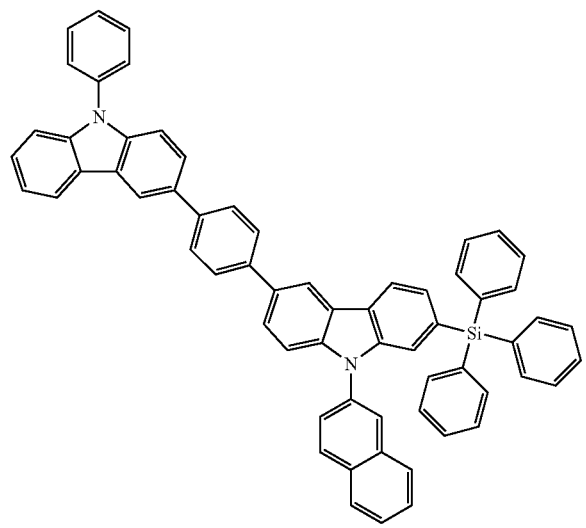
H1-296
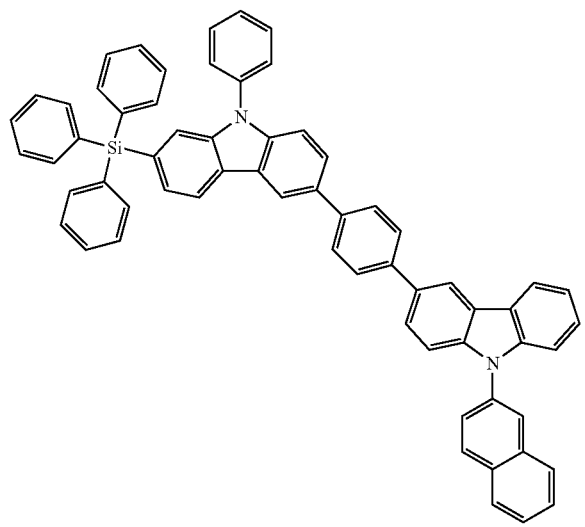
H1-299
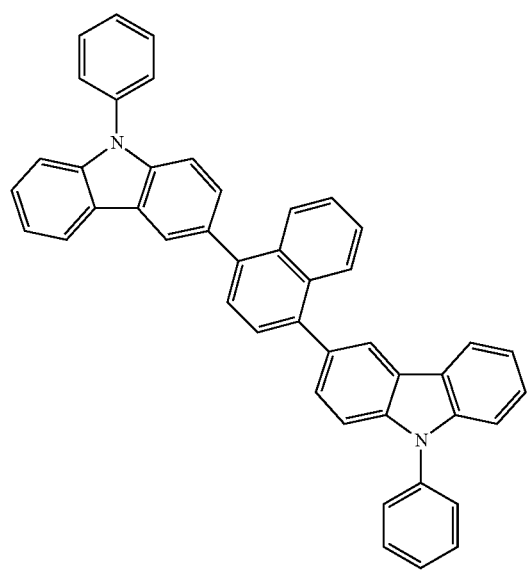
H1-300
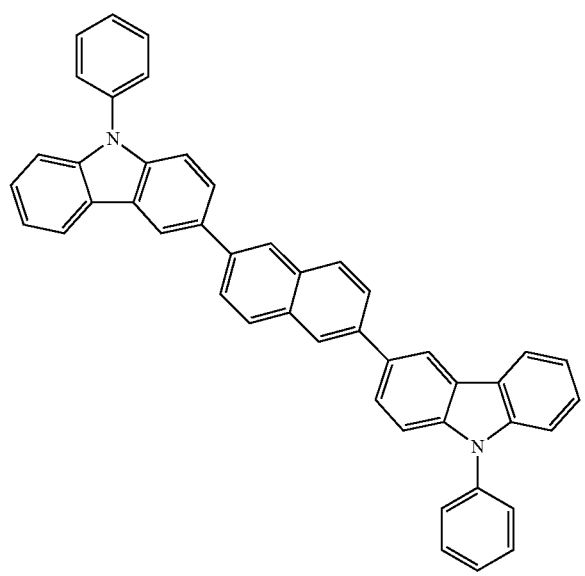

H1-301
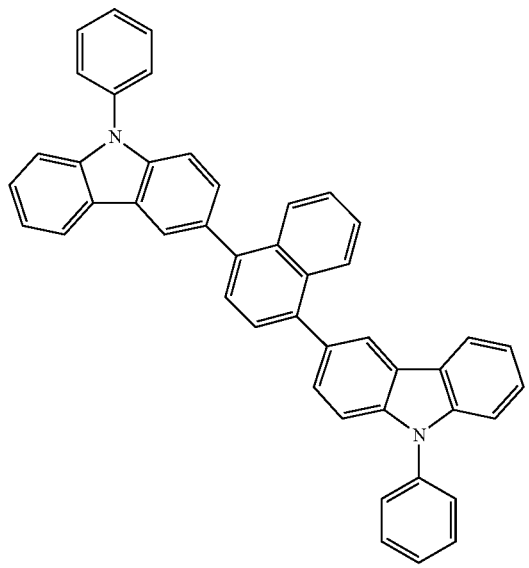
H1-302
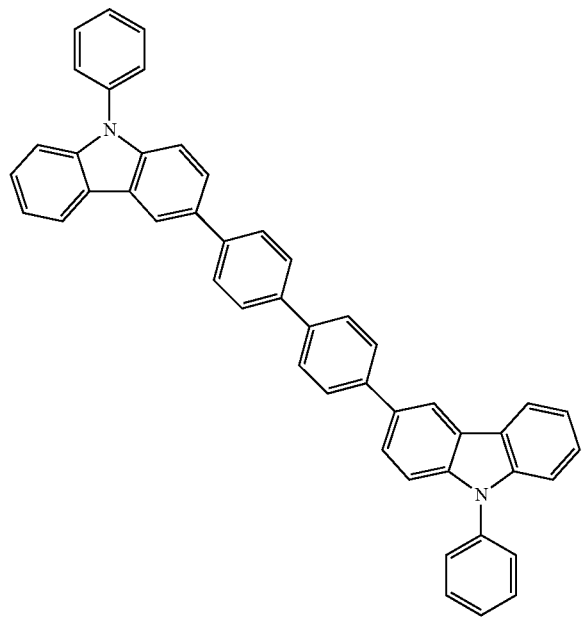
I1-303
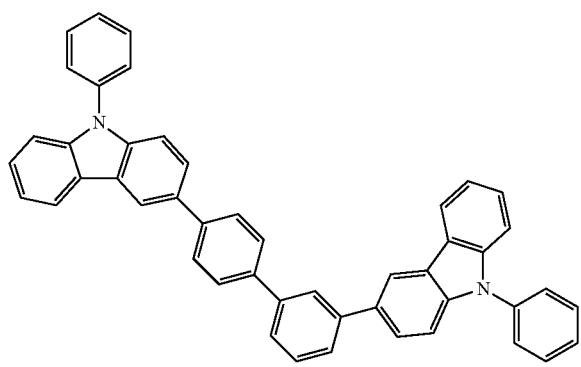
I1-304
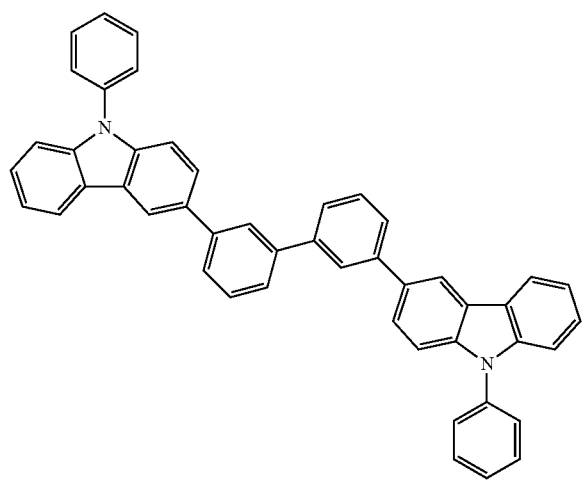

H1-305
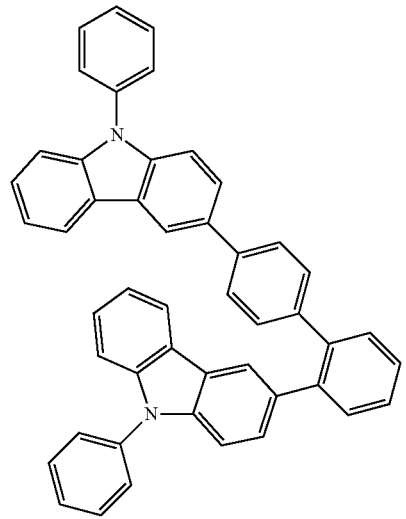
H1-306
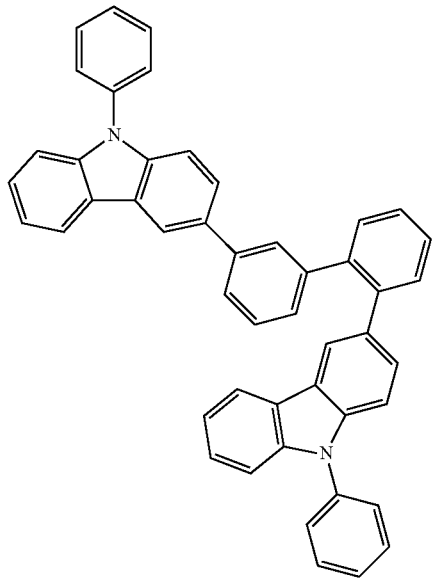
H1-307
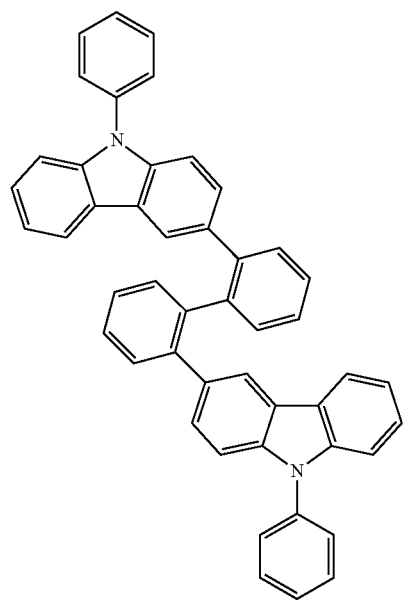
H1-308
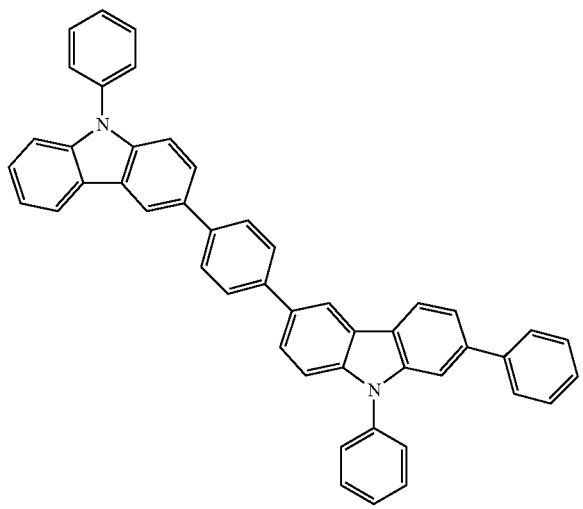

-continued
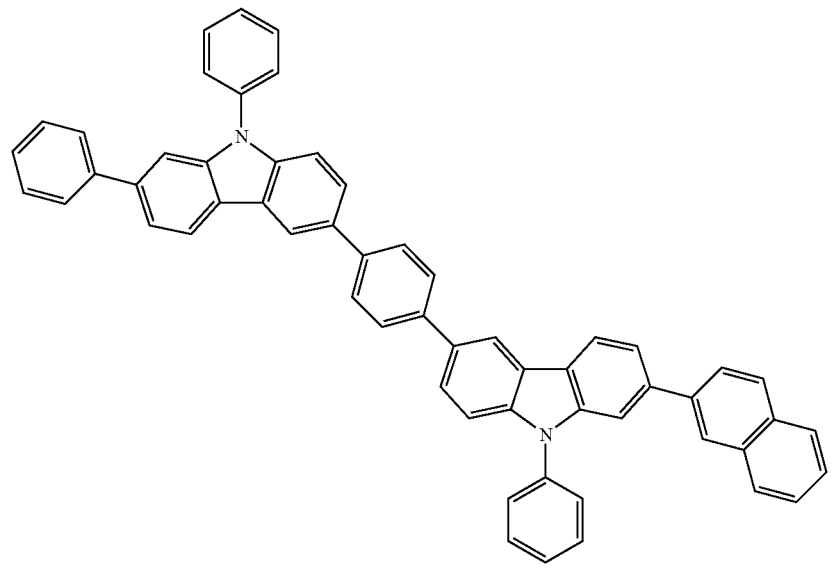
H1-310
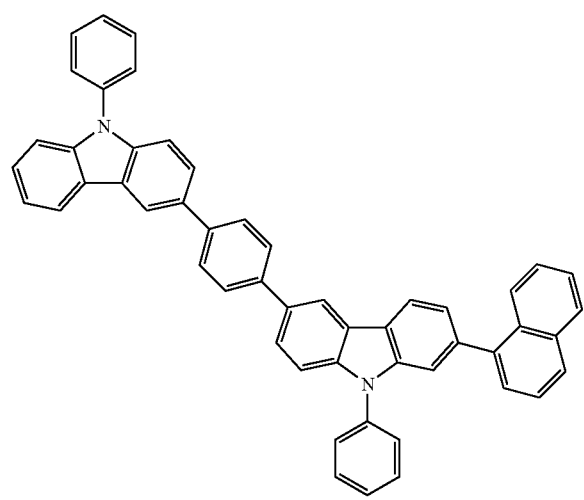
H1-311
H1-312

H1-313
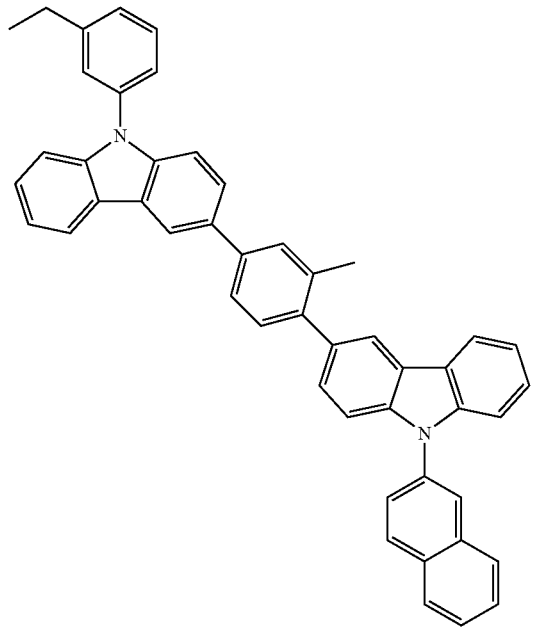
H1-314
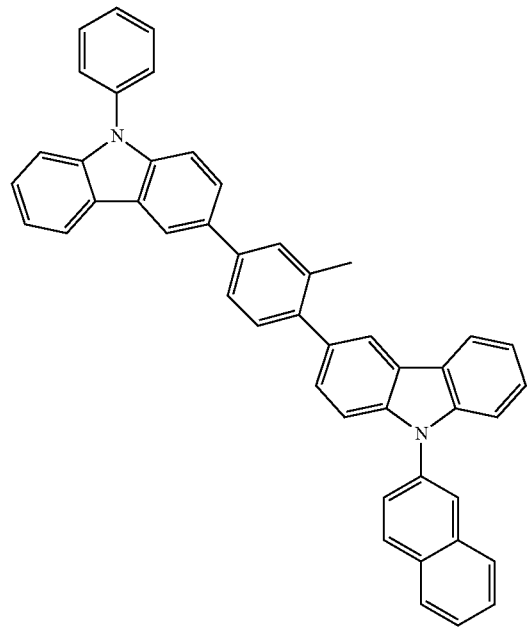
H1-315
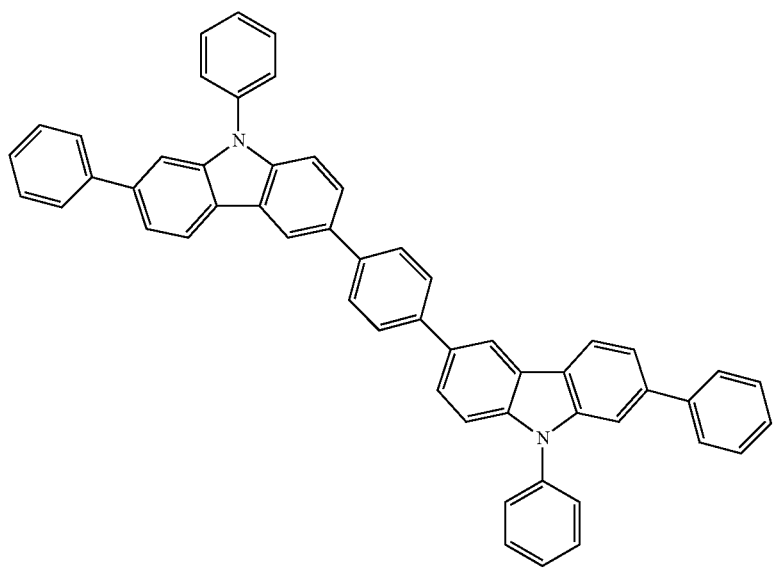

H1-316
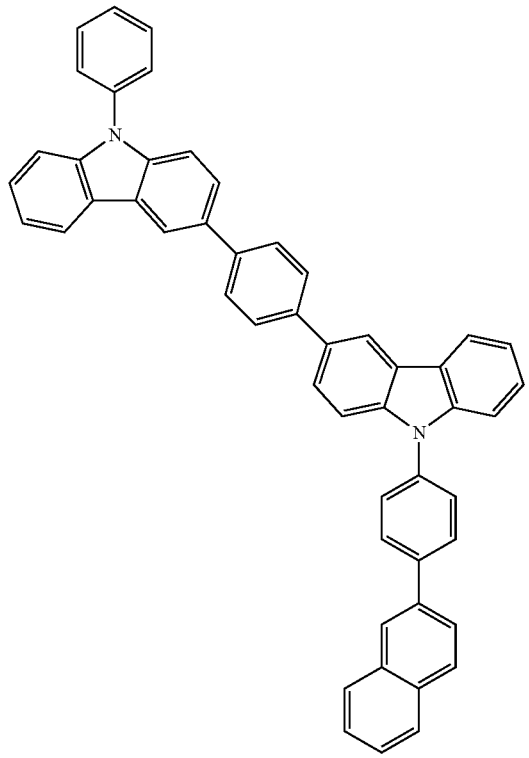
H1-317
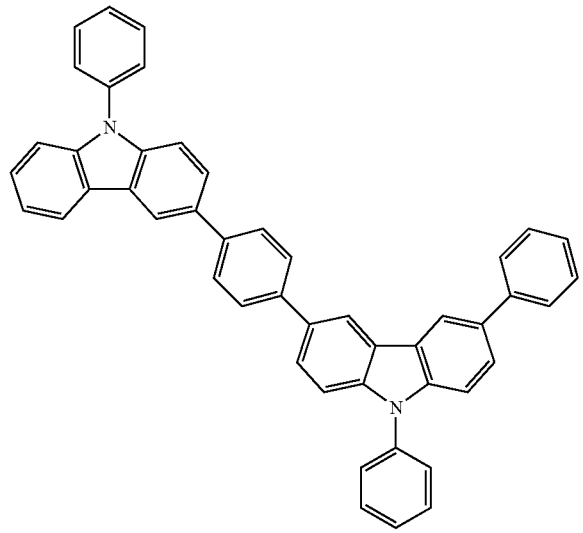
H1-321
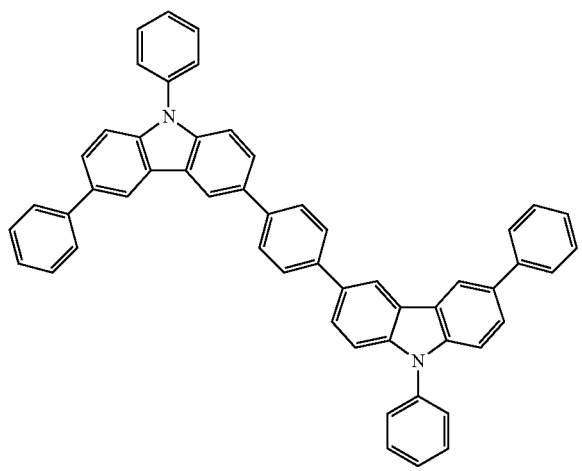
H1-323
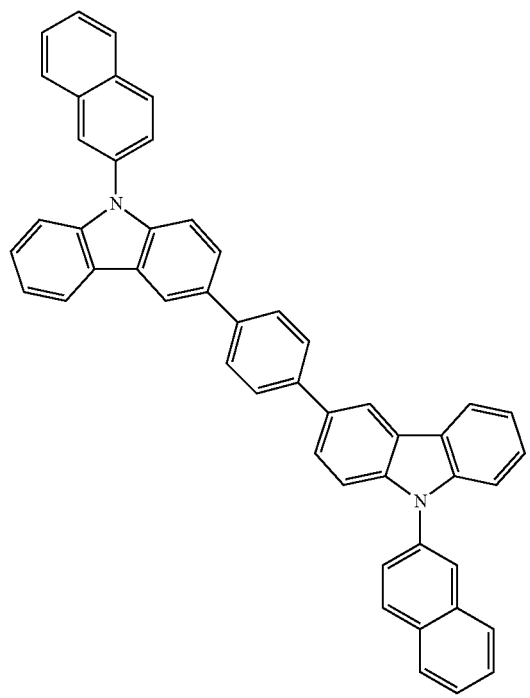

-continued
H1-324
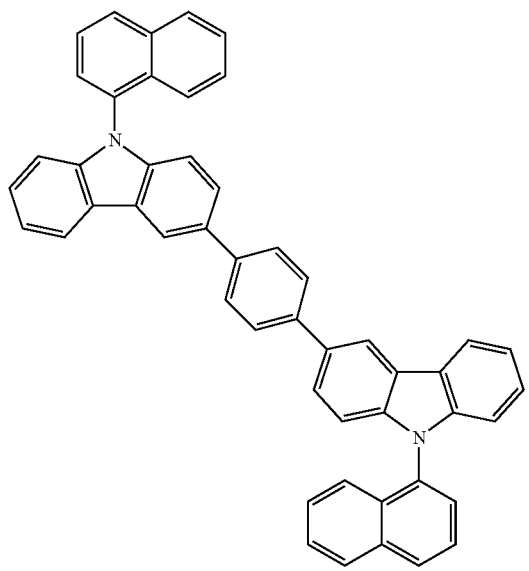
H1-326
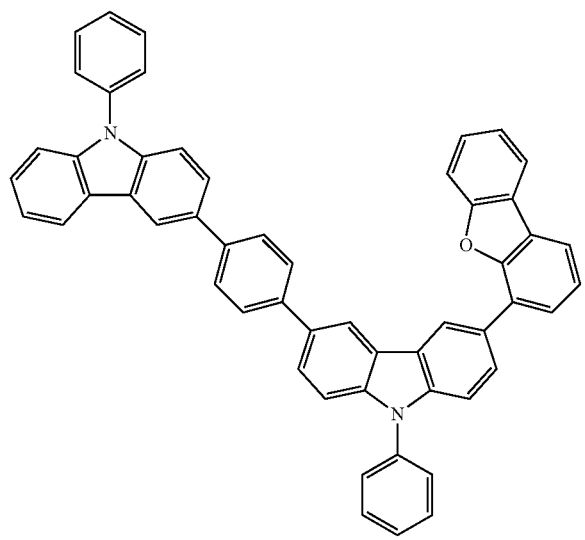
H1-327
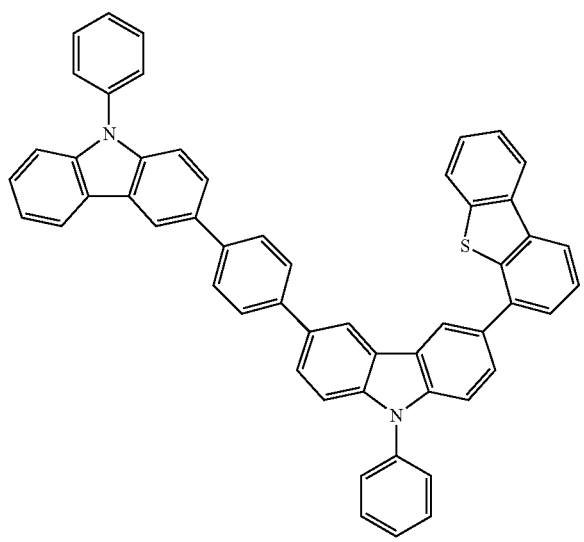
H1-328
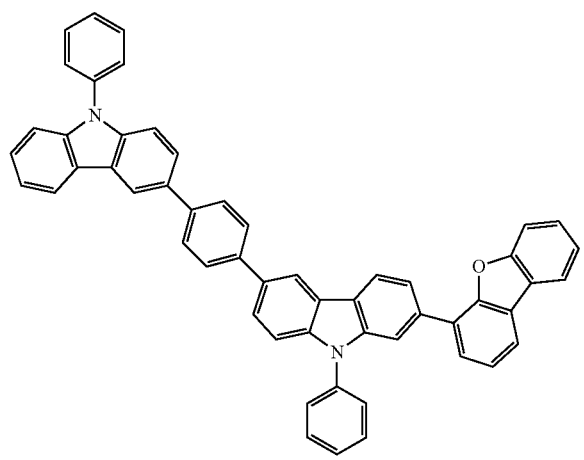

-continued
H1-329
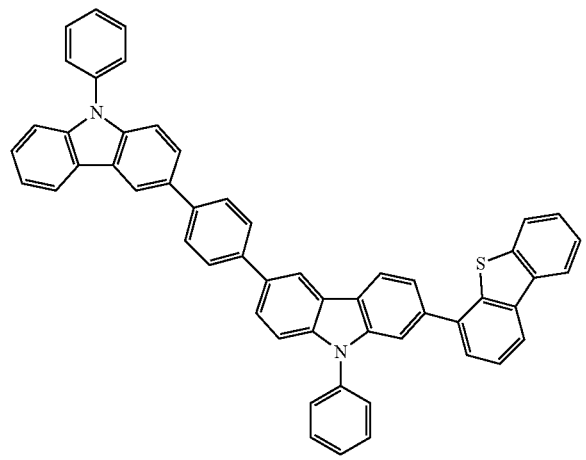
H1-334
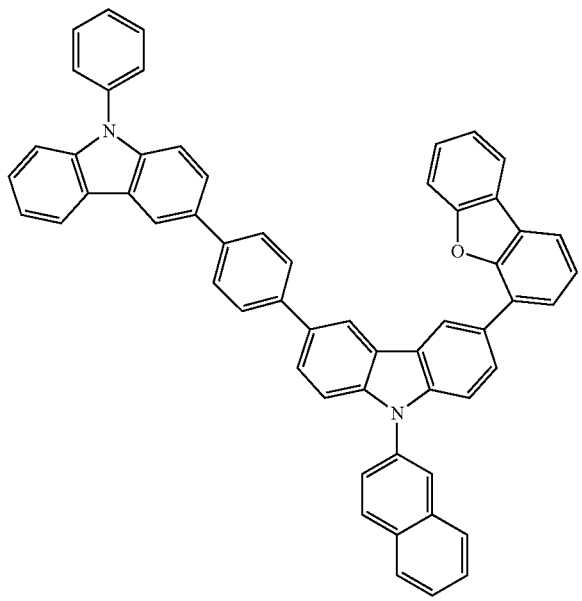
H1-335
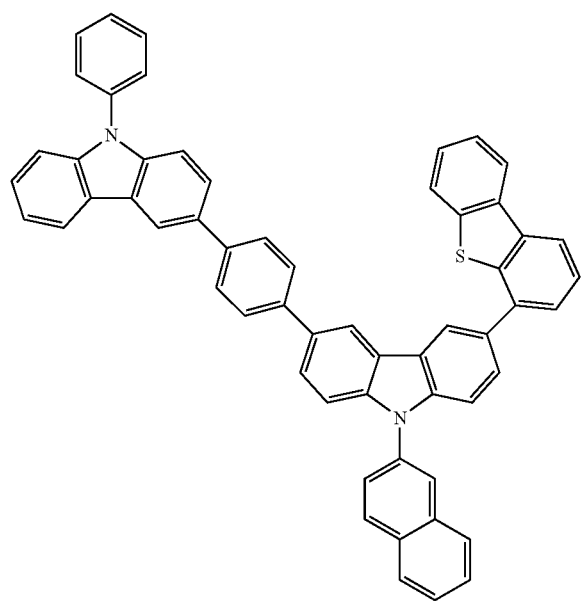
H1-336
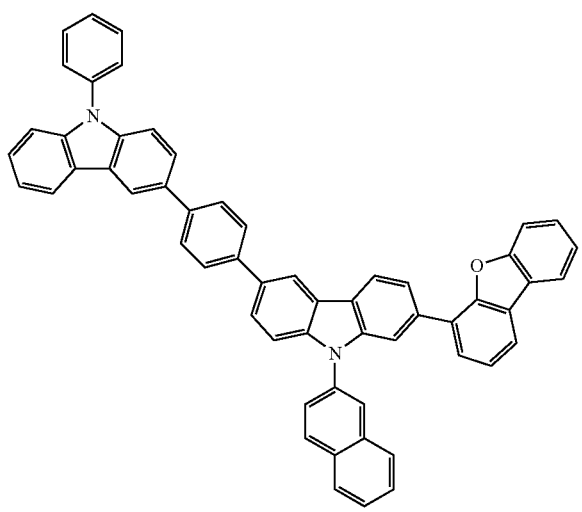

-continued
H1-337
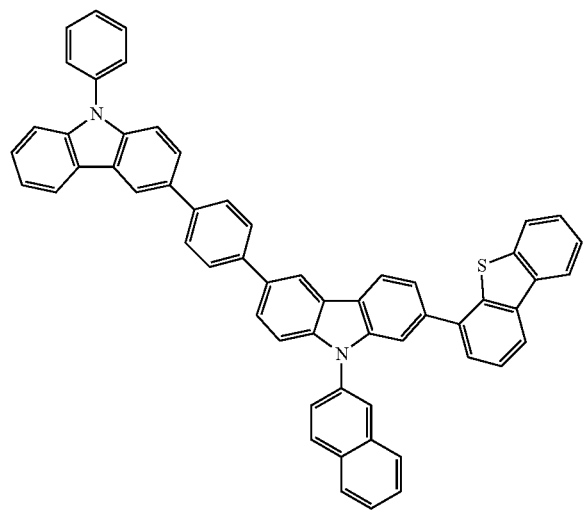
H1-342
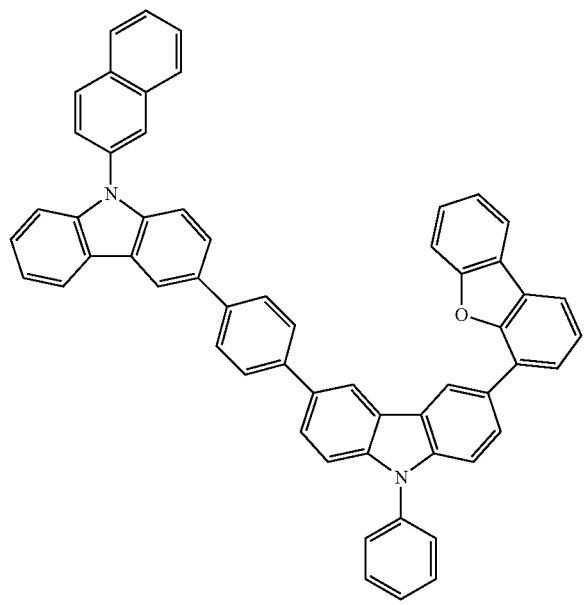
H1-343
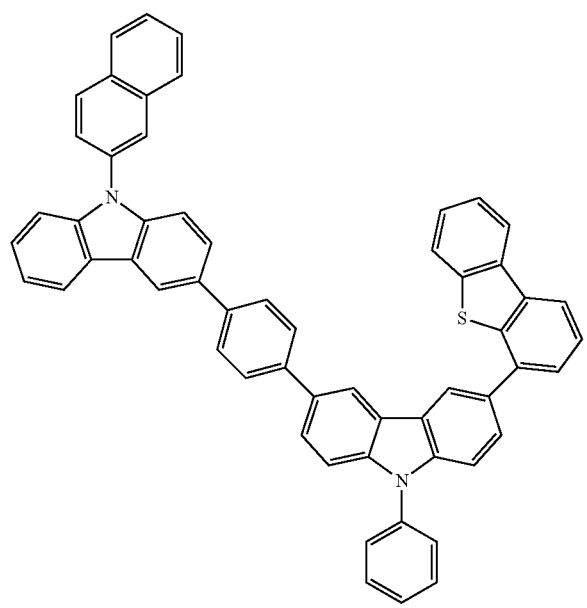
H1-344
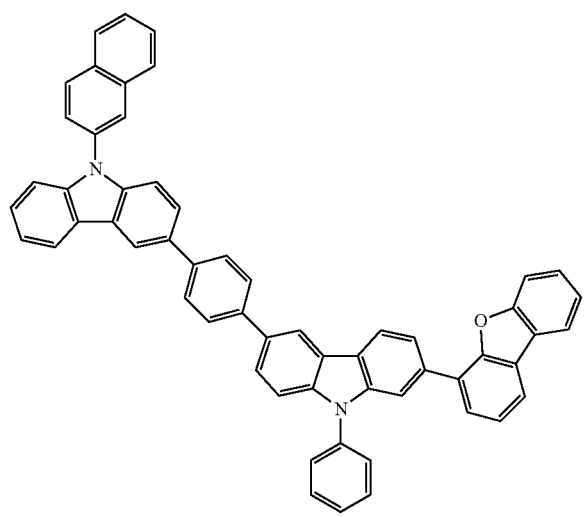

H1-345
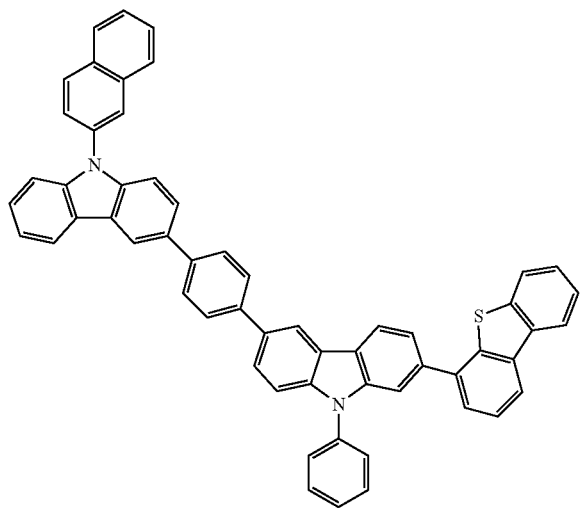
H1-346
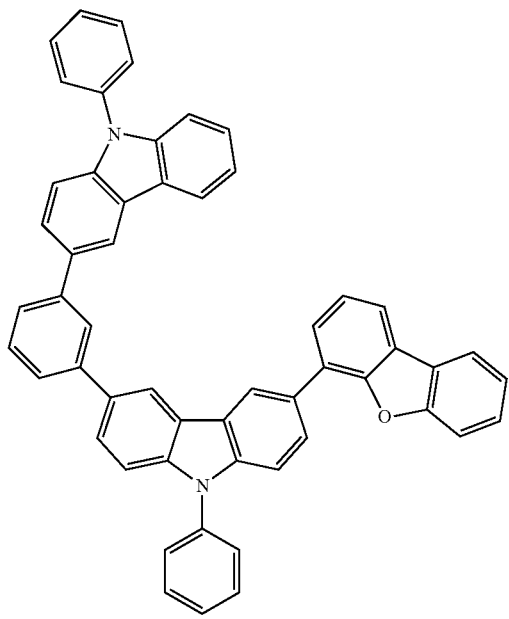
H1-347
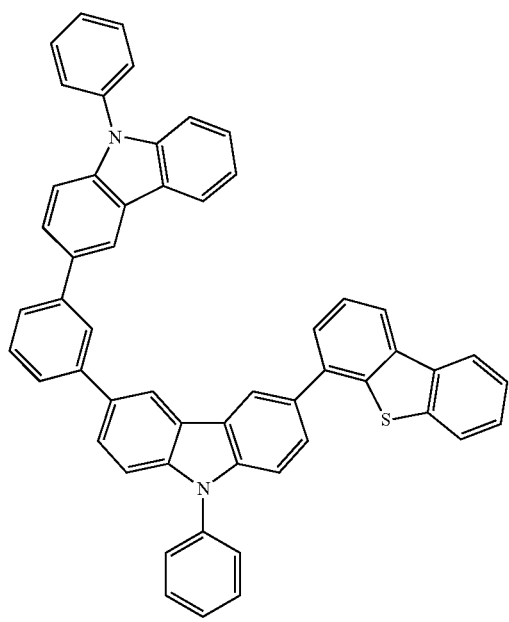
H1-348
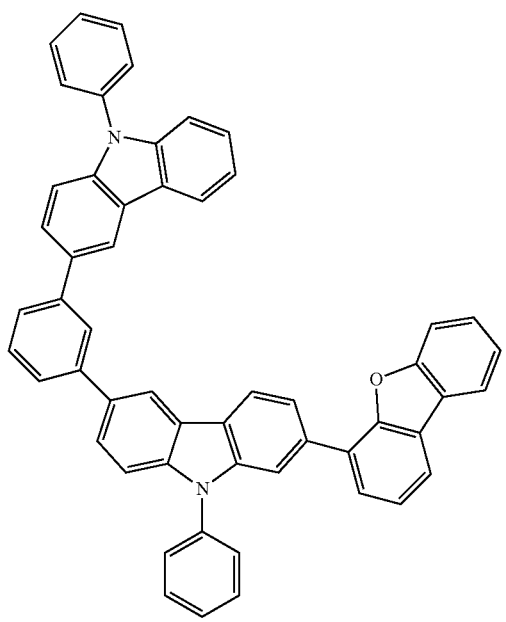

H1-349
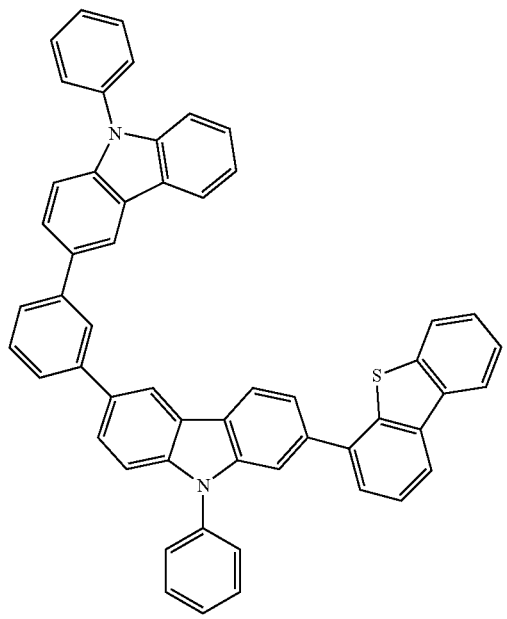
H1-369
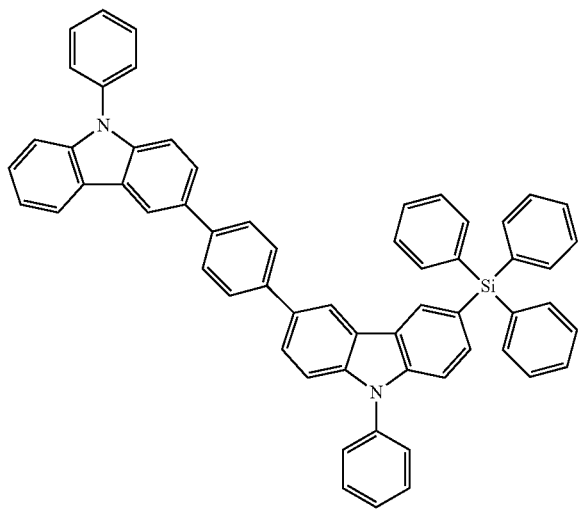
H1-371
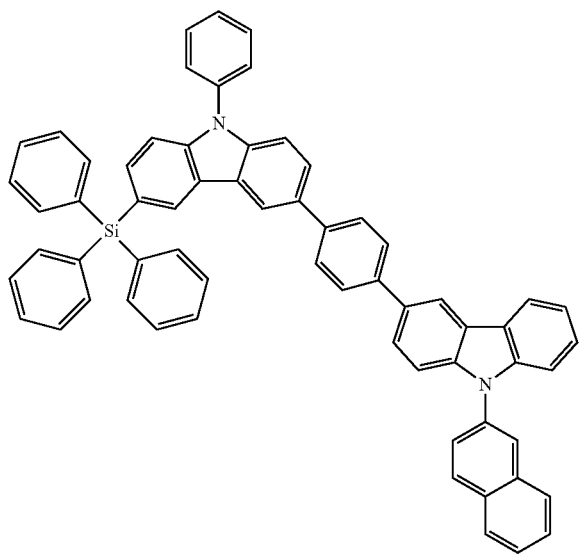
H1-372
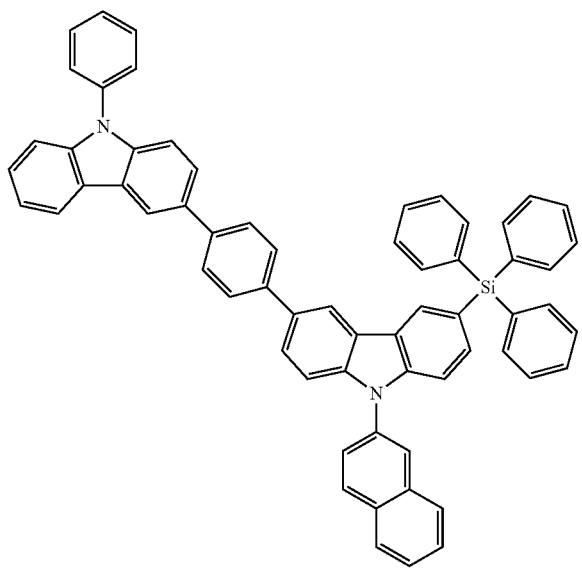

-continued
H1-380
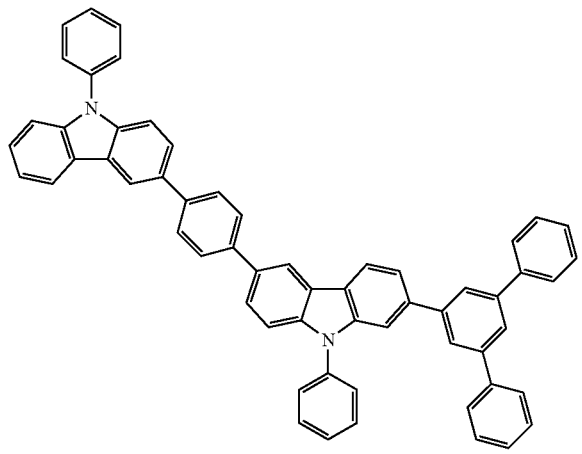
H1-381
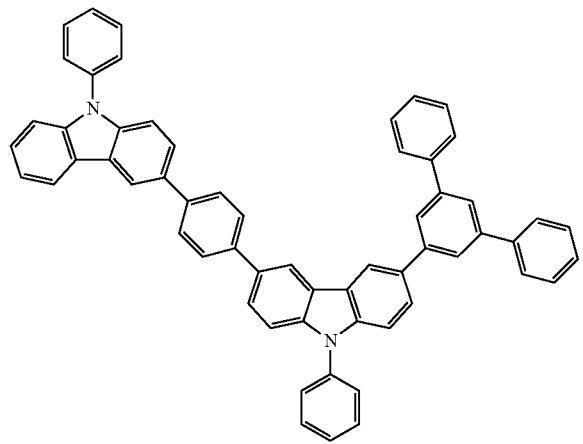
H1-382
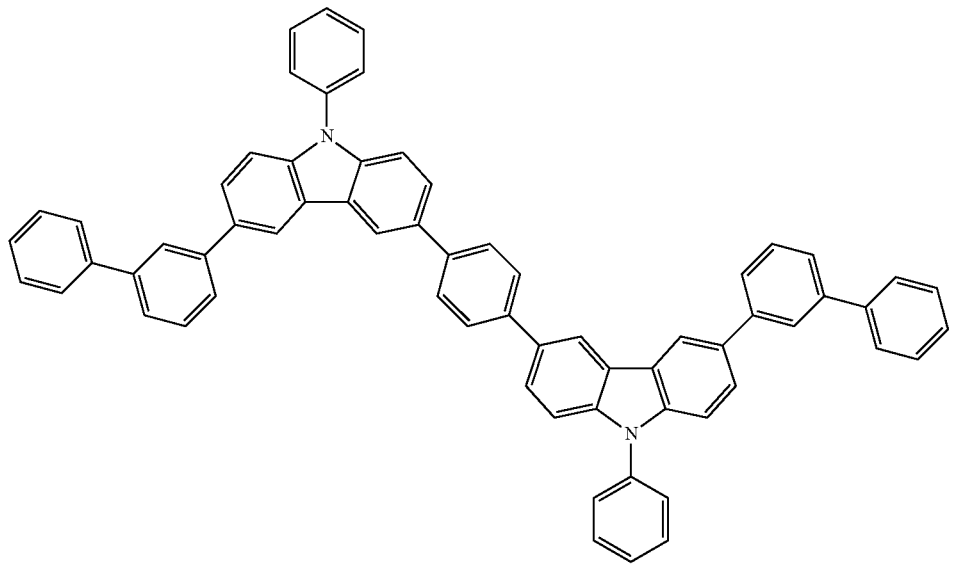
H1-383
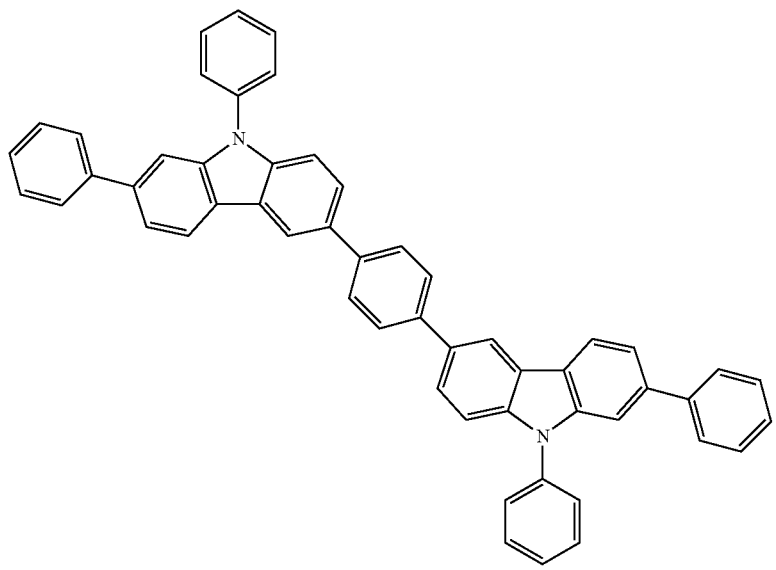

-continued
H1-384
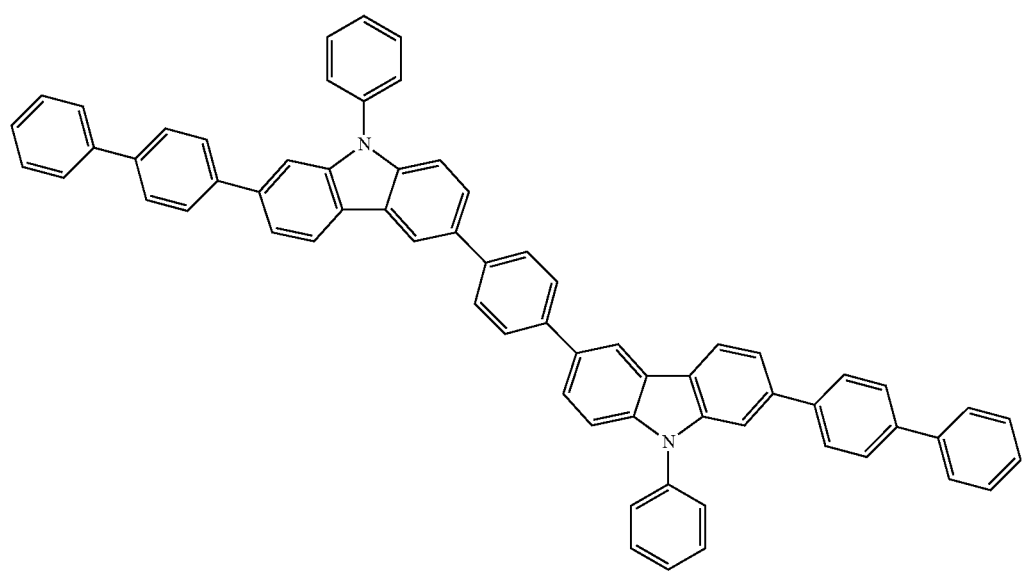
H1-385
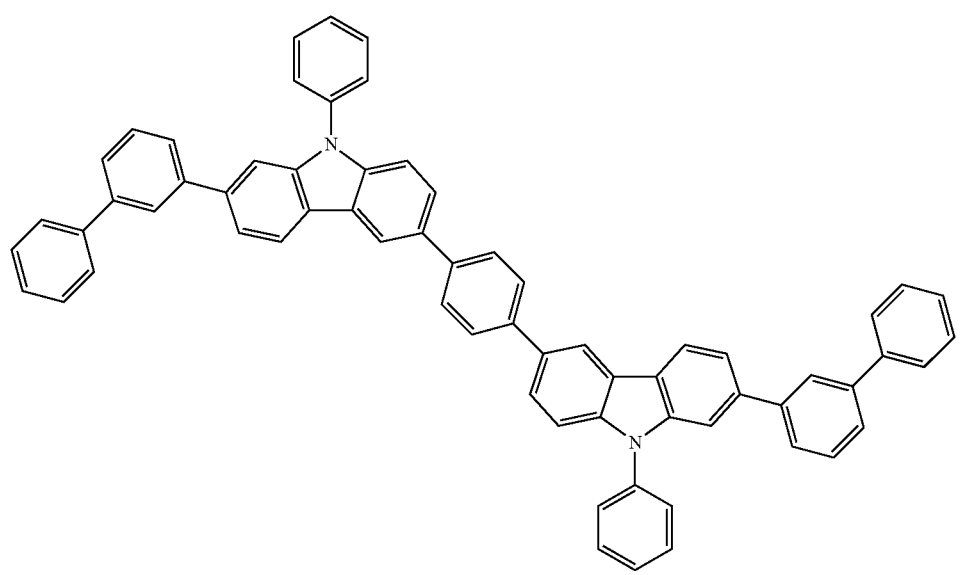
H1-386  H1-387
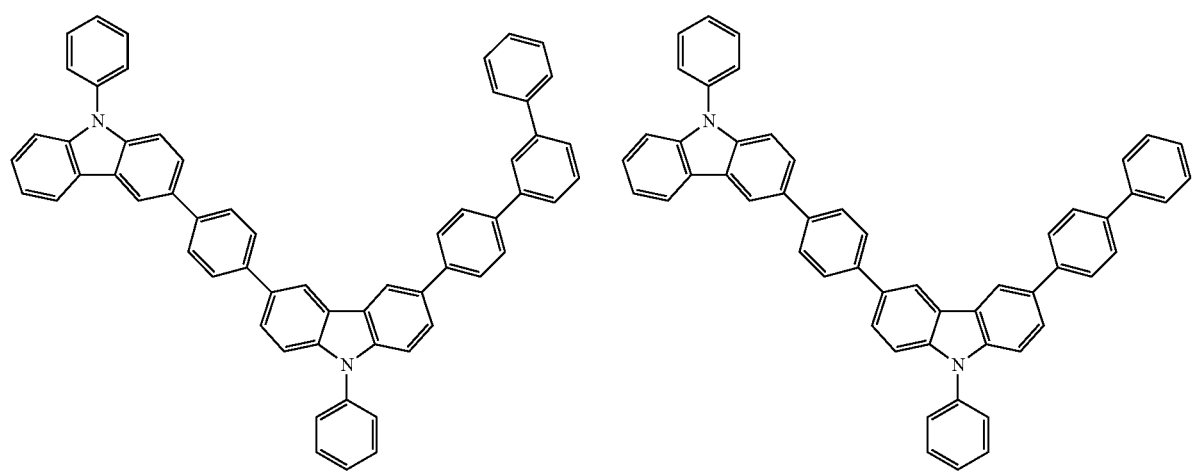

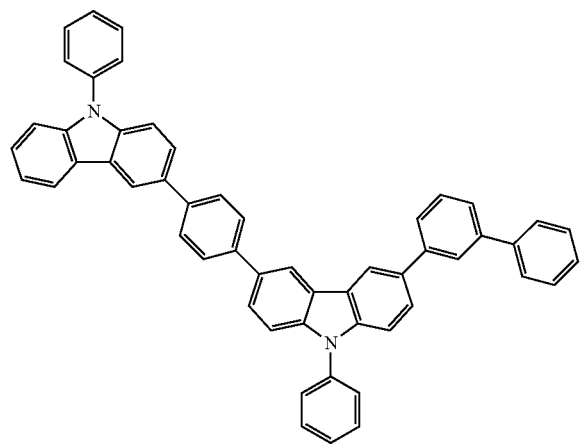
H1-388
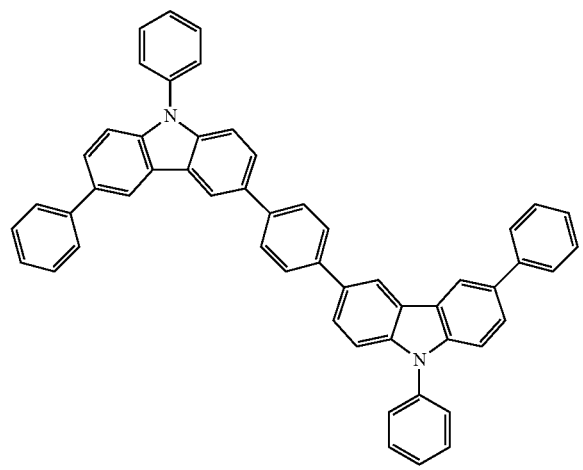
H1-389
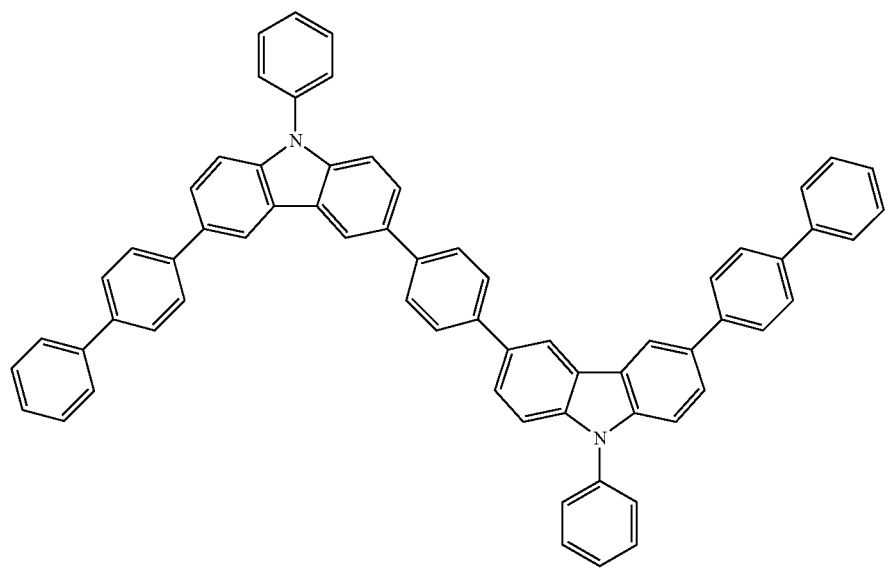
H1-390

H1-391
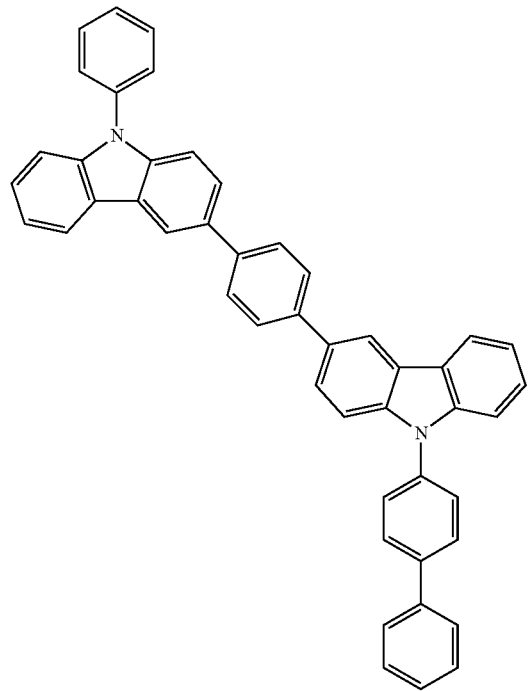
H1-392
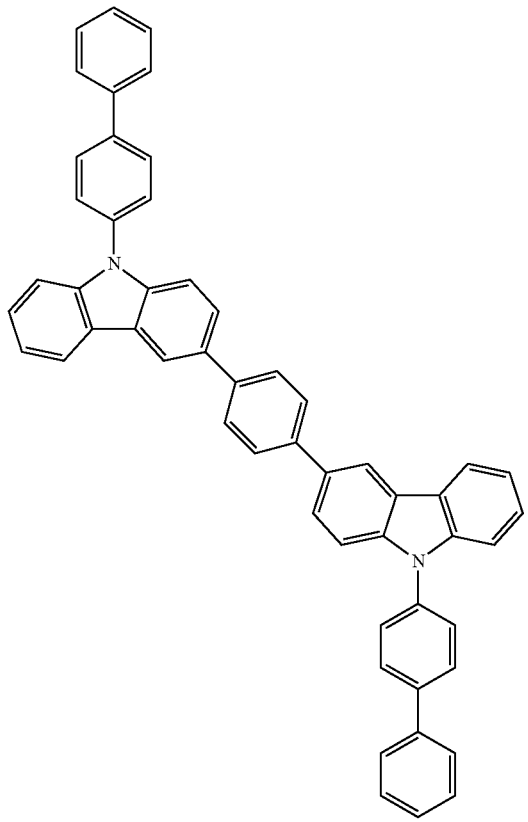
H1-393
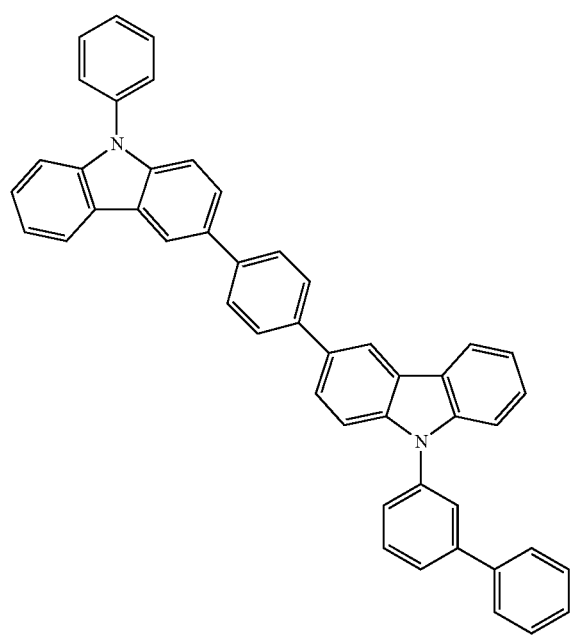
H1-394
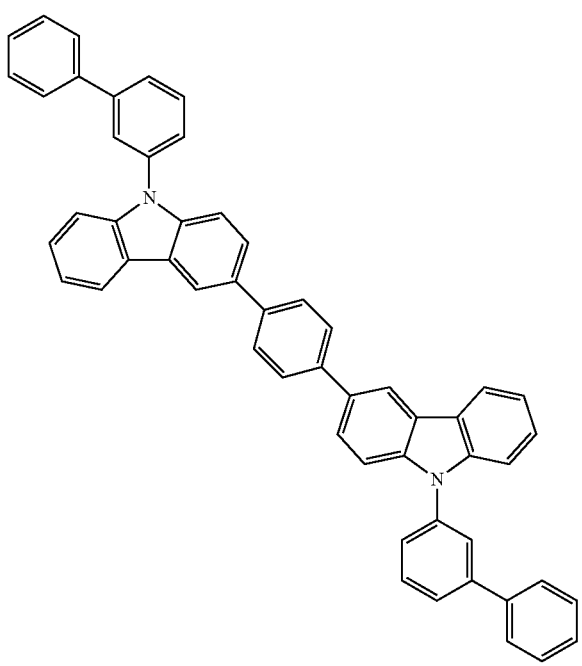

H1-395
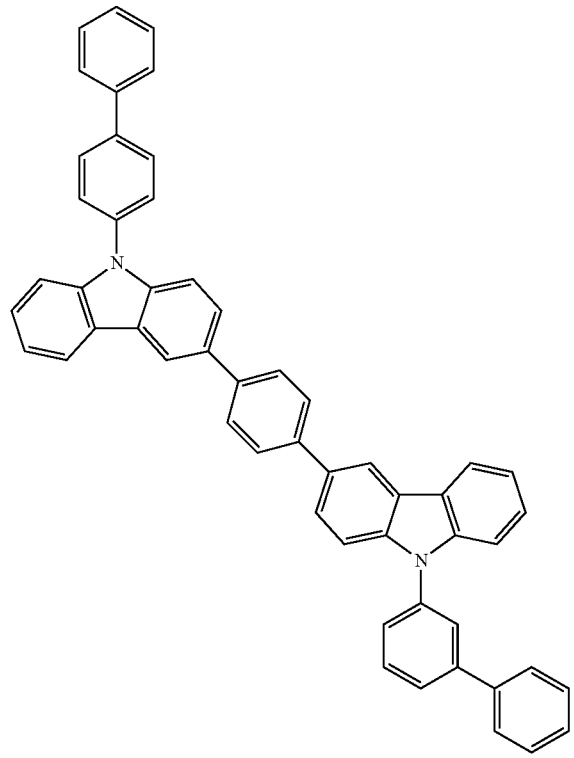
H1-412
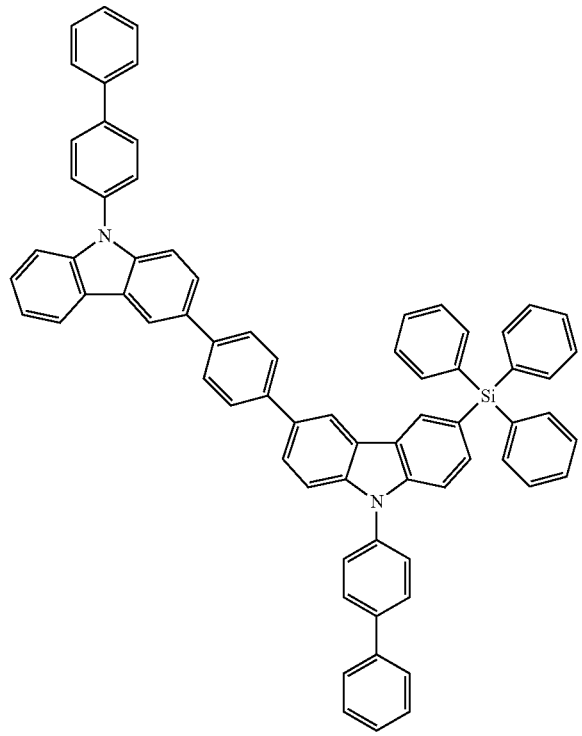
H1-414
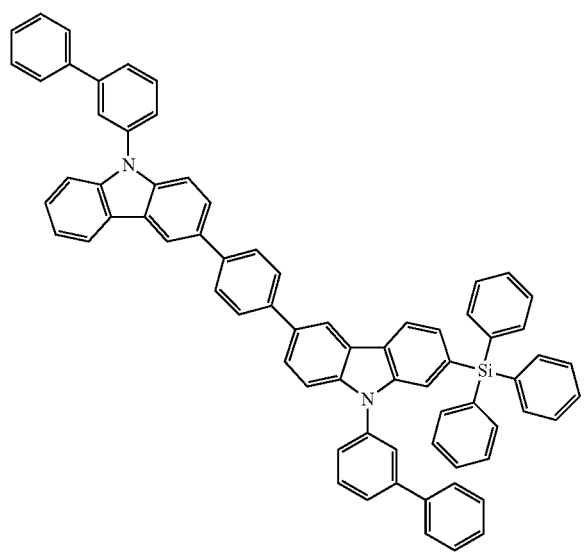
H1-416
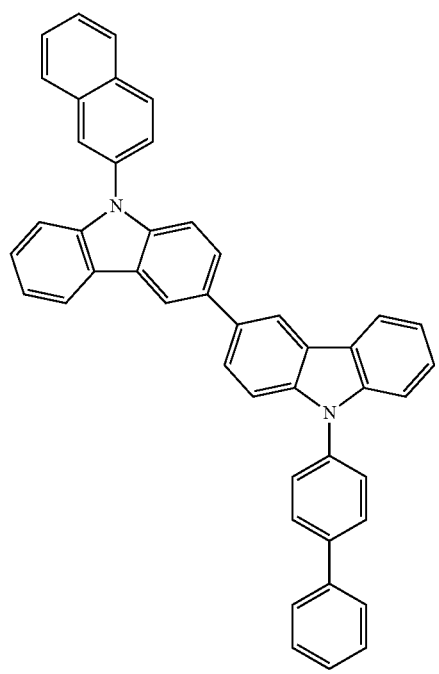

H1-417
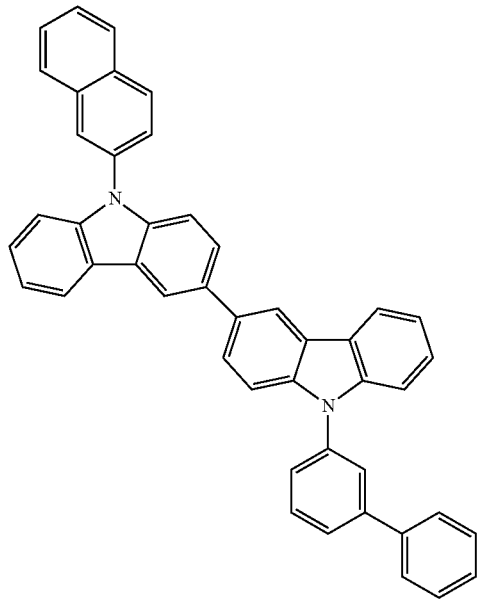
H1-418
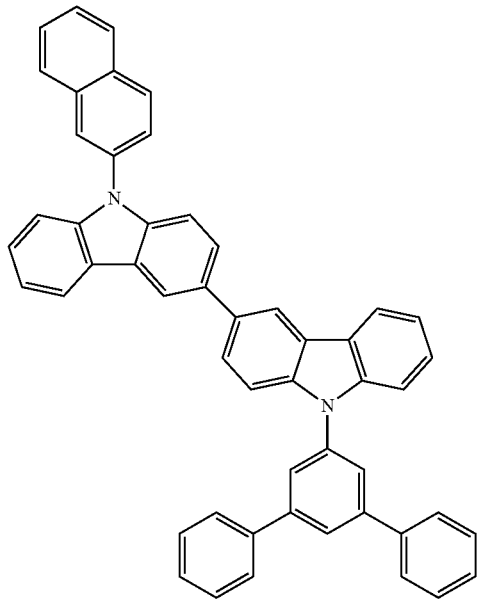
H1-419
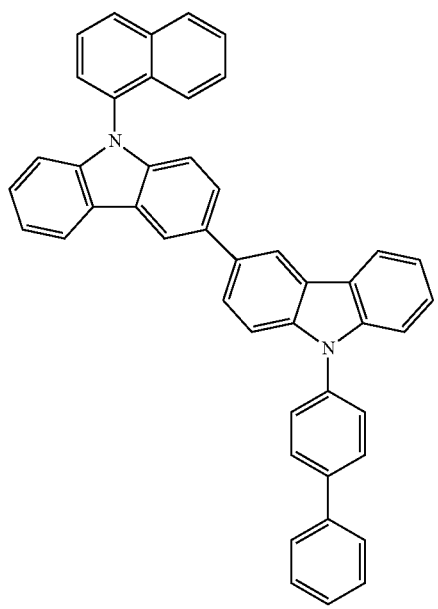
H1-420
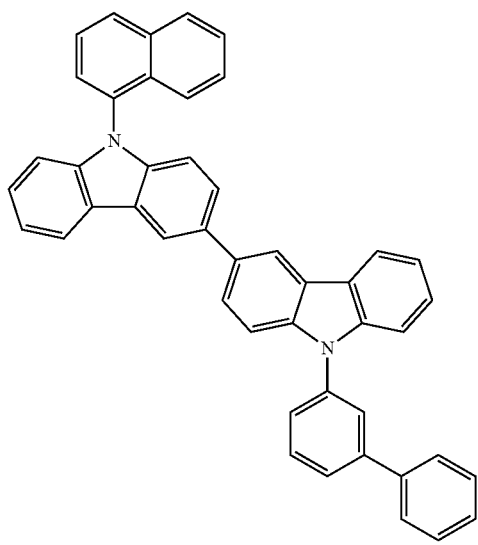

H1-421
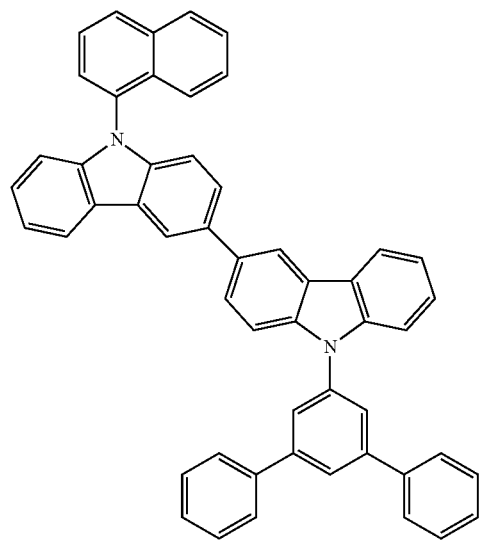
H1-422
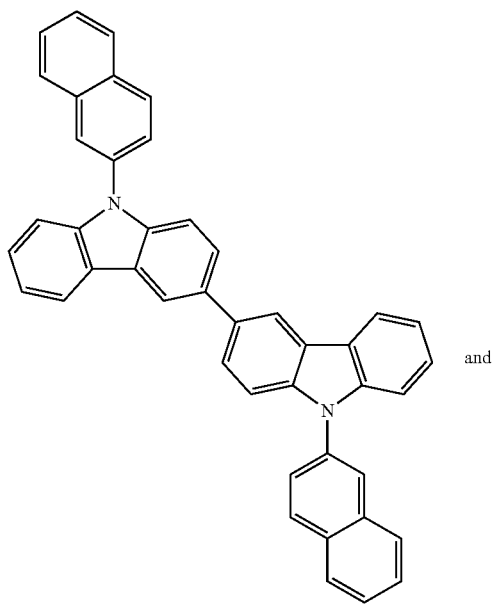
and
H1-423
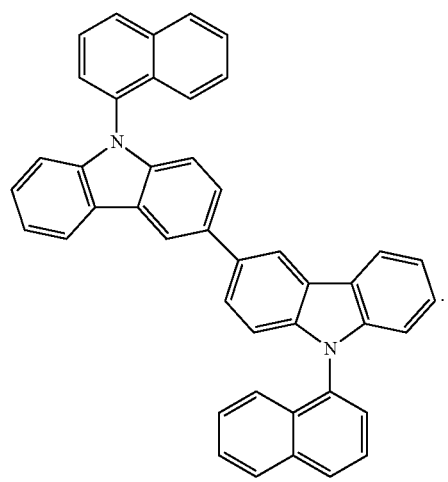
10. The organic electroluminescent device according to claim 1, wherein the compound of formula 2 is selected from the group consisting of:
H2-15
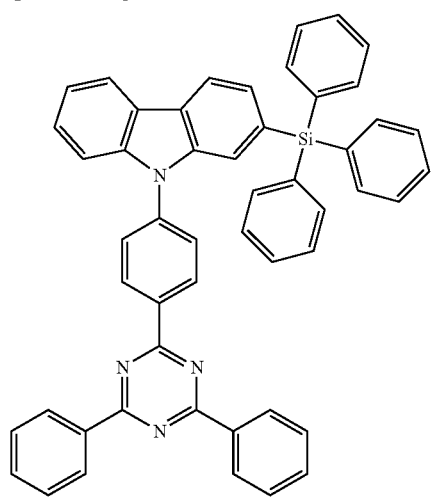
-continued
H2-31
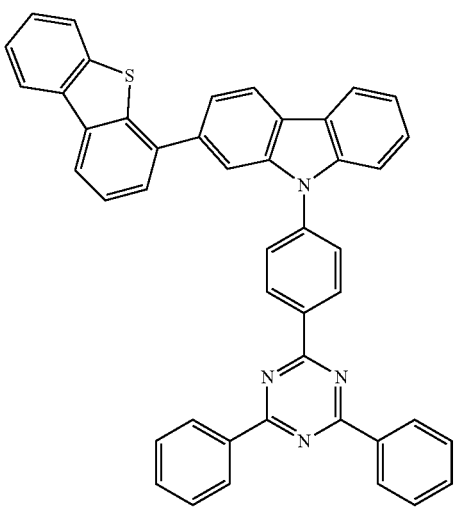

H2-32
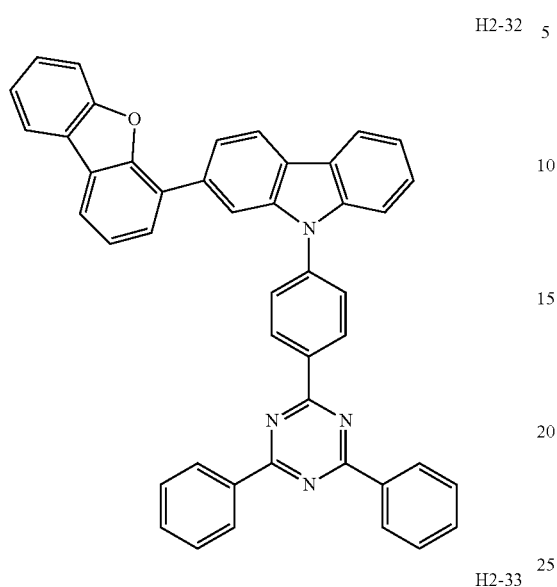
H2-33
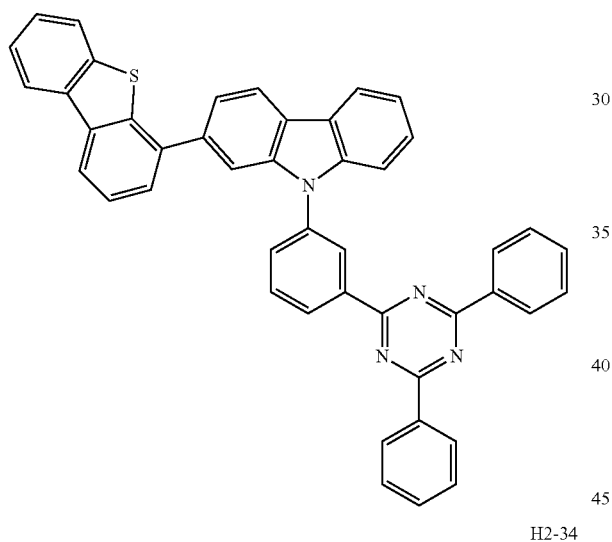
H2-34
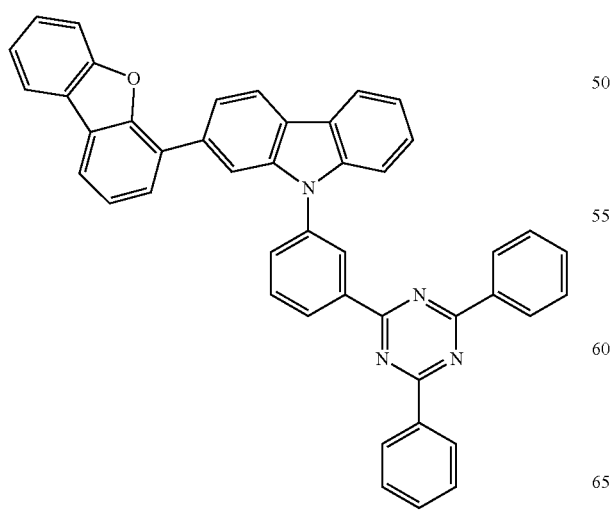
H2-35
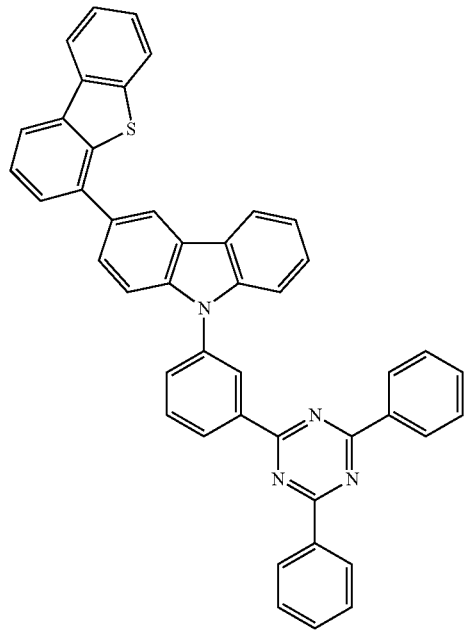
H2-41
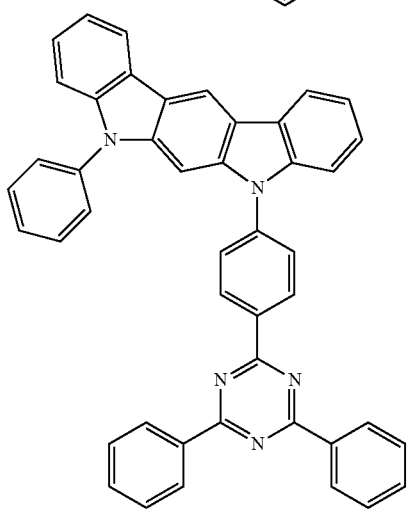
H2-42
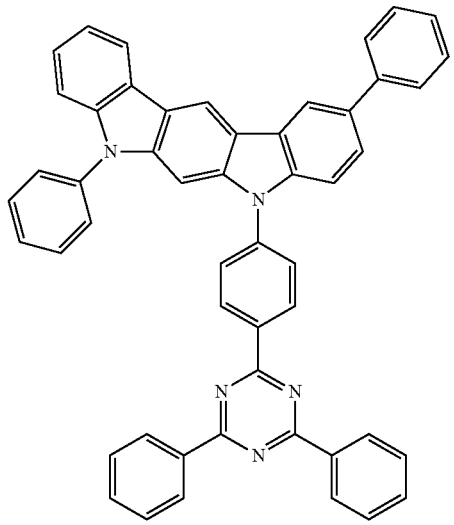

H2-43
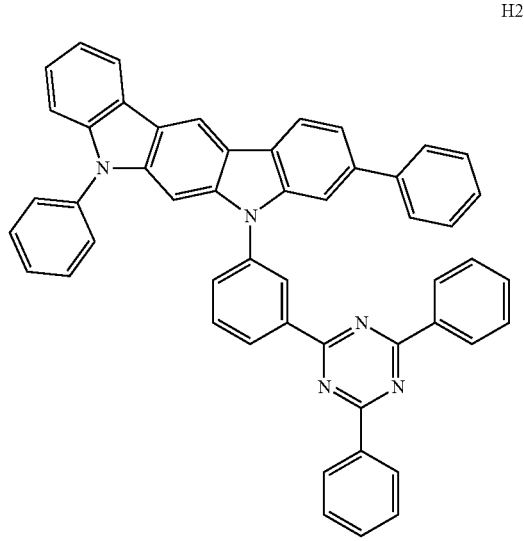
H2-44
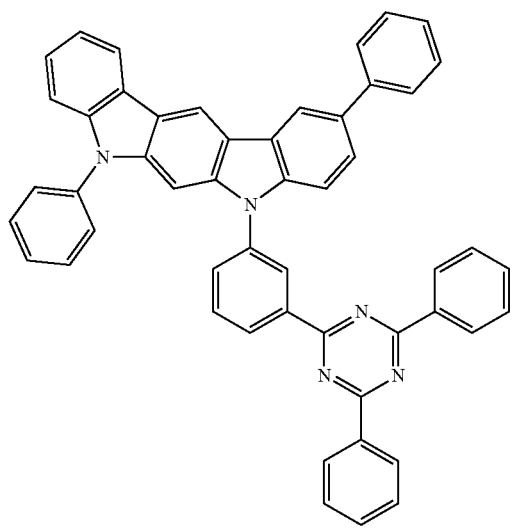
H2-45
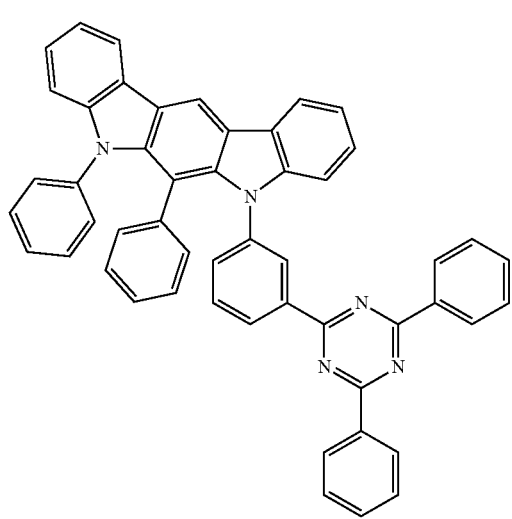
H2-46
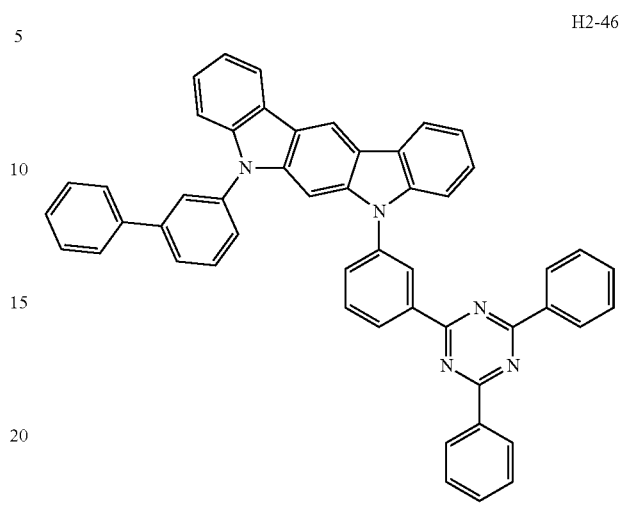
H2-47
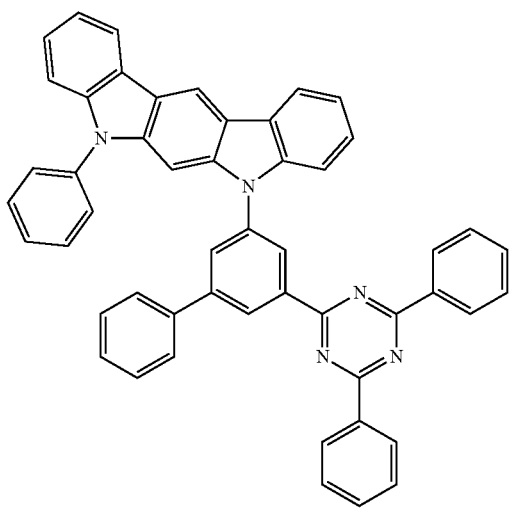
H2-48
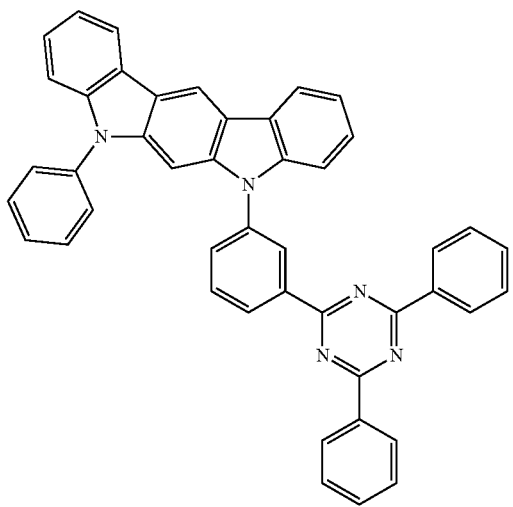

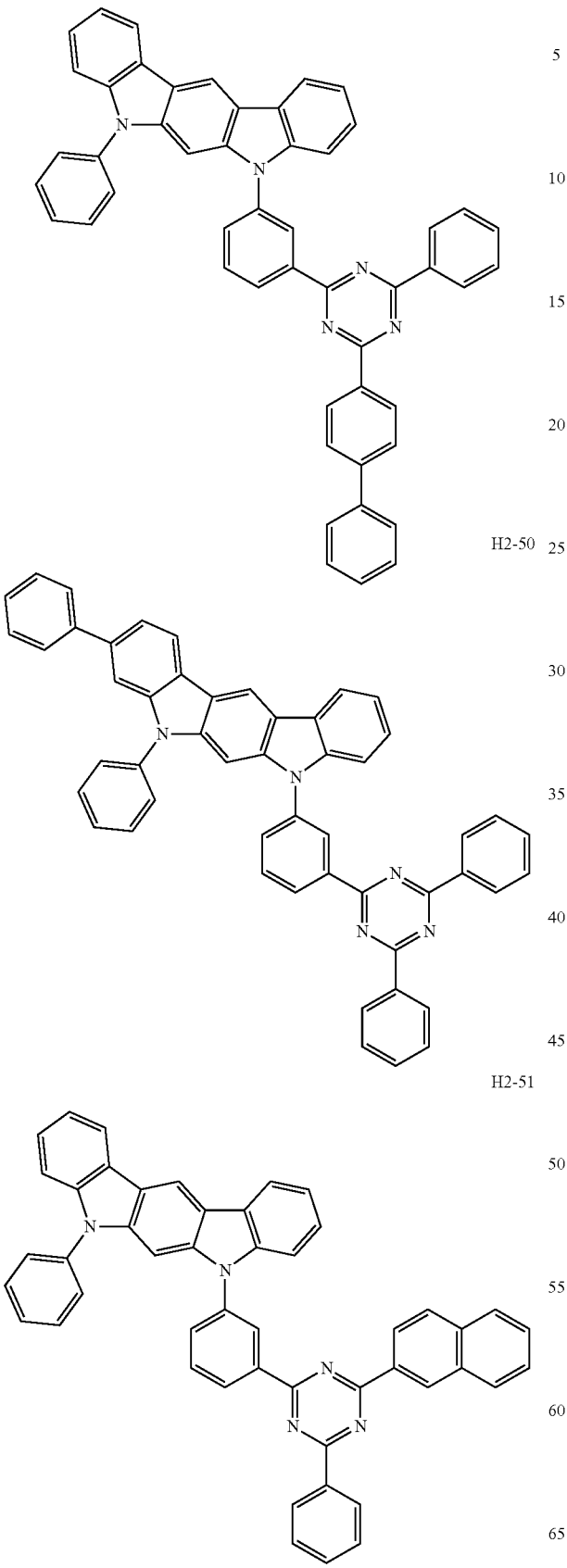
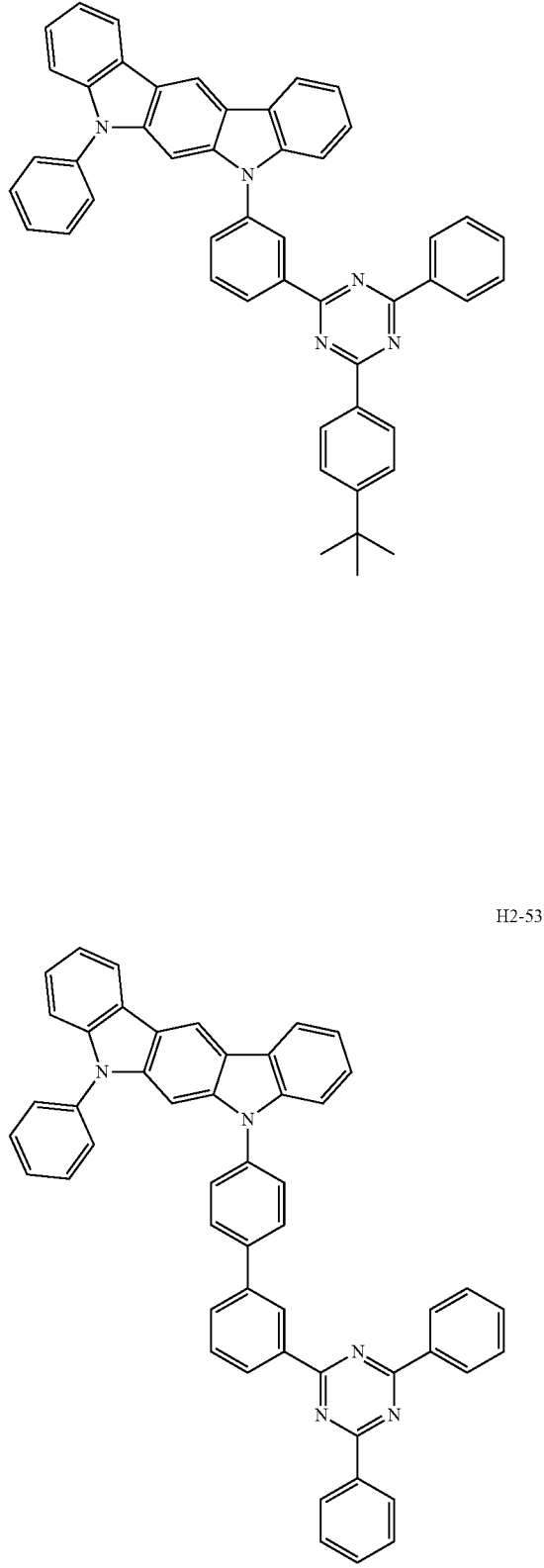

H2-54
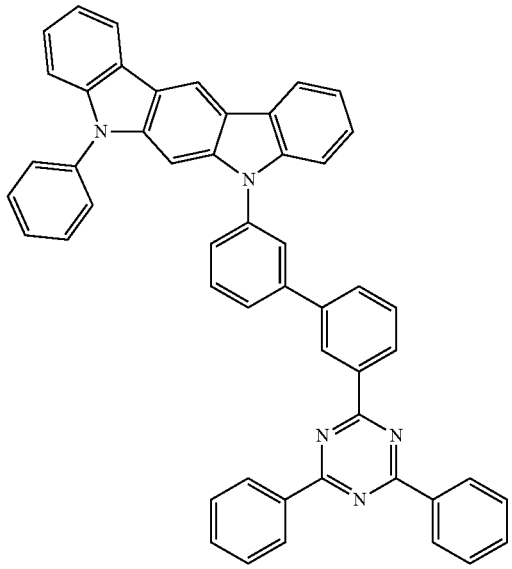
H2-55
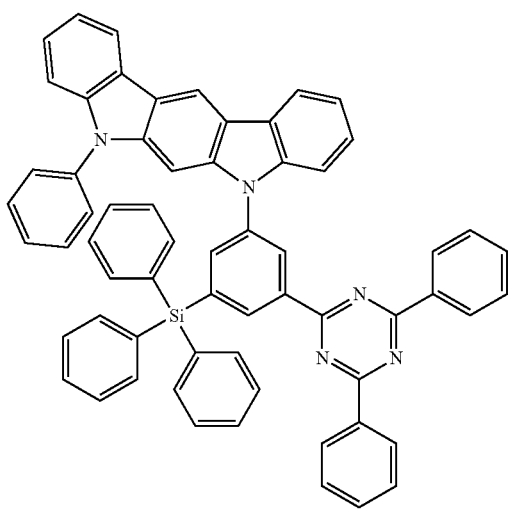
H2-56
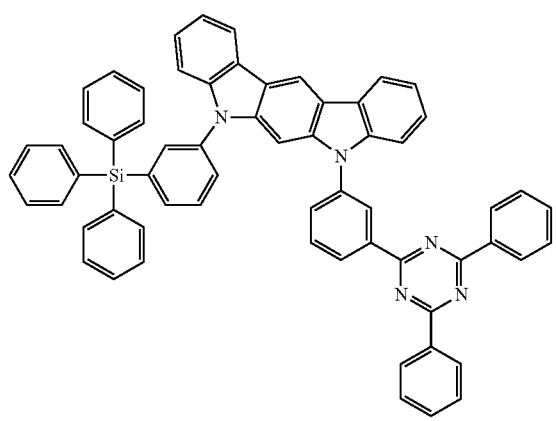
H2-57
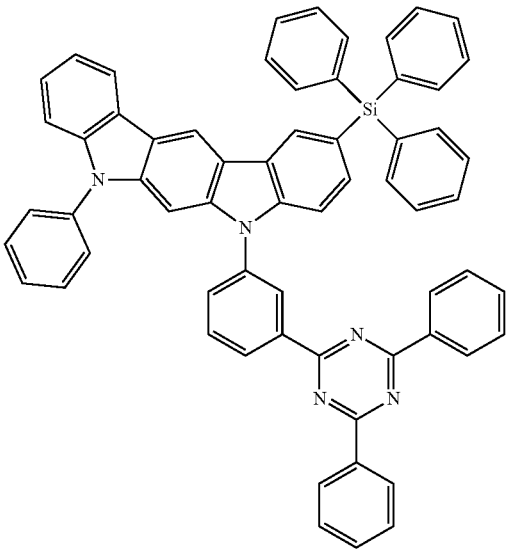
H2-58
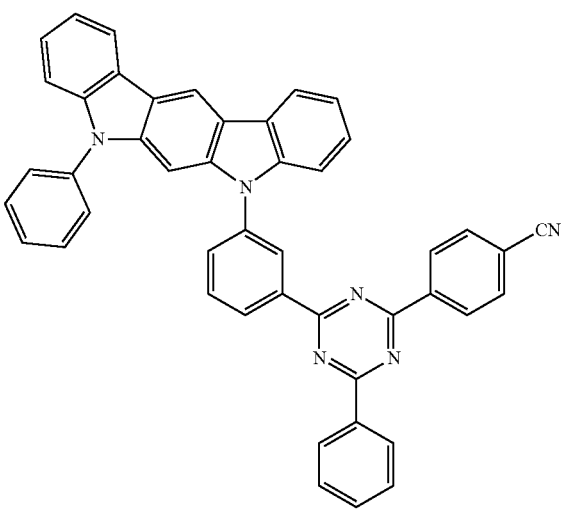
H2-59
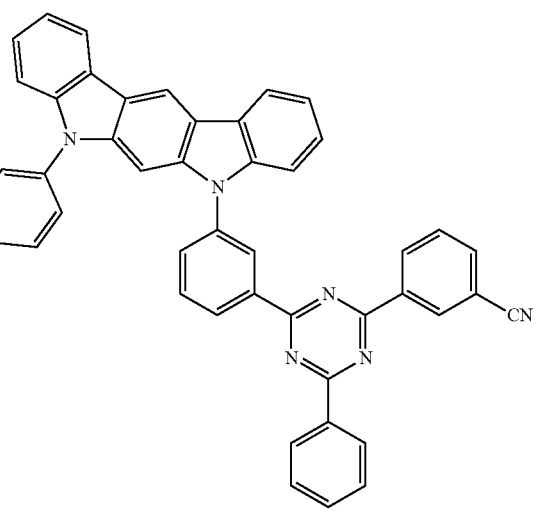

H2-60
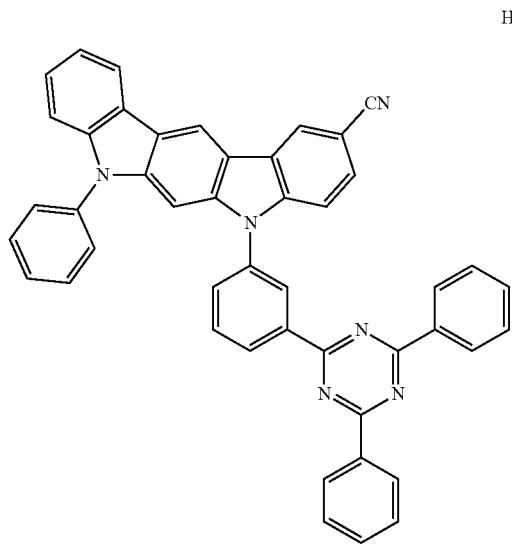
H2-61
H2-62
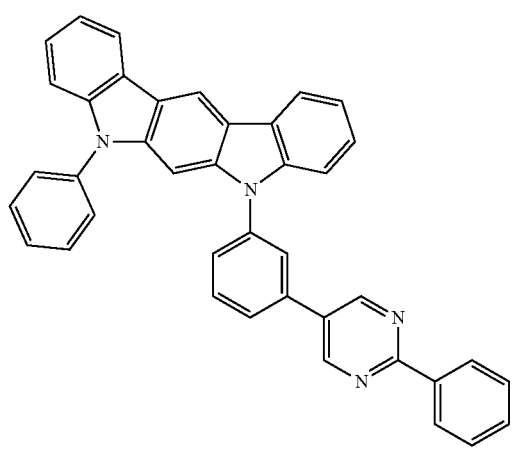
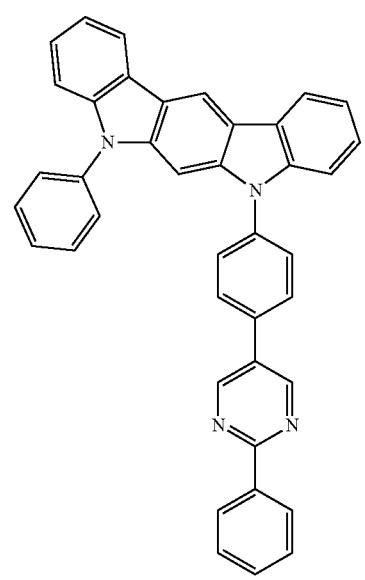
H2-63
H2-64
H2-66
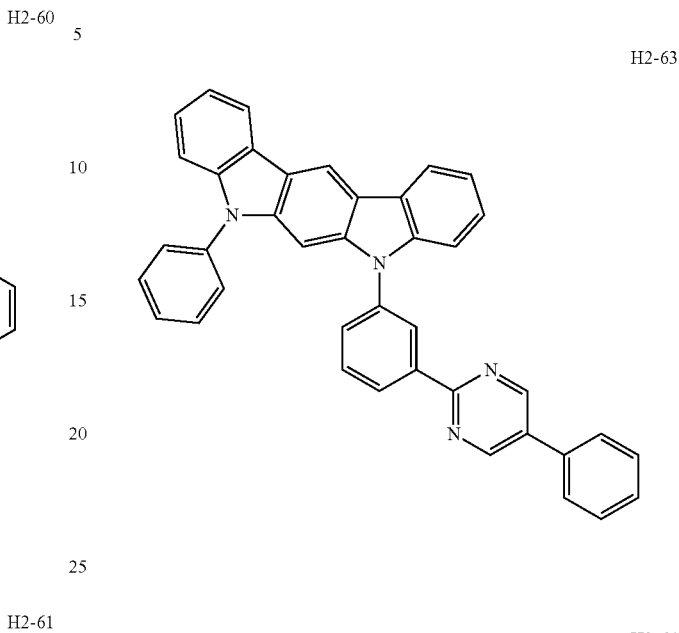
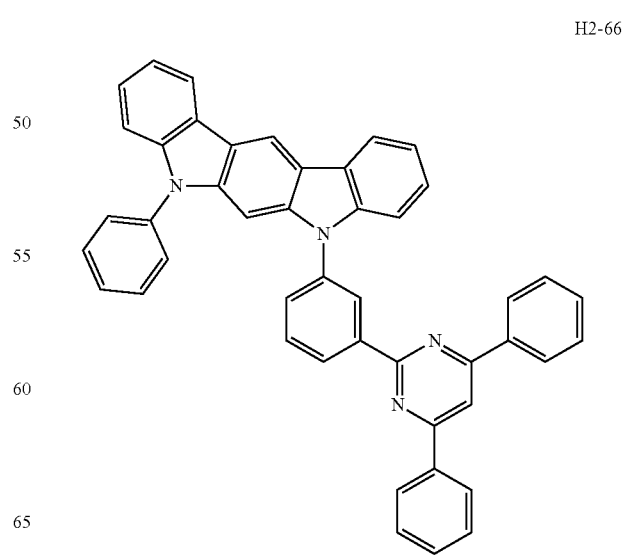

H2-67
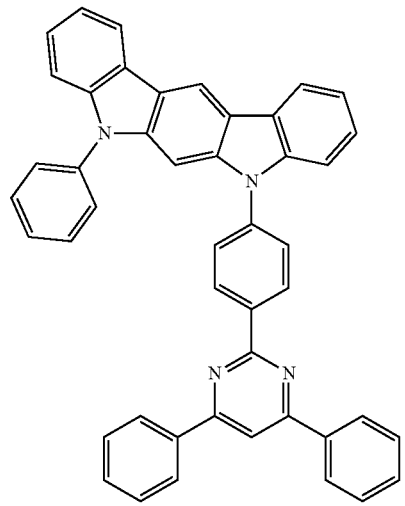
H2-69
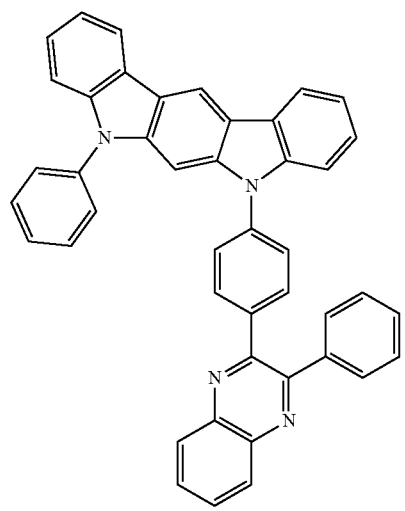
H2-70
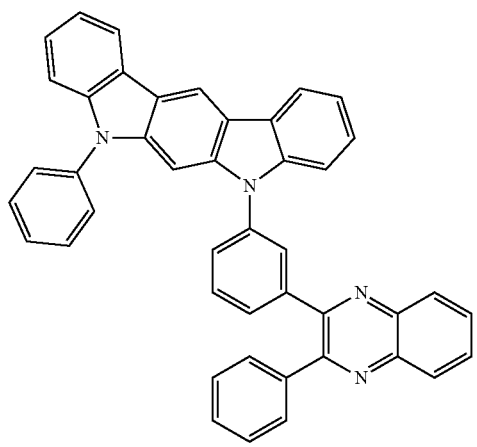
H2-72
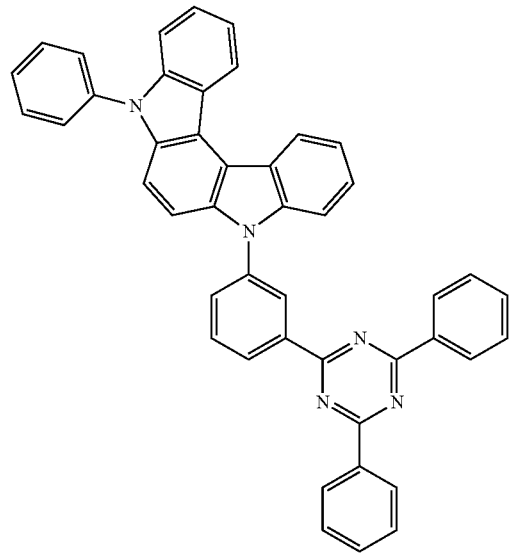
H2-79
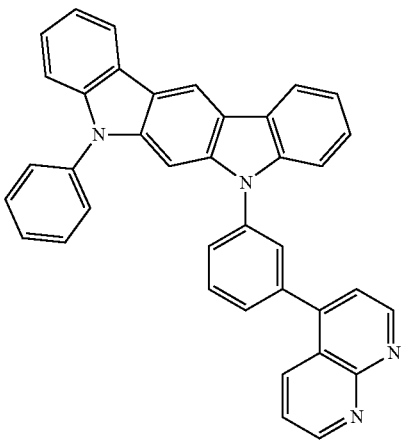
H2-80
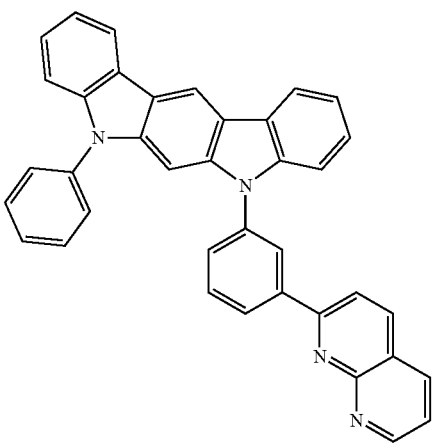

H2-81
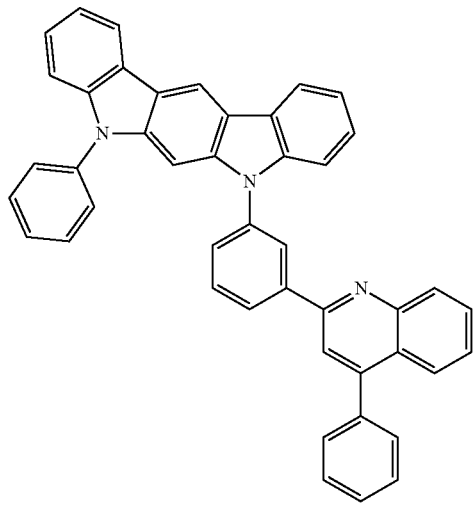
H2-82
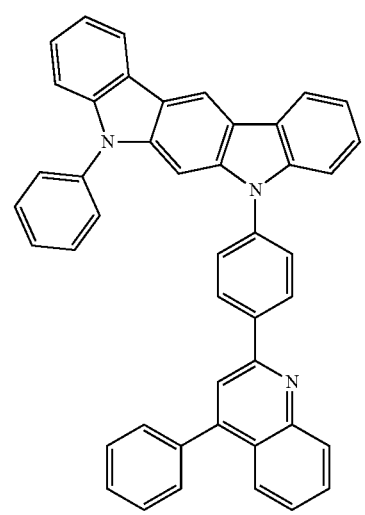
H2-83
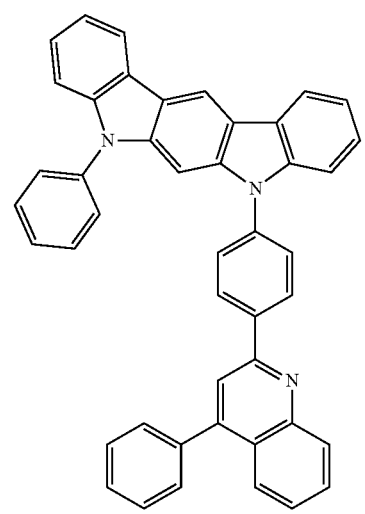
H2-84
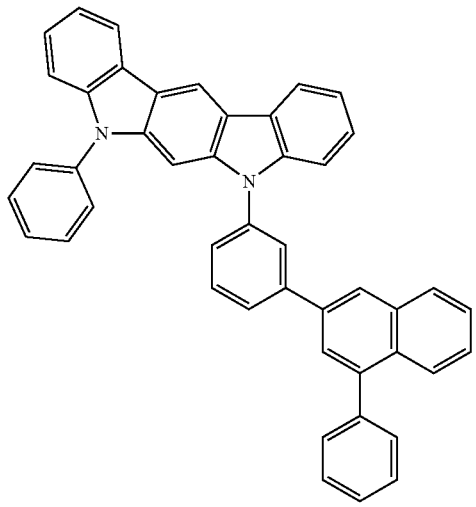
H2-85
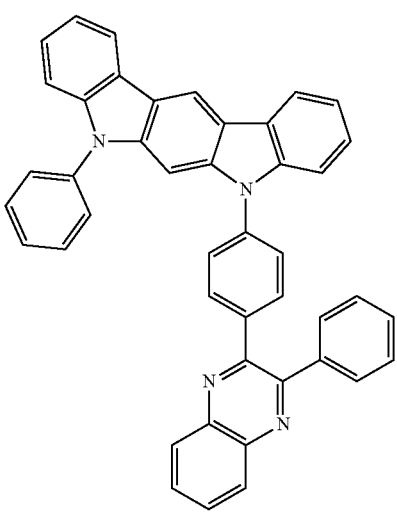
H2-87
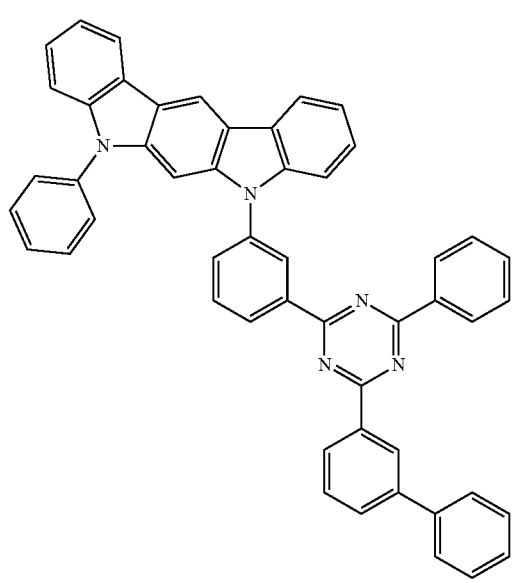

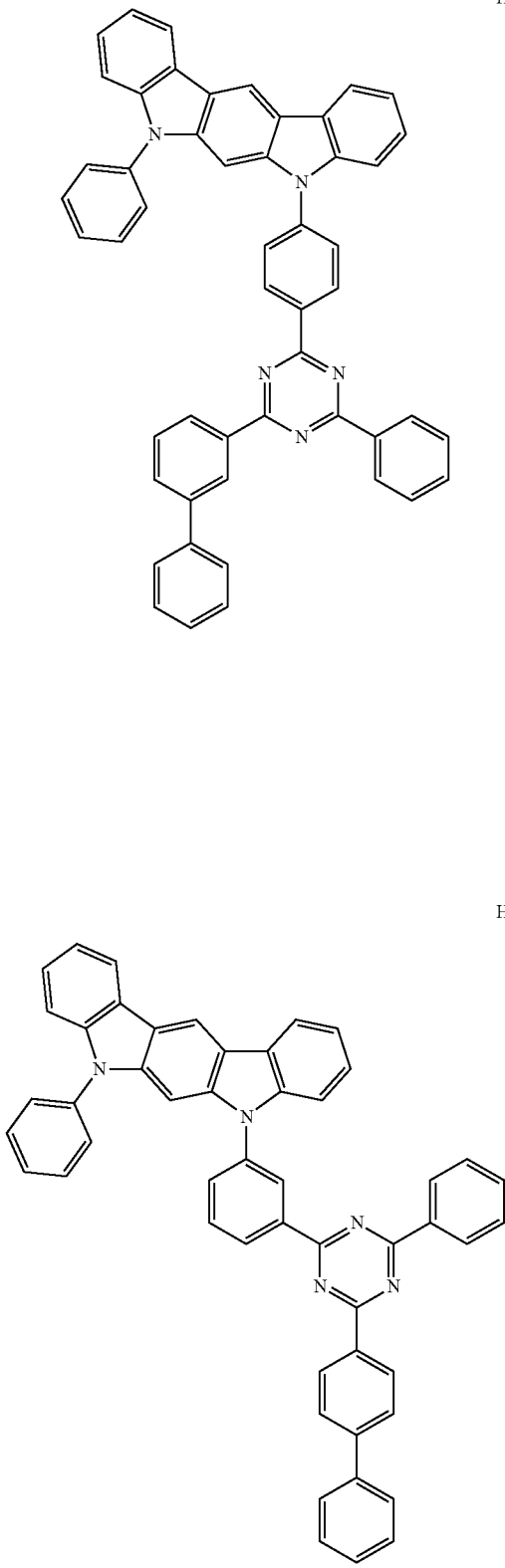
H2-88
H2-89
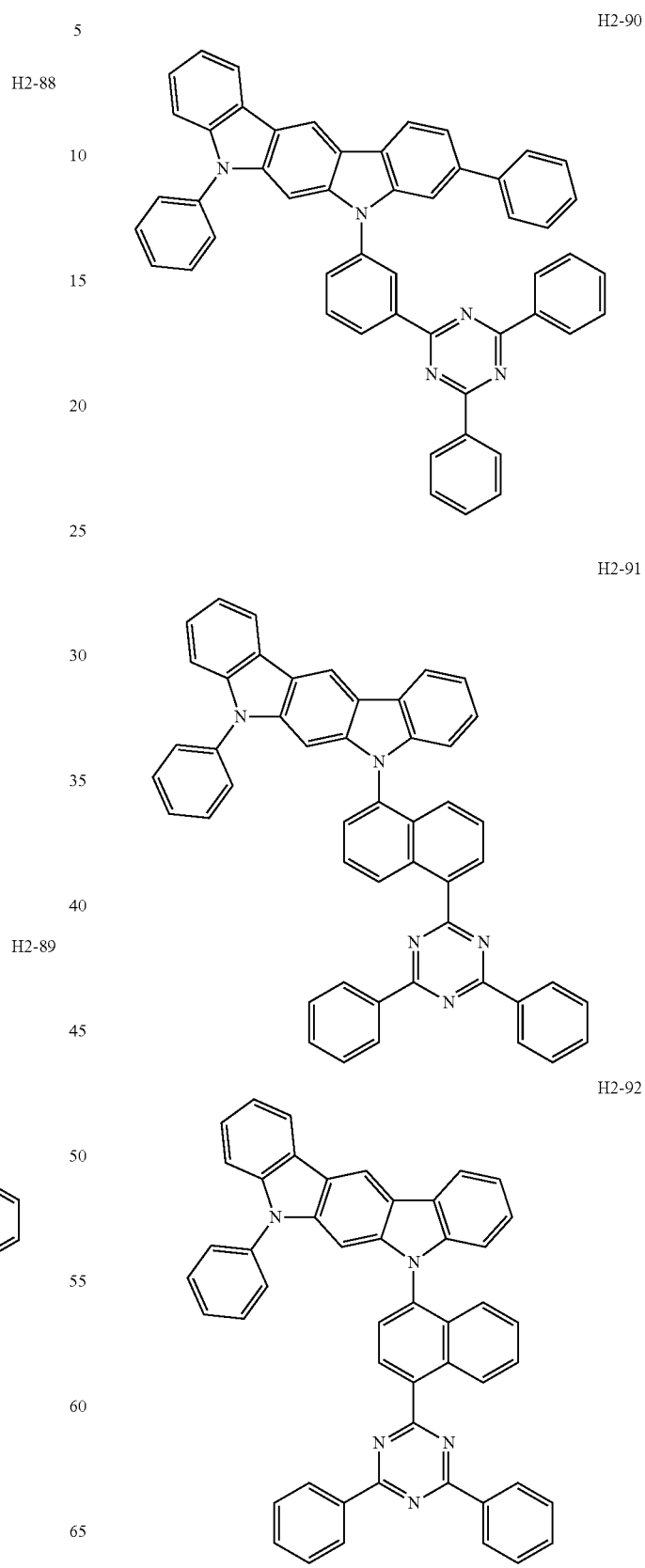
H2-90
H2-91
H2-92

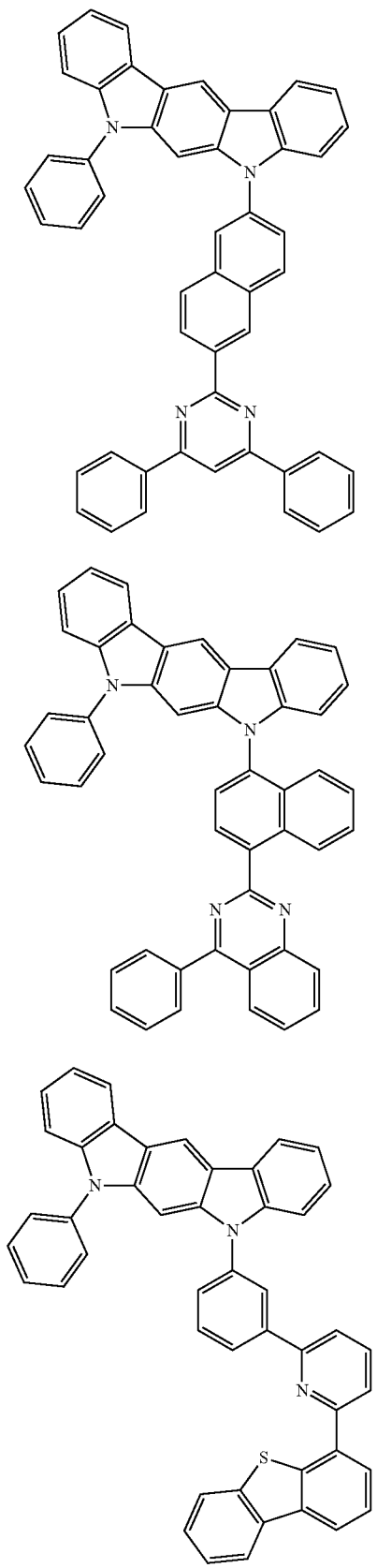
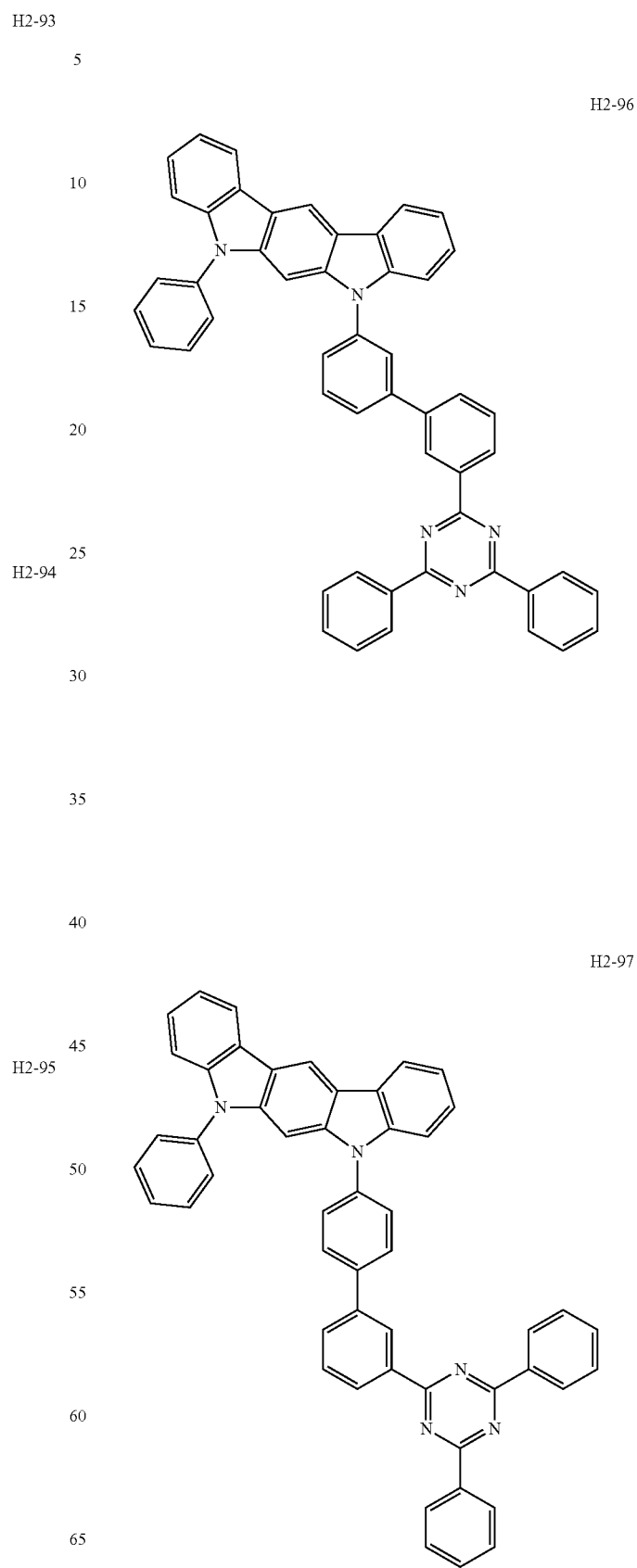

H2-98
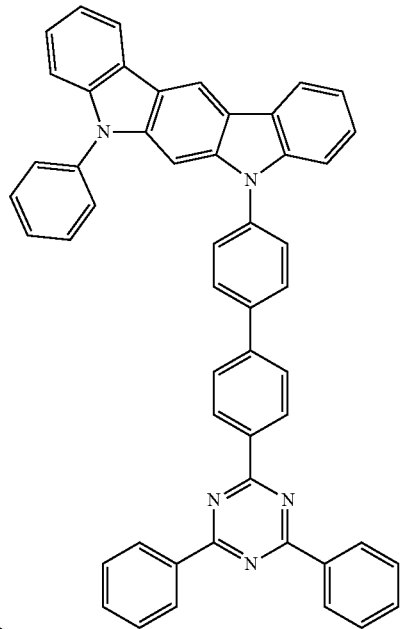
H2-99
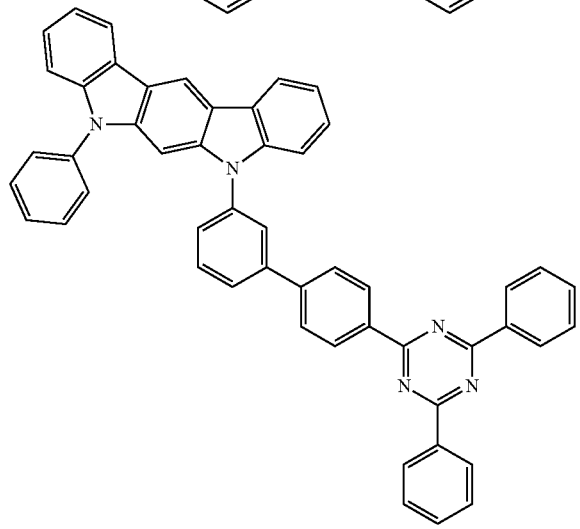
H2-100
H2-101
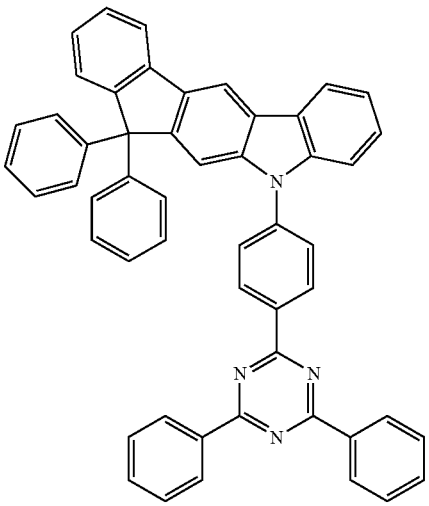
H2-102
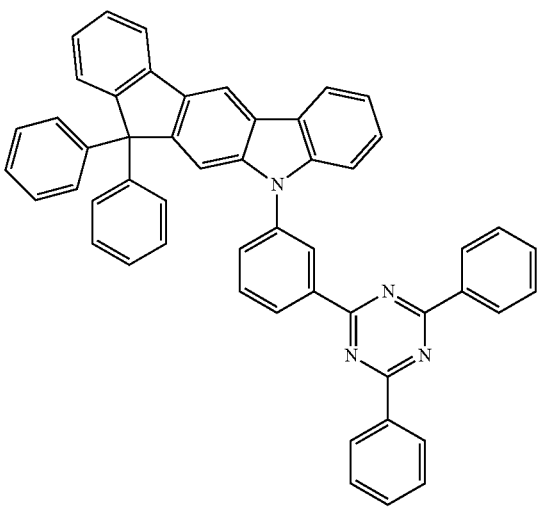
H2-105
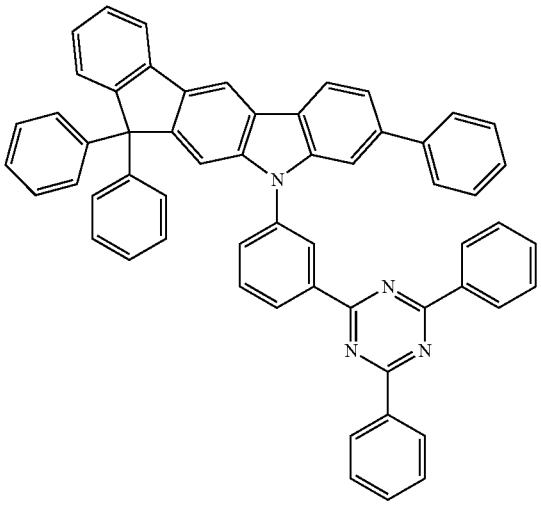

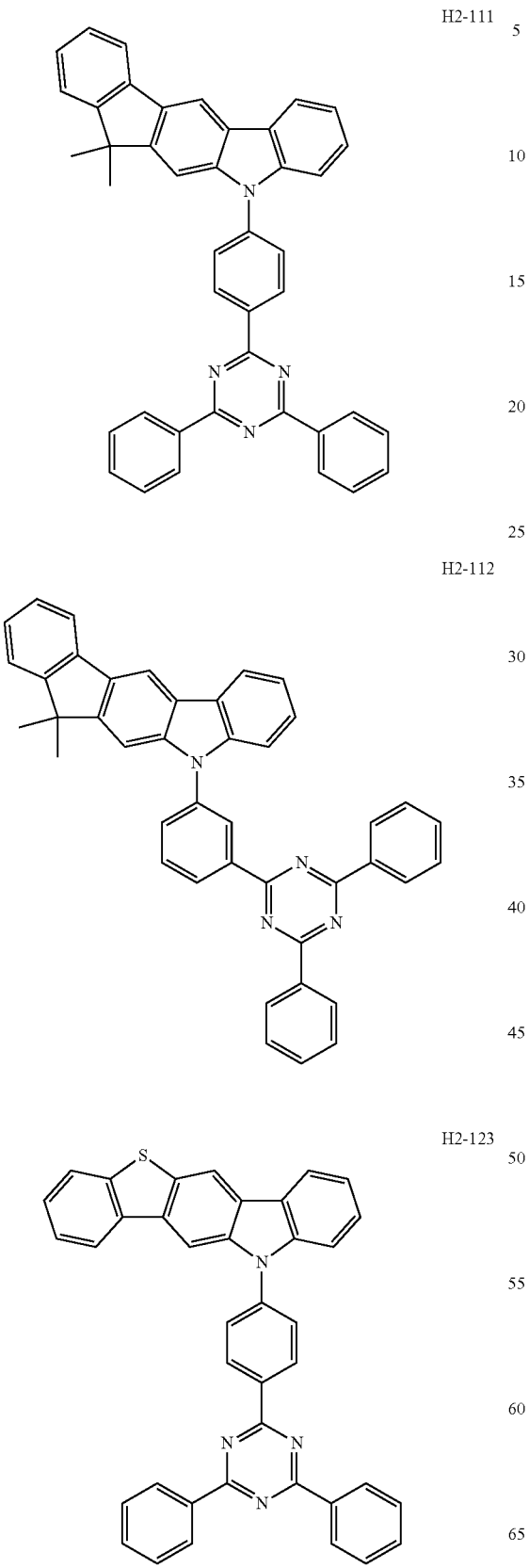
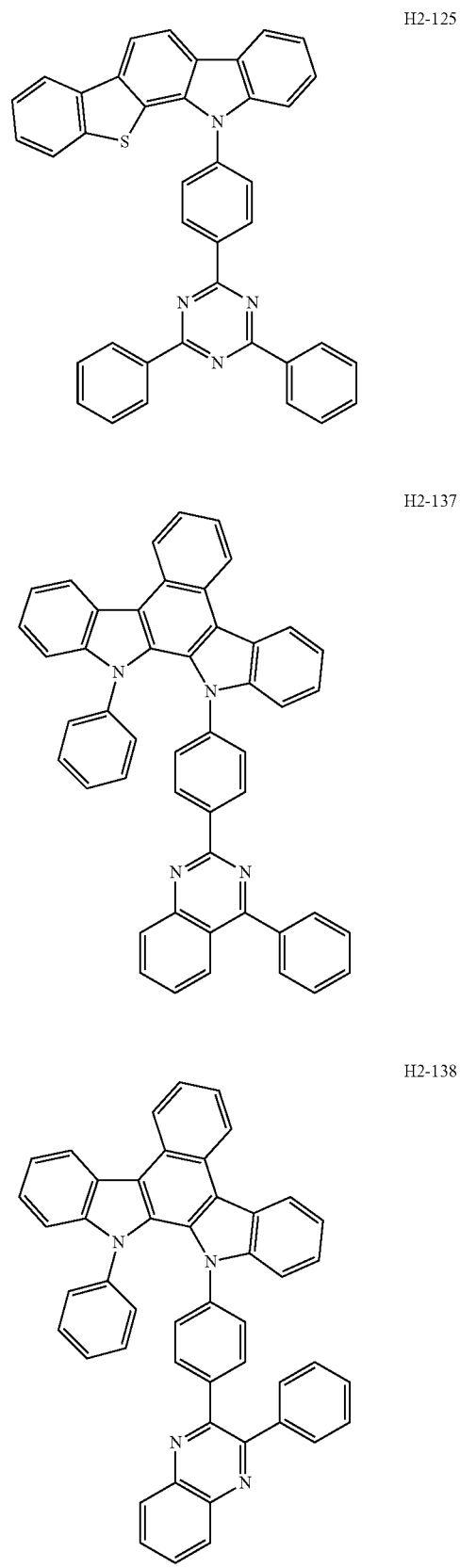

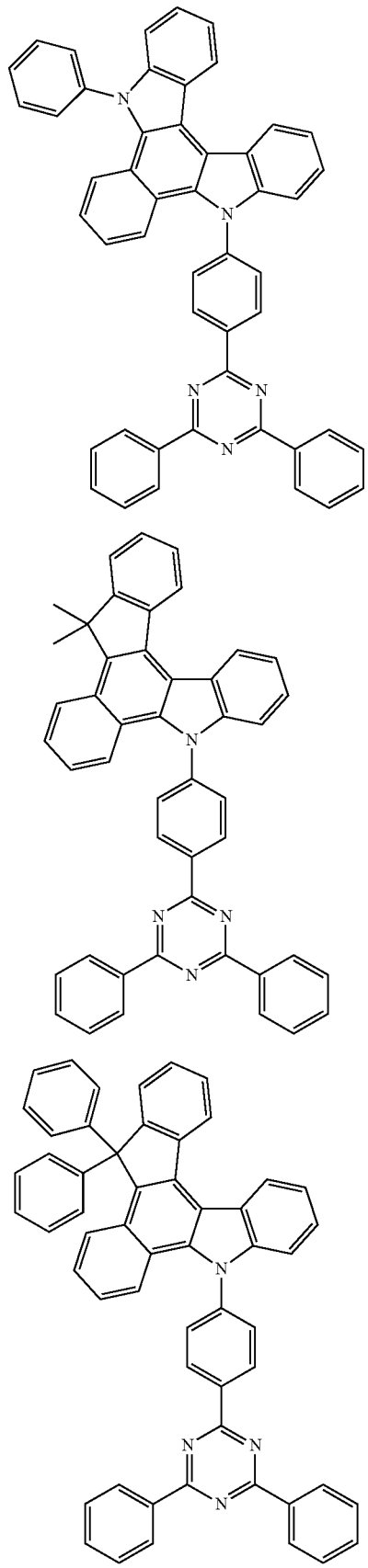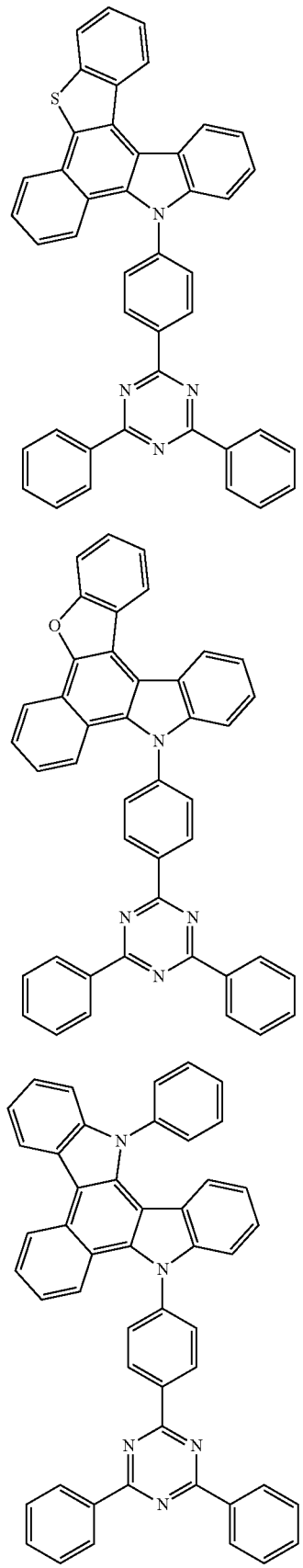

H2-145
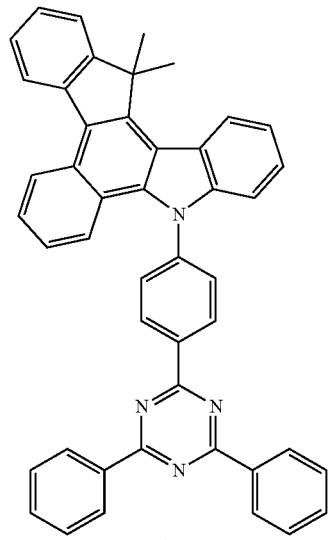
H2-146
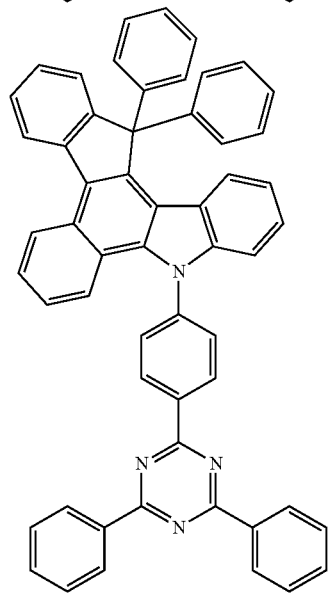
H2-147
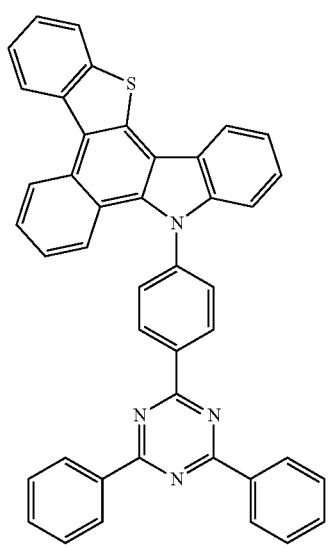
H2-148
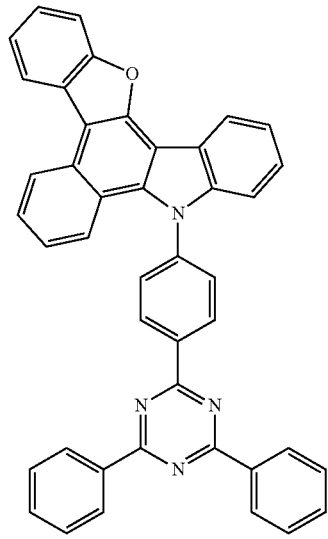
H2-149
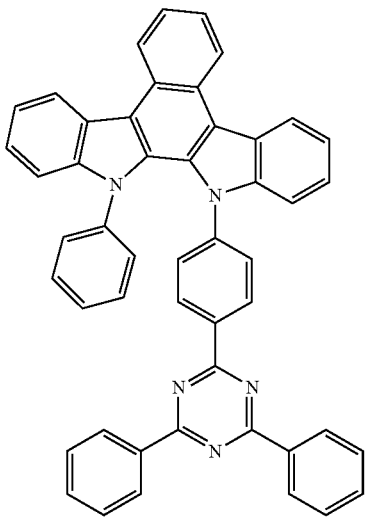
H2-150
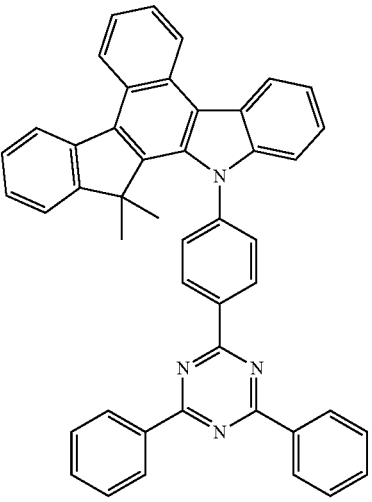

H2-151
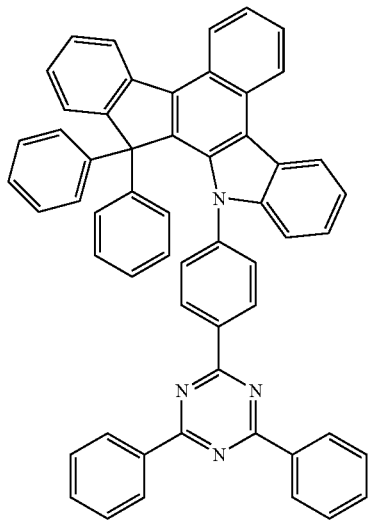
H2-152
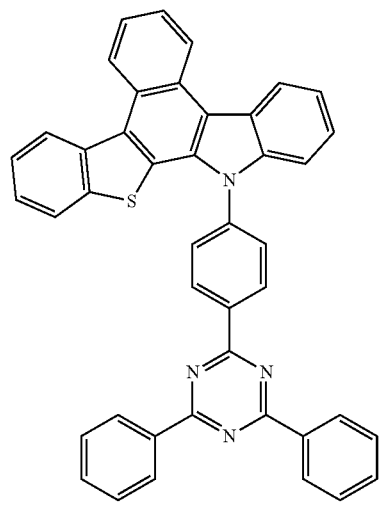
H2-153
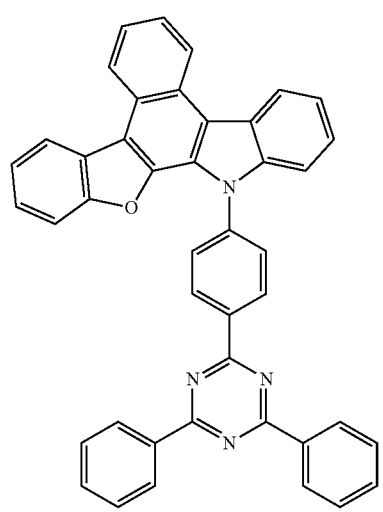
H2-161
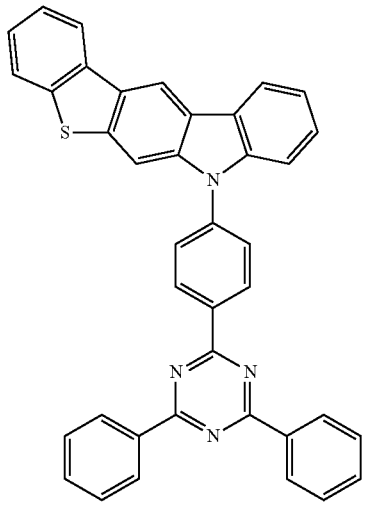
H2-163
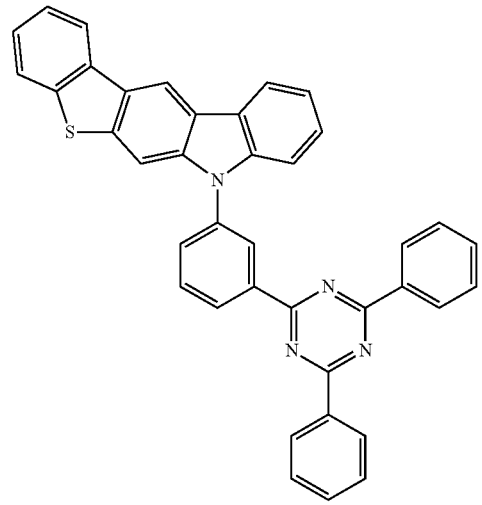
H2-166
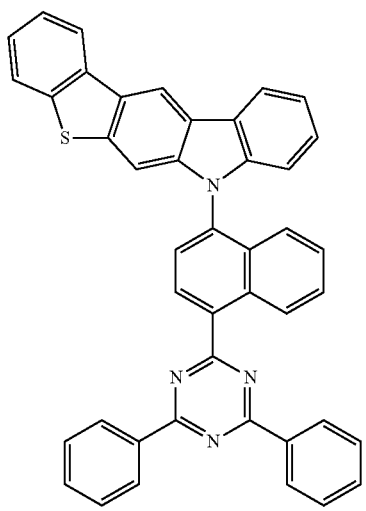

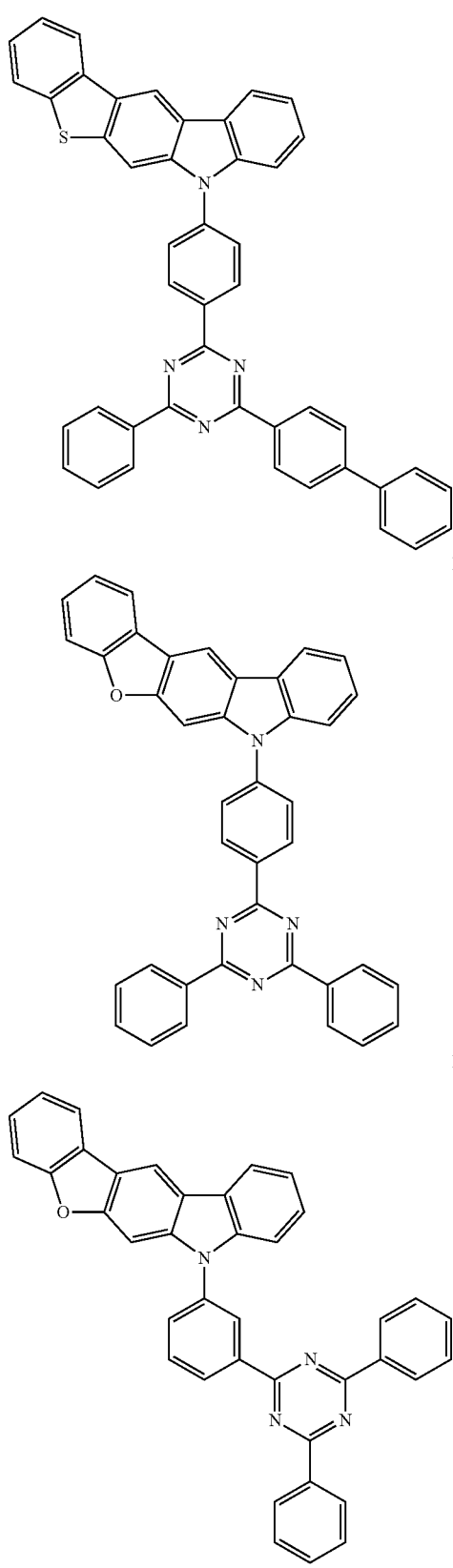
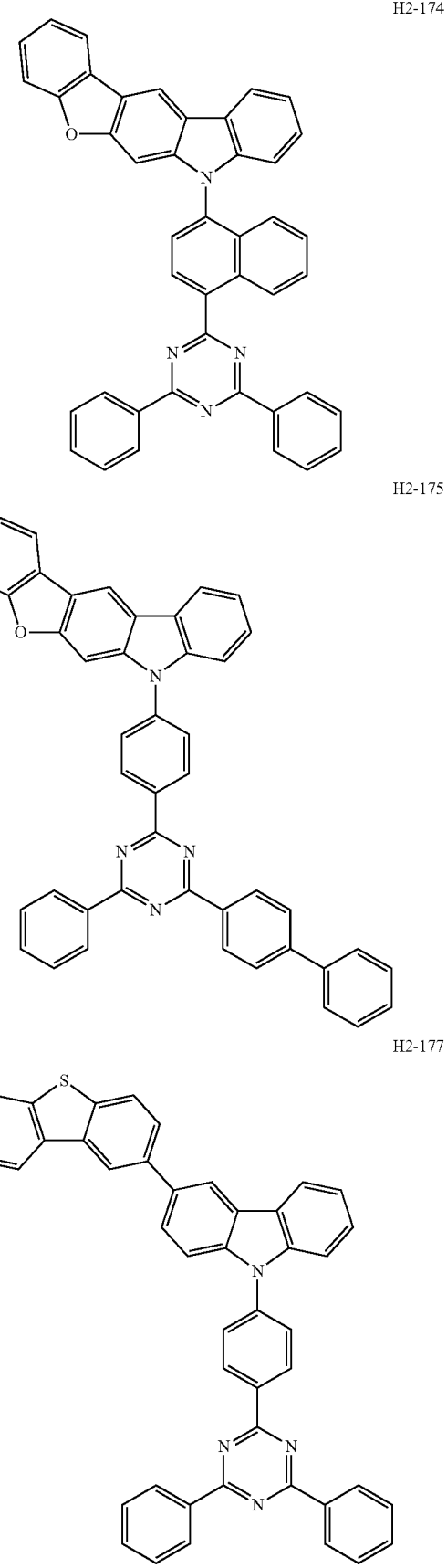

H2-179
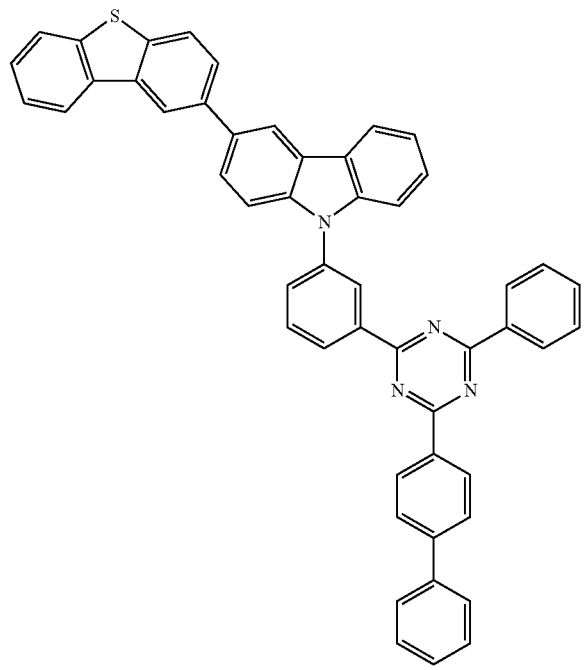
H2-180
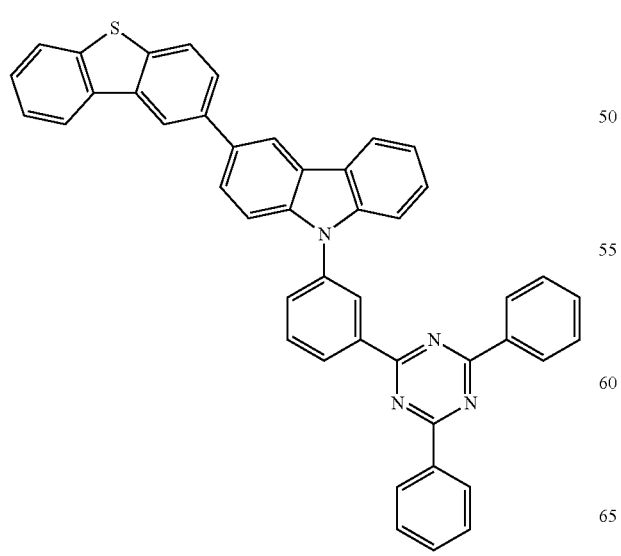
H2-181
H2-183
H2-185
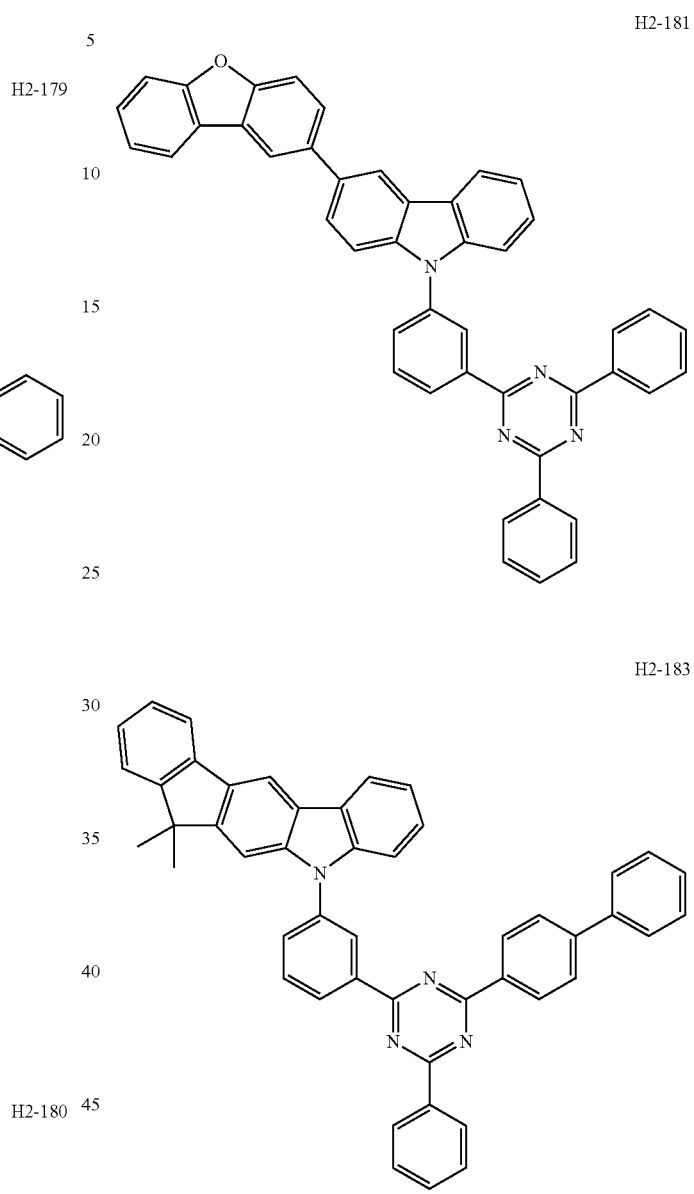

605
-continued
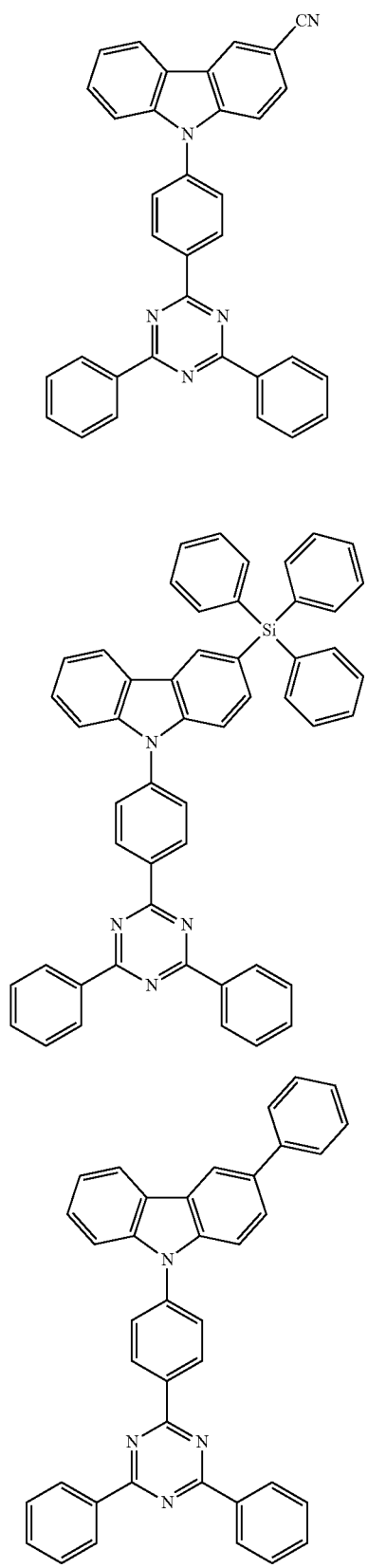
H2-187
H2-188
H2-189
606
-continued
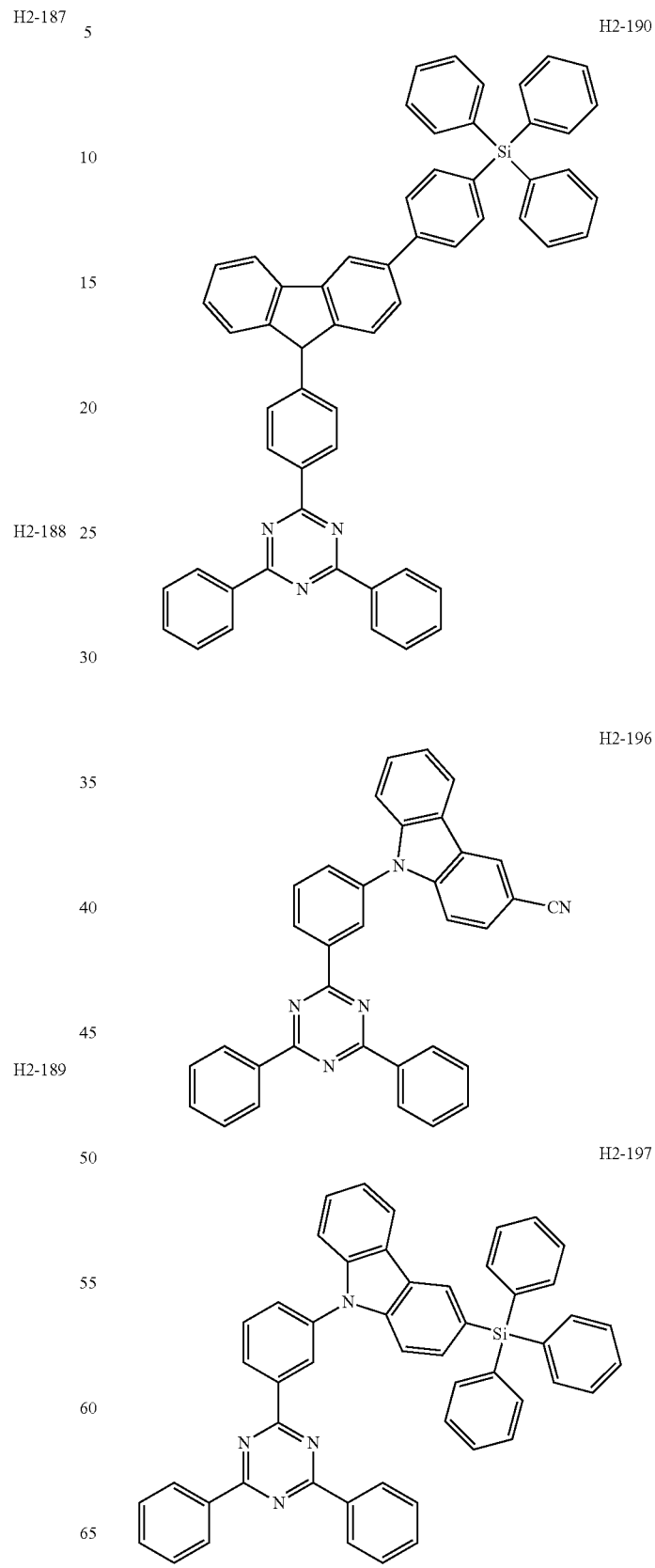
H2-190
H2-196
H2-197

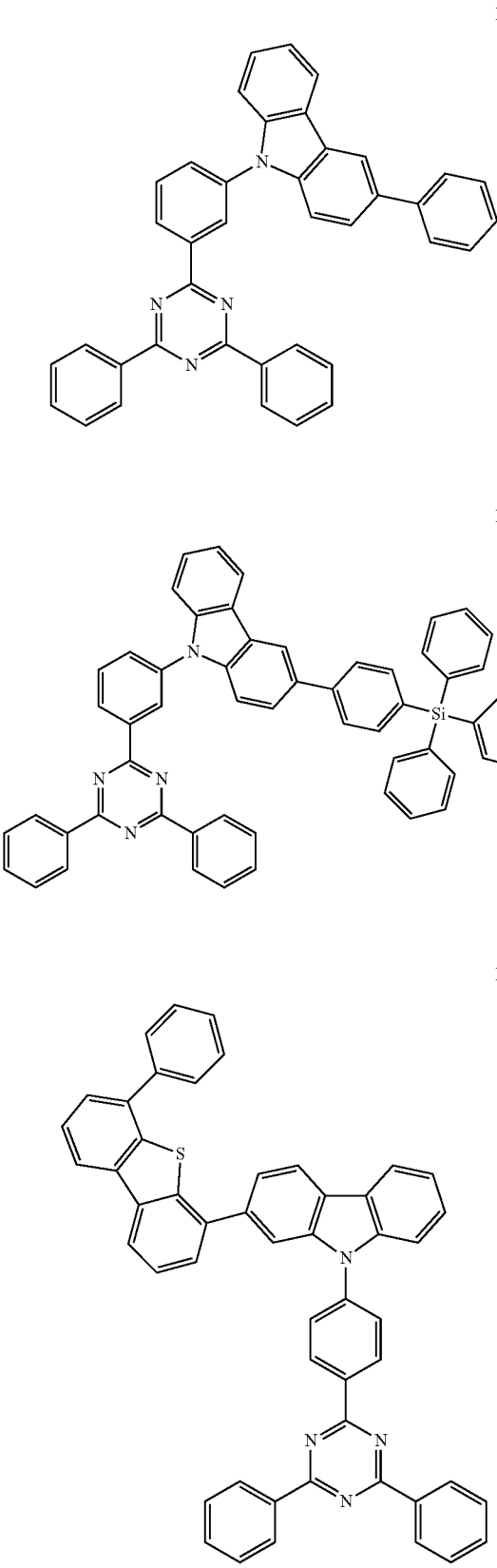
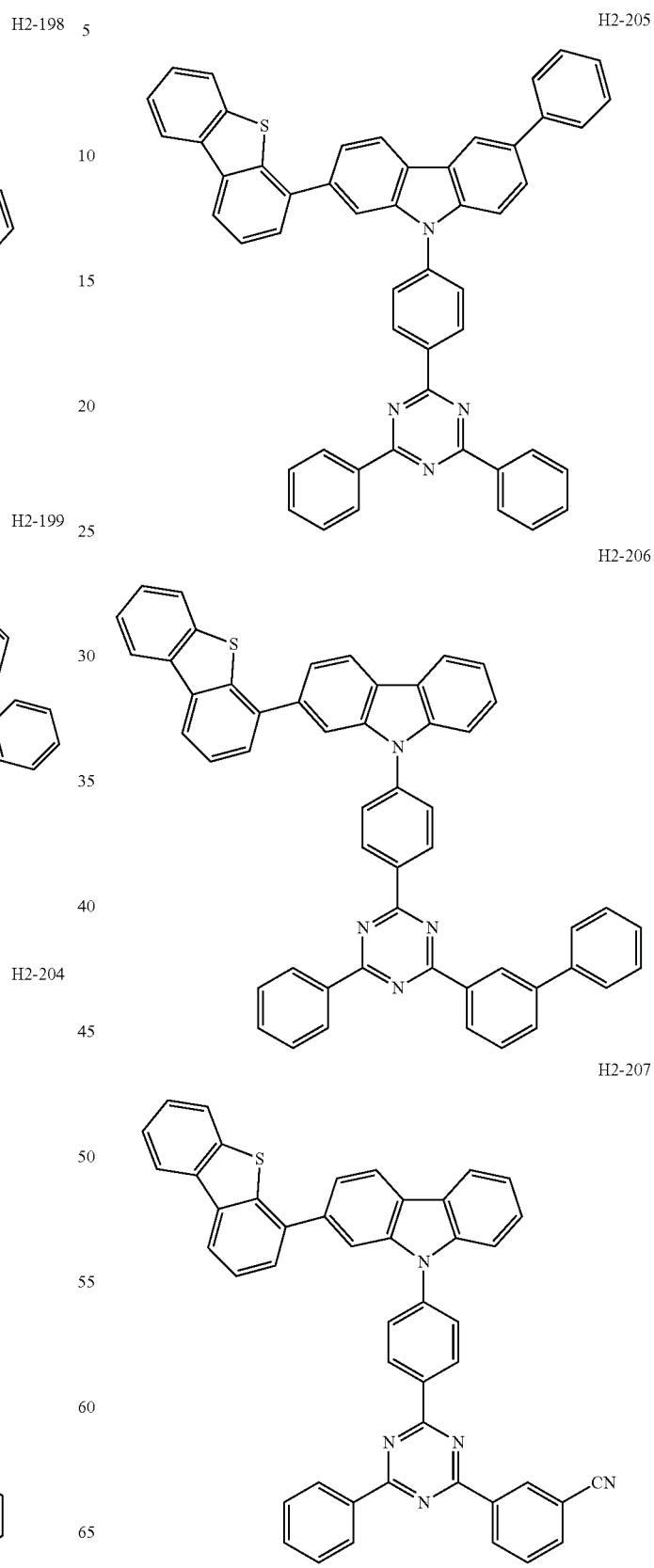

-continued
H2-208
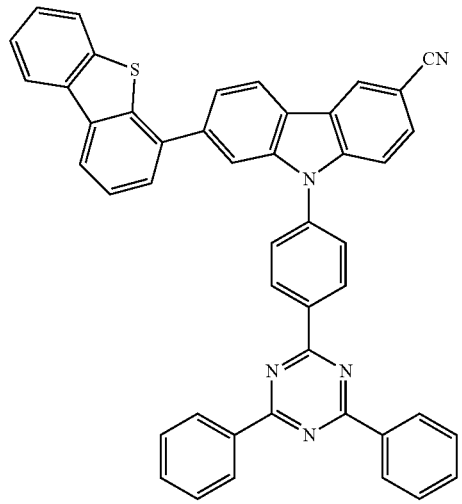
H2-209
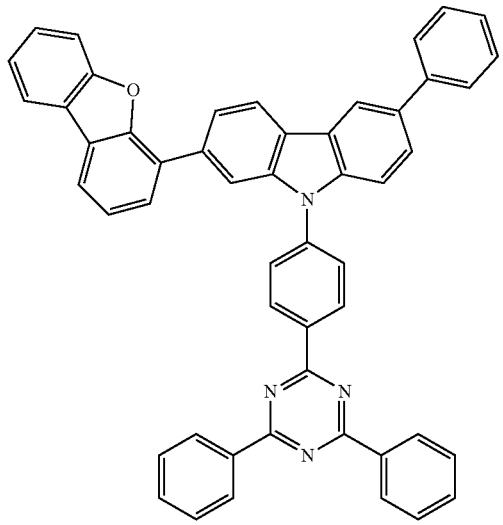
H2-210
-continued
H2-211
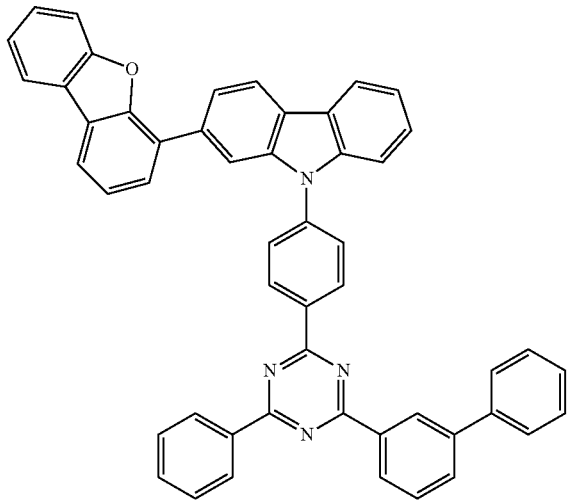
H2-212
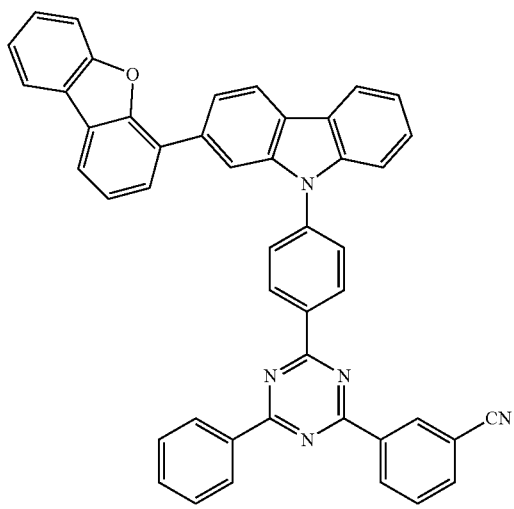
H2-213
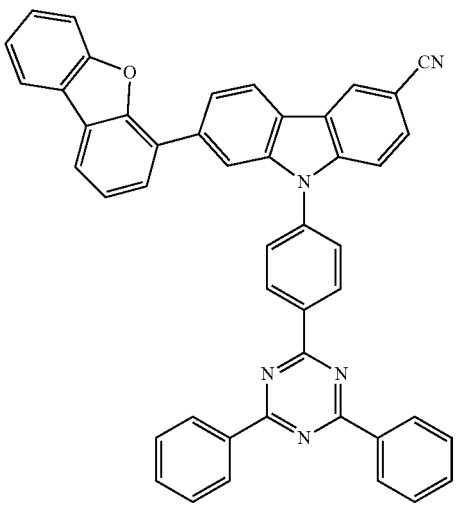

H2-214
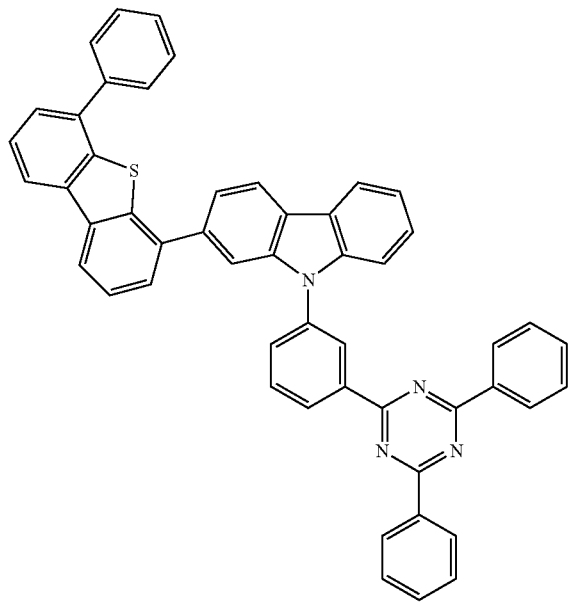
H2-215
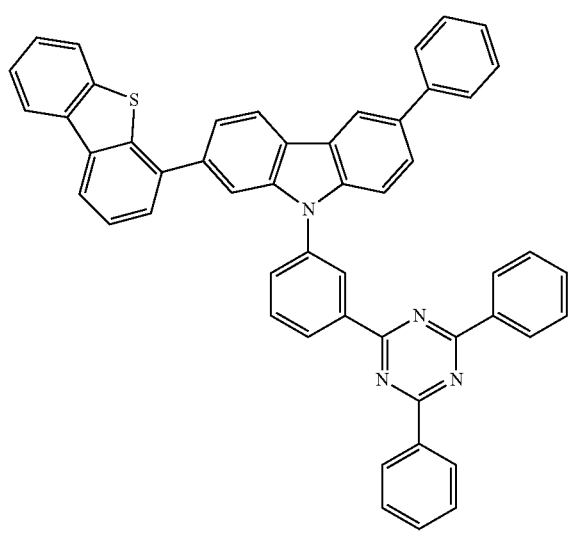
H2-216
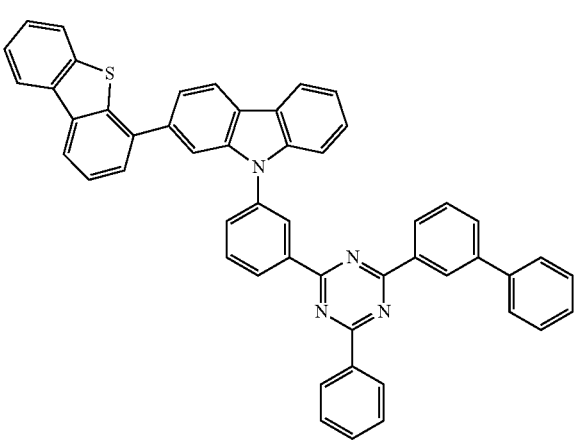
H2-217
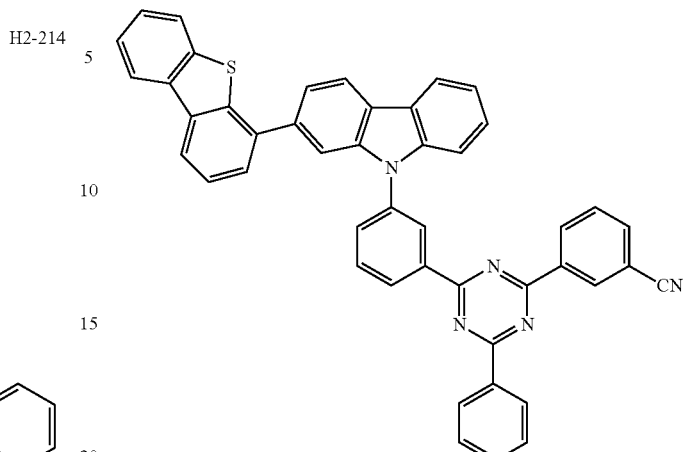
H2-218
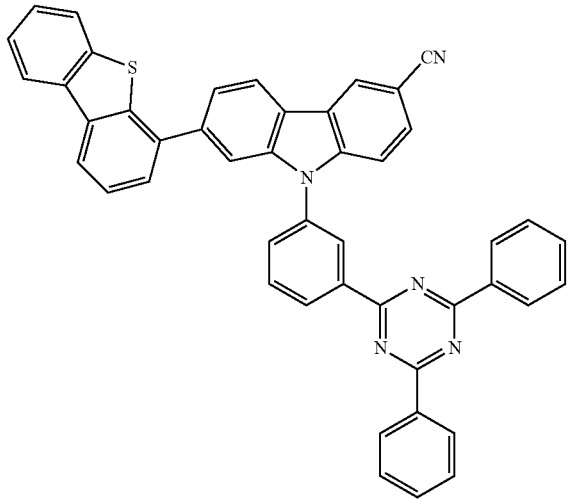
H2-219
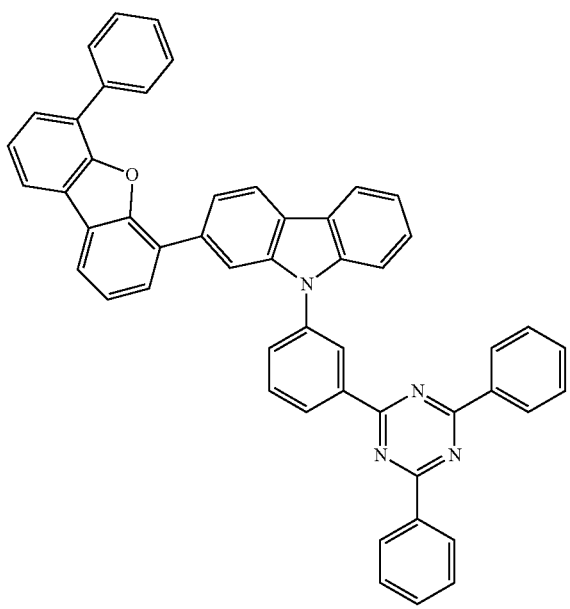

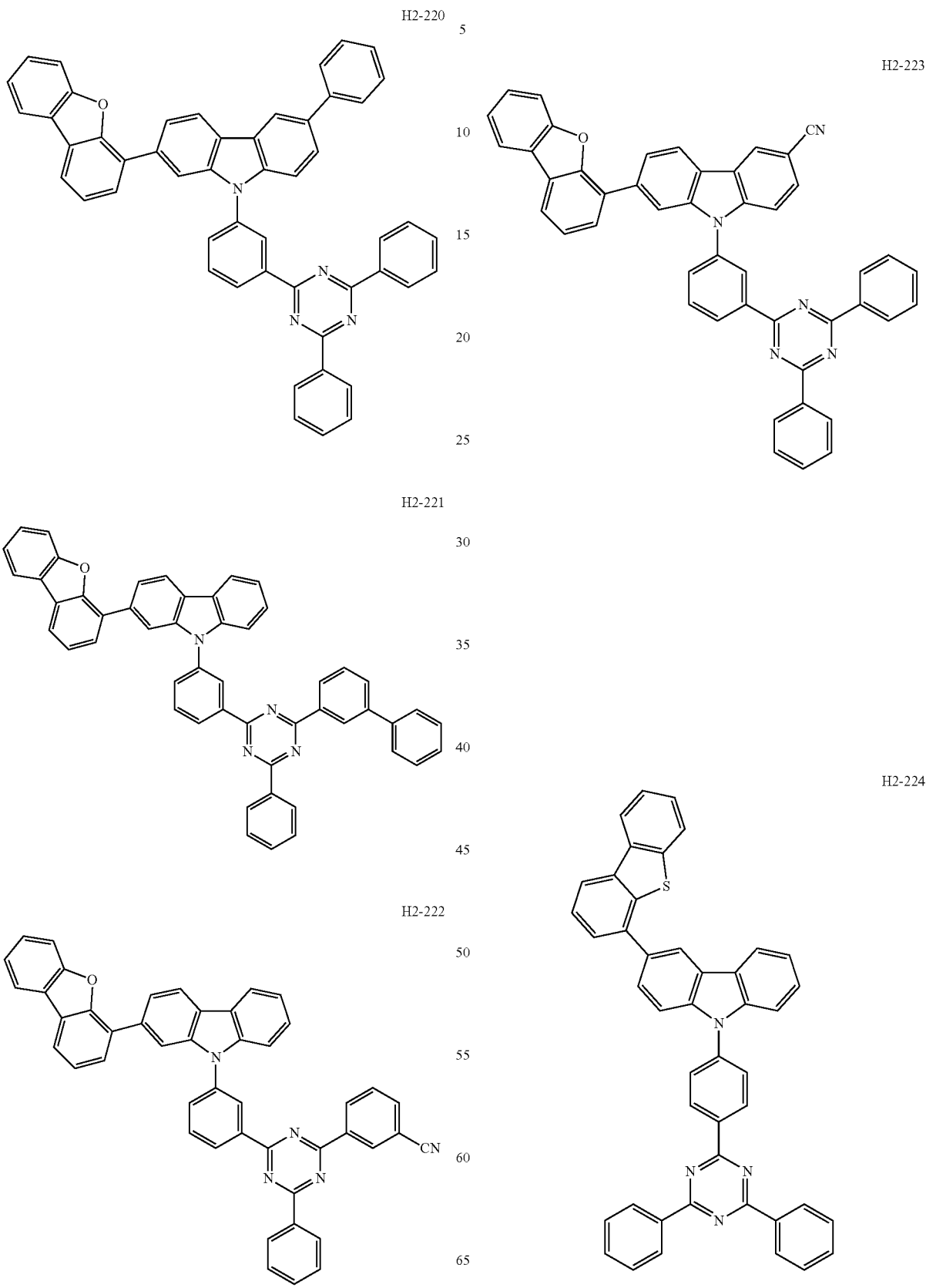

H2-225
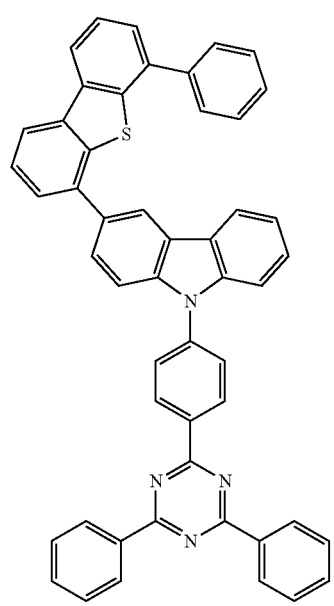
H2-227
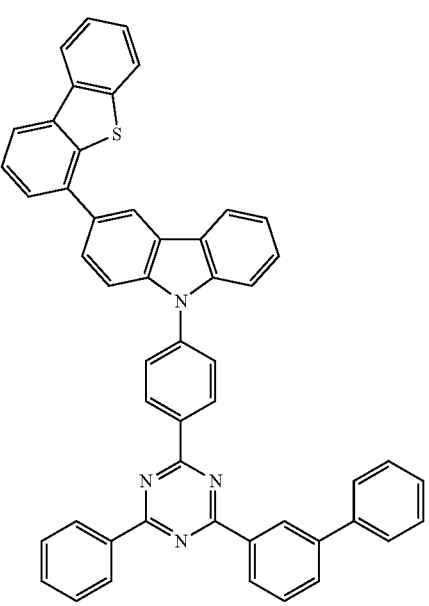
H2-226
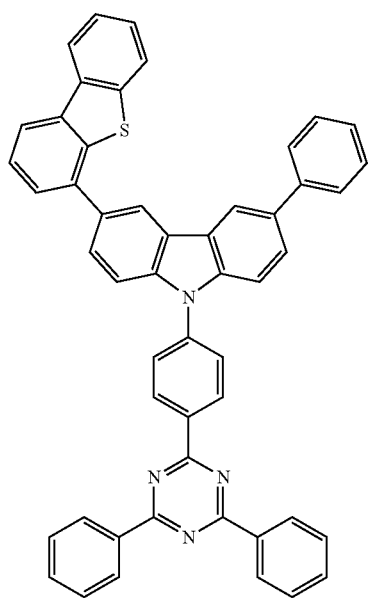
H2-228
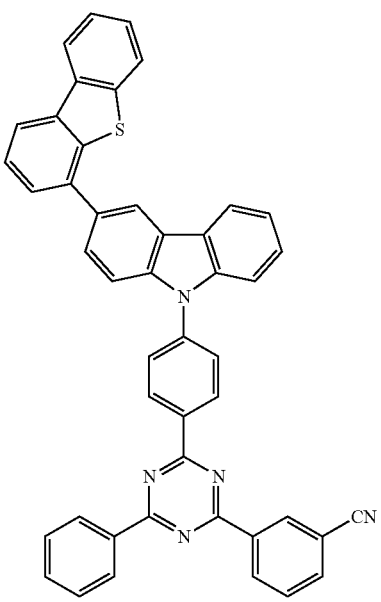

-continued
H2-229
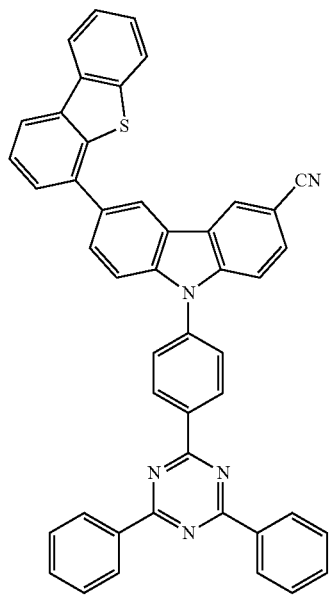
H2-230
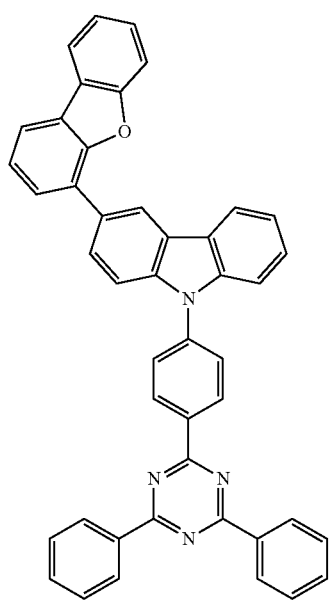
-continued
H2-231
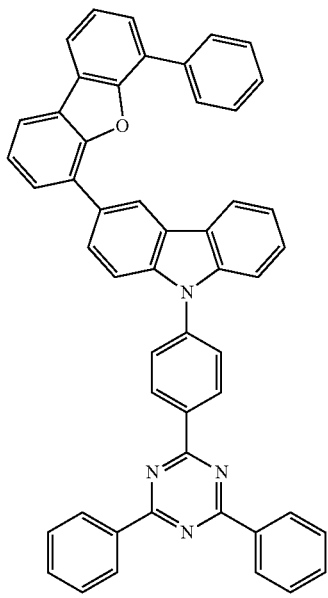
H2-232
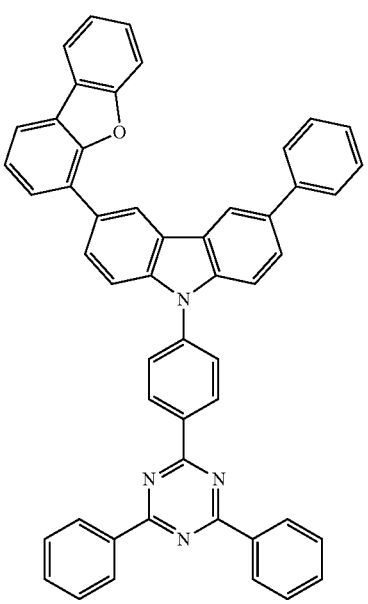

H2-233
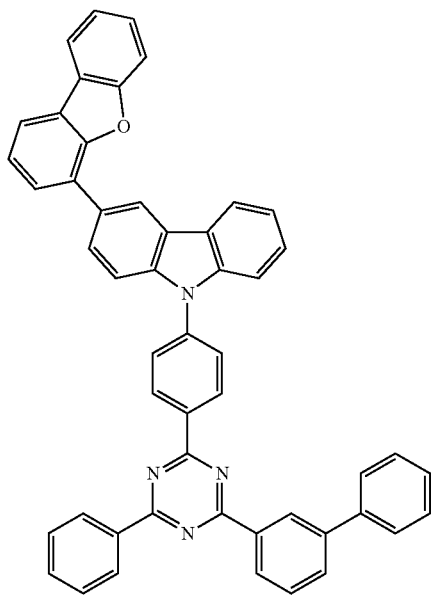
H2-234
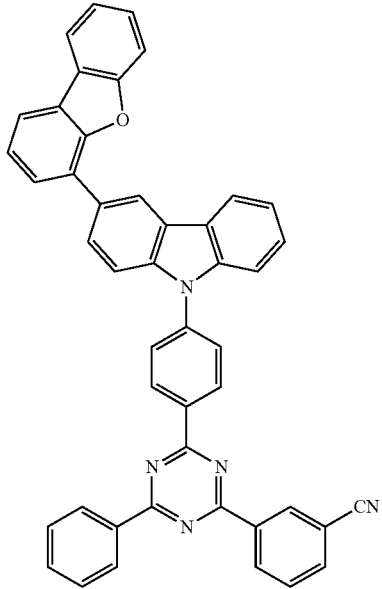
H2-235
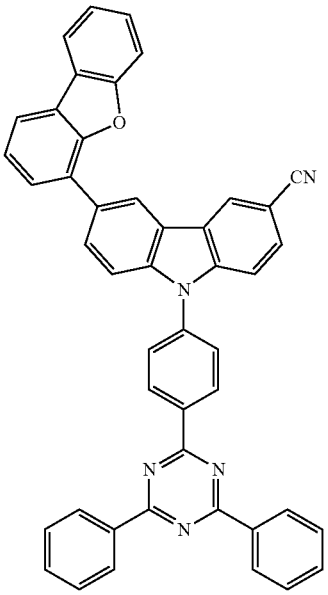
H2-236
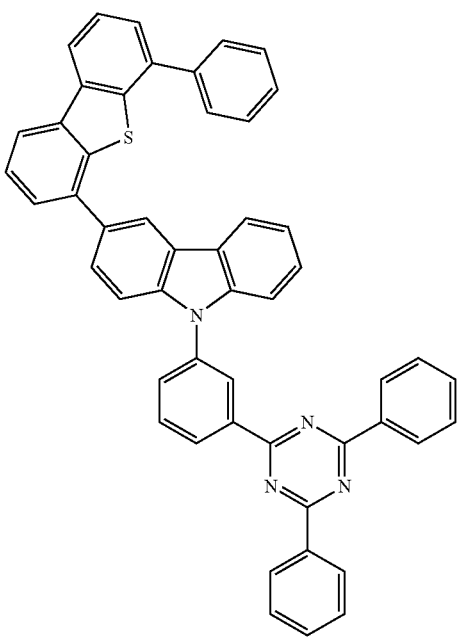

H2-237
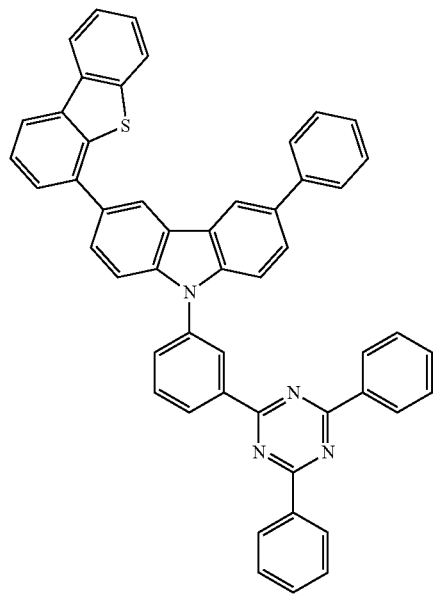
H2-238
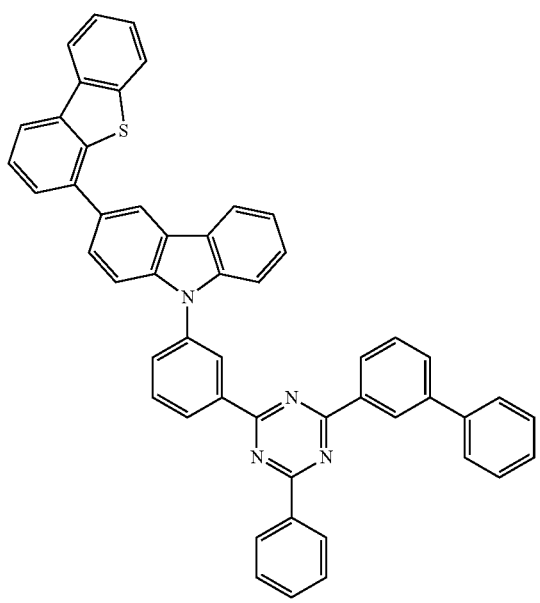
H2-239
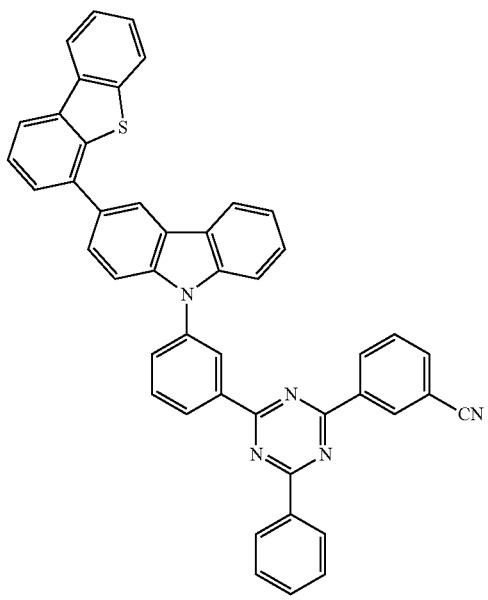
H2-240
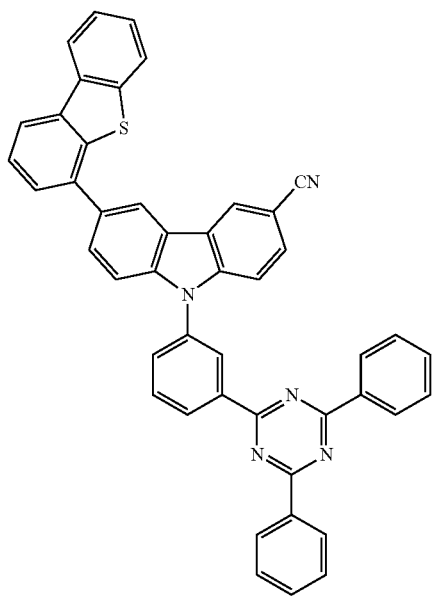

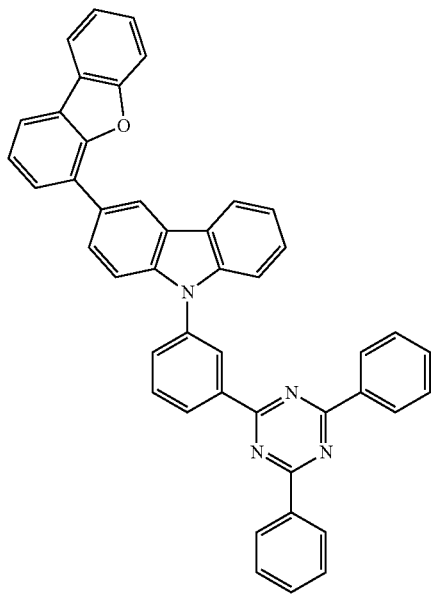
H2-241
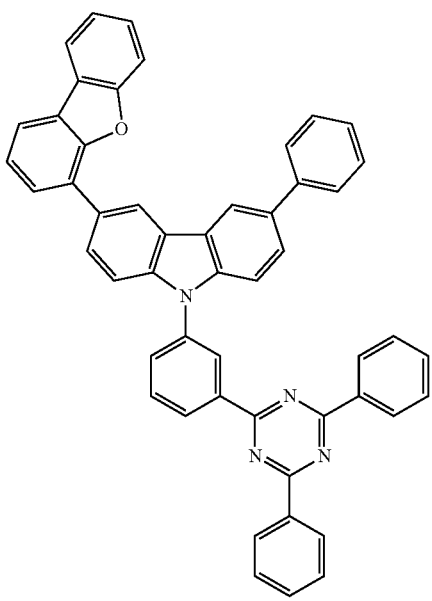
H2-243
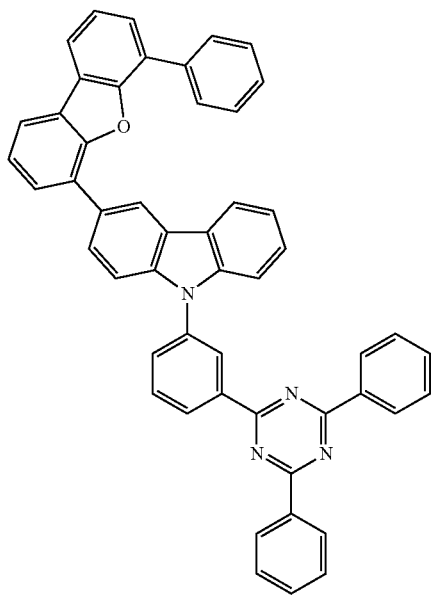
H2-242
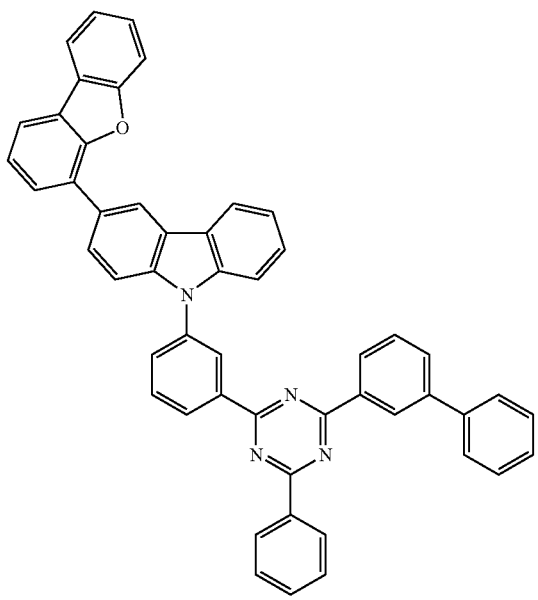
H2-244

H2-245
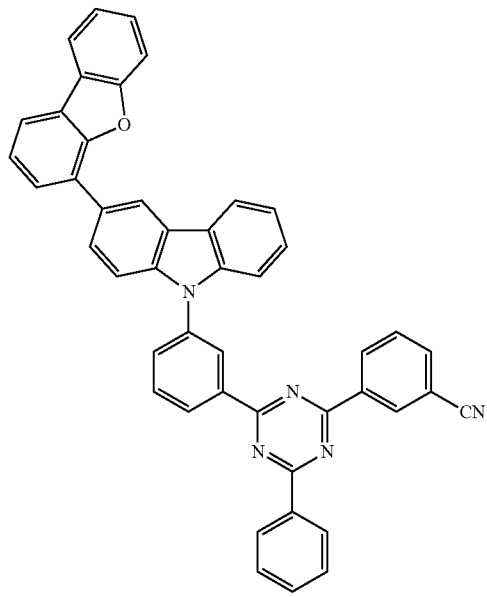
H2-246
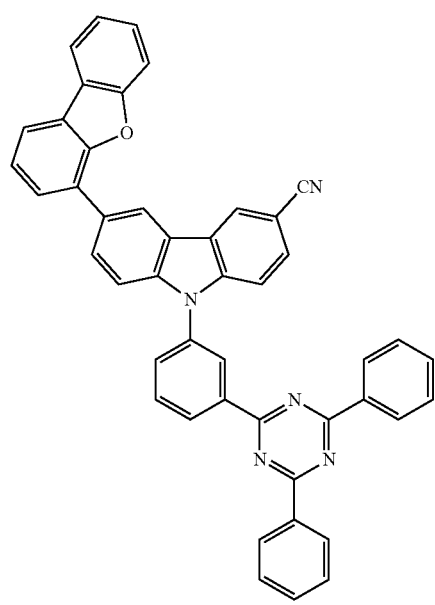
H2-251
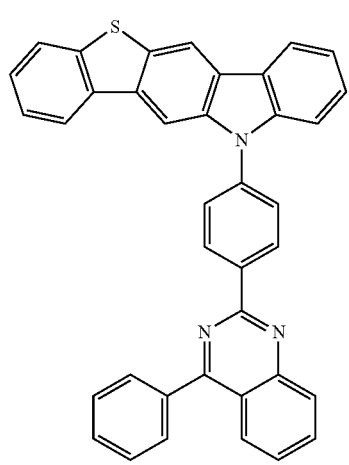
H2-252
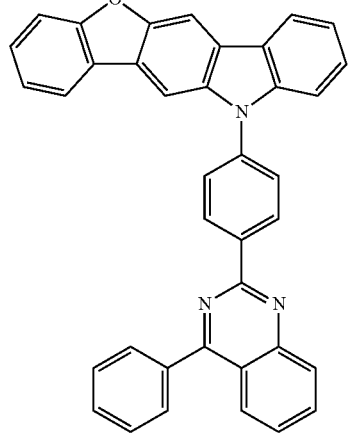
H2-253
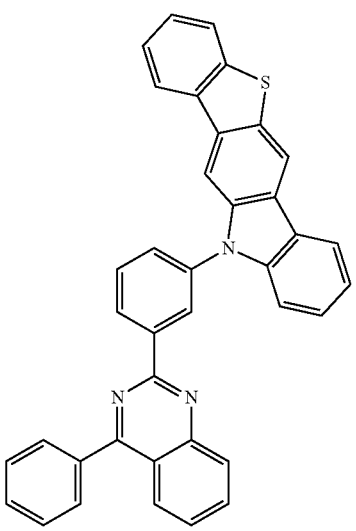
H2-254
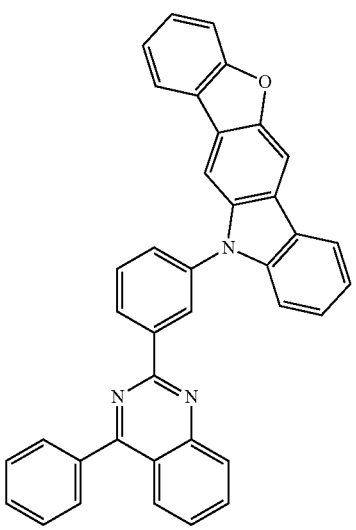

H2-258 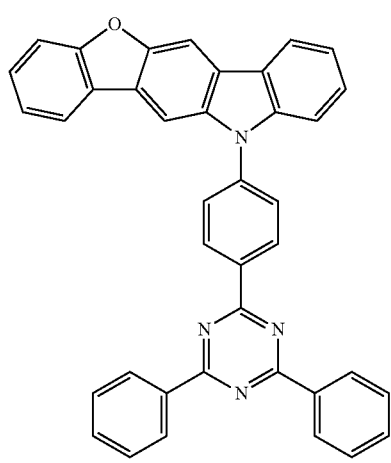
H2-259 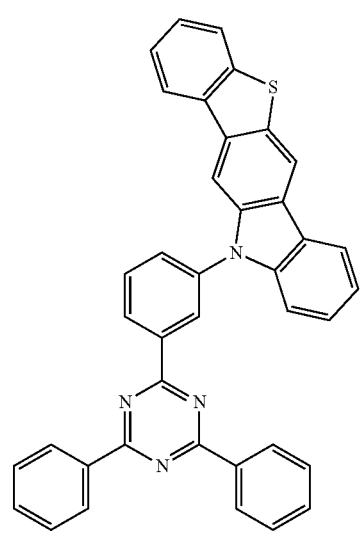
H2-260 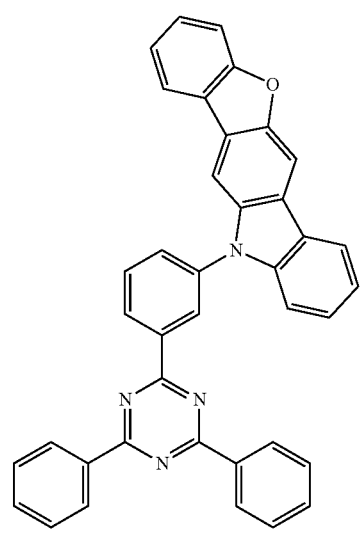
H2-265 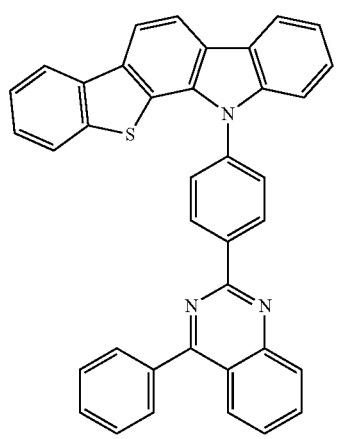
H2-266 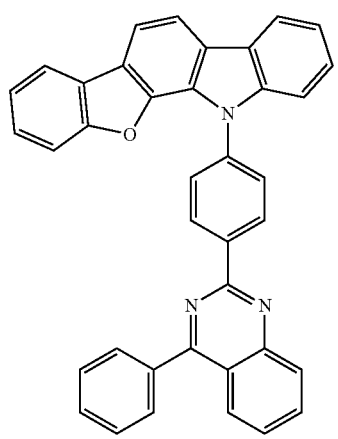
H2-267 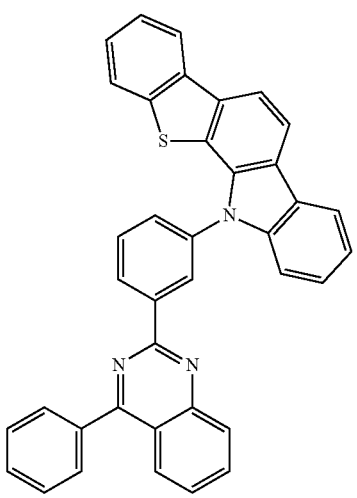

H2-268
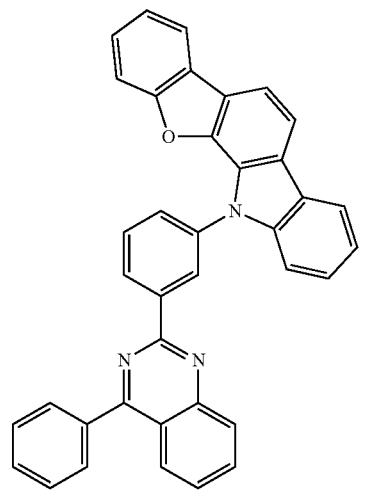
H2-272
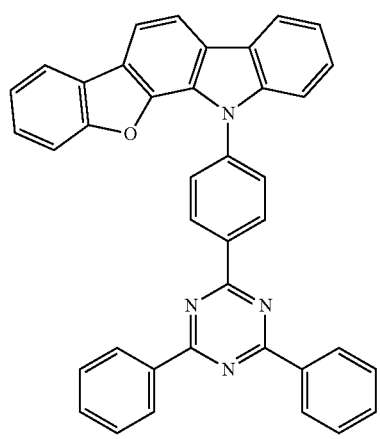
H2-273
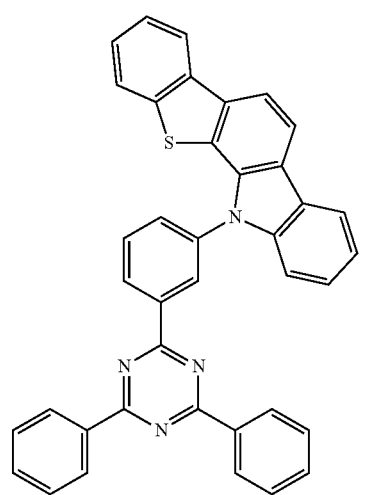
H2-274
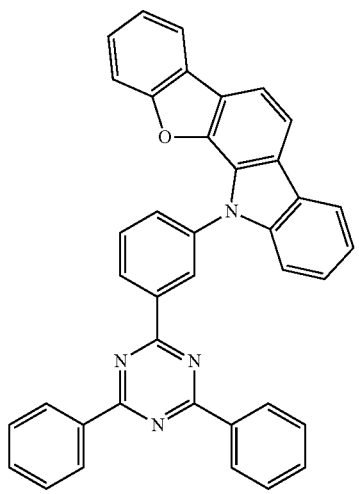
H2-279
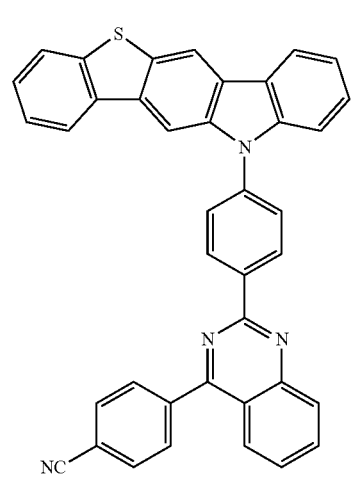
H2-280
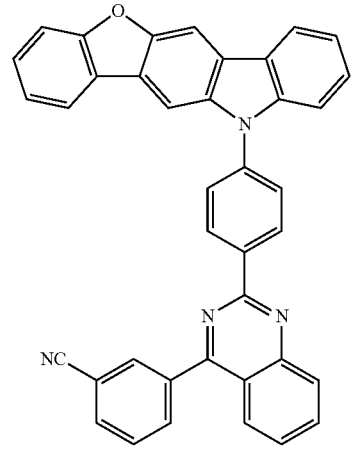

-continued
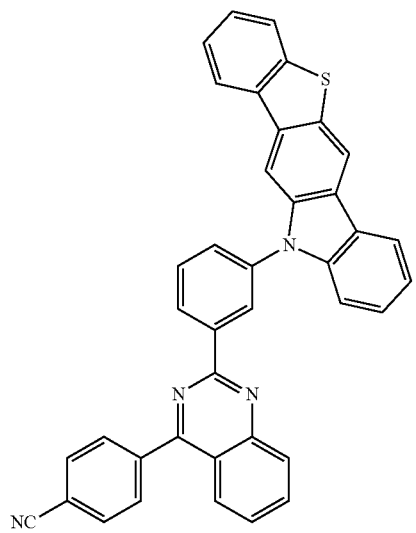
H2-281
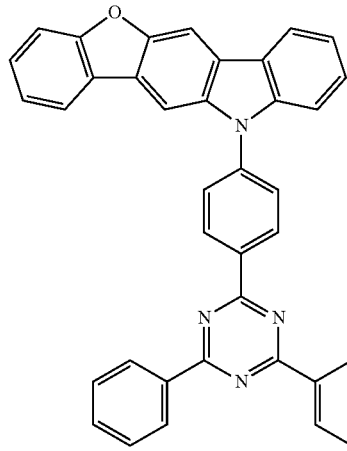
H2-288
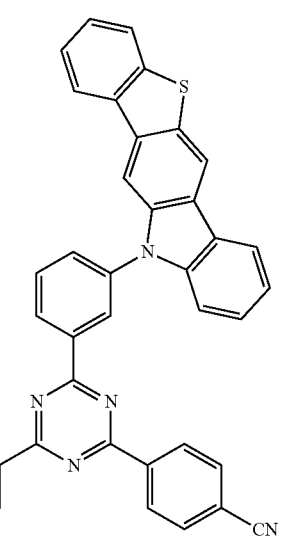
H2-282
H2-289
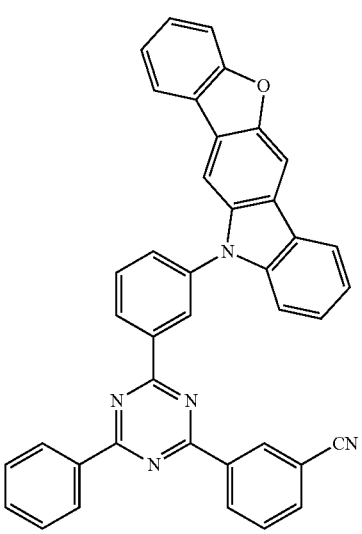
H2-287
H2-290

H2-295
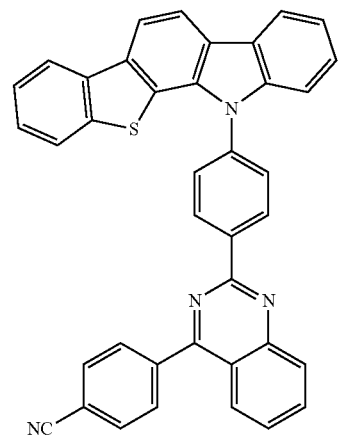
H2-296
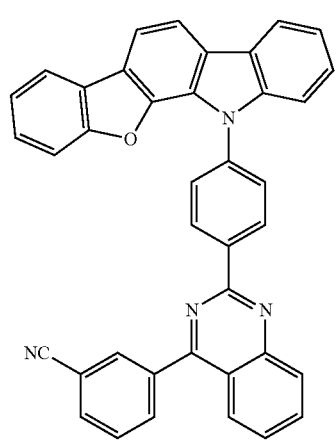
H2-297
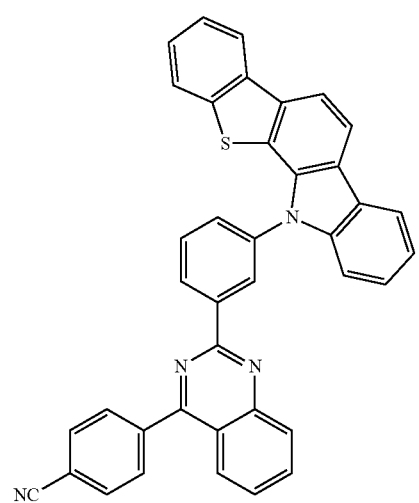
H2-298
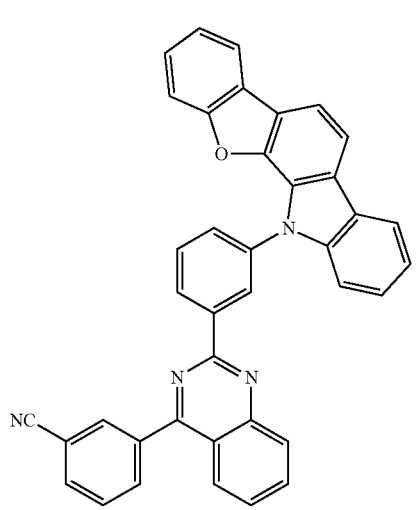
H2-303
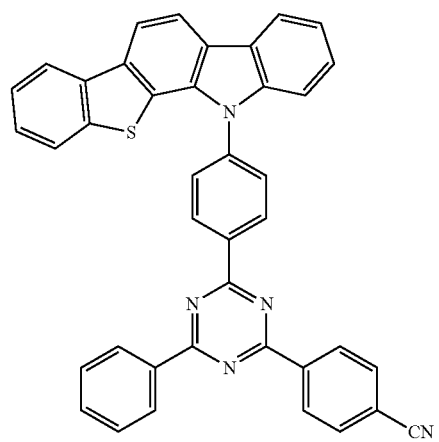
H2-304
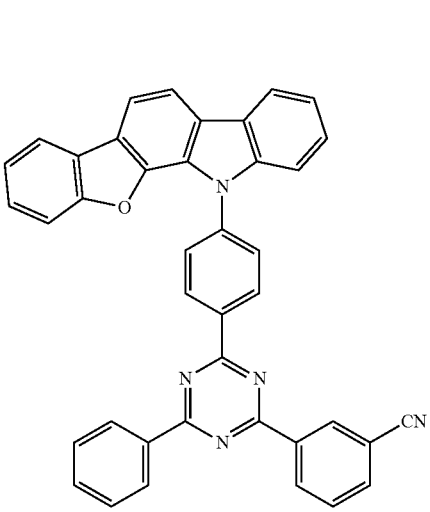

H2-305
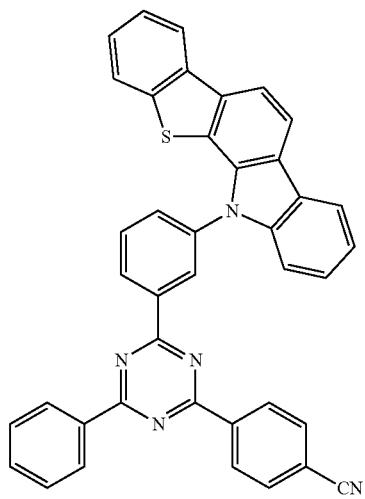
H2-306
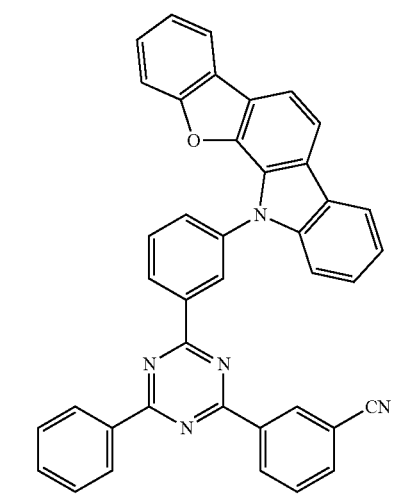
H2-311
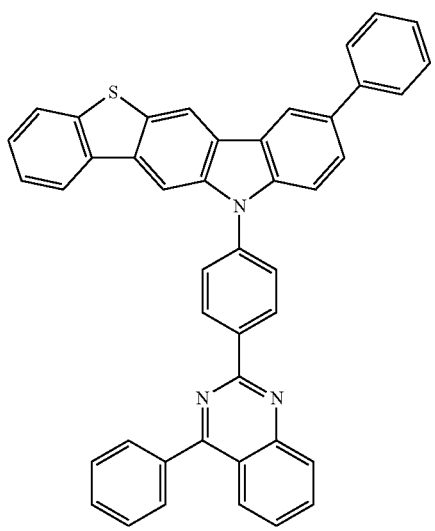
H2-312
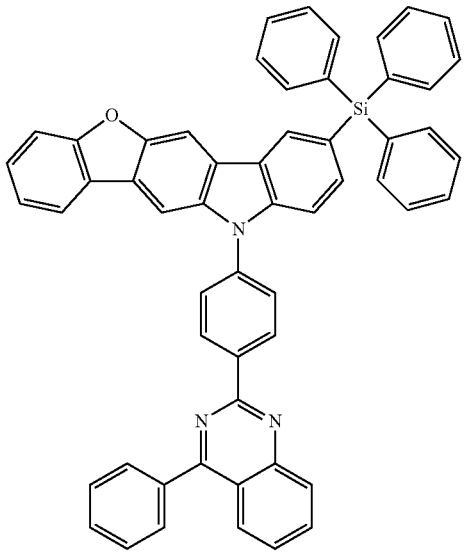
H2-313
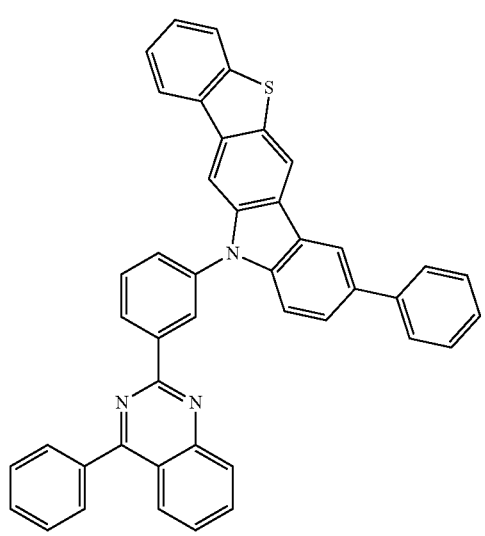
H2-314
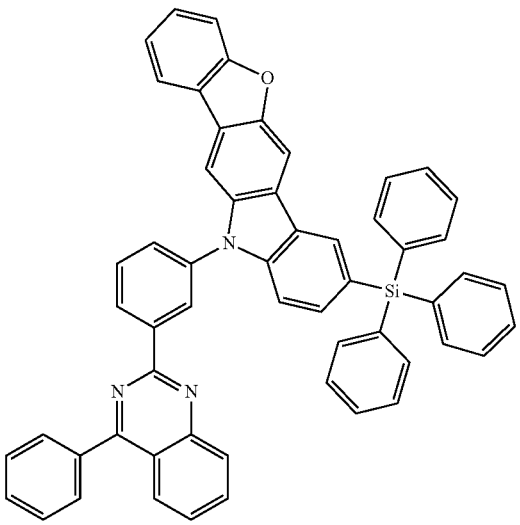

637
-continued
638
-continued
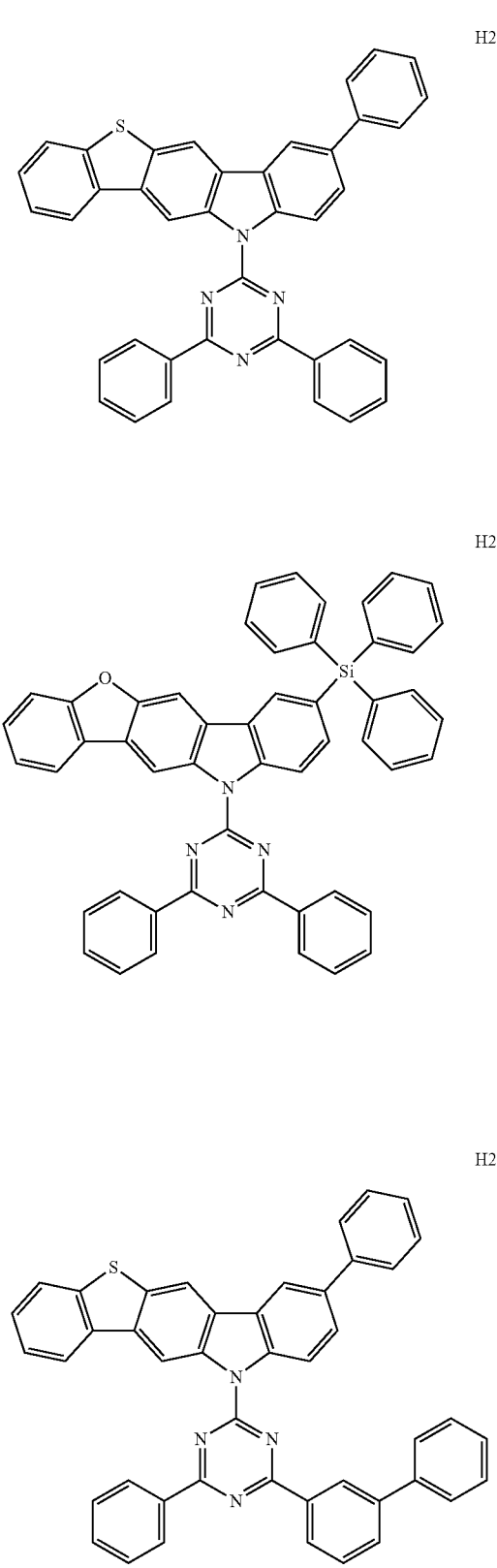
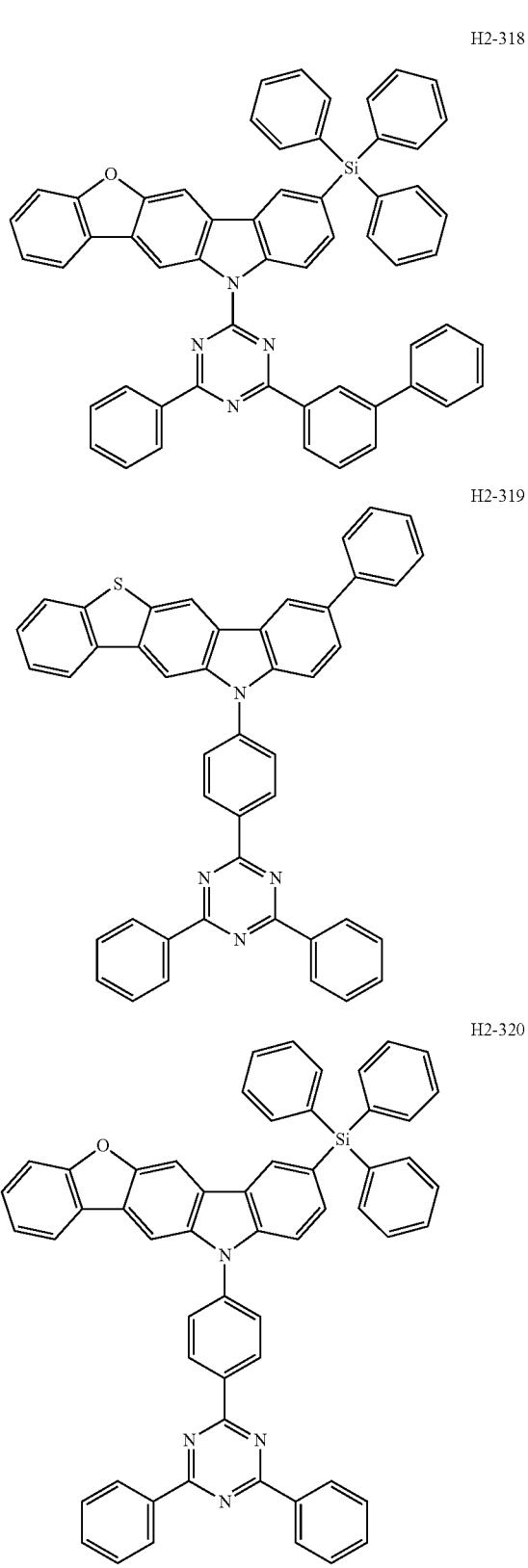

-continued
H2-321
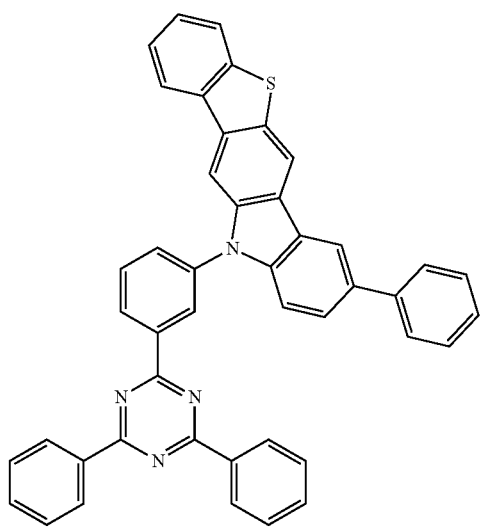
H2-322
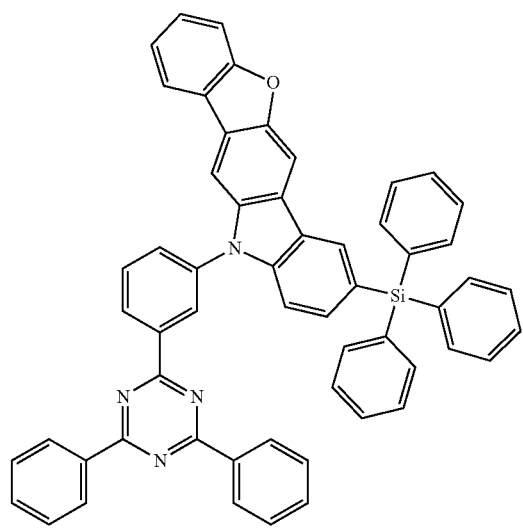
H2-327
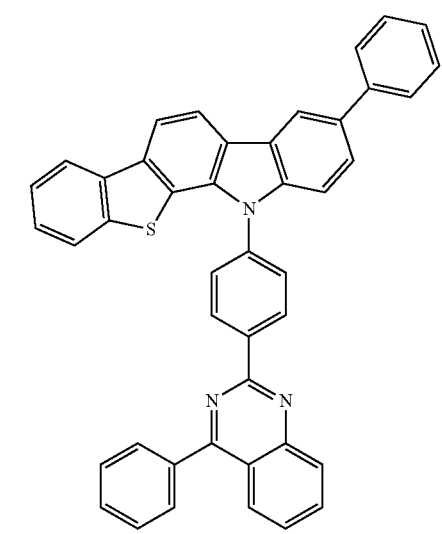
-continued
H2-328
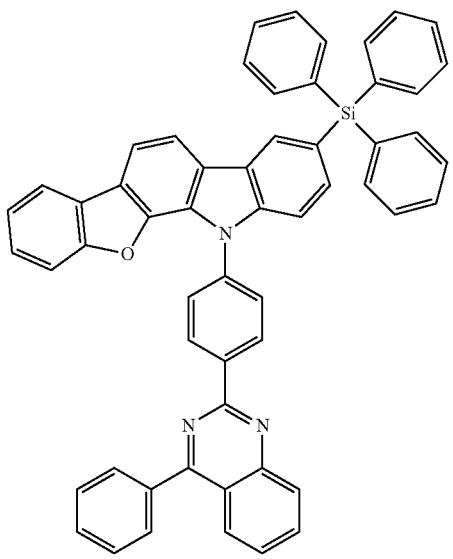
H2-329
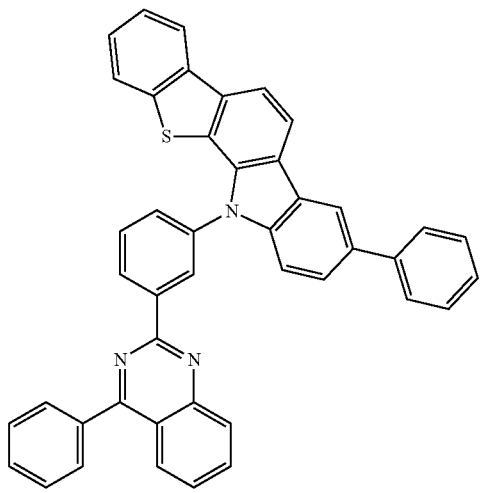
H2-330
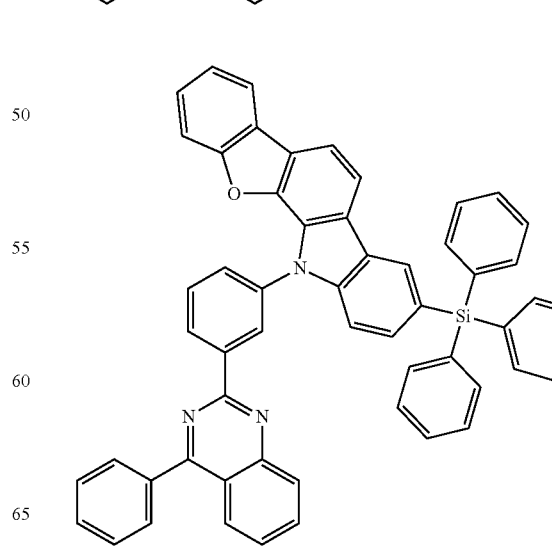

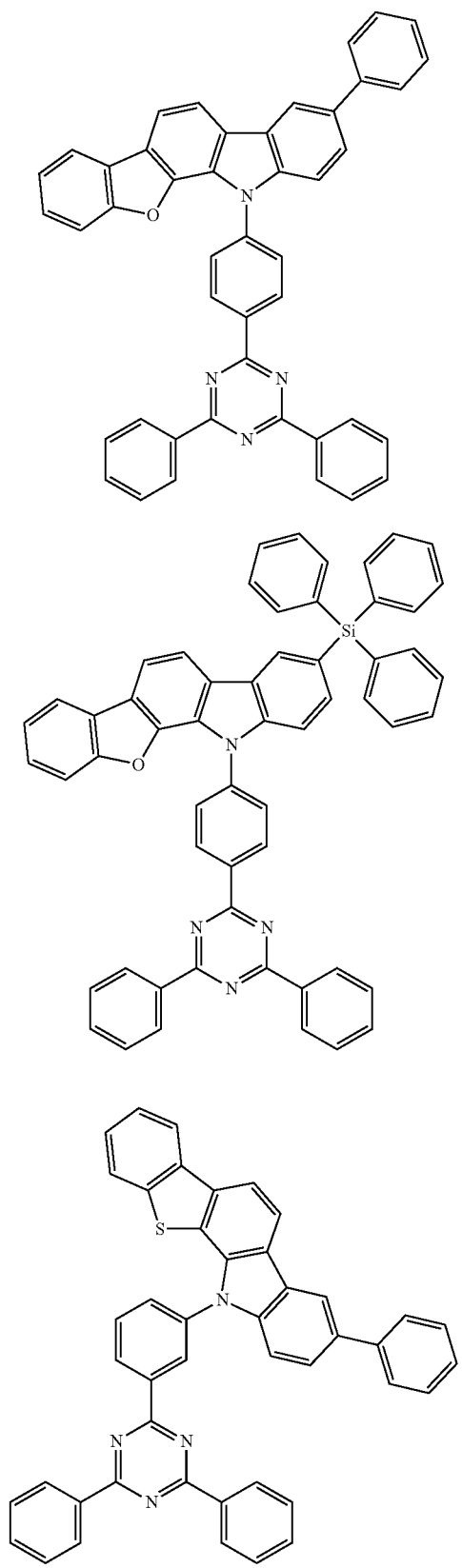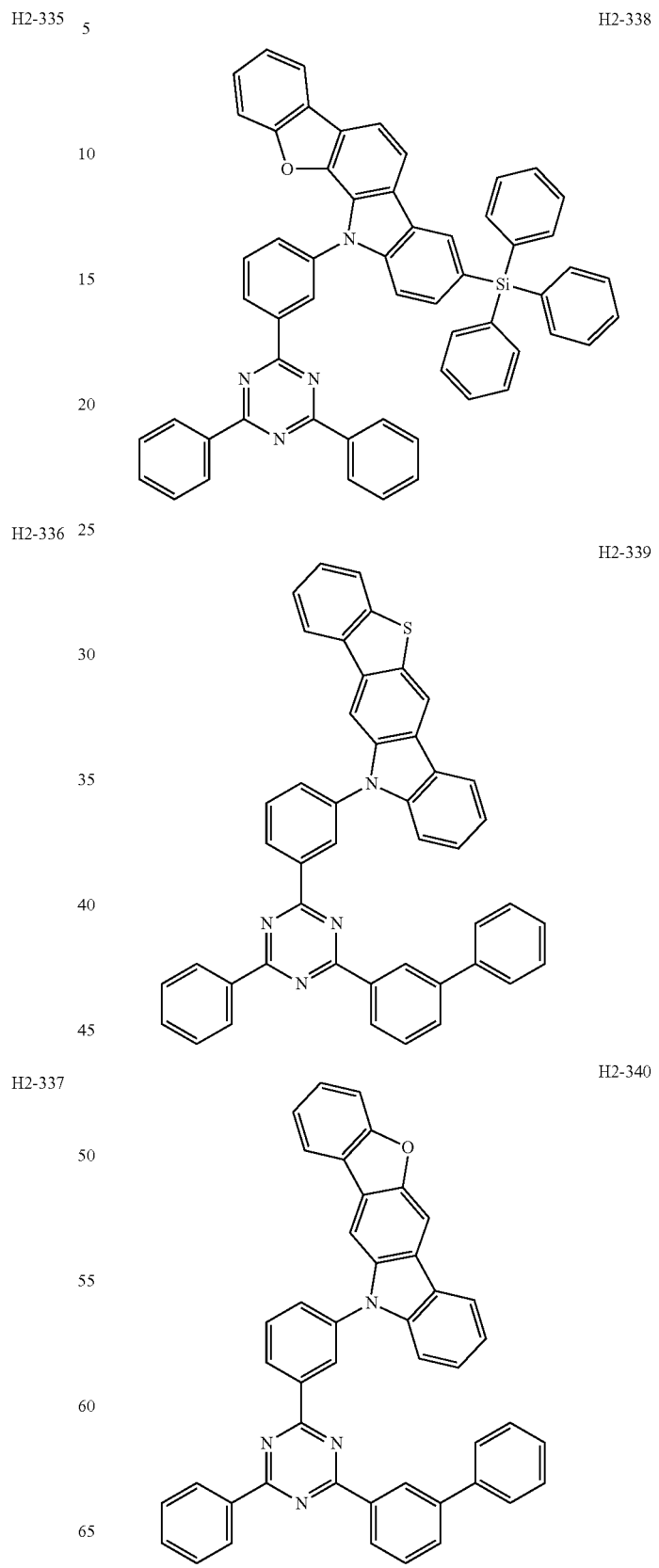

H2-341
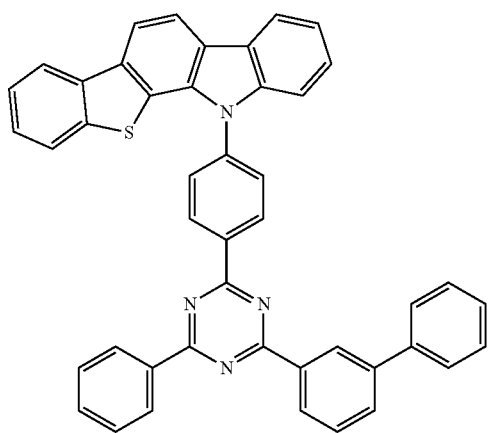
H2-342
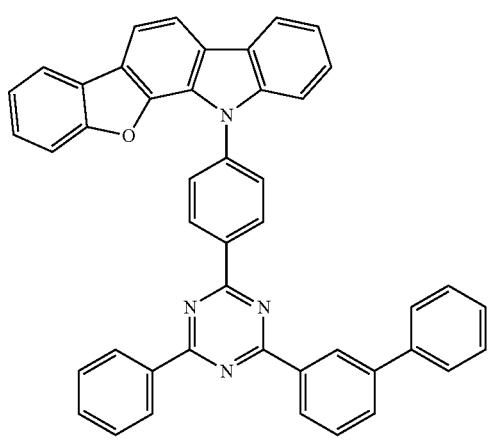
H2-343
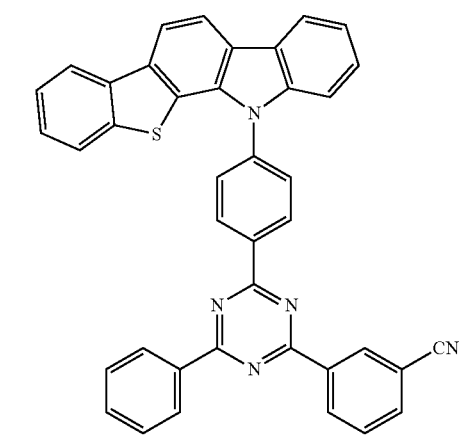
H2-344
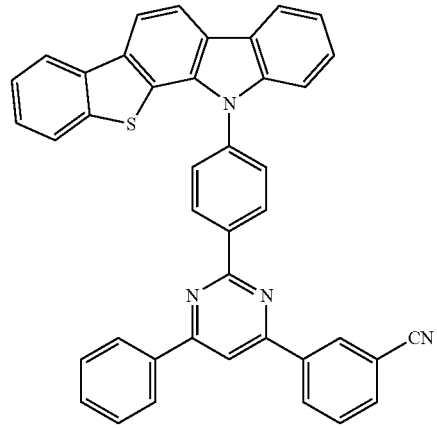
H2-345
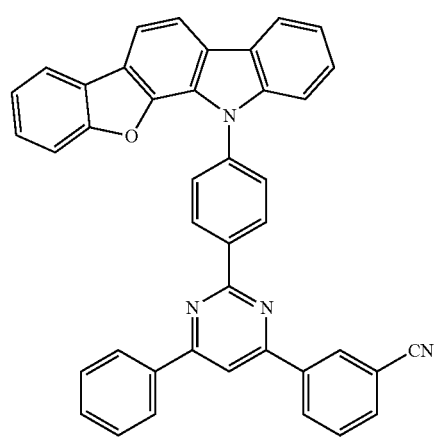
H2-346
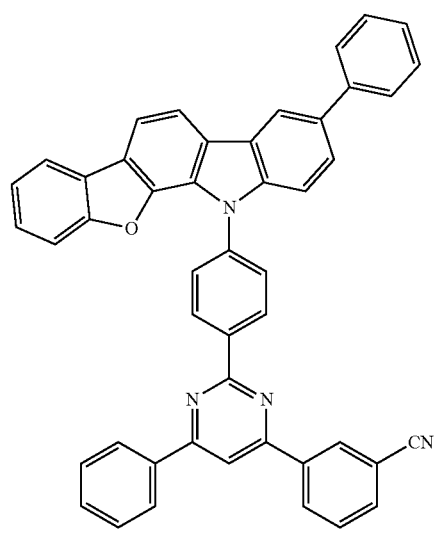

H2-347
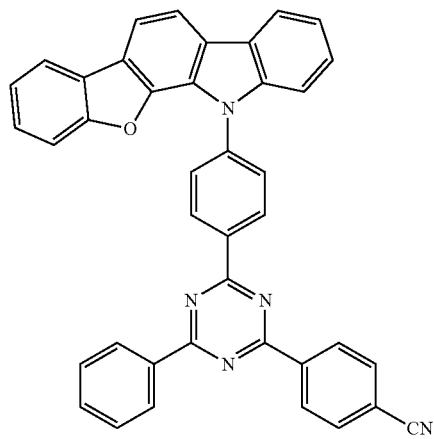
H2-348
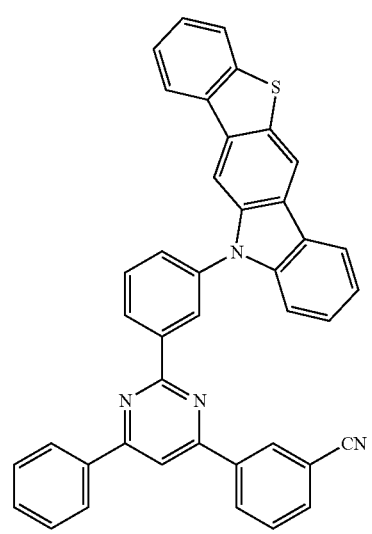
H2-349
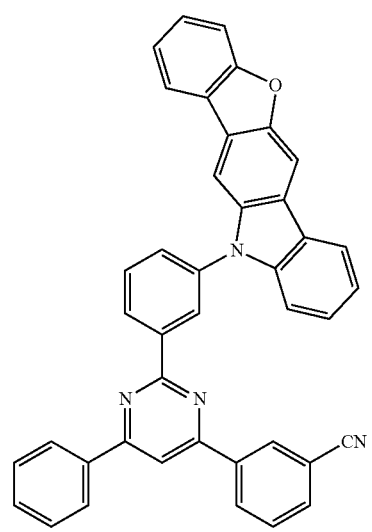
H2-350
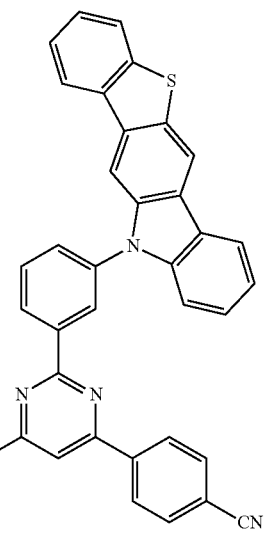
H2-351
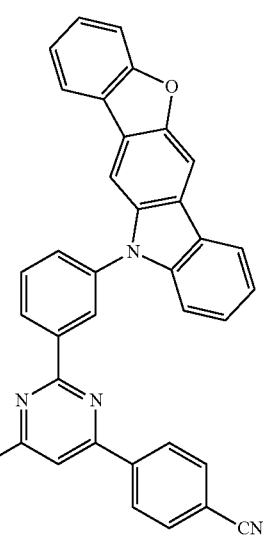
H2-352
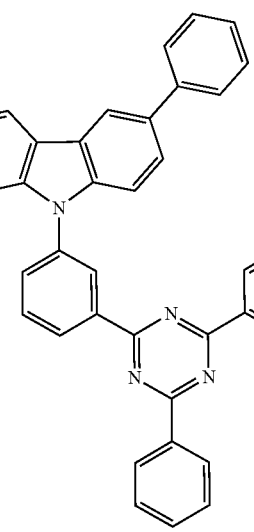

H2-353
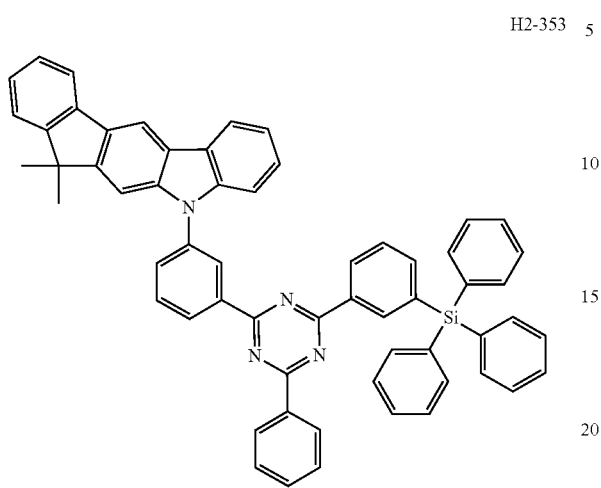
H2-354
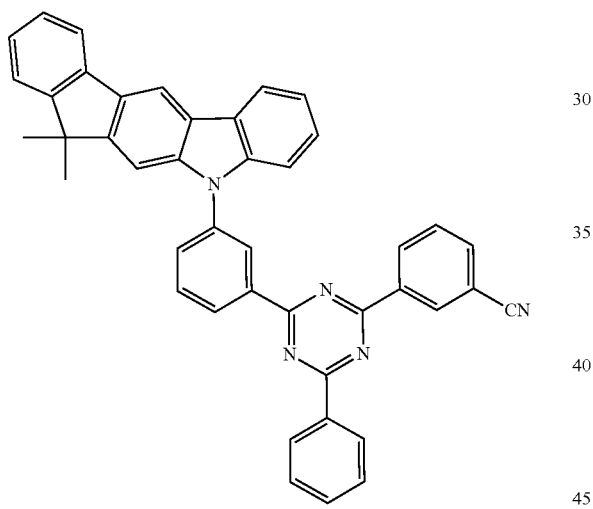
H2-355
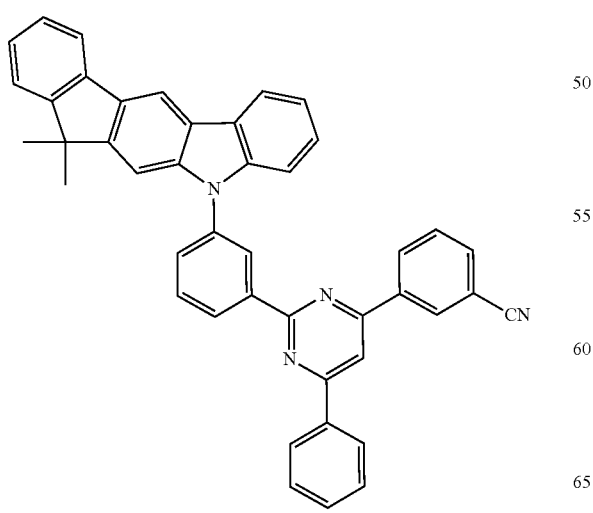
H2-356
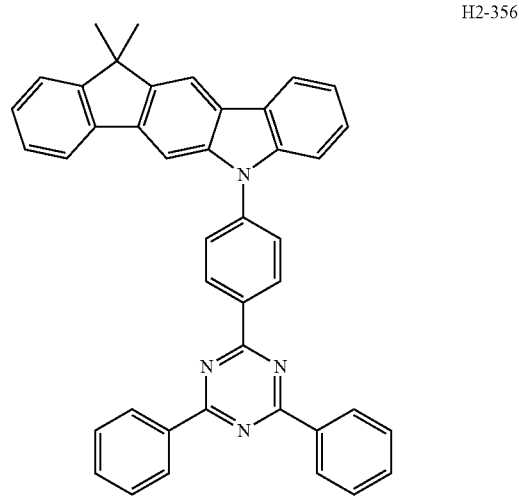
H2-357
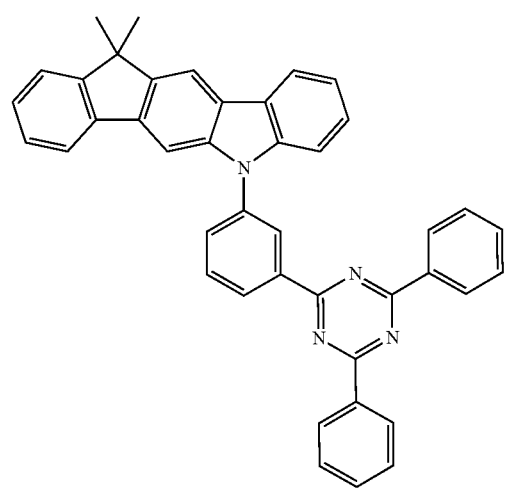
H2-360
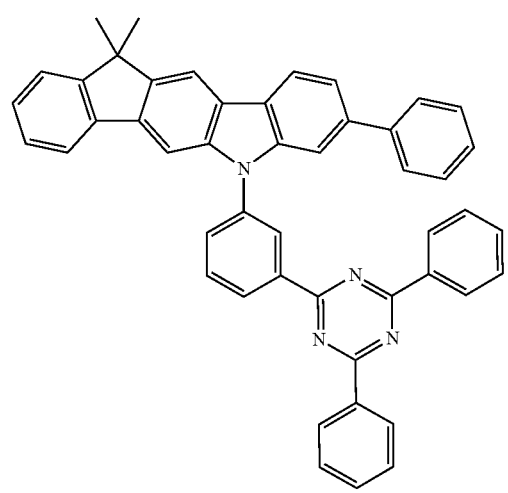

H2-366
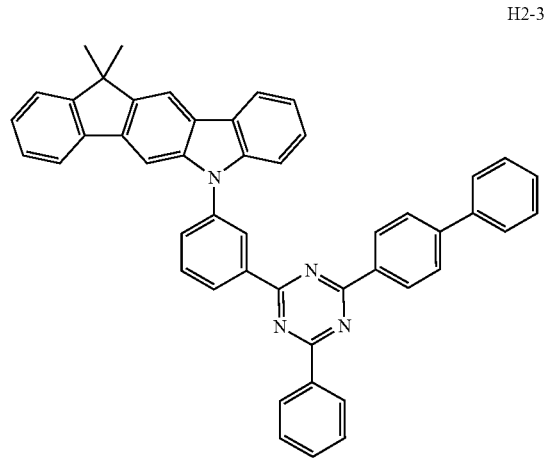
H2-370
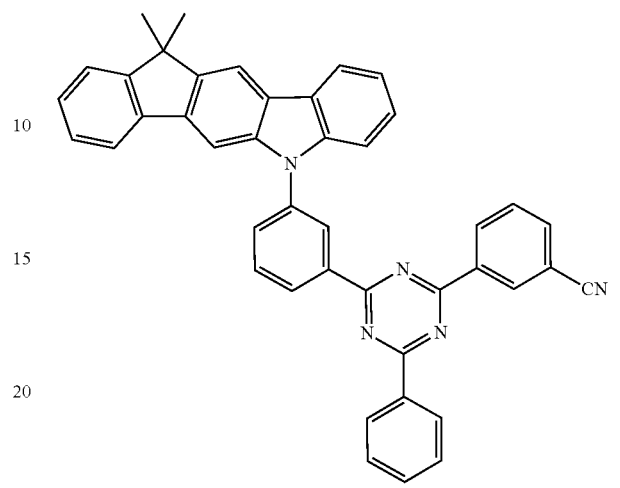
H2-368
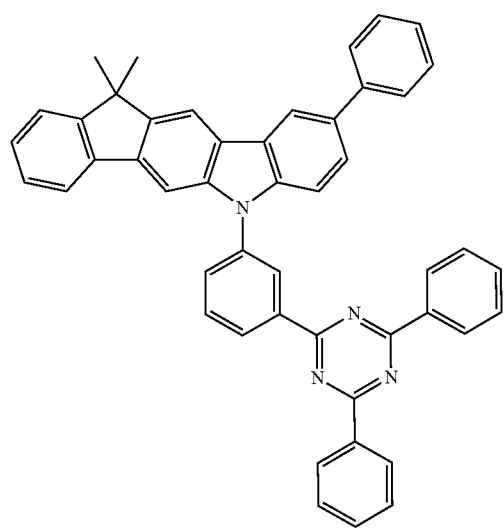
H2-371
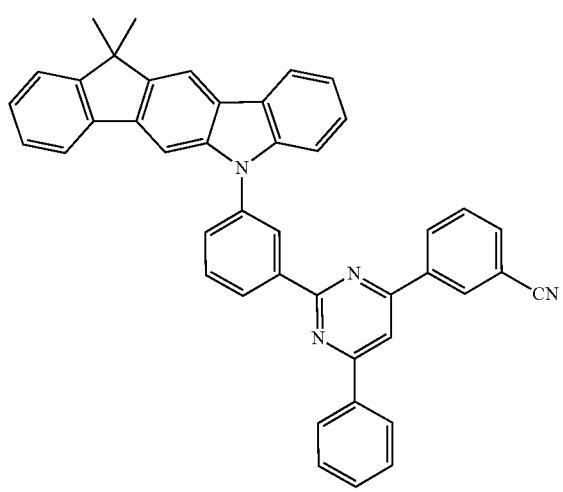
H2-369
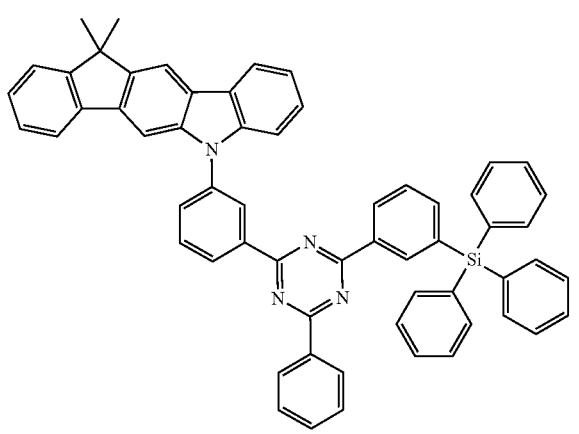
H2-372
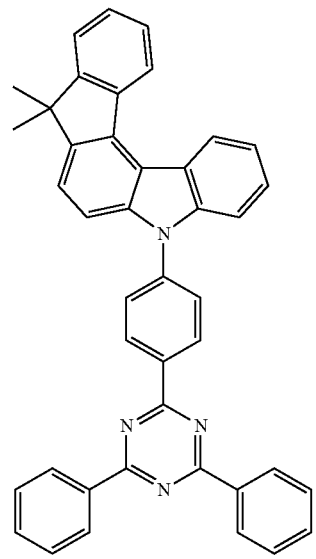

651
-continued
H2-373
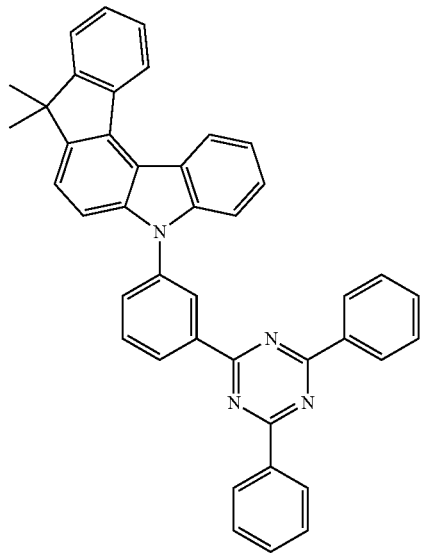
H2-376
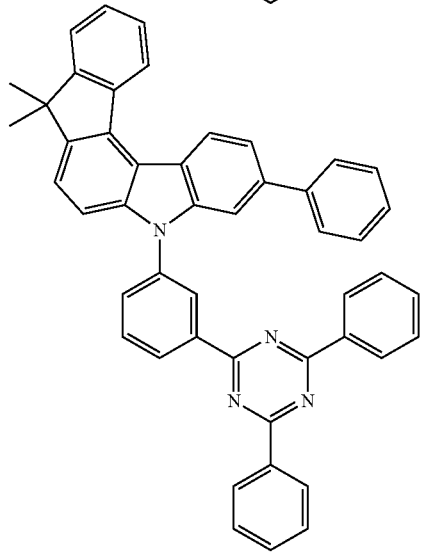
H2-382
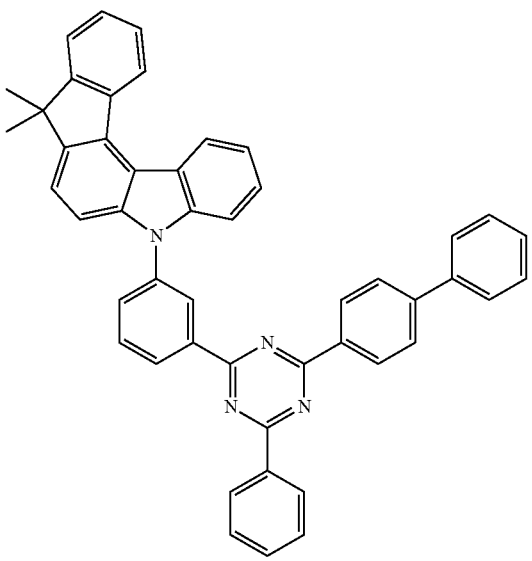
652
-continued
H2-384
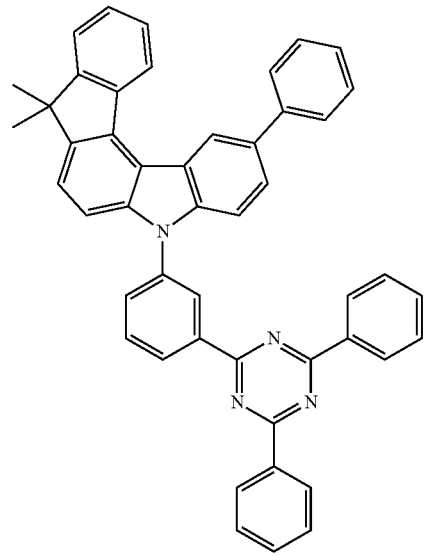
H2-385
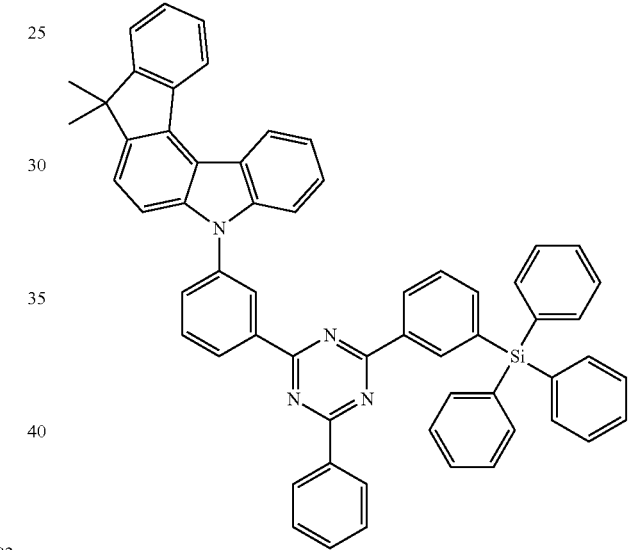
H2-386
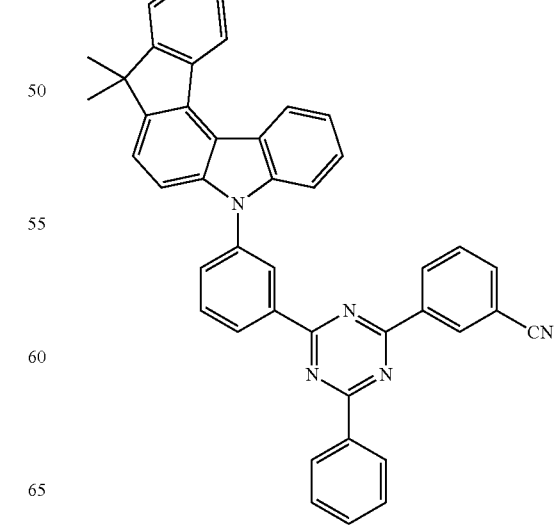

H2-387
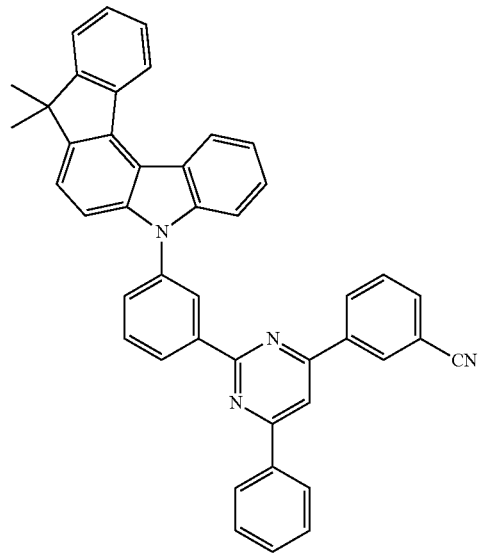
H2-388
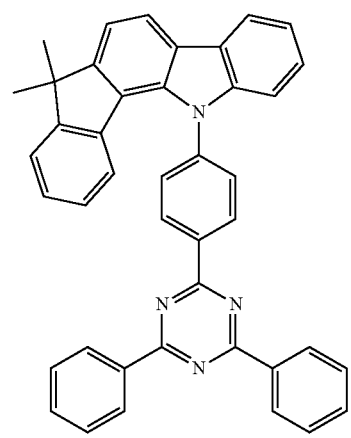
H2-389
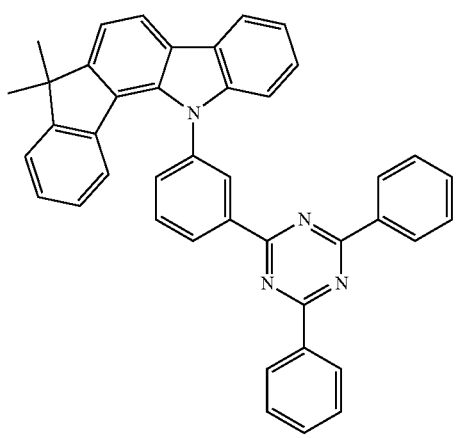
H2-392
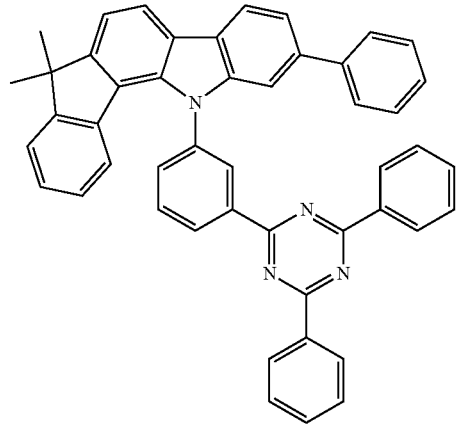
H2-398
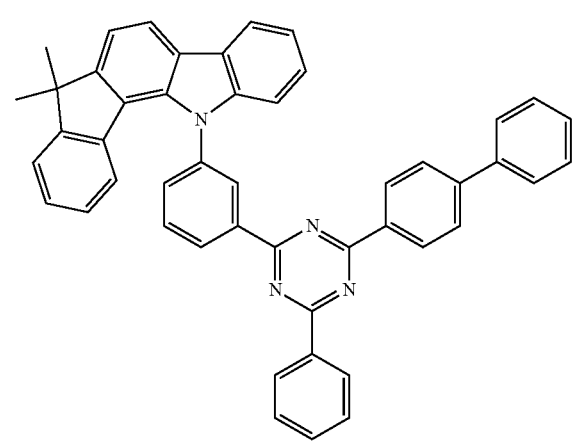
H2-400
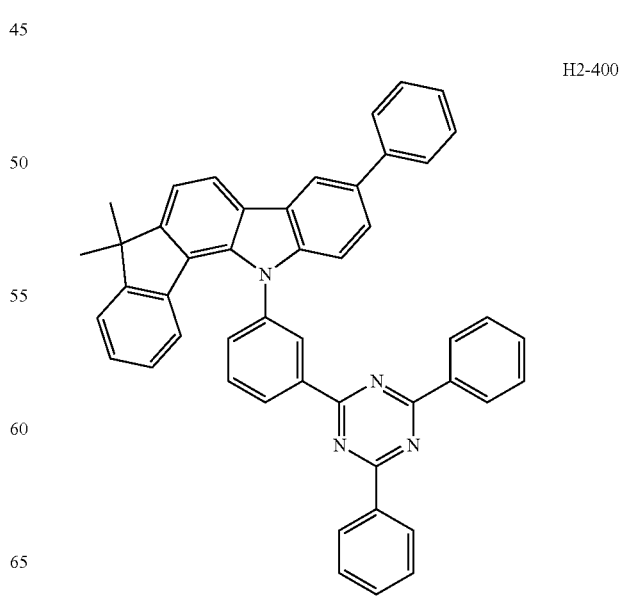

-continued
H2-401
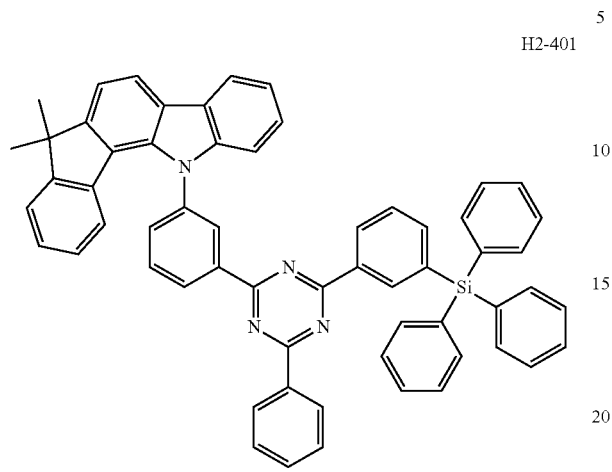
H2-404
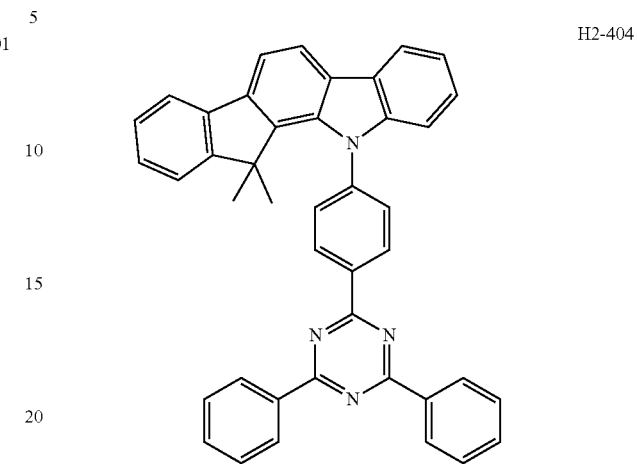
-continued
H2-402
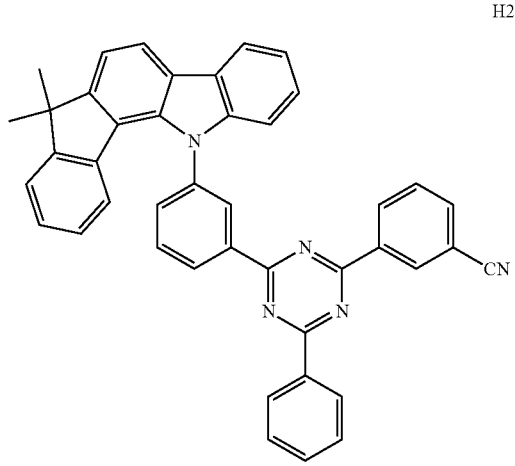
H2-405
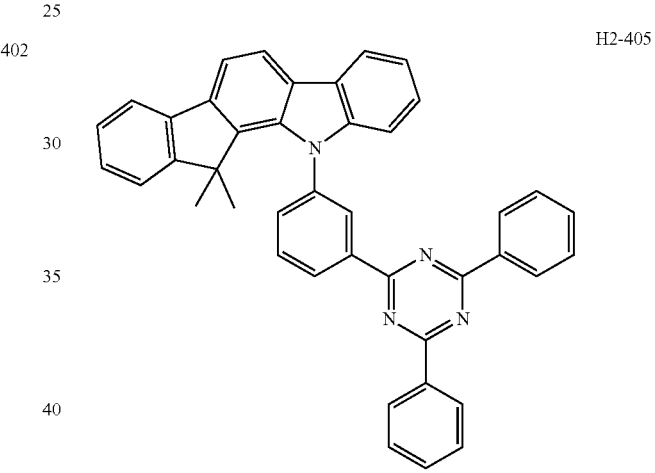
H2-403
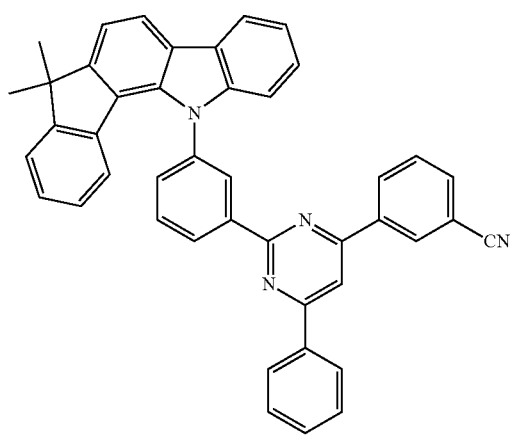
H2-408
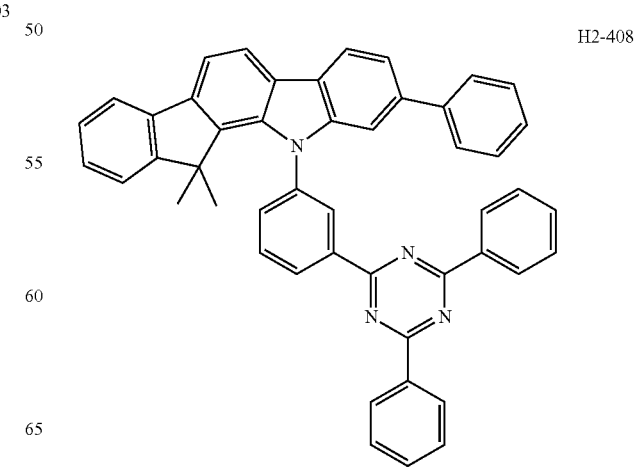

H2-414
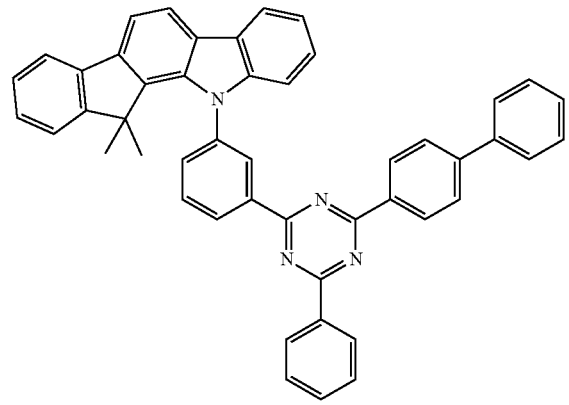
H2-418
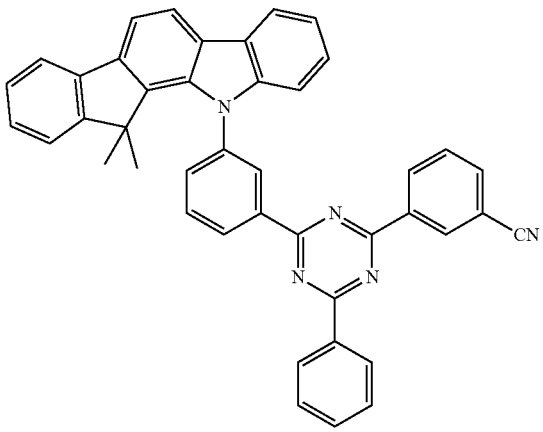
H2-416
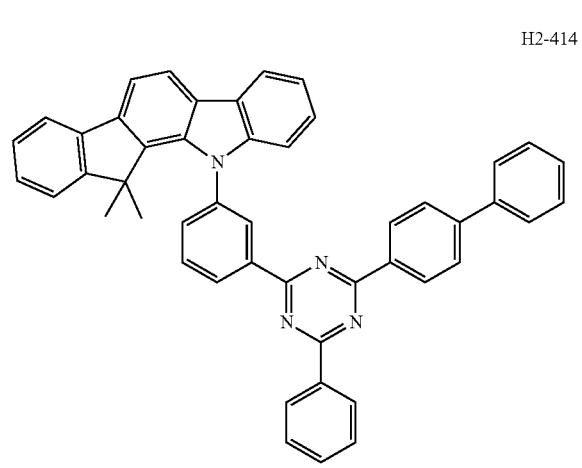
H2-419
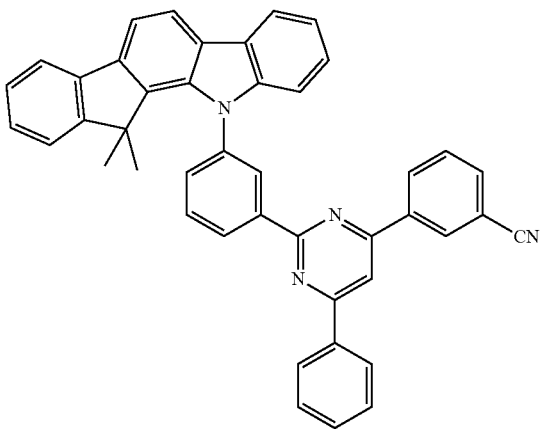
H2-417
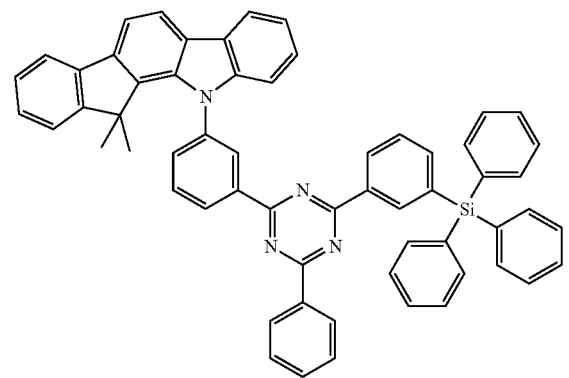
H2-420
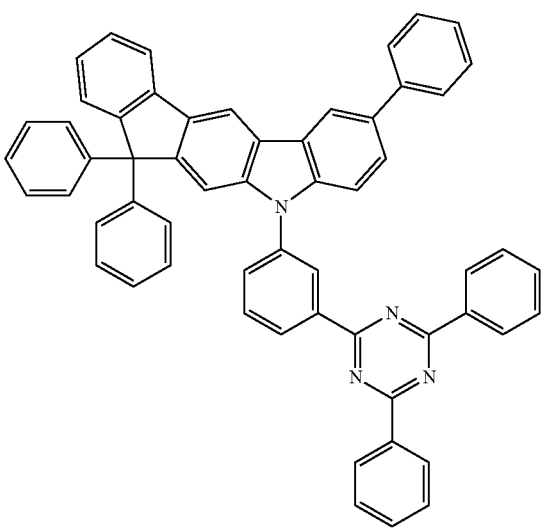

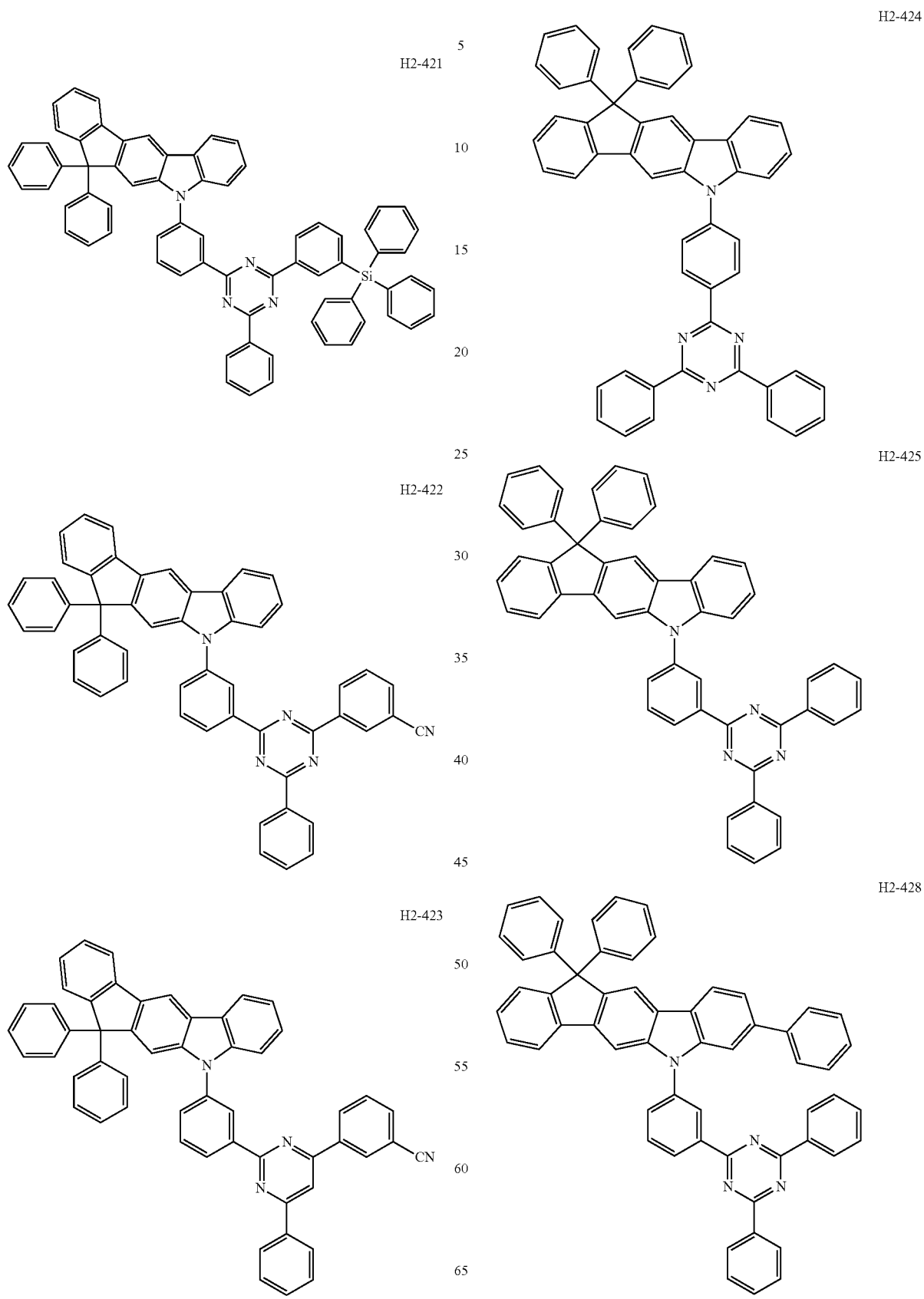

H2-434
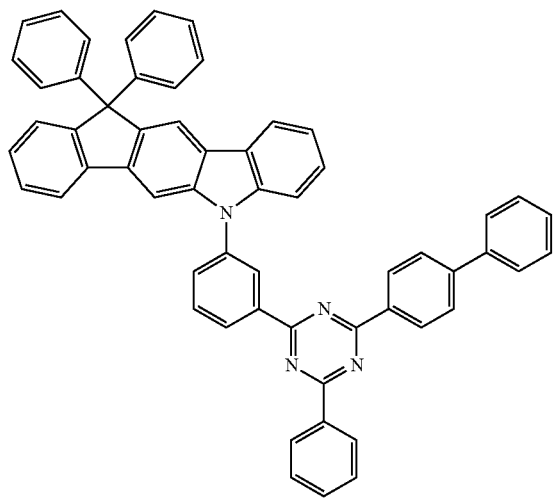
H2-436
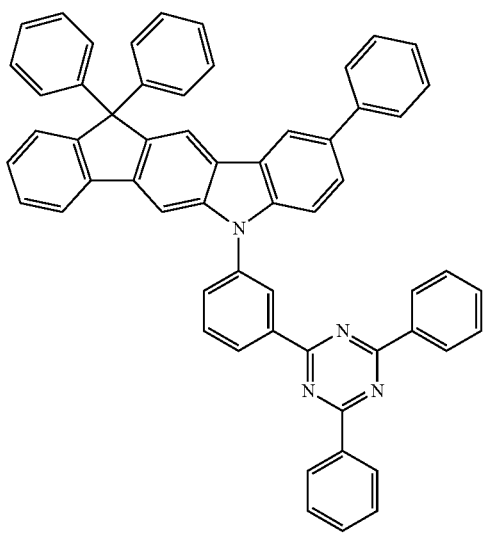
H2-437
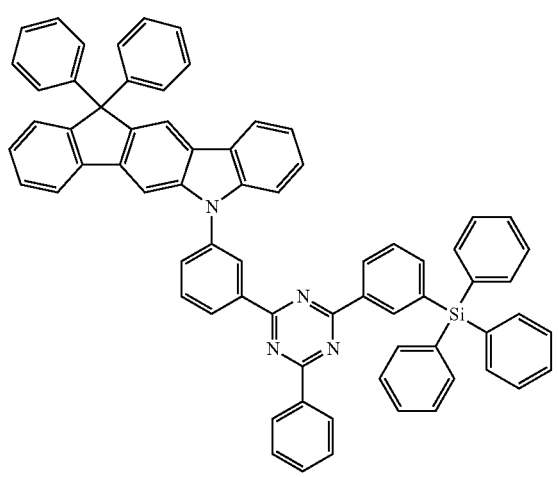
H2-438
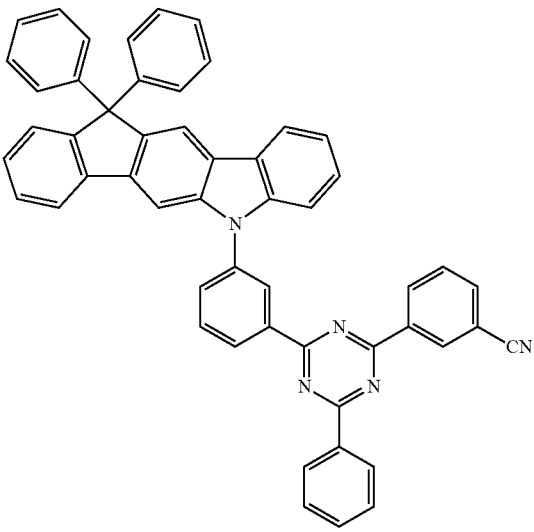
H2-439
H2-440
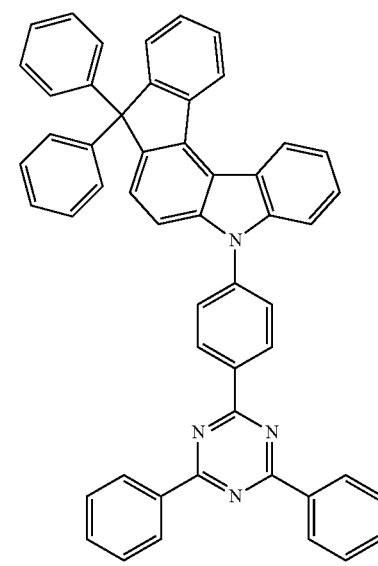

663
-continued
H2-441
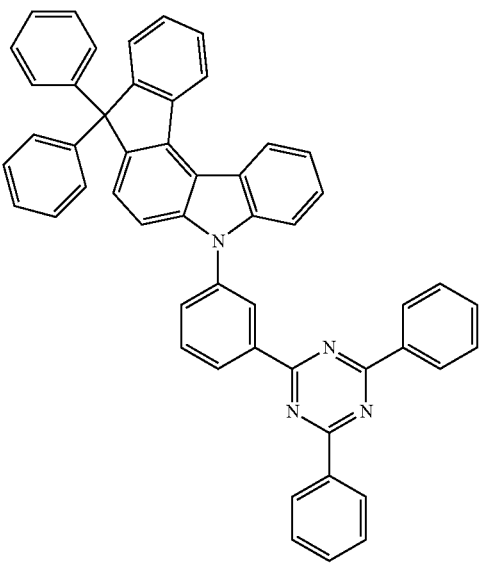
H2-444
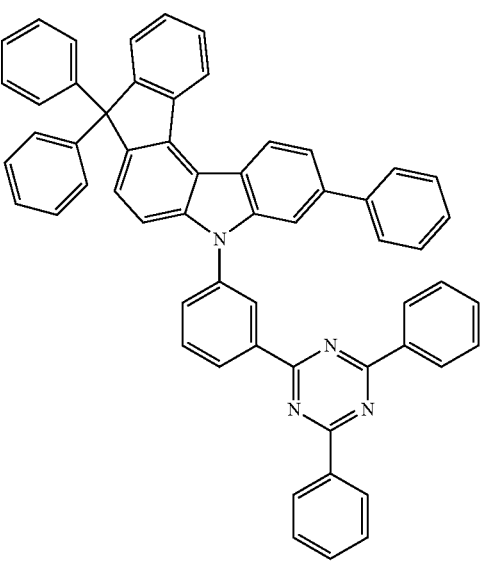
H2-450
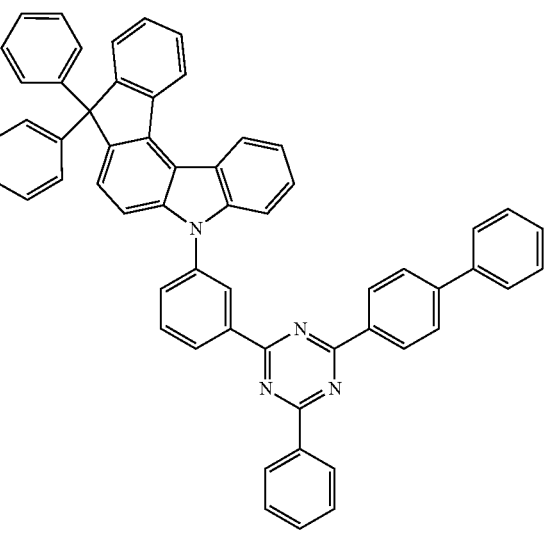
664
-continued
H2-452
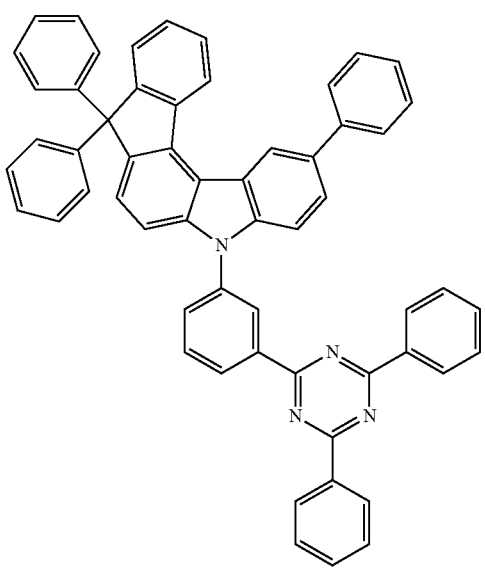
H2-453
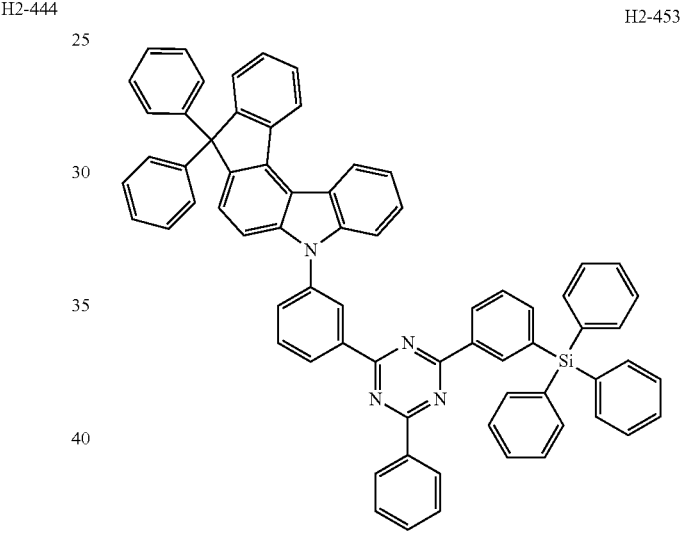
H2-454
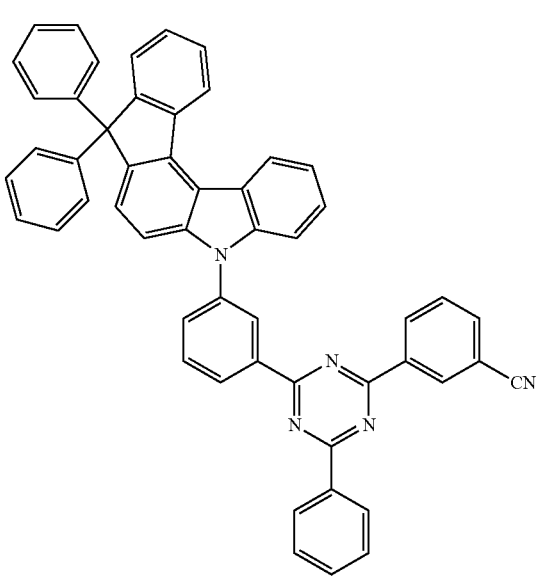

H2-455
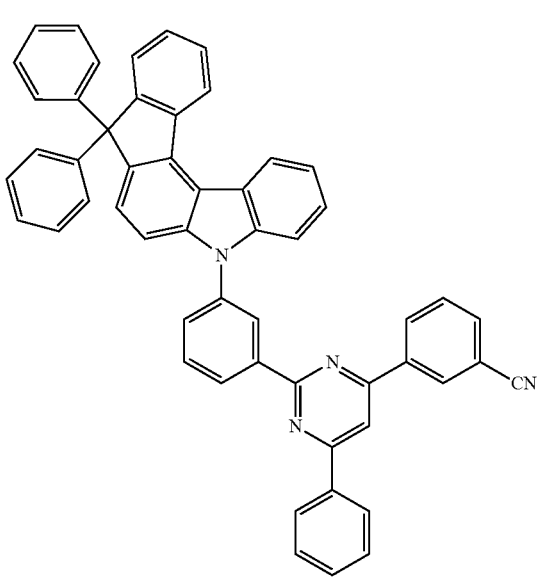
H2-456
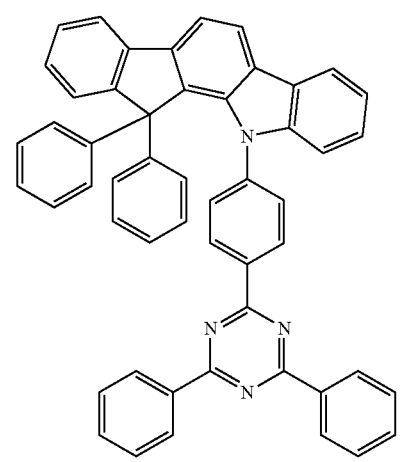
H2-457
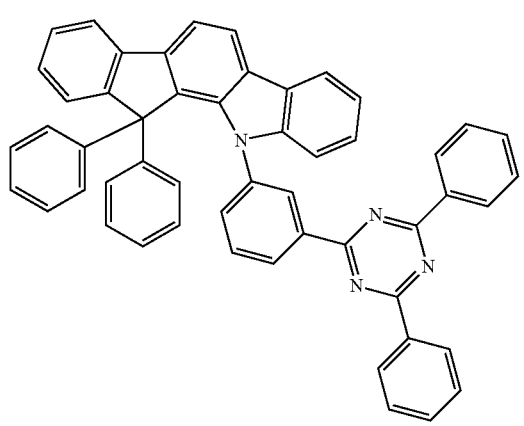
H2-460
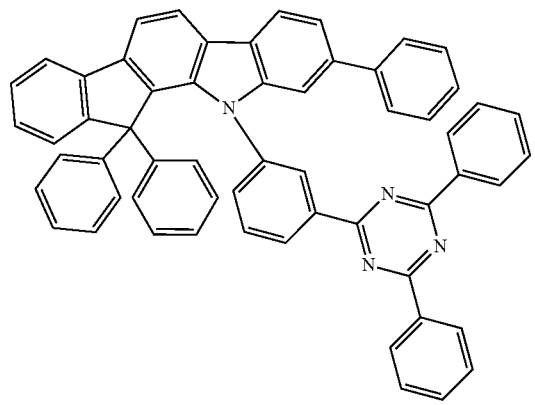
H2-466
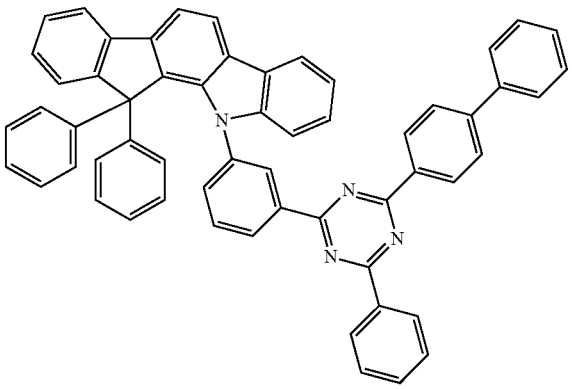
H2-468
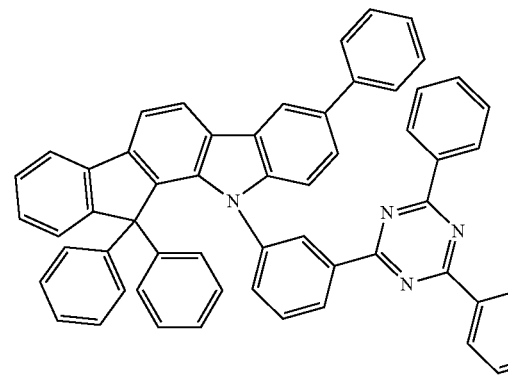
H2-469
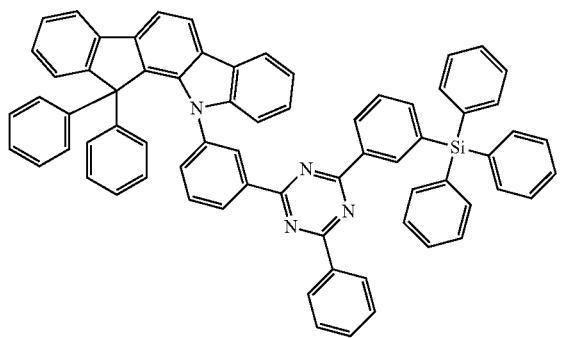

H2-470
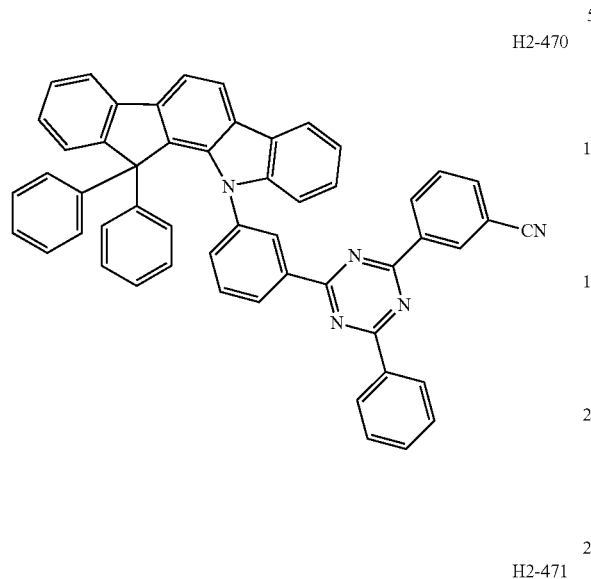
H2-471
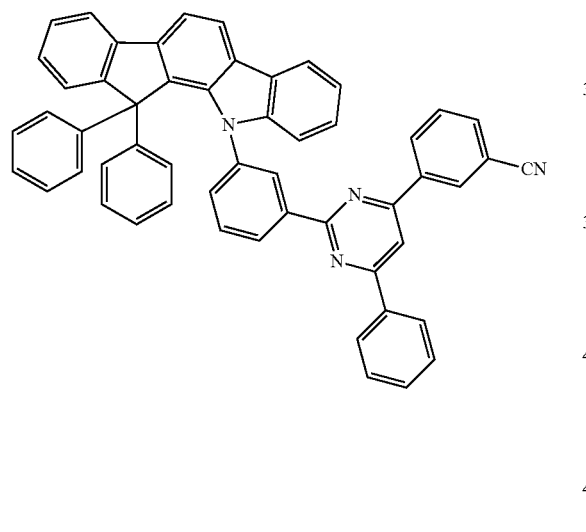
H2-474
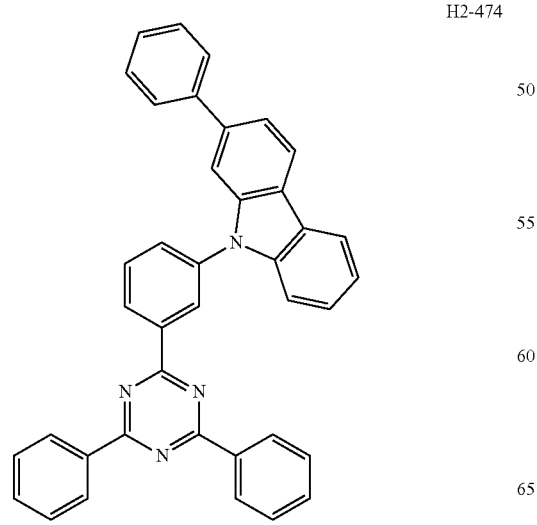
H2-476
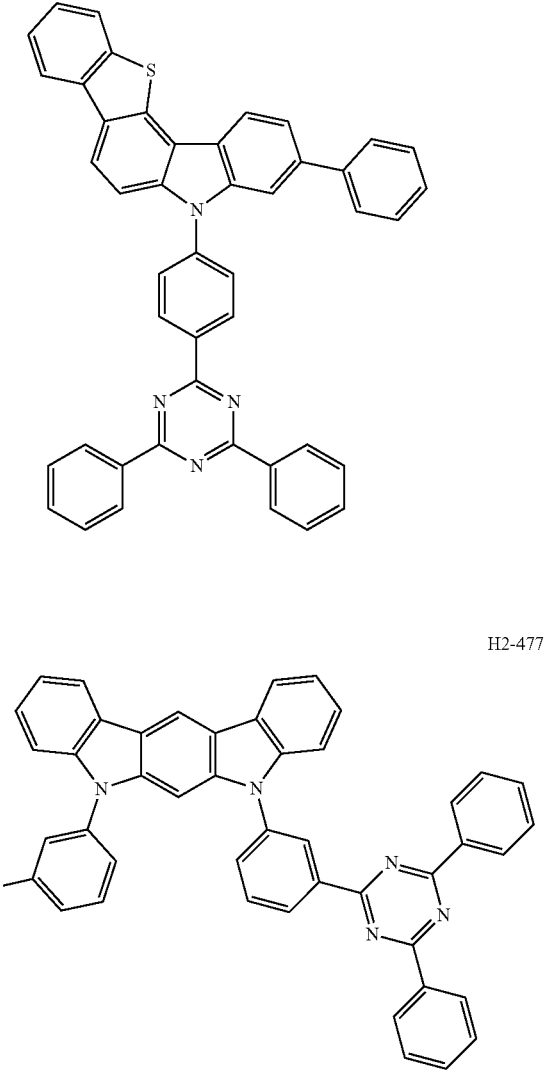
H2-477
H2-479
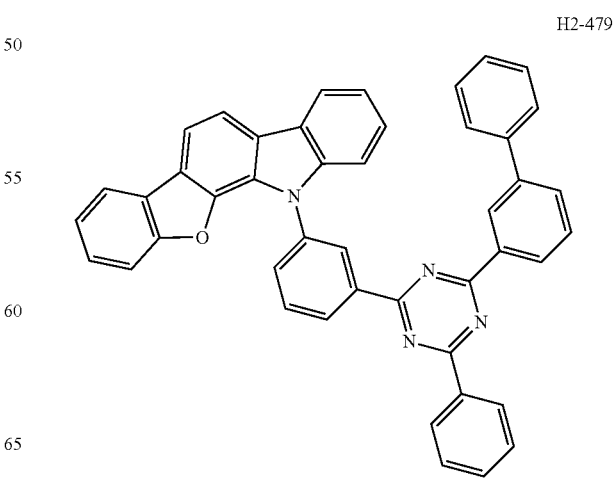

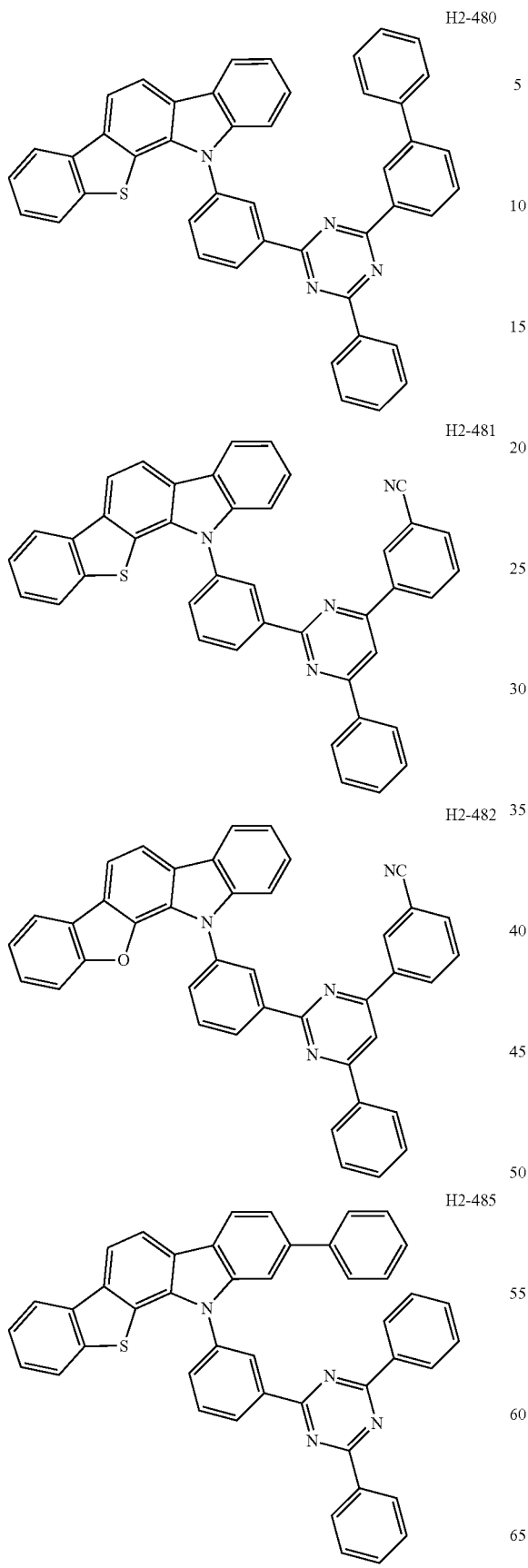
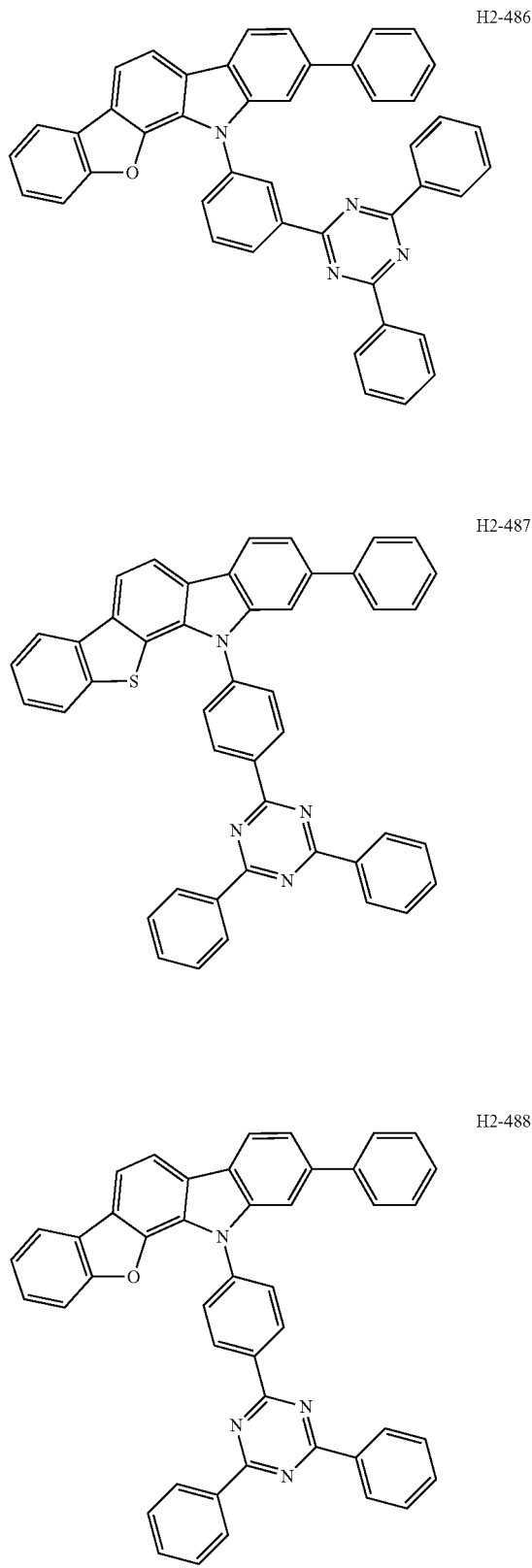

H2-489
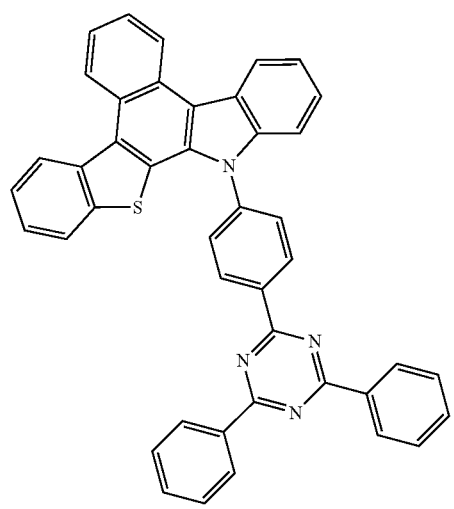
H2-490
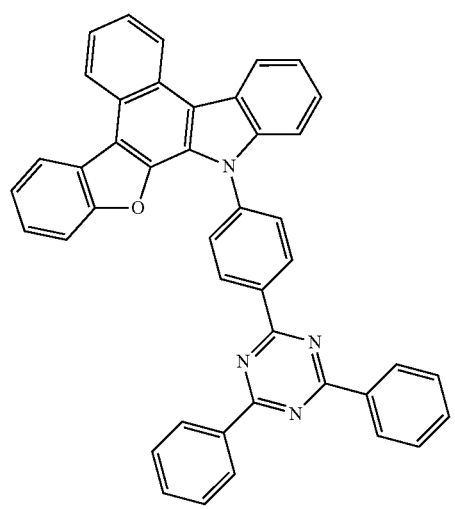
H2-491
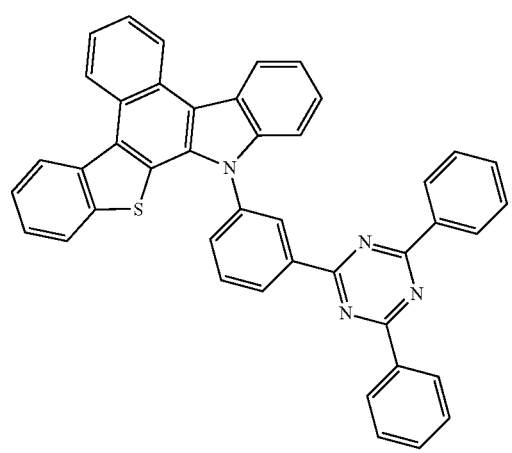
and
H2-492
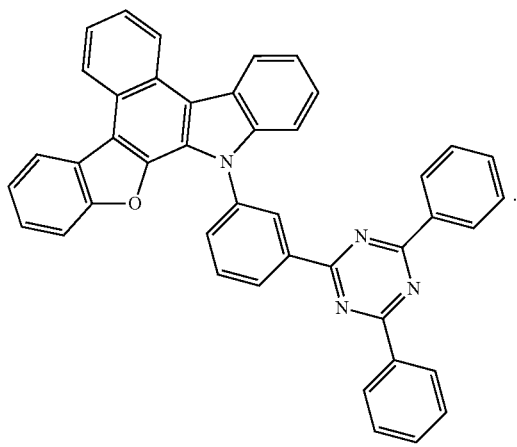
.
11. The organic electroluminescent device according to claim 1, wherein the compound of formula 3 is selected from the group consisting of:
H4-3
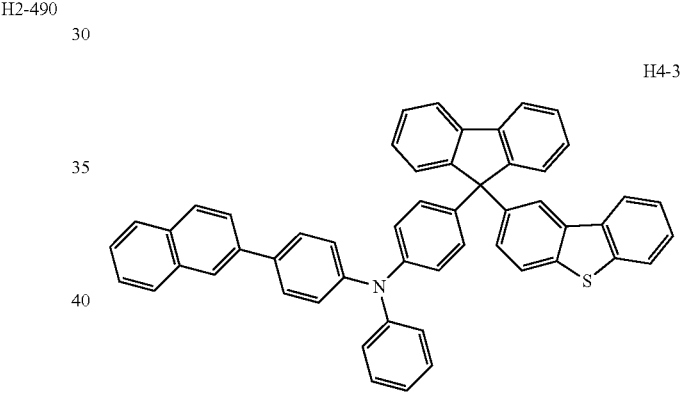
H4-4
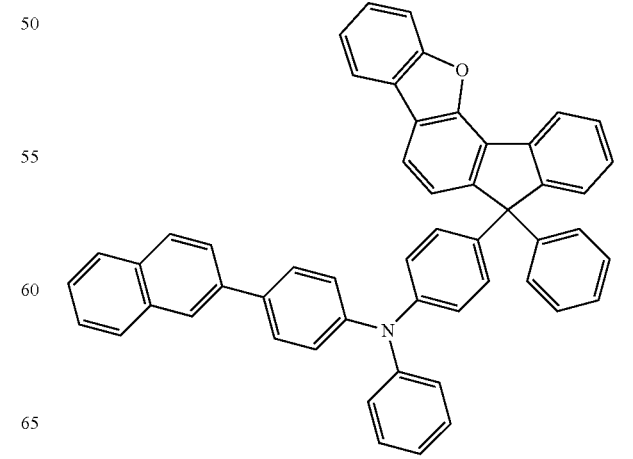

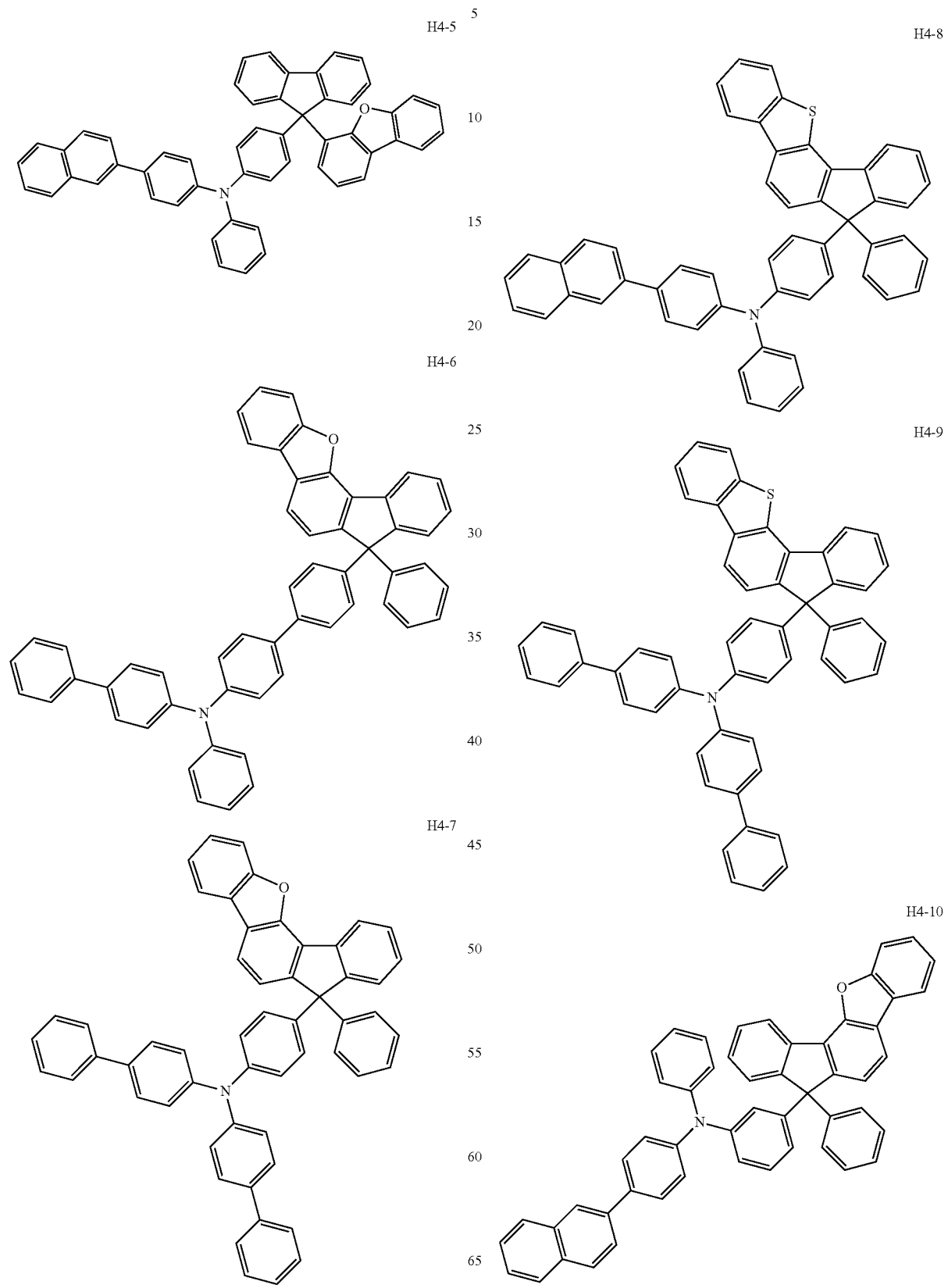

H4-11
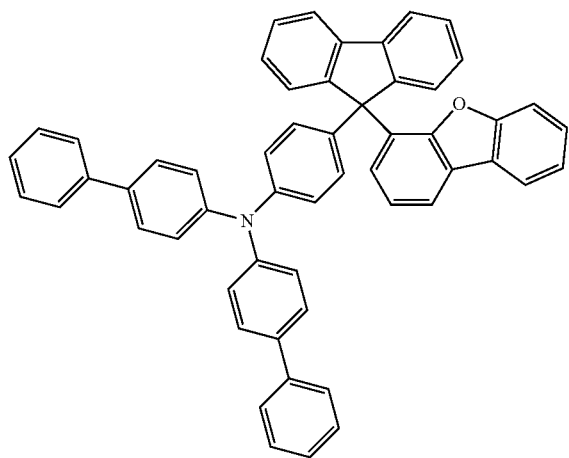
H4-12
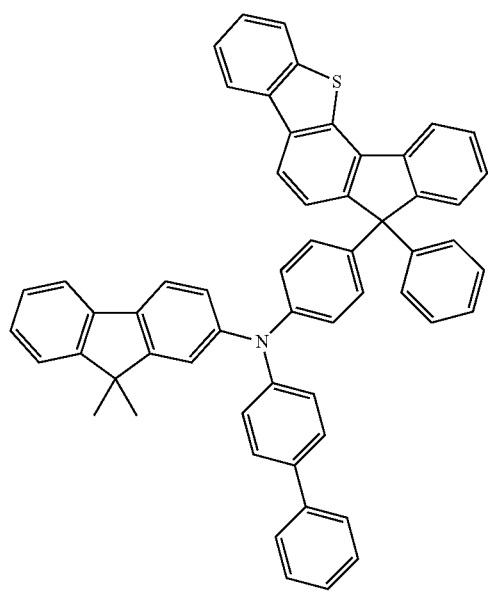
H4-13
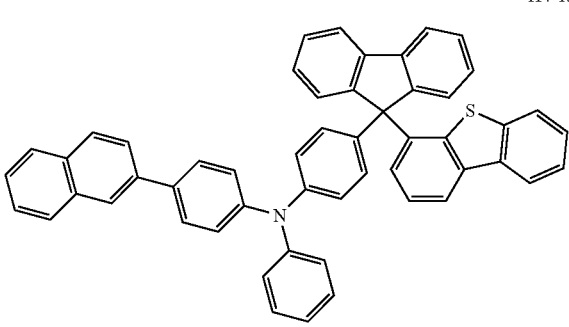
H4-14
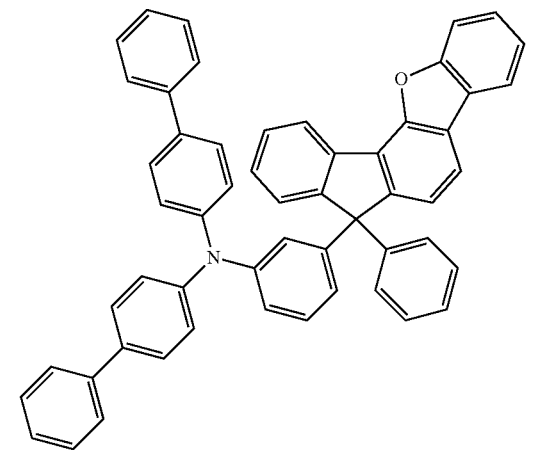
H4-15
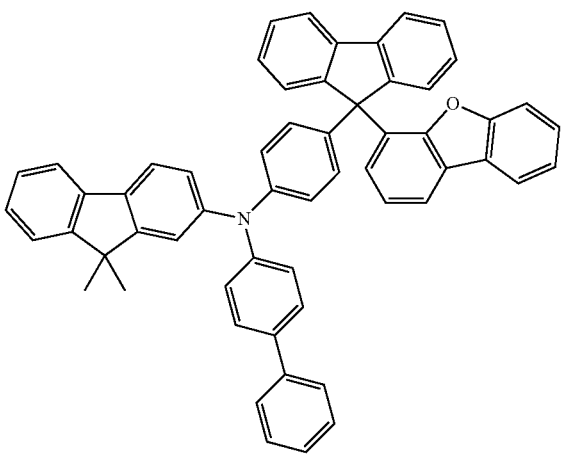
H4-16
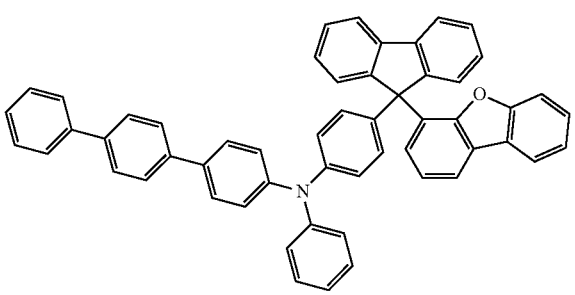
H4-17
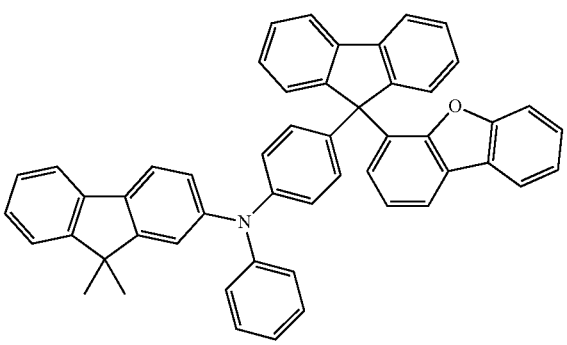

677
-continued
H4-18
H4-19
H4-20
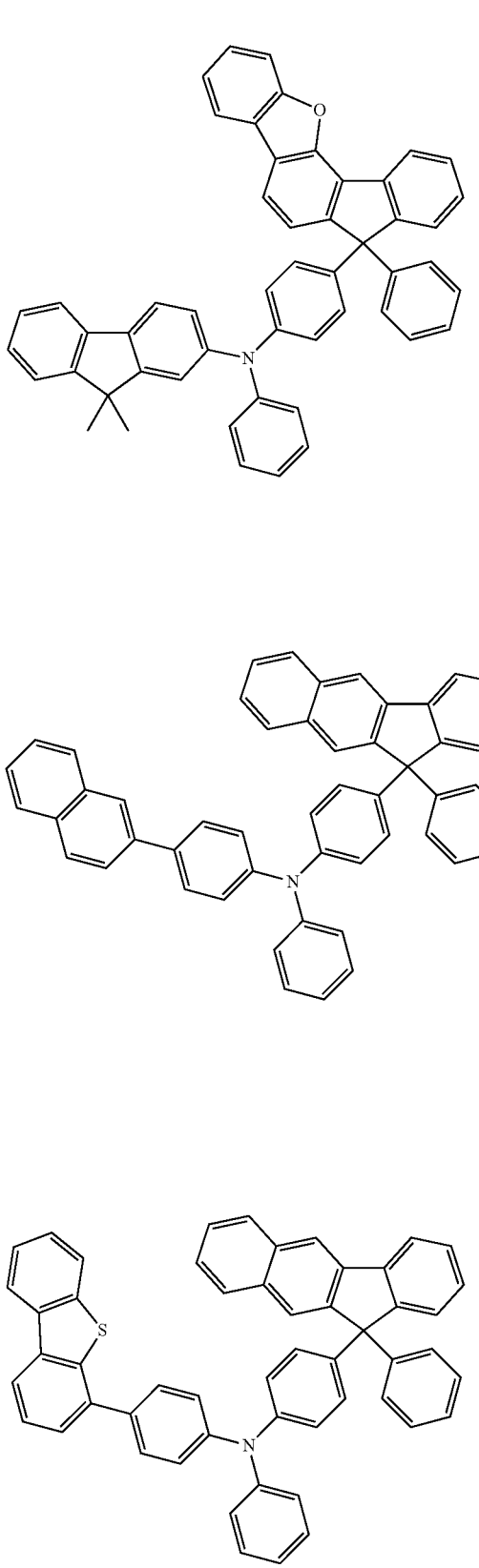
678
-continued
H4-22
H4-23
H4-24
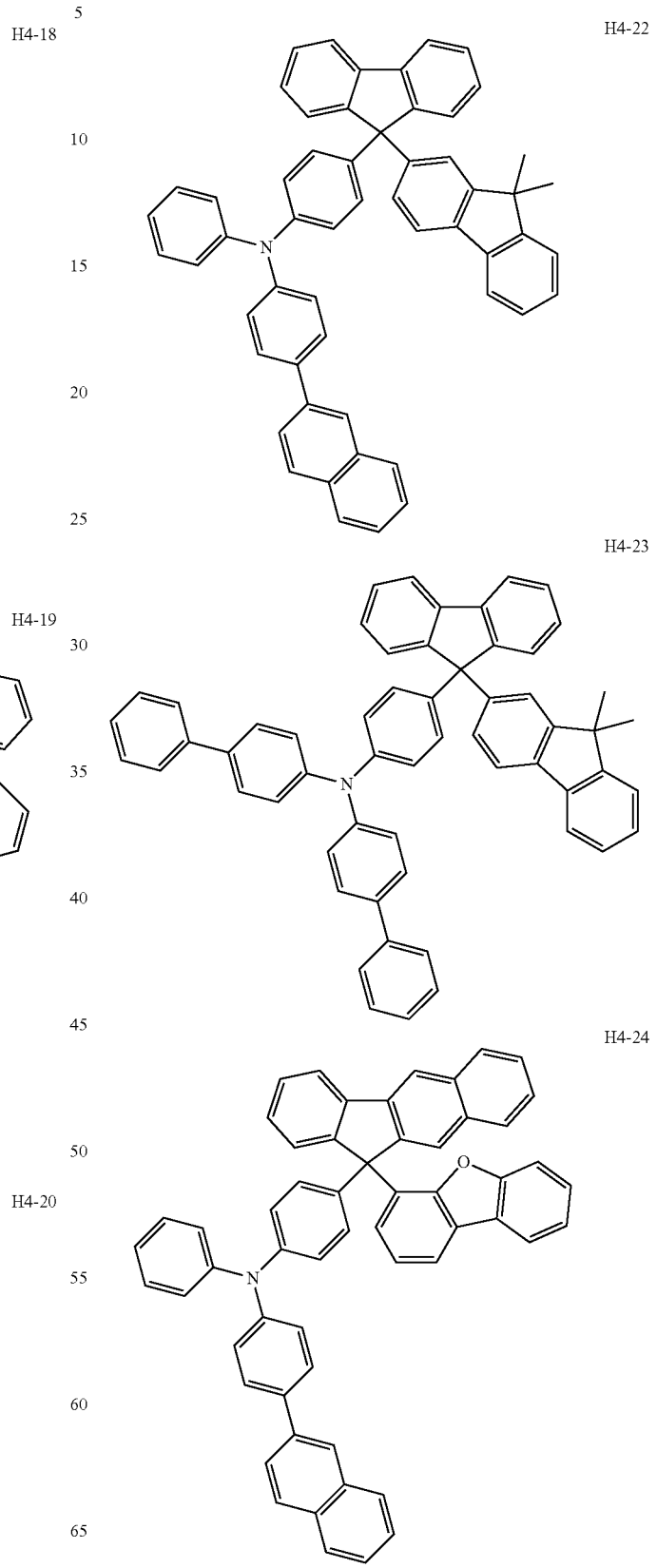

H4-25
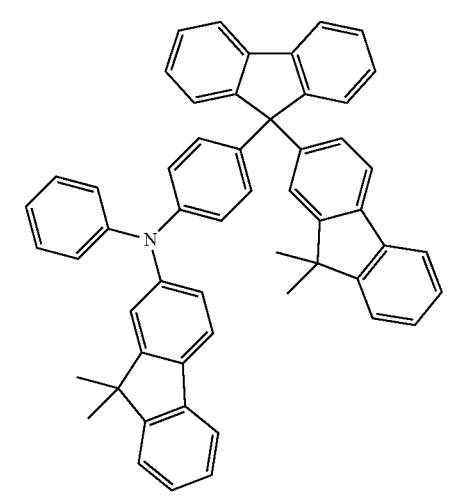
H4-26
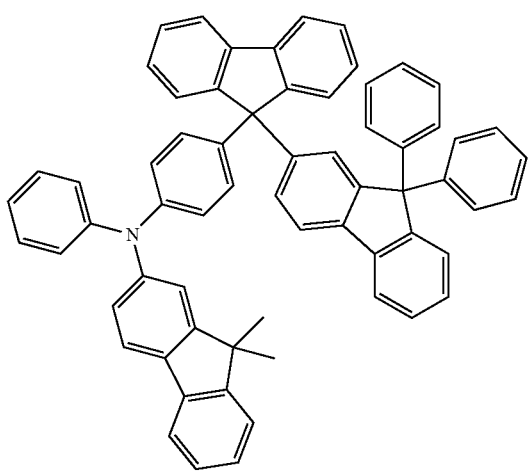
H4-27
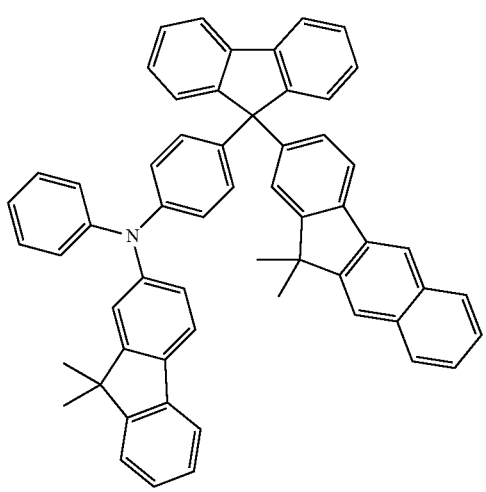
H4-28
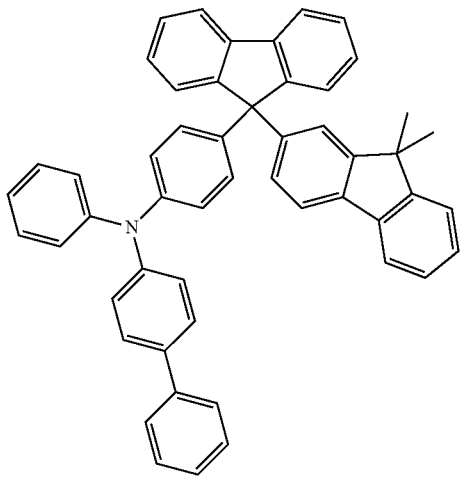
H4-33
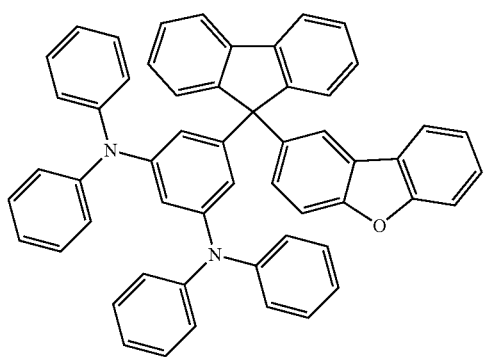
H4-34
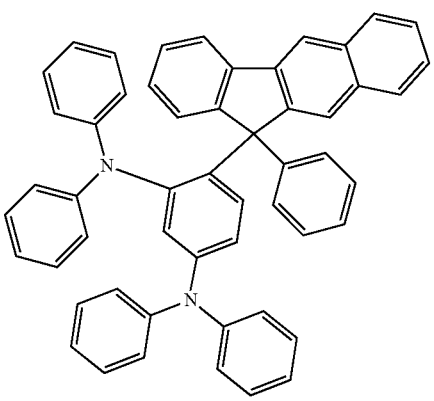
H4-35
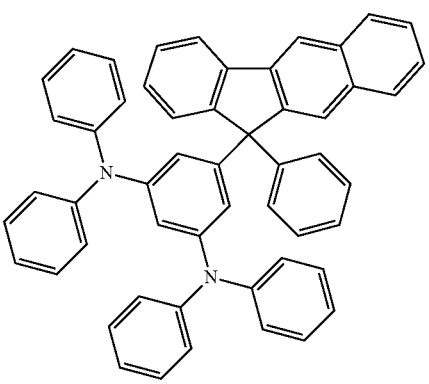
and -continued
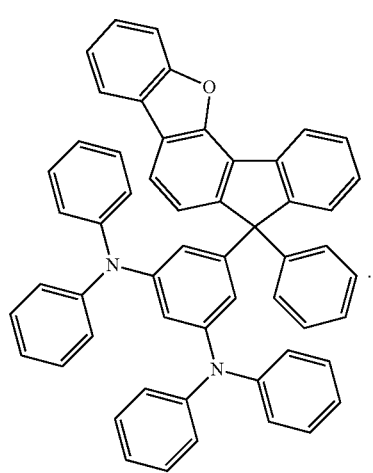
H4-37